United States Patent
Tanaka et al.

(10) Patent No.: US 11,459,325 B2
(45) Date of Patent: Oct. 4, 2022

(54) HETEROCYCLIC COMPOUND

(71) Applicant: Takeda Pharmaceutical Company Limited, Osaka (JP)

(72) Inventors: Yuta Tanaka, Kanagawa (JP); Tomohiro Ohashi, Kanagawa (JP); Zenichi Ikeda, Kanagawa (JP); Yuta Tanaka, Kanagawa (JP); Florian Pünner, Kanagawa (JP); Takeshi Yamamoto, Kanagawa (JP); Keiko Kakegawa, Kanagawa (JP); Fumiaki Kikuchi, Kanagawa (JP); Nao Morishita, Kanagawa (JP); Takahito Kasahara, Kanagawa (JP); Masaki Seto, Kanagawa (JP); Minoru Nakamura, Kanagawa (JP); Kazuaki Takami, Kanagawa (JP); Masataka Murakami, Kanagawa (JP); Masaki Daini, Kanagawa (JP); Satoshi Mikami, Kanagawa (JP); Minoru Sasaki, Kanagawa (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 75 days.

(21) Appl. No.: 16/961,476

(22) PCT Filed: Jan. 30, 2019

(86) PCT No.: PCT/JP2019/003044
§ 371 (c)(1),
(2) Date: Jul. 10, 2020

(87) PCT Pub. No.: WO2019/151269
PCT Pub. Date: Aug. 8, 2019

(65) Prior Publication Data
US 2021/0087186 A1    Mar. 25, 2021

(30) Foreign Application Priority Data

Jan. 31, 2018  (JP) .................. 2018-015264

(51) Int. Cl.
| | |
|---|---|
| *C07D 471/04* | (2006.01) |
| *C07D 487/04* | (2006.01) |
| *C07D 491/048* | (2006.01) |
| *C07D 495/04* | (2006.01) |
| *C07D 519/00* | (2006.01) |
| *A61P 25/28* | (2006.01) |

(52) U.S. Cl.
CPC ............ *C07D 471/04* (2013.01); *A61P 25/28* (2018.01); *C07D 487/04* (2013.01); *C07D 491/048* (2013.01); *C07D 495/04* (2013.01); *C07D 519/00* (2013.01)

(58) Field of Classification Search
CPC ............ C07D 471/04; C07D 487/04; C07D 491/048; C07D 495/04; C07D 519/00; A61P 25/28
See application file for complete search history.

(56) References Cited

U.S. PATENT DOCUMENTS

| | | | |
|---|---|---|---|
| 2014/0249145 A1 | 9/2014 | Marugan et al. |
| 2014/0255381 A1 | 9/2014 | Bourque et al. |
| 2014/0371460 A1 | 12/2014 | Bourque et al. |
| 2015/0065469 A1 | 3/2015 | Marugan et al. |
| 2016/0207933 A1 | 7/2016 | Bourque et al. |

(Continued)

FOREIGN PATENT DOCUMENTS

| | | |
|---|---|---|
| EP | 1 953 147 A1 | 8/2008 |
| WO | WO-2012/078855 A1 | 6/2012 |

(Continued)

OTHER PUBLICATIONS

PubChem CID 69663535, National Center for Biotechnology Information. PubChem Compound Summary for CID 69663535. https://pubchem.ncbi.nlm.nih.gov/compound/69663535. Accessed Dec. 8, 2021, create date Dec. 1, 2012. (Year: 2012).*

(Continued)

*Primary Examiner* — Laura L Stockton
(74) *Attorney, Agent, or Firm* — Foley & Lardner LLP

(57) ABSTRACT

The present invention provides a compound having a glucosylceramide lowering action (e.g., promoting glucosylceramide metabolism, inhibition of glucosylceramide synthesis, promoting glucosylceramide catabolism, etc.), which is expected to be useful as an agent for the prophylaxis or treatment of lysosome diseases (e.g., Gaucher's disease), neurodegenerative diseases (e.g., Parkinson's disease, Lewy body dementia, multiple-system atrophy) and the like.

The present invention relates to a compound represented by the formula (I):

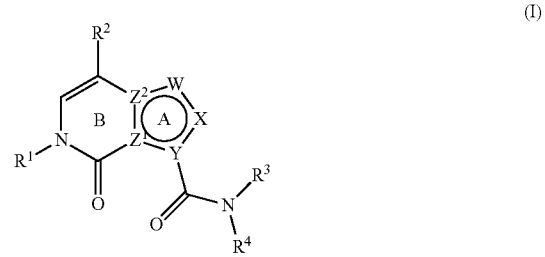

wherein each symbol is as described in the specification, or a salt thereof.

10 Claims, No Drawings

(56) References Cited

U.S. PATENT DOCUMENTS

| | | |
|---|---|---|
| 2016/0346284 A1 | 12/2016 | Marugan et al. |
| 2017/0002013 A1 | 1/2017 | Krainc et al. |
| 2017/0183354 A1 | 6/2017 | Skerlj et al. |
| 2017/0333435 A1 | 11/2017 | Skerlj et al. |
| 2017/0334916 A1 | 11/2017 | Skerlj et al. |
| 2017/0355702 A1 | 12/2017 | Skerlj et al. |
| 2018/0037586 A1 | 2/2018 | Krainc et al. |
| 2018/0185368 A1 | 7/2018 | Skerlj et al. |
| 2018/0263988 A1 | 9/2018 | Marugan et al. |
| 2018/0305367 A1 | 10/2018 | Krainc et al. |
| 2019/0092789 A1 | 3/2019 | Skerlj et al. |
| 2019/0112316 A1 | 4/2019 | Skerlj et al. |
| 2019/0152980 A1 | 5/2019 | Krainc et al. |
| 2019/0216813 A1 | 7/2019 | Skerlj et al. |
| 2019/0389856 A1 | 12/2019 | Skerlj et al. |
| 2019/0389865 A1 | 12/2019 | Skerlj et al. |
| 2019/0389866 A1 | 12/2019 | Skerlj et al. |
| 2020/0010474 A1 | 1/2020 | Krainc et al. |
| 2020/0030331 A1 | 1/2020 | Skerlj et al. |
| 2020/0048266 A1 | 2/2020 | Bourque et al. |
| 2020/0115383 A1 | 4/2020 | Bryan et al. |

FOREIGN PATENT DOCUMENTS

| | | |
|---|---|---|
| WO | WO-2012/129084 A1 | 9/2012 |
| WO | WO-2013/148333 A1 | 10/2013 |
| WO | WO-2016/073889 A1 | 5/2016 |
| WO | WO-2016/073891 A1 | 5/2016 |
| WO | WO-2016/073895 A1 | 5/2016 |
| WO | WO-2017/004408 A1 | 1/2017 |
| WO | WO-2017/040877 A1 | 3/2017 |
| WO | WO-2017/040879 A1 | 3/2017 |
| WO | WO-2017/192841 A1 | 11/2017 |
| WO | WO-2017/192929 A1 | 11/2017 |
| WO | WO-2017/192930 A1 | 11/2017 |
| WO | WO-2017/192931 A1 | 11/2017 |
| WO | WO-2017/204319 A1 | 11/2017 |
| WO | WO-2018/234342 A1 | 12/2018 |

OTHER PUBLICATIONS

Geiger et al., "Next-generation sequencing reveals substantial genetic contribution to dementia with Lewy bodies," Neurobiol. Dis., Oct. 2016, 94:55-62.

Marshall et al., "CNS-accessible Inhibitor of Glucosylceramide Synthase for Substrate Reduction Therapy of Neuronopathic Gaucher Disease," Molecular Therapy, Jun. 2016, 24(6):1019-1029.

Schapira, Anthony H.V., "Glucocerebrosidase and Parkinson disease: Recent advances," Molecular and Cellular Neuroscience, 2015, 66(Pt.A):37-42.

\* cited by examiner

HETEROCYCLIC COMPOUND

TECHNICAL FIELD

The present invention relates to a heterocyclic compound having a glucosylceramide or glucosylsphingosine (hereinafter sometimes collectively to be abbreviated as "glucosylceramide") lowering action (e.g., promoting glucosylceramide metabolism, inhibition of glucosylceramide synthesis, promoting glucosylceramide catabolism, etc.), which is useful for the treatment of lysosome diseases (e.g., Gaucher's disease), neurodegenerative diseases (e.g., Parkinson's disease, Lewy body dementia, multiple-system atrophy) and the like, a medicament containing same, and the like.

BACKGROUND OF THE INVENTION

Glucosylceramidase (gene symbol: GBA) is an enzyme which hydrolyze glycolipids, glucosylceramide and glucosylsphingosine. GBA is known as a gene responsible for Gaucher's disease which is one of autosomal recessively inheritable diseases. For the treatment of Gaucher's disease, GBA protein replacement or glucosylceramide synthetase inhibitor can be used. However, both have poor brain penetration, and their efficacy on central nervous symptom is not sufficient (Non-Patent Document 1). Moreover, GBA mutation has recently been shown to be a genetic risk factor for the development of Parkinson's disease or Lewy body dementia (Non-Patent Document 2 and Non-Patent Document 3). The above suggests that glucosylceramide and glucosylsphingosine lowering agents may serve as preventive or therapeutic agents for neurodegenerative diseases such as Gaucher's disease, Parkinson's disease, and Lewy body dementia.

As heterocyclic compounds, the following compounds are known.

Patent Document 1 describes that a compound represented by the following formula (I):

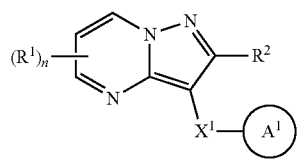

wherein each symbol is as defined in Patent Document 1, is useful for the treatment of Gaucher's disease, Parkinson's disease, Lewy body disease, dementia, multiple-system atrophy and the like.

Patent Document 2 describes that a compound represented by the following formula (I):

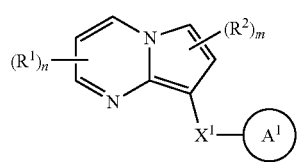

wherein each symbol is as defined in Patent Document 2, is useful for the treatment of Gaucher's disease, Parkinson's disease, Lewy body disease, dementia, multiple-system atrophy and the like.

Patent Document 3 describes that a compound represented by the following formula (I):

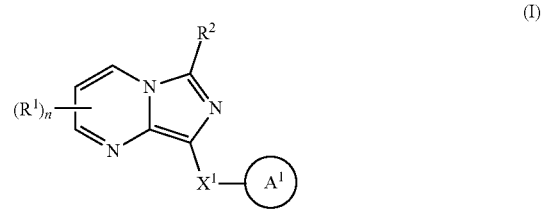

wherein each symbol is as defined in Patent Document 3, is useful for the treatment of Gaucher's disease, Parkinson's disease, Lewy body disease, dementia, multiple-system atrophy and the like.

Patent Document 4 describes that a compound represented by the following formula (I) or (II):

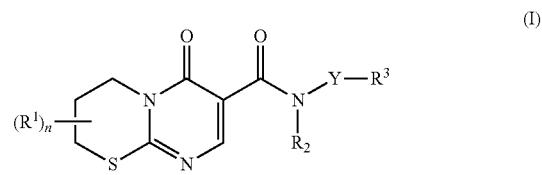

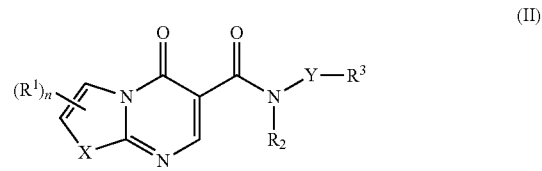

wherein each symbol is as defined in Patent Document 4, is useful for the treatment of Gaucher's disease, Parkinson's disease, Lewy body disease, dementia, multiple-system atrophy and the like.

Patent Document 5 describes that a compound represented by the following formula (I):

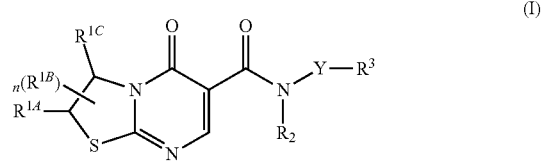

wherein each symbol is as defined in Patent Document 5, is useful for the treatment of Gaucher's disease, Parkinson's disease, Lewy body disease, dementia, multiple-system atrophy and the like.

Patent Document 6 describes that a compound represented by the following formula (A-I), (B-I) or (C-I):

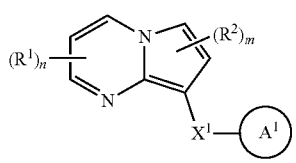
(A-I)

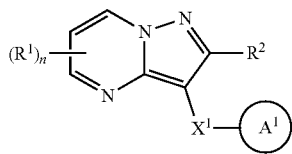
(B-I)

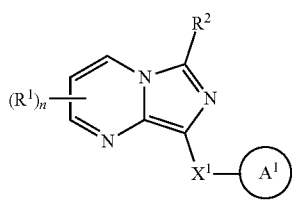
(C-I)

wherein each symbol is as defined in Patent Document 6, is useful for the treatment of Gaucher's disease, Parkinson's disease, Lewy body disease, dementia, multiple-system atrophy and the like.

Patent Document 7 describes that compounds represented by the following formula (I) or (II):

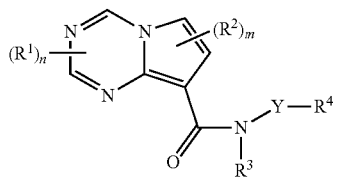
(I)

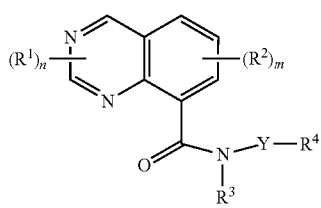
(II)

wherein each symbol is as defined in Patent Document 7, is useful for the treatment of Gaucher's disease, Parkinson's disease, Lewy body disease, dementia, multiple-system atrophy and the like.

Patent Document 8 describes that compounds represented by the following formulas (I) to (VII):

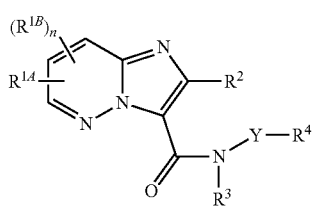
(I)

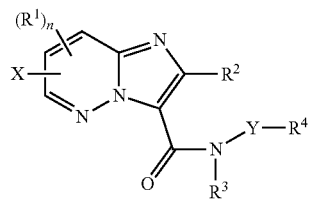
(II)

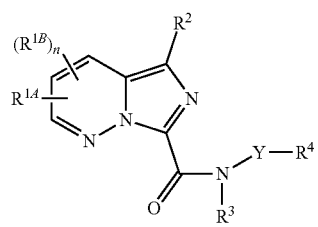
(III)

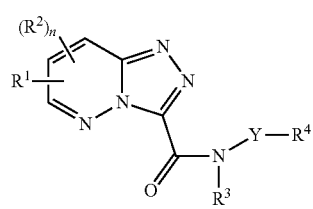
(IV)

(V)

(VI)

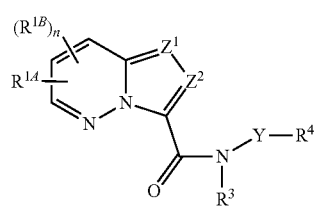
(VII)

wherein each symbol is as defined in Patent Document 8, are useful for the treatment of Gaucher's disease, Parkinson's disease, Lewy body disease, dementia, multiple-system atrophy and the like.

Patent Document 9 describes that compounds represented by the following formulas (I) to (III):

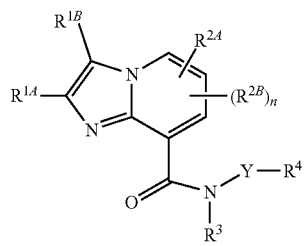

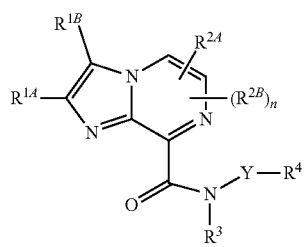

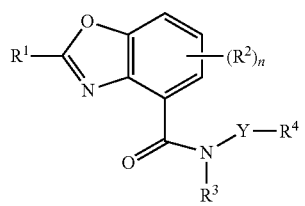

wherein each symbol is as defined in Patent Document 9, is useful for the treatment of Gaucher's disease, Parkinson's disease, Lewy body disease, dementia, multiple-system atrophy and the like.

Patent Document 10 describes that a compound represented by the following formula (I):

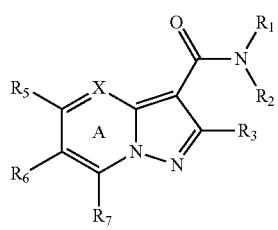

wherein each symbol is as defined in Patent Document 10, is useful for the treatment of Gaucher's disease and the like.

Patent Document 11 describes that a compound represented by the following formula (I):

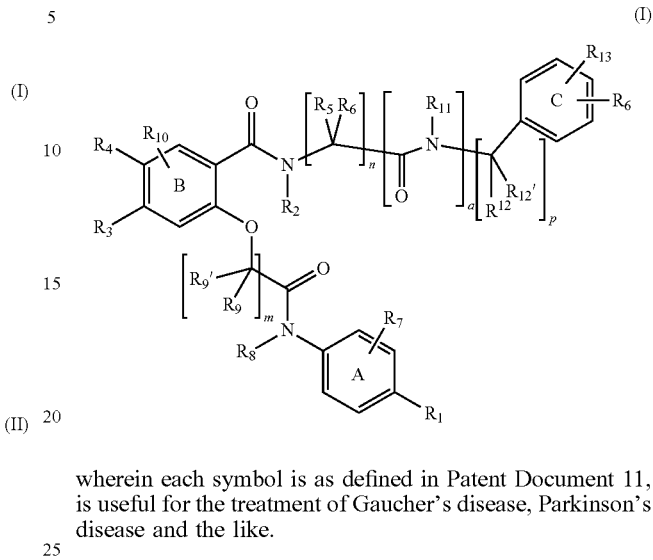

wherein each symbol is as defined in Patent Document 11, is useful for the treatment of Gaucher's disease, Parkinson's disease and the like.

DOCUMENT LIST

Patent Document

Patent Document 1: WO 2016/073895
Patent Document 2: WO 2016/073891
Patent Document 3: WO 2016/073889
Patent Document 4: WO 2017/040877
Patent Document 5: WO 2017/040879
Patent Document 6: WO 2017/192841
Patent Document 7: WO 2017/192929
Patent Document 8: WO 2017/192930
Patent Document 9: WO 2017/192931
Patent Document 10: WO 2012/078855
Patent Document 11: WO 2013/148333

Non-Patent Document

Non-Patent Document 1: Marshall, J., et al., Mol Ther, 2016. 24(6): p. 1019-1029.
Non-Patent Document 2: Schapira, A. H., Mol Cell Neurosci, 2015. 66(Pt A): p. 37-42.
Non-Patent Document 3: Geiger, J. T., et al., Neurobiol Dis, 2016. 94: p. 55-62.

SUMMARY OF THE INVENTION

Problems to be Solved by the Invention

An object of the present invention is to provide a compound having a glucosylceramide lowering action (e.g., promoting glucosylceramide metabolism, inhibition of glucosylceramide synthesis, promoting glucosylceramide catabolism, etc.), which is useful as an agent for the prophylaxis or treatment of lysosome diseases (e.g., Gaucher's disease), neurodegenerative diseases (e.g., Parkinson's disease, Lewy body dementia, multiple-system atrophy) and the like.

Means of Solving the Problems

The present inventors have conducted intensive studies in an attempt to solve the above-mentioned problems and found that a compound represented by the following formula (I) has a glucosylceramide lowering action (e.g., promoting glucosylceramide metabolism, inhibition of glucosylceramide synthesis, promoting glucosylceramide catabolism, etc.), and therefore, the compound is useful as an agent for the prophylaxis or treatment of lysosome diseases (e.g., Gaucher's disease), neurodegenerative diseases (e.g., Parkinson's disease, Lewy body dementia, multiple-system atrophy) and the like, which resulted in the completion of the present invention.

Accordingly, the present invention provides the following.

[1]

A compound represented by the formula (I):

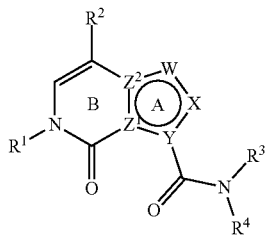

wherein
Ring A is a 5-membered aromatic heterocycle,
Ring B is an optionally further substituted 6-membered nitrogen-containing non-aromatic heterocycle,
W is $CR^5$, $NR^6$, N, O or S,
X is $CR^7$, $NR^8$ or N,
Y is C or N,
$Z^1$ and $Z^2$ are each independently C or N,
$R^1$ is a substituent,
as to $R^2$
(1) when W is $CR^5$, $NR^6$ or N, then $R^2$ is a hydrogen atom or a substituent,
(2) when W is O or S, then $R^2$ is a substituent,
$R^3$ and $R^4$ are each independently a hydrogen atom or a substituent, or
$R^3$ and $R^4$ are bonded to each other to form, together with the adjacent nitrogen atom, an optionally further substituted nitrogen-containing heterocycle,
$R^5$ and $R^7$ are each independently a hydrogen atom or a substituent, and
$R^6$ and $R^8$ are each independently a substituent,
or a salt thereof (hereinafter sometimes to be referred to as compound (I)).

[2] The compound or salt of the above-mentioned [1], wherein
Ring A is pyrrole, pyrazole, thiophene, furan or imidazole;
Ring B is dihydropyridine, tetrahydropyridine, tetrahydropyrazine or tetrahydropyrimidine;
W is $NR^6$ wherein $R^6$ is a $C_{1-6}$ alkyl group or a benzyl group, N, O or S;
X is $CR^7$ wherein $R^7$ is a hydrogen atom or a $C_{1-6}$ alkyl group, $NR^8$ wherein $R^8$ is a $C_{1-6}$ alkyl group, or N;
Y is C;
$Z^1$—$Z^2$ is C=C, C—C, C—N or N—N;
$R^1$ is
(1) a $C_{1-6}$ alkyl group optionally substituted by 1 to 3 substituents selected from
  (a) a halogen atom, and
  (b) a cyano group,
(2) a phenyl group optionally substituted by 1 to 3 substituents selected from
  (a) an optionally halogenated $C_{1-6}$ alkoxy group, and
  (b) a halogen atom, or
(3) a benzyl group optionally substituted by 1 to 3 $C_{1-6}$ alkoxy groups;
as to $R^2$
(1) when W is $NR^6$ or N, then $R^2$ is a hydrogen atom, a halogen atom, a $C_{1-6}$ alkyl group, a $C_{3-6}$ cycloalkyl group or a phenyl group,
(2) when W is O or S, then $R^2$ is a $C_{1-6}$ alkyl group; and
$R^3$ and $R^4$ are each independently
(1) a hydrogen atom,
(2) a $C_{1-6}$ alkyl group optionally substituted by 1 to 3 substituents selected from
  (a) a halogen atom,
  (b) a cyano group,
  (c) a $C_{3-6}$ cycloalkyl group,
  (d) a phenyl group optionally substituted by 1 to 3 halogen atoms,
  (e) a pyridyl group optionally substituted by 1 to 3 $C_{1-6}$ alkoxy groups,
  (f) a pyrazolyl group optionally substituted by 1 to 3 substituents selected from
    (i) a $C_{1-6}$ alkyl group, and
    (ii) a phenyl group optionally substituted by 1 to 3 substituents selected from a halogen atom and a $C_{1-6}$ alkyl group,
  (g) a triazolyl group optionally substituted by 1 or 2 substituents selected from
    (i) a $C_{1-6}$ alkyl group, and
    (ii) a phenyl group,
  (h) an oxadiazolyl group optionally substituted by phenyl group(s) optionally substituted by 1 to 3 halogen atoms,
  (i) a thiazolyl group optionally substituted by 1 or 2 substituents selected from
    (i) a $C_{1-6}$ alkyl group, and
    (ii) a phenyl group, and
  (j) a thienyl group optionally substituted by 1 to 3 phenyl groups optionally substituted by 1 to 3 halogen atoms,
(3) a $C_{3-6}$ cycloalkyl group optionally substituted by 1 to 3 substituents selected from
  (a) a halogen atom,
  (b) a cyano group,
  (c) an optionally halogenated $C_{1-6}$ alkyl group,
  (d) a $C_{1-6}$ alkoxy group,
  (e) a $C_{1-6}$ alkoxy-carbonylamino group,
  (f) a phenyl group optionally substituted by 1 to 3 halogen atoms,
  (g) a phenoxy group,
  (h) a benzyloxy group, and
  (i) a pyridyl group,
(4) a bicyclo[1.1.1]pentyl group optionally substituted by 1 to 3 substituents selected from
  (a) an optionally halogenated $C_{1-6}$ alkyl group, and
  (b) a phenyl group,
(5) an indanyl group optionally substituted by 1 to 3 halogen atoms,
(6) a tetrahydronaphthyl group,
(7) a dihydrobenzocyclobutenyl group,
(8) a phenyl group optionally substituted by 1 to 3 substituents selected from
  (a) a $C_{1-6}$ alkyl group optionally substituted by 1 to 3 hydroxy groups,
  (b) a $C_{1-6}$ alkoxy group,
  (c) a phenoxy group,
  (d) a benzyloxy group, and
  (e) a morpholinyl group, (9) a pyrazolyl group optionally substituted by 1 to 3 substituents selected from
  (a) an optionally halogenated $C_{1-6}$ alkyl group, and
  (b) a benzyl group optionally substituted by 1 to 3 halogen atoms,
(10) an imidazolyl group optionally substituted by 1 to 3 phenyl groups,
(11) a pyridyl group optionally substituted by 1 to 3 substituents selected from
  (a) a cyano group,
  (b) an optionally halogenated $C_{1-6}$ alkyl group,
  (c) an optionally halogenated $C_{1-6}$ alkoxy group,
  (d) a phenoxy group, and
  (e) a $C_{3-10}$ cycloalkyl group,
(12) a pyrrolidinyl group optionally substituted by 1 to 3 benzyl groups,
(13) a piperidyl group optionally substituted by 1 to 3 substituents selected from
  (a) a $C_{1-6}$ alkyl group optionally substituted by 1 to 3 $C_{3-6}$ cycloalkyl groups,
  (b) a $C_{1-6}$ alkoxy-carbonyl group,
  (c) a phenyl group optionally substituted by 1 to 3 halogen atoms, and
  (d) a benzyl group,
(14) a tetrahydrofuryl group optionally substituted by 1 to 3 phenyl groups, or
(15) a dihydrochromenyl group optionally substituted by 1 to 3 $C_{1-6}$ alkyl groups, or
$R^3$ and $R^4$ are bonded to each other to form, together with the adjacent nitrogen atom,
(1) an azetidine ring optionally further substituted by 1 to 3 substituents selected from
  (a) a $C_{1-6}$ alkyl group optionally substituted by 1 to 3 $C_{1-6}$ alkoxy groups,
  (b) an optionally halogenated $C_{1-6}$ alkoxy group,
  (c) a $C_{3-6}$ cycloalkyl group,
  (d) a phenyl group optionally substituted by 1 to 3 halogen atoms,
  (e) a phenoxy group,
  (f) a benzyl group, and
  (g) a benzyloxy group,
(2) a pyrrolidine ring optionally further substituted by 1 to 3 substituents selected from
  (a) a halogen atom,
  (b) an optionally halogenated $C_{1-6}$ alkoxy group,
  (c) a phenyl group optionally substituted by 1 to 3 substituents selected from
    (i) a halogen atom,
    (ii) an optionally halogenated $C_{1-6}$ alkyl group, and
    (iii) a $C_{1-6}$ alkoxy group,
  (d) a benzyl group, and
  (e) a benzyloxy group,
(3) a piperidine ring optionally further substituted by 1 to 3 substituents selected from
  (a) a $C_{1-6}$ alkoxy group optionally substituted by 1 to 3 substituents selected from
    (i) a halogen atom, and
    (ii) a $C_{3-6}$ cycloalkyl group,
  (b) a phenyl group optionally substituted by 1 to 3 substituents selected from
    (i) a halogen atom, and
    (ii) a $C_{1-6}$ alkoxy group,
  (c) a phenoxy group optionally substituted by 1 to 3 substituents selected from
    (i) a halogen atom,
    (ii) a cyano group,
    (iii) an optionally halogenated $C_{1-6}$ alkyl group, and
    (iv) an optionally halogenated $C_{1-6}$ alkoxy group,
  (d) a benzyl group,
  (e) a benzyloxy group,
  (f) a pyridyloxy group,
  (g) a pyrazinyloxy group,
  (h) a pyrimidinyloxy group,
  (i) a thiazolyloxy group, and
  (j) a piperidyloxy group optionally substituted by 1 to 3 $C_{1-6}$ alkoxy-carbonyl groups,
(4) an indoline ring optionally further substituted by 1 to 3 $C_{1-6}$ alkoxy groups,
(5) an isoindoline ring optionally further substituted by 1 to 3 $C_{1-6}$ alkoxy groups,
(6) a tetrahydroquinoline ring optionally further substituted by 1 to 3 $C_{1-6}$ alkoxy groups,
(7) a tetrahydroisoquinoline ring optionally further substituted by 1 to 3 substituents selected from
  (a) a halogen atom,
  (b) a $C_{1-6}$ alkyl group, and
  (c) a $C_{1-6}$ alkoxy group,
(8) a 3-azabicyclo[3.1.0]hexane ring optionally further substituted by 1 to 3 substituents selected from
  (a) a halogen atom,
  (b) a $C_{1-6}$ alkyl group optionally substituted by 1 to 3 substituents selected from
    (i) a halogen atom,
    (ii) a cyano group,
    (iii) a $C_{1-6}$ alkoxy group, and
    (iv) a mono- or di-$C_{1-6}$ alkylamino group,
  (c) a phenyl group optionally substituted by 1 to 3 substituents selected from
    (i) a halogen atom,
    (ii) an optionally halogenated $C_{1-6}$ alkyl group, and
    (iii) an optionally halogenated $C_{1-6}$ alkoxy group,
  (d) a naphthyl group, and
  (e) a thienyl group,
  (f) a pyrazolyl group optionally substituted by 1 to 3 of optionally halogenated $C_{1-6}$ alkyl groups,
  (g) a pyridyl group optionally substituted by 1 to 3 halogen atoms, and
  (h) a pyrimidinyl group optionally substituted by 1 to 3 halogen atoms,
(9) a 3-azabicyclo[4.1.0]heptane ring optionally further substituted by 1 to 3 substituents selected from
  (a) a halogen atom, and
  (b) a phenyl group optionally substituted by 1 to 3 substituents selected from
    (i) a halogen atom,
    (ii) a $C_{1-6}$ alkyl group, and
    (iii) a $C_{1-6}$ alkoxy group,
(10) a 1-azaspiro[3.3]heptane ring,
(11) a 6-oxa-1-azaspiro[3.5]nonane ring,
(12) a 6-oxa-1-azaspiro[3.3]heptane ring, or
(13) a 6-oxa-1-azaspiro[3.4]octane ring.

[3] The compound or salt of the above-mentioned [2], wherein the partial structure represented by the following formula:

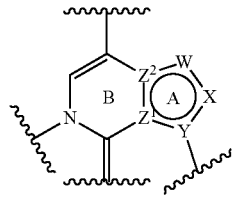

is a partial structure represented by the following formula:

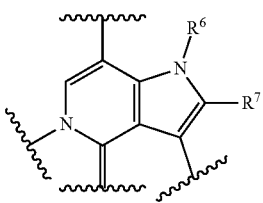

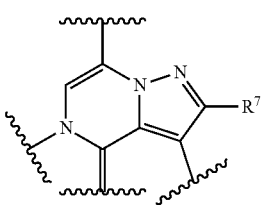

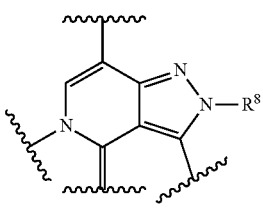

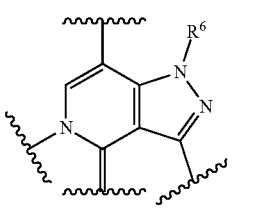

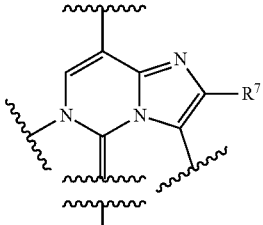

or

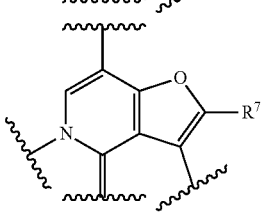

wherein $R^6$ is a $C_{1-6}$ alkyl group or a benzyl group, $R^7$ is a hydrogen atom or a $C_{1-6}$ alkyl group, and $R^8$ is a $C_{1-6}$ alkyl group.

[4] The compound or salt of the above-mentioned [1], wherein the partial structure represented by the following formula:

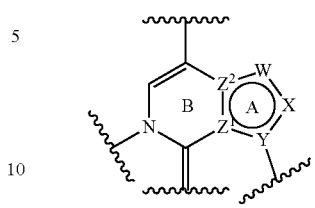

is a partial structure represented by the following formula:

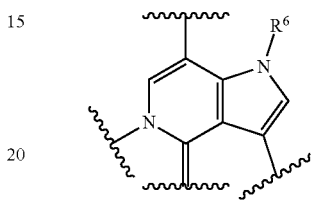

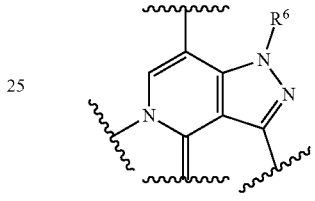

or wherein $R^6$ is a $C_{1-6}$ alkyl group;
$R^1$ is
(1) a $C_{1-6}$ alkyl group optionally substituted by 1 to 3 substituents selected from
  (a) a halogen atom, and
  (b) a cyano group, or
(2) a phenyl group optionally substituted by 1 to 3 substituents selected from
  (a) an optionally halogenated $C_{1-6}$ alkoxy group, and
  (b) a halogen atom;
$R^2$ is a hydrogen atom or a $C_{1-6}$ alkyl group;
$R^3$ is a hydrogen atom, and
$R^4$ is
(1) a $C_{1-6}$ alkyl group optionally substituted by 1 to 3 substituents selected from
  (a) a phenyl group optionally substituted by 1 to 3 halogen atoms,
  (b) an oxadiazolyl group optionally substituted by phenyl group(s) optionally substituted by 1 to 3 halogen atoms, and
  (c) a thienyl group optionally substituted by 1 to 3 phenyl groups optionally substituted by 1 to 3 halogen atoms,
(2) a $C_{3-6}$ cycloalkyl group optionally substituted by 1 to 3 substituents selected from
  (a) a $C_{1-6}$ alkoxy group, and
  (b) a phenyl group optionally substituted by 1 to 3 halogen atoms,
(3) a phenyl group optionally substituted by 1 to 3 substituents selected from
  (a) a benzyloxy group,
  (b) a morpholinyl group, and
  (c) a $C_{1-6}$ alkyl group optionally substituted by 1 to 3 hydroxy groups, or
(4) a pyridyl group optionally substituted by 1 to 3 substituents selected from
  (a) a cyano group,
  (b) an optionally halogenated $C_{1-6}$ alkoxy group, and
  (c) a $C_{3-10}$ cycloalkyl group, or $R^3$ and $R^4$ are bonded to each other to form, together with the adjacent nitrogen atom,
(1) an azetidine ring optionally further substituted by 1 to 3 phenyl groups,
(2) a pyrrolidine ring optionally further substituted by 1 to 3 substituents selected from
   (a) a halogen atom, and
   (b) a phenyl group optionally substituted by 1 to 3 halogen atoms,
(3) a piperidine ring optionally further substituted by 1 to 3 substituents selected from
   (a) a phenyl group optionally substituted by 1 to 3 halogen atoms, and
   (b) a phenoxy group optionally substituted by 1 to 3 substituents selected from
     (i) a halogen atom,
     (ii) an optionally halogenated $C_{1-6}$ alkyl group, and
     (iii) an optionally halogenated $C_{1-6}$ alkoxy group, or
(4) a 3-azabicyclo[3.1.0]hexane ring optionally further substituted by 1 to 3 substituents selected from
   (a) a halogen atom,
   (b) a phenyl group optionally substituted by 1 to 3 substituents selected from
     (i) a halogen atom,
     (ii) an optionally halogenated $C_{1-6}$ alkyl group, and
     (iii) an optionally halogenated $C_{1-6}$ alkoxy group, and
   (c) a naphthyl group.

[5] N-(trans-4-Butoxycyclohexyl)-1,5,7-trimethyl-4-oxo-4,5-dihydro-1H-pyrrolo[3,2-c]pyridine-3-carboxamide or a salt thereof.

[6] 1-Methyl-N-(4-(morpholin-4-yl)phenyl)-4-oxo-5-(2-(2,2,2-trifluoroethoxy)phenyl)-4,5-dihydro-1H-pyrrolo[3,2-c]pyridine-3-carboxamide or a salt thereof.

[7] N-[4-(2-Hydroxypropan-2-yl)phenyl]-7-methyl-4-oxo-5-[2-(2,2,2-trifluoroethoxy)phenyl]-4,5-dihydropyrazolo[1,5-a]pyrazine-3-carboxamide or a salt thereof.

[8] A medicament comprising the compound or salt of the above-mentioned [1].

[9] The medicament of the above-mentioned [8], which is a glucosylceramide lowering agent.

[10] The medicament of the above-mentioned [8], which is an agent for the prophylaxis or treatment of a lysosome disease or a neurodegenerative disease.

[11] The compound or salt of the above-mentioned [1] for use in the prophylaxis or treatment of a lysosome disease or a neurodegenerative disease.

[12] A method of lowering glucosylceramide in a mammal, which comprises administering an effective amount of the compound or salt of the above-mentioned [1] to the mammal.

[13] A method for the prophylaxis or treatment of a lysosome disease or a neurodegenerative disease in a mammal, which comprises administering an effective amount of the compound or salt of the above-mentioned [1] to the mammal.

[14] Use of the compound or salt of the above-mentioned [1] for the manufacture of an agent for the prophylaxis or treatment of a lysosome disease or a neurodegenerative disease.

Effect of the Invention

According to the present invention, a compound having an excellent glucosylceramide lowering action (e.g., promoting glucosylceramide metabolism, inhibition of glucosylceramide synthesis, promoting glucosylceramide catabolism, etc.), which is useful as an agent for the prophylaxis or treatment of lysosome diseases (e.g., Gaucher's disease), neurodegenerative diseases (e.g., Parkinson's disease, Lewy body dementia, multiple-system atrophy) and the like, can be provided.

DETAILED DESCRIPTION OF THE INVENTION

The present invention is explained in detail in the following.

The definition of each substituent used in the present specification is described in detail in the following. Unless otherwise specified, each substituent has the following definition.

In the present specification, examples of the "halogen atom" include fluorine, chlorine, bromine and iodine.

In the present specification, examples of the "$C_{1-6}$ alkyl group" include methyl, ethyl, propyl, isopropyl, butyl, isobutyl, sec-butyl, tert-butyl, pentyl, isopentyl, neopentyl, 1-ethylpropyl, hexyl, isohexyl, 1,1-dimethylbutyl, 2,2-dimethylbutyl, 3,3-dimethylbutyl and 2-ethylbutyl.

In the present specification, examples of the "optionally halogenated $C_{1-6}$ alkyl group" include a $C_{1-6}$ alkyl group optionally having 1 to 7, preferably 1 to 5, halogen atoms. Specific examples thereof include methyl, chloromethyl, difluoromethyl, trichloromethyl, trifluoromethyl, ethyl, 2-bromoethyl, 2,2,2-trifluoroethyl, tetrafluoroethyl, pentafluoroethyl, propyl, 2,2-difluoropropyl, 3,3,3-trifluoropropyl, isopropyl, butyl, 4,4,4-trifluorobutyl, isobutyl, sec-butyl, tert-butyl, pentyl, isopentyl, neopentyl, 5,5,5-trifluoropentyl, hexyl and 6,6,6-trifluorohexyl.

In the present specification, examples of the "$C_{2-6}$ alkenyl group" include ethenyl, 1-propenyl, 2-propenyl, 2-methyl-1-propenyl, 1-butenyl, 2-butenyl, 3-butenyl, 3-methyl-2-butenyl, 1-pentenyl, 2-pentenyl, 3-pentenyl, 4-pentenyl, 4-methyl-3-pentenyl, 1-hexenyl, 3-hexenyl and 5-hexenyl.

In the present specification, examples of the "$C_{2-6}$ alkynyl group" include ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and 4-methyl-2-pentynyl.

In the present specification, examples of the "$C_{3-10}$ cycloalkyl group" include cyclopropyl, cyclobutyl, cyclopentyl, cyclohexyl, cycloheptyl, cyclooctyl, bicyclo[2.2.1]heptyl, bicyclo[2.2.2]octyl, bicyclo[3.2.1]octyl and adamantyl.

In the present specification, examples of the "optionally halogenated $C_{3-10}$ cycloalkyl group" include a $C_{3-10}$ cycloalkyl group optionally having 1 to 7, preferably 1 to 5, halogen atoms. Specific examples thereof include cyclopropyl, 2,2-difluorocyclopropyl, 2,3-difluorocyclopropyl, cyclobutyl, difluorocyclobutyl, cyclopentyl, cyclohexyl, cycloheptyl and cyclooctyl.

In the present specification, examples of the "$C_{3-10}$ cycloalkenyl group" include cyclopropenyl, cyclobutenyl, cyclopentenyl, cyclohexenyl, cycloheptenyl and cyclooctenyl.

In the present specification, examples of the "$C_{6-14}$ aryl group" include phenyl, 1-naphthyl, 2-naphthyl, 1-anthryl, 2-anthryl and 9-anthryl.

In the present specification, examples of the "$C_{1-6}$ aralkyl group" include benzyl, phenethyl, naphthylmethyl and phenylpropyl.

In the present specification, examples of the "$C_{1-6}$ alkoxy group" include methoxy, ethoxy, propoxy, isopropoxy, butoxy, isobutoxy, sec-butoxy, tert-butoxy, pentyloxy and hexyloxy.

In the present specification, examples of the "optionally halogenated $C_{1-6}$ alkoxy group" include a $C_{1-6}$ alkoxy group optionally having 1 to 7, preferably 1 to 5, halogen atoms. Specific examples thereof include methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentyloxy and hexyloxy.

In the present specification, examples of the "$C_{3-10}$ cycloalkyloxy group" include cyclopropyloxy, cyclobutyloxy, cyclopentyloxy, cyclohexyloxy, cycloheptyloxy and cyclooctyloxy.

In the present specification, examples of the "$C_{1-6}$ alkylthio group" include methylthio, ethylthio, propylthio, isopropylthio, butylthio, sec-butylthio, tert-butylthio, pentylthio and hexylthio.

In the present specification, examples of the "optionally halogenated $C_{1-6}$ alkylthio group" include a $C_{1-6}$ alkylthio group optionally having 1 to 7, preferably 1 to 5, halogen atoms. Specific examples thereof include methylthio, difluoromethylthio, trifluoromethylthio, ethylthio, propylthio, isopropylthio, butylthio, 4,4,4-trifluorobutylthio, pentylthio and hexylthio.

In the present specification, examples of the "$C_{1-6}$ alkyl-carbonyl group" include acetyl, propanoyl, butanoyl, 2-methylpropanoyl, pentanoyl, 3-methylbutanoyl, 2-methylbutanoyl, 2,2-dimethylpropanoyl, hexanoyl and heptanoyl.

In the present specification, examples of the "optionally halogenated $C_{1-6}$ alkyl-carbonyl group" include a $C_{1-6}$ alkyl-carbonyl group optionally having 1 to 7, preferably 1 to 5, halogen atoms. Specific examples thereof include acetyl, chloroacetyl, trifluoroacetyl, trichloroacetyl, propanoyl, butanoyl, pentanoyl and hexanoyl.

In the present specification, examples of the "$C_{1-6}$ alkoxy-carbonyl group" include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl and hexyloxycarbonyl.

In the present specification, examples of the "$C_{6-14}$ aryl-carbonyl group" include benzoyl, 1-naphthoyl and 2-naphthoyl.

In the present specification, examples of the "$C_{7-16}$ aralkyl-carbonyl group" include phenylacetyl and phenylpropionyl.

In the present specification, examples of the "5- to 14-membered aromatic heterocyclylcarbonyl group" include nicotinoyl, isonicotinoyl, thenoyl and furoyl.

In the present specification, examples of the "3- to 14-membered non-aromatic heterocyclylcarbonyl group" include morpholinylcarbonyl, piperidinylcarbonyl and pyrrolidinylcarbonyl.

In the present specification, examples of the "mono- or di-$C_{1-6}$ alkyl-carbamoyl group" include methylcarbamoyl, ethylcarbamoyl, dimethylcarbamoyl, diethylcarbamoyl and N-ethyl-N-methylcarbamoyl.

In the present specification, examples of the "mono- or di-$C_{7-16}$ aralkyl-carbamoyl group" include benzylcarbamoyl and phenethylcarbamoyl.

In the present specification, examples of the "$C_{1-6}$ alkylsulfonyl group" include methylsulfonyl, ethylsulfonyl, propylsulfonyl, isopropylsulfonyl, butylsulfonyl, sec-butylsulfonyl and tert-butylsulfonyl.

In the present specification, examples of the "optionally halogenated $C_{1-6}$ alkylsulfonyl group" include a $C_{1-6}$ alkylsulfonyl group optionally having 1 to 7, preferably 1 to 5, halogen atoms. Specific examples thereof include methylsulfonyl, difluoromethylsulfonyl, trifluoromethylsulfonyl, ethylsulfonyl, propylsulfonyl, isopropylsulfonyl, butylsulfonyl, 4,4,4-trifluorobutylsulfonyl, pentylsulfonyl and hexylsulfonyl.

In the present specification, examples of the "$C_{6-14}$ arylsulfonyl group" include phenylsulfonyl, 1-naphthylsulfonyl and 2-naphthylsulfonyl.

In the present specification, examples of the "substituent" include a halogen atom, a cyano group, a nitro group, an optionally substituted hydrocarbon group, an optionally substituted heterocyclic group, an acyl group, an optionally substituted amino group, an optionally substituted carbamoyl group, an optionally substituted thiocarbamoyl group, an optionally substituted sulfamoyl group, an optionally substituted hydroxy group, an optionally substituted sulfanyl (SH) group and an optionally substituted silyl group.

In the present specification, examples of the "hydrocarbon group" (including "hydrocarbon group" of "optionally substituted hydrocarbon group") include a $C_{1-6}$ alkyl group, a $C_{2-6}$ alkenyl group, a $C_{2-6}$ alkynyl group, a $C_{3-10}$ cycloalkyl group, a $C_{3-10}$ cycloalkenyl group, a $C_{6-14}$ aryl group and a $C_{7-16}$ aralkyl group.

In the present specification, examples of the "optionally substituted hydrocarbon group" include a hydrocarbon group optionally having substituent(s) selected from the following Substituent group A.

[Substituent Group A]
(1) a halogen atom,
(2) a nitro group,
(3) a cyano group,
(4) an oxo group,
(5) a hydroxy group,
(6) an optionally halogenated $C_{1-6}$ alkoxy group,
(7) a $C_{6-14}$ aryloxy group (e.g., phenoxy, naphthoxy),
(8) a $C_{7-16}$ aralkyloxy group (e.g., benzyloxy),
(9) a 5- to 14-membered aromatic heterocyclyloxy group (e.g., pyridyloxy),
(10) a 3- to 14-membered non-aromatic heterocyclyloxy group (e.g., morpholinyloxy, piperidinyloxy),
(11) a $C_{1-6}$ alkyl-carbonyloxy group (e.g., acetoxy, propanoyloxy),
(12) a $C_{6-14}$ aryl-carbonyloxy group (e.g., benzoyloxy, 1-naphthoyloxy, 2-naphthoyloxy),
(13) a $C_{1-6}$ alkoxy-carbonyloxy group (e.g., methoxycarbonyloxy, ethoxycarbonyloxy, propoxycarbonyloxy, butoxycarbonyloxy),
(14) a mono- or di-$C_{1-6}$ alkyl-carbamoyloxy group (e.g., methylcarbamoyloxy, ethylcarbamoyloxy, dimethylcarbamoyloxy, diethylcarbamoyloxy),
(15) a $C_{6-14}$ aryl-carbamoyloxy group (e.g., phenylcarbamoyloxy, naphthylcarbamoyloxy),
(16) a 5- to 14-membered aromatic heterocyclylcarbonyloxy group (e.g., nicotinoyloxy),
(17) a 3- to 14-membered non-aromatic heterocyclylcarbonyloxy group (e.g., morpholinylcarbonyloxy, piperidinylcarbonyloxy),
(18) an optionally halogenated $C_{1-6}$ alkylsulfonyloxy group (e.g., methylsulfonyloxy, trifluoromethylsulfonyloxy),
(19) a $C_{6-14}$ arylsulfonyloxy group optionally substituted by a $C_{1-6}$ alkyl group (e.g., phenylsulfonyloxy, toluenesulfonyloxy),
(20) an optionally halogenated $C_{1-6}$ alkylthio group,
(21) a 5- to 14-membered aromatic heterocyclic group,
(22) a 3- to 14-membered non-aromatic heterocyclic group,
(23) a formyl group,
(24) a carboxy group,
(25) an optionally halogenated $C_{1-6}$ alkyl-carbonyl group,
(26) a $C_{6-14}$ aryl-carbonyl group,

(27) a 5- to 14-membered aromatic heterocyclylcarbonyl group,
(28) a 3- to 14-membered non-aromatic heterocyclylcarbonyl group,
(29) a $C_{1-6}$ alkoxy-carbonyl group,
(30) a $C_{6-14}$ aryloxy-carbonyl group (e.g., phenyloxycarbonyl, 1-naphthyloxycarbonyl, 2-naphthyloxycarbonyl),
(31) a $C_{7-16}$ aralkyloxy-carbonyl group (e.g., benzyloxycarbonyl, phenethyloxycarbonyl),
(32) a carbamoyl group,
(33) a thiocarbamoyl group,
(34) a mono- or di-$C_{1-6}$ alkyl-carbamoyl group,
(35) a $C_{6-14}$ aryl-carbamoyl group (e.g., phenylcarbamoyl),
(36) a 5- to 14-membered aromatic heterocyclylcarbamoyl group (e.g., pyridylcarbamoyl, thienylcarbamoyl),
(37) a 3- to 14-membered non-aromatic heterocyclylcarbamoyl group (e.g., morpholinylcarbamoyl, piperidinylcarbamoyl),
(38) an optionally halogenated $C_{1-6}$ alkylsulfonyl group,
(39) a $C_{6-14}$ arylsulfonyl group,
(40) a 5- to 14-membered aromatic heterocyclylsulfonyl group (e.g., pyridylsulfonyl, thienylsulfonyl),
(41) an optionally halogenated $C_{1-6}$ alkylsulfinyl group,
(42) a $C_{6-14}$ arylsulfinyl group (e.g., phenylsulfinyl, 1-naphthylsulfinyl, 2-naphthylsulfinyl),
(43) a 5- to 14-membered aromatic heterocyclylsulfinyl group (e.g., pyridylsulfinyl, thienylsulfinyl),
(44) an amino group,
(45) a mono- or di-$C_{1-6}$ alkylamino group (e.g., methylamino, ethylamino, propylamino, isopropylamino, butylamino, dimethylamino, diethylamino, dipropylamino, dibutylamino, N-ethyl-N-methylamino),
(46) a mono- or di-$C_{6-14}$ arylamino group (e.g., phenylamino),
(47) a 5- to 14-membered aromatic heterocyclylamino group (e.g., pyridylamino),
(48) a $C_{7-16}$ aralkylamino group (e.g., benzylamino),
(49) a formylamino group,
(50) a $C_{1-6}$ alkyl-carbonylamino group (e.g., acetylamino, propanoylamino, butanoylamino),
(51) a ($C_{1-6}$ alkyl) ($C_{1-6}$ alkyl-carbonyl) amino group (e.g., N-acetyl-N-methylamino),
(52) a $C_{6-14}$ aryl-carbonylamino group (e.g., phenylcarbonylamino, naphthylcarbonylamino),
(53) a $C_{1-6}$ alkoxy-carbonylamino group (e.g., methoxycarbonylamino, ethoxycarbonylamino, propoxycarbonylamino, butoxycarbonylamino, tert-butoxycarbonylamino),
(54) a $C_{7-16}$ aralkyloxy-carbonylamino group (e.g., benzyloxycarbonylamino),
(55) a $C_{1-6}$ alkylsulfonylamino group (e.g., methylsulfonylamino, ethylsulfonylamino),
(56) a $C_{6-14}$ arylsulfonylamino group optionally substituted by a $C_{1-6}$ alkyl group (e.g., phenylsulfonylamino, toluenesulfonylamino),
(57) an optionally halogenated $C_{1-6}$ alkyl group,
(58) a $C_{2-6}$ alkenyl group,
(59) a $C_{2-6}$ alkynyl group,
(60) a $C_{3-10}$ cycloalkyl group,
(61) a $C_{3-10}$ cycloalkenyl group, and
(62) a $C_{6-14}$ aryl group.

The number of the above-mentioned substituents in the "optionally substituted hydrocarbon group" is, for example, 1 to 5, preferably 1 to 3. When the number of the substituents is two or more, the respective substituents may be the same or different.

In the present specification, examples of the "heterocyclic group" (including "heterocyclic group" of "optionally substituted heterocyclic group") include (i) an aromatic heterocyclic group, (ii) a non-aromatic heterocyclic group and (iii) a 7- to 10-membered bridged heterocyclic group, each containing, as a ring-constituting atom besides carbon atom, 1 to 4 heteroatoms selected from a nitrogen atom, a sulfur atom and an oxygen atom.

In the present specification, examples of the "aromatic heterocyclic group" (including "5- to 14-membered aromatic heterocyclic group") include a 5- to 14-membered (preferably 5- to 10-membered) aromatic heterocyclic group containing, as a ring-constituting atom besides carbon atom, 1 to 4 heteroatoms selected from a nitrogen atom, a sulfur atom and an oxygen atom.

Preferable examples of the "aromatic heterocyclic group" include 5- or 6-membered monocyclic aromatic heterocyclic groups such as thienyl, furyl, pyrrolyl, imidazolyl, pyrazolyl, thiazolyl, isothiazolyl, oxazolyl, isoxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, triazinyl and the like; and 8- to 14-membered fused polycyclic (preferably bi or tricyclic) aromatic heterocyclic groups such as benzothiophenyl, benzofuranyl, benzimidazolyl, benzoxazolyl, benzisoxazolyl, benzothiazolyl, benzisothiazolyl, benzotriazolyl, imidazopyridinyl, thienopyridinyl, furopyridinyl, pyrrolopyridinyl, pyrazolopyridinyl, oxazolopyridinyl, thiazolopyridinyl, imidazopyrazinyl, imidazopyrimidinyl, thienopyrimidinyl, furopyrimidinyl, pyrrolopyrimidinyl, pyrazolopyrimidinyl, oxazolopyrimidinyl, thiazolopyrimidinyl, pyrazolotriazinyl, naphtho[2,3-b]thienyl, phenoxathiinyl, indolyl, isoindolyl, 1H-indazolyl, purinyl, isoquinolyl, quinolyl, phthalazinyl, naphthyridinyl, quinoxalinyl, quinazolinyl, cinnolinyl, carbazolyl, j-carbolinyl, phenanthridinyl, acridinyl, phenazinyl, phenothiazinyl, phenoxazinyl and the like.

In the present specification, examples of the "non-aromatic heterocyclic group" (including "3- to 14-membered non-aromatic heterocyclic group") include a 3- to 14-membered (preferably 4- to 10-membered) non-aromatic heterocyclic group containing, as a ring-constituting atom besides carbon atom, 1 to 4 heteroatoms selected from a nitrogen atom, a sulfur atom and an oxygen atom.

Preferable examples of the "non-aromatic heterocyclic group" include 3- to 8-membered monocyclic non-aromatic heterocyclic groups such as aziridinyl, oxiranyl, thiiranyl, azetidinyl, oxetanyl, thietanyl, tetrahydrothienyl, tetrahydrofuranyl, pyrrolinyl, pyrrolidinyl, imidazolinyl, imidazolidinyl, oxazolinyl, oxazolidinyl, pyrazolinyl, pyrazolidinyl, thiazolinyl, thiazolidinyl, tetrahydroisothiazolyl, tetrahydrooxazolyl, tetrahydroisooxazolyl, piperidinyl, piperazinyl, tetrahydropyridinyl, dihydropyridinyl, dihydrothiopyranyl, tetrahydropyrimidinyl, tetrahydropyridazinyl, dihydropyranyl, tetrahydropyranyl, tetrahydrothiopyranyl, morpholinyl, thiomorpholinyl, azepanyl, diazepanyl, azepinyl, oxepanyl, azocanyl, diazocanyl and the like; and 9- to 14-membered fused polycyclic (preferably bi or tricyclic) non-aromatic heterocyclic groups such as dihydrobenzofuranyl, dihydrobenzimidazolyl, dihydrobenzoxazolyl, dihydrobenzothiazolyl, dihydrobenzisothiazolyl, dihydronaphtho[2,3-b]thienyl, tetrahydroisoquinolyl, tetrahydroquinolyl, 4H-quinolizinyl, indolinyl, isoindolinyl, tetrahydrothieno[2,3-c]pyridinyl, tetrahydrobenzazepinyl, tetrahydroquinoxalinyl, tetrahydrophenanthridinyl, hexahydrophenothiazinyl, hexahydrophenoxazinyl, tetrahydrophthalazinyl, tetrahydronaphthyridinyl, tetrahydroquinazolinyl, tetrahydrocinnolinyl, tetrahydrocarbazolyl, tetrahydro-β-carbolinyl, tetrahydroacrydinyl, tetrahydrophenazinyl, tetrahydrothioxanthenyl, octahydroisoquinolyl and the like.

In the present specification, preferable examples of the "7- to 10-membered bridged heterocyclic group" include quinuclidinyl and 7-azabicyclo[2.2.1]heptanyl.

In the present specification, examples of the "nitrogen-containing heterocyclic group" include a "heterocyclic group" containing at least one nitrogen atom as a ring-constituting atom.

In the present specification, examples of the "optionally substituted heterocyclic group" include a heterocyclic group optionally having substituent(s) selected from the above-mentioned Substituent group A.

The number of the substituents in the "optionally substituted heterocyclic group" is, for example, 1 to 3. When the number of the substituents is two or more, the respective substituents may be the same or different.

In the present specification, examples of the "acyl group" include a formyl group, a carboxy group, a carbamoyl group, a thiocarbamoyl group, a sulfino group, a sulfo group, a sulfamoyl group and a phosphono group, each optionally having "1 or 2 substituents selected from a $C_{1-6}$ alkyl group, a $C_{2-6}$ alkenyl group, a $C_{3-10}$ cycloalkyl group, a $C_{3-10}$ cycloalkenyl group, a $C_{6-14}$ aryl group, a $C_{7-16}$ aralkyl group, a 5- to 14-membered aromatic heterocyclic group and a 3- to 14-membered non-aromatic heterocyclic group, each of which optionally has 1 to 3 substituents selected from a halogen atom, an optionally halogenated $C_{1-6}$ alkoxy group, a hydroxy group, a nitro group, a cyano group, an amino group and a carbamoyl group".

Examples of the "acyl group" also include a hydrocarbon-sulfonyl group, a heterocyclylsulfonyl group, a hydrocarbon-sulfinyl group and a heterocyclylsulfinyl group.

Here, the hydrocarbon-sulfonyl group means a hydrocarbon group-bonded sulfonyl group, the heterocyclylsulfonyl group means a heterocyclic group-bonded sulfonyl group, the hydrocarbon-sulfinyl group means a hydrocarbon group-bonded sulfinyl group and the heterocyclylsulfinyl group means a heterocyclic group-bonded sulfinyl group.

Preferable examples of the "acyl group" include a formyl group, a carboxy group, a $C_{1-6}$ alkyl-carbonyl group, a $C_{2-6}$ alkenyl-carbonyl group (e.g., crotonoyl), a $C_{3-10}$ cycloalkyl-carbonyl group (e.g., cyclobutanecarbonyl, cyclopentanecarbonyl, cyclohexanecarbonyl, cycloheptanecarbonyl), a $C_{3-10}$ cycloalkenyl-carbonyl group (e.g., 2-cyclohexenecarbonyl), a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a $C_{6-14}$ aryloxy-carbonyl group (e.g., phenyloxycarbonyl, naphthyloxycarbonyl), a $C_{7-16}$ aralkyloxy-carbonyl group (e.g., benzyloxycarbonyl, phenethyloxycarbonyl), a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl), a mono- or di-$C_{6-14}$ aryl-carbamoyl group (e.g., phenylcarbamoyl), a mono- or di-$C_{7-16}$ aralkyl-carbamoyl group, a 5- to 14-membered aromatic heterocyclylcarbamoyl group (e.g., pyridylcarbamoyl), a thiocarbamoyl group, a mono- or di-$C_{1-6}$ alkyl-thiocarbamoyl group (e.g., methylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a 5- to 14-membered aromatic heterocyclylthiocarbamoyl group (e.g., pyridylthiocarbamoyl), a sulfino group, a $C_{1-6}$ alkylsulfinyl group (e.g., methylsulfinyl, ethylsulfinyl), a sulfo group, a $C_{1-6}$ alkylsulfonyl group, a $C_{6-14}$ arylsulfonyl group, a phosphono group and a mono- or di-$C_{1-6}$ alkylphosphono group (e.g., dimethylphosphono, diethylphosphono, diisopropylphosphono, dibutylphosphono).

In the present specification, examples of the "optionally substituted amino group" include an amino group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from Substituent group A".

Preferable examples of the optionally substituted amino group include an amino group, a mono- or di-(optionally halogenated $C_{1-6}$ alkyl) amino group (e.g., methylamino, trifluoromethylamino, dimethylamino, ethylamino, diethylamino, propylamino, dibutylamino), a mono- or di-$C_{2-6}$ alkenylamino group (e.g., diallylamino), a mono- or di-$C_{3-10}$ cycloalkylamino group (e.g., cyclopropylamino, cyclohexylamino), a mono- or di-$C_{6-14}$ arylamino group (e.g., phenylamino), a mono- or di-$C_{7-16}$ aralkylamino group (e.g., benzylamino, dibenzylamino), a mono- or di-(optionally halogenated $C_{1-6}$ alkyl)-carbonylamino group (e.g., acetylamino, propionylamino), a mono- or di-$C_{6-14}$ aryl-carbonylamino group (e.g., benzoylamino), a mono- or di-$C_{7-16}$ aralkyl-carbonylamino group (e.g., benzylcarbonylamino), a mono- or di-5- to 14-membered aromatic heterocyclylcarbonylamino group (e.g., nicotinoylamino, isonicotinoylamino), a mono- or di-3- to 14-membered non-aromatic heterocyclylcarbonylamino group (e.g., piperidinylcarbonylamino), a mono- or di-$C_{1-6}$ alkoxy-carbonylamino group (e.g., tert-butoxycarbonylamino), a 5- to 14-membered aromatic heterocyclylamino group (e.g., pyridylamino), a carbamoylamino group, a (mono- or di-$C_{1-6}$ alkyl-carbamoyl) amino group (e.g., methylcarbamoylamino), a (mono- or di-$C_{7-16}$ aralkyl-carbamoyl) amino group (e.g., benzylcarbamoylamino), a $C_{1-6}$ alkylsulfonylamino group (e.g., methylsulfonylamino, ethylsulfonylamino), a $C_{6-14}$ arylsulfonylamino group (e.g., phenylsulfonylamino), a ($C_{1-6}$ alkyl)($C_{1-6}$ alkyl-carbonyl) amino group (e.g., N-acetyl-N-methylamino) and a ($C_{1-6}$ alkyl)($C_{6-14}$ aryl-carbonyl) amino group (e.g., N-benzoyl-N-methylamino).

In the present specification, examples of the "optionally substituted carbamoyl group" include a carbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from Substituent group A".

Preferable examples of the optionally substituted carbamoyl group include a carbamoyl group, a mono- or di-$C_{1-6}$ alkyl-carbamoyl group, a mono- or di-$C_{2-6}$ alkenyl-carbamoyl group (e.g., diallylcarbamoyl), a mono- or di-$C_{3-10}$ cycloalkyl-carbamoyl group (e.g., cyclopropylcarbamoyl, cyclohexylcarbamoyl), a mono- or di-$C_{6-14}$ aryl-carbamoyl group (e.g., phenylcarbamoyl), a mono- or di-$C_{7-16}$ aralkyl-carbamoyl group, a mono- or di-$C_{1-6}$ alkyl-carbonyl-carbamoyl group (e.g., acetylcarbamoyl, propionylcarbamoyl), a mono- or di-$C_{6-14}$ aryl-carbonyl-carbamoyl group (e.g., benzoylcarbamoyl) and a 5- to 14-membered aromatic heterocyclylcarbamoyl group (e.g., pyridylcarbamoyl).

In the present specification, examples of the "optionally substituted thiocarbamoyl group" include a thiocarbamoyl group optionally having "1 or 2 substituents selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from Substituent group A".

Preferable examples of the optionally substituted thiocarbamoyl group include a thiocarbamoyl group, a mono- or di-$C_{1-6}$ alkyl-thiocarbamoyl group (e.g., methylthiocarbamoyl, ethylthiocarbamoyl, dimethylthiocarbamoyl, diethylthiocarbamoyl, N-ethyl-N-methylthiocarbamoyl), a mono- or di-$C_{2-6}$ alkenyl-thiocarbamoyl group (e.g., diallylthiocarbamoyl), a mono- or di-$C_{3-10}$ cycloalkyl-thiocarbamoyl group (e.g., cyclopropylthiocarbamoyl, cyclohexylthiocarbamoyl), a mono- or di-$C_{6-14}$ aryl-thiocarbamoyl group (e.g., phenylthiocarbamoyl), a mono- or di-$C_{7-16}$ aralkyl-thiocarbamoyl group (e.g., benzylthiocarbamoyl, phenethylthiocarbamoyl), a mono- or di-$C_{1-6}$ alkyl-carbonyl-thiocarbamoyl group (e.g., acetylthiocarbamoyl, propionylthiocarbamoyl), a mono- or di-$C_{6-14}$ aryl-carbonyl-thiocarbamoyl group (e.g., benzoylthiocarbamoyl) and a 5- to 14-membered aromatic heterocyclylthiocarbamoyl group (e.g., pyridylthiocarbamoyl).

In the present specification, examples of the "optionally substituted sulfamoyl group" include a sulfamoyl group optionally having "1 or 2 substituents selected from a $C_{1-6}$ alkyl group, a $C_{2-6}$ alkenyl group, a $C_{3-10}$ cycloalkyl group, a $C_6$-14 aryl group, a $C_{7-16}$ aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a C-s alkoxy-carbonyl group, a 5- to 14-membered aromatic heterocyclic group, a carbamoyl group, a mono- or di-$C_{1-6}$ alkyl-carbamoyl group and a mono- or di-$C_{7-16}$ aralkyl-carbamoyl group, each of which optionally has 1 to 3 substituents selected from Substituent group A".

Preferable examples of the optionally substituted sulfamoyl group include a sulfamoyl group, a mono- or di-$C_{1-6}$ alkyl-sulfamoyl group (e.g., methylsulfamoyl, ethylsulfamoyl, dimethylsulfamoyl, diethylsulfamoyl, N-ethyl-N-methylsulfamoyl), a mono- or di-$C_{2-6}$ alkenyl-sulfamoyl group (e.g., diallylsulfamoyl), a mono- or di-$C_{3-10}$ cycloalkyl-sulfamoyl group (e.g., cyclopropylsulfamoyl, cyclohexylsulfamoyl), a mono- or di-$C_{6-14}$ aryl-sulfamoyl group (e.g., phenylsulfamoyl), a mono- or di-$C_{7-16}$ aralkyl-sulfamoyl group (e.g., benzylsulfamoyl, phenethylsulfamoyl), a mono- or di-$C_{1-6}$ alkyl-carbonyl-sulfamoyl group (e.g., acetylsulfamoyl, propionylsulfamoyl), a mono- or di-$C_{6-14}$ aryl-carbonyl-sulfamoyl group (e.g., benzoylsulfamoyl) and a 5- to 14-membered aromatic heterocyclylsulfamoyl group (e.g., pyridylsulfamoyl).

In the present specification, examples of the "optionally substituted hydroxy group" include a hydroxy group optionally having "a substituent selected from a $C_{1-6}$ alkyl group, a $C_{2-6}$ alkenyl group, a $C_{3-10}$ cycloalkyl group, a $C_{6-14}$ aryl group, a $C_7$-16 aralkyl group, a $C_{1-6}$ alkyl-carbonyl group, a $C_{6-14}$ aryl-carbonyl group, a $C_{7-16}$ aralkyl-carbonyl group, a 5- to 14-membered aromatic heterocyclylcarbonyl group, a 3- to 14-membered non-aromatic heterocyclylcarbonyl group, a $C_{1-6}$ alkoxy-carbonyl group, a 5- to 14-membered aromatic heterocyclic group, a carbamoyl group, a mono- or di-$C_{1-6}$ alkyl-carbamoyl group, a mono- or di-$C_{7-16}$ aralkyl-carbamoyl group, a $C_{1-6}$ alkylsulfonyl group and a $C_{6-14}$ arylsulfonyl group, each of which optionally has 1 to 3 substituents selected from Substituent group A".

Preferable examples of the optionally substituted hydroxy group include a hydroxy group, a $C_{1-6}$ alkoxy group, a $C_{2-6}$ alkenyloxy group (e.g., allyloxy, 2-butenyloxy, 2-pentenyloxy, 3-hexenyloxy), a $C_{3-10}$ cycloalkyloxy group (e.g., cyclohexyloxy), a $C_{6-14}$ aryloxy group (e.g., phenoxy, naphthyloxy), a $C_{7-16}$ aralkyloxy group (e.g., benzyloxy, phenethyloxy), a $C_{1-6}$ alkyl-carbonyloxy group (e.g., acetyloxy, propionyloxy, butyryloxy, isobutyryloxy, pivaloyloxy), a $C_{6-14}$ aryl-carbonyloxy group (e.g., benzoyloxy), a $C_{7-16}$ aralkyl-carbonyloxy group (e.g., benzylcarbonyloxy), a 5- to 14-membered aromatic heterocyclylcarbonyloxy group (e.g., nicotinoyloxy), a 3- to 14-membered non-aromatic heterocyclylcarbonyloxy group (e.g., piperidinylcarbonyloxy), a $C_{1-6}$ alkoxy-carbonyloxy group (e.g., tert-butoxycarbonyloxy), a 5- to 14-membered aromatic heterocyclyloxy group (e.g., pyridyloxy), a carbamoyloxy group, a $C_{1-6}$ alkyl-carbamoyloxy group (e.g., methylcarbamoyloxy), a $C_{7-16}$ aralkyl-carbamoyloxy group (e.g., benzylcarbamoyloxy), a $C_{1-6}$ alkylsulfonyloxy group (e.g., methylsulfonyloxy, ethylsulfonyloxy) and a $C_{6-14}$ arylsulfonyloxy group (e.g., phenylsulfonyloxy).

In the present specification, examples of the "optionally substituted sulfanyl group" include a sulfanyl group optionally having "a substituent selected from a $C_{1-6}$ alkyl group, a $C_{2-6}$ alkenyl group, a $C_{3-10}$ cycloalkyl group, a $C_{6-14}$ aryl group, a $C_{7-16}$ aralkyl group, a $C_{1-6}$ alkyl-carbonyl group, a $C_{6-14}$ aryl-carbonyl group and a 5- to 14-membered aromatic heterocyclic group, each of which optionally has 1 to 3 substituents selected from Substituent group A" and a halogenated sulfanyl group.

Preferable examples of the optionally substituted sulfanyl group include a sulfanyl (—SH) group, a $C_{1-6}$ alkylthio group, a $C_{2-6}$ alkenylthio group (e.g., allylthio, 2-butenylthio, 2-pentenylthio, 3-hexenylthio), a $C_{3-10}$ cycloalkylthio group (e.g., cyclohexylthio), a $C_{6-14}$ arylthio group (e.g., phenylthio, naphthylthio), a $C_{7-16}$ aralkylthio group (e.g., benzylthio, phenethylthio), a $C_{1-6}$ alkyl-carbonylthio group (e.g., acetylthio, propionylthio, butyrylthio, isobutyrylthio, pivaloylthio), a $C_{6-14}$ aryl-carbonylthio group (e.g., benzoylthio), a 5- to 14-membered aromatic heterocyclylthio group (e.g., pyridylthio) and a halogenated thio group (e.g., pentafluorothio).

In the present specification, examples of the "optionally substituted silyl group" include a silyl group optionally having "1 to 3 substituents selected from a $C_{1-6}$ alkyl group, a $C_{2-6}$ alkenyl group, a $C_{3-10}$ cycloalkyl group, a $C_{6-14}$ aryl group and a $C_{7-16}$ aralkyl group, each of which optionally has 1 to 3 substituents selected from Substituent group A".

Preferable examples of the optionally substituted silyl group include a tri-$C_{1-6}$ alkylsilyl group (e.g., trimethylsilyl, tert-butyl(dimethyl)silyl).

In the present specification, examples of the "heterocycle" include an aromatic heterocycle and a non-aromatic heterocycle, each containing, as a ring-constituting atom besides carbon atom, 1 to 4 hetero atoms selected from a nitrogen atom, a sulfur atom and an oxygen atom.

In the present specification, examples of the "aromatic heterocycle" include a 5- to 14-membered (preferably 5- to 10-membered) aromatic heterocycle containing, as a ring-constituting atom besides carbon atom, 1 to 4 hetero atoms selected from a nitrogen atom, a sulfur atom and an oxygen atom. Preferable examples of the "aromatic heterocycle" include 5- or 6-membered monocyclic aromatic heterocycles such as thiophene, furan, pyrrole, imidazole, pyrazole, thiazole, isothiazole, oxazole, isoxazole, pyridine, pyrazine, pyrimidine, pyridazine, 1,2,4-oxadiazole, 1,3,4-oxadiazole, 1,2,4-thiadiazole, 1,3,4-thiadiazole, triazole, tetrazole, triazine and the like; and
8- to 14-membered fused polycyclic (preferably bi or tricyclic) aromatic heterocycles such as benzothiophene, benzofuran, benzimidazole, benzoxazole, benzisoxazole, benzothiazole, benzisothiazole, benzotriazole, imidazopyridine, thienopyridine, furopyridine, pyrrolopyridine, pyrazolopyridine, oxazolopyridine, thiazolopyridine, imidazopyrazine, imidazopyrimidine, thienopyrimidine, furopyrimidine, pyrrolopyrimidine, pyrazolopyrimidine, oxazolopyrimidine, thiazolopyrimidine, pyrazolopyrimidine, pyrazolotriazine, naphtho[2,3-b]thiophene, phenoxathiin, indole, isoindole, 1H-indazole, purine, isoquinoline, quinoline, phthalazine, naphthyridine, quinoxaline, quinazoline, cinnoline, carbazole, β-carboline, phenanthridine, acridine, phenazine, phenothiazine, phenoxazine and the like.

In the present specification, examples of the "non-aromatic heterocycle" include a 3- to 14-membered (preferably 4- to 10-membered) non-aromatic heterocycle containing, as a ring-constituting atom besides carbon atom, 1 to 4 hetero atoms selected from a nitrogen atom, a sulfur atom and an oxygen atom. Preferable examples of the "non-aromatic heterocycle" include 3- to 8-membered monocyclic non-aromatic heterocycles such as aziridine, oxirane, thiirane, azetidine, oxetane, thietane, tetrahydrothiophene, tetrahydrofuran, pyrroline, pyrrolidine, imidazoline, imidazolidine, oxazoline, oxazolidine, pyrazoline, pyrazolidine, thiazoline, thiazolidine, tetrahydroisothiazole, tetrahydrooxazole, tetrahydroisoxazole, piperidine, piperazine, tetrahydropyridine, dihydropyridine, dihydrothiopyran, tetrahydropyrimidine, tetrahydropyridazine, dihydropyran, tetrahydropyran, tetrahydrothiopyran, morpholine, thiomorpholine, azepane, diazepane, azepine, azocane, diazocane, oxepane and the like; and 9- to 14-membered fused polycyclic (preferably bi or tricyclic) non-aromatic heterocycles such as dihydrobenzofuran, dihydrobenzimidazole, dihydrobenzoxazole, dihydrobenzothiazole, dihydrobenzisothiazole, dihydronaphtho[2,3-b]thiophene, tetrahydroisoquinoline, tetrahydroquinoline, 4H-quinolizine, indoline, isoindoline, tetrahydrothieno[2,3-c]pyridine, tetrahydrobenzazepine, tetrahydroquinoxaline, tetrahydrophenanthridine, hexahydrophenothiazine, hexahydrophenoxazine, tetrahydrophthalazine, tetrahydronaphthyridine, tetrahydroquinazoline, tetrahydrocinnoline, tetrahydrocarbazole, tetrahydro-β-carboline, tetrahydroacridine, tetrahydrophenazine, tetrahydrothioxanthene, octahydroisoquinoline and the like.

In the present specification, examples of the "nitrogen-containing heterocycle" include a "heterocycle" containing at least one nitrogen atom as a ring-constituting atom.

The definition of each symbol in the formula (I) is explained in detail below.

Ring A is a 5-membered aromatic heterocycle.

Examples of the "5-membered aromatic heterocycle" represented by Ring A include a 5-membered aromatic heterocycle, from among the "aromatic heterocycle". Specific examples thereof include thiophene, furan, pyrrole, imidazole, pyrazole, isothiazole, isoxazole, 1,2,3-triazole, 1,2,4-triazole and the like.

Ring A is preferably pyrrole, pyrazole, thiophene or furan.

As another embodiment, Ring A is preferably pyrrole, pyrazole, thiophene, furan or imidazole.

In this embodiment, Ring A is more preferably pyrrole, pyrazole or imidazole.

Ring A is particularly preferably pyrrole or pyrazole.

Ring B is an optionally further substituted 6-membered nitrogen-containing non-aromatic heterocycle.

Examples of the "6-membered nitrogen-containing non-aromatic heterocycle" of the "optionally further substituted 6-membered nitrogen-containing non-aromatic heterocycle" represented by Ring B include a 6-membered non-aromatic heterocycle containing at least one nitrogen atom as a ring-constituting atom, from among the "non-aromatic heterocycle". Specific examples thereof include tetrahydropyridine, dihydropyridine, tetrahydropyrimidine, tetrahydropyrazine and the like. The "6-membered nitrogen-containing non-aromatic heterocycle" of the "optionally further substituted 6-membered nitrogen-containing non-aromatic heterocycle" represented by Ring B is preferably dihydropyridine, tetrahydropyridine, tetrahydropyrazine or tetrahydropyrimidine, more preferably dihydropyridine or tetrahydropyrazine.

The "6-membered nitrogen-containing non-aromatic heterocycle" of the "optionally further substituted 6-membered nitrogen-containing non-aromatic heterocycle" represented by Ring B is optionally substituted, for example, by substituent(s) selected from the above-mentioned Substituent Group A. The number of the substituents is, for example, 1 to 3. When the number of the substituents is 2 or more, the respective substituents may be the same or different.

Ring B is preferably dihydropyridine, tetrahydropyridine or tetrahydropyrazine.

As another embodiment, Ring B is preferably dihydropyridine, tetrahydropyridine, tetrahydropyrazine or tetrahydropyrimidine.

In this embodiment, Ring B is more preferably dihydropyridine, tetrahydropyrazine or tetrahydropyrimidine.

Ring B is particularly preferably dihydropyridine or tetrahydropyrazine.

W is $CR^5$, $NR^6$, N, O or S.

$R^5$ is a hydrogen atom or a substituent.

$R^6$ is a substituent.

$R^6$ is preferably an optionally substituted $C_{1-6}$ alkyl group (e.g., methyl, ethyl) or an optionally substituted $C_{7-16}$ aralkyl group (e.g., benzyl).

The "$C_{1-6}$ alkyl group" of the above-mentioned "optionally substituted $C_{1-6}$ alkyl group" is optionally substituted, for example, by substituent(s) selected from the above-mentioned Substituent Group A. The number of the substituents is, for example, 1 to 3. When the number of the substituents is 2 or more, the respective substituents may be the same or different.

"$C_{7-16}$ aralkyl group" of the above-mentioned "optionally substituted $C_{7-16}$ aralkyl group" is optionally substituted, for example, by substituent(s) selected from the above-mentioned Substituent Group A. The number of the substituents is, for example, 1 to 3. When the number of the substituents is 2 or more, the respective substituents may be the same or different.

$R^6$ is more preferably a $C_{1-6}$ alkyl group (e.g., methyl, ethyl) or a $C_{7-16}$ aralkyl group (e.g., benzyl).

$R^6$ is further more preferably a $C_{1-6}$ alkyl group (e.g., methyl, ethyl) or a benzyl group.

$R^6$ is even more preferably a $C_{1-6}$ alkyl group (e.g., methyl).

As another embodiment, $R^6$ is more preferably an optionally substituted $C_{1-6}$ alkyl group (e.g., methyl).

W is preferably $NR^6$ wherein $R^6$ is as defined above, N, O or S.

W is more preferably $NR^6$ wherein $R^6$ is an optionally substituted $C_{1-6}$ alkyl group (e.g., methyl, ethyl) or an optionally substituted $C_{7-16}$ aralkyl group (e.g., benzyl), N, O or S.

W is further more preferably $NR^6$ wherein $R^6$ is a $C_{1-6}$ alkyl group (e.g., methyl, ethyl) or a $C_{7-16}$ aralkyl group (e.g., benzyl), N, O or S.

W is still more preferably $NR^6$ wherein $R^6$ is a $C_{1-6}$ alkyl group (e.g., methyl, ethyl) or a benzyl group, N, O or S.

W is even more preferably $NR^6$ wherein $R^6$ is a $C_{1-6}$ alkyl group (e.g., methyl), or N.

As another embodiment, W is more preferably $NR^6$ wherein $R^6$ is as defined above, or N.

In this embodiment, W is further more preferably $NR^6$ wherein $R^6$ is an optionally substituted $C_{1-6}$ alkyl group (e.g., methyl), or N.

X is $CR^7$, $NR^9$ or N.

$R^7$ is a hydrogen atom or a substituent.

$R^8$ is a substituent.

$R^7$ is preferably a hydrogen atom or an optionally substituted $C_{1-6}$ alkyl group (e.g., methyl).

The "$C_{1-6}$ alkyl group" of the above-mentioned "optionally substituted $C_{1-6}$ alkyl group" is optionally substituted, for example, by substituent(s) selected from the above-mentioned Substituent Group A. The number of the substituents is, for example, 1 to 3. When the number of the substituents is 2 or more, the respective substituents may be the same or different.

$R^7$ is more preferably a hydrogen atom or a $C_{1-6}$ alkyl group (e.g., methyl).

$R^7$ is further more preferably a hydrogen atom.

$R^8$ is preferably an optionally substituted $C_{1-6}$ alkyl group (e.g., methyl).

The "$C_{1-6}$ alkyl group" of the above-mentioned "optionally substituted $C_{1-6}$ alkyl group" is optionally substituted, for example, by substituent(s) selected from the above-mentioned Substituent Group A. The number of the substituents is, for example, 1 to 3. When the number of the substituents is 2 or more, the respective substituents may be the same or different.

$R^8$ is more preferably a $C_{1-6}$ alkyl group (e.g., methyl).

X is preferably $CR^7$ wherein $R^7$ is a hydrogen atom or an optionally substituted $C_{1-6}$ alkyl group (e.g., methyl), $NR^8$ wherein $R^8$ is an optionally substituted $C_{1-6}$ alkyl group (e.g., methyl), or N.

X is more preferably $CR^7$ wherein $R^7$ is a hydrogen atom or a $C_{1-6}$ alkyl group (e.g., methyl), $NR^8$ wherein R is a $C_{1-6}$ alkyl group (e.g., methyl), or N.

X is further more preferably CH or N.

Y is C or N.

Y is preferably C.

$Z^1$ and $Z^2$ are each independently C or N.

$Z^1$ is preferably C.

$Z^1$—$Z^2$ is C=C, C—C, C—N or N—C.

$Z^1$—$Z^2$ is preferably C=C, C—C or C—N.

As another embodiment, $Z^1$—$Z^2$ is preferably C=C, C—N or N—C.

$Z^1$—$Z^2$ is more preferably C=C or C—N.

The fused ring moiety composed of Ring A and Ring B, i.e., the partial structure represented by the following formula:

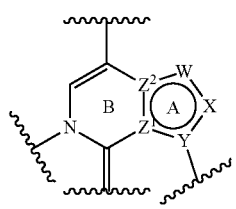

is a partial structure represented by the following formula:

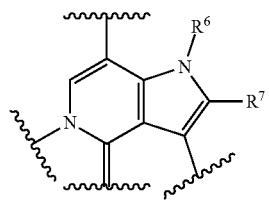

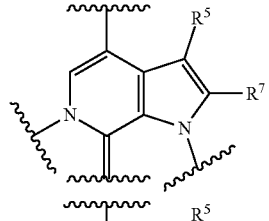

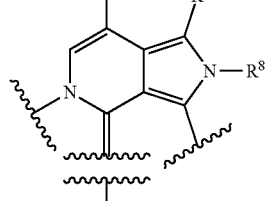

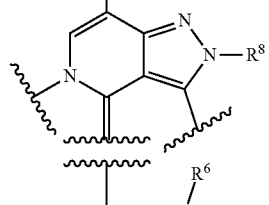

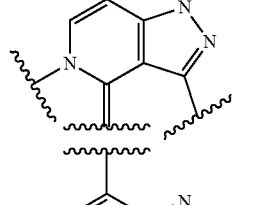

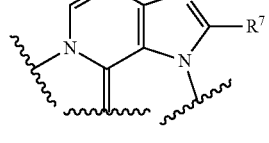

-continued

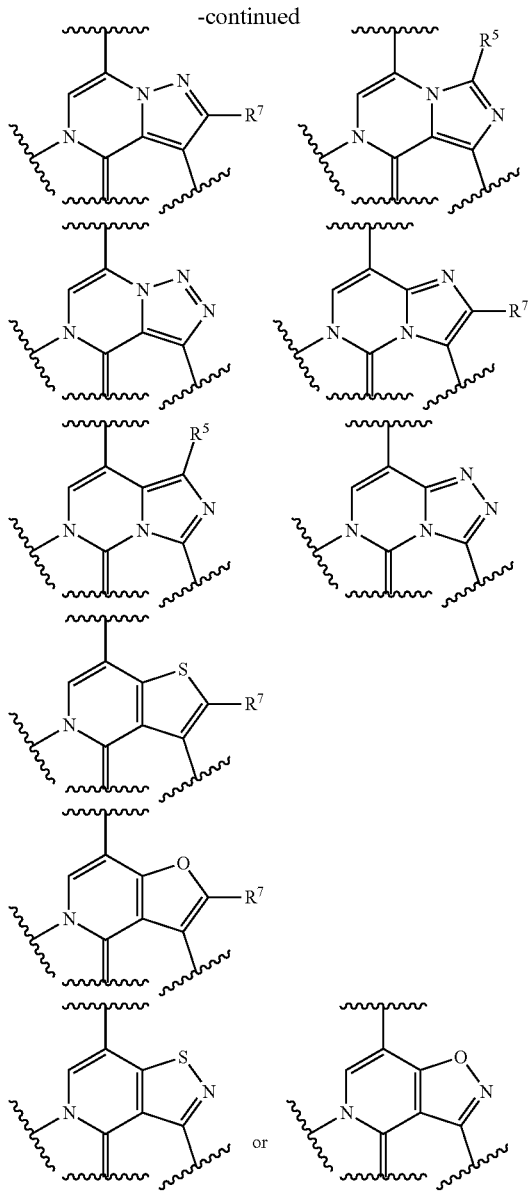

wherein each symbol is as defined above, preferably, $R^5$ is a hydrogen atom or a $C_{1-6}$ alkyl group (e.g., methyl), $R^6$ is a $C_{1-6}$ alkyl group (e.g., methyl, ethyl) or a $C_{7-16}$ aralkyl group (e.g., benzyl), $R^7$ is a hydrogen atom or a $C_{1-6}$ alkyl group (e.g., methyl), and $R^8$ is a $C_{1-6}$ alkyl group (e.g., methyl).

The fused ring moiety composed of Ring A and Ring B, i.e., the partial structure represented by the following formula:

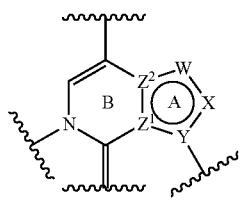

is preferably a partial structure represented by the following formula:

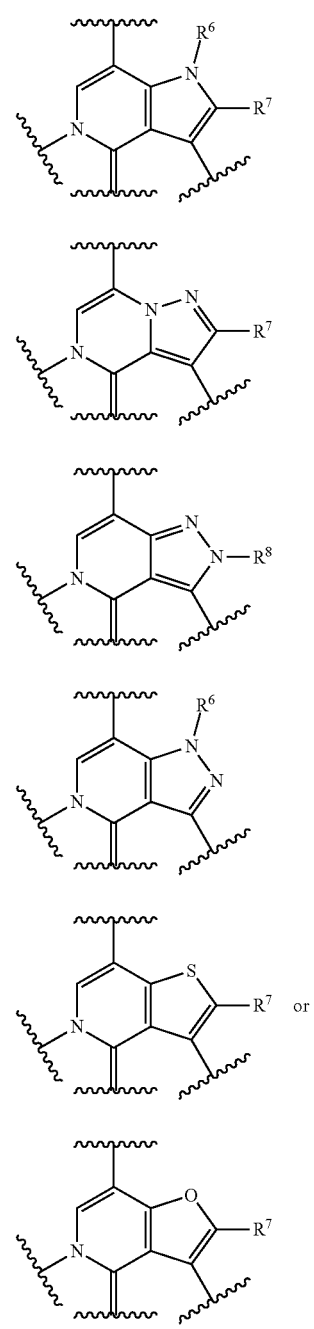

wherein each symbol is as defined above, preferably, $R^6$ is a $C_{1-6}$ alkyl group (e.g., methyl, ethyl) or a $C_{7-16}$ aralkyl group (e.g., benzyl), $R^7$ is a hydrogen atom or a $C_{1-6}$ alkyl group (e.g., methyl), and $R^8$ is a $C_{1-6}$ alkyl group (e.g., methyl), more preferably, $R^6$ is a $C_{1-6}$ alkyl group (e.g., methyl, ethyl) or a benzyl group, $R^7$ is a hydrogen atom or a $C_{1-6}$ alkyl group (e.g., methyl), and $R^8$ is a $C_{1-6}$ alkyl group (e.g., methyl).

As another embodiment, the above-mentioned partial structure is preferably a partial structure represented by the following formula:

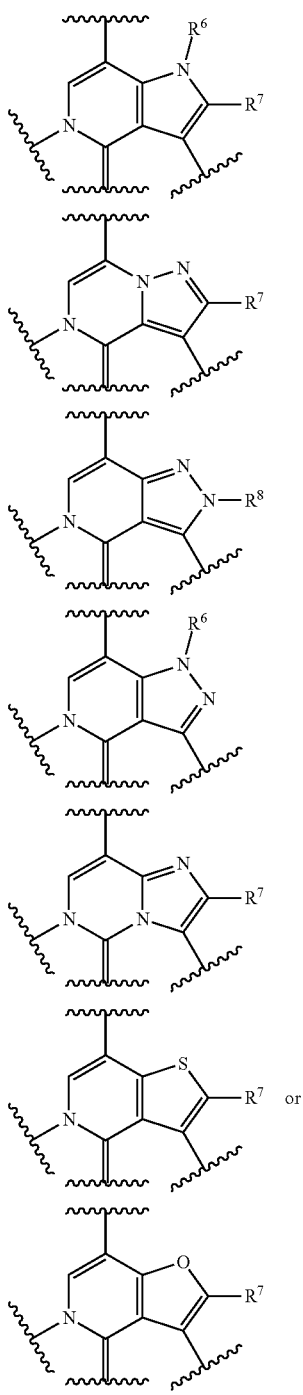

wherein each symbol is as defined above, preferably, $R^6$ is a $C_{1-6}$ alkyl group (e.g., methyl, ethyl) or a $C_{7-16}$ aralkyl group (e.g., benzyl), $R^7$ is a hydrogen atom or a $C_{1-6}$ alkyl group (e.g., methyl), and $R^8$ is a $C_{1-6}$ alkyl group (e.g., methyl), more preferably, $R^6$ is a $C_{1-6}$ alkyl group (e.g., methyl, ethyl) or a benzyl group, $R^7$ is a hydrogen atom or a $C_{1-6}$ alkyl group (e.g., methyl), and $R^8$ is a $C_{1-6}$ alkyl group (e.g., methyl).

The fused ring moiety composed of Ring A and Ring B, i.e., the partial structure represented by the following formula:

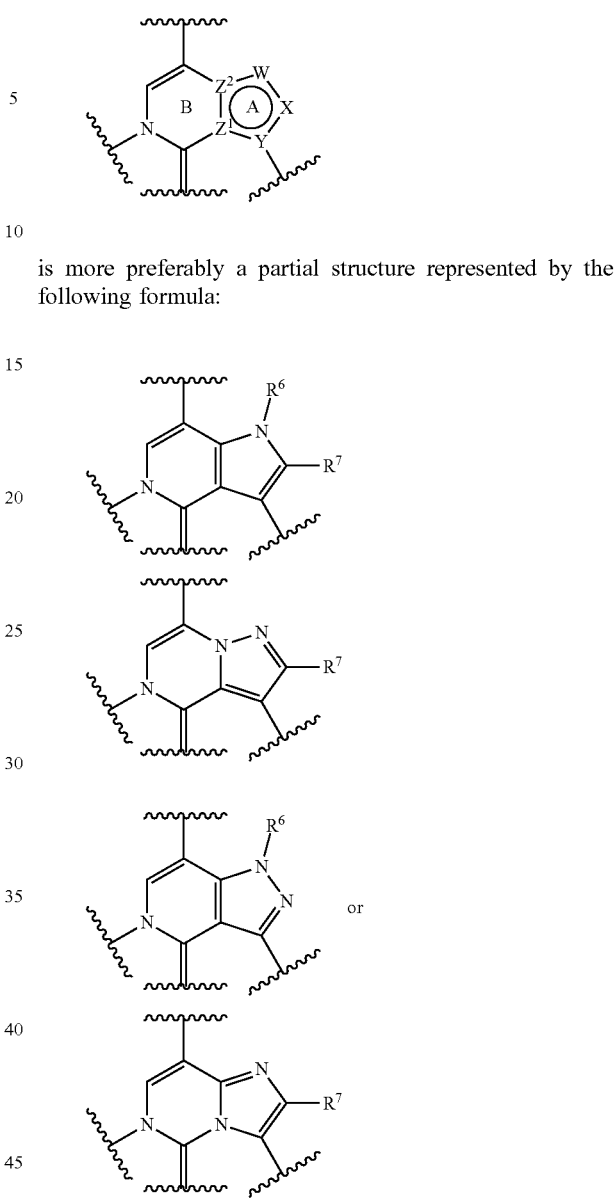

is more preferably a partial structure represented by the following formula:

wherein each symbol is as defined above, preferably, $R^6$ is a $C_{1-6}$ alkyl group (e.g., methyl, ethyl) or a $C_{7-16}$ aralkyl group (e.g., benzyl), and $R^7$ is a hydrogen atom or a $C_{1-6}$ alkyl group (e.g., methyl), more preferably, $R^6$ is a $C_{1-6}$ alkyl group (e.g., methyl, ethyl) or a benzyl group, and $R^7$ is a hydrogen atom or a $C_{1-6}$ alkyl group (e.g., methyl), further more preferably a partial structure represented by the following formula:

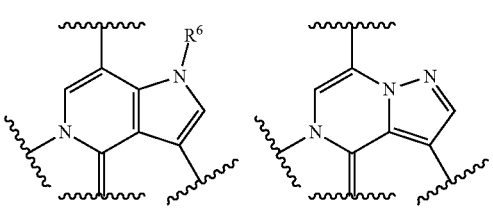

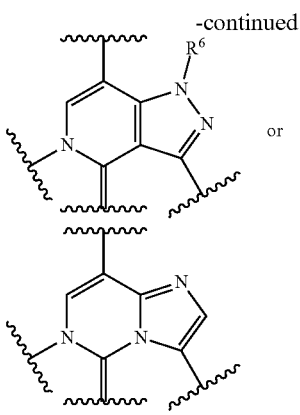

wherein each symbol is as defined above, preferably, $R^6$ is a $C_{1-6}$ alkyl group (e.g., methyl),
particularly preferably a partial structure represented by the following formula:

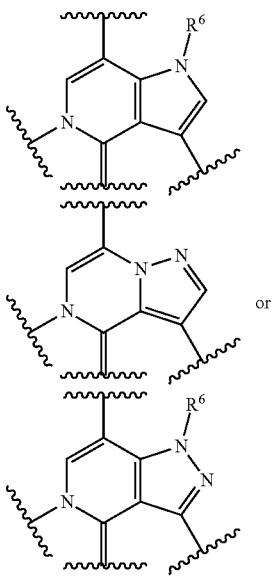

wherein each symbol is as defined above, preferably, $R^6$ is a $C_{1-6}$ alkyl group (e.g., methyl).

$R^1$ is a substituent.

$R^1$ is preferably an optionally substituted $C_{1-6}$ alkyl group (e.g., methyl, ethyl) or an optionally substituted $C_{6-14}$ aryl group (e.g., phenyl).

As another embodiment, $R^1$ is preferably an optionally substituted $C_{1-6}$ alkyl group (e.g., methyl, ethyl), an optionally substituted $C_{6-14}$ aryl group (e.g., phenyl) or an optionally substituted $C_{7-16}$ aralkyl group (e.g., benzyl).

The "$C_{1-6}$ alkyl group" of the above-mentioned "optionally substituted $C_{1-6}$ alkyl group" is optionally substituted, for example, by substituent(s) selected from the above-mentioned Substituent Group A. The number of the substituents is, for example, 1 to 3. When the number of the substituents is 2 or more, the respective substituents may be the same or different.

The "$C_{6-14}$ aryl group" of the above-mentioned "optionally substituted $C_{6-14}$ aryl group" is optionally substituted, for example, by substituent(s) selected from the above-mentioned Substituent Group A. The number of the substituents is, for example, 1 to 3. When the number of the substituents is 2 or more, the respective substituents may be the same or different.

The "$C_{7-16}$ aralkyl group" of the above-mentioned "optionally substituted $C_{7-16}$ aralkyl group" is optionally substituted, for example, by substituent(s) selected from the above-mentioned Substituent Group A. The number of the substituents is, for example, 1 to 3. When the number of the substituents is 2 or more, the respective substituents may be the same or different.

$R^1$ is more preferably
(1) a $C_{1-6}$ alkyl group (e.g., methyl, ethyl) optionally substituted by 1 to 3 substituents selected from
  (a) a halogen atom (e.g., a fluorine atom), and
  (b) a cyano group, or
(2) a $C_{6-14}$ aryl group (e.g., phenyl) optionally substituted by 1 to 3 substituents selected from
  (a) an optionally halogenated $C_{1-6}$ alkoxy group (e.g., methoxy, 2,2,2-trifluoroethoxy), and
  (b) a halogen atom (e.g., a fluorine atom).

As another embodiment, $R^1$ is more preferably
(1) a $C_{1-6}$ alkyl group (e.g., methyl, ethyl) optionally substituted by 1 to 3 substituents selected from
  (a) a halogen atom (e.g., a fluorine atom), and
  (b) a cyano group,
(2) a $C_{6-14}$ aryl group (e.g., phenyl) optionally substituted by 1 to 3 substituents selected from
  (a) an optionally halogenated $C_{1-6}$ alkoxy group (e.g., methoxy, 2,2,2-trifluoroethoxy), and
  (b) a halogen atom (e.g., a fluorine atom), or
(3) a $C_{7-16}$ aralkyl group (e.g., benzyl) optionally substituted by 1 to 3 $C_{1-6}$ alkoxy groups (e.g., methoxy).

In this embodiment, $R^1$ is further more preferably
(1) a $C_{1-6}$ alkyl group (e.g., methyl, ethyl) optionally substituted by 1 to 3 substituents selected from
  (a) a halogen atom (e.g., a fluorine atom), and
  (b) a cyano group,
(2) a phenyl group optionally substituted by 1 to 3 substituents selected from
  (a) an optionally halogenated $C_{1-6}$ alkoxy group (e.g., methoxy, 2,2,2-trifluoroethoxy), and
  (b) a halogen atom (e.g., a fluorine atom), or
(3) a benzyl group optionally substituted by 1 to 3 $C_{1-6}$ alkoxy groups (e.g., methoxy).

$R^1$ is even more preferably
(1) a $C_{1-6}$ alkyl group (e.g., methyl, ethyl) optionally substituted by 1 to 3 substituents selected from
  (a) a halogen atom (e.g., a fluorine atom), and
  (b) a cyano group, or
(2) a phenyl group optionally substituted by 1 to 3 substituents selected from
  (a) an optionally halogenated $C_{1-6}$ alkoxy group (e.g., methoxy, 2,2,2-trifluoroethoxy), and
  (b) a halogen atom (e.g., a fluorine atom).

$R^1$ is particularly preferably
(1) a $C_{1-6}$ alkyl group (e.g., methyl) optionally substituted by 1 to 3 cyano groups, or
(2) a phenyl group optionally substituted by 1 to 3 of optionally halogenated $C_{1-6}$ alkoxy groups (e.g., methoxy, 2,2,2-trifluoroethoxy).

As to $R^2$
(1) when W is $CR^5$, $NR^6$ or N, then $R^2$ is a hydrogen atom or a substituent,
(2) when W is O or S, then $R^2$ is a substituent.

Preferably
(1) when W is $NR^6$ or N, then $R^2$ is a hydrogen atom, a halogen atom (e.g., a chlorine atom, a bromine atom), an optionally substituted $C_{1-6}$ alkyl group (e.g., methyl, ethyl), an optionally substituted $C_{3-10}$ cycloalkyl group (e.g., cyclopropyl) or an optionally substituted $C_{6-14}$ aryl group (e.g., phenyl), (2) when W is O or S, then $R^2$ is an optionally substituted $C_{1-6}$ alkyl group (e.g., methyl).

The "$C_{1-6}$ alkyl group" of the above-mentioned "optionally substituted $C_{1-6}$ alkyl group" is optionally substituted, for example, by substituent(s) selected from the above-mentioned Substituent Group A. The number of the substituents is, for example, 1 to 3. When the number of the substituents is 2 or more, the respective substituents may be the same or different.

The "$C_{3-10}$ cycloalkyl group" of the above-mentioned "optionally substituted $C_{3-10}$ cycloalkyl group" is optionally substituted, for example, by substituent(s) selected from the above-mentioned Substituent Group A. The number of the substituents is, for example, 1 to 3. When the number of the substituents is 2 or more, the respective substituents may be the same or different.

The "$C_{6-14}$ aryl group" of the above-mentioned "optionally substituted $C_{6-14}$ aryl group" is optionally substituted, for example, by substituent(s) selected from the above-mentioned Substituent Group A. The number of the substituents is, for example, 1 to 3. When the number of the substituents is 2 or more, the respective substituents may be the same or different.

More preferably
(1) when W is $NR^6$ or N, then $R^2$ is a hydrogen atom, a halogen atom (e.g., a chlorine atom, a bromine atom), a $C_{1-6}$ alkyl group (e.g., methyl, ethyl), a $C_{3-10}$ cycloalkyl group (e.g., cyclopropyl) or a $C_{6-14}$ aryl group (e.g., phenyl),
(2) when W is O or S, then $R^2$ is a $C_{1-6}$ alkyl group (e.g., methyl).

Further more preferably
(1) when W is $NR^6$ or N, then $R^2$ is a hydrogen atom, a halogen atom (e.g., a chlorine atom, a bromine atom), a $C_{1-6}$ alkyl group (e.g., methyl, ethyl), a $C_{3-6}$ cycloalkyl group (e.g., cyclopropyl) or a phenyl group,
(2) when W is O or S, then $R^2$ is a $C_{1-6}$ alkyl group (e.g., methyl).

Even more preferably, (1) when W is $NR^6$ or N, then $R^2$ is a hydrogen atom or a $C_{1-6}$ alkyl group (e.g., methyl).

$R^3$ and $R^4$ are each independently a hydrogen atom or a substituent, or $R^3$ and $R^4$ are bonded to each other to form, together with the adjacent nitrogen atom, an optionally further substituted nitrogen-containing heterocycle.

The "nitrogen-containing heterocycle" of the "optionally further substituted nitrogen-containing heterocycle" formed by $R^3$ and $R^4$ bonded to each other, together with the adjacent nitrogen atom, may be a bridged ring, and specific examples thereof include a 6- to 9-membered nitrogen-containing bridged ring such as 3-azabicyclo[3.1.0]hexane, 3-azabicyclo[4.1.0]heptane and the like, and the like.

The "nitrogen-containing heterocycle" of the "optionally further substituted nitrogen-containing heterocycle" formed by $R^3$ and $R^4$ bonded to each other, together with the adjacent nitrogen atom, may be a spiro ring, and specific examples thereof include a 6- to 9-membered nitrogen-containing spiro ring such as 1-azaspiro[3.3]heptane, 6-oxa-1-azaspiro[3.5]nonane, 6-oxa-1-azaspiro[3.3]heptane, 6-oxa-1-azaspiro[3.4]octane and the like, and the like.

The "nitrogen-containing heterocycle" of the "optionally further substituted nitrogen-containing heterocycle" formed by $R^3$ and $R^4$ bonded to each other, together with the adjacent nitrogen atom, is optionally substituted, for example, by substituent(s) selected from the above-mentioned Substituent Group A. The number of the substituents is, for example, 1 to 3. When the number of the substituents is 2 or more, the respective substituents may be the same or different. In addition, the Substituent Group A is an optionally further substituted by substituent(s) selected from the above-mentioned Substituent Group A. The number of the substituents is, for example, 1 to 3. When the number of the substituents is 2 or more, the respective substituents may be the same or different.

The "nitrogen-containing heterocycle" of the "optionally further substituted nitrogen-containing heterocycle" formed by $R^3$ and $R^4$ bonded to each other, together with the adjacent nitrogen atom, is preferably a 3- to 8-membered monocyclic non-aromatic nitrogen-containing heterocycle (e.g., azetidine, pyrrolidine, piperidine), a 9- to 14-membered fused polycyclic (preferably bi- or tri-cyclic) non-aromatic nitrogen-containing heterocycle (e.g., indoline, isoindoline, tetrahydroquinoline, tetrahydroisoquinoline), a 6- to 9-membered nitrogen-containing bridged ring (e.g., 3-azabicyclo[3.1.0]hexane, 3-azabicyclo[4.1.0]heptane), or a 6- to 9-membered nitrogen-containing spiro ring (e.g., 1-azaspiro[3.3]heptane, 6-oxa-1-azaspiro[3.5]nonane, 6-oxa-1-azaspiro[3.3]heptane, 6-oxa-1-azaspiro[3.4]octane).

$R^3$ and $R^4$ are preferably each independently
(1) a hydrogen atom,
(2) an optionally substituted $C_{1-6}$ alkyl group (e.g., methyl, isopropyl, tert-butyl),
(3) a $C_{3-10}$ cycloalkyl group optionally fused with a benzene ring (the $C_{3-10}$ cycloalkyl may be a bridged ring group, e.g., cyclopropyl, cyclobutyl, cyclopentyl, cyclohexyl, bicyclo[1.1.1]pentyl (e.g., bicyclo[1.1.1]pentan-1-yl), indanyl (e.g., indan-1-yl), tetrahydronaphthyl (e.g., 1,2,3,4-tetrahydronaphthalen-2-yl), dihydrobenzocyclobutenyl (e.g., dihydrobenzocyclobuten-1-yl)), which is optionally substituted,
(4) an optionally substituted $C_{6-14}$ aryl group (e.g., phenyl),
(5) an optionally substituted 5- to 14-membered aromatic heterocyclic group (preferably a 5- to 6-membered monocyclic aromatic heterocyclic group (e.g., pyrazolyl, imidazolyl, pyridyl)), or
(6) an optionally substituted 3- to 14-membered non-aromatic heterocyclic group (preferably a 3- to 8-membered monocyclic non-aromatic heterocyclic group (e.g., pyrrolidinyl, piperidyl, tetrahydrofuryl), or a 9- to 14-membered fused polycyclic (preferably bi- or tri-cyclic) non-aromatic heterocyclic group (e.g., dihydrochromenyl (e.g., 3,4-dihydro-2H-chromen-4-yl))), or $R^3$ and $R^4$ are bonded to each other to form, together with the adjacent nitrogen atom, an optionally further substituted 3- to 14-membered non-aromatic nitrogen-containing heterocycle (preferably a 3- to 8-membered monocyclic non-aromatic nitrogen-containing heterocycle (e.g., azetidine, pyrrolidine, piperidine), a 9- to 14-membered fused polycyclic (preferably bi- or tri-cyclic) non-aromatic nitrogen-containing heterocycle (e.g., indoline, isoindoline, tetrahydroquinoline, tetrahydroisoquinoline), a 6- to 9-membered nitrogen-containing bridged ring (e.g., 3-azabicyclo[3.1.0]hexane, 3-azabicyclo[4.1.0]heptane), or a 6- to 9-membered nitrogen-containing spiro ring (e.g., 1-azaspiro[3.3]heptane, 6-oxa-1-azaspiro[3.5]nonane, 6-oxa-1-azaspiro[3.3]heptane, 6-oxa-1-azaspiro[3.4]octane)).

The "$C_{1-6}$ alkyl group" of the above-mentioned "optionally substituted $C_{1-6}$ alkyl group" is optionally substituted, for example, by substituent(s) selected from the above-mentioned Substituent Group A. The number of the substituents is, for example, 1 to 3. When the number of the substituents is 2 or more, the respective substituents may be the same or different. In addition, the Substituent Group A is an optionally further substituted by substituent(s) selected from the above-mentioned Substituent Group A. The number of the substituents is, for example, 1 to 3. When the number of the substituents is 2 or more, the respective substituents may be the same or different.

The "$C_{3-10}$ cycloalkyl group" of the above-mentioned "optionally substituted $C_{3-10}$ cycloalkyl group" may be fused with a benzene ring. Specific examples thereof include indanyl (e.g., indan-1-yl), tetrahydronaphthyl (e.g., 1,2,3,4-tetrahydronaphthalen-2-yl), dihydrobenzocyclobutenyl (e.g., dihydrobenzocyclobuten-1-yl) and the like.

"$C_{3-10}$ cycloalkyl group" of the above-mentioned "optionally substituted $C_{3-10}$ cycloalkyl group" may be a bridged ring group. Specific examples thereof include bicyclo[1.1.1]pentyl (e.g., bicyclo[1.1.1]pentan-1-yl) and the like.

The "$C_{3-10}$ cycloalkyl group" of the above-mentioned "optionally substituted $C_{3-10}$ cycloalkyl group" is optionally substituted, for example, by substituent(s) selected from the above-mentioned Substituent Group A. The number of the substituents is, for example, 1 to 3. When the number of the substituents is 2 or more, the respective substituents may be the same or different. In addition, the Substituent Group A is an optionally further substituted by substituent(s) selected from the above-mentioned Substituent Group A. The number of the substituents is, for example, 1 to 3. When the number of the substituents is 2 or more, the respective substituents may be the same or different.

"$C_{6-14}$ aryl group" of the above-mentioned "optionally substituted $C_{6-14}$ aryl group" is optionally substituted, for example, by substituent(s) selected from the above-mentioned Substituent Group A. The number of the substituents is, for example, 1 to 3. When the number of the substituents is 2 or more, the respective substituents may be the same or different. In addition, the Substituent Group A is an optionally further substituted by substituent(s) selected from the above-mentioned Substituent Group A. The number of the substituents is, for example, 1 to 3. When the number of the substituents is 2 or more, the respective substituents may be the same or different.

$R^3$ and $R^4$ are more preferably each independently
(1) a hydrogen atom,
(2) a $C_{1-6}$ alkyl group (e.g., methyl, isopropyl, tert-butyl) optionally substituted by 1 to 3 substituents selected from
  (a) a halogen atom (e.g., a fluorine atom),
  (b) a cyano group,
  (c) a $C_{3-10}$ cycloalkyl group (e.g., cyclopropyl, cyclohexyl),
  (d) a $C_{6-14}$ aryl group (e.g., phenyl) optionally substituted by 1 to 3 halogen atoms (e.g., a chlorine atom), and
  (e) a 5- to 14-membered aromatic heterocyclic group (preferably a 5- to 6-membered monocyclic aromatic heterocyclic group (e.g., pyridyl, pyrazolyl, triazolyl, oxadiazolyl, thiazolyl, thienyl)) optionally substituted by 1 to 3 substituents selected from
    (i) a $C_{1-6}$ alkyl group (e.g., methyl),
    (ii) a $C_{1-6}$ alkoxy group (e.g., methoxy), and
    (iii) a $C_{6-14}$ aryl group (e.g., phenyl) optionally substituted by 1 to 3 substituents selected from a halogen atom (e.g., a chlorine atom) and a $C_{1-6}$ alkyl group (e.g., methyl),
(3) a $C_{3-10}$ cycloalkyl group optionally fused with a benzene ring (the $C_{3-10}$ cycloalkyl may be a bridged ring group, e.g., cyclopropyl, cyclobutyl, cyclopentyl, cyclohexyl, bicyclo[1.1.1]pentyl (e.g., bicyclo[1.1.1]pentan-1-yl), indanyl (e.g., indan-1-yl), tetrahydronaphthyl (e.g., 1,2,3,4-tetrahydronaphthalen-2-yl), dihydrobenzocyclobutenyl (e.g., dihydrobenzocyclobuten-1-yl)), which is optionally substituted by 1 to 3 substituents selected from
  (a) a halogen atom (e.g., a fluorine atom, a chlorine atom),
  (b) a cyano group,
  (c) an optionally halogenated $C_{1-6}$ alkyl group (e.g., trifluoromethyl),
  (d) a $C_{1-6}$ alkoxy group (e.g., methoxy, propoxy, butoxy),
  (e) a $C_{1-6}$ alkoxy-carbonylamino group (e.g., tert-butoxycarbonylamino),
  (f) a $C_{6-14}$ aryl group (e.g., phenyl) optionally substituted by 1 to 3 halogen atoms (e.g., a chlorine atom),
  (g) a $C_{6-14}$ aryloxy group (e.g., phenoxy),
  (h) a $C_{7-16}$ aralkyloxy group (e.g., benzyloxy), and
  (i) a 5- to 14-membered aromatic heterocyclic group (preferably a 5- to 6-membered monocyclic aromatic heterocyclic group (e.g., pyridyl)),
(4) a $C_{6-14}$ aryl group (e.g., phenyl) optionally substituted by 1 to 3 substituents selected from
  (a) a $C_{1-6}$ alkyl group (e.g., ethyl),
  (b) a $C_{1-6}$ alkoxy group (e.g., methoxy, ethoxy),
  (c) a $C_{6-14}$ aryloxy group (e.g., phenoxy),
  (d) a $C_{7-16}$ aralkyloxy group (e.g., benzyloxy), and
  (e) a 3- to 14-membered non-aromatic heterocyclic group (preferably a 3- to 8-membered monocyclic non-aromatic heterocyclic group (e.g., morpholinyl)),
(5) a 5- to 14-membered aromatic heterocyclic group (preferably a 5- to 6-membered monocyclic aromatic heterocyclic group (e.g., pyrazolyl, imidazolyl, pyridyl)) optionally substituted by 1 to 3 substituents selected from
  (a) a cyano group,
  (b) an optionally halogenated $C_{1-6}$ alkyl group (e.g., methyl, trifluoromethyl, 2,2,2-trifluoroethyl),
  (c) a $C_{1-6}$ alkoxy group (e.g., methoxy),
  (d) a $C_{6-14}$ aryl group (e.g., phenyl),
  (e) a $C_{6-14}$ aryloxy group (e.g., phenoxy), and
  (f) a $C_{7-16}$ aralkyl group (e.g., benzyl) optionally substituted by 1 to 3 halogen atoms (e.g., a fluorine atom), or
(6) a 3- to 14-membered non-aromatic heterocyclic group (preferably a 3- to 8-membered monocyclic non-aromatic heterocyclic group (e.g., pyrrolidinyl, piperidyl, tetrahydrofuryl), or a 9- to 14-membered fused polycyclic (preferably bi- or tri-cyclic) non-aromatic heterocyclic group (e.g., dihydrochromenyl (e.g., 3,4-dihydro-2H-chromen-4-yl))) optionally substituted by 1 to 3 substituents selected from
  (a) a $C_{1-6}$ alkyl group (e.g., methyl) optionally substituted by 1 to 3 $C_{3-10}$ cycloalkyl groups (e.g., cyclopropyl),
  (b) a $C_{1-6}$ alkoxy-carbonyl group (e.g., tert-butoxycarbonyl),
  (c) a $C_{6-14}$ aryl group (e.g., phenyl) optionally substituted by 1 to 3 halogen atoms (e.g., a fluorine atom, a chlorine atom), and
  (d) a $C_{7-16}$ aralkyl group (e.g., benzyl), or $R^3$ and $R^4$ are bonded to each other to form, together with the adjacent nitrogen atom, a 3- to 14-membered non-aromatic nitrogen-containing heterocycle (preferably a 3- to 8-membered monocyclic non-aromatic nitrogen-containing heterocycle (e.g., azetidine, pyrrolidine, piperidine), a 9- to 14-membered fused polycyclic (preferably bi- or tri-cyclic) non-aromatic nitrogen-containing heterocycle (e.g., indoline, isoindoline, tetrahydroquinoline, tetrahydroisoquinoline), a 6- to 9-membered nitrogen-containing bridged ring (e.g., 3-azabicyclo[3.1.0]hexane, 3-azabicyclo[4.1.0]heptane), or a 6- to 9-membered nitrogen-containing spiro ring (e.g., 1-azaspiro[3.3]heptane, 6-oxa-1-azaspiro[3.5]nonane, 6-oxa-1-azaspiro[3.3]heptane, 6-oxa-1-azaspiro[3.4]octane)) optionally further substituted by 1 to 3 substituents selected from (a) a halogen atom (e.g., a fluorine atom, a chlorine atom, a bromine atom),
(b) a $C_{1-6}$ alkyl group (e.g., methyl, isopropyl) optionally substituted by 1 to 3 substituents selected from
  (i) a halogen atom (e.g., a fluorine atom),
  (ii) a cyano group,
  (iii) a $C_{1-6}$ alkoxy group (e.g., methoxy), and
  (iv) a mono- or di-$C_{1-6}$ alkylamino group (e.g., dimethylamino),
(c) a $C_{1-6}$ alkoxy group (e.g., methoxy, ethoxy) optionally substituted by 1 to 3 substituents selected from
  (i) a halogen atom (e.g., a fluorine atom), and
  (ii) a $C_{3-10}$ cycloalkyl group (e.g., cyclopropyl),
(d) a $C_{3-10}$ cycloalkyl group (e.g., cyclopropyl),
(e) a $C_{6-14}$ aryl group (e.g., phenyl, naphthyl) optionally substituted by 1 to 3 substituents selected from
  (i) a halogen atom (e.g., a fluorine atom, a chlorine atom, a bromine atom),
  (ii) an optionally halogenated $C_{1-6}$ alkyl group (e.g., methyl, trifluoromethyl), and
  (iii) an optionally halogenated $C_{1-6}$ alkoxy group (e.g., methoxy, trifluoromethoxy),
(f) a $C_{6-14}$ aryloxy group (e.g., phenoxy) optionally substituted by 1 to 3 substituents selected from
  (i) a halogen atom (e.g., a fluorine atom, a chlorine atom),
  (ii) a cyano group,
  (iii) an optionally halogenated $C_{1-6}$ alkyl group (e.g., methyl, trifluoromethyl), and
  (iv) an optionally halogenated $C_{1-6}$ alkoxy group (e.g., methoxy, trifluoromethoxy),
(g) a $C_{7-16}$ aralkyl group (e.g., benzyl),
(h) a $C_{7-16}$ aralkyloxy group (e.g., benzyloxy),
(i) a 5- to 14-membered aromatic heterocyclic group (preferably a 5- to 6-membered monocyclic aromatic heterocyclic group (e.g., thienyl)),
(j) a 5- to 14-membered aromatic heterocyclyloxy group (preferably a 5- to 6-membered monocyclic aromatic heterocyclyloxy group (e.g., pyridyloxy, pyrazinyloxy, pyrimidinyloxy, thiazolyloxy)), and
(k) a 3- to 14-membered non-aromatic heterocyclyloxy group (preferably a 3- to 8-membered monocyclic non-aromatic heterocyclyloxy group (e.g., piperidyloxy)) optionally substituted by 1 to 3 $C_{1-6}$ alkoxy-carbonyl groups (e.g., tert-butoxycarbonyl).

$R^3$ and $R^4$ are further more preferably each independently
(1) a hydrogen atom,
(2) a $C_{1-6}$ alkyl group (e.g., methyl, isopropyl, tert-butyl) optionally substituted by 1 to 3 substituents selected from
  (a) a halogen atom (e.g., a fluorine atom),
  (b) a cyano group,
  (c) a $C_{3-10}$ cycloalkyl group (e.g., cyclopropyl, cyclohexyl),
  (d) a $C_{6-14}$ aryl group (e.g., phenyl) optionally substituted by 1 to 3 halogen atoms (e.g., a chlorine atom), and
  (e) a 5- to 14-membered aromatic heterocyclic group (preferably a 5- to 6-membered monocyclic aromatic heterocyclic group (e.g., pyridyl, pyrazolyl, triazolyl, oxadiazolyl, thiazolyl, thienyl)) optionally substituted by 1 to 3 substituents selected from
    (i) a $C_{1-6}$ alkyl group (e.g., methyl),
    (ii) a $C_{1-6}$ alkoxy group (e.g., methoxy), and
    (iii) a $C_{6-14}$ aryl group (e.g., phenyl) optionally substituted by 1 to 3 substituents selected from a halogen atom (e.g., a chlorine atom) and a $C_{1-6}$ alkyl group (e.g., methyl),
(3) a $C_{3-6}$ cycloalkyl group (e.g., cyclopropyl, cyclobutyl, cyclopentyl, cyclohexyl) optionally substituted by 1 to 3 substituents selected from
  (a) a halogen atom (e.g., a fluorine atom),
  (b) a cyano group,
  (c) an optionally halogenated $C_{1-6}$ alkyl group (e.g., trifluoromethyl),
  (d) a $C_{1-6}$ alkoxy group (e.g., methoxy, propoxy, butoxy),
  (e) a $C_{1-6}$ alkoxy-carbonylamino group (e.g., tert-butoxycarbonylamino),
  (f) a $C_{6-14}$ aryl group (e.g., phenyl) optionally substituted by 1 to 3 halogen atoms (e.g., a chlorine atom),
  (g) a $C_{6-14}$ aryloxy group (e.g., phenoxy),
  (h) a $C_{7-16}$ aralkyloxy group (e.g., benzyloxy), and
  (i) a 5- to 14-membered aromatic heterocyclic group (preferably a 5- to 6-membered monocyclic aromatic heterocyclic group (e.g., pyridyl)),
(4) a bicyclo[1.1.1]pentyl group (e.g., bicyclo[1.1.1]pentan-1-yl) optionally substituted by 1 to 3 substituents selected from
  (a) an optionally halogenated $C_{1-6}$ alkyl group (e.g., trifluoromethyl), and
  (b) a $C_{6-14}$ aryl group (e.g., phenyl),
(5) an indanyl group (e.g., indan-1-yl) optionally substituted by 1 to 3 halogen atoms (e.g., a chlorine atom),
(6) a tetrahydronaphthyl group (e.g., 1,2,3,4-tetrahydronaphthalen-2-yl),
(7) a dihydrobenzocyclobutenyl group (e.g., dihydrobenzocyclobuten-1-yl,
(8) a phenyl group optionally substituted by 1 to 3 substituents selected from
  (a) a $C_{1-6}$ alkyl group (e.g., ethyl),
  (b) a $C_{1-6}$ alkoxy group (e.g., methoxy, ethoxy),
  (c) a $C_{6-14}$ aryloxy group (e.g., phenoxy),
  (d) a $C_{7-16}$ aralkyloxy group (e.g., benzyloxy), and
  (e) a 3- to 14-membered non-aromatic heterocyclic group (preferably a 3- to 8-membered monocyclic non-aromatic heterocyclic group (e.g., morpholinyl)),
(9) a pyrazolyl group optionally substituted by 1 to 3 substituents selected from
  (a) an optionally halogenated $C_{1-6}$ alkyl group (e.g., methyl, trifluoromethyl, 2,2,2-trifluoroethyl), and
  (b) a $C_{7-16}$ aralkyl group (e.g., benzyl) optionally substituted by 1 to 3 halogen atoms (e.g., a fluorine atom),
(10) an imidazolyl group optionally substituted by 1 to 3 $C_{6-14}$ aryl groups (e.g., phenyl),
(11) a pyridyl group optionally substituted by 1 to 3 substituents selected from
  (a) a cyano group,
  (b) an optionally halogenated $C_{1-6}$ alkyl group (e.g., trifluoromethyl),
  (c) a $C_{1-6}$ alkoxy group (e.g., methoxy), and
  (d) a $C_{6-14}$ aryloxy group (e.g., phenoxy),
(12) a pyrrolidinyl group optionally substituted by 1 to 3 $C_{7-16}$ aralkyl groups (e.g., benzyl),
(13) a piperidyl group optionally substituted by 1 to 3 substituents selected from
  (a) a $C_{1-6}$ alkyl group (e.g., methyl) optionally substituted by 1 to 3 $C_{3-10}$ cycloalkyl groups (e.g., cyclopropyl),
  (b) a $C_{1-6}$ alkoxy-carbonyl group (e.g., tert-butoxycarbonyl),
  (c) a $C_{6-14}$ aryl group (e.g., phenyl) optionally substituted by 1 to 3 halogen atoms (e.g., a fluorine atom, a chlorine atom), and
  (d) a $C_{7-16}$ aralkyl group (e.g., benzyl),
(14) a tetrahydrofuryl group optionally substituted by 1 to 3 $C_{6-14}$ aryl groups (e.g., phenyl), or

(15) a dihydrochromenyl group (e.g., 3,4-dihydro-2H-chromen-4-yl) optionally substituted by 1 to 3 $C_{1-6}$ alkyl groups (e.g., methyl), or $R^3$ and $R^4$ are bonded to each other to form, together with the adjacent nitrogen atom, (1) an azetidine ring optionally further substituted by 1 to 3 substituents selected from
- (a) a $C_{1-6}$ alkyl group (e.g., methyl, isopropyl) optionally substituted by 1 to 3 $C_{1-6}$ alkoxy groups (e.g., methoxy),
- (b) an optionally halogenated $C_{1-6}$ alkoxy group (e.g., methoxy, difluoromethoxy),
- (c) a $C_{3-10}$ cycloalkyl group (e.g., cyclopropyl),
- (d) a $C_{6-14}$ aryl group (e.g., phenyl) optionally substituted by 1 to 3 halogen atoms (e.g., a fluorine atom, a chlorine atom, a bromine atom),
- (e) a $C_{6-14}$ aryloxy group (e.g., phenoxy),
- (f) a $C_{7-16}$ aralkyl group (e.g., benzyl), and
- (g) a $C_{7-16}$ aralkyloxy group (e.g., benzyloxy), (2) a pyrrolidine ring optionally further substituted by 1 to 3 substituents selected from
- (a) a halogen atom (e.g., a fluorine atom),
- (b) an optionally halogenated $C_{1-6}$ alkoxy group (e.g., methoxy, trifluoromethoxy),
- (c) a $C_{6-14}$ aryl group (e.g., phenyl) optionally substituted by 1 to 3 substituents selected from
  - (i) a halogen atom (e.g., a chlorine atom),
  - (ii) an optionally halogenated $C_{1-6}$ alkyl group (e.g., trifluoromethyl), and
  - (iii) a $C_{1-6}$ alkoxy group (e.g., methoxy),
- (d) a $C_{7-16}$ aralkyl group (e.g., benzyl), and
- (e) a $C_{7-16}$ aralkyloxy group (e.g., benzyloxy), (3) a piperidine ring optionally further substituted by 1 to 3 substituents selected from
- (a) a $C_{1-6}$ alkoxy group (e.g., methoxy, ethoxy) optionally substituted by 1 to 3 substituents selected from
  - (i) a halogen atom (e.g., a fluorine atom), and
  - (ii) a $C_{3-10}$ cycloalkyl group (e.g., cyclopropyl),
- (b) a $C_{6-14}$ aryl group (e.g., phenyl) optionally substituted by 1 to 3 substituents selected from
  - (i) a halogen atom (e.g., a chlorine atom), and
  - (ii) a $C_{1-6}$ alkoxy group (e.g., methoxy),
- (c) a $C_{6-14}$ aryloxy group (e.g., phenoxy) optionally substituted by 1 to 3 substituents selected from
  - (i) a halogen atom (e.g., a fluorine atom, a chlorine atom),
  - (ii) a cyano group,
  - (iii) an optionally halogenated $C_{1-6}$ alkyl group (e.g., methyl, trifluoromethyl), and
  - (iv) an optionally halogenated $C_{1-6}$ alkoxy group (e.g., methoxy, trifluoromethoxy),
- (d) a $C_{7-16}$ aralkyl group (e.g., benzyl),
- (e) a $C_{7-16}$ aralkyloxy group (e.g., benzyloxy),
- (f) a 5- to 14-membered aromatic heterocyclyloxy group (preferably a 5- to 6-membered monocyclic aromatic heterocyclyloxy group (e.g., pyridyloxy, pyrazinyloxy, pyrimidinyloxy, thiazolyloxy)), and
- (g) a 3- to 14-membered non-aromatic heterocyclyloxy group (preferably a 3- to 8-membered monocyclic non-aromatic heterocyclyloxy group (e.g., piperidyloxy)) optionally substituted by 1 to 3 $C_{1-6}$ alkoxycarbonyl groups (e.g., tert-butoxycarbonyl), (4) an indoline ring optionally further substituted by 1 to 3 $C_{1-6}$ alkoxy groups (e.g., methoxy), (5) an isoindoline ring optionally further substituted by 1 to 3 $C_{1-6}$ alkoxy groups (e.g., methoxy), (6) a tetrahydroquinoline ring optionally further substituted by 1 to 3 $C_{1-6}$ alkoxy groups (e.g., methoxy), (7) a tetrahydroisoquinoline ring optionally further substituted by 1 to 3 substituents selected from
- (a) a halogen atom (e.g., a chlorine atom, a bromine atom),
- (b) a $C_{1-6}$ alkyl group (e.g., methyl), and
- (c) a $C_{1-6}$ alkoxy group (e.g., methoxy), (8) a 3-azabicyclo[3.1.0]hexane ring optionally further substituted by 1 to 3 substituents selected from
- (a) a halogen atom (e.g., a fluorine atom),
- (b) a $C_{1-6}$ alkyl group (e.g., methyl) optionally substituted by 1 to 3 substituents selected from
  - (i) a halogen atom (e.g., a fluorine atom),
  - (ii) a cyano group,
  - (iii) a $C_{1-6}$ alkoxy group (e.g., methoxy), and
  - (iv) a mono- or di-$C_{1-6}$ alkylamino group (e.g., dimethylamino),
- (c) a $C_{6-14}$ aryl group (e.g., phenyl, naphthyl) optionally substituted by 1 to 3 substituents selected from
  - (i) a halogen atom (e.g., a fluorine atom, a chlorine atom),
  - (ii) an optionally halogenated $C_{1-6}$ alkyl group (e.g., methyl, trifluoromethyl), and
  - (iii) an optionally halogenated $C_{1-6}$ alkoxy group (e.g., methoxy, trifluoromethoxy), and
- (d) a 5- to 14-membered aromatic heterocyclic group (preferably a 5- to 6-membered monocyclic aromatic heterocyclic group (e.g., thienyl)), (9) a 3-azabicyclo[4.1.0]heptane ring optionally further substituted by 1 to 3 substituents selected from
- (a) a halogen atom (e.g., a fluorine atom), and
- (b) a $C_{6-14}$ aryl group (e.g., phenyl) optionally substituted by 1 to 3 substituents selected from
  - (i) a halogen atom (e.g., a chlorine atom),
  - (ii) a $C_{1-6}$ alkyl group (e.g., methyl), and
  - (iii) a $C_{1-6}$ alkoxy group (e.g., methoxy),

(10) a 1-azaspiro[3.3]heptane ring,
(11) a 6-oxa-1-azaspiro[3.5]nonane ring,
(12) a 6-oxa-1-azaspiro[3.3]heptane ring, or
(13) a 6-oxa-1-azaspiro[3.4]octane ring.

$R^3$ and $R^4$ are still more preferably each independently
(1) a hydrogen atom,
(2) a $C_{1-6}$ alkyl group (e.g., methyl, isopropyl, tert-butyl) optionally substituted by 1 to 3 substituents selected from
- (a) a halogen atom (e.g., a fluorine atom),
- (b) a cyano group,
- (c) a $C_{3-6}$ cycloalkyl group (e.g., cyclopropyl, cyclohexyl),
- (d) a phenyl group optionally substituted by 1 to 3 halogen atoms (e.g., a chlorine atom),
- (e) a pyridyl group optionally substituted by 1 to 3 $C_{1-6}$ alkoxy groups (e.g., methoxy),
- (f) a pyrazolyl group optionally substituted by 1 to 3 substituents selected from
  - (i) a $C_{1-6}$ alkyl group (e.g., methyl), and
  - (ii) a phenyl group optionally substituted by 1 to 3 substituents selected from a halogen atom (e.g., a chlorine atom) and a C-s alkyl group (e.g., methyl),
- (g) a triazolyl group optionally substituted by 1 or 2 substituents selected from
  - (i) a $C_{1-6}$ alkyl group (e.g., methyl), and
  - (ii) a phenyl group,
- (h) an oxadiazolyl group optionally substituted by phenyl group(s) optionally substituted by 1 to 3 halogen atoms (e.g., a chlorine atom), (i) a thiazolyl group optionally substituted by 1 or 2 substituents selected from
   (i) a $C_{1-6}$ alkyl group (e.g., methyl), and
   (ii) a phenyl group, and
(j) a thienyl group optionally substituted by 1 to 3 phenyl groups optionally substituted by 1 to 3 halogen atoms (e.g., a chlorine atom),
(3) a $C_{3-6}$ cycloalkyl group (e.g., cyclopropyl, cyclobutyl, cyclopentyl, cyclohexyl) optionally substituted by 1 to 3 substituents selected from
   (a) a halogen atom (e.g., a fluorine atom),
   (b) a cyano group,
   (c) an optionally halogenated $C_{1-6}$ alkyl group (e.g., trifluoromethyl),
   (d) a $C_{1-6}$ alkoxy group (e.g., methoxy, propoxy, butoxy),
   (e) a $C_{1-6}$ alkoxy-carbonylamino group (e.g., tert-butoxy-carbonylamino),
   (f) a phenyl group optionally substituted by 1 to 3 halogen atoms (e.g., a chlorine atom),
   (g) a phenoxy group,
   (h) a benzyloxy group, and
   (i) a pyridyl group,
(4) a bicyclo[1.1.1]pentyl group (e.g., bicyclo[1.1.1]pentan-1-yl) optionally substituted by 1 to 3 substituents selected from
   (a) an optionally halogenated $C_{1-6}$ alkyl group (e.g., trifluoromethyl), and
   (b) a phenyl group,
(5) an indanyl group (e.g., indan-1-yl) optionally substituted by 1 to 3 halogen atoms (e.g., a chlorine atom),
(6) a tetrahydronaphthyl group (e.g., 1,2,3,4-tetrahydronaphthalen-2-yl),
(7) a dihydrobenzocyclobutenyl group (e.g., dihydrobenzocyclobuten-1-yl,
(8) a phenyl group optionally substituted by 1 to 3 substituents selected from
   (a) a $C_{1-6}$ alkyl group (e.g., ethyl),
   (b) a $C_{1-6}$ alkoxy group (e.g., methoxy, ethoxy),
   (c) a phenoxy group,
   (d) a benzyloxy group, and
   (e) a morpholinyl group,
(9) a pyrazolyl group optionally substituted by 1 to 3 substituents selected from
   (a) an optionally halogenated $C_{1-6}$ alkyl group (e.g., methyl, trifluoromethyl, 2,2,2-trifluoroethyl), and
   (b) a benzyl group optionally substituted by 1 to 3 halogen atoms (e.g., a fluorine atom),
(10) an imidazolyl group optionally substituted by 1 to 3 phenyl groups,
(11) a pyridyl group optionally substituted by 1 to 3 substituents selected from
   (a) a cyano group,
   (b) an optionally halogenated $C_{1-6}$ alkyl group (e.g., trifluoromethyl),
   (c) a $C_{1-6}$ alkoxy group (e.g., methoxy), and
   (d) a phenoxy group,
(12) a pyrrolidinyl group optionally substituted by 1 to 3 so benzyl groups,
(13) a piperidyl group optionally substituted by 1 to 3 substituents selected from
   (a) a $C_{1-6}$ alkyl group (e.g., methyl) optionally substituted by 1 to 3 $C_{3-6}$ cycloalkyl groups (e.g., cyclopropyl),
   (b) a $C_{1-6}$ alkoxy-carbonyl group (e.g., tert-butoxycarbonyl),
   (c) a phenyl group optionally substituted by 1 to 3 halogen atoms (e.g., a fluorine atom, a chlorine atom), and
   (d) a benzyl group,
(14) a tetrahydrofuryl group optionally substituted by 1 to 3 phenyl groups, or
(15) a dihydrochromenyl group (e.g., 3,4-dihydro-2H-chromen-4-yl) optionally substituted by 1 to 3 $C_{1-6}$ alkyl groups (e.g., methyl), or $R^3$ and $R^4$ are bonded to each other to form, together with the adjacent nitrogen atom,
(1) an azetidine ring optionally further substituted by 1 to 3 substituents selected from
   (a) a $C_{1-6}$ alkyl group (e.g., methyl, isopropyl) optionally substituted by 1 to 3 $C_{1-6}$ alkoxy groups (e.g., methoxy),
   (b) an optionally halogenated $C_{1-6}$ alkoxy group (e.g., methoxy, difluoromethoxy),
   (c) a $C_{3-6}$ cycloalkyl group (e.g., cyclopropyl),
   (d) a phenyl group optionally substituted by 1 to 3 halogen atoms (e.g., a fluorine atom, a chlorine atom, a bromine atom),
   (e) a phenoxy group,
   (f) a benzyl group, and
   (g) a benzyloxy group,
(2) a pyrrolidine ring optionally further substituted by 1 to 3 substituents selected from
   (a) a halogen atom (e.g., a fluorine atom),
   (b) an optionally halogenated $C_{1-6}$ alkoxy group (e.g., methoxy, trifluoromethoxy),
   (c) a phenyl group optionally substituted by 1 to 3 substituents selected from
      (i) a halogen atom (e.g., a chlorine atom),
      (ii) an optionally halogenated $C_{1-6}$ alkyl group (e.g., trifluoromethyl), and
      (iii) a $C_{1-6}$ alkoxy group (e.g., methoxy),
   (d) a benzyl group, and
   (e) a benzyloxy group,
(3) a piperidine ring optionally further substituted by 1 to 3 substituents selected from
   (a) a $C_{1-6}$ alkoxy group (e.g., methoxy, ethoxy) optionally substituted by 1 to 3 substituents selected from
      (i) a halogen atom (e.g., a fluorine atom), and
      (ii) a $C_{3-6}$ cycloalkyl group (e.g., cyclopropyl),
   (b) a phenyl group optionally substituted by 1 to 3 substituents selected from
      (i) a halogen atom (e.g., a chlorine atom), and
      (ii) a $C_{1-6}$ alkoxy group (e.g., methoxy),
   (c) a phenoxy group optionally substituted by 1 to 3 substituents selected from
      (i) a halogen atom (e.g., a fluorine atom, a chlorine atom),
      (ii) a cyano group,
      (iii) an optionally halogenated $C_{1-6}$ alkyl group (e.g., methyl, trifluoromethyl), and
      (iv) an optionally halogenated $C_{1-6}$ alkoxy group (e.g., methoxy, trifluoromethoxy),
   (d) a benzyl group,
   (e) a benzyloxy group,
   (f) a pyridyloxy group,
   (g) a pyrazinyloxy group,
   (h) a pyrimidinyloxy group,
   (i) a thiazolyloxy group, and
   (j) a piperidyloxy group optionally substituted by 1 to 3 $C_{1-6}$ alkoxy-carbonyl groups (e.g., tert-butoxycarbonyl),
(4) an indoline ring optionally further substituted by 1 to 3 $C_{1-6}$ alkoxy groups (e.g., methoxy),
(5) an isoindoline ring optionally further substituted by 1 to 3 $C_{1-6}$ alkoxy groups (e.g., methoxy), (6) a tetrahydroquinoline ring optionally further substituted by 1 to 3 $C_{1-6}$ alkoxy groups (e.g., methoxy),
(7) a tetrahydroisoquinoline ring optionally further substituted by 1 to 3 substituents selected from
  (a) a halogen atom (e.g., a chlorine atom, a bromine atom),
  (b) a $C_{1-6}$ alkyl group (e.g., methyl), and
  (c) a $C_{1-6}$ alkoxy group (e.g., methoxy),
(8) a 3-azabicyclo[3.1.0]hexane ring optionally further substituted by 1 to 3 substituents selected from
  (a) a halogen atom (e.g., a fluorine atom),
  (b) a $C_{1-6}$ alkyl group (e.g., methyl) optionally substituted by 1 to 3 substituents selected from
    (i) a halogen atom (e.g., a fluorine atom),
    (ii) a cyano group,
    (iii) a $C_{1-6}$ alkoxy group (e.g., methoxy), and
    (iv) a mono- or di-$C_{1-6}$ alkylamino group (e.g., dimethylamino),
  (c) a phenyl group optionally substituted by 1 to 3 substituents selected from
    (i) a halogen atom (e.g., a fluorine atom, a chlorine atom),
    (ii) an optionally halogenated $C_{1-6}$ alkyl group (e.g., methyl, trifluoromethyl), and
    (iii) an optionally halogenated $C_{1-6}$ alkoxy group (e.g., methoxy, trifluoromethoxy),
  (d) a naphthyl group, and
  (e) a thienyl group,
(9) a 3-azabicyclo[4.1.0]heptane ring optionally further substituted by 1 to 3 substituents selected from
  (a) a halogen atom (e.g., a fluorine atom), and
  (b) a phenyl group optionally substituted by 1 to 3 substituents selected from
    (i) a halogen atom (e.g., a chlorine atom),
    (ii) a $C_{1-6}$ alkyl group (e.g., methyl), and
    (iii) a $C_{1-6}$ alkoxy group (e.g., methoxy),
(10) a 1-azaspiro[3.3]heptane ring,
(11) a 6-oxa-1-azaspiro[3.5]nonane ring,
(12) a 6-oxa-1-azaspiro[3.3]heptane ring, or
(13) a 6-oxa-1-azaspiro[3.4]octane ring.

Even more preferably, $R^3$ is a hydrogen atom, and $R^4$ is
(1) a $C_{1-6}$ alkyl group (e.g., methyl, isopropyl) optionally substituted by 1 to 3 substituents selected from
  (a) a phenyl group optionally substituted by 1 to 3 halogen atoms (e.g., a chlorine atom),
  (b) an oxadiazolyl group optionally substituted by phenyl group(s) optionally substituted by 1 to 3 halogen atoms (e.g., a chlorine atom), and
  (c) a thienyl group optionally substituted by 1 to 3 phenyl groups optionally substituted by 1 to 3 halogen atoms (e.g., a chlorine atom),
(2) a $C_{3-6}$ cycloalkyl group (e.g., cyclobutyl, cyclopentyl, cyclohexyl) optionally substituted by 1 to 3 substituents selected from
  (a) a $C_{1-6}$ alkoxy group (e.g., butoxy), and
  (b) a phenyl group optionally substituted by 1 to 3 halogen atoms (e.g., a chlorine atom),
(3) a phenyl group optionally substituted by 1 to 3 substituents selected from
  (a) a benzyloxy group, and
  (b) a morpholinyl group, or
(4) a pyridyl group optionally substituted by 1 to 3 substituents selected from
  (a) a cyano group, and
  (b) a $C_{1-6}$ alkoxy group (e.g., methoxy), or $R^3$ and $R^4$ are bonded to each other to form, together with the adjacent nitrogen atom,
(1) an azetidine ring optionally further substituted by 1 to 3 phenyl groups,
(2) a pyrrolidine ring optionally further substituted by 1 to 3 substituents selected from
  (a) a halogen atom (e.g., a fluorine atom), and
  (b) a phenyl group optionally substituted by 1 to 3 halogen atoms (e.g., a chlorine atom),
(3) a piperidine ring optionally further substituted by 1 to 3 substituents selected from
  (a) a phenyl group optionally substituted by 1 to 3 halogen atoms (e.g., a chlorine atom), and
  (b) a phenoxy group optionally substituted by 1 to 3 substituents selected from
    (i) a halogen atom (e.g., a chlorine atom),
    (ii) an optionally halogenated $C_{1-6}$ alkyl group (e.g., trifluoromethyl), and
    (iii) an optionally halogenated $C_{1-6}$ alkoxy group (e.g., trifluoromethoxy), or
(4) a 3-azabicyclo[3.1.0]hexane ring optionally further substituted by 1 to 3 substituents selected from
  (a) a halogen atom (e.g., a fluorine atom),
  (b) a phenyl group optionally substituted by 1 to 3 substituents selected from
    (i) a halogen atom (e.g., a fluorine atom, a chlorine atom),
    (ii) an optionally halogenated $C_{1-6}$ alkyl group (e.g., methyl, trifluoromethyl), and
    (iii) an optionally halogenated $C_{1-6}$ alkoxy group (e.g., methoxy, trifluoromethoxy), and
  (c) a naphthyl group.

Particularly preferably, $R^3$ is a hydrogen atom, and $R^4$ is
(1) a $C_{3-6}$ cycloalkyl group (e.g., cyclohexyl) optionally substituted by 1 to 3 $C_{1-6}$ alkoxy groups (e.g., butoxy), or
(2) a phenyl group optionally substituted by 1 to 3 morpholinyl groups.

As another embodiment, $R^3$ and $R^4$ are more preferably each independently
(1) a hydrogen atom,
(2) a $C_{1-6}$ alkyl group (e.g., methyl, isopropyl, tert-butyl) optionally substituted by 1 to 3 substituents selected from
  (a) a halogen atom (e.g., a fluorine atom),
  (b) a cyano group,
  (c) a $C_{3-10}$ cycloalkyl group (e.g., cyclopropyl, cyclohexyl),
  (d) a $C_{6-14}$ aryl group (e.g., phenyl) optionally substituted by 1 to 3 halogen atoms (e.g., a chlorine atom), and
  (e) a 5- to 14-membered aromatic heterocyclic group (preferably a 5- to 6-membered monocyclic aromatic heterocyclic group (e.g., pyridyl, pyrazolyl, triazolyl, oxadiazolyl, thiazolyl, thienyl)) optionally substituted by 1 to 3 substituents selected from
    (i) a $C_{1-6}$ alkyl group (e.g., methyl),
    (ii) a $C_{1-6}$ alkoxy group (e.g., methoxy), and
    (iii) a $C_{6-14}$ aryl group (e.g., phenyl) optionally substituted by 1 to 3 substituents selected from a halogen atom (e.g., a chlorine atom) and a $C_{1-6}$ alkyl group (e.g., methyl),
(3) a $C_{3-10}$ cycloalkyl group optionally fused with a benzene ring (the $C_{3-10}$ cycloalkyl may be a bridged ring group, e.g., cyclopropyl, cyclobutyl, cyclopentyl, cyclohexyl, bicyclo[1.1.1]pentyl (e.g., bicyclo[1.1.1]pentan-1-yl), indanyl (e.g., indan-1-yl), tetrahydronaphthyl (e.g., 1,2,3,4-tetrahydronaphthalen-2-yl), dihydrobenzocyclobutenyl (e.g., dihydrobenzocyclobuten-1-yl)), which is optionally substituted by 1 to 3 substituents selected from
  (a) a halogen atom (e.g., a fluorine atom, a chlorine atom),
  (b) a cyano group, (c) an optionally halogenated $C_{1-6}$ alkyl group (e.g., trifluoromethyl),
(d) a $C_{1-6}$ alkoxy group (e.g., methoxy, propoxy, butoxy),
(e) a $C_{1-6}$ alkoxy-carbonylamino group (e.g., tert-butoxycarbonylamino),
(f) a $C_{6-14}$ aryl group (e.g., phenyl) optionally substituted by 1 to 3 halogen atoms (e.g., a chlorine atom),
(g) a $C_{6-14}$ aryloxy group (e.g., phenoxy),
(h) a $C_{7-16}$ aralkyloxy group (e.g., benzyloxy), and
(i) a 5- to 14-membered aromatic heterocyclic group (preferably a 5- to 6-membered monocyclic aromatic heterocyclic group (e.g., pyridyl)), (4) a $C_{6-14}$ aryl group (e.g., phenyl) optionally substituted by 1 to 3 substituents selected from
(a) a $C_{1-6}$ alkyl group (e.g., ethyl, isopropyl) optionally substituted by 1 to 3 hydroxy groups,
(b) a $C_{1-6}$ alkoxy group (e.g., methoxy, ethoxy),
(c) a $C_{6-14}$ aryloxy group (e.g., phenoxy),
(d) a $C_{7-16}$ aralkyloxy group (e.g., benzyloxy), and
(e) a 3- to 14-membered non-aromatic heterocyclic group (preferably a 3- to 8-membered monocyclic non-aromatic heterocyclic group (e.g., morpholinyl)), (5) a 5- to 14-membered aromatic heterocyclic group (preferably a 5- to 6-membered monocyclic aromatic heterocyclic group (e.g., pyrazolyl, imidazolyl, pyridyl)) optionally substituted by 1 to 3 substituents selected from
(a) a cyano group,
(b) an optionally halogenated $C_{1-6}$ alkyl group (e.g., methyl, trifluoromethyl, 2,2,2-trifluoroethyl),
(c) an optionally halogenated $C_{1-6}$ alkoxy group (e.g., methoxy, difluoromethoxy, 2,2,2-trifluoroethoxy),
(d) a $C_{6-14}$ aryl group (e.g., phenyl),
(e) a $C_{6-14}$ aryloxy group (e.g., phenoxy),
(f) a $C_{7-16}$ aralkyl group (e.g., benzyl) optionally substituted by 1 to 3 halogen atoms (e.g., a fluorine atom), and
(g) a $C_{3-10}$ cycloalkyl group (e.g., cyclopropyl), or (6) a 3- to 14-membered non-aromatic heterocyclic group (preferably a 3- to 8-membered monocyclic non-aromatic heterocyclic group (e.g., pyrrolidinyl, piperidyl, tetrahydrofuryl), or a 9- to 14-membered fused polycyclic (preferably bi- or tri-cyclic) non-aromatic heterocyclic group (e.g., dihydrochromenyl (e.g., 3,4-dihydro-2H-chromen-4-yl))) optionally substituted by 1 to 3 substituents selected from
(a) a $C_{1-6}$ alkyl group (e.g., methyl) optionally substituted by 1 to 3 $C_{3-10}$ cycloalkyl groups (e.g., cyclopropyl),
(b) a $C_{1-6}$ alkoxy-carbonyl group (e.g., tert-butoxycarbonyl),
(c) a $C_{6-14}$ aryl group (e.g., phenyl) optionally substituted by 1 to 3 halogen atoms (e.g., a fluorine atom, a chlorine atom), and
(d) a $C_{7-16}$ aralkyl group (e.g., benzyl), or $R^3$ and $R^4$ are bonded to each other to form, together with the adjacent nitrogen atom, a 3- to 14-membered non-aromatic nitrogen-containing heterocycle (preferably a 3- to 8-membered monocyclic non-aromatic nitrogen-containing heterocycle (e.g., azetidine, pyrrolidine, piperidine), a 9- to 14-membered fused polycyclic (preferably bi- or tri-cyclic) non-aromatic nitrogen-containing heterocycle (e.g., indoline, isoindoline, tetrahydroquinoline, tetrahydroisoquinoline), a 6- to 9-membered nitrogen-containing bridged ring (e.g., 3-azabicyclo[3.1.0]hexane, 3-azabicyclo[4.1.0]heptane), or a 6- to 9-membered nitrogen-containing spiro ring (e.g., 1-azaspiro[3.3]heptane, 6-oxa-1-azaspiro[3.5]nonane, 6-oxa-1-azaspiro[3.3]heptane, 6-oxa-1-azaspiro[3.4]octane)) optionally further substituted by 1 to 3 substituents selected from (a) a halogen atom (e.g., a fluorine atom, a chlorine atom, a bromine atom),
(b) a $C_{1-6}$ alkyl group (e.g., methyl, isopropyl) optionally substituted by 1 to 3 substituents selected from
(i) a halogen atom (e.g., a fluorine atom),
(ii) a cyano group,
(iii) a $C_{1-6}$ alkoxy group (e.g., methoxy), and
(iv) a mono- or di-$C_{1-6}$ alkylamino group (e.g., dimethylamino),
(c) a $C_{1-6}$ alkoxy group (e.g., methoxy, ethoxy) optionally substituted by 1 to 3 substituents selected from
(i) a halogen atom (e.g., a fluorine atom), and
(ii) a $C_{3-10}$ cycloalkyl group (e.g., cyclopropyl),
(d) a $C_{3-10}$ cycloalkyl group (e.g., cyclopropyl),
(e) a $C_{6-14}$ aryl group (e.g., phenyl, naphthyl) optionally substituted by 1 to 3 substituents selected from
(i) a halogen atom (e.g., a fluorine atom, a chlorine atom, a bromine atom),
(ii) an optionally halogenated $C_{1-6}$ alkyl group (e.g., methyl, trifluoromethyl), and
(iii) an optionally halogenated $C_{1-6}$ alkoxy group (e.g., methoxy, trifluoromethoxy),
(f) a $C_{6-14}$ aryloxy group (e.g., phenoxy) optionally substituted by 1 to 3 substituents selected from
(i) a halogen atom (e.g., a fluorine atom, a chlorine atom),
(ii) a cyano group,
(iii) an optionally halogenated $C_{1-6}$ alkyl group (e.g., methyl, trifluoromethyl), and
(iv) an optionally halogenated $C_{1-6}$ alkoxy group (e.g., methoxy, trifluoromethoxy),
(g) a $C_{7-16}$ aralkyl group (e.g., benzyl),
(h) a $C_{7-16}$ aralkyloxy group (e.g., benzyloxy),
(i) a 5- to 14-membered aromatic heterocyclic group (preferably a 5- to 6-membered monocyclic aromatic heterocyclic group (e.g., thienyl, pyrazolyl, pyridyl, pyrimidinyl)) optionally substituted by 1 to 3 substituents selected from
(i) a halogen atom (e.g., a chlorine atom), and
(ii) an optionally halogenated $C_{1-6}$ alkyl group (e.g., 2,2,2-trifluoroethyl),
(j) a 5- to 14-membered aromatic heterocyclyloxy group (preferably a 5- to 6-membered monocyclic aromatic heterocyclyloxy group (e.g., pyridyloxy, pyrazinyloxy, pyrimidinyloxy, thiazolyloxy)), and
(k) a 3- to 14-membered non-aromatic heterocyclyloxy group (preferably a 3- to 8-membered monocyclic non-aromatic heterocyclyloxy group (e.g., piperidyloxy)) optionally substituted by 1 to 3 $C_{1-6}$ alkoxy-carbonyl groups (e.g., tert-butoxycarbonyl).

In this embodiment, $R^3$ and $R^4$ are further more preferably each independently
(1) a hydrogen atom,
(2) a $C_{1-6}$ alkyl group (e.g., methyl, isopropyl, tert-butyl) optionally substituted by 1 to 3 substituents selected from
(a) a halogen atom (e.g., a fluorine atom),
(b) a cyano group,
(c) a $C_{3-10}$ cycloalkyl group (e.g., cyclopropyl, cyclohexyl),
(d) a $C_{6-14}$ aryl group (e.g., phenyl) optionally substituted by 1 to 3 halogen atoms (e.g., a chlorine atom), and (e) a 5- to 14-membered aromatic heterocyclic group (preferably a 5- to 6-membered monocyclic aromatic heterocyclic group (e.g., pyridyl, pyrazolyl, triazolyl, oxadiazolyl, thiazolyl, thienyl)) optionally substituted by 1 to 3 substituents selected from (i) a $C_{1-6}$ alkyl group (e.g., methyl),
(ii) a $C_{1-6}$ alkoxy group (e.g., methoxy), and
(iii) a $C_{6-14}$ aryl group (e.g., phenyl) optionally substituted by 1 to 3 substituents selected from a halogen atom (e.g., a chlorine atom) and a $C_{1-6}$ alkyl group (e.g., methyl), (3) a $C_{3-6}$ cycloalkyl group (e.g., cyclopropyl, cyclobutyl, cyclopentyl, cyclohexyl) optionally substituted by 1 to 3 substituents selected from
(a) a halogen atom (e.g., a fluorine atom),
(b) a cyano group,
(c) an optionally halogenated $C_{1-6}$ alkyl group (e.g., trifluoromethyl),
(d) a $C_{1-6}$ alkoxy group (e.g., methoxy, propoxy, butoxy),
(e) a $C_{1-6}$ alkoxy-carbonylamino group (e.g., tert-butoxy-carbonylamino),
(f) a $C_{6-14}$ aryl group (e.g., phenyl) optionally substituted by 1 to 3 halogen atoms (e.g., a chlorine atom),
(g) a $C_{6-14}$ aryloxy group (e.g., phenoxy),
(h) a $C_{7-16}$ aralkyloxy group (e.g., benzyloxy), and
(i) a 5- to 14-membered aromatic heterocyclic group (preferably a 5- to 6-membered monocyclic aromatic heterocyclic group (e.g., pyridyl)), (4) a bicyclo[1.1.1]pentyl group (e.g., bicyclo[1.1.1]pentan-1-yl) optionally substituted by 1 to 3 substituents selected from
(a) an optionally halogenated $C_{1-6}$ alkyl group (e.g., trifluoromethyl), and
(b) a $C_{6-14}$ aryl group (e.g., phenyl), (5) an indanyl group (e.g., indan-1-yl) optionally substituted by 1 to 3 halogen atoms (e.g., a chlorine atom),
(6) a tetrahydronaphthyl group (e.g., 1,2,3,4-tetrahydronaphthalen-2-yl),
(7) a dihydrobenzocyclobutenyl group (e.g., dihydrobenzocyclobuten-1-yl,
(8) a phenyl group optionally substituted by 1 to 3 substituents selected from
(a) a $C_{1-6}$ alkyl group (e.g., ethyl, isopropyl) optionally substituted by 1 to 3 hydroxy groups,
(b) a $C_{1-6}$ alkoxy group (e.g., methoxy, ethoxy),
(c) a $C_{6-14}$ aryloxy group (e.g., phenoxy),
(d) a $C_{7-16}$ aralkyloxy group (e.g., benzyloxy), and
(e) a 3- to 14-membered non-aromatic heterocyclic group (preferably a 3- to 8-membered monocyclic non-aromatic heterocyclic group (e.g., morpholinyl)), (9) a pyrazolyl group optionally substituted by 1 to 3 substituents selected from
(a) an optionally halogenated $C_{1-6}$ alkyl group (e.g., methyl, trifluoromethyl, 2,2,2-trifluoroethyl), and
(b) a $C_{7-16}$ aralkyl group (e.g., benzyl) optionally substituted by 1 to 3 halogen atoms (e.g., a fluorine atom),

(10) an imidazolyl group optionally substituted by 1 to 3 $C_{6-14}$ aryl groups (e.g., phenyl),
(11) a pyridyl group optionally substituted by 1 to 3 substituents selected from
(a) a cyano group,
(b) an optionally halogenated $C_{1-6}$ alkyl group (e.g., trifluoromethyl),
(c) an optionally halogenated $C_{1-6}$ alkoxy group (e.g., methoxy, difluoromethoxy, 2,2,2-trifluoroethoxy),
(d) a $C_{6-14}$ aryloxy group (e.g., phenoxy), and
(e) a $C_{3-10}$ cycloalkyl group (e.g., cyclopropyl).

(12) a pyrrolidinyl group optionally substituted by 1 to 3 $C_{7-16}$ aralkyl groups (e.g., benzyl),
(13) a piperidyl group optionally substituted by 1 to 3 substituents selected from
(a) a $C_{1-6}$ alkyl group (e.g., methyl) optionally substituted by 1 to 3 $C_{3-10}$ cycloalkyl groups (e.g., cyclopropyl),
(b) a $C_{1-6}$ alkoxy-carbonyl group (e.g., tert-butoxycarbonyl),
(c) a $C_{6-14}$ aryl group (e.g., phenyl) optionally substituted by 1 to 3 halogen atoms (e.g., a fluorine atom, a chlorine atom), and
(d) a $C_{7-16}$ aralkyl group (e.g., benzyl),

(14) a tetrahydrofuryl group optionally substituted by 1 to 3 $C_{6-14}$ aryl groups (e.g., phenyl), or
(15) a dihydrochromenyl group (e.g., 3,4-dihydro-2H-chromen-4-yl) optionally substituted by 1 to 3 $C_{1-6}$ alkyl groups (e.g., methyl), or $R^3$ and $R^4$ are bonded to each other to form, together with the adjacent nitrogen atom,
(1) an azetidine ring optionally further substituted by 1 to 3 substituents selected from
(a) a $C_{1-6}$ alkyl group (e.g., methyl, isopropyl) optionally substituted by 1 to 3 $C_{1-6}$ alkoxy groups (e.g., methoxy),
(b) an optionally halogenated $C_{1-6}$ alkoxy group (e.g., methoxy, difluoromethoxy),
(c) a $C_{3-10}$ cycloalkyl group (e.g., cyclopropyl),
(d) a $C_{6-14}$ aryl group (e.g., phenyl) optionally substituted by 1 to 3 halogen atoms (e.g., a fluorine atom, a chlorine atom, a bromine atom),
(e) a $C_{6-14}$ aryloxy group (e.g., phenoxy),
(f) a $C_{7-16}$ aralkyl group (e.g., benzyl), and
(g) a $C_{7-16}$ aralkyloxy group (e.g., benzyloxy), (2) a pyrrolidine ring optionally further substituted by 1 to 3 substituents selected from
(a) a halogen atom (e.g., a fluorine atom),
(b) an optionally halogenated $C_{1-6}$ alkoxy group (e.g., methoxy, trifluoromethoxy),
(c) a $C_{6-14}$ aryl group (e.g., phenyl) optionally substituted by 1 to 3 substituents selected from
(i) a halogen atom (e.g., a chlorine atom),
(ii) an optionally halogenated $C_{1-6}$ alkyl group (e.g., trifluoromethyl), and
(iii) a $C_{1-6}$ alkoxy group (e.g., methoxy),
(d) a $C_{7-16}$ aralkyl group (e.g., benzyl), and
(e) a $C_{7-16}$ aralkyloxy group (e.g., benzyloxy), (3) a piperidine ring optionally further substituted by 1 to 3 substituents selected from
(a) a $C_{1-6}$ alkoxy group (e.g., methoxy, ethoxy) optionally substituted by 1 to 3 substituents selected from
(i) a halogen atom (e.g., a fluorine atom), and
(ii) a $C_{3-10}$ cycloalkyl group (e.g., cyclopropyl),
(b) a $C_{6-14}$ aryl group (e.g., phenyl) optionally substituted by 1 to 3 substituents selected from
(i) a halogen atom (e.g., a chlorine atom), and
(ii) a $C_{1-6}$ alkoxy group (e.g., methoxy),
(c) a $C_{6-14}$ aryloxy group (e.g., phenoxy) optionally substituted by 1 to 3 substituents selected from
(i) a halogen atom (e.g., a fluorine atom, a chlorine atom),
(ii) a cyano group,
(iii) an optionally halogenated $C_{1-6}$ alkyl group (e.g., methyl, trifluoromethyl), and
(iv) an optionally halogenated $C_{1-6}$ alkoxy group (e.g., methoxy, trifluoromethoxy),
(d) a $C_{7-16}$ aralkyl group (e.g., benzyl),
(e) a $C_{7-16}$ aralkyloxy group (e.g., benzyloxy),
(f) a 5- to 14-membered aromatic heterocyclyloxy group (preferably a 5- to 6-membered monocyclic aromatic heterocyclyloxy group (e.g., pyridyloxy, pyrazinyloxy, pyrimidinyloxy, thiazolyloxy)), and
(g) a 3- to 14-membered non-aromatic heterocyclyloxy group (preferably a 3- to 8-membered monocyclic non-aromatic heterocyclyloxy group (e.g., piperidyloxy)) optionally substituted by 1 to 3 $C_{1-6}$ alkoxycarbonyl groups (e.g., tert-butoxycarbonyl), (4) an indoline ring optionally further substituted by 1 to 3 $C_{1-6}$ alkoxy groups (e.g., methoxy), (5) an isoindoline ring optionally further substituted by 1 to 3 $C_{1-6}$ alkoxy groups (e.g., methoxy), (6) a tetrahydroquinoline ring optionally further substituted by 1 to 3 $C_{1-6}$ alkoxy groups (e.g., methoxy), (7) a tetrahydroisoquinoline ring optionally further substituted by 1 to 3 substituents selected from
- (a) a halogen atom (e.g., a chlorine atom, a bromine atom),
- (b) a $C_{1-6}$ alkyl group (e.g., methyl), and
- (c) a $C_{1-6}$ alkoxy group (e.g., methoxy), (8) a 3-azabicyclo[3.1.0]hexane ring optionally further substituted by 1 to 3 substituents selected from
- (a) a halogen atom (e.g., a fluorine atom),
- (b) a $C_{1-6}$ alkyl group (e.g., methyl) optionally substituted by 1 to 3 substituents selected from
  - (i) a halogen atom (e.g., a fluorine atom),
  - (ii) a cyano group,
  - (iii) a $C_{1-6}$ alkoxy group (e.g., methoxy), and
  - (iv) a mono- or di-$C_{1-6}$ alkylamino group (e.g., dimethylamino),
- (c) a $C_{6-14}$ aryl group (e.g., phenyl, naphthyl) optionally substituted by 1 to 3 substituents selected from
  - (i) a halogen atom (e.g., a fluorine atom, a chlorine atom),
  - (ii) an optionally halogenated $C_{1-6}$ alkyl group (e.g., methyl, trifluoromethyl), and
  - (iii) an optionally halogenated $C_{1-6}$ alkoxy group (e.g., methoxy, trifluoromethoxy), and
- (d) a 5- to 14-membered aromatic heterocyclic group (preferably a 5- to 6-membered monocyclic aromatic heterocyclic group (e.g., thienyl, pyrazolyl, pyridyl, pyrimidinyl)) optionally substituted by 1 to 3 substituents selected from
  - (i) a halogen atom (e.g., a chlorine atom), and
  - (ii) an optionally halogenated $C_{1-6}$ alkyl group (e.g., 2,2,2-trifluoroethyl), (9) a 3-azabicyclo[4.1.0]heptane ring optionally further substituted by 1 to 3 substituents selected from
- (a) a halogen atom (e.g., a fluorine atom), and
- (b) a $C_{6-14}$ aryl group (e.g., phenyl) optionally substituted by 1 to 3 substituents selected from
  - (i) a halogen atom (e.g., a chlorine atom),
  - (ii) a $C_{1-6}$ alkyl group (e.g., methyl), and
  - (iii) a $C_{1-6}$ alkoxy group (e.g., methoxy),

(10) a 1-azaspiro[3.3]heptane ring,
(11) a 6-oxa-1-azaspiro[3.5]nonane ring,
(12) a 6-oxa-1-azaspiro[3.3]heptane ring, or
(13) a 6-oxa-1-azaspiro[3.4]octane ring.

In this embodiment, $R^3$ and $R^4$ are still more preferably each independently
(1) a hydrogen atom,
(2) a $C_{1-6}$ alkyl group (e.g., methyl, isopropyl, tert-butyl) optionally substituted by 1 to 3 substituents selected from
- (a) a halogen atom (e.g., a fluorine atom),
- (b) a cyano group,
- (c) a $C_{3-6}$ cycloalkyl group (e.g., cyclopropyl, cyclohexyl),
- (d) a phenyl group optionally substituted by 1 to 3 halogen atoms (e.g., a chlorine atom),
- (e) a pyridyl group optionally substituted by 1 to 3 $C_{1-6}$ alkoxy groups (e.g., methoxy),
- (f) a pyrazolyl group optionally substituted by 1 to 3 substituents selected from
  - (i) a $C_{1-6}$ alkyl group (e.g., methyl), and
  - (ii) a phenyl group optionally substituted by 1 to 3 substituents selected from a halogen atom (e.g., a chlorine atom) and a $C_{1-6}$ alkyl group (e.g., methyl),
- (g) a triazolyl group optionally substituted by 1 or 2 substituents selected from
  - (i) a $C_{1-6}$ alkyl group (e.g., methyl), and
  - (ii) a phenyl group,
- (h) an oxadiazolyl group optionally substituted by phenyl group(s) optionally substituted by 1 to 3 halogen atoms (e.g., a chlorine atom),
- (i) a thiazolyl group optionally substituted by 1 or 2 substituents selected from
  - (i) a $C_{1-6}$ alkyl group (e.g., methyl), and
  - (ii) a phenyl group, and
- (j) a thienyl group optionally substituted by 1 to 3 phenyl groups optionally substituted by 1 to 3 halogen atoms (e.g., a chlorine atom), (3) a $C_{3-6}$ cycloalkyl group (e.g., cyclopropyl, cyclobutyl, cyclopentyl, cyclohexyl) optionally substituted by 1 to 3 substituents selected from
- (a) a halogen atom (e.g., a fluorine atom),
- (b) a cyano group,
- (c) an optionally halogenated $C_{1-6}$ alkyl group (e.g., trifluoromethyl),
- (d) a $C_{1-6}$ alkoxy group (e.g., methoxy, propoxy, butoxy),
- (e) a $C_{1-6}$ alkoxy-carbonylamino group (e.g., tert-butoxycarbonylamino),
- (f) a phenyl group optionally substituted by 1 to 3 halogen atoms (e.g., a chlorine atom),
- (g) a phenoxy group,
- (h) a benzyloxy group, and
- (i) a pyridyl group, (4) a bicyclo[1.1.1]pentyl group (e.g., bicyclo[1.1.1]pentan-1-yl) optionally substituted by 1 to 3 substituents selected from
- (a) an optionally halogenated $C_{1-6}$ alkyl group (e.g., trifluoromethyl), and
- (b) a phenyl group, (5) an indanyl group (e.g., indan-1-yl) optionally substituted by 1 to 3 halogen atoms (e.g., a chlorine atom), (6) a tetrahydronaphthyl group (e.g., 1,2,3,4-tetrahydronaphthalen-2-yl), (7) a dihydrobenzocyclobutenyl group (e.g., dihydrobenzocyclobuten-1-yl, (8) a phenyl group optionally substituted by 1 to 3 substituents selected from
- (a) a $C_{1-6}$ alkyl group (e.g., ethyl, isopropyl) optionally substituted by 1 to 3 hydroxy groups,
- (b) a $C_{1-6}$ alkoxy group (e.g., methoxy, ethoxy),
- (c) a phenoxy group,
- (d) a benzyloxy group, and
- (e) a morpholinyl group, (9) a pyrazolyl group optionally substituted by 1 to 3 substituents selected from
- (a) an optionally halogenated $C_{1-6}$ alkyl group (e.g., methyl, trifluoromethyl, 2,2,2-trifluoroethyl), and
- (b) a benzyl group optionally substituted by 1 to 3 halogen atoms (e.g., a fluorine atom),

(10) an imidazolyl group optionally substituted by 1 to 3 phenyl groups,

(11) a pyridyl group optionally substituted by 1 to 3 substituents selected from
- (a) a cyano group,
- (b) an optionally halogenated $C_{1-6}$ alkyl group (e.g., trifluoromethyl), (c) an optionally halogenated $C_{1-6}$ alkoxy group (e.g., methoxy, difluoromethoxy, 2,2,2-trifluoroethoxy),
(d) a phenoxy group, and
(e) a $C_{3-10}$ cycloalkyl group (e.g., cyclopropyl),
(12) a pyrrolidinyl group optionally substituted by 1 to 3 benzyl groups,
(13) a piperidyl group optionally substituted by 1 to 3 substituents selected from
    (a) a $C_{1-6}$ alkyl group (e.g., methyl) optionally substituted by 1 to 3 $C_{3-6}$ cycloalkyl groups (e.g., cyclopropyl),
    (b) a $C_{1-6}$ alkoxy-carbonyl group (e.g., tert-butoxycarbonyl),
    (c) a phenyl group optionally substituted by 1 to 3 halogen atoms (e.g., a fluorine atom, a chlorine atom), and
    (d) a benzyl group,
(14) a tetrahydrofuryl group optionally substituted by 1 to 3 phenyl groups, or
(15) a dihydrochromenyl group (e.g., 3,4-dihydro-2H-chromen-4-yl) optionally substituted by 1 to 3 $C_{1-6}$ alkyl groups (e.g., methyl), or
$R^3$ and $R^4$ are bonded to each other to form, together with the adjacent nitrogen atom,
(1) an azetidine ring optionally further substituted by 1 to 3 substituents selected from
    (a) a $C_{1-6}$ alkyl group (e.g., methyl, isopropyl) optionally substituted by 1 to 3 $C_{1-6}$ alkoxy groups (e.g., methoxy),
    (b) an optionally halogenated $C_{1-6}$ alkoxy group (e.g., methoxy, difluoromethoxy),
    (c) a $C_{3-6}$ cycloalkyl group (e.g., cyclopropyl),
    (d) a phenyl group optionally substituted by 1 to 3 halogen atoms (e.g., a fluorine atom, a chlorine atom, a bromine atom),
    (e) a phenoxy group,
    (f) a benzyl group, and
    (g) a benzyloxy group,
(2) a pyrrolidine ring optionally further substituted by 1 to 3 substituents selected from
    (a) a halogen atom (e.g., a fluorine atom),
    (b) an optionally halogenated $C_{1-6}$ alkoxy group (e.g., methoxy, trifluoromethoxy),
    (c) a phenyl group optionally substituted by 1 to 3 substituents selected from
        (i) a halogen atom (e.g., a chlorine atom),
        (ii) an optionally halogenated $C_{1-6}$ alkyl group (e.g., trifluoromethyl), and
        (iii) a $C_{1-6}$ alkoxy group (e.g., methoxy),
    (d) a benzyl group, and
    (e) a benzyloxy group,
(3) a piperidine ring optionally further substituted by 1 to 3 substituents selected from
    (a) a $C_{1-6}$ alkoxy group (e.g., methoxy, ethoxy) optionally substituted by 1 to 3 substituents selected from
        (i) a halogen atom (e.g., a fluorine atom), and
        (ii) a $C_{3-6}$ cycloalkyl group (e.g., cyclopropyl),
    (b) a phenyl group optionally substituted by 1 to 3 substituents selected from
        (i) a halogen atom (e.g., a chlorine atom), and
        (ii) a $C_{1-6}$ alkoxy group (e.g., methoxy),
    (c) a phenoxy group optionally substituted by 1 to 3 substituents selected from
        (i) a halogen atom (e.g., a fluorine atom, a chlorine atom),
        (ii) a cyano group,
        (iii) an optionally halogenated $C_{1-6}$ alkyl group (e.g., methyl, trifluoromethyl), and
        (iv) an optionally halogenated $C_{1-6}$ alkoxy group (e.g., methoxy, trifluoromethoxy),
    (d) a benzyl group,
    (e) a benzyloxy group,
    (f) a pyridyloxy group,
    (g) a pyrazinyloxy group,
    (h) a pyrimidinyloxy group,
    (i) a thiazolyloxy group, and
    (j) a piperidyloxy group optionally substituted by 1 to 3 $C_{1-6}$ alkoxy-carbonyl groups (e.g., tert-butoxycarbonyl),
(4) an indoline ring optionally further substituted by 1 to 3 $C_{1-6}$ alkoxy groups (e.g., methoxy),
(5) an isoindoline ring optionally further substituted by 1 to 3 $C_{1-6}$ alkoxy groups (e.g., methoxy),
(6) a tetrahydroquinoline ring optionally further substituted by 1 to 3 $C_{1-6}$ alkoxy groups (e.g., methoxy),
(7) a tetrahydroisoquinoline ring optionally further substituted by 1 to 3 substituents selected from
    (a) a halogen atom (e.g., a chlorine atom, a bromine atom),
    (b) a $C_{1-6}$ alkyl group (e.g., methyl), and
    (c) a $C_{1-6}$ alkoxy group (e.g., methoxy),
(8) a 3-azabicyclo[3.1.0]hexane ring optionally further substituted by 1 to 3 substituents selected from
    (a) a halogen atom (e.g., a fluorine atom),
    (b) a $C_{1-6}$ alkyl group (e.g., methyl) optionally substituted by 1 to 3 substituents selected from
        (i) a halogen atom (e.g., a fluorine atom),
        (ii) a cyano group,
        (iii) a $C_{1-6}$ alkoxy group (e.g., methoxy), and
        (iv) a mono- or di-$C_{1-6}$ alkylamino group (e.g., dimethylamino),
    (c) a phenyl group optionally substituted by 1 to 3 substituents selected from
        (i) a halogen atom (e.g., a fluorine atom, a chlorine atom),
        (ii) an optionally halogenated $C_{1-6}$ alkyl group (e.g., methyl, trifluoromethyl), and
        (iii) an optionally halogenated $C_{1-6}$ alkoxy group (e.g., methoxy, trifluoromethoxy),
    (d) a naphthyl group,
    (e) a thienyl group,
    (f) a pyrazolyl group optionally substituted by 1 to 3 of optionally halogenated $C_{1-6}$ alkyl groups (e.g., 2,2,2-trifluoroethyl),
    (g) a pyridyl group optionally substituted by 1 to 3 halogen atoms (e.g., a chlorine atom), and
    (h) a pyrimidinyl group optionally substituted by 1 to 3 halogen atoms (e.g., a chlorine atom),
(9) a 3-azabicyclo[4.1.0]heptane ring optionally further substituted by 1 to 3 substituents selected from
    (a) a halogen atom (e.g., a fluorine atom), and
    (b) a phenyl group optionally substituted by 1 to 3 substituents selected from
        (i) a halogen atom (e.g., a chlorine atom),
        (ii) a $C_{1-6}$ alkyl group (e.g., methyl), and
        (iii) a $C_{1-6}$ alkoxy group (e.g., methoxy),
(10) a 1-azaspiro[3.3]heptane ring,
(11) a 6-oxa-1-azaspiro[3.5]nonane ring,
(12) a 6-oxa-1-azaspiro[3.3]heptane ring, or
(13) a 6-oxa-1-azaspiro[3.4]octane ring.

Even more preferably, $R^3$ is a hydrogen atom, and $R^4$ is
(1) a $C_{1-6}$ alkyl group (e.g., methyl, isopropyl) optionally substituted by 1 to 3 substituents selected from
   (a) a phenyl group optionally substituted by 1 to 3 halogen atoms (e.g., a chlorine atom),
   (b) an oxadiazolyl group optionally substituted by phenyl group(s) optionally substituted by 1 to 3 halogen atoms (e.g., a chlorine atom), and
   (c) a thienyl group optionally substituted by 1 to 3 phenyl groups optionally substituted by 1 to 3 halogen atoms (e.g., a chlorine atom),
(2) a $C_{3-6}$ cycloalkyl group (e.g., cyclobutyl, cyclopentyl, cyclohexyl) optionally substituted by 1 to 3 substituents selected from
   (a) a $C_{1-6}$ alkoxy group (e.g., butoxy), and
   (b) a phenyl group optionally substituted by 1 to 3 halogen atoms (e.g., a chlorine atom),
(3) a phenyl group optionally substituted by 1 to 3 substituents selected from
   (a) a benzyloxy group,
   (b) a morpholinyl group, and
   (c) a $C_{1-6}$ alkyl group (e.g., isopropyl) optionally substituted by 1 to 3 hydroxy groups, or
(4) a pyridyl group optionally substituted by 1 to 3 substituents selected from
   (a) a cyano group,
   (b) an optionally halogenated $C_{1-6}$ alkoxy group (e.g., methoxy, difluoromethoxy, 2,2,2-trifluoroethoxy), and
   (c) a $C_{3-10}$ cycloalkyl group (e.g., cyclopropyl), or
$R^3$ and $R^4$ are bonded to each other to form, together with the adjacent nitrogen atom,
(1) an azetidine ring optionally further substituted by 1 to 3 phenyl groups,
(2) a pyrrolidine ring optionally further substituted by 1 to 3 substituents selected from
   (a) a halogen atom (e.g., a fluorine atom), and
   (b) a phenyl group optionally substituted by 1 to 3 halogen atoms (e.g., a chlorine atom),
(3) a piperidine ring optionally further substituted by 1 to 3 substituents selected from
   (a) a phenyl group optionally substituted by 1 to 3 halogen atoms (e.g., a chlorine atom), and
   (b) a phenoxy group optionally substituted by 1 to 3 substituents selected from
      (i) a halogen atom (e.g., a chlorine atom),
      (ii) an optionally halogenated $C_{1-6}$ alkyl group (e.g., trifluoromethyl), and
      (iii) an optionally halogenated $C_{1-6}$ alkoxy group (e.g., trifluoromethoxy), or
(4) a 3-azabicyclo[3.1.0]hexane ring optionally further substituted by 1 to 3 substituents selected from
   (a) a halogen atom (e.g., a fluorine atom),
   (b) a phenyl group optionally substituted by 1 to 3 substituents selected from
      (i) a halogen atom (e.g., a fluorine atom, a chlorine atom),
      (ii) an optionally halogenated $C_{1-6}$ alkyl group (e.g., methyl, trifluoromethyl), and
      (iii) an optionally halogenated $C_{1-6}$ alkoxy group (e.g., methoxy, trifluoromethoxy), and
   (c) a naphthyl group.

Particularly preferably $R^3$ is a hydrogen atom, and $R^4$ is
(1) a $C_{3-6}$ cycloalkyl group (e.g., cyclohexyl) optionally substituted by 1 to 3 $C_{1-6}$ alkoxy groups (e.g., butoxy), or
(2) a phenyl group optionally substituted by 1 to 3 substituents selected from
   (a) a morpholinyl group, and
   (b) a $C_{1-6}$ alkyl group (e.g., isopropyl) optionally substituted by 1 to 3 hydroxy groups.

Preferable examples of compound (I) include the following compounds:
[Compound A-1]
Compound (I) wherein
Ring A is a 5-membered aromatic heterocycle;
Ring B is an optionally further substituted 6-membered nitrogen-containing non-aromatic heterocycle;
W is $NR^6$ wherein $R^6$ is an optionally substituted $C_{1-6}$ alkyl group (e.g., methyl, ethyl) or an optionally substituted $C_{7-16}$ aralkyl group (e.g., benzyl), N, O or S;
X is $CR^7$ wherein $R^7$ is a hydrogen atom or an optionally substituted $C_{1-6}$ alkyl group (e.g., methyl), $NR^8$ wherein $R^8$ is an optionally substituted $C_{1-6}$ alkyl group (e.g., methyl), or N;
Y is C;
$Z^1$ and $Z^2$ are each independently C or N;
$R^1$ is an optionally substituted $C_{1-6}$ alkyl group (e.g., methyl, ethyl) or an optionally substituted $C_{6-14}$ aryl group (e.g., phenyl);
as to $R^2$
(1) when W is NR or N, then $R^2$ is a hydrogen atom, a halogen atom (e.g., a chlorine atom, a bromine atom), an optionally substituted $C_{1-6}$ alkyl group (e.g., methyl, ethyl), an optionally substituted $C_{3-10}$ cycloalkyl group (e.g., cyclopropyl) or an optionally substituted $C_{6-14}$ aryl group (e.g., phenyl),
(2) when W is O or S, then $R^2$ is an optionally substituted $C_{1-6}$ alkyl group (e.g., methyl); and
$R^3$ and $R^4$ are each independently
(1) a hydrogen atom,
(2) an optionally substituted $C_{1-6}$ alkyl group (e.g., methyl, isopropyl, tert-butyl),
(3) a $C_{3-10}$ cycloalkyl group optionally fused with a benzene ring (the $C_{3-10}$ cycloalkyl may be a bridged ring group, e.g., cyclopropyl, cyclobutyl, cyclopentyl, cyclohexyl, bicyclo[1.1.1]pentyl (e.g., bicyclo[1.1.1]pentan-1-yl), indanyl (e.g., indan-1-yl), tetrahydronaphthyl (e.g., 1,2,3,4-tetrahydronaphthalen-2-yl), dihydrobenzocyclobutenyl (e.g., dihydrobenzocyclobuten-1-yl)), which is optionally substituted,
(4) an optionally substituted $C_{6-14}$ aryl group (e.g., phenyl),
(5) an optionally substituted 5- to 14-membered aromatic heterocyclic group (preferably a 5- to 6-membered monocyclic aromatic heterocyclic group (e.g., pyrazolyl, imidazolyl, pyridyl)), or
(6) an optionally substituted 3- to 14-membered non-aromatic heterocyclic group (preferably a 3- to 8-membered monocyclic non-aromatic heterocyclic group (e.g., pyrrolidinyl, piperidyl, tetrahydrofuryl), or a 9- to 14-membered fused polycyclic (preferably bi- or tri-cyclic) non-aromatic heterocyclic group (e.g., dihydrochromenyl (e.g., 3,4-dihydro-2H-chromen-4-yl))), or
$R^3$ and $R^4$ are bonded to each other to form, together with the adjacent nitrogen atom, an optionally further substituted 3- to 14-membered non-aromatic nitrogen-containing heterocycle (preferably a 3- to 8-membered monocyclic non-aromatic nitrogen-containing heterocycle (e.g., azetidine, pyrrolidine, piperidine), a 9- to 14-membered fused polycyclic (preferably bi- or tri-cyclic) non-aromatic nitrogen-containing heterocycle (e.g., indoline, isoindoline, tetrahydroquinoline, tetrahydroisoquinoline), a 6- to 9-membered nitrogen-containing bridged ring (e.g., 3-azabicyclo[3.1.0]hexane, 3-azabicyclo[4.1.0]heptane), or a 6- to 9-membered nitrogen-containing spiro ring (e.g., 1-azaspiro[3.3]heptane, 6-oxa-1-azaspiro[3.5]nonane, 6-oxa-1-azaspiro[3.3]heptane, 6-oxa-1-azaspiro[3.4]octane)).

[Compound B-1]

Compound (I) wherein

Ring A is pyrrole, pyrazole, thiophene or furan;

Ring B is dihydropyridine, tetrahydropyridine or tetrahydropyrazine;

W is $NR^6$ wherein $R^6$ is a $C_{1-6}$ alkyl group (e.g., methyl, ethyl) or a $C_{7-16}$ aralkyl group (e.g., benzyl), N, O or S;

X is $CR^7$ wherein $R^7$ is a hydrogen atom or a $C_{1-6}$ alkyl group (e.g., methyl), $NR^8$ wherein $R^8$ is a $C_{1-6}$ alkyl group (e.g., methyl), or N;

Y is C;

$Z^1$—$Z^2$ is C=C, C—C or C—N;

[preferably, the partial structure represented by the following formula:

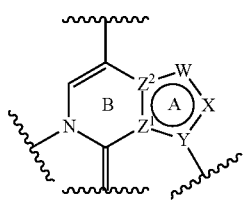

is a partial structure represented by the following formula:

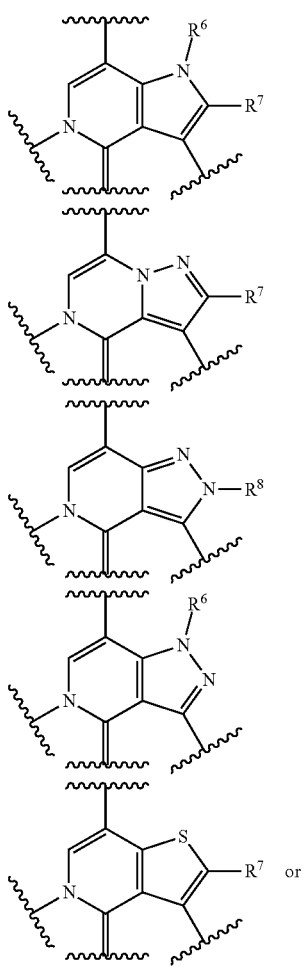

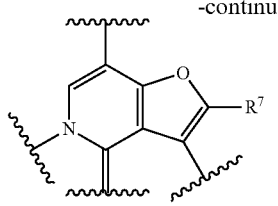

wherein $R^6$ is a $C_{1-6}$ alkyl group (e.g., methyl, ethyl) or a $C_{7-16}$ aralkyl group (e.g., benzyl), $R^7$ is a hydrogen atom or a $C_{1-6}$ alkyl group (e.g., methyl), and $R^8$ is a $C_{1-6}$ alkyl group (e.g., methyl)]

$R^1$ is (1) a $C_{1-6}$ alkyl group (e.g., methyl, ethyl) optionally substituted by 1 to 3 substituents selected from
 (a) a halogen atom (e.g., a fluorine atom), and
 (b) a cyano group, or (2) a $C_{6-14}$ aryl group (e.g., phenyl) optionally substituted by 1 to 3 substituents selected from
 (a) an optionally halogenated $C_{1-6}$ alkoxy group (e.g., methoxy, 2,2,2-trifluoroethoxy), and
 (b) a halogen atom (e.g., a fluorine atom);

as to $R^2$ (1) when W is $NR^6$ or N, then $R^2$ is a hydrogen atom, a halogen atom (e.g., a chlorine atom, a bromine atom), a $C_{1-6}$ alkyl group (e.g., methyl, ethyl), a $C_{3-10}$ cycloalkyl group (e.g., cyclopropyl) or a $C_{6-14}$ aryl group (e.g., phenyl), (2) when W is O or S, then $R^2$ is a $C_{1-6}$ alkyl group (e.g., methyl); and $R^3$ and $R^4$ are each independently (1) a hydrogen atom, (2) a $C_{1-6}$ alkyl group (e.g., methyl, isopropyl, tert-butyl) optionally substituted by 1 to 3 substituents selected from
 (a) a halogen atom (e.g., a fluorine atom),
 (b) a cyano group,
 (c) a $C_{3-10}$ cycloalkyl group (e.g., cyclopropyl, cyclohexyl),
 (d) a $C_{6-14}$ aryl group (e.g., phenyl) optionally substituted by 1 to 3 halogen atoms (e.g., a chlorine atom), and
 (e) a 5- to 14-membered aromatic heterocyclic group (preferably a 5- to 6-membered monocyclic aromatic heterocyclic group (e.g., pyridyl, pyrazolyl, triazolyl, oxadiazolyl, thiazolyl, thienyl)) optionally substituted by 1 to 3 substituents selected from
  (i) a $C_{1-6}$ alkyl group (e.g., methyl),
  (ii) a $C_{1-6}$ alkoxy group (e.g., methoxy), and
  (iii) a $C_{6-14}$ aryl group (e.g., phenyl) optionally substituted by 1 to 3 substituents selected from a halogen atom (e.g., a chlorine atom) and a $C_{1-6}$ alkyl group (e.g., methyl), (3) a $C_{3-10}$ cycloalkyl group optionally fused with a benzene ring (the $C_{3-10}$ cycloalkyl may be a bridged ring group, e.g., cyclopropyl, cyclobutyl, cyclopentyl, cyclohexyl, bicyclo[1.1.1]pentyl (e.g., bicyclo[1.1.1]pentan-1-yl), indanyl (e.g., indan-1-yl), tetrahydronaphthyl (e.g., 1,2,3,4-tetrahydronaphthalen-2-yl), dihydrobenzocyclobutenyl (e.g., dihydrobenzocyclobuten-1-yl)), which is optionally substituted by 1 to 3 substituents selected from
 (a) a halogen atom (e.g., a fluorine atom, a chlorine atom),
 (b) a cyano group,
 (c) an optionally halogenated $C_{1-6}$ alkyl group (e.g., trifluoromethyl),
 (d) a $C_{1-6}$ alkoxy group (e.g., methoxy, propoxy, butoxy),
 (e) a $C_{1-6}$ alkoxy-carbonylamino group (e.g., tert-butoxycarbonylamino), (f) a $C_{6-14}$ aryl group (e.g., phenyl) optionally substituted by 1 to 3 halogen atoms (e.g., a chlorine atom),
(g) a $C_{6-14}$ aryloxy group (e.g., phenoxy),
(h) a $C_{7-16}$ aralkyloxy group (e.g., benzyloxy), and
(i) a 5- to 14-membered aromatic heterocyclic group (preferably a 5- to 6-membered monocyclic aromatic heterocyclic group (e.g., pyridyl)),
(4) a $C_{6-14}$ aryl group (e.g., phenyl) optionally substituted by 1 to 3 substituents selected from
  (a) a $C_{1-6}$ alkyl group (e.g., ethyl),
  (b) a $C_{1-6}$ alkoxy group (e.g., methoxy, ethoxy),
  (c) a $C_{6-14}$ aryloxy group (e.g., phenoxy),
  (d) a $C_{7-16}$ aralkyloxy group (e.g., benzyloxy), and
  (e) a 3- to 14-membered non-aromatic heterocyclic group (preferably a 3- to 8-membered monocyclic non-aromatic heterocyclic group (e.g., morpholinyl)),
(5) a 5- to 14-membered aromatic heterocyclic group (preferably a 5- to 6-membered monocyclic aromatic heterocyclic group (e.g., pyrazolyl, imidazolyl, pyridyl)) optionally substituted by 1 to 3 substituents selected from
  (a) a cyano group,
  (b) an optionally halogenated $C_{1-6}$ alkyl group (e.g., methyl, trifluoromethyl, 2,2,2-trifluoroethyl),
  (c) a $C_{1-6}$ alkoxy group (e.g., methoxy),
  (d) a $C_{6-14}$ aryl group (e.g., phenyl),
  (e) a $C_{6-14}$ aryloxy group (e.g., phenoxy), and
  (f) a $C_{7-16}$ aralkyl group (e.g., benzyl) optionally substituted by 1 to 3 halogen atoms (e.g., a fluorine atom), or
(6) a 3- to 14-membered non-aromatic heterocyclic group (preferably a 3- to 8-membered monocyclic non-aromatic heterocyclic group (e.g., pyrrolidinyl, piperidyl, tetrahydrofuryl), or a 9- to 14-membered fused polycyclic (preferably bi- or tri-cyclic) non-aromatic heterocyclic group (e.g., dihydrochromenyl (e.g., 3,4-dihydro-2H-chromen-4-yl))) optionally substituted by 1 to 3 substituents selected from
  (a) a $C_{1-6}$ alkyl group (e.g., methyl) optionally substituted by 1 to 3 $C_{3-10}$ cycloalkyl groups (e.g., cyclopropyl),
  (b) a $C_{1-6}$ alkoxy-carbonyl group (e.g., tert-butoxycarbonyl),
  (c) a $C_{6-14}$ aryl group (e.g., phenyl) optionally substituted by 1 to 3 halogen atoms (e.g., a fluorine atom, a chlorine atom), and
  (d) a $C_{7-16}$ aralkyl group (e.g., benzyl), or
$R^3$ and $R^4$ are bonded to each other to form, together with the adjacent nitrogen atom, a 3- to 14-membered non-aromatic nitrogen-containing heterocycle (preferably a 3- to 8-membered monocyclic non-aromatic nitrogen-containing heterocycle (e.g., azetidine, pyrrolidine, piperidine), a 9- to 14-membered fused polycyclic (preferably bi- or tri-cyclic) non-aromatic nitrogen-containing heterocycle (e.g., indoline, isoindoline, tetrahydroquinoline, tetrahydroisoquinoline), a 6- to 9-membered nitrogen-containing bridged ring (e.g., 3-azabicyclo[3.1.0]hexane, 3-azabicyclo[4.1.0]heptane), or a 6- to 9-membered nitrogen-containing spiro ring (e.g., 1-azaspiro[3.3]heptane, 6-oxa-1-azaspiro[3.5]nonane, 6-oxa-1-azaspiro[3.3]heptane, 6-oxa-1-azaspiro[3.4]octane)) optionally further substituted by 1 to 3 substituents selected from
  (a) a halogen atom (e.g., a fluorine atom, a chlorine atom, a bromine atom),
  (b) a $C_{1-6}$ alkyl group (e.g., methyl, isopropyl) optionally substituted by 1 to 3 substituents selected from
    (i) a halogen atom (e.g., a fluorine atom),
    (ii) a cyano group,
    (iii) a $C_{1-6}$ alkoxy group (e.g., methoxy), and
    (iv) a mono- or di-$C_{1-6}$ alkylamino group (e.g., dimethylamino), (c) a $C_{1-6}$ alkoxy group (e.g., methoxy, ethoxy) optionally substituted by 1 to 3 substituents selected from
  (i) a halogen atom (e.g., a fluorine atom), and
  (ii) a $C_{3-10}$ cycloalkyl group (e.g., cyclopropyl),
(d) a $C_{3-10}$ cycloalkyl group (e.g., cyclopropyl),
(e) a $C_{6-14}$ aryl group (e.g., phenyl, naphthyl) optionally substituted by 1 to 3 substituents selected from
  (i) a halogen atom (e.g., a fluorine atom, a chlorine atom, a bromine atom),
  (ii) an optionally halogenated $C_{1-6}$ alkyl group (e.g., methyl, trifluoromethyl), and
  (iii) an optionally halogenated $C_{1-6}$ alkoxy group (e.g., methoxy, trifluoromethoxy),
(f) a $C_{6-14}$ aryloxy group (e.g., phenoxy) optionally substituted by 1 to 3 substituents selected from
  (i) a halogen atom (e.g., a fluorine atom, a chlorine atom),
  (ii) a cyano group,
  (iii) an optionally halogenated $C_{1-6}$ alkyl group (e.g., methyl, trifluoromethyl), and
  (iv) an optionally halogenated $C_{1-6}$ alkoxy group (e.g., methoxy, trifluoromethoxy),
(g) a $C_{7-16}$ aralkyl group (e.g., benzyl),
(h) a $C_{7-16}$ aralkyloxy group (e.g., benzyloxy),
(i) a 5- to 14-membered aromatic heterocyclic group (preferably a 5- to 6-membered monocyclic aromatic heterocyclic group (e.g., thienyl)),
(j) a 5- to 14-membered aromatic heterocyclyloxy group (preferably a 5- to 6-membered monocyclic aromatic heterocyclyloxy group (e.g., pyridyloxy, pyrazinyloxy, pyrimidinyloxy, thiazolyloxy)), and
(k) a 3- to 14-membered non-aromatic heterocyclyloxy group (preferably a 3- to 8-membered monocyclic non-aromatic heterocyclyloxy group (e.g., piperidyloxy)) optionally substituted by 1 to 3 $C_{1-6}$ alkoxy-carbonyl groups (e.g., tert-butoxycarbonyl).

[Compound C-1]

Compound (I) wherein

Ring A is pyrrole, pyrazole, thiophene or furan;

Ring B is dihydropyridine, tetrahydropyridine or tetrahydropyrazine;

W is $NR^6$ wherein $R^6$ is a $C_{1-6}$ alkyl group (e.g., methyl, ethyl) or a benzyl group, N, O or S;

X is $CR^7$ wherein $R^7$ is a hydrogen atom or a $C_{1-6}$ alkyl group (e.g., methyl), $NR^8$ wherein $R^8$ is a $C_{1-6}$ alkyl group (e.g., methyl), or N;

Y is C;

$Z^1$—$Z^2$ is C=C, C—C or C—N;

[preferably, the partial structure represented by the following formula:

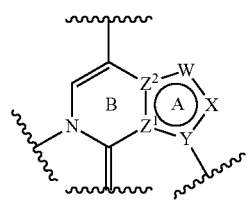

is a partial structure represented by the following formula:

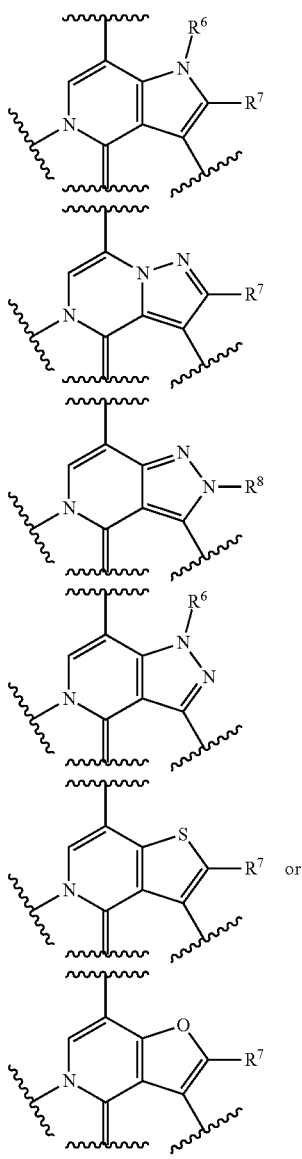

wherein $R^6$ is a $C_{1-6}$ alkyl group (e.g., methyl, ethyl) or a benzyl group, $R^7$ is a hydrogen atom or a $C_{1-6}$ alkyl group (e.g., methyl), and $R^8$ is a $C_{1-6}$ alkyl group (e.g., methyl)]
$R^1$ is
(1) a $C_{1-6}$ alkyl group (e.g., methyl, ethyl) optionally substituted by 1 to 3 substituents selected from
    (a) a halogen atom (e.g., a fluorine atom), and
    (b) a cyano group, or
(2) a phenyl group optionally substituted by 1 to 3 substituents selected from
    (a) an optionally halogenated $C_{1-6}$ alkoxy group (e.g., methoxy, 2,2,2-trifluoroethoxy), and
    (b) a halogen atom (e.g., a fluorine atom);
as to $R^2$
(1) when W is $NR^6$ or N, then $R^2$ is a hydrogen atom, a halogen atom (e.g., a chlorine atom, a bromine atom), a $C_{1-6}$ alkyl group (e.g., methyl, ethyl), a $C_{3-6}$ cycloalkyl group (e.g., cyclopropyl) or a phenyl group,
(2) when W is O or S, then $R^2$ is a $C_{1-6}$ alkyl group (e.g., methyl); and
$R^3$ and $R^4$ are each independently
(1) a hydrogen atom,
(2) a $C_{1-6}$ alkyl group (e.g., methyl, isopropyl, tert-butyl) optionally substituted by 1 to 3 substituents selected from
    (a) a halogen atom (e.g., a fluorine atom),
    (b) a cyano group,
    (c) a $C_{3-10}$ cycloalkyl group (e.g., cyclopropyl, cyclohexyl),
    (d) a $C_{6-14}$ aryl group (e.g., phenyl) optionally substituted by 1 to 3 halogen atoms (e.g., a chlorine atom), and
    (e) a 5- to 14-membered aromatic heterocyclic group (preferably a 5- to 6-membered monocyclic aromatic heterocyclic group (e.g., pyridyl, pyrazolyl, triazolyl, oxadiazolyl, thiazolyl, thienyl)) optionally substituted by 1 to 3 substituents selected from
        (i) a $C_{1-6}$ alkyl group (e.g., methyl),
        (ii) a $C_{1-6}$ alkoxy group (e.g., methoxy), and
        (iii) a $C_{6-14}$ aryl group (e.g., phenyl) optionally substituted by 1 to 3 substituents selected from a halogen atom (e.g., a chlorine atom) and a $C_{1-6}$ alkyl group (e.g., methyl),
(3) a $C_{3-6}$ cycloalkyl group (e.g., cyclopropyl, cyclobutyl, cyclopentyl, cyclohexyl) optionally substituted by 1 to 3 substituents selected from
    (a) a halogen atom (e.g., a fluorine atom),
    (b) a cyano group,
    (c) an optionally halogenated $C_{1-6}$ alkyl group (e.g., trifluoromethyl),
    (d) a $C_{1-6}$ alkoxy group (e.g., methoxy, propoxy, butoxy),
    (e) a $C_{1-6}$ alkoxy-carbonylamino group (e.g., tert-butoxycarbonylamino),
    (f) a $C_{6-14}$ aryl group (e.g., phenyl) optionally substituted by 1 to 3 halogen atoms (e.g., a chlorine atom),
    (g) a $C_{6-14}$ aryloxy group (e.g., phenoxy),
    (h) a $C_{7-16}$ aralkyloxy group (e.g., benzyloxy), and
    (i) a 5- to 14-membered aromatic heterocyclic group (preferably a 5- to 6-membered monocyclic aromatic heterocyclic group (e.g., pyridyl)),
(4) a bicyclo[1.1.1]pentyl group (e.g., bicyclo[1.1.1]pentan-1-yl) optionally substituted by 1 to 3 substituents selected from
    (a) an optionally halogenated $C_{1-6}$ alkyl group (e.g., trifluoromethyl), and
    (b) a $C_{6-14}$ aryl group (e.g., phenyl),
(5) an indanyl group (e.g., indan-1-yl) optionally substituted by 1 to 3 halogen atoms (e.g., a chlorine atom),
(6) a tetrahydronaphthyl group (e.g., 1,2,3,4-tetrahydronaphthalen-2-yl),
(7) a dihydrobenzocyclobutenyl group (e.g., dihydrobenzocyclobuten-1-yl,
(8) a phenyl group optionally substituted by 1 to 3 substituents selected from
    (a) a $C_{1-6}$ alkyl group (e.g., ethyl),
    (b) a $C_{1-6}$ alkoxy group (e.g., methoxy, ethoxy),
    (c) a $C_{6-14}$ aryloxy group (e.g., phenoxy),
    (d) a $C_{7-16}$ aralkyloxy group (e.g., benzyloxy), and (e) a 3- to 14-membered non-aromatic heterocyclic group (preferably a 3- to 8-membered monocyclic non-aromatic heterocyclic group (e.g., morpholinyl)),
(9) a pyrazolyl group optionally substituted by 1 to 3 substituents selected from
    (a) an optionally halogenated $C_{1-6}$ alkyl group (e.g., methyl, trifluoromethyl, 2,2,2-trifluoroethyl), and
    (b) a $C_{7-16}$ aralkyl group (e.g., benzyl) optionally substituted by 1 to 3 halogen atoms (e.g., a fluorine atom),
(10) an imidazolyl group optionally substituted by 1 to 3 $C_{6-14}$ aryl groups (e.g., phenyl),

(11) a pyridyl group optionally substituted by 1 to 3 substituents selected from
  (a) a cyano group,
  (b) an optionally halogenated $C_{1-6}$ alkyl group (e.g., trifluoromethyl),
  (c) a $C_{1-6}$ alkoxy group (e.g., methoxy), and
  (d) a $C_{6-14}$ aryloxy group (e.g., phenoxy),
(12) a pyrrolidinyl group optionally substituted by 1 to 3 $C_{7-16}$ aralkyl groups (e.g., benzyl),
(13) a piperidyl group optionally substituted by 1 to 3 substituents selected from
  (a) a $C_{1-6}$ alkyl group (e.g., methyl) optionally substituted by 1 to 3 $C_{3-10}$ cycloalkyl groups (e.g., cyclopropyl),
  (b) a $C_{1-6}$ alkoxy-carbonyl group (e.g., tert-butoxycarbonyl),
  (c) a $C_{6-14}$ aryl group (e.g., phenyl) optionally substituted by 1 to 3 halogen atoms (e.g., a fluorine atom, a chlorine atom), and
  (d) a $C_{7-16}$ aralkyl group (e.g., benzyl),
(14) a tetrahydrofuryl group optionally substituted by 1 to 3 $C_{6-14}$ aryl groups (e.g., phenyl), or
(15) a dihydrochromenyl group (e.g., 3,4-dihydro-2H-chromen-4-yl) optionally substituted by 1 to 3 $C_{1-6}$ alkyl groups (e.g., methyl), or
$R^3$ and $R^4$ are bonded to each other to form, together with the adjacent nitrogen atom,
(1) an azetidine ring optionally further substituted by 1 to 3 substituents selected from
  (a) a $C_{1-6}$ alkyl group (e.g., methyl, isopropyl) optionally substituted by 1 to 3 $C_{1-6}$ alkoxy groups (e.g., methoxy),
  (b) an optionally halogenated $C_{1-6}$ alkoxy group (e.g., methoxy, difluoromethoxy),
  (c) a $C_{3-10}$ cycloalkyl group (e.g., cyclopropyl),
  (d) a $C_{6-14}$ aryl group (e.g., phenyl) optionally substituted by 1 to 3 halogen atoms (e.g., a fluorine atom, a chlorine atom, a bromine atom),
  (e) a $C_{6-14}$ aryloxy group (e.g., phenoxy),
  (f) a $C_{7-16}$ aralkyl group (e.g., benzyl), and
  (g) a $C_{7-16}$ aralkyloxy group (e.g., benzyloxy),
(2) a pyrrolidine ring optionally further substituted by 1 to 3 substituents selected from
  (a) a halogen atom (e.g., a fluorine atom),
  (b) an optionally halogenated $C_{1-6}$ alkoxy group (e.g., methoxy, trifluoromethoxy),
  (c) a $C_{6-14}$ aryl group (e.g., phenyl) optionally substituted by 1 to 3 substituents selected from
    (i) a halogen atom (e.g., a chlorine atom),
    (ii) an optionally halogenated $C_{1-6}$ alkyl group (e.g., trifluoromethyl), and
    (iii) a $C_{1-6}$ alkoxy group (e.g., methoxy),
  (d) a $C_{7-16}$ aralkyl group (e.g., benzyl), and
  (e) a $C_{7-16}$ aralkyloxy group (e.g., benzyloxy),
(3) a piperidine ring optionally further substituted by 1 to 3 substituents selected from
  (a) a $C_{1-6}$ alkoxy group (e.g., methoxy, ethoxy) optionally substituted by 1 to 3 substituents selected from
    (i) a halogen atom (e.g., a fluorine atom), and
    (ii) a $C_{3-10}$ cycloalkyl group (e.g., cyclopropyl),
  (b) a $C_{6-14}$ aryl group (e.g., phenyl) optionally substituted by 1 to 3 substituents selected from
    (i) a halogen atom (e.g., a chlorine atom), and
    (ii) a $C_{1-6}$ alkoxy group (e.g., methoxy),
  (c) a $C_{6-14}$ aryloxy group (e.g., phenoxy) optionally substituted by 1 to 3 substituents selected from
    (i) a halogen atom (e.g., a fluorine atom, a chlorine atom),
    (ii) a cyano group,
    (iii) an optionally halogenated $C_{1-6}$ alkyl group (e.g., methyl, trifluoromethyl), and
    (iv) an optionally halogenated $C_{1-6}$ alkoxy group (e.g., methoxy, trifluoromethoxy),
  (d) a $C_{7-16}$ aralkyl group (e.g., benzyl),
  (e) a $C_{7-16}$ aralkyloxy group (e.g., benzyloxy),
  (f) a 5- to 14-membered aromatic heterocyclyloxy group (preferably a 5- to 6-membered monocyclic aromatic heterocyclyloxy group (e.g., pyridyloxy, pyrazinyloxy, pyrimidinyloxy, thiazolyloxy)), and
  (g) a 3- to 14-membered non-aromatic heterocyclyloxy group (preferably a 3- to 8-membered monocyclic non-aromatic heterocyclyloxy group (e.g., piperidyloxy)) optionally substituted by 1 to 3 $C_{1-6}$ alkoxy-carbonyl groups (e.g., tert-butoxycarbonyl),
(4) an indoline ring optionally further substituted by 1 to 3 $C_{1-6}$ alkoxy groups (e.g., methoxy),
(5) an isoindoline ring optionally further substituted by 1 to 3 $C_{1-6}$ alkoxy groups (e.g., methoxy),
(6) a tetrahydroquinoline ring optionally further substituted by 1 to 3 $C_{1-6}$ alkoxy groups (e.g., methoxy),
(7) a tetrahydroisoquinoline ring optionally further substituted by 1 to 3 substituents selected from
  (a) a halogen atom (e.g., a chlorine atom, a bromine atom),
  (b) a $C_{1-6}$ alkyl group (e.g., methyl), and
  (c) a $C_{1-6}$ alkoxy group (e.g., methoxy),
(8) a 3-azabicyclo[3.1.0]hexane ring optionally further substituted by 1 to 3 substituents selected from
  (a) a halogen atom (e.g., a fluorine atom),
  (b) a $C_{1-6}$ alkyl group (e.g., methyl) optionally substituted by 1 to 3 substituents selected from
    (i) a halogen atom (e.g., a fluorine atom),
    (ii) a cyano group,
    (iii) a $C_{1-6}$ alkoxy group (e.g., methoxy), and
    (iv) a mono- or di-$C_{1-6}$ alkylamino group (e.g., dimethylamino),
  (c) a $C_{6-14}$ aryl group (e.g., phenyl, naphthyl) optionally substituted by 1 to 3 substituents selected from
    (i) a halogen atom (e.g., a fluorine atom, a chlorine atom),
    (ii) an optionally halogenated $C_{1-6}$ alkyl group (e.g., methyl, trifluoromethyl), and
    (iii) an optionally halogenated $C_{1-6}$ alkoxy group (e.g., methoxy, trifluoromethoxy), and
  (d) a 5- to 14-membered aromatic heterocyclic group (preferably a 5- to 6-membered monocyclic aromatic heterocyclic group (e.g., thienyl)),
(9) a 3-azabicyclo[4.1.0]heptane ring optionally further substituted by 1 to 3 substituents selected from
  (a) a halogen atom (e.g., a fluorine atom), and
  (b) a $C_{6-14}$ aryl group (e.g., phenyl) optionally substituted by 1 to 3 substituents selected from
    (i) a halogen atom (e.g., a chlorine atom),
    (ii) a $C_{1-6}$ alkyl group (e.g., methyl), and
    (iii) a $C_{1-6}$ alkoxy group (e.g., methoxy),
(10) a 1-azaspiro[3.3]heptane ring,
(11) a 6-oxa-1-azaspiro[3.5]nonane ring,
(12) a 6-oxa-1-azaspiro[3.3]heptane ring, or
(13) a 6-oxa-1-azaspiro[3.4]octane ring.
[Compound D-1]
  Compound (I) wherein
Ring A is pyrrole, pyrazole, thiophene or furan;
Ring B is dihydropyridine, tetrahydropyridine or tetrahydropyrazine;

W is $NR^6$ wherein $R^6$ is a $C_{1-6}$ alkyl group (e.g., methyl, ethyl) or a benzyl group, N, O or S;

X is $CR^7$ wherein $R^7$ is a hydrogen atom or a $C_{1-6}$ alkyl group (e.g., methyl), $NR^8$ wherein $R^8$ is a $C_{1-6}$ alkyl group (e.g., methyl), or N;

Y is C;

$Z^1$—$Z^2$ is C=C, C—C or C—N;

[preferably, the partial structure represented by the following formula:

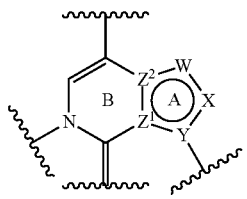

is a partial structure represented by the following formula:

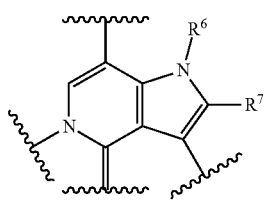

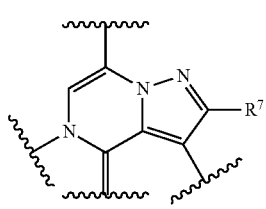

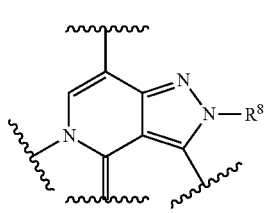

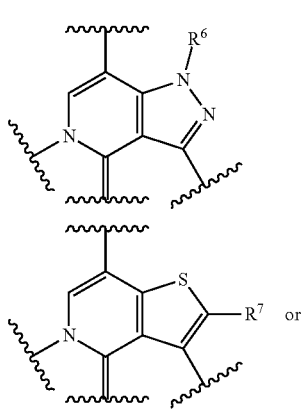 or

-continued

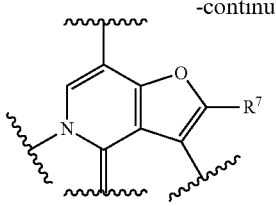

wherein $R^6$ is a $C_{1-6}$ alkyl group (e.g., methyl, ethyl) or a benzyl group, $R^7$ is a hydrogen atom or a $C_{1-6}$ alkyl group (e.g., methyl), and $R^8$ is a $C_{1-6}$ alkyl group (e.g., methyl)]

$R^1$ is (1) a $C_{1-6}$ alkyl group (e.g., methyl, ethyl) optionally substituted by 1 to 3 substituents selected from
 (a) a halogen atom (e.g., a fluorine atom), and
 (b) a cyano group, or
(2) a phenyl group optionally substituted by 1 to 3 substituents selected from
 (a) an optionally halogenated $C_{1-6}$ alkoxy group (e.g., methoxy, 2,2,2-trifluoroethoxy), and
 (b) a halogen atom (e.g., a fluorine atom);

as to $R^2$ (1) when W is $NR^6$ or N, then $R^2$ is a hydrogen atom, a halogen atom (e.g., a chlorine atom, a bromine atom), a $C_{1-6}$ alkyl group (e.g., methyl, ethyl), a $C_{3-6}$ cycloalkyl group (e.g., cyclopropyl) or a phenyl group, (2) when W is O or S, then $R^2$ is a $C_{1-6}$ alkyl group (e.g., methyl); and $R^3$ and $R^4$ are each independently
(1) a hydrogen atom,
(2) a $C_{1-6}$ alkyl group (e.g., methyl, isopropyl, tert-butyl) optionally substituted by 1 to 3 substituents selected from
 (a) a halogen atom (e.g., a fluorine atom),
 (b) a cyano group,
 (c) a $C_{3-6}$ cycloalkyl group (e.g., cyclopropyl, cyclohexyl),
 (d) a phenyl group optionally substituted by 1 to 3 halogen atoms (e.g., a chlorine atom),
 (e) a pyridyl group optionally substituted by 1 to 3 $C_{1-6}$ alkoxy groups (e.g., methoxy),
 (f) a pyrazolyl group optionally substituted by 1 to 3 substituents selected from
  (i) a $C_{1-6}$ alkyl group (e.g., methyl), and
  (ii) a phenyl group optionally substituted by 1 to 3 substituents selected from a halogen atom (e.g., a chlorine atom) and a $C_{1-6}$ alkyl group (e.g., methyl),
 (g) a triazolyl group optionally substituted by 1 or 2 substituents selected from
  (i) a $C_{1-6}$ alkyl group (e.g., methyl), and
  (ii) a phenyl group,
 (h) an oxadiazolyl group optionally substituted by phenyl group(s) optionally substituted by 1 to 3 halogen atoms (e.g., a chlorine atom),
 (i) a thiazolyl group optionally substituted by 1 or 2 substituents selected from
  (i) a $C_{1-6}$ alkyl group (e.g., methyl), and
  (ii) a phenyl group, and
 (j) a thienyl group optionally substituted by 1 to 3 phenyl groups optionally substituted by 1 to 3 halogen atoms (e.g., a chlorine atom),
(3) a $C_{3-6}$ cycloalkyl group (e.g., cyclopropyl, cyclobutyl, cyclopentyl, cyclohexyl) optionally substituted by 1 to 3 substituents selected from
 (a) a halogen atom (e.g., a fluorine atom),
 (b) a cyano group, (c) an optionally halogenated $C_{1-6}$ alkyl group (e.g., trifluoromethyl),
(d) a $C_{1-6}$ alkoxy group (e.g., methoxy, propoxy, butoxy),
(e) a $C_{1-6}$ alkoxy-carbonylamino group (e.g., tert-butoxycarbonylamino),
(f) a phenyl group optionally substituted by 1 to 3 halogen atoms (e.g., a chlorine atom),
(g) a phenoxy group,
(h) a benzyloxy group, and
(i) a pyridyl group,
(4) a bicyclo[1.1.1]pentyl group (e.g., bicyclo[1.1.1]pentan-1-yl) optionally substituted by 1 to 3 substituents selected from
(a) an optionally halogenated $C_{1-6}$ alkyl group (e.g., trifluoromethyl), and
(b) a phenyl group,
(5) an indanyl group (e.g., indan-1-yl) optionally substituted by 1 to 3 halogen atoms (e.g., a chlorine atom),
(6) a tetrahydronaphthyl group (e.g., 1,2,3,4-tetrahydronaphthalen-2-yl),
(7) a dihydrobenzocyclobutenyl group (e.g., dihydrobenzocyclobuten-1-yl,
(8) a phenyl group optionally substituted by 1 to 3 substituents selected from
(a) a $C_{1-6}$ alkyl group (e.g., ethyl),
(b) a $C_{1-6}$ alkoxy group (e.g., methoxy, ethoxy),
(c) a phenoxy group,
(d) a benzyloxy group, and
(e) a morpholinyl group,
(9) a pyrazolyl group optionally substituted by 1 to 3 substituents selected from
(a) an optionally halogenated $C_{1-6}$ alkyl group (e.g., methyl, trifluoromethyl, 2,2,2-trifluoroethyl), and
(b) a benzyl group optionally substituted by 1 to 3 halogen atoms (e.g., a fluorine atom),
(10) an imidazolyl group optionally substituted by 1 to 3 phenyl groups,
(11) a pyridyl group optionally substituted by 1 to 3 substituents selected from
(a) a cyano group,
(b) an optionally halogenated $C_{1-6}$ alkyl group (e.g., trifluoromethyl),
(c) a $C_{1-6}$ alkoxy group (e.g., methoxy), and
(d) a phenoxy group,
(12) a pyrrolidinyl group optionally substituted by 1 to 3 benzyl groups,
(13) a piperidyl group optionally substituted by 1 to 3 substituents selected from
(a) a $C_{1-6}$ alkyl group (e.g., methyl) optionally substituted by 1 to 3 $C_{3-6}$ cycloalkyl groups (e.g., cyclopropyl),
(b) a $C_{1-6}$ alkoxy-carbonyl group (e.g., tert-butoxycarbonyl),
(c) a phenyl group optionally substituted by 1 to 3 halogen atoms (e.g., a fluorine atom, a chlorine atom), and
(d) a benzyl group,
(14) a tetrahydrofuryl group optionally substituted by 1 to 3 phenyl groups, or
(15) a dihydrochromenyl group (e.g., 3,4-dihydro-2H-chromen-4-yl) optionally substituted by 1 to 3 $C_{1-6}$ alkyl groups (e.g., methyl), or
$R^3$ and $R^4$ are bonded to each other to form, together with the adjacent nitrogen atom,
(1) an azetidine ring optionally further substituted by 1 to 3 substituents selected from
(a) a $C_{1-6}$ alkyl group (e.g., methyl, isopropyl) optionally substituted by 1 to 3 $C_{1-6}$ alkoxy groups (e.g., methoxy),
(b) an optionally halogenated $C_{1-6}$ alkoxy group (e.g., methoxy, difluoromethoxy),
(c) a $C_{3-6}$ cycloalkyl group (e.g., cyclopropyl),
(d) a phenyl group optionally substituted by 1 to 3 halogen atoms (e.g., a fluorine atom, a chlorine atom, a bromine atom),
(e) a phenoxy group,
(f) a benzyl group, and
(g) a benzyloxy group,
(2) a pyrrolidine ring optionally further substituted by 1 to 3 substituents selected from
(a) a halogen atom (e.g., a fluorine atom),
(b) an optionally halogenated $C_{1-6}$ alkoxy group (e.g., methoxy, trifluoromethoxy),
(c) a phenyl group optionally substituted by 1 to 3 substituents selected from
(i) a halogen atom (e.g., a chlorine atom),
(ii) an optionally halogenated $C_{1-6}$ alkyl group (e.g., trifluoromethyl), and
(iii) a $C_{1-6}$ alkoxy group (e.g., methoxy),
(d) a benzyl group, and
(e) a benzyloxy group,
(3) a piperidine ring optionally further substituted by 1 to 3 substituents selected from
(a) a $C_{1-6}$ alkoxy group (e.g., methoxy, ethoxy) optionally substituted by 1 to 3 substituents selected from
(i) a halogen atom (e.g., a fluorine atom), and
(ii) a $C_{3-6}$ cycloalkyl group (e.g., cyclopropyl),
(b) a phenyl group optionally substituted by 1 to 3 substituents selected from
(i) a halogen atom (e.g., a chlorine atom), and
(ii) a $C_{1-6}$ alkoxy group (e.g., methoxy),
(c) a phenoxy group optionally substituted by 1 to 3 substituents selected from
(i) a halogen atom (e.g., a fluorine atom, a chlorine atom),
(ii) a cyano group,
(iii) an optionally halogenated $C_{1-6}$ alkyl group (e.g., methyl, trifluoromethyl), and
(iv) an optionally halogenated $C_{1-6}$ alkoxy group (e.g., methoxy, trifluoromethoxy),
(d) a benzyl group,
(e) a benzyloxy group,
(f) a pyridyloxy group,
(g) a pyrazinyloxy group,
(h) a pyrimidinyloxy group,
(i) a thiazolyloxy group, and
(j) a piperidyloxy group optionally substituted by 1 to 3 $C_{1-6}$ alkoxy-carbonyl groups (e.g., tert-butoxycarbonyl),
(4) an indoline ring optionally further substituted by 1 to 3 $C_{1-6}$ alkoxy groups (e.g., methoxy),
(5) an isoindoline ring optionally further substituted by 1 to 3 $C_{1-6}$ alkoxy groups (e.g., methoxy),
(6) a tetrahydroquinoline ring optionally further substituted by 1 to 3 $C_{1-6}$ alkoxy groups (e.g., methoxy),
(7) a tetrahydroisoquinoline ring optionally further substituted by 1 to 3 substituents selected from
(a) a halogen atom (e.g., a chlorine atom, a bromine atom),
(b) a $C_{1-6}$ alkyl group (e.g., methyl), and
(c) a $C_{1-6}$ alkoxy group (e.g., methoxy),
(8) a 3-azabicyclo[3.1.0]hexane ring optionally further substituted by 1 to 3 substituents selected from
(a) a halogen atom (e.g., a fluorine atom),
(b) a $C_{1-6}$ alkyl group (e.g., methyl) optionally substituted by 1 to 3 substituents selected from (i) a halogen atom (e.g., a fluorine atom),
(ii) a cyano group,
(iii) a $C_{1-6}$ alkoxy group (e.g., methoxy), and
(iv) a mono- or di-$C_{1-6}$ alkylamino group (e.g., dimethylamino),
(c) a phenyl group optionally substituted by 1 to 3 substituents selected from
(i) a halogen atom (e.g., a fluorine atom, a chlorine atom),
(ii) an optionally halogenated $C_{1-6}$ alkyl group (e.g., methyl, trifluoromethyl), and
(iii) an optionally halogenated $C_{1-6}$ alkoxy group (e.g., methoxy, trifluoromethoxy),
(d) a naphthyl group, and
(e) a thienyl group,
(9) a 3-azabicyclo[4.1.0]heptane ring optionally further substituted by 1 to 3 substituents selected from
(a) a halogen atom (e.g., a fluorine atom), and
(b) a phenyl group optionally substituted by 1 to 3 substituents selected from
(i) a halogen atom (e.g., a chlorine atom),
(ii) a $C_{1-6}$ alkyl group (e.g., methyl), and
(iii) a $C_{1-6}$ alkoxy group (e.g., methoxy),
(10) a 1-azaspiro[3.3]heptane ring,
(11) a 6-oxa-1-azaspiro[3.5]nonane ring,
(12) a 6-oxa-1-azaspiro[3.3]heptane ring, or
(13) a 6-oxa-1-azaspiro[3.4]octane ring.
[Compound E-1]
Compound (I) wherein
Ring A is pyrrole or pyrazole;
Ring B is dihydropyridine or tetrahydropyrazine;
W is $NR^6$ wherein $R^6$ is a $C_{1-6}$ alkyl group (e.g., methyl), or N;
X is CH or N;
Y is C;
$Z^1$—$Z^2$ is C═C or C—N;
[preferably, the partial structure represented by the following formula:

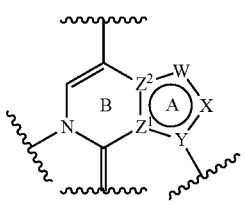

is a partial structure represented by the following formula:

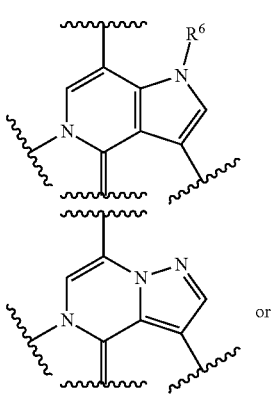

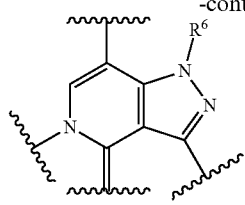

wherein $R^6$ is a $C_{1-6}$ alkyl group (e.g., methyl)]
$R^1$ is
(1) a $C_{1-6}$ alkyl group (e.g., methyl, ethyl) optionally substituted by 1 to 3 substituents selected from
(a) a halogen atom (e.g., a fluorine atom), and
(b) a cyano group, or
(2) a phenyl group optionally substituted by 1 to 3 substituents selected from
(a) an optionally halogenated $C_{1-6}$ alkoxy group (e.g., methoxy, 2,2,2-trifluoroethoxy), and
(b) a halogen atom (e.g., a fluorine atom);
$R^2$ is a hydrogen atom or a $C_{1-6}$ alkyl group (e.g., methyl);
$R^3$ is a hydrogen atom, and
$R^4$ is
(1) a $C_{1-6}$ alkyl group (e.g., methyl, isopropyl) optionally substituted by 1 to 3 substituents selected from
(a) a phenyl group optionally substituted by 1 to 3 halogen atoms (e.g., a chlorine atom),
(b) an oxadiazolyl group optionally substituted by phenyl group(s) optionally substituted by 1 to 3 halogen atoms (e.g., a chlorine atom), and
(c) a thienyl group optionally substituted by 1 to 3 phenyl groups optionally substituted by 1 to 3 halogen atoms (e.g., a chlorine atom),
(2) a $C_{3-6}$ cycloalkyl group (e.g., cyclobutyl, cyclopentyl, cyclohexyl) optionally substituted by 1 to 3 substituents selected from
(a) a $C_{1-6}$ alkoxy group (e.g., butoxy), and
(b) a phenyl group optionally substituted by 1 to 3 halogen atoms (e.g., a chlorine atom),
(3) a phenyl group optionally substituted by 1 to 3 substituents selected from
(a) a benzyloxy group, and
(b) a morpholinyl group, or
(4) a pyridyl group optionally substituted by 1 to 3 substituents selected from
(a) a cyano group, and
(b) a $C_{1-6}$ alkoxy group (e.g., methoxy), or
$R^3$ and $R^4$ are bonded to each other to form, together with the adjacent nitrogen atom,
(1) an azetidine ring optionally further substituted by 1 to 3 phenyl groups,
(2) a pyrrolidine ring optionally further substituted by 1 to 3 substituents selected from
(a) a halogen atom (e.g., a fluorine atom), and
(b) a phenyl group optionally substituted by 1 to 3 halogen atoms (e.g., a chlorine atom),
(3) a piperidine ring optionally further substituted by 1 to 3 substituents selected from
(a) a phenyl group optionally substituted by 1 to 3 halogen atoms (e.g., a chlorine atom), and
(b) a phenoxy group optionally substituted by 1 to 3 substituents selected from
(i) a halogen atom (e.g., a chlorine atom),
(ii) an optionally halogenated $C_{1-6}$ alkyl group (e.g., trifluoromethyl), and (iii) an optionally halogenated $C_{1-6}$ alkoxy group (e.g., trifluoromethoxy), or
(4) a 3-azabicyclo[3.1.0]hexane ring optionally further substituted by 1 to 3 substituents selected from
  (a) a halogen atom (e.g., a fluorine atom),
  (b) a phenyl group optionally substituted by 1 to 3 substituents selected from
    (i) a halogen atom (e.g., a fluorine atom, a chlorine atom),
    (ii) an optionally halogenated $C_{1-6}$ alkyl group (e.g., methyl, trifluoromethyl), and
    (iii) an optionally halogenated $C_{1-6}$ alkoxy group (e.g., methoxy, trifluoromethoxy), and
  (c) a naphthyl group.

[Compound F-1]

The above-mentioned Compound E wherein
$R^1$ is
(1) a $C_{1-6}$ alkyl group (e.g., methyl) optionally substituted by 1 to 3 cyano groups, or
(2) a phenyl group optionally substituted by 1 to 3 of optionally halogenated $C_{1-6}$ alkoxy groups (e.g., methoxy, 2,2,2-trifluoroethoxy); and
$R^4$ is
(1) a $C_{3-6}$ cycloalkyl group (e.g., cyclohexyl) optionally substituted by 1 to 3 $C_{1-6}$ alkoxy groups (e.g., butoxy), or
(2) a phenyl group optionally substituted by 1 to 3 morpholinyl groups.

[Compound A-2]

Compound (I) wherein
Ring A is a 5-membered aromatic heterocycle;
Ring B is an optionally further substituted 6-membered nitrogen-containing non-aromatic heterocycle;
W is $NR^6$ wherein $R^6$ is an optionally substituted $C_{1-6}$ alkyl group (e.g., methyl, ethyl) or an optionally substituted $C_{7-16}$ aralkyl group (e.g., benzyl), N, O or S;
X is $CR^7$ wherein $R^7$ is a hydrogen atom or an optionally substituted $C_{1-6}$ alkyl group (e.g., methyl), $NR^8$ wherein $R^8$ is an optionally substituted $C_{1-6}$ alkyl group (e.g., methyl), or N;
Y is C;
$Z^1$ and $Z^2$ are each independently C or N;
$R^1$ is an optionally substituted $C_{1-6}$ alkyl group (e.g., methyl, ethyl), an optionally substituted $C_{6-14}$ aryl group (e.g., phenyl) or an optionally substituted $C_{7-16}$ aralkyl group (e.g., benzyl);
as to $R^2$
(1) when W is $NR^6$ or N, then $R^2$ is a hydrogen atom, a halogen atom (e.g., a chlorine atom, a bromine atom), an optionally substituted $C_{1-6}$ alkyl group (e.g., methyl, ethyl), an optionally substituted $C_{3-10}$ cycloalkyl group (e.g., cyclopropyl) or an optionally substituted $C_{6-14}$ aryl group (e.g., phenyl),
(2) when W is O or S, then $R^2$ is an optionally substituted $C_{1-6}$ alkyl group (e.g., methyl); and
$R^3$ and $R^4$ are each independently
(1) a hydrogen atom,
(2) an optionally substituted $C_{1-6}$ alkyl group (e.g., methyl, isopropyl, tert-butyl),
(3) a $C_{3-10}$ cycloalkyl group optionally fused with a benzene ring (the $C_{3-10}$ cycloalkyl may be a bridged ring group, e.g., cyclopropyl, cyclobutyl, cyclopentyl, cyclohexyl, bicyclo[1.1.1]pentyl (e.g., bicyclo[1.1.1]pentan-1-yl), indanyl (e.g., indan-1-yl), tetrahydronaphthyl (e.g., 1,2,3,4-tetrahydronaphthalen-2-yl), dihydrobenzocyclobutenyl (e.g., dihydrobenzocyclobuten-1-yl)), which is and optionally substituted,
(4) an optionally substituted $C_{6-14}$ aryl group (e.g., phenyl),
(5) an optionally substituted 5- to 14-membered aromatic heterocyclic group (preferably a 5- to 6-membered monocyclic aromatic heterocyclic group (e.g., pyrazolyl, imidazolyl, pyridyl)), or
(6) an optionally substituted 3- to 14-membered non-aromatic heterocyclic group (preferably a 3- to 8-membered monocyclic non-aromatic heterocyclic group (e.g., pyrrolidinyl, piperidyl, tetrahydrofuryl), or a 9- to 14-membered fused polycyclic (preferably bi- or tri-cyclic) non-aromatic heterocyclic group (e.g., dihydrochromenyl (e.g., 3,4-dihydro-2H-chromen-4-yl))), or
$R^3$ and $R^4$ are bonded to each other to form, together with the adjacent nitrogen atom, an optionally further substituted 3- to 14-membered non-aromatic nitrogen-containing heterocycle (preferably a 3- to 8-membered monocyclic non-aromatic nitrogen-containing heterocycle (e.g., azetidine, pyrrolidine, piperidine), a 9- to 14-membered fused polycyclic (preferably bi- or tri-cyclic) non-aromatic nitrogen-containing heterocycle (e.g., indoline, isoindoline, tetrahydroquinoline, tetrahydroisoquinoline), a 6- to 9-membered nitrogen-containing bridged ring (e.g., 3-azabicyclo[3.1.0]hexane, 3-azabicyclo[4.1.0]heptane), or a 6- to 9-membered nitrogen-containing spiro ring (e.g., 1-azaspiro[3.3]heptane, 6-oxa-1-azaspiro[3.5]nonane, 6-oxa-1-azaspiro[3.3]heptane, 6-oxa-1-azaspiro[3.4]octane)).

[Compound B-2]

Compound (I) wherein
Ring A is pyrrole, pyrazole, thiophene, furan or imidazole;
Ring B is dihydropyridine, tetrahydropyridine, tetrahydropyrazine or tetrahydropyrimidine;
W is $NR^6$ wherein $R^6$ is a $C_{1-6}$ alkyl group (e.g., methyl, ethyl) or a $C_{7-16}$ aralkyl group (e.g., benzyl), N, O or S;
X is $CR^7$ wherein $R^7$ is a hydrogen atom or a $C_{1-6}$ alkyl group (e.g., methyl), $NR^8$ wherein $R^8$ is a $C_{1-6}$ alkyl group (e.g., methyl), or N;
Y is C;
$Z^1$—$Z^2$ is C=C, C—C, C—N or N—C;
[preferably, the partial structure represented by the following formula:

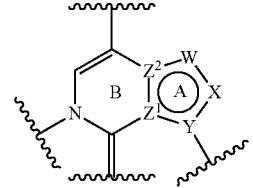

is a partial structure represented by the following formula:

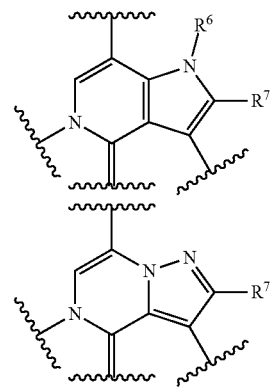

-continued

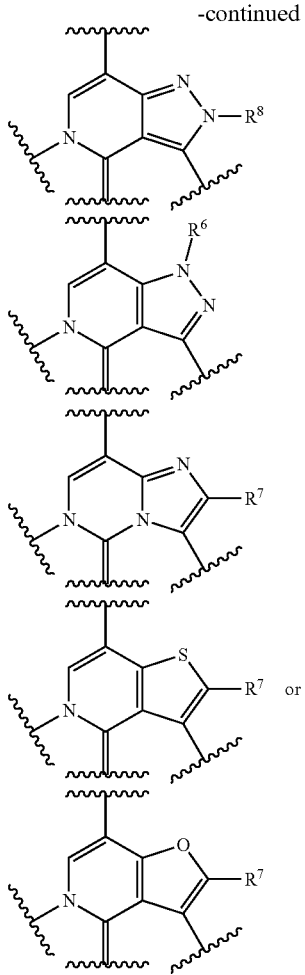

wherein $R^6$ is a $C_{1-6}$ alkyl group (e.g., methyl, ethyl) or a $C_{7-16}$ aralkyl group (e.g., benzyl), $R^7$ is a hydrogen atom or a $C_{1-6}$ alkyl group (e.g., methyl), and $R^8$ is a $C_{1-6}$ alkyl group (e.g., methyl)]

$R^1$ is (1) a $C_{1-6}$ alkyl group (e.g., methyl, ethyl) optionally substituted by 1 to 3 substituents selected from
  (a) a halogen atom (e.g., a fluorine atom), and
  (b) a cyano group,
(2) a $C_{6-14}$ aryl group (e.g., phenyl) optionally substituted by 1 to 3 substituents selected from
  (a) an optionally halogenated $C_{1-6}$ alkoxy group (e.g., methoxy, 2,2,2-trifluoroethoxy), and
  (b) a halogen atom (e.g., a fluorine atom), or
(3) a $C_{7-16}$ aralkyl group (e.g., benzyl) optionally substituted by 1 to 3 $C_{1-6}$ alkoxy groups (e.g., methoxy);

as to $R^2$ (1) when W is $NR^6$ or N, then $R^2$ is a hydrogen atom, a halogen atom (e.g., a chlorine atom, a bromine atom), a $C_{1-6}$ alkyl group (e.g., methyl, ethyl), a $C_{3-10}$ cycloalkyl group (e.g., cyclopropyl) or a $C_{6-14}$ aryl group (e.g., phenyl),
(2) when W is O or S, then $R^2$ is a $C_{1-6}$ alkyl group (e.g., methyl); and $R^3$ and $R^4$ are each independently
(1) a hydrogen atom,
(2) a $C_{1-6}$ alkyl group (e.g., methyl, isopropyl, tert-butyl) optionally substituted by 1 to 3 substituents selected from
  (a) a halogen atom (e.g., a fluorine atom),
  (b) a cyano group,
  (c) a $C_{3-10}$ cycloalkyl group (e.g., cyclopropyl, cyclohexyl),
  (d) a $C_{6-14}$ aryl group (e.g., phenyl) optionally substituted by 1 to 3 halogen atoms (e.g., a chlorine atom), and
  (e) a 5- to 14-membered aromatic heterocyclic group (preferably a 5- to 6-membered monocyclic aromatic heterocyclic group (e.g., pyridyl, pyrazolyl, triazolyl, oxadiazolyl, thiazolyl, thienyl)) optionally substituted by 1 to 3 substituents selected from
    (i) a $C_{1-6}$ alkyl group (e.g., methyl),
    (ii) a $C_{1-6}$ alkoxy group (e.g., methoxy), and
    (iii) a $C_{6-14}$ aryl group (e.g., phenyl) optionally substituted by 1 to 3 substituents selected from a halogen atom (e.g., a chlorine atom) and a $C_{1-6}$ alkyl group (e.g., methyl),
(3) a $C_{3-10}$ cycloalkyl group optionally fused with a benzene ring (the $C_{3-10}$ cycloalkyl may be a bridged ring group, e.g., cyclopropyl, cyclobutyl, cyclopentyl, cyclohexyl, bicyclo[1.1.1]pentyl (e.g., bicyclo[1.1.1]pentan-1-yl), indanyl (e.g., indan-1-yl), tetrahydronaphthyl (e.g., 1,2,3,4-tetrahydronaphthalen-2-yl), dihydrobenzocyclobutenyl (e.g., dihydrobenzocyclobuten-1-yl)), which is optionally substituted by 1 to 3 substituents selected from
  (a) a halogen atom (e.g., a fluorine atom, a chlorine atom),
  (b) a cyano group,
  (c) an optionally halogenated $C_{1-6}$ alkyl group (e.g., trifluoromethyl),
  (d) a $C_{1-6}$ alkoxy group (e.g., methoxy, propoxy, butoxy),
  (e) a $C_{1-6}$ alkoxy-carbonylamino group (e.g., tert-butoxycarbonylamino),
  (f) a $C_{6-14}$ aryl group (e.g., phenyl) optionally substituted by 1 to 3 halogen atoms (e.g., a chlorine atom),
  (g) a $C_{6-14}$ aryloxy group (e.g., phenoxy),
  (h) a $C_{7-16}$ aralkyloxy group (e.g., benzyloxy), and
  (i) a 5- to 14-membered aromatic heterocyclic group (preferably a 5- to 6-membered monocyclic aromatic heterocyclic group (e.g., pyridyl)),
(4) a $C_{6-14}$ aryl group (e.g., phenyl) optionally substituted by 1 to 3 substituents selected from
  (a) a $C_{1-6}$ alkyl group (e.g., ethyl, isopropyl) optionally substituted by 1 to 3 hydroxy groups,
  (b) a $C_{1-6}$ alkoxy group (e.g., methoxy, ethoxy),
  (c) a $C_{6-14}$ aryloxy group (e.g., phenoxy),
  (d) a $C_{7-16}$ aralkyloxy group (e.g., benzyloxy), and
  (e) a 3- to 14-membered non-aromatic heterocyclic group (preferably a 3- to 8-membered monocyclic non-aromatic heterocyclic group (e.g., morpholinyl)),
(5) a 5- to 14-membered aromatic heterocyclic group (preferably a 5- to 6-membered monocyclic aromatic heterocyclic group (e.g., pyrazolyl, imidazolyl, pyridyl)) optionally substituted by 1 to 3 substituents selected from
  (a) a cyano group,
  (b) an optionally halogenated $C_{1-6}$ alkyl group (e.g., methyl, trifluoromethyl, 2,2,2-trifluoroethyl),
  (c) an optionally halogenated $C_{1-6}$ alkoxy group (e.g., methoxy, difluoromethoxy, 2,2,2-trifluoroethoxy),
  (d) a $C_{6-14}$ aryl group (e.g., phenyl),
  (e) a $C_{6-14}$ aryloxy group (e.g., phenoxy),
  (f) a $C_{7-16}$ aralkyl group (e.g., benzyl) optionally substituted by 1 to 3 halogen atoms (e.g., a fluorine atom), and
  (g) a $C_{3-10}$ cycloalkyl group (e.g., cyclopropyl), or
(6) a 3- to 14-membered non-aromatic heterocyclic group (preferably a 3- to 8-membered monocyclic non-aromatic heterocyclic group (e.g., pyrrolidinyl, piperidyl, tetrahydrofuryl), or a 9- to 14-membered fused polycyclic (preferably bi- or tri-cyclic) non-aromatic heterocyclic group (e.g., dihydrochromenyl (e.g., 3,4-dihydro-2H-chromen-4-yl))) optionally substituted by 1 to 3 substituents selected from
  (a) a $C_{1-6}$ alkyl group (e.g., methyl) optionally substituted by 1 to 3 $C_{3-10}$ cycloalkyl groups (e.g., cyclopropyl),
  (b) a $C_{1-6}$ alkoxy-carbonyl group (e.g., tert-butoxycarbonyl),
  (c) a $C_{6-14}$ aryl group (e.g., phenyl) optionally substituted by 1 to 3 halogen atoms (e.g., a fluorine atom, a chlorine atom), and
  (d) a $C_{7-16}$ aralkyl group (e.g., benzyl), or $R^3$ and $R^4$ are bonded to each other to form, together with the adjacent nitrogen atom, a 3- to 14-membered non-aromatic nitrogen-containing heterocycle (preferably a 3- to 8-membered monocyclic non-aromatic nitrogen-containing heterocycle (e.g., azetidine, pyrrolidine, piperidine), a 9- to 14-membered fused polycyclic (preferably bi- or tri-cyclic) non-aromatic nitrogen-containing heterocycle (e.g., indoline, isoindoline, tetrahydroquinoline, tetrahydroisoquinoline), a 6- to 9-membered nitrogen-containing bridged ring (e.g., 3-azabicyclo[3.1.0]hexane, 3-azabicyclo[4.1.0]heptane), or a 6- to 9-membered nitrogen-containing spiro ring (e.g., 1-azaspiro[3.3]heptane, 6-oxa-1-azaspiro[3.5]nonane, 6-oxa-1-azaspiro[3.3]heptane, 6-oxa-1-azaspiro[3.4]octane)) optionally further substituted by 1 to 3 substituents selected from
  (a) a halogen atom (e.g., a fluorine atom, a chlorine atom, a bromine atom),
  (b) a $C_{1-6}$ alkyl group (e.g., methyl, isopropyl) optionally substituted by 1 to 3 substituents selected from
    (i) a halogen atom (e.g., a fluorine atom),
    (ii) a cyano group,
    (iii) a $C_{1-6}$ alkoxy group (e.g., methoxy), and
    (iv) a mono- or di-$C_{1-6}$ alkylamino group (e.g., dimethylamino),
  (c) a $C_{1-6}$ alkoxy group (e.g., methoxy, ethoxy) optionally substituted by 1 to 3 substituents selected from
    (i) a halogen atom (e.g., a fluorine atom), and
    (ii) a $C_{3-10}$ cycloalkyl group (e.g., cyclopropyl),
  (d) a $C_{3-10}$ cycloalkyl group (e.g., cyclopropyl),
  (e) a $C_{6-14}$ aryl group (e.g., phenyl, naphthyl) optionally substituted by 1 to 3 substituents selected from
    (i) a halogen atom (e.g., a fluorine atom, a chlorine atom, a bromine atom),
    (ii) an optionally halogenated $C_{1-6}$ alkyl group (e.g., methyl, trifluoromethyl), and
    (iii) an optionally halogenated $C_{1-6}$ alkoxy group (e.g., methoxy, trifluoromethoxy),
  (f) a $C_{6-14}$ aryloxy group (e.g., phenoxy) optionally substituted by 1 to 3 substituents selected from
    (i) a halogen atom (e.g., a fluorine atom, a chlorine atom),
    (ii) a cyano group,
    (iii) an optionally halogenated $C_{1-6}$ alkyl group (e.g., methyl, trifluoromethyl), and
    (iv) an optionally halogenated $C_{1-6}$ alkoxy group (e.g., methoxy, trifluoromethoxy),
  (g) a $C_{7-16}$ aralkyl group (e.g., benzyl),
  (h) a $C_{7-16}$ aralkyloxy group (e.g., benzyloxy),
  (i) a 5- to 14-membered aromatic heterocyclic group (preferably a 5- to 6-membered monocyclic aromatic heterocyclic group (e.g., thienyl, pyrazolyl, pyridyl, pyrimidinyl)) optionally substituted by 1 to 3 substituents selected from
    (i) a halogen atom (e.g., a chlorine atom), and
    (ii) an optionally halogenated $C_{1-6}$ alkyl group (e.g., 2,2,2-trifluoroethyl),
  (j) a 5- to 14-membered aromatic heterocyclyloxy group (preferably a 5- to 6-membered monocyclic aromatic heterocyclyloxy group (e.g., pyridyloxy, pyrazinyloxy, pyrimidinyloxy, thiazolyloxy)), and
  (k) a 3- to 14-membered non-aromatic heterocyclyloxy group (preferably a 3- to 8-membered monocyclic non-aromatic heterocyclyloxy group (e.g., piperidyloxy)) optionally substituted by 1 to 3 $C_{1-6}$ alkoxy-carbonyl groups (e.g., tert-butoxycarbonyl).

[Compound C-2]
Compound (I) wherein
Ring A is pyrrole, pyrazole, thiophene, furan or imidazole;
Ring B is dihydropyridine, tetrahydropyridine, tetrahydropyrazine or tetrahydropyrimidine;
W is $NR^6$ wherein $R^6$ is a $C_{1-6}$ alkyl group (e.g., methyl, ethyl) or a benzyl group, N, O or S;
X is $CR^7$ wherein $R^7$ is a hydrogen atom or a $C_{1-6}$ alkyl group (e.g., methyl), $NR^6$ wherein $R^8$ is a $C_{1-6}$ alkyl group (e.g., methyl), or N;
Y is C;
$Z^1$—$Z^2$ is C═C, C—C, C—N or N—C;
[preferably, the partial structure represented by the following formula:

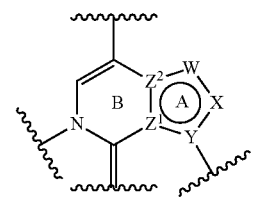

is a partial structure represented by the following formula:

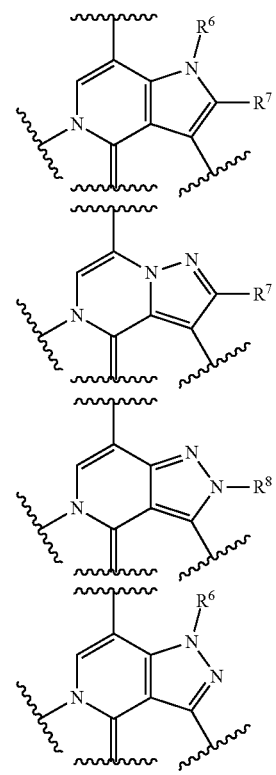

-continued

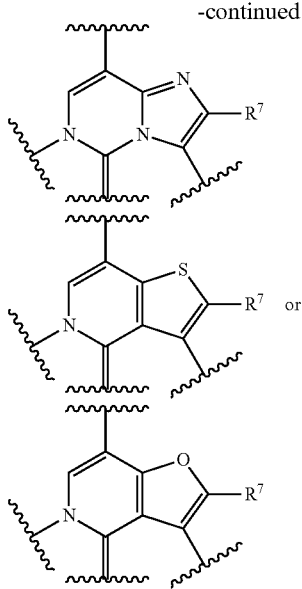

wherein R⁶ is a $C_{1-6}$ alkyl group (e.g., methyl, ethyl) or a benzyl group, R⁷ is a hydrogen atom or a $C_{1-6}$ alkyl group (e.g., methyl), and R⁸ is a $C_{1-6}$ alkyl group (e.g., methyl)]
R¹ is
(1) a $C_{1-6}$ alkyl group (e.g., methyl, ethyl) optionally substituted by 1 to 3 substituents selected from
  (a) a halogen atom (e.g., a fluorine atom), and
  (b) a cyano group,
(2) a phenyl group optionally substituted by 1 to 3 substituents selected from
  (a) an optionally halogenated $C_{1-6}$ alkoxy group (e.g., methoxy, 2,2,2-trifluoroethoxy), and
  (b) a halogen atom (e.g., a fluorine atom), or
(3) a benzyl group optionally substituted by 1 to 3 $C_{1-6}$ alkoxy groups (e.g., methoxy);
as to R²
(1) when W is NR⁶ or N, then R² is a hydrogen atom, a halogen atom (e.g., a chlorine atom, a bromine atom), a $C_{1-6}$ alkyl group (e.g., methyl, ethyl), a $C_{3-6}$ cycloalkyl group (e.g., cyclopropyl) or a phenyl group,
(2) when W is O or S, then R² is a $C_{1-6}$ alkyl group (e.g., methyl); and
R³ and R⁴ are each independently
(1) a hydrogen atom,
(2) a $C_{1-6}$ alkyl group (e.g., methyl, isopropyl, tert-butyl) optionally substituted by 1 to 3 substituents selected from
  (a) a halogen atom (e.g., a fluorine atom),
  (b) a cyano group,
  (c) a $C_{3-10}$ cycloalkyl group (e.g., cyclopropyl, cyclohexyl),
  (d) a $C_{6-14}$ aryl group (e.g., phenyl) optionally substituted by 1 to 3 halogen atoms (e.g., a chlorine atom), and
  (e) a 5- to 14-membered aromatic heterocyclic group (preferably a 5- to 6-membered monocyclic aromatic heterocyclic group (e.g., pyridyl, pyrazolyl, triazolyl, oxadiazolyl, thiazolyl, thienyl)) optionally substituted by 1 to 3 substituents selected from
    (i) a $C_{1-6}$ alkyl group (e.g., methyl),
    (ii) a $C_{1-6}$ alkoxy group (e.g., methoxy), and
    (iii) a $C_{6-14}$ aryl group (e.g., phenyl) optionally substituted by 1 to 3 substituents selected from a halogen atom (e.g., a chlorine atom) and a $C_{1-6}$ alkyl group (e.g., methyl),
(3) a $C_{3-6}$ cycloalkyl group (e.g., cyclopropyl, cyclobutyl, cyclopentyl, cyclohexyl) optionally substituted by 1 to 3 substituents selected from
  (a) a halogen atom (e.g., a fluorine atom),
  (b) a cyano group,
  (c) an optionally halogenated $C_{1-6}$ alkyl group (e.g., trifluoromethyl),
  (d) a $C_{1-6}$ alkoxy group (e.g., methoxy, propoxy, butoxy),
  (e) a $C_{1-6}$ alkoxy-carbonylamino group (e.g., tert-butoxycarbonylamino),
  (f) a $C_{6-14}$ aryl group (e.g., phenyl) optionally substituted by 1 to 3 halogen atoms (e.g., a chlorine atom),
  (g) a $C_{6-14}$ aryloxy group (e.g., phenoxy),
  (h) a $C_{7-16}$ aralkyloxy group (e.g., benzyloxy), and
  (i) a 5- to 14-membered aromatic heterocyclic group (preferably a 5- to 6-membered monocyclic aromatic heterocyclic group (e.g., pyridyl)),
(4) a bicyclo[1.1.1]pentyl group (e.g., bicyclo[1.1.1]pentan-1-yl) optionally substituted by 1 to 3 substituents selected from
  (a) an optionally halogenated $C_{1-6}$ alkyl group (e.g., trifluoromethyl), and
  (b) a $C_{6-14}$ aryl group (e.g., phenyl),
(5) an indanyl group (e.g., indan-1-yl) optionally substituted by 1 to 3 halogen atoms (e.g., a chlorine atom),
(6) a tetrahydronaphthyl group (e.g., 1,2,3,4-tetrahydronaphthalen-2-yl),
(7) a dihydrobenzocyclobutenyl group (e.g., dihydrobenzocyclobuten-1-yl,
(8) a phenyl group optionally substituted by 1 to 3 substituents selected from
  (a) a $C_{1-6}$ alkyl group (e.g., ethyl, isopropyl) optionally substituted by 1 to 3 hydroxy groups,
  (b) a $C_{1-6}$ alkoxy group (e.g., methoxy, ethoxy),
  (c) a $C_{6-14}$ aryloxy group (e.g., phenoxy),
  (d) a $C_{7-16}$ aralkyloxy group (e.g., benzyloxy), and
  (e) a 3- to 14-membered non-aromatic heterocyclic group (preferably a 3- to 8-membered monocyclic non-aromatic heterocyclic group (e.g., morpholinyl)),
(9) a pyrazolyl group optionally substituted by 1 to 3 substituents selected from
  (a) an optionally halogenated $C_{1-6}$ alkyl group (e.g., methyl, trifluoromethyl, 2,2,2-trifluoroethyl), and
  (b) a $C_{7-16}$ aralkyl group (e.g., benzyl) optionally substituted by 1 to 3 halogen atoms (e.g., a fluorine atom),
(10) an imidazolyl group optionally substituted by 1 to 3 $C_{6-14}$ aryl groups (e.g., phenyl),
(11) a pyridyl group optionally substituted by 1 to 3 substituents selected from
  (a) a cyano group,
  (b) an optionally halogenated $C_{1-6}$ alkyl group (e.g., trifluoromethyl),
  (c) an optionally halogenated $C_{1-6}$ alkoxy group (e.g., methoxy, difluoromethoxy, 2,2,2-trifluoroethoxy),
  (d) a $C_{6-14}$ aryloxy group (e.g., phenoxy), and
  (e) a $C_{3-10}$ cycloalkyl group (e.g., cyclopropyl),
(12) a pyrrolidinyl group optionally substituted by 1 to 3 $C_{7-16}$ aralkyl groups (e.g., benzyl),
(13) a piperidyl group optionally substituted by 1 to 3 substituents selected from
  (a) a $C_{1-6}$ alkyl group (e.g., methyl) optionally substituted by 1 to 3 $C_{3-10}$ cycloalkyl groups (e.g., cyclopropyl),
  (b) a $C_{1-6}$ alkoxy-carbonyl group (e.g., tert-butoxycarbonyl), (c) a $C_{6-14}$ aryl group (e.g., phenyl) optionally substituted by 1 to 3 halogen atoms (e.g., a fluorine atom, a chlorine atom), and
(d) a $C_{7-16}$ aralkyl group (e.g., benzyl),
(14) a tetrahydrofuryl group optionally substituted by 1 to 3 $C_{6-14}$ aryl groups (e.g., phenyl), or
(15) a dihydrochromenyl group (e.g., 3,4-dihydro-2H-chromen-4-yl) optionally substituted by 1 to 3 $C_{1-6}$ alkyl groups (e.g., methyl), or
$R^3$ and $R^4$ are bonded to each other to form, together with the adjacent nitrogen atom,
(1) an azetidine ring optionally further substituted by 1 to 3 substituents selected from
 (a) a $C_{1-6}$ alkyl group (e.g., methyl, isopropyl) optionally substituted by 1 to 3 $C_{1-6}$ alkoxy groups (e.g., methoxy),
 (b) an optionally halogenated $C_{1-6}$ alkoxy group (e.g., methoxy, difluoromethoxy),
 (c) a $C_{3-10}$ cycloalkyl group (e.g., cyclopropyl),
 (d) a $C_{6-14}$ aryl group (e.g., phenyl) optionally substituted by 1 to 3 halogen atoms (e.g., a fluorine atom, a chlorine atom, a bromine atom),
 (e) a $C_{6-14}$ aryloxy group (e.g., phenoxy),
 (f) a $C_{7-16}$ aralkyl group (e.g., benzyl), and
 (g) a $C_{7-16}$ aralkyloxy group (e.g., benzyloxy),
(2) a pyrrolidine ring optionally further substituted by 1 to 3 substituents selected from
 (a) a halogen atom (e.g., a fluorine atom),
 (b) an optionally halogenated $C_{1-6}$ alkoxy group (e.g., methoxy, trifluoromethoxy),
 (c) a $C_{6-14}$ aryl group (e.g., phenyl) optionally substituted by 1 to 3 substituents selected from
  (i) a halogen atom (e.g., a chlorine atom),
  (ii) an optionally halogenated $C_{1-6}$ alkyl group (e.g., trifluoromethyl), and
  (iii) a $C_{1-6}$ alkoxy group (e.g., methoxy),
 (d) a $C_{7-16}$ aralkyl group (e.g., benzyl), and
 (e) a $C_{7-16}$ aralkyloxy group (e.g., benzyloxy),
(3) a piperidine ring optionally further substituted by 1 to 3 substituents selected from
 (a) a $C_{1-6}$ alkoxy group (e.g., methoxy, ethoxy) optionally substituted by 1 to 3 substituents selected from
  (i) a halogen atom (e.g., a fluorine atom), and
  (ii) a $C_{3-10}$ cycloalkyl group (e.g., cyclopropyl),
 (b) a $C_{6-14}$ aryl group (e.g., phenyl) optionally substituted by 1 to 3 substituents selected from
  (i) a halogen atom (e.g., a chlorine atom), and
  (ii) a $C_{1-6}$ alkoxy group (e.g., methoxy),
 (c) a $C_{6-14}$ aryloxy group (e.g., phenoxy) optionally substituted by 1 to 3 substituents selected from
  (i) a halogen atom (e.g., a fluorine atom, a chlorine atom),
  (ii) a cyano group,
  (iii) an optionally halogenated $C_{1-6}$ alkyl group (e.g., methyl, trifluoromethyl), and
  (iv) an optionally halogenated $C_{1-6}$ alkoxy group (e.g., methoxy, trifluoromethoxy),
 (d) a $C_{7-16}$ aralkyl group (e.g., benzyl),
 (e) a $C_{7-16}$ aralkyloxy group (e.g., benzyloxy),
 (f) a 5- to 14-membered aromatic heterocyclyloxy group (preferably a 5- to 6-membered monocyclic aromatic heterocyclyloxy group (e.g., pyridyloxy, pyrazinyloxy, pyrimidinyloxy, thiazolyloxy)), and
 (g) a 3- to 14-membered non-aromatic heterocyclyloxy group (preferably a 3- to 8-membered monocyclic non-aromatic heterocyclyloxy group (e.g., piperidyloxy)) optionally substituted by 1 to 3 $C_{1-6}$ alkoxycarbonyl groups (e.g., tert-butoxycarbonyl),
(4) an indoline ring optionally further substituted by 1 to 3 $C_{1-6}$ alkoxy groups (e.g., methoxy),
(5) an isoindoline ring optionally further substituted by 1 to 3 $C_{1-6}$ alkoxy groups (e.g., methoxy),
(6) a tetrahydroquinoline ring optionally further substituted by 1 to 3 $C_{1-6}$ alkoxy groups (e.g., methoxy),
(7) a tetrahydroisoquinoline ring optionally further substituted by 1 to 3 substituents selected from
 (a) a halogen atom (e.g., a chlorine atom, a bromine atom),
 (b) a $C_{1-6}$ alkyl group (e.g., methyl), and
 (c) a $C_{1-6}$ alkoxy group (e.g., methoxy),
(8) a 3-azabicyclo[3.1.0]hexane ring optionally further substituted by 1 to 3 substituents selected from
 (a) a halogen atom (e.g., a fluorine atom),
 (b) a $C_{1-6}$ alkyl group (e.g., methyl) optionally substituted by 1 to 3 substituents selected from
  (i) a halogen atom (e.g., a fluorine atom),
  (ii) a cyano group,
  (iii) a $C_{1-6}$ alkoxy group (e.g., methoxy), and
  (iv) a mono- or di-$C_{1-6}$ alkylamino group (e.g., dimethylamino),
 (c) a $C_{6-14}$ aryl group (e.g., phenyl, naphthyl) optionally substituted by 1 to 3 substituents selected from
  (i) a halogen atom (e.g., a fluorine atom, a chlorine atom),
  (ii) an optionally halogenated $C_{1-6}$ alkyl group (e.g., methyl, trifluoromethyl), and
  (iii) an optionally halogenated $C_{1-6}$ alkoxy group (e.g., methoxy, trifluoromethoxy), and
 (d) a 5- to 14-membered aromatic heterocyclic group (preferably a 5- to 6-membered monocyclic aromatic heterocyclic group (e.g., thienyl, pyrazolyl, pyridyl, pyrimidinyl)) optionally substituted by 1 to 3 substituents selected from
  (i) a halogen atom (e.g., a chlorine atom), and
  (ii) an optionally halogenated $C_{1-6}$ alkyl group (e.g., 2,2,2-trifluoroethyl),
(9) a 3-azabicyclo[4.1.0]heptane ring optionally further substituted by 1 to 3 substituents selected from
 (a) a halogen atom (e.g., a fluorine atom), and
 (b) a $C_{6-14}$ aryl group (e.g., phenyl) optionally substituted by 1 to 3 substituents selected from
  (i) a halogen atom (e.g., a chlorine atom),
  (ii) a $C_{1-6}$ alkyl group (e.g., methyl), and
  (iii) a $C_{1-6}$ alkoxy group (e.g., methoxy),
(10) a 1-azaspiro[3.3]heptane ring,
(11) a 6-oxa-1-azaspiro[3.5]nonane ring,
(12) a 6-oxa-1-azaspiro[3.3]heptane ring, or
(13) a 6-oxa-1-azaspiro[3.4]octane ring.
[Compound D-2]
Compound (I) wherein
Ring A is pyrrole, pyrazole, thiophene, furan or imidazole;
Ring B is dihydropyridine, tetrahydropyridine, tetrahydropyrazine or tetrahydropyrimidine;
W is $NR^6$ wherein $R^6$ is a $C_{1-6}$ alkyl group (e.g., methyl, ethyl) or a benzyl group, N, O or S;
X is $CR^7$ wherein $R^7$ is a hydrogen atom or a $C_{1-6}$ alkyl group (e.g., methyl), $NR^8$ wherein $R^8$ is a $C_{1-6}$ alkyl group (e.g., methyl), or N;
Y is C;
$Z^1$—$Z^2$ is C=C, C—C, C—N or N—C;

[preferably, the partial structure represented by the following formula:

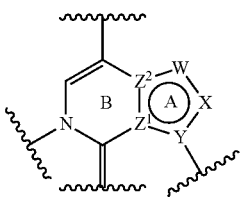

is a the partial structure represented by the following formula:

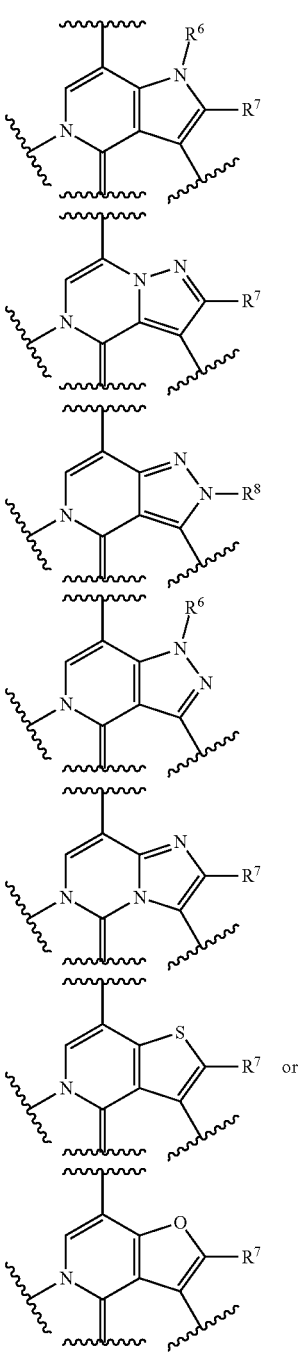

wherein $R^6$ is a $C_{1-6}$ alkyl group (e.g., methyl, ethyl) or a benzyl group, $R^7$ is a hydrogen atom or a $C_{1-6}$ alkyl group (e.g., methyl), and $R^8$ is a $C_{1-6}$ alkyl group (e.g., methyl)]
$R^1$ is
(1) a $C_{1-6}$ alkyl group (e.g., methyl, ethyl) optionally substituted by 1 to 3 substituents selected from
  (a) a halogen atom (e.g., a fluorine atom), and
  (b) a cyano group,
(2) a phenyl group optionally substituted by 1 to 3 substituents selected from
  (a) an optionally halogenated $C_{1-6}$ alkoxy group (e.g., methoxy, 2,2,2-trifluoroethoxy), and
  (b) a halogen atom (e.g., a fluorine atom), or
(3) a benzyl group optionally substituted by 1 to 3 $C_{1-6}$ alkoxy groups (e.g., methoxy);
as to $R^2$
(1) when W is $NR^6$ or N, then $R^2$ is a hydrogen atom, a halogen atom (e.g., a chlorine atom, a bromine atom), a $C_{1-6}$ alkyl group (e.g., methyl, ethyl), a $C_{3-6}$ cycloalkyl group (e.g., cyclopropyl) or a phenyl group,
(2) when W is O or S, then $R^2$ is a $C_{1-6}$ alkyl group (e.g., methyl); and
$R^3$ and $R^4$ are each independently
(1) a hydrogen atom,
(2) a $C_{1-6}$ alkyl group (e.g., methyl, isopropyl, tert-butyl) optionally substituted by 1 to 3 substituents selected from
  (a) a halogen atom (e.g., a fluorine atom),
  (b) a cyano group,
  (c) a $C_{3-6}$ cycloalkyl group (e.g., cyclopropyl, cyclohexyl),
  (d) a phenyl group optionally substituted by 1 to 3 halogen atoms (e.g., a chlorine atom),
  (e) a pyridyl group optionally substituted by 1 to 3 $C_{1-6}$ alkoxy groups (e.g., methoxy),
  (f) a pyrazolyl group optionally substituted by 1 to 3 substituents selected from
    (i) a $C_{1-6}$ alkyl group (e.g., methyl), and
    (ii) a phenyl group optionally substituted by 1 to 3 substituents selected from a halogen atom (e.g., a chlorine atom) and a $C_{1-6}$ alkyl group (e.g., methyl),
  (g) a triazolyl group optionally substituted by 1 or 2 substituents selected from
    (i) a $C_{1-6}$ alkyl group (e.g., methyl), and
    (ii) a phenyl group,
  (h) an oxadiazolyl group optionally substituted by phenyl group(s) optionally substituted by 1 to 3 halogen atoms (e.g., a chlorine atom),
  (i) a thiazolyl group optionally substituted by 1 or 2 substituents selected from
    (i) a $C_{1-6}$ alkyl group (e.g., methyl), and
    (ii) a phenyl group, and
  (j) a thienyl group optionally substituted by 1 to 3 phenyl groups optionally substituted by 1 to 3 halogen atoms (e.g., a chlorine atom),
(3) a $C_{3-6}$ cycloalkyl group (e.g., cyclopropyl, cyclobutyl, cyclopentyl, cyclohexyl) optionally substituted by 1 to 3 substituents selected from
  (a) a halogen atom (e.g., a fluorine atom),
  (b) a cyano group,
  (c) an optionally halogenated C-s alkyl group (e.g., trifluoromethyl),
  (d) a $C_{1-6}$ alkoxy group (e.g., methoxy, propoxy, butoxy),
  (e) a $C_{1-6}$ alkoxy-carbonylamino group (e.g., tert-butoxycarbonylamino),
  (f) a phenyl group optionally substituted by 1 to 3 halogen atoms (e.g., a chlorine atom),
  (g) a phenoxy group, (h) a benzyloxy group, and
(i) a pyridyl group,
(4) a bicyclo[1.1.1]pentyl group (e.g., bicyclo[1.1.1]pentan-1-yl) optionally substituted by 1 to 3 substituents selected from
   (a) an optionally halogenated C-s alkyl group (e.g., trifluoromethyl), and
   (b) a phenyl group,
(5) an indanyl group (e.g., indan-1-yl) optionally substituted by 1 to 3 halogen atoms (e.g., a chlorine atom),
(6) a tetrahydronaphthyl group (e.g., 1,2,3,4-tetrahydronaphthalen-2-yl),
(7) a dihydrobenzocyclobutenyl group (e.g., dihydrobenzocyclobuten-1-yl,
(8) a phenyl group optionally substituted by 1 to 3 substituents selected from
   (a) a Ca-s alkyl group (e.g., ethyl, isopropyl) optionally substituted by 1 to 3 hydroxy groups,
   (b) a $C_1$_s alkoxy group (e.g., methoxy, ethoxy),
   (c) a phenoxy group,
   (d) a benzyloxy group, and
   (e) a morpholinyl group,
(9) a pyrazolyl group optionally substituted by 1 to 3 substituents selected from
   (a) an optionally halogenated $C_{1-6}$ alkyl group (e.g., methyl, trifluoromethyl, 2,2,2-trifluoroethyl), and
   (b) a benzyl group optionally substituted by 1 to 3 halogen atoms (e.g., a fluorine atom),
(10) an imidazolyl group optionally substituted by 1 to 3 phenyl groups,
(11) a pyridyl group optionally substituted by 1 to 3 substituents selected from
   (a) a cyano group,
   (b) an optionally halogenated $C_{1-6}$ alkyl group (e.g., trifluoromethyl),
   (c) an optionally halogenated $C_{1-6}$ alkoxy group (e.g., methoxy, difluoromethoxy, 2,2,2-trifluoroethoxy),
   (d) a phenoxy group, and
   (e) a $C_{3-10}$ cycloalkyl group (e.g., cyclopropyl),
(12) a pyrrolidinyl group optionally substituted by 1 to 3 benzyl groups,
(13) a piperidyl group optionally substituted by 1 to 3 substituents selected from
   (a) a $C_{1-6}$ alkyl group (e.g., methyl) optionally substituted by 1 to 3 $C_{3-6}$ cycloalkyl groups (e.g., cyclopropyl),
   (b) a $C_{1-6}$ alkoxy-carbonyl group (e.g., tert-butoxycarbonyl),
   (c) a phenyl group optionally substituted by 1 to 3 halogen atoms (e.g., a fluorine atom, a chlorine atom), and
   (d) a benzyl group,
(14) a tetrahydrofuryl group optionally substituted by 1 to 3 phenyl groups, or
(15) a dihydrochromenyl group (e.g., 3,4-dihydro-2H-chromen-4-yl) optionally substituted by 1 to 3 $C_{1-6}$ alkyl groups (e.g., methyl), or
$R^3$ and $R^4$ are bonded to each other to form, together with the adjacent nitrogen atom,
(1) an azetidine ring optionally further substituted by 1 to 3 substituents selected from
   (a) a $C_{1-6}$ alkyl group (e.g., methyl, isopropyl) optionally substituted by 1 to 3 $C_{1-6}$ alkoxy groups (e.g., methoxy),
   (b) an optionally halogenated $C_1$ alkoxy group (e.g., methoxy, difluoromethoxy),
   (c) a $C_{3-6}$ cycloalkyl group (e.g., cyclopropyl),
   (d) a phenyl group optionally substituted by 1 to 3 halogen atoms (e.g., a fluorine atom, a chlorine atom, a bromine atom),
   (e) a phenoxy group,
   (f) a benzyl group, and
   (g) a benzyloxy group,
(2) a pyrrolidine ring optionally further substituted by 1 to 3 substituents selected from
   (a) a halogen atom (e.g., a fluorine atom),
   (b) an optionally halogenated $C_{1-6}$ alkoxy group (e.g., methoxy, trifluoromethoxy),
   (c) a phenyl group optionally substituted by 1 to 3 substituents selected from
      (i) a halogen atom (e.g., a chlorine atom),
      (ii) an optionally halogenated C-s alkyl group (e.g., trifluoromethyl), and
      (iii) a $C_{1-6}$ alkoxy group (e.g., methoxy),
   (d) a benzyl group, and
   (e) a benzyloxy group,
(3) a piperidine ring optionally further substituted by 1 to 3 substituents selected from
   (a) a $C_{1-6}$ alkoxy group (e.g., methoxy, ethoxy) optionally substituted by 1 to 3 substituents selected from
      (i) a halogen atom (e.g., a fluorine atom), and
      (ii) a Ce cycloalkyl group (e.g., cyclopropyl),
   (b) a phenyl group optionally substituted by 1 to 3 substituents selected from
      (i) a halogen atom (e.g., a chlorine atom), and
      (ii) a $C_{1-6}$ alkoxy group (e.g., methoxy),
   (c) a phenoxy group optionally substituted by 1 to 3 substituents selected from
      (i) a halogen atom (e.g., a fluorine atom, a chlorine atom),
      (ii) a cyano group,
      (iii) an optionally halogenated $C_{1-6}$ alkyl group (e.g., methyl, trifluoromethyl), and
      (iv) an optionally halogenated $C_{1-6}$ alkoxy group (e.g., methoxy, trifluoromethoxy),
   (d) a benzyl group,
   (e) a benzyloxy group,
   (f) a pyridyloxy group,
   (g) a pyrazinyloxy group,
   (h) a pyrimidinyloxy group,
   (i) a thiazolyloxy group, and
   (j) a piperidyloxy group optionally substituted by 1 to 3 $C_{1-6}$ alkoxy-carbonyl groups (e.g., tert-butoxycarbonyl),
(4) an indoline ring optionally further substituted by 1 to 3 $C_{1-6}$ alkoxy groups (e.g., methoxy),
(5) an isoindoline ring optionally further substituted by 1 to 3 $C_{1-6}$ alkoxy groups (e.g., methoxy),
(6) a tetrahydroquinoline ring optionally further substituted by 1 to 3 $C_{1-6}$ alkoxy groups (e.g., methoxy),
(7) a tetrahydroisoquinoline ring optionally further substituted by 1 to 3 substituents selected from
   (a) a halogen atom (e.g., a chlorine atom, a bromine atom), (b) a $C_{1-6}$ alkyl group (e.g., methyl), and
   (c) a $C_{1-6}$ alkoxy group (e.g., methoxy),
(8) a 3-azabicyclo[3.1.0]hexane ring optionally further substituted by 1 to 3 substituents selected from
   (a) a halogen atom (e.g., a fluorine atom),
   (b) a $C_{1-6}$ alkyl group (e.g., methyl) optionally substituted by 1 to 3 substituents selected from
      (i) a halogen atom (e.g., a fluorine atom),
      (ii) a cyano group,
      (iii) a $C_{1-6}$ alkoxy group (e.g., methoxy), and (iv) a mono- or di-$C_{1-6}$ alkylamino group (e.g., dimethylamino),
(c) a phenyl group optionally substituted by 1 to 3 substituents selected from
  (i) a halogen atom (e.g., a fluorine atom, a chlorine atom),
  (ii) an optionally halogenated $C_{1-6}$ alkyl group (e.g., methyl, trifluoromethyl), and
  (iii) an optionally halogenated $C_{1-6}$ alkoxy group (e.g., methoxy, trifluoromethoxy),
(d) a naphthyl group,
(e) a thienyl group,
(f) a pyrazolyl group optionally substituted by 1 to 3 of optionally halogenated $C_{1-6}$ alkyl groups (e.g., 2,2,2-trifluoroethyl),
(g) a pyridyl group optionally substituted by 1 to 3 halogen atoms (e.g., a chlorine atom), and
(h) a pyrimidinyl group optionally substituted by 1 to 3 halogen atoms (e.g., a chlorine atom),
(9) a 3-azabicyclo[4.1.0]heptane ring optionally further substituted by 1 to 3 substituents selected from
  (a) a halogen atom (e.g., a fluorine atom), and
  (b) a phenyl group optionally substituted by 1 to 3 substituents selected from
    (i) a halogen atom (e.g., a chlorine atom),
    (ii) a $C_{1-6}$ alkyl group (e.g., methyl), and
    (iii) a $C_{1-6}$ alkoxy group (e.g., methoxy),
(10) a 1-azaspiro[3.3]heptane ring,
(11) a 6-oxa-1-azaspiro[3.5]nonane ring,
(12) a 6-oxa-1-azaspiro[3.3]heptane ring, or
(13) a 6-oxa-1-azaspiro[3.4]octane ring.

[Compound E-2]
Compound (I) wherein
the partial structure represented by the following formula:

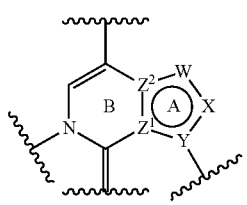

is a partial structure represented by the following formula:

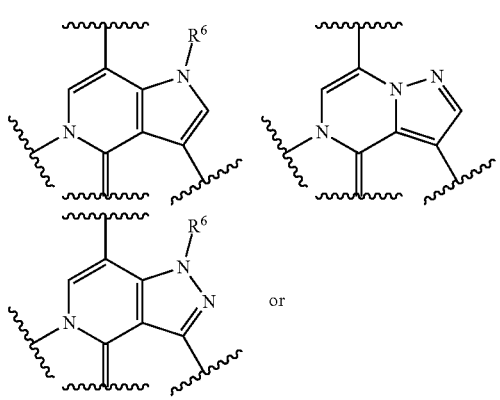

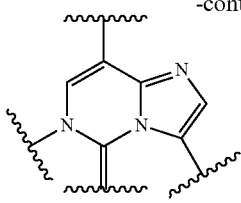

wherein $R^6$ is a $C_{1-6}$ alkyl group (e.g., methyl);
$R^1$ is
(1) a $C_{1-6}$ alkyl group (e.g., methyl, ethyl) optionally substituted by 1 to 3 substituents selected from
  (a) a halogen atom (e.g., a fluorine atom), and
  (b) a cyano group, or
(2) a phenyl group optionally substituted by 1 to 3 substituents selected from
  (a) an optionally halogenated $C_{1-6}$ alkoxy group (e.g., methoxy, 2,2,2-trifluoroethoxy), and
  (b) a halogen atom (e.g., a fluorine atom);
$R^2$ is a hydrogen atom or a $C_{1-6}$ alkyl group (e.g., methyl);
$R^3$ is a hydrogen atom, and
$R^4$ is
(1) a $C_{1-6}$ alkyl group (e.g., methyl, isopropyl) optionally substituted by 1 to 3 substituents selected from
  (a) a phenyl group optionally substituted by 1 to 3 halogen atoms (e.g., a chlorine atom),
  (b) an oxadiazolyl group optionally substituted by phenyl group(s) optionally substituted by 1 to 3 halogen atoms (e.g., a chlorine atom), and
  (c) a thienyl group optionally substituted by 1 to 3 phenyl groups optionally substituted by 1 to 3 halogen atoms (e.g., a chlorine atom),
(2) a $C_{3-6}$ cycloalkyl group (e.g., cyclobutyl, cyclopentyl, cyclohexyl) optionally substituted by 1 to 3 substituents selected from
  (a) a $C_{1-6}$ alkoxy group (e.g., butoxy), and
  (b) a phenyl group optionally substituted by 1 to 3 halogen atoms (e.g., a chlorine atom),
(3) a phenyl group optionally substituted by 1 to 3 substituents selected from
  (a) a benzyloxy group,
  (b) a morpholinyl group, and
  (c) a $C_{1-6}$ alkyl group (e.g., isopropyl) optionally substituted by 1 to 3 hydroxy groups, or
(4) a pyridyl group optionally substituted by 1 to 3 substituents selected from
  (a) a cyano group,
  (b) an optionally halogenated $C_{1-6}$ alkoxy group (e.g., methoxy, difluoromethoxy, 2,2,2-trifluoroethoxy), and
  (c) a $C_{3-10}$ cycloalkyl group (e.g., cyclopropyl), or
$R^3$ and $R^4$ are bonded to each other to form, together with the adjacent nitrogen atom,
(1) an azetidine ring optionally further substituted by 1 to 3 phenyl groups,
(2) a pyrrolidine ring optionally further substituted by 1 to 3 substituents selected from
  (a) a halogen atom (e.g., a fluorine atom), and
  (b) a phenyl group optionally substituted by 1 to 3 halogen atoms (e.g., a chlorine atom),
(3) a piperidine ring optionally further substituted by 1 to 3 substituents selected from
  (a) a phenyl group optionally substituted by 1 to 3 halogen atoms (e.g., a chlorine atom), and
  (b) a phenoxy group optionally substituted by 1 to 3 substituents selected from (i) a halogen atom (e.g., a chlorine atom),
(ii) an optionally halogenated $C_{1-6}$ alkyl group (e.g., trifluoromethyl), and
(iii) an optionally halogenated $C_{1-6}$ alkoxy group (e.g., trifluoromethoxy), or
(4) a 3-azabicyclo[3.1.0]hexane ring optionally further substituted by 1 to 3 substituents selected from
(a) a halogen atom (e.g., a fluorine atom),
(b) a phenyl group optionally substituted by 1 to 3 substituents selected from
(i) a halogen atom (e.g., a fluorine atom, a chlorine atom),
(ii) an optionally halogenated $C_{1-6}$ alkyl group (e.g., methyl, trifluoromethyl), and
(iii) an optionally halogenated $C_{1-6}$ alkoxy group (e.g., methoxy, trifluoromethoxy), and
(c) a naphthyl group.

[Compound F-2]
Compound (I) wherein
the partial structure represented by the following formula:

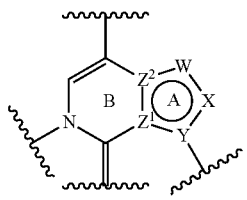

is a partial structure represented by the following formula:

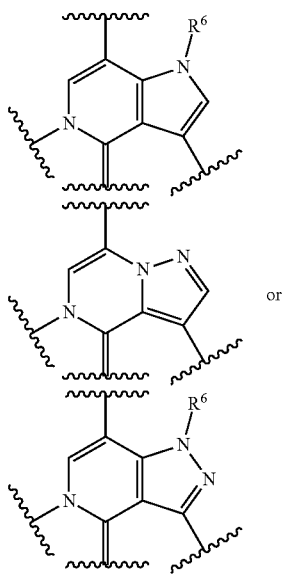

wherein $R^6$ is a $C_{1-6}$ alkyl group (e.g., methyl);
$R^1$ is
(1) a $C_{1-6}$ alkyl group (e.g., methyl) optionally substituted by 1 to 3 cyano groups, or
(2) a phenyl group optionally substituted by 1 to 3 of optionally halogenated $C_{1-6}$ alkoxy groups (e.g., methoxy, 2,2,2-trifluoroethoxy);
$R^2$ is a hydrogen atom or a $C_{1-6}$ alkyl group (e.g., methyl);
$R^3$ is a hydrogen atom, and
$R^4$ is
(1) a $C_{3-6}$ cycloalkyl group (e.g., cyclohexyl) optionally substituted by 1 to 3 $C_{1-6}$ alkoxy groups (e.g., butoxy), or
(2) a phenyl group optionally substituted by 1 to 3 substituents selected from
(a) a morpholinyl group, and
(b) a $C_{1-6}$ alkyl group (e.g., isopropyl) optionally substituted by 1 to 3 hydroxy groups.

[Compound G]
N-(trans-4-butoxycyclohexyl)-1,5,7-trimethyl-4-oxo-4,5-dihydro-1H-pyrrolo[3,2-c]pyridine-3-carboxamide or a salt thereof.
1-methyl-N-(4-(morpholin-4-yl)phenyl)-4-oxo-5-(2-(2,2,2-trifluoroethoxy)phenyl)-4,5-dihydro-1H-pyrrolo[3,2-c]pyridine-3-carboxamide or a salt thereof.
N-[4-(2-hydroxypropan-2-yl)phenyl]-7-methyl-4-oxo-5-[2-(2,2,2-trifluoroethoxy)phenyl]-4,5-dihydropyrazolo[1,5-a]pyrazine-3-carboxamide or a salt thereof.

Specific examples of compound (I) include the compounds of Examples 1 to 353.

When compound (I) is a salt, examples of the salt include metal salts, ammonium salts, salts with organic base, salts with inorganic acid, salts with organic acid, and salts with basic or acidic amino acid. Preferable examples of the metal salt include alkali metal salts such as sodium salts, potassium salts and the like; alkali earth metal salts such as calcium salts, magnesium salts, barium salts and the like; and aluminum salts. Preferable examples of the salt with organic base include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like. Preferable examples of the salt with inorganic acid include salts with hydrochloric acid, hydrobromic acid, nitric acid, sulfuric acid, phosphoric acid and the like. Preferable examples of the salt with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like. Preferable examples of the salts with basic amino acid include salts with arginine, lysine, ornithine and the like. Preferable examples of the salt with acidic amino acid include salts with aspartic acid, glutamic acid and the like. Among them, a pharmaceutically acceptable salt is preferable. For example, when a compound has an acidic functional group, examples of the salt include inorganic salts such as alkali metal salts (e.g., sodium salt, potassium salt etc.), alkaline earth metal salts (e.g., calcium salt, magnesium salt, barium salt etc.) and the like, ammonium salt etc., and when a compound has a basic functional group, examples of the salt include salts with inorganic acid such as hydrochloric acid, hydrobromic acid, nitric acid, sulfuric acid, phosphoric acid and the like, and salts with organic acid such as acetic acid, phthalic acid, fumaric acid, oxalic acid, tartaric acid, maleic acid, citric acid, succinic acid, methanesulfonic acid, p-toluenesulfonic acid and the like.

When compound (I) contains isomers such as tautomers, optical isomers, stereoisomers, position isomers and rotational isomers, any of isomers or mixture are also encompassed in the compound of the present invention. Further, when compound (I) contains an optical isomer, the optical isomer separated from the racemate is encompassed in compound (I).

Compound (I) can be obtained in the crystal form. Either single crystalline form or crystalline mixture can be encompassed in compound (I).

Compound (I) can be a pharmaceutically acceptable co-crystal or a co-crystal salt. The co-crystal or co-crystal salt as used herein means a crystalline material composed of two or more unique solids at room temperature, each of which has distinctive physical characteristics such as structure, melting point, and heats of fusion, hygroscopicity, solubility, and stability. A co-crystal or a co-crystal salt can be produced according to co-crystallization method known per se.

Compound (I) may be a solvate (e.g., a hydrate) or a non-solvate and both are encompassed in compound (I).

Compounds labeled with or substituted by isotopes (e.g., $^2H$, $^3H$, $^{11}C$, $^{14}C$, $^{18}F$, $^{35}S$, $^{125}I$, etc.) are also encompassed in compound (I). The compound labeled with or substituted by isotopes can be used as, for example, a tracer used for Positron Emission Tomography (PET) (PET tracer), and are expected to be useful in the field of medical diagnosis and the like.

The production method of the compound of the present invention is explained below.

The raw material compound and reagent used and the compound obtained in each step in the following production method may be each in a form of a salt, and examples of such salt include those similar to the salts of the compound of the present invention and the like.

When the compound obtained in each step is a free form, it can be converted to the objective salt according to a method known per se. When the compound obtained in each step is a salt, it can be converted to the objective free form or the other salt according to a method known per se.

The compound obtained in each step can be used directly as the reaction mixture or as a crude product for the next reaction. Alternatively, the compound obtained in each step can be isolated and purified from a reaction mixture according to a method known per se, for example, a separation means such as concentration, crystallization, recrystallization, distillation, solvent extraction, fractional distillation, column chromatography and the like.

When the raw material compound and reagent used in each step are commercially available, the commercially available product can also be used directly.

In the reaction in each step, while the reaction time varies depending on the kind of the reagent and solvent to be used, it is generally 1 min-48 hr, preferably 10 min-8 hr, unless otherwise specified.

In the reaction in each step, while the reaction temperature varies depending on the kind of the reagent and solvent to be used, it is generally −78° C.-300° C., preferably −78° C.-150° C., unless otherwise specified.

In the reaction in each step, while the pressure varies depending on the kind of the reagent and solvent to be used, it is generally 1 atm-20 atm, preferably 1 atm-3 atm, unless otherwise specified.

Microwave synthesizer such as Initiator manufactured by Biotage and the like may be used for the reaction in each step. While the reaction temperature varies depending on the kind of the reagent and solvent to be used, it is generally room temperature-300° C., preferably 50° C.-250° C., unless otherwise specified. While the reaction time varies depending on the kind of the reagent and solvent to be used, it is generally 1 min-48 hr, preferably 1 min-8 hr, unless otherwise specified.

In the reaction in each step, the reagent is used in an amount of 0.5 equivalents-20 equivalents, preferably 0.8 equivalents-5 equivalents, relative to the substrate, unless otherwise specified. When the reagent is used as a catalyst, the reagent is used in an amount of 0.001 equivalent-1 equivalent, preferably 0.01 equivalent-0.2 equivalent, relative to the substrate. When the reagent is used as a reaction solvent, the reagent is used in a solvent amount.

Unless otherwise specified, the reaction in each step is carried out without solvent, or by dissolving or suspending the raw material compound in a suitable solvent. Examples of the solvent include those described in Examples and the following solvents.
alcohols: methanol, ethanol, tert-butyl alcohol, 2-methoxyethanol and the like;
ethers: diethyl ether, diphenyl ether, tetrahydrofuran, 1,2-dimethoxyethane and the like;
aromatic hydrocarbons: chlorobenzene, toluene, xylene and the like;
saturated hydrocarbons: cyclohexane, hexane and the like;
amides: N,N-dimethylformamide, N-methylpyrrolidone and the like;
halogenated hydrocarbons: dichloromethane, carbon tetrachloride and the like;
nitriles: acetonitrile and the like;
sulfoxides: dimethyl sulfoxide and the like;
aromatic organic bases: pyridine and the like;
anhydrides: acetic anhydride and the like;
organic acids: formic acid, acetic acid, trifluoroacetic acid and the like;
inorganic acids: hydrochloric acid, sulfuric acid and the like;
esters: ethyl acetate and the like;
ketones: acetone, methyl ethyl ketone and the like; water.

The above-mentioned solvent can be used in a mixture of two or more kinds thereof in an appropriate ratio.

When a base is used for the reaction in each step, examples thereof include those described in Examples and the following bases.
inorganic bases: sodium hydroxide, magnesium hydroxide, sodium carbonate, calcium carbonate, sodium hydrogen carbonate and the like;
organic bases: triethylamine, diethylamine, pyridine, 4-dimethylaminopyridine, N,N-dimethylaniline, 1,4-diazabicyclo[2.2.2]octane, 1,8-diazabicyclo[5.4.0]-7-undecene, imidazole, piperidine and the like;
metal alkoxides: sodium ethoxide, potassium tert-butoxide and the like;
alkali metal hydrides: sodium hydride and the like;
metal amides: sodium amide, lithium diisopropylamide, lithium hexamethyldisilazide and the like;
organic lithiums: n-butyllithium and the like.

When an acid or an acid catalyst is used for the reaction in each step, examples thereof include those described in Examples and the following acids and acid catalysts.
inorganic acids: hydrochloric acid, sulfuric acid, nitric acid, hydrobromic acid, phosphoric acid and the like;
organic acids: acetic acid, trifluoroacetic acid, citric acid, p-toluenesulfonic acid, 10-camphorsulfonic acid and the like;
Lewis acid: boron trifluoride diethyl ether complex, zinc iodide, anhydrous aluminum chloride, anhydrous zinc chloride, anhydrous iron chloride and the like.

Unless otherwise specified, the reaction in each step is carried out according to a method known per se, for example, the method described in Jikken Kagaku Kouza, 5th Edition, vol. 13-19 (the Chemical Society of Japan ed.); Shin Jikken Kagaku Kouza, vol. 14-15 (the Chemical Society of Japan ed.); Fine Organic Chemistry, Revised 2nd Edition (L. F. Tietze, Th. Eicher, Nankodo); Organic Name Reactions, the Reaction Mechanism and Essence, Revised Edition (Hideo Togo, Kodansha); ORGANIC SYNTHESES Collective Volume I-VII (John Wiley & Sons Inc.); Modern Organic Synthesis in the Laboratory A Collection of Standard Experimental Procedures (Jie Jack Li, OXFORD UNIVERSITY); Comprehensive Heterocyclic Chemistry III, Vol. 1-Vol. 14 (Elsevier Japan); Strategic Applications of Named Reactions in Organic Synthesis (translated by Kiyoshi Tomioka, Kagakudojin); Comprehensive Organic Transformations (VCH Publishers Inc.), 1989, or the like, or the method described in Examples.

In each step, the protection or deprotection reaction of an functional group is carried out according to a method known per se, for example, the method described in "Protective Groups in Organic Synthesis, 4th Ed", Wiley-Interscience, Inc., 2007 (Theodora W. Greene, Peter G. M. Wuts); "Protecting Groups 3rd Ed." Thieme, 2004 (P. J. Kocienski), or the like, or the method described in Examples.

Examples of the protecting group for a hydroxy group of an alcohol and the like and a phenolic hydroxy group include ether-type protecting groups such as methoxymethyl ether, benzyl ether, tert-butyldimethylsilyl ether, tetrahydropyranyl ether and the like; carboxylate ester-type protecting groups such as acetate ester and the like; sulfonate ester-type protecting groups such as methanesulfonate ester and the like; carbonate ester-type protecting groups such as tert-butylcarbonate and the like, and the like.

Examples of the protecting group for a carbonyl group of an aldehyde include acetal-type protecting groups such as dimethylacetal and the like; cyclic acetal-type protecting groups such as 1,3-dioxane and the like, and the like.

Examples of the protecting group for a carbonyl group of a ketone include ketal-type protecting groups such as dimethylketal and the like; cyclic ketal-type protecting groups such as 1,3-dioxane and the like; oxime-type protecting groups such as O-methyloxime and the like; hydrazone-type protecting groups such as N,N-dimethylhydrazone and the like, and the like.

Examples of the protecting group for a carboxyl group include ester-type protecting groups such as methyl ester and the like; amide-type protecting groups such as N,N-dimethylamide and the like, and the like.

Examples of the protecting group for a thiol include ether-type protecting groups such as benzyl thioether and the like; ester-type protecting groups such as thioacetate ester, thiocarbonate, thiocarbamate and the like, and the like.

Examples of the protecting group for an amino group and an aromatic heterocycle such as imidazole, pyrrole, indole and the like include carbamate-type protecting groups such as benzyl carbamate and the like; amide-type protecting groups such as acetamide and the like; alkyl amine-type protecting groups such as N-triphenylmethylamine and the like; sulfonamide-type protecting groups such as methanesulfonamide and the like, and the like.

The protecting groups can be removed according to a method known per se, for example, by employing a method using acid, base, ultraviolet rays, hydrazine, phenylhydrazine, sodium N-methyldithiocarbamate, tetrabutylammonium fluoride, palladium acetate, trialkylsilyl halide (e.g., trimethylsilyl iodide, trimethylsilyl bromide) and the like, a reduction method, and the like.

When reduction reaction is carried out in each step, examples of the reducing agent to be used include metal hydrides such as lithium aluminum hydride, sodium triacetoxyborohydride, sodium cyanoborohydride, diisobutylaluminum hydride (DIBAL-H), sodium borohydride, tetramethylammonium triacetoxyborohydride and the like; boranes such as borane tetrahydrofuran complex and the like; Raney nickel; Raney cobalt; hydrogen; formic acid; triethylsilane and the like. When carbon-carbon double bond or triple bond is reduced, a method using a catalyst such as palladium-carbon, Lindlar's catalyst and the like may be employed.

When oxidation reaction is carried out in each step, examples of the oxidizing agent to be used include peroxides such as m-chloroperbenzoic acid (mCPBA), hydrogen peroxide, tert-butylhydroperoxide and the like; perchlorates such as tetrabutylammonium perchlorate and the like; chlorates such as sodium chlorate and the like; chlorites such as sodium chlorite and the like; periodates such as sodium periodate and the like; hypervalent iodine reagents such as iodosylbenzene and the like; reagents containing manganese such as manganese dioxide, potassium permanganate and the like; leads such as lead tetraacetate and the like; reagents containing chromium such as pyridinium chlorochromate (PCC), pyridinium dichromate (PDC), Jones reagent and the like; halogen compounds such as N-bromosuccinimide (NBS) and the like; oxygen; ozone; sulfur trioxide-pyridine complex; osmium tetroxide; selenium dioxide; 2,3-dichloro-5,6-dicyano-1,4-benzoquinone (DDQ) and the like.

When radical cyclization reaction is carried out in each step, examples of the radical initiator to be used include azo compounds such as azobisisobutyronitrile (AIBN) and the like; water-soluble radical initiators such as 4-4'-azobis-4-cyanopentanoic acid (ACPA) and the like; triethylboron in the presence of air or oxygen; benzoyl peroxide and the like. Examples of the radical reagent to be used include tributylstannane, tristrimethylsilylsilane, 1,1,2,2-tetraphenyldisilane, diphenylsilane, samarium iodide and the like.

When Wittig reaction is carried out in each step, examples of the Wittig reagent to be used include alkylidene phosphoranes and the like. The alkylidene phosphoranes can be prepared according to a method known per se, for example, by reacting a phosphonium salt with a strong base.

When Horner-Emmons reaction is carried out in each step, examples of the reagent to be used include phosphonoacetates such as methyl dimethylphosphonoacetate, ethyl diethylphosphonoacetate and the like; and bases such as alkali metal hydrides, organic lithiums and the like.

When Friedel-Crafts reaction is carried out in each step, a combination of a Lewis acid and an acid chloride or a combination of a Lewis acid and an alkylating agent (e.g., an alkyl halide, an alcohol, an olefin etc.) is used as a reagent. Alternatively, an organic acid or an inorganic acid can also be used instead of a Lewis acid, and an anhydride such as acetic anhydride and the like can also be used instead of an acid chloride.

When aromatic nucleophilic substitution reaction is carried out in each step, a nucleophile (e.g., an amine, imidazole etc.) and a base (e.g., an organic base etc.) are used as a reagent.

When nucleophilic addition reaction by a carbo anion, nucleophilic 1,4-addition reaction (Michael addition reaction) by a carbo anion or nucleophilic substitution reaction by a carbo anion is carried out in each step, and examples of the base to be used for generation of the carbo anion include organic lithiums, metal alkoxides, inorganic bases, organic bases and the like.

When Grignard reaction is carried out in each step, examples of the Grignard reagent to be used include arylmagnesium halides such as phenylmagnesium bromide and the like; and alkylmagnesium halides such as methylmagnesium bromide and the like. The Grignard reagent can be prepared according to a method known per se, for example, by reacting an alkyl halide or an aryl halide with a metal magnesium in an ether or tetrahydrofuran as a solvent.

When Knoevenagel condensation reaction is carried out in each step, a compound having an activated methylene group with two electron withdrawing groups (e.g., malonic acid, diethyl malonate, malononitrile etc.) and a base (e.g., an organic base, a metal alkoxide, an inorganic base) are used as a reagent.

When Vilsmeier-Haack reaction is carried out in each step, phosphoryl chloride and an amide derivative (e.g., N,N-dimethylformamide etc.) are used as a reagent.

When azidation reaction of an alcohol, an alkyl halide or a sulfonate is carried out in each step, examples of the azidating agent to be used include diphenylphosphorylazide (DPPA), trimethylsilylazide, sodium azide and the like. For example, for the azidation reaction of an alcohol, a method using diphenylphosphorylazide and 1,8-diazabicyclo[5.4.0]undec-7-ene (DBU), a method using trimethylsilylazide and a Lewis acid, and the like are employed.

When reductive amination reaction is carried out in each step, examples of the reducing agent to be used include sodium triacetoxyborohydride, sodium cyanoborohydride, hydrogen, formic acid and the like. When the substrate is an amine compound, examples of the carbonyl compound to be used include paraformaldehyde, aldehydes such as acetaldehyde and the like, and ketones such as cyclohexanone and the like. When the substrate is a carbonyl compound, examples of the amine to be used include ammonia, primary amines such as methylamine and the like; secondary amines such as dimethylamine and the like, and the like.

When Mitsunobu reaction is carried out in each step, an azodicarboxylate (e.g., diethyl azodicarboxylate (DEAD), diisopropyl azodicarboxylate (DIAD) etc.) and triphenylphosphine are used as a reagent.

When esterification reaction, amidation reaction or urea formation reaction is carried out in each step, examples of the reagent to be used include acyl halides such as acid chlorides, acid bromides and the like; activated carboxylic acids such as anhydrides, activated esters, sulfates and the like. Examples of the activating agent of the carboxylic acid include carbodiimide condensing agents such as 1-ethyl-3-(3-dimethylaminopropyl)carbodiimide hydrochloride (WSCD) and the like; triazine condensing agents such as 4-(4,6-dimethoxy-1,3,5-triazin-2-yl)-4-methylmorpholinium chloride n-hydrate (DMT-MM) and the like; carbonate condensing agents such as 1,1-carbonyldiimidazole (CDI) and the like; diphenylphosphoryl azide (DPPA); benzotriazol-1-yloxy-trisdimethylaminophosphonium salt (BOP reagent); 2-chloro-1-methyl-pyridinium iodide (Mukaiyama reagent); thionyl chloride; lower alkyl haloformates such as ethyl chloroformate and the like; O-(7-azabenzotriazol-1-yl)-N,N,N',N'-tetramethyluronium hexafluorophosphorate (HATU); sulfuric acid; combinations thereof and the like. When carbodiimide condensing agent is used, an additive such as 1-hydroxybenzotriazole (HOBt), N-hydroxysuccinimide (HOSu), dimethylaminopyridine (DMAP) and the like may be added to the reaction system.

When coupling reaction is carried out in each step, examples of the metal catalyst to be used include palladium compounds such as palladium(II) acetate, tetrakis(triphenylphosphine)palladium(0), dichlorobis(triphenylphosphine)palladium(II), dichlorobis(triethylphosphine)palladium(II), tris(dibenzylideneacetone)dipalladium(0), 1,1'-bis(diphenylphosphino)ferrocenepalladium(II) chloride and the like; nickel compounds such as tetrakis(triphenylphosphine)nickel(0) and the like; rhodium compounds such as tris(triphenylphosphine)rhodium(III) chloride and the like; cobalt compounds; copper compounds such as copper oxide, copper(I) iodide and the like; platinum compounds and the like. In addition, a base can be added to the reaction system, and examples thereof include inorganic bases and the like.

When thiocarbonylation reaction is carried out in each step, phosphorus pentasulfide is typically used as the thiocarbonylating agent. Alternatively, a reagent having a 1,3,2,4-dithiadiphosphetane-2,4-disulfide structure (e.g., 2,4-bis(4-methoxyphenyl)-1,3,2,4-dithiadiphosphetane-2,4-disulfide (Lawesson reagent) etc.) can also be used instead of phosphorus pentasulfide.

When halogenation reaction is carried out in each step, examples of the halogenating agent to be used include N-iodosuccinimide, N-bromosuccinimide (NBS), N-chlorosuccinimide (NCS), bromine, sulfuryl chloride and the like. In addition, the reaction can be accelerated by subjecting a radical initiator such as heat, light, benzoyl peroxide, azobisisobutyronitrile and the like to the reaction system reaction.

When halogenation reaction of a hydroxy group is carried out in each step, examples of the halogenating agent to be used include hydrohalic acids and acid halides of inorganic acids, specifically, hydrochloric acid, thionyl chloride, phosphorus oxychloride and the like for chlorination, 48% hydrobromic acid and the like for bromination. In addition, a method of producing an alkyl halide by reacting an alcohol with triphenylphosphine and carbon tetrachloride or carbon tetrabromide or the like can be employed. Alternatively, a method of producing an alkyl halide via two steps comprising converting an alcohol to the corresponding sulfonate, and then reacting the sulfonate with lithium bromide, lithium chloride or sodium iodide can also be employed.

When Arbuzov reaction is carried out in each step, examples of the reagent to be used include alkyl halides such as ethyl bromoacetate and the like; and phosphites such as triethyl phosphite, tri(isopropyl) phosphite and the like.

When sulfonate esterification reaction is carried out in each step, examples of the sulfonating agent to be used include methanesulfonyl chloride, p-toluenesulfonyl chloride, methanesulfonic anhydride, p-toluenesulfonic anhydride and the like.

When hydrolysis reaction is carried out in each step, an acid or a base is used as a reagent. For acid hydrolysis reaction of tert-butyl ester, formic acid, triethylsilane and the like may be added to reductively-trap tert-butyl cation which is by-produced.

When dehydration reaction is carried out in each step, examples of the dehydrating agent to be used include sulfuric acid, diphosphorus pentaoxide, phosphorus oxychloride, N,N'-dicyclohexylcarbodiimide, alumina, polyphosphoric acid and the like.

When alkylation reaction is carried out in each step, a combination of an electrophile (e.g., an alkyl halide etc.) and a base (e.g., an organic base, an inorganic base, a metal alkoxide, a metal amide etc.) is used as a reagent.

Compound (I) can be synthesized according to the following Production Methods A to N or a method analogous thereto. Each symbol in the formulas of the schemes is as defined above, unless otherwise specified. HAL is a halogen atom (e.g., a chlorine atom, a bromine atom, iodine atom). $R^9$ is an optionally substituted $C_{1-6}$ alkyl group (e.g., methyl, ethyl). $R^{10}$ is a hydrogen atom or a substituent.

Moreover, when desired, compound (I) can be synthesized by performing deprotection reaction, amidation reaction, urea formation, alkylation reaction, Mitsunobu reaction, oxidation reaction, reduction reaction, halogenation reaction, coupling reaction, nucleophilic addition reaction by a carbo anion, Grignard reaction, dehydration reaction and the like singly or two or more thereof in combination.

Production Method A

Among compound (I), the below-mentioned compound (Ia) can be produced according to the following method.

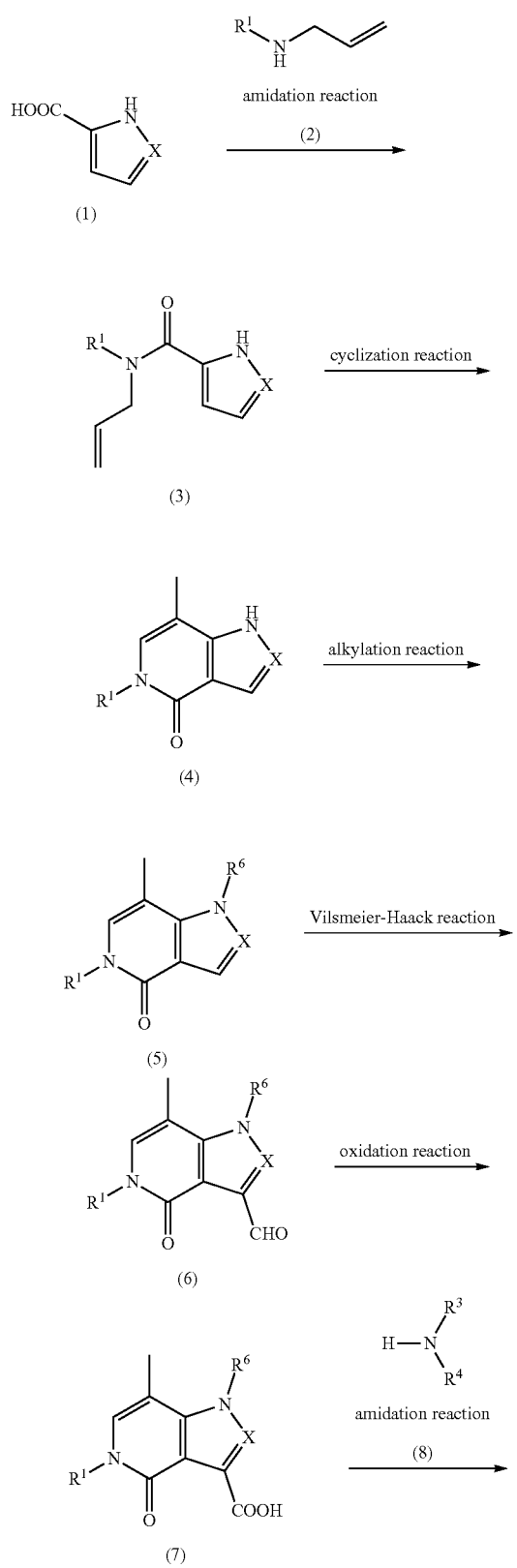

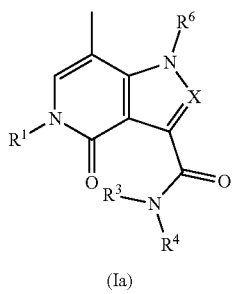

Compound (3) can be produced by subjecting compound (1) to an amidation reaction with compound (2).

Compound (4) can be produced by subjecting compound (3) to a cyclization reaction. Examples of the reagent to be used in the cyclization reaction include a combination of a metal catalyst and an oxidizing agent. Examples of the metal catalyst include dichlorobis(acetonitrile)palladium(II) and the like. Examples of the oxidizing agent include 1,4-benzoquinone and the like.

Compound (5) can be produced by subjecting compound (4) to an alkylation reaction (in case where $R^6$ is an optionally substituted $C_{1-6}$ alkyl group).

Compound (6) can be produced by subjecting compound (5) to the Vilsmeier-Haack reaction.

Compound (7) can be produced by subjecting compound (6) to an oxidation reaction.

Compound (Ia) can be produced by subjecting compound (7) to an amidation reaction with compound (8).

Compound (5) used in Production Method A can also be produced according to the following method.

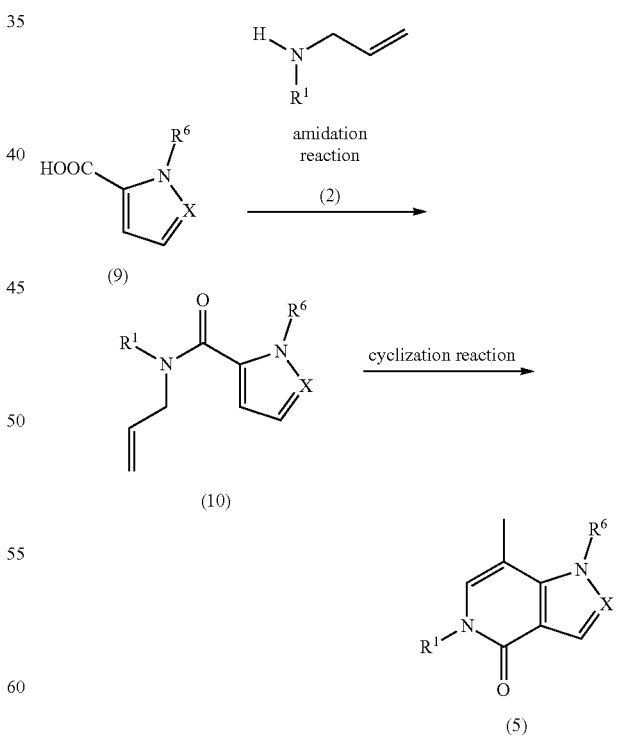

Compound (10) can be produced by subjecting compound (9) to an amidation reaction with compound (2).

Compound (5) can be produced by subjecting compound (10) to a cyclization reaction. Examples of the reagent to be used in the cyclization reaction include a combination of a metal catalyst and an oxidizing agent. Examples of the metal catalyst include dichlorobis(acetonitrile)palladium(II) and the like. Examples of the oxidizing agent include 1,4-benzoquinone and the like.

Production Method B

Among compound (I), the below-mentioned compound (Ib) can be produced according to the following method.

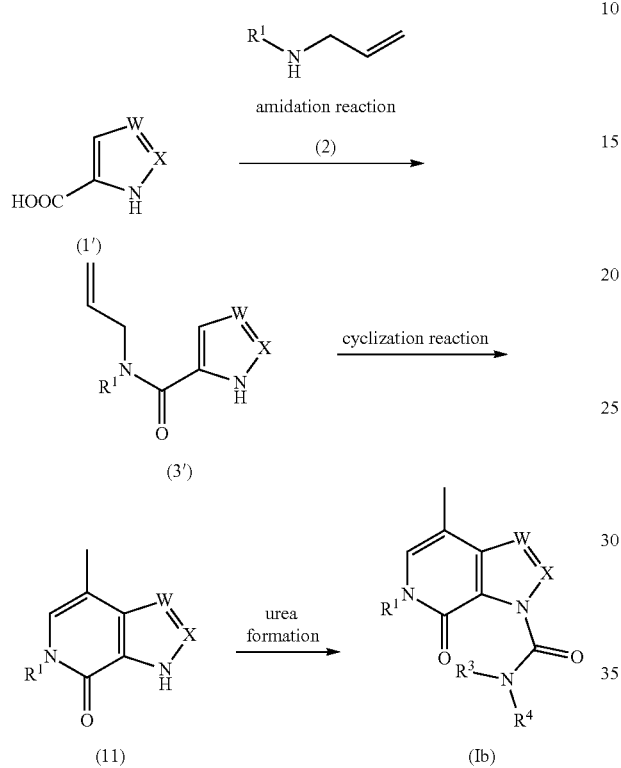

Compound (3') can be produced by subjecting compound (1') to an amidation reaction with compound (2).

Compound (11) can be produced by subjecting compound (3') to a cyclization reaction. Examples of the reagent to be used in the cyclization reaction include a combination of a metal catalyst and an oxidizing agent. Examples of the metal catalyst include dichlorobis(acetonitrile)palladium(II) and the like. Examples of the oxidizing agent include 1,4-benzoquinone and the like.

Compound (Ib) can be produced by subjecting compound (11) to an urea formation. Examples of the reagent to be used in the urea formation include an isocyanate derivative (in case where $R^3$ is a hydrogen atom, and $R^4$ is a substituent) and the like, in addition to the above-mentioned reagents.

Production Method C

Among compound (I), the below-mentioned compound (Ic) can be produced according to the following method.

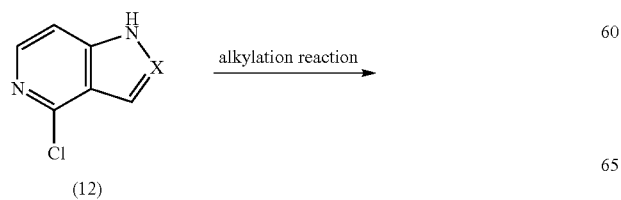

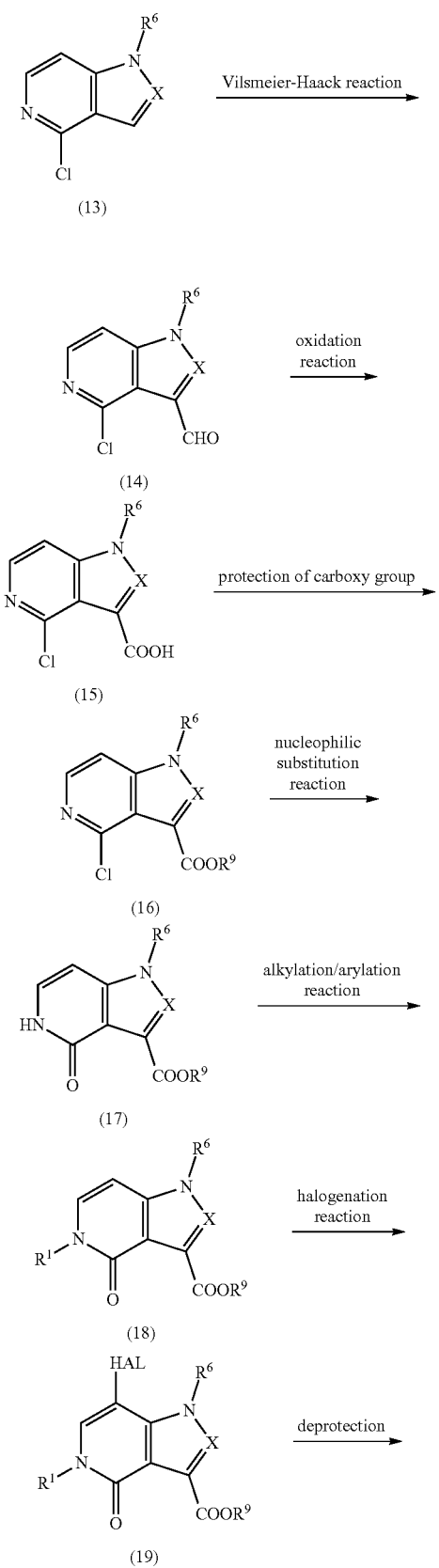

-continued

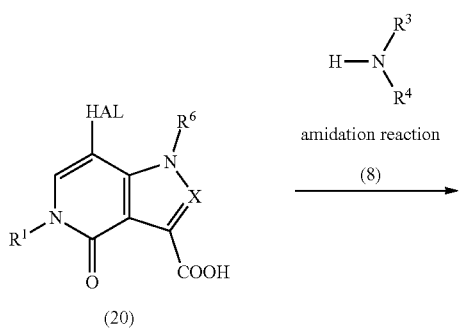

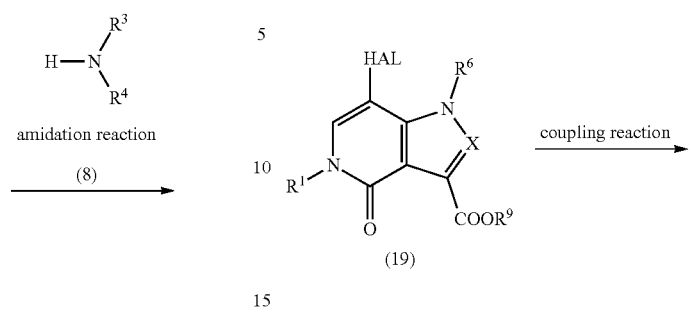

Production Method D

Among compound (I), the below-mentioned compound (Id) can be produced according to the following method.

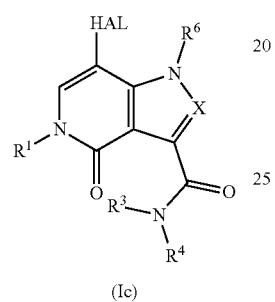

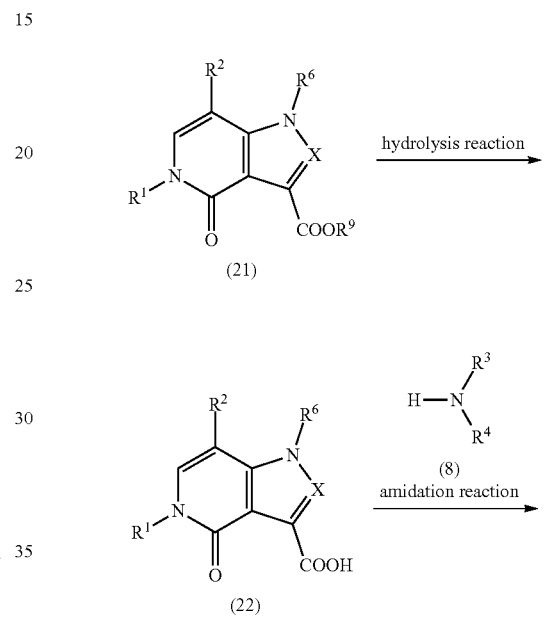

Compound (13) can be produced by subjecting compound (12) to an alkylation reaction (in case where $R^6$ is an optionally substituted $C_{1-6}$ alkyl group).

Compound (14) can be produced by subjecting compound (13) to the Vilsmeier-Haack reaction.

Compound (15) can be produced by subjecting compound (14) to an oxidation reaction.

Compound (16) can be produced by subjecting compound (15) to protection of the carboxy group.

Compound (17) can be produced by subjecting compound (16) to a nucleophilic substitution reaction. Examples of the reagent to be used include acetic acid, sodium acetate and the like.

Compound (18) can be produced by subjecting compound (17) to an alkylation reaction or an arylation reaction (in case where $R^1$ is an optionally substituted $C_{1-6}$ alkyl group or an optionally substituted $C_{6-14}$ aryl group). Examples of the reagent to be used in the arylation reaction include a combination of an aryl boronic acid, a metal reagent and a base. Examples of the metal reagent include copper acetate. Examples of the base include the above-mentioned organic bases (triethylamine, pyridine, diisopropylethylamine, etc.). A molecular sieve may be added depending on the condition.

Compound (19) can be produced by subjecting compound (18) to a halogenation reaction.

Compound (20) can be produced by subjecting compound (19) to a deprotection reaction.

Compound (Ic) can be produced by subjecting compound (20) to an amidation reaction with compound (8).

Compound (19) can be produced from compound (12) according to the above-mentioned Production Method C.

Compound (21) can be produced by subjecting compound (19) to a coupling reaction with a trialkyltin derivative or a boronic acid derivative corresponding to $R^2$. When $R^2$ is an optionally substituted $C_{2-6}$ alkenyl group or an optionally substituted $C_{2-6}$ alkynyl group, the resulting compound can be subjected to a reduction reaction to convert $R^2$ to an optionally substituted $C_{2-6}$ alkyl group. Examples of the catalyst to be used include the above-mentioned catalysts (e.g., palladium-carbon, etc.).

Compound (22) can be produced by subjecting compound (21) to a hydrolysis reaction.

Compound (Id) can be produced by subjecting compound (22) to an amidation reaction with compound (8).

Production Method E

Among compound (I), the below-mentioned compound (Ie) can be produced according to the following method.

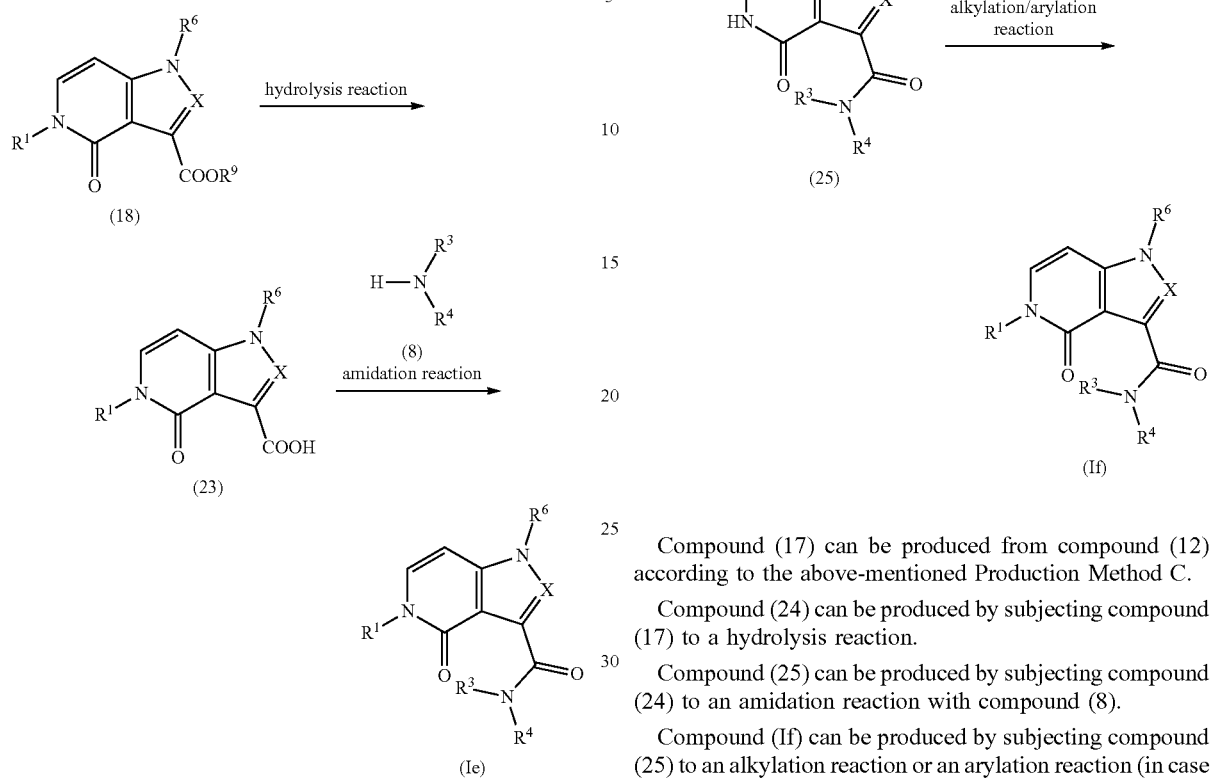

Compound (18) can be produced from compound (12) according to the above-mentioned Production Method C.

Compound (23) can be produced by subjecting compound (18) to a hydrolysis reaction.

Compound (Ie) can be produced by subjecting compound (23) to an amidation reaction with compound (8).

Production Method F

Among compound (I), the below-mentioned compound (If) can be produced according to the following method.

Compound (17) can be produced from compound (12) according to the above-mentioned Production Method C.

Compound (24) can be produced by subjecting compound (17) to a hydrolysis reaction.

Compound (25) can be produced by subjecting compound (24) to an amidation reaction with compound (8).

Compound (If) can be produced by subjecting compound (25) to an alkylation reaction or an arylation reaction (in case where $R^1$ is an optionally substituted $C_{1-6}$ alkyl group or an optionally substituted $C_{6-14}$ aryl group). Examples of the reagent to be used in the arylation reaction include a combination of an aryl boronic acid, a metal reagent or a base. Examples of the metal reagent include copper acetate. Examples of the base include the above-mentioned organic bases (triethylamine, pyridine, diisopropylethylamine, etc.). A molecular sieve may be added depending on the condition.

Production Method G

Among compound (I), the below-mentioned compound (Ig) can be produced according to the following method.

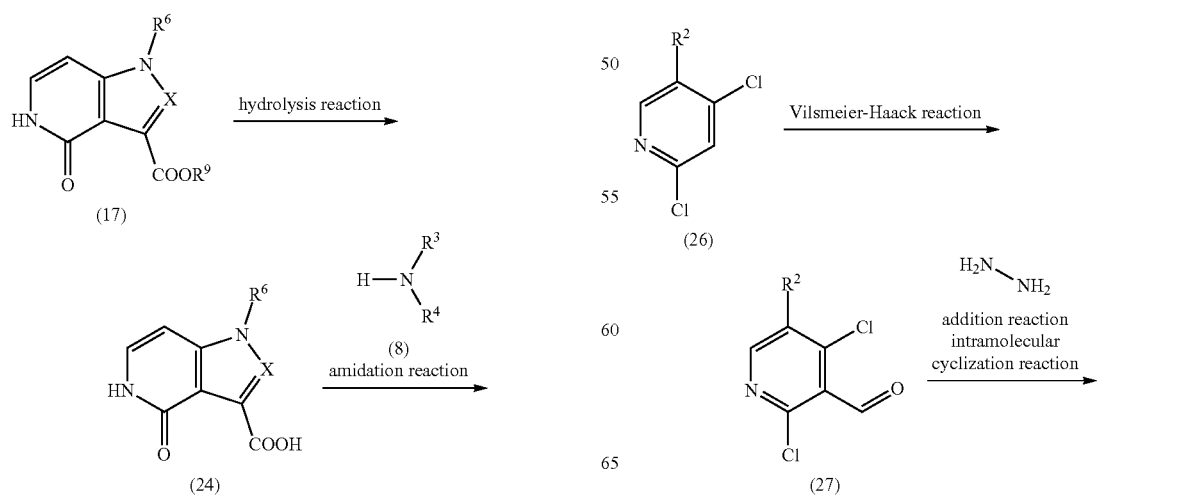

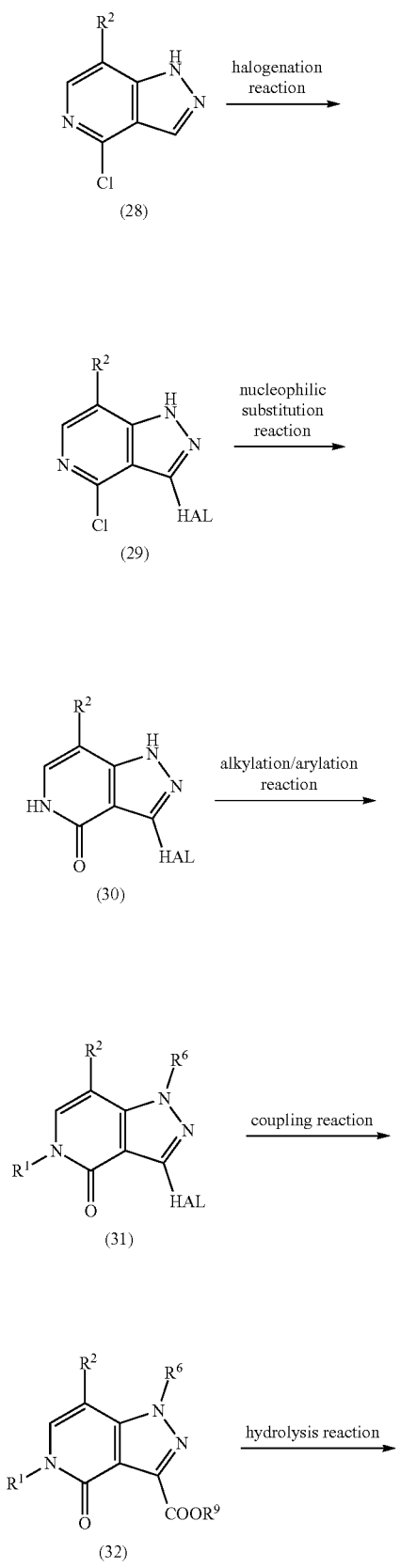

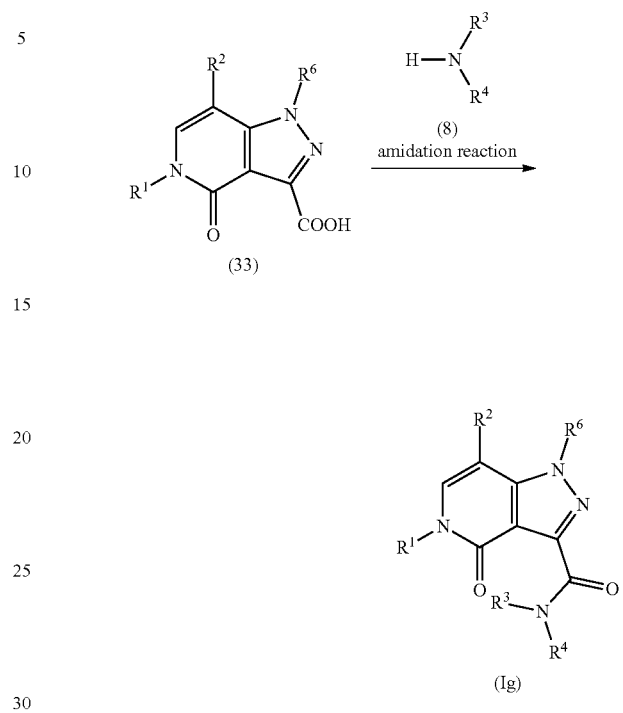

Compound (27) can be produced by subjecting compound (26) to the Vilsmeier-Haack reaction.

Compound (28) can be produced by subjecting compound (27) to an addition reaction of hydrazine, followed by an intramolecular cyclization reaction. Examples of reagent to be used in the addition reaction include hydrazine hydrate and the like.

Compound (29) can be produced by subjecting compound (28) to a halogenation reaction.

Compound (30) can be produced by subjecting compound (29) to a nucleophilic substitution reaction. Examples of the reagent to be used include acetic acid and the like.

Compound (31) can be produced by subjecting compound (30) to an alkylation reaction or an arylation reaction (in case where $R^1$ and $R^6$ are each an optionally substituted $C_{1-6}$ alkyl group or an optionally substituted $C_{6-14}$ aryl group). Examples of the reagent to be used in the arylation reaction include a combination of an aryl boronic acid, a metal reagent or a base. Examples of the metal reagent include copper acetate. Examples of the base include the above-mentioned organic bases (triethylamine, pyridine, diisopropylethylamine, etc.). A molecular sieve may be added depending on the condition.

Compound (32) can be produced by subjecting compound (31) to a coupling reaction with carbon monoxide in the presence of an alcohol corresponding to $R^9$.

Compound (33) can be produced by subjecting compound (32) to a hydrolysis reaction.

Compound (Ig) can be produced by subjecting compound (33) to an amidation reaction with compound (8).

Compound (32) used in Production Method G can also be produced according to the following method.

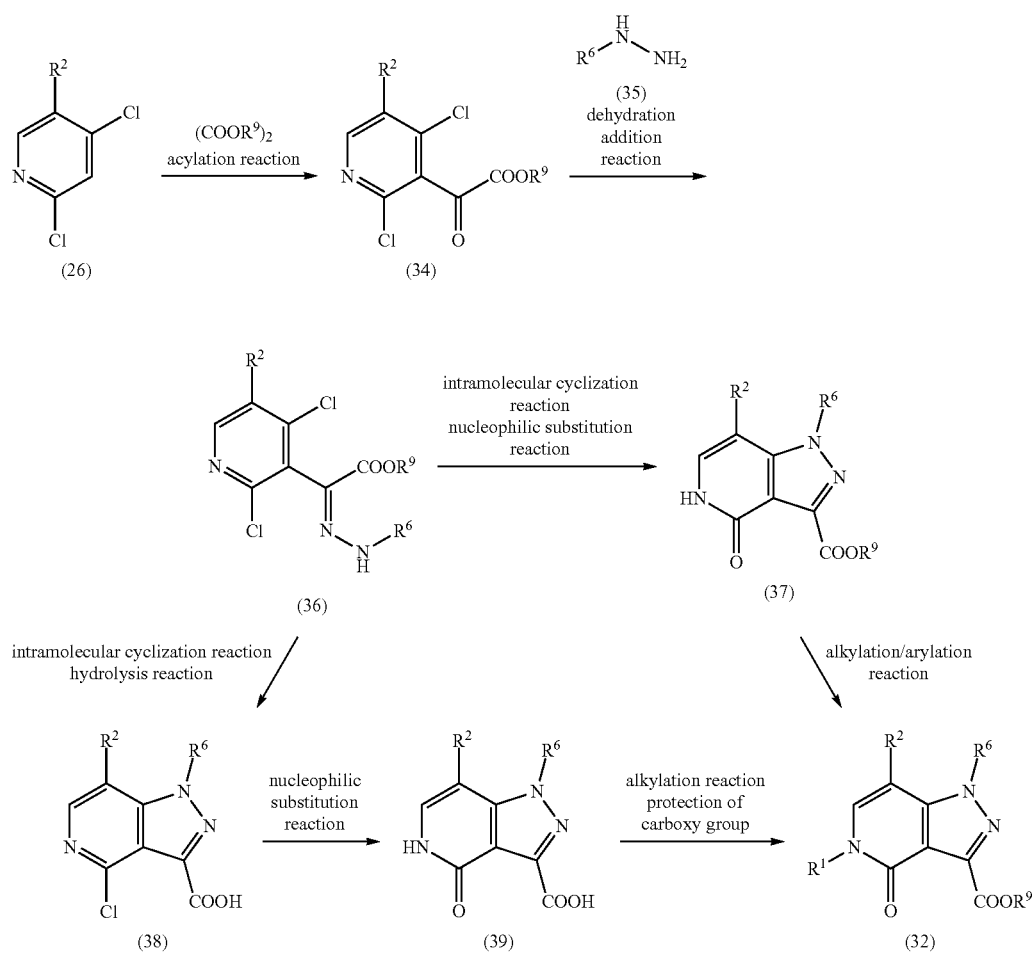

Compound (34) can be produced by subjecting compound (26) to an acylation reaction. Examples of the reagent to be used include a combination of a base and an oxalate. Examples of the base include lithium diisopropylamide and the like.

Compound (36) can be produced by subjecting compound (34) to a dehydration addition reaction with compound (35).

Compound (37) can be produced by subjecting compound (36) to an intramolecular cyclization reaction, followed by a nucleophilic substitution reaction. Examples of the reagent to be used include sodium hydride and the like.

Compound (38) can be produced by subjecting compound (36) to an intramolecular cyclization reaction, followed by a hydrolysis reaction. Examples of the reagent to be used include sodium hydride and the like.

Compound (39) can be produced by subjecting compound (38) to a nucleophilic substitution reaction. Examples of the reagent to be used include sodium hydroxide and the like.

Compound (32) can be produced by subjecting compound (37) to an alkylation or an arylation reaction (in case where $R^1$ is an optionally substituted $C_{1-6}$ alkyl group or an optionally substituted $C_{6-14}$ aryl group). Examples of the reagent to be used in the arylation reaction include a combination of an aryl boronic acid (phenylboronic acid, etc.), a metal reagent and a base. Examples of the metal reagent include copper acetate. Examples of the base include the above-mentioned organic bases (triethylamine, pyridine, diisopropylethylamine, etc.). A molecular sieve may be added depending on the condition.

Compound (32) can also be produced by subjecting compound (39) to an alkylation reaction, followed by a protection reaction of the carboxy group.

Production Method H

Among compound (I), the below-mentioned compound (Ih) can be produced according to the following method.

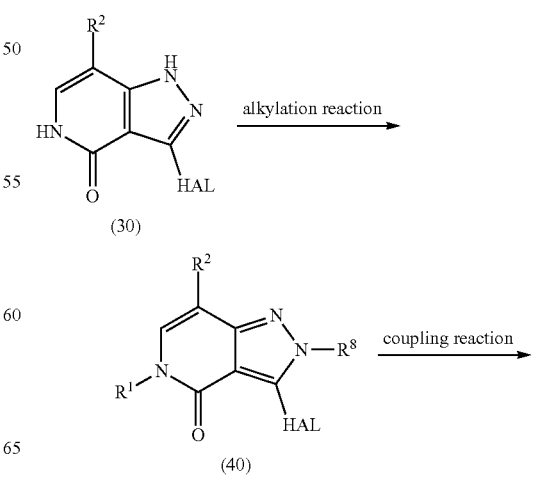

-continued

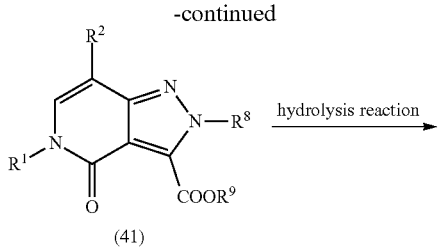

(41)

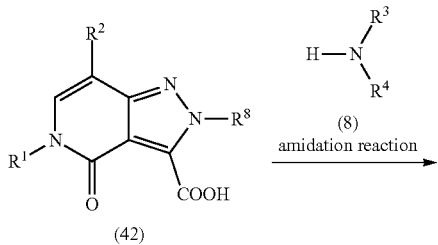

(42)

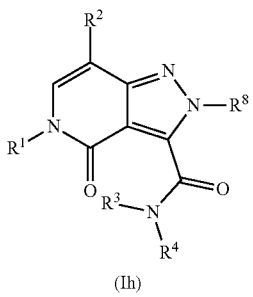

(Ih)

Compound (30) can be produced from compound (26) according to the above-mentioned Production Method G.

Compound (40) can be produced by subjecting compound (30) to an alkylation reaction (in case where $R^1$ and $R^8$ are both optionally substituted $C_{1-6}$ alkyl groups).

Compound (41) can be produced by subjecting compound (40) to a coupling reaction with carbon monoxide, in the presence of an alcohol corresponding to $R^9$.

Compound (42) can be produced by subjecting compound (41) to a hydrolysis reaction.

Compound (Ih) can be produced by subjecting compound (42) to an amidation reaction with compound (8).

Production Method I

Among compound (I), the below-mentioned compound (Ii) can be produced according to the following method.

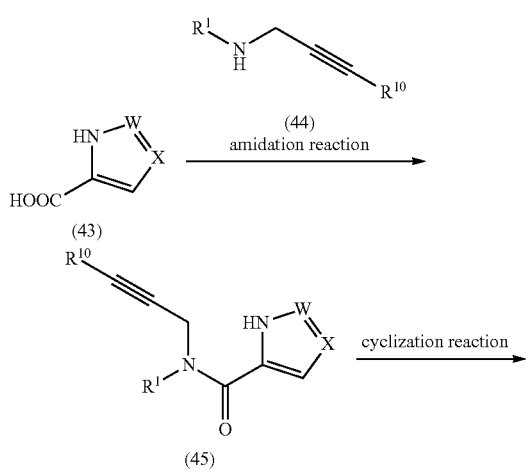

-continued

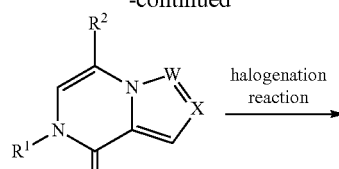

(46)

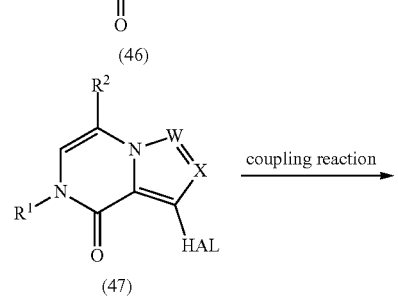

(47)

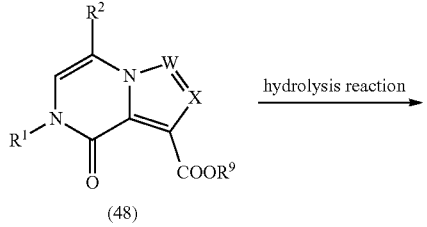

(48)

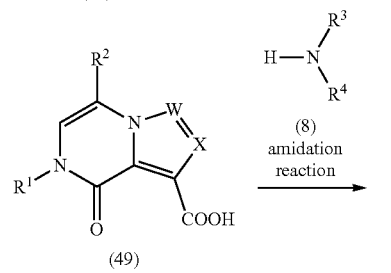

(49)

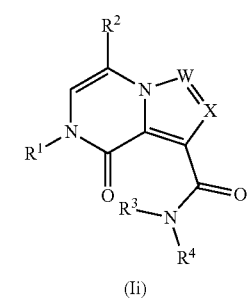

(Ii)

Compound (45) can be produced by subjecting compound (43) to an amidation reaction with compound (44).

Compound (46) can be produced by subjecting compound (45) to a cyclization reaction. Examples of the reagent to be used include DBU and the like.

Compound (47) can be produced by subjecting compound (46) to a halogenation reaction.

Compound (48) can be produced by subjecting compound (47) to a coupling reaction with carbon monoxide, in the presence of an alcohol corresponding to $R^9$.

Compound (49) can be produced by subjecting compound (48) to a hydrolysis reaction.

Compound (Ii) can be produced by subjecting compound (49) to an amidation reaction with compound (8).

Compound (47) used in Production Method I can also be produced according to the following method.

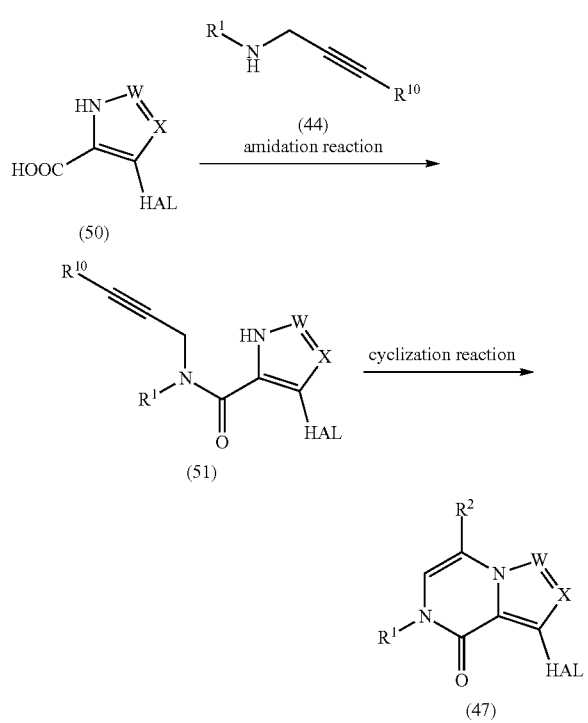

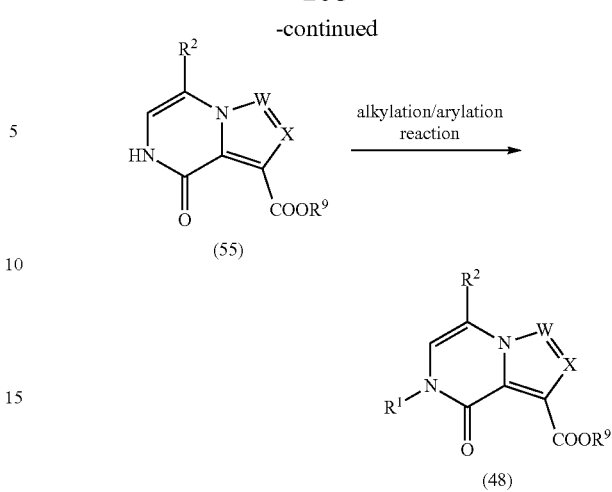

Compound (51) can be produced by subjecting compound (50) to an amidation reaction with compound (44).

Compound (47) can be produced by subjecting compound (51) to a cyclization reaction. Examples of the reagent to be used include DBU and the like.

Compound (48) used in Production Method I can also be produced according to the following method.

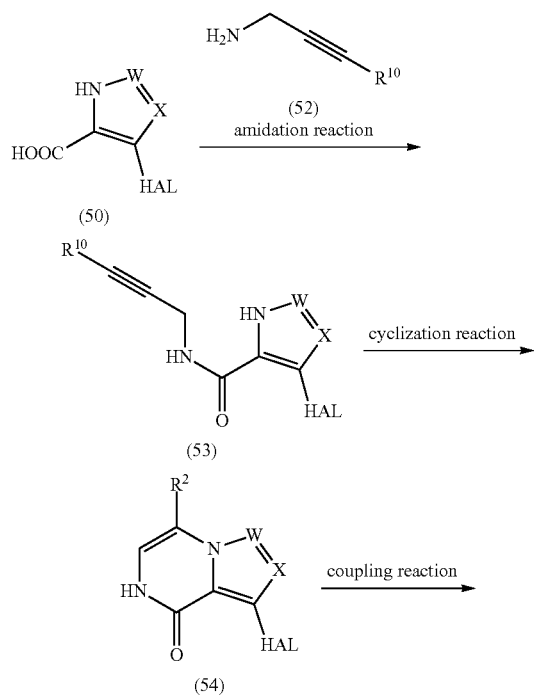

Compound (53) can be produced by subjecting compound (50) to an amidation reaction with compound (52).

Compound (54) can be produced by subjecting compound (53) to a cyclization reaction. Examples of the reagent to be used include DBU and the like.

Compound (55) can be produced by subjecting compound (54) to a coupling reaction with carbon monoxide, in the presence of an alcohol corresponding to $R^9$.

Compound (48) can be produced by subjecting compound (55) to an alkylation or an arylation reaction (in case where $R^1$ is an optionally substituted $C_{1-6}$ alkyl group or an optionally substituted $C_{6-14}$ aryl group). Examples of the reagent to be used in the arylation reaction include a combination of an aryl boronic acid (phenylboronic acid, etc.), a metal reagent and a base. Examples of the metal reagent include copper acetate. Examples of the base include the above-mentioned organic bases (triethylamine, pyridine, diisopropylethylamine, etc.). A molecular sieve may be added depending on the condition.

Compound (49) used in Production Method I can also be produced according to the following method.

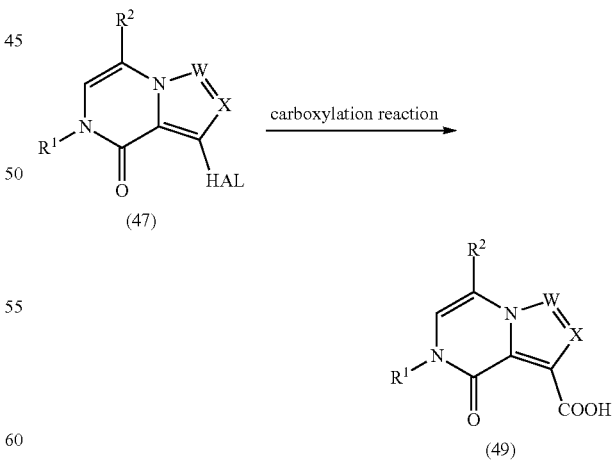

Compound (49) can be produced by subjecting compound (47) to a carboxylation reaction. Examples of the reagent to be used in the carboxylation reaction include isopropylmagnesium chloride-lithium chloride complex, carbon dioxide and the like.

Production Method J

Among compound (I), the below-mentioned compound (Ij) can be produced according to the following method.

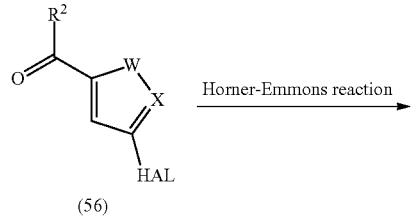
(56)

Horner-Emmons reaction →

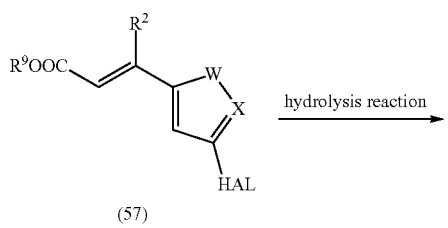
(57)

hydrolysis reaction →

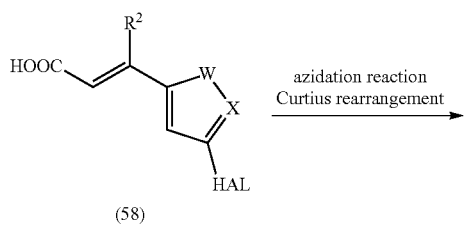
(58)

azidation reaction
Curtius rearrangement →

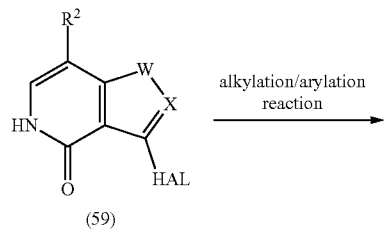
(59)

alkylation/arylation reaction →

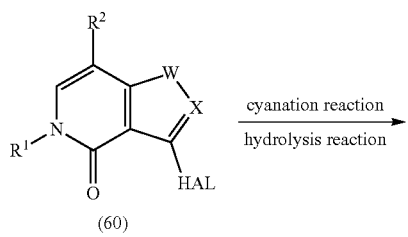
(60)

cyanation reaction
hydrolysis reaction →

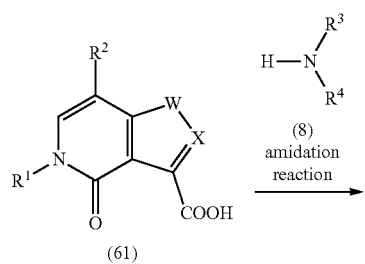
(61)

$$H-N\begin{array}{c}R^3\\R^4\end{array}$$
(8)
amidation reaction →

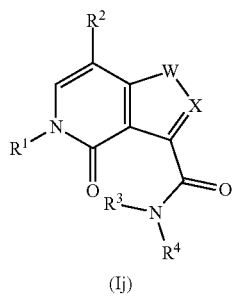
(Ij)

Compound (57) can be produced by subjecting compound (56) to the Horner-Emmons reaction with a dialkylphosphonoacetate corresponding to $R^9$.

Compound (58) can be produced by subjecting compound (57) to a hydrolysis reaction.

Compound (59) can be produced by subjecting compound (58) to an azidation reaction, followed by a cyclization reaction accompanying the Curtius rearrangement. Examples of the reagent to be used in the azidation reaction include DPPA and the like.

Compound (60) can be produced by subjecting compound (59) to an alkylation reaction or an arylation reaction (in case where $R^1$ is an optionally substituted $C_{1-6}$ alkyl group or an optionally substituted $C_{6-14}$ aryl group). Examples of the reagent to be used in the arylation reaction include a combination of an aryl boronic acid, a metal reagent and a base. Examples of the metal reagent include copper acetate. Examples of the base include the above-mentioned organic bases (triethylamine, pyridine, diisopropylethylamine, etc.). A molecular sieve may be added depending on the condition.

Compound (61) can be produced by subjecting compound (60) to a cyanation reaction, followed by a hydrolysis reaction. Examples of the reagent to be used in the cyanation reaction include copper cyanide and the like.

Compound (Ij) can be produced by subjecting compound (61) to an amidation reaction with compound (8).

Production Method K

Among compound (I), the below-mentioned compound (Ik) can be produced according to the following method.

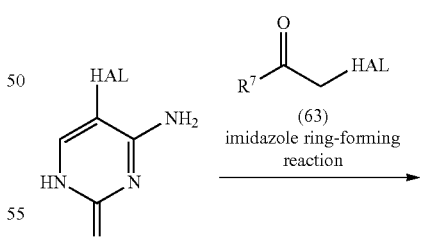
(62)

(63)
imidazole ring-forming reaction →

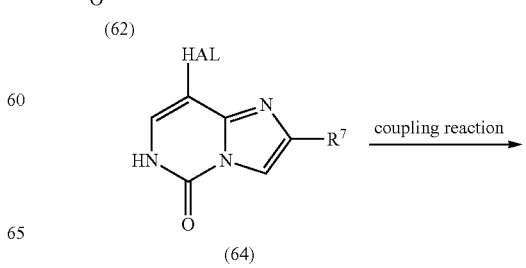
(64)

coupling reaction →

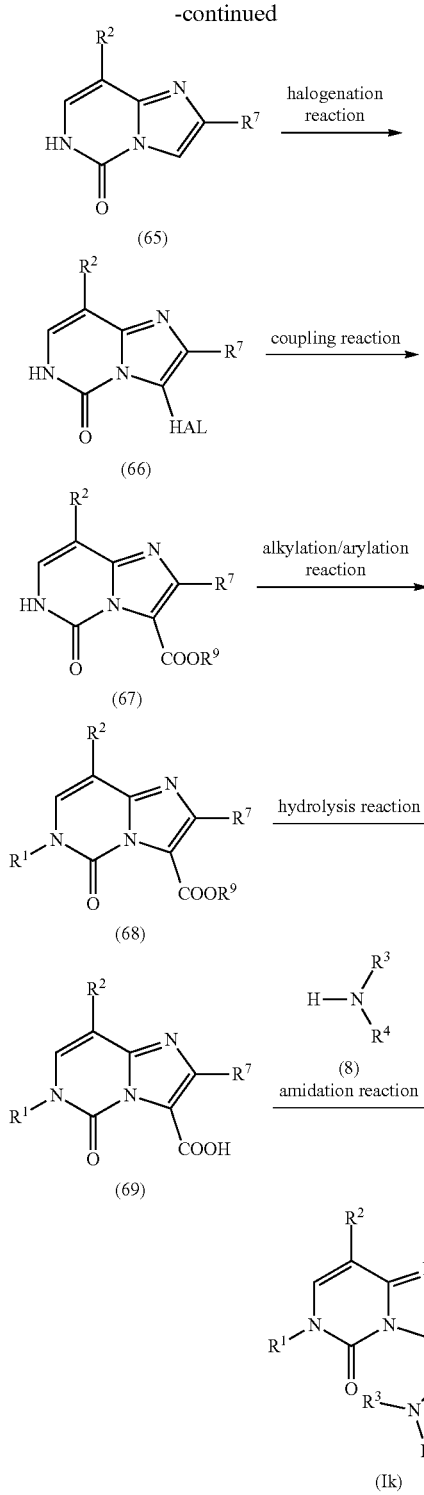

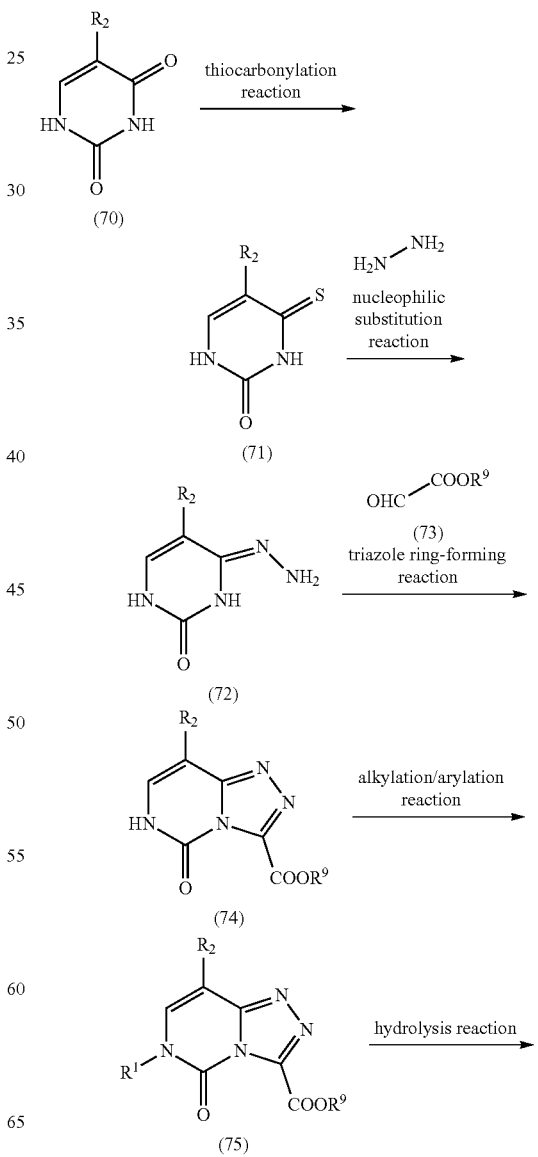

Compound (67) can be produced by subjecting compound (66) to a coupling reaction with carbon monoxide, in the presence of an alcohol corresponding to $R^9$.

Compound (68) can be produced by subjecting compound (67) to an alkylation reaction or an arylation reaction (in case where $R^1$ is an optionally substituted $C_{1-6}$ alkyl group or an optionally substituted $C_{6-14}$ aryl group). Examples of the reagent to be used in the arylation reaction include a combination of an aryl boronic acid, a metal reagent and a base. Examples of the metal reagent include copper acetate. Examples of the base include the above-mentioned organic bases (triethylamine, pyridine, diisopropylethylamine, etc.). A molecular sieve may be added depending on the condition.

Compound (69) can be produced by subjecting compound (68) to a hydrolysis reaction.

Compound (Ik) can be produced by subjecting compound (69) to an amidation reaction with compound (8).

Production Method L

Among compound (I), the below-mentioned compound (Il) can be produced according to the following method.

Compound (64) can be produced by subjecting compound (62) to an imidazole ring-forming reaction with compound (63).

Compound (65) can be produced by subjecting compound (64) to a coupling reaction with a trialkyltin derivative or a boronic acid derivative corresponding to $R^2$.

Compound (66) can be produced by subjecting compound (65) to a halogenation reaction.

113
-continued

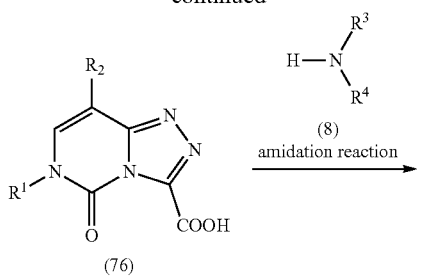

(76)

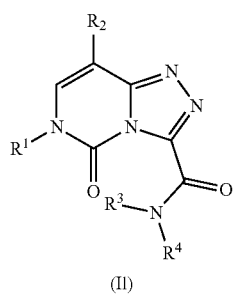

(II)

Compound (71) can be produced by subjecting compound (70) to a thiocarbonylation reaction.

Compound (72) can be produced by subjecting compound (71) to a nucleophilic substitution reaction. Examples of the reagent to be used include hydrazine hydrate and the like.

Compound (74) can be produced by subjecting compound (72) to a triazole ring-forming reaction with compound (73). Examples of the base to be used include the above-mentioned bases (e.g., pyridine, triethylamine) and the like.

Compound (75) can be produced by subjecting compound (74) to an alkylation reaction or an arylation reaction (in case where $R^1$ is an optionally substituted $C_{1-6}$ alkyl group or an optionally substituted $C_{6-14}$ aryl group). Examples of the reagent to be used in the arylation reaction include a combination of an aryl boronic acid, a metal reagent and a base. Examples of the metal reagent include copper acetate. Examples of the base include the above-mentioned organic bases (triethylamine, pyridine, diisopropylethylamine, etc.). A molecular sieve may be added depending on the condition.

Compound (76) can be produced by subjecting compound (75) to a hydrolysis reaction.

Compound (II) can be produced by subjecting compound (76) to an amidation reaction with compound (8).

114

Production Method M

Among compound (I), the below-mentioned compound (Im) can be produced according to the following method.

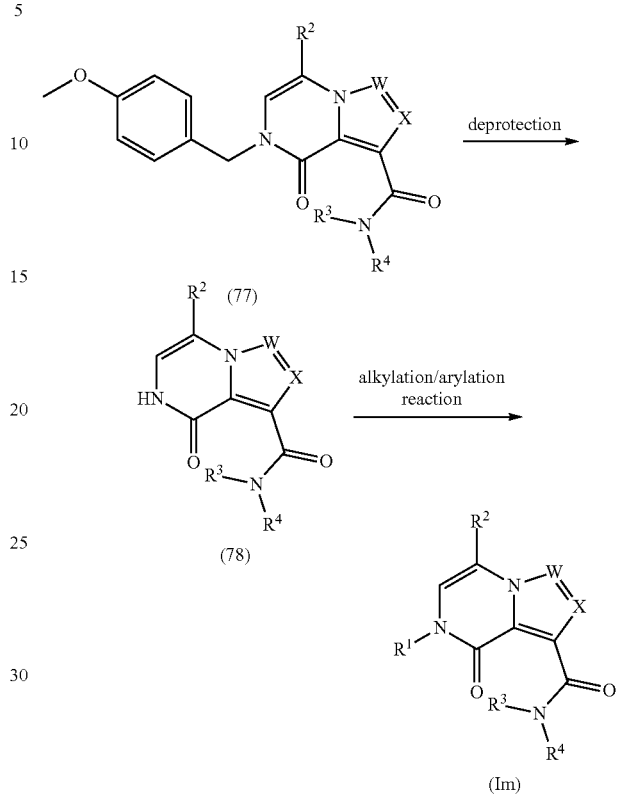

Compound (78) can be produced by subjecting compound (77) to a deprotection reaction.

Compound (Im) can be produced by subjecting compound (78) to an alkylation reaction or an arylation reaction (in case where $R^1$ is an optionally substituted $C_{1-6}$ alkyl group or an optionally substituted $C_{6-14}$ aryl group). Examples of the reagent to be used in the arylation reaction include a combination of an aryl boronic acid, a metal reagent and a base. Examples of the metal reagent include copper acetate. Examples of the base include the above-mentioned organic bases (triethylamine, pyridine, diisopropylethylamine, etc.). A molecular sieve may be added depending on the condition.

Production Method N

Among compound (I), the below-mentioned compound (In) can be produced according to the following method.

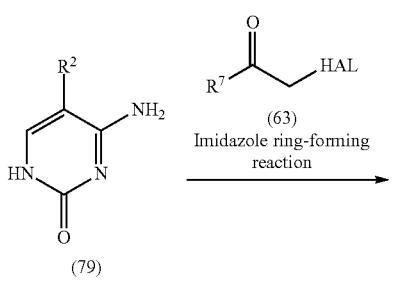

-continued

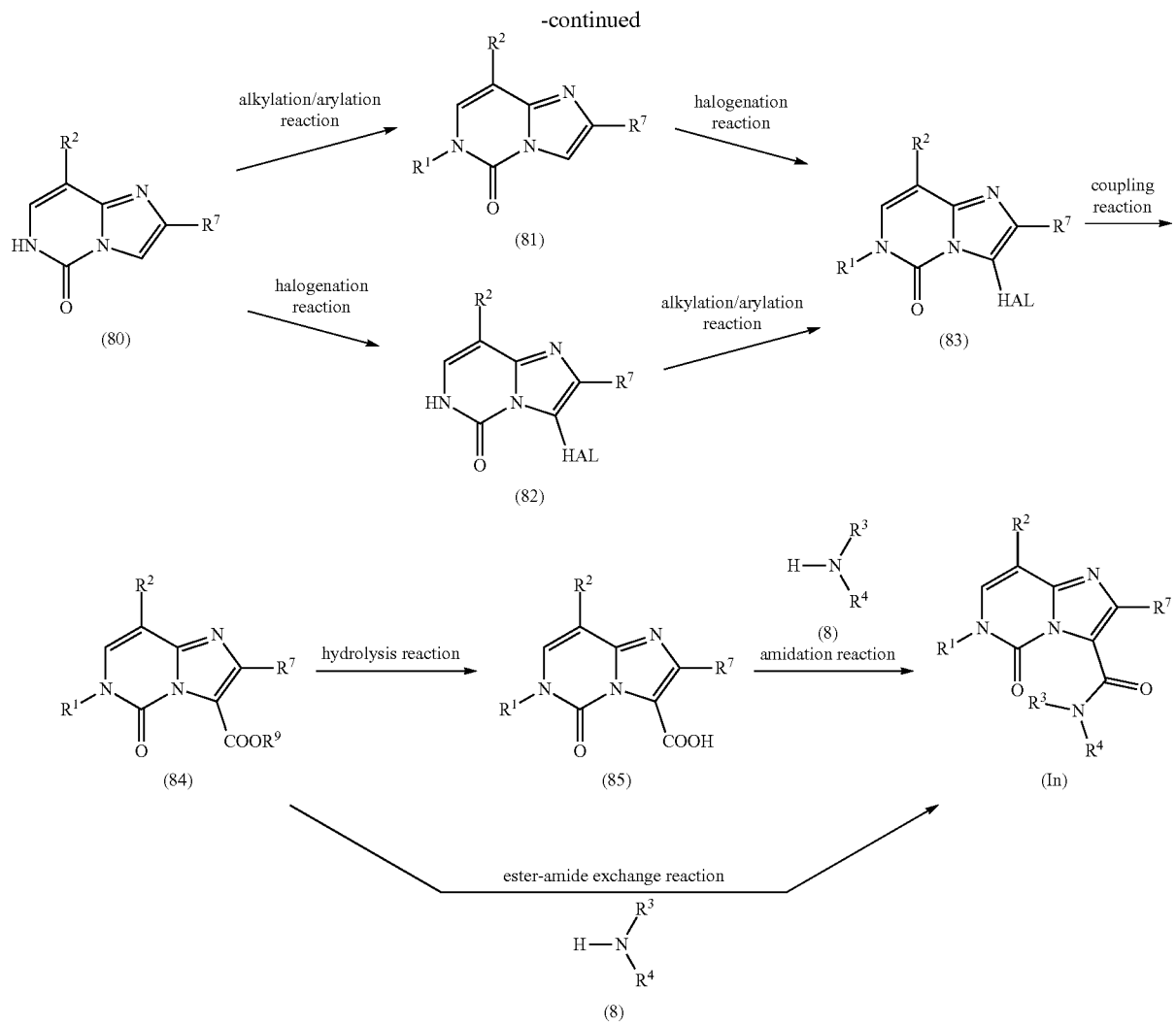

Compound (80) can be produced by subjecting compound (79) to an imidazole ring-forming reaction with compound (63).

Compound (81) can be produced by subjecting compound (80) to an alkylation reaction or an arylation reaction (in case is where $R^1$ is an optionally substituted $C_{1-6}$ alkyl group or an optionally substituted $C_{6-14}$ aryl group). Examples of the reagent to be used in the arylation reaction include a combination of an aryl boronic acid, a metal reagent and a base. Examples of the metal reagent include copper acetate. Examples of the base include the above-mentioned organic bases (triethylamine, pyridine, diisopropylethylamine, etc.). A molecular sieve may be added depending on the condition.

Compound (82) can be produced by subjecting compound (80) to a halogenation reaction.

Compound (83) can be produced by subjecting compound (81) to a halogenation reaction.

Compound (83) can be produced by subjecting compound (82) to an alkylation reaction or an arylation reaction (in case where $R^1$ is an optionally substituted $C_{1-6}$ alkyl group or an optionally substituted $C_{6-14}$ aryl group). Examples of the reagent to be used in the arylation reaction include a combination of an aryl boronic acid, a metal reagent and a base. Examples of the metal reagent include copper acetate.

Examples of the base include the above-mentioned organic bases (triethylamine, pyridine, diisopropylethylamine, etc.). A molecular sieve may be added depending on the condition.

Compound (84) can be produced by subjecting compound (83) to a coupling reaction with carbon monoxide, in the presence of an alcohol corresponding to $R^9$.

Compound (85) can be produced by subjecting compound (84) to a hydrolysis reaction.

Compound (In) can be produced by subjecting compound (85) to an amidation reaction with compound (8).

Compound (In) can also be produced by subjecting compound (84) to an ester-amide exchange reaction with compound (8). Examples of the reagent to be used include trimethylaluminium and the like.

Compounds (1), (1'), (2), (8), (9), (12), (26), (35), (43), (44), (50), (52), (56), (62), (63), (70), (73), (77) and (79), which are used as a raw material in each production method, may be commercially available products, or can be produced according to a method known per se or a method analogous thereto.

As for the configurational isomers (E, Z forms) of compound (I), they can be isolated and purified when isomerization occurs, for example, according to a conventional separation means such as extraction, recrystallization, distillation, chromatography and the like to obtain a pure compound. In addition, the corresponding pure isomer can also be obtained by isomerizing a double bond using heating, an acid catalyst, a transition metal complex, a metal catalyst, a radical catalyst, light irradiation, a strong base catalyst and the like, according to the method described in Shin Jikken Kagaku Kouza 14 (The Chemical Society of Japan ed.), pages 251 to 253, 4th Edition Jikken Kagaku Kouza 19 (The Chemical Society of Japan ed.), pages 273 to 274 or a method analogous thereto.

Compound (I) contains a stereoisomer depending on the kind of a substituent, and each stereoisomer and a mixture thereof are encompassed in the present invention.

When the objective product is obtained as a free form by the above-mentioned reaction, it can be converted to a salt according to a conventional method, or when the objective product is obtained as a salt, it can be converted to a free form or other salt according to a conventional method. The thus-obtained compound (I) can also be isolated and purified from a reaction mixture according to a known method such as transfer, concentration, solvent extraction, distillation, crystallization, recrystallization, chromatography and the like.

When compound (I) contains a configurational isomer, a diastereomer, a conformer and the like, each can be isolated according to the above-mentioned separation and purification methods, if desired. In addition, when compound (I) is racemic, d-form and l-form or S-form and R-form can be isolated according to a conventional optical resolution.

The thus-obtained compound (I), other reaction intermediate therefor and starting compounds thereof can be isolated and purified from a reaction mixture according to a method known per se, for example, extraction, concentration, neutralization, filtration, distillation, recrystallization, column chromatography, thin layer chromatography, preparative high performance liquid chromatography (preparative HPLC), moderate-pressure preparative liquid chromatography (moderate-pressure preparative LC) and the like.

A salt of compound (I) can be produced according to a method known per se. For example, when compound (I) is a basic compound, it can be produced by adding an inorganic acid or organic acid, or when compound (I) is an acidic compound, by adding an organic base or inorganic base.

When compound (I) contains an optical isomer, each optical isomer and a mixture thereof are encompassed in the scope of the present invention, and these isomers can be subjected to optical resolution or can be produced respectively, according to a method known per se, if desired.

The compound of the present invention is expected to be useful for mammals (e.g., mouse, rat, hamster, rabbit, cat, dog, bovine, sheep, monkey, human etc.) as an agent for the prophylaxis or treatment of diseases, for example, (1) psychiatric diseases [e.g., depression, major depression, bipolar depression, dysthymic disorder, emotional disorder (seasonal affective disorder and the like), recurrent depression, postpartum depression, stress disorder, depression symptom, mania, anxiety, generalized anxiety disorder, anxiety syndrome, panic disorder, phobia, social phobia, social anxiety disorder, obsessive disorder, post-traumatic stress syndrome, post-traumatic stress disorder, Tourette syndrome, autism, fragile X syndrome, Rett syndrome, adjustment disorder, bipolar disorder, neurosis, schizophrenia (e.g., positive symptom, negative symptom, cognitive impairment), chronic fatigue syndrome, anxiety neurosis, compulsive neurosis, panic disorder, epilepsy, anxiety disorder, anxiety, anxious mental state, emotional abnormality, cyclothymia, nervous erethism, faint, addiction, low sex drive, attention deficit hyperactivity disorder (ADHD), psychotic major depression, refractory major depression, treatment-resistant depression, depressive disorder, catalepsy, hebephrenic schizophrenia, paranoid schizophrenia], (2) neurodegenerative diseases [e.g., Alzheimer's disease, Alzheimer-type senile dementia, Parkinson's disease, Huntington's disease, multi-infarct dementia, frontotemporal dementia, dementia Parkinson's type, progressive supranuclear palsy, Pick's syndrome, corticobasal degeneration, Down's disease, vascular dementia, postencephalitic parkinsonism, Lewy body dementia, multiple-system atrophy, HIV dementia, amyotrophic lateral sclerosis (ALS), motor neurogenesis disease (MND), Creutzfeldt-Jakob disease or prion disease, cerebral palsy, progressive supranuclear palsy, traumatic brain injury, glaucoma, multiple sclerosis, neuromyelitis optica (NMO), postoperative cognitive dysfunction (POCD), postoperative delirium (POD), delirium], (3) age-related cognition memory disorders [e.g., age-related memory disorders, senile dementia], (4) sleep disorders [e.g., intrinsic sleep disorders (e.g., psychophysiological insomnia and the like), extrinsic sleep disorder, circadian rhythm disorders (e.g., time zone change syndrome (jet lag), shift work sleep disorder, irregular sleep-wake pattern, delayed sleep phase syndrome, advanced sleep phase syndrome, non-24-hour sleep-wake and the like), parasomnia, sleep disorders associated with internal medical or psychiatric disorder (e.g., chronic obstructive pulmonary diseases, Alzheimer's disease, Parkinson's disease, cerebrovascular dementia, schizophrenia, depression, anxiety neurosis), stress insomnia, insomnia, insomniac neurosis, sleep apnea syndrome], (5) respiratory depression caused by anesthetics, traumatic disease, or neurodegenerative disease and the like, (6) traumatic brain injury, cerebral apoplexy, cerebral edema, cerebral ischemia, ischemia, neurotic anorexia, eating disorder, anorexia nervosa, hyperorexia, other eating disorder, alcohol dependence, alcohol abuse, alcoholic amnesia, alcohol paranoia, alcohol preference, alcohol withdrawal, alcoholic insanity, alcohol poisoning, alcoholic jealousy, alcoholic mania, alcohol-dependent psychiatric disorder, alcoholic insanity, pharmacophilia, pharmacophobia, pharmacomania, drug withdrawal, migraine, stress headache, catatonic headache, diabetic neuropathy, obesity, diabetes, muscular spasm, Meniere's disease, autonomic ataxia, alopecia, glaucoma, hypertension, cardiac disease, tachycardia, congestive cardiac failure, hyperventilation, bronchial asthma, apnea, sudden infant death syndrome, inflammatory disease, allergic disease, impotence, climacteric disorder, infertility, neoplasms (e.g., cancer, liver neoplasms, colonic neoplasms, breast neoplasms, prostatic neoplasms, neuroblastoma, bone neoplasms, mouth neoplasms, mastocytoma, cholangiocarcinoma, Lewis lung carcinoma etc.), immunodeficiency syndrome caused by HIV infection, immunodeficiency syndrome caused by stress, cerebrospinal meningitis, acromegaly, incontinence, metabolic syndrome, osteoporosis, peptic ulcer, irritable bowel syndrome, inflammatory bowel disease, ulcerative colitis, Crohn's disease, stress gastrointestinal disorder, stress vomiting, diarrhea, constipation, postoperative ileus, rheumatoid arthritis, osteoarthritis, functional dyspepsia, hyperalgesia, insulin resistance, dementia pugilistica, nausea, vomiting, neoplasm metastasis, brain injuries, seizure, body weight changes, weight gain, weight loss, colitis, alcoholism, hypothermia, fatty liver, atherosclerosis, infection, muscle spasticity, hypertension, stroke, malignant migrating partial seizures of infancy, diabetes mellitus, type 2 diabetes mellitus, dyslipidaemia, visceral obesity, ocular hypotension, anorexia, fibrosis, myocardial infarction, cachexia, induced psychotic disorder, ataxia, AIDS wasting syndrome, cirrhotic cardiomyopathy, uremic pruritus, neurobehavioral manifestations, Tubulointerstitial nephritis and uveitis syndrome, interstitial cystitis, retinitis pigmentosa, autoimmune diseases, coronary artery disease, aspirin-induced asthma, platelet storage pool deficiency, diabetic embryopathy, Arthus type urticaria, asthma, toxic oil syndrome, otitis and the like, (7) pain (e.g., inflammatory pain, cancerous pain, neuropathic pain, acute pain, pain associated with peripheral neuropathy, central pain, fibromyalgia, vassooclussive painful crises in sickle cell disease, multiple sclerosis-mediated spasticity or pain, functional chest pain, complex regional pain syndrome etc.), (8) lysosome diseases [e.g., Gaucher's disease, Krabbe's disease, Niemann-Pick syndrome]
and the like.

Since the compound of the present invention has an excellent glucosylceramide lowering action (e.g., promoting glucosylceramide metabolism, inhibition of glucosylceramide synthesis, promoting glucosylceramide catabolism, etc.), a superior prophylactic or therapeutic effect for the above-mentioned diseases may be expected.

Since the compound of the present invention has an excellent glucosylceramide lowering action (e.g., promoting glucosylceramide metabolism, inhibition of glucosylceramide synthesis, promoting glucosylceramide catabolism, etc.), a superior prophylactic or therapeutic effect for lysosome diseases (e.g., Gaucher's disease), neurodegenerative diseases (e.g., Parkinson's disease, Lewy body dementia, multiple-system atrophy) and the like may be expected.

Compound (I) can be used as a prodrug.

A prodrug of compound (I) means a compound which is converted to compound (I) with a reaction due to an enzyme, an gastric acid, etc. under the physiological condition in the living body, that is, a compound which is converted to compound (I) with oxidation, reduction, hydrolysis, etc. according to an enzyme; a compound which is converted to compound (I) by hydrolysis etc. due to gastric acid, etc.

A prodrug for compound (I) may be a compound obtained by subjecting an amino group in compound (I) to an acylation, alkylation or phosphorylation (e.g., a compound obtained by subjecting an amino group in compound (I) to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation or tert-butylation, etc.); a compound obtained by subjecting a hydroxy group in compound (I) to an acylation, alkylation, phosphorylation or boration (e.g., a compound obtained by subjecting an hydroxy group in compound (I) to an acetylation, palmitoylation, propanoylation, pivaloylation, succinylation, fumarylation, alanylation or dimethylaminomethylcarbonylation, etc.); a compound obtained by subjecting a carboxyl group in compound (I) to an esterification or amidation (e.g., a compound obtained by subjecting a carboxyl group in compound (I) to an ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification or methylamidation, etc.) and the like. Any of these compounds can be produced from compound (I) by a method known per se. The prodrug of compound (I) may be a compound that converts to compound (I) under physiological conditions as described in Development of Pharmaceutical Products, vol. 7, Molecule Design, 163-198, Hirokawa Shoten (1990).

The compound of the present invention is superior in vivo kinetics (e.g., plasma drug half-life, intracerebral transferability, metabolic stability), shows low toxicity (e.g., more superior as a medicament in terms of acute toxicity, chronic toxicity, genetic toxicity, reproductive toxicity, cardiotoxicity, drug interaction, carcinogenicity etc.). The compound of the present invention is directly used as a medicament or a pharmaceutical composition mixed with a pharmaceutically acceptable carrier or the like to be orally or parenterally administered to mammals (e.g., humans, monkeys, cows, horses, pigs, mice, rats, hamsters, rabbits, cats, dogs, sheep and goats) in safety. Examples of the "parenteral" include intravenous, intramuscular, subcutaneous, intra-organ, intranasal, intradermal, instillation, intracerebral, intrarectal, intravaginal, intraperitoneal and intratumor administrations, administration to the vicinity of tumor etc. and direct administration to the lesion.

While the dose of the compound of the present invention varies depending on the administration route, symptom and the like, when, for example, the compound is orally administered to a patient with Parkinson's disease (adult, body weight 40-80 kg, for example, 60 kg), it is, for example, 0.001-1000 mg/kg body weight/day, preferably 0.01-100 mg/kg body weight/day, more preferably 0.1-10 mg/kg body weight/day. This amount can be administered in 1 to 3 portions per day.

A medicament containing the compound of the present invention can be used alone or as a pharmaceutical composition containing the compound of the present invention and a pharmaceutically acceptable carrier according to a method known per se as a production method of a pharmaceutical preparation (e.g., the method described in the Japanese Pharmacopoeia etc.). A medicament containing the compound of the present invention can be safely administered in the form of, for example, tablet (including sugar-coated tablet, film-coated tablet, sublingual tablet, orally disintegrating tablet, buccal and the like), pill, powder, granule, capsule (including soft capsule, microcapsule), troche, syrup, liquid, emulsion, suspension, release control preparation (e.g., immediate-release preparation, sustained-release preparation, sustained-release microcapsule), aerosol, film (e.g., orally disintegrating film, oral mucosa-adhesive film), injection (e.g., subcutaneous injection, intravenous injection, intramuscular injection, intraperitoneal injection), drip infusion, transdermal absorption type preparation, ointment, lotion, adhesive preparation, suppository (e.g., rectal suppository, vaginal suppository), pellet, nasal preparation, pulmonary preparation (inhalant), eye drop and the like, orally or parenterally (e.g., intravenous, intramuscular, subcutaneous, intraorgan, intranasal, intradermal, instillation, intracerebral, intrarectal, intravaginal, intraperitoneal administrations, and administration to the lesion).

As the aforementioned "pharmaceutically acceptable carrier", various organic or inorganic carriers conventionally used as preparation materials (starting materials) can be used. For example, excipient, lubricant, binder, disintegrant and the like are used for solid preparations, and solvent, solubilizing agent, suspending agent, isotonicity agent, buffer, soothing agent and the like are used for liquid preparations. Where necessary, preparation additives such as preservative, antioxidant, colorant, sweetening agent and the like can also be used.

Examples of the excipient include lactose, sucrose, D-mannitol, starch, corn starch, crystalline cellulose, light anhydrous silicic acid and the like.

Examples of the lubricant include magnesium stearate, calcium stearate, talc, colloidal silica and the like.

Examples of the binder include crystalline cellulose, white sugar, D-mannitol, dextrin, hydroxypropylcellulose, hydroxypropylmethylcellulose, polyvinylpyrrolidone, starch, sucrose, gelatin, methylcellulose, carboxymethylcellulose sodium and the like.

Examples of the disintegrant include starch, carboxymethylcellulose, carboxymethylcellulose calcium, sodium carboxymethyl starch, L-hydroxypropylcellulose and the like.

Examples of the solvent include water for injection, alcohol, propylene glycol, Macrogol, sesame oil, corn oil, olive oil and the like.

Examples of the solubilizing agent include polyethylene glycol, propylene glycol, D-mannitol, benzyl benzoate, ethanol, trisaminomethane, cholesterol, triethanolamine, sodium carbonate, sodium citrate and the like.

Examples of the suspending agent include surfactants such as stearyl triethanolamine, sodium lauryl sulfate, laurylaminopropionic acid, lecithin, benzalkonium chloride, benzetonium chloride, glycerin monostearate and the like; hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose and the like; and the like.

Examples of the isotonicity agent include glucose, D-sorbitol, sodium chloride, glycerin, D-mannitol and the like.

Examples of the buffer include buffer solutions such as phosphates, acetates, carbonates, citrates and the like.

Examples of the soothing agent include benzyl alcohol and the like.

Examples of the preservative include p-oxybenzoates, chlorobutanol, benzyl alcohol, phenylethyl alcohol, dehydroacetic acid, sorbic acid and the like.

Examples of the antioxidant include sulfite, ascorbic acid, α-tocopherol and the like.

While the pharmaceutical composition varies according to the dosage form, administration method, carrier and the like, it can be produced according to a conventional method by adding the compound of the present invention in a proportion of generally 0.01-100% (w/w), preferably 0.1-95% (w/w), of the total amount of the preparation.

The compound of the present invention can be used in combination with other active ingredients (hereinafter to be abbreviated as concomitant drug).

Examples of the concomitant drug include the following, benzodiazepine (chlordiazepoxide, diazepam, potassium clorazepate, lorazepam, clonazepam, alprazolam etc.), L-type calcium channel inhibitor (pregabalin etc.), tricyclic or tetracyclic antidepressant (imipramine hydrochloride, amitriptyline hydrochloride, desipramine hydrochloride, clomipramine hydrochloride etc.), selective serotonin reuptake inhibitor (fluvoxamine maleate, fluoxetine hydrochloride, citalopram hydrobromide, sertraline hydrochloride, paroxetine hydrochloride, escitalopram oxalate etc.), serotonin-noradrenaline reuptake inhibitor (venlafaxine hydrochloride, duloxetine hydrochloride, desvenlafaxine hydrochloride etc.), noradrenaline reuptake inhibitor (reboxetine mesylate etc.), noradrenaline-dopamine reuptake inhibitor (bupropion hydrochloride etc.), mirtazapine, trazodone hydrochloride, nefazodone hydrochloride, bupropion hydrochloride, setiptiline maleate, 5-HT$_{1A}$ agonist (buspirone hydrochloride, tandospirone citrate, osemozotan hydrochloride etc.), 5-HT$_3$ antagonist (Cyamemazine etc.), heart non-selective βinhibitor (propranolol hydrochloride, oxprenolol hydrochloride etc.), histamine H$_1$ antagonist (hydroxyzine hydrochloride etc.), therapeutic drug for schizophrenia (chlorpromazine, haloperidol, sulpiride, clozapine, trifluoperazine hydrochloride, fluphenazine hydrochloride, olanzapine, quetiapine fumarate, risperidone, aripiprazole etc.), CRF antagonist, other antianxiety drug (meprobamate etc.), tachykinin antagonist (MK-869, saredutant etc.), medicament that acts on metabotropic glutamate receptor, CCK antagonist, β3 adrenaline antagonist (amibegron hydrochloride etc.), GAT-1 inhibitor (tiagabine hydrochloride etc.), N-type calcium channel inhibitor, carbonic anhydrase II inhibitor, NMDA glycine moiety agonist, NMDA antagonist (memantine etc.), peripheral benzodiazepine receptor agonist, vasopressin antagonist, vasopressin V1b antagonist, vasopressin Via antagonist, phosphodiesterase inhibitor, opioid antagonist, opioid agonist, uridine, nicotinic acid receptor agonist, thyroid hormone (T3, T4), TSH, TRH, MAO inhibitor (phenelzine sulfate, tranylcypromine sulfate, moclobemide etc.), 5-HT$_{2A}$ antagonist, 5-HT$_{2A}$ inverse agonist, COMT inhibitor (entacapone etc.), therapeutic drug for bipolar disorder (lithium carbonate, sodium valproate, lamotrigine, riluzole, felbamate etc.), cannabinoid CB1 antagonist (rimonabant etc.), FAAH inhibitor, sodium channel inhibitor, anti-ADHD drug (methylphenidate hydrochloride, methamphetamine hydrochloride etc.), therapeutic drug for alcoholism, therapeutic drug for autism, therapeutic drug for chronic fatigue syndrome, therapeutic drug for spasm, therapeutic drug for fibromyalgia syndrome, therapeutic drug for headache, therapeutic drug for insomnia (etizolam, zopiclone, triazolam, zolpidem, ramelteon, indiplon etc.), therapeutic drug for quitting smoking, therapeutic drug for myasthenia gravis, therapeutic drug for cerebral infarction, therapeutic drug for mania, therapeutic drug for hypersomnia, therapeutic drug for pain, therapeutic drug for dysthymia, therapeutic drug for autonomic ataxia, therapeutic drug for male and female sexual dysfunction, therapeutic drug for migraine, therapeutic drug for pathological gambler, therapeutic drug for restless legs syndrome, therapeutic drug for substance addiction, therapeutic drug for alcohol-related syndrome, therapeutic drug for irritable bowel syndrome, therapeutic drug for Alzheimer's disease (donepezil, galanthamine, memantine, rivastigmine etc.), therapeutic drug for Parkinson's disease (levodopa, carbidopa, benserazide, selegiline, zonisamide, entacapone, amantadine, talipexole, pramipexole, apomorphine, cabergoline, bromocriptine, istradefylline, trihexyphenidyl, promethazine, pergolide, etc.), therapeutic drug for Huntington's disease (chlorpromazine hydrochloride, haloperidol, reserpine etc.), therapeutic drug for Gaucher's disease (imiglucerase, taliglucerase alfa, velaglucerase alfa, eliglustat, miglustat, etc.), therapeutic drug for ALS (riluzole etc., neurotrophic factor etc.), therapeutic drug for multiple sclerosis (molecular target drug such as fingolimod, interferon beta 1b, natalizumab and the like, etc.), antiepilepsy drug (phenytoin, carbamazepine, phenobarbital, primidone, zonisamide, sodium valproate, ethosuximide, diazepam, nitrazepam, clonazepam, clobazam, gabapentin, topiramate, lamotrigine, levetiracetam, stiripentol, rufinamide, etc.), therapeutic drug for lipid abnormality such as cholesterol-lowering drug (statin series (pravastatin sodium, atrovastatin, simvastatin, rosuvastatin etc.), fibrate (clofibrate etc.), squalene synthetase inhibitor), therapeutic drug for abnormal behavior or suppressant of dromomania due to dementia (sedatives, antianxiety drug etc.), apoptosis inhibitor, antiobesity drug, therapeutic drug for diabetes, therapeutic drug for hypertension, therapeutic drug for hypotension, therapeutic drug for rheumatism (DMARD), anti-cancer agent, therapeutic drug for parathyroid (PTH), calcium receptor antagonist, sex hormone or a derivative thereof (progesterone, estradiol, estradiol benzoate etc.), neuronal differentiation promoter, nerve regeneration promoter, non-steroidal anti-inflammatory drug (meloxicam, tenoxicam, indomethacin, ibuprofen, celecoxib, rofecoxib, aspirin etc.), steroid (dexamethasone, cortisone acetate etc.), anti-cytokine drug (TNF inhibitor, MAP kinase inhibitor etc.), antibody medicament, nucleic acid or nucleic acid derivative, aptamer drug and the like.

By combining the compound of the present invention and a concomitant drug, a superior effect such as
(1) the dose can be reduced as compared to single administration of the compound of the present invention or a concomitant drug,
(2) the drug to be combined with the compound of the present invention can be selected according to the condition of patients (mild case, severe case and the like),
(3) the period of treatment can be set longer by selecting a concomitant drug having different action and mechanism from the compound of the present invention,
(4) a sustained treatment effect can be designed by selecting a concomitant drug having different action and mechanism from the compound of the present invention,
(5) a synergistic effect can be afforded by a combined use of the compound of the present invention and a concomitant drug, and the like, can be achieved.

Hereinafter the compound of the present invention and a concomitant drug used in combination are referred to as the "combination agent of the present invention".

When using the combination agent of the present invention, the administration time of the compound of the present invention and the concomitant drug is not restricted, and the compound of the present invention or a pharmaceutical composition thereof and the concomitant drug or a pharmaceutical composition thereof can be administered to an administration subject simultaneously, or may be administered at different times. The dosage of the concomitant drug may be determined according to the dose clinically used, and can be appropriately selected depending on an administration subject, administration route, disease, combination and the like.

The administration mode of the concomitant drug of the present invention is not particularly restricted, and it is sufficient that the compound of the present invention and the concomitant drug are combined in administration. Examples of such administration mode include the following methods: (1) administration of a single preparation obtained by simultaneously processing the compound of the present invention and the concomitant drug, (2) simultaneous administration of two kinds of preparations of the compound of the present invention and the concomitant drug, which have been separately produced, by the same administration route, (3) administration of two kinds of preparations of the compound of the present invention and the concomitant drug, which have been separately produced, by the same administration route in a staggered manner, (4) simultaneous administration of two kinds of preparations of the compound of the present invention and the concomitant drug, which have been separately produced, by different administration routes, (5) administration of two kinds of preparations of the compound of the present invention and the concomitant drug, which have been separately produced, by different administration routes in a staggered manner (for example, administration in the order of the compound of the present invention and the concomitant drug, or in the reverse order) and the like.

The combination agent of the present invention exhibits low toxicity. For example, the compound of the present invention or (and) the aforementioned concomitant drug can be combined with a pharmacologically acceptable carrier according to the known method to prepare a pharmaceutical composition such as tablets (including sugar-coated tablet and film-coated tablet), powders, granules, capsules (including soft capsule), liquids, injections, suppositories, sustained-release agents, etc. These compositions can be administered safely orally or non-orally (e.g., topical, rectal, intravenous administration etc.). Injection can be administered intravenously, intramuscularly, subcutaneously, or by intraorgan administration or directly to the lesion.

Examples of the pharmacologically acceptable carriers usable for the production of the combination agent of the present invention include those similar to the above-mentioned carriers.

The mixing ratio of the compound of the present invention to the concomitant drug in the combination agent of the present invention can be appropriately selected depending on an administration subject, administration route, diseases and the like.

For example, the content of the compound of the present invention in the combination agent of the present invention differs depending on the form of a preparation, and usually from about 0.01 to about 100 wt %, preferably from about 0.1 to about 50 wt %, further preferably from about 0.5 to about 20 wt %, based on the preparation.

The content of the concomitant drug in the combination agent of the present invention differs depending on the form of a preparation, and usually from about 0.01 to about 100 wt %, preferably from about 0.1 to about 50 wt %, further preferably from about 0.5 to about 20 wt %, based on the preparation.

EXAMPLES

The present invention is explained in detail in the following by referring to Examples, Experimental Examples and Formulation Examples, which are not to be construed as limitative, and the invention may be changed within the scope of the present invention.

In the following Examples, the "room temperature" generally means about 10° C. to about 35° C. The ratios indicated for mixed solvents are volume mixing ratios, unless otherwise specified. % means wt %, unless otherwise specified.

The elution by column chromatography in the Examples was performed under the observation by TLC (Thin Layer Chromatography) unless otherwise specified. In the observation by TLC, 60 $F_{254}$ manufactured by Merck was used as a TLC plate, the solvent used as an elution solvent in column chromatography was used as a developing solvent, and UV detector was used for the detection. In silica gel column chromatography, the indication of NH means use of aminopropylsilane-bonded silica gel and the indication of Diol means use of 3-(2,3-dihydroxypropoxy)propylsilane-bonded silica gel. In preparative HPLC (high performance liquid chromatography), the indication of C18 means use of octadecyl-bonded silica gel. The ratio for elution solvent is, unless otherwise specified, a volume mixing ratio.

For the analysis of $^1$H NMR, ACD/SpecManager (trade name) software and the like were used. Peaks of a hydroxyl group, an amino group and the like, having very mild proton peak, are not sometimes described.

MS was measured by LC/MS. As the ionization method, ESI method, or APCI method was used. The data indicates actual measured value (found). While molecular ion peak is generally observed, a fragment ion is sometimes observed.

In the case of a salt, a molecular ion peak or fragment ion peak of free form is generally observed.

In Examples, the following abbreviations are used.

mp: melting point
MS: mass spectrum
M: mol concentration
N: normality
CDCl$_3$: deuterochloroform
DMSO-d$_6$: deuterodimethyl sulfoxide
$^1$H NMR: proton nuclear magnetic resonance
LC/MS: liquid chromatograph mass spectrometer
ESI: electron spray ionization
APCI: atmospheric pressure chemical ionization
HATU: (dimethylamino)-N,N-dimethyl(3H-[1,2,3]triazolo[4,5-b]pyridin-3-yloxy)methaneiminium hexafluorophosphate
CDI: 1,1'-carbonyldiimidazole
DPPA: diphenyl phosphorazidate
DIPEA: N-ethyl-N-isopropylpropan-2-amine
DMA: N,N-dimethylacetamide
DMF: N,N-dimethylformamide
THF: tetrahydrofuran
MeOH: methanol
EtOH: ethanol
Pd(PPh$_3$)$_4$: tetrakis(triphenylphosphine)palladium(0)
DMSO: dimethyl sulfoxide
DBU: 2,3,4,6,7,8,9,10-octahydropyrimido[1,2-a]azepine
TEA: triethylamine
NaHMDS: sodium 1,1,1,3,3,3-hexamethyldisilazane-2-ide
DMAP: N,N-dimethyl-4-aminopyridine Example 1

N-benzyl-1,5,7-trimethyl-4-oxo-4,5-dihydro-1H-pyrrolo[3,2-c]pyridine-3-carboxamide A) 1,5,7-trimethyl-1,5-dihydro-4H-pyrrolo[3,2-c]pyridin-4-one To a solution of 5,7-dimethyl-1,5-dihydro-4H-pyrrolo[3,2-c]pyridin-4-one (825 mg) in DMF (15 mL) was added sodium hydride (60% in oil, 261.2 mg) at 0° C., and the mixture was stirred at room temperature for 30 min. To the reaction mixture was added iodomethane (0.477 mL) at 0° C., and the mixture was stirred at 0° C. for 2 hr. To the reaction mixture was added aqueous sodium hydrogencarbonate solution, and the mixture was extracted with ethyl acetate. To the aqueous layer was added sodium chloride, and the mixture was extracted with THF. The organic layers were combined, washed with saturated brine, dried over anhydrous sodium sulfate, and concentrated under reduced pressure. The residue was purified by silica gel column chromatography (NH, hexane/ethyl acetate/methanol) to give the title compound (650 mg).
MS: [M+H]$^+$ 177.2.

B) 1,5,7-trimethyl-4-oxo-4,5-dihydro-1H-pyrrolo[3,2-c]pyridine-3-carbaldehyde

To DMF (3 mL) was added oxalyl chloride (0.388 mL) at 0° C., and the mixture was stirred at 0° C. for 30 min, and then for 1 hr while allowed to be warm to room temperature. A solution of 1,5,7-trimethyl-1,5-dihydro-4H-pyrrolo[3,2-c]pyridin-4-one (519.5 mg) in DMF (7.5 mL) was added thereto at 0° C., and the mixture was stirred at room temperature for 3 hr, and then at 80° C. for 2 hr. To the reaction mixture was added aqueous sodium hydrogencarbonate solution, and the mixture was extracted with ethyl acetate. To the aqueous layer was added sodium chloride, and the mixture was extracted with THF. The organic layers were combined, dried over anhydrous sodium sulfate, and concentrated under reduced pressure. The residue was purified by silica gel column chromatography (hexane/ethyl acetate/methanol) to give the title compound (262 mg).
MS: [M+H]$^+$ 205.1.

C) 1,5,7-trimethyl-4-oxo-4,5-dihydro-1H-pyrrolo[3,2-c]pyridine-3-carboxylic Acid To a solution of 1,5,7-trimethyl-4-oxo-4,5-dihydro-1H-pyrrolo[3,2-c]pyridine-3-carbaldehyde (159.3 mg) in DMSO (2 mL) were added an aqueous solution (0.5 mL) of sodium dihydrogenphosphate (291 mg) and an aqueous solution (0.5 mL) of sodium chlorite (214.3 mg) at 15° C., and the mixture was stirred at room temperature for 2 hr. The reaction mixture was acidified with 6M hydrochloric acid, and diluted with water. The precipitate was collected by filtration to give the title compound (121 mg).
MS: [M+H]$^+$ 221.2.

D) N-benzyl-1,5,7-trimethyl-4-oxo-4,5-dihydro-1H-pyrrolo[3,2-c]pyridine-3-carboxamide To a mixture of 1,5,7-trimethyl-4-oxo-4,5-dihydro-1H-pyrrolo[3,2-c]pyridine-3-carboxylic acid (80 mg), THF (1.5 mL) and DMF (0.01 mL) was added oxalyl chloride (0.041 mL), and the mixture was stirred at room temperature for 3 hr. The reaction mixture was concentrated under reduced pressure, and suspended in DMA (1.5 mL). Benzylamine (46.7 mg) was added dropwise thereto at 0° C., and the mixture was stirred at 0° C. for 1 hr, and then at room temperature for 1 hr. To the reaction mixture was added aqueous sodium hydrogencarbonate solution, and the mixture was extracted with ethyl acetate. The organic layer was separated, dried over anhydrous magnesium sulfate, and concentrated under reduced pressure. The residue was purified by silica gel column chromatography (NH, hexane/ethyl acetate/methanol) to give the title compound (6.5 mg).
$^1$H NMR (300 MHz, DMSO-d$_6$) δ 2.42 (3H, d, J=0.8 Hz), 3.46 (3H, s), 4.00 (3H, s), 4.50 (2H, d, J=6.0 Hz), 7.19-7.37 (6H, m), 7.75 (1H, s), 11.74 (1H, t, J=5.7 Hz).

Example 2

N-(trans-4-butoxycyclohexyl)-1,5,7-trimethyl-4-oxo-4,5-dihydro-1H-pyrrolo[3,2-c]pyridine-3-carboxamide A) Tert-butyl (trans-4-(but-2-en-1-yloxy)cyclohexyl)carbamate To a solution of tert-butyl(trans-4-hydroxycyclohexyl)carbamate (1 g) in DMF (10 mL) was added sodium hydride (60% in oil, 246.7 mg) at 0° C., and the mixture was stirred at 0° C. for 15 min. Crotyl bromide (0.621 mL) was added dropwise thereto at 0° C., and the mixture was stirred overnight at room temperature. Sodium hydride (60% in oil, 122.7 mg) and crotyl bromide (0.310 mL) were added thereto, and the mixture was stirred at 50° C. for 5 hr. To the reaction mixture was added aqueous sodium hydrogencarbonate solution, and the mixture was extracted with ethyl acetate. The organic layer was separated, washed with saturated brine, dried over anhydrous magnesium sulfate, and concentrated under reduced pressure. The residue was purified by silica gel column chromatography (hexane/ethyl acetate) to give the title compound (514 mg).

$^1$H NMR (300 MHz, DMSO-$d_6$) δ 1.05-1.24 (4H, m), 1.37 (9H, s), 1.56-1.68 (3H, m), 1.69-1.82 (2H, m), 1.90 (2H, d, J=3.8 Hz), 3.06-3.24 (2H, m), 3.78-4.04 (2H, m), 5.40-5.72 (2H, m), 6.68 (1H, d, J=7.7 Hz).

B) Tert-butyl (trans-4-butoxycyclohexyl)carbamate

A mixture of tert-butyl (trans-4-(but-2-en-1-yloxy)cyclohexyl)carbamate (7.2 g), 10% palladium-carbon (1.40.25 g) and MeOH (150 mL) was stirred overnight under normal pressure of hydrogen atmosphere at room temperature. The catalyst was removed by filtration, and the filtrate was concentrated under reduced pressure. The residue was dissolved in ethyl acetate (100 mL), and the solution was dried over anhydrous magnesium sulfate, and concentrated under reduced pressure to give the title compound (7.08 g).

$^1$H NMR (300 MHz, DMSO-$d_6$) δ 0.79-0.94 (3H, m), 1.04-1.20 (4H, m), 1.23-1.50 (13H, m), 1.73 (2H, brs), 1.85-1.99 (2H, m), 3.02-3.25 (2H, m), 3.36 (2H, t, J=6.3 Hz), 6.68 (1H, d, J=7.2 Hz).

C) trans-4-butoxycyclohexanamine Hydrochloride

To a solution of tert-butyl (trans-4-butoxycyclohexyl) carbamate (7.7 g) in ethyl acetate (70 mL) was added 4M hydrogen chloride-ethyl acetate solution (35 mL), and the mixture was stirred at 60° C. for 4.5 hr. The reaction mixture was concentrated under reduced pressure, and the precipitate was collected by filtration, and washed with hexane and diisopropyl ether to give the title compound (5.67 g).

$^1$H NMR (300 MHz, DMSO-$d_6$) δ 0.81-0.92 (3H, m), 1.09-1.52 (8H, m), 1.85-2.05 (4H, m), 2.87-3.02 (1H, m), 3.07-3.22 (1H, m), 3.38 (2H, t, J=6.4 Hz), 7.94 (3H, brs).

D) N-(trans-4-butoxycyclohexyl)-1,5,7-trimethyl-4-oxo-4,5-dihydro-1H-pyrrolo[3,2-c]pyridine-3-carboxamide To a mixture of 1,5,7-trimethyl-4-oxo-4,5-dihydro-1H-pyrrolo[3,2-c]pyridine-3-carboxylic acid (100 mg), DMF (0.01 mL) and THF (2 mL) was added oxalyl chloride (0.06 mL) at room temperature, and the mixture was stirred at room temperature for 1 hr. The reaction mixture was concentrated under reduced pressure, to the residue were added THF (2 mL), TEA (0.253 mL) and trans-4-butoxycyclohexanamine hydrochloride (111.3 mg) at 0° C., and the mixture was stirred at room temperature for 2 hr. To the reaction mixture was added aqueous sodium hydrogencarbonate solution, and the mixture was extracted with ethyl acetate. The organic layer was separated, dried over anhydrous magnesium sulfate, and concentrated under reduced pressure. The residue was purified by silica gel column chromatography (NH, ethyl acetate/methanol) to give the title compound (100 mg).

$^1$H NMR (300 MHz, DMSO-$d_6$) δ 0.81-0.93 (3H, m), 1.18-1.39 (6H, m), 1.39-1.53 (2H, m), 1.94 (4H, dd, J=10.7, 4.7 Hz), 2.40 (3H, s), 3.18-3.30 (1H, m), 3.39 (2H, t, J=6.4 Hz), 3.47 (3H, s), 3.70 (1H, brs), 3.97 (3H, s), 7.22 (1H, s), 7.67 (1H, s), 11.26 (1H, d, J=7.2 Hz).

Example 3

N-(trans-4-butoxycyclohexyl)-1-ethyl-5,7-dimethyl-4-oxo-4,5-dihydro-1H-pyrrolo[3,2-c]pyridine-3-carboxamide

A) 1-ethyl-5,7-dimethyl-1,5-dihydro-4H-pyrrolo[3,2-c]pyridin-4-one

To a solution of 5,7-dimethyl-1,5-dihydro-4H-pyrrolo[3,2-c]pyridin-4-one (471.6 mg) in DMF (10 mL) was added sodium hydride (60% in oil, 153.9 mg) at 0° C., and the mixture was stirred at room temperature for 30 min. Iodoethane (0.35 mL) was added dropwise thereto at room temperature, and the mixture was stirred overnight at room temperature. To the reaction mixture was added aqueous sodium hydrogencarbonate solution, and the mixture was extracted with ethyl acetate. To the aqueous layer was added sodium chloride, and the mixture was extracted with THF. The organic layers were combined, dried over anhydrous sodium sulfate, and concentrated under reduced pressure. The residue was purified by silica gel column chromatography (NH, hexane/ethyl acetate/methanol) to give the title compound (374 mg).

MS: [M+H]$^+$ 191.2.

B) 1-ethyl-5,7-dimethyl-4-oxo-4,5-dihydro-1H-pyrrolo[3,2-c]pyridine-3-carbaldehyde To DMF (2 mL) was added dropwise oxalyl chloride (0.26 mL) at 0° C., and the mixture was stirred at 0° C. for 30 min, and then for 2.5 hr while allowed to be warm to room temperature. A solution of 1-ethyl-5,7-dimethyl-1,5-dihydro-4H-pyrrolo[3,2-c]pyridin-4-one (369.5 mg) in DMF (5 mL) was added dropwise thereto at 0° C., and the mixture was stirred at room temperature for 2.5 hr, and then at 80° C. for 1.5 hr. To the reaction mixture was added aqueous sodium hydrogencarbonate solution, and the mixture was extracted with ethyl acetate. To the aqueous layer was added sodium chloride, and the mixture was extracted with THF. The organic layers were combined, dried over anhydrous sodium sulfate, and concentrated under reduced pressure. The residue was purified by silica gel column chromatography (hexane/ethyl acetate/methanol) to give the title compound (240 mg).

MS: [M+H]$^+$ 219.2.

C) 1-ethyl-5,7-dimethyl-4-oxo-4,5-dihydro-1H-pyrrolo[3,2-c]pyridine-3-carboxylic Acid To a suspension of 1-ethyl-5,7-dimethyl-4-oxo-4,5-dihydro-1H-pyrrolo[3,2-c]pyridine-3-carbaldehyde (238 mg) in DMSO (4 mL) were added an aqueous solution (0.6 mL) of sodium dihydrogenphosphate (267.1 mg), and an aqueous solution (0.6 mL) of sodium chlorite (249.7 mg) at 15° C., and the mixture was stirred overnight at room temperature. The reaction mixture was adjusted to pH=2-3 with 6M hydrochloric acid. The precipitate was collected by filtration, and washed with water to give the title compound (137 mg).

MS: [M+H]$^+$ 235.1.

D) N-(trans-4-butoxycyclohexyl)-1-ethyl-5,7-dimethyl-4-oxo-4,5-dihydro-1H-pyrrolo[3,2-c]pyridine-3-carboxamide To a mixture of 1-ethyl-5,7-dimethyl-4-oxo-4,5-dihydro-1H-pyrrolo[3,2-c]pyridine-3-carboxylic acid (60.3 mg), THF (1.25 mL) and DMF (0.01 mL) was added oxalyl chloride (0.034 mL), and the mixture was stirred at room temperature for 1 hr. The reaction mixture was concentrated under reduced pressure, and to the residue was added THF (1.5 mL). TEA (0.144 mL) and trans-4-butoxycyclohexanamine hydrochloride (62.6 mg) were added thereto at 0° C., and the mixture was stirred at room temperature for 2 hr. To the reaction mixture was added aqueous sodium hydrogencarbonate solution, and the mixture was extracted with ethyl acetate. The organic layer was separated, dried over anhydrous magnesium sulfate, and concentrated under reduced pressure. The residue was purified by silica gel column chromatography (NH, ethyl acetate/methanol) to give the title compound (48.2 mg).

$^1$H NMR (300 MHz, DMSO-$d_6$) δ 0.80-0.94 (3H, m), 1.22-1.39 (9H, m), 1.40-1.53 (2H, m), 1.94 (4H, dd, J=10.3, 4.8 Hz), 2.39 (3H, s), 3.30 (1H, s), 3.39 (2H, t, J=6.5 Hz), 3.48 (3H, s), 3.62-3.80 (1H, m), 4.33 (2H, q, J=7.2 Hz), 7.26 (1H, d, J=0.9 Hz), 7.74 (1H, s), 11.30 (1H, d, J=7.2 Hz).

Example 4

1-benzyl-N-(trans-4-butoxycyclohexyl)-5,7-dimethyl-4-oxo-4,5-dihydro-1H-pyrrolo[3,2-c]pyridine-3-carboxamide A) 1-benzyl-5,7-dimethyl-1,5-dihydro-4H-pyrrolo[3,2-c]pyridin-4-one To a solution of 5,7-dimethyl-1,5-dihydro-4H-pyrrolo[3,2-c]pyridin-4-one (474.2 mg) in DMF (10 mL) was added sodium hydride (60% in oil, 138.9 mg) at 0° C., and the mixture was stirred at room temperature for 1.5 hr. Benzyl bromide (0.45 mL) was added dropwise thereto, and the mixture was stirred at room temperature for 4 hr. To the reaction mixture was added aqueous sodium hydrogencarbonate solution, and the mixture was extracted with ethyl acetate. To the aqueous layer was added sodium chloride, and the mixture was extracted with THF. The organic layers were combined, dried over magnesium sulfate, and concentrated under reduced pressure. The residue was purified by silica gel column chromatography (NH, hexane/ethyl acetate/methanol) to give the title compound (564 mg).

MS: [M+H]$^+$ 253.2.

B) 1-benzyl-5,7-dimethyl-4-oxo-4,5-dihydro-1H-pyrrolo[3,2-c]pyridine-3-carbaldehyde To DMF (5 mL) was added dropwise oxalyl chloride (0.4 mL) at 0° C., and the mixture was stirred at 0° C. for 30 min, and then for 2.5 hr while allowed to be warm to room temperature. A solution of 1-benzyl-5,7-dimethyl-1,5-dihydro-4H-pyrrolo[3,2-c]pyridin-4-one (560 mg) in DMF (7 mL) was added dropwise thereto at 0° C., and the mixture was stirred at room temperature for 2.5 hr, and then at 80° C. for 1.5 hr. To the reaction mixture was added aqueous sodium hydrogencarbonate solution, and the mixture was extracted with ethyl acetate. To the aqueous layer was added sodium chloride, and the mixture was extracted with THF. The organic layers were combined, dried over anhydrous sodium sulfate, and concentrated under reduced pressure. The residue was purified by silica gel column chromatography (hexane/ethyl acetate/methanol) to give the title compound (290 mg).

MS: [M+H]$^+$ 281.2.

C) 1-benzyl-5,7-dimethyl-4-oxo-4,5-dihydro-1H-pyrrolo[3,2-c]pyridine-3-carboxylic Acid To a solution of 1-benzyl-5,7-dimethyl-4-oxo-4,5-dihydro-1H-pyrrolo[3,2-c]pyridine-3-carbaldehyde (288 mg) in DMSO (5 mL) were added an aqueous solution (0.7 mL) of sodium dihydrogenphosphate (248.7 mg), and an aqueous solution (0.7 mL) of sodium chlorite (248.3 mg) at 0° C., and the mixture was stirred overnight at room temperature. The reaction mixture was adjusted to pH=2-3 with 6M hydrochloric acid, and the precipitate was collected by filtration, and washed with water to give the title compound (183 mg).

MS: [M+H]$^+$ 297.2.

D) 1-benzyl-N-(trans-4-butoxycyclohexyl)-5,7-dimethyl-4-oxo-4,5-dihydro-1H-pyrrolo[3,2-c]pyridine-3-carboxamide To a mixture of 1-benzyl-5,7-dimethyl-4-oxo-4,5-dihydro-1H-pyrrolo[3,2-c]pyridine-3-carboxylic acid (60.2 mg), THF (1 mL) and DMF (0.01 mL) was added oxalyl chloride (0.027 mL), and the mixture was stirred at room temperature for 2.5 hr. The reaction mixture was concentrated under reduced pressure, and the residue was suspended in THF (1.5 mL). TEA (0.113 mL) and trans-4-butoxycyclohexanamine hydrochloride (50.1 mg) were added thereto at 0° C., and the mixture was stirred at room temperature for 4 hr. To the reaction mixture was added aqueous sodium hydrogencarbonate solution, and the mixture was extracted with a mixed solvent of ethyl acetate/THF=1/1. The organic layer was separated, dried over anhydrous magnesium sulfate, and concentrated under reduced pressure. The residue was purified by silica gel column chromatography (NH, hexane/ethyl acetate/methanol) to give the title compound (18.3 mg).

$^1$H NMR (300 MHz, DMSO-$d_6$) δ 0.88 (3H, t, J=7.3 Hz), 1.24-1.40 (6H, m), 1.40-1.54 (2H, m), 1.86-2.04 (4H, m), 2.14 (3H, s), 3.22-3.29 (1H, m), 3.40 (2H, t, J=6.4 Hz), 3.47 (3H, s), 3.63-3.81 (1H, m), 5.63 (2H, s), 6.90 (2H, d, J=6.8 Hz), 7.21 (1H, d, J=0.9 Hz), 7.23-7.39 (3H, m), 7.82 (1H, s), 11.34 (1H, d, J=7.2 Hz).

Example 5

N-(trans-4-butoxycyclohexyl)-1,2,5,7-tetramethyl-4-oxo-4,5-dihydro-1H-pyrrolo[3,2-c]pyridine-3-carboxamide A) N-allyl-N,5-dimethyl-1H-pyrrole-2-carboxamide To a mixture of 5-methyl-1H-pyrrole-2-carboxylic acid (5 g), THF (100 mL) and DMF (0.5 mL) was added oxalyl chloride (4.5 mL), and the mixture was stirred at room temperature for 1.25 hr. The reaction mixture was concentrated under reduced pressure, and the residue was suspended in THF (100 mL). N-Methylprop-2-en-1-amine (4.5 mL) and TEA (19 mL) were added thereto at 0° C., and the mixture was stirred overnight at room temperature. To the reaction mixture was added aqueous sodium hydrogencarbonate solution, and the mixture was extracted with ethyl acetate. The organic layer was separated, washed with water and saturated brine, dried over anhydrous magnesium sulfate, and concentrated under reduced pressure. The residue was purified by silica gel column chromatography (hexane/ethyl acetate) to give the title compound (5.43 g).

$^1$H NMR (300 MHz, DMSO-d$_6$) δ 2.18 (3H, s), 3.04 (3H, s), 4.10 (2H, d, J=5.1 Hz), 5.08-5.25 (2H, m), 5.74-5.96 (2H, m), 6.39 (1H, t, J=2.9 Hz), 11.16 (1H, brs).

B) 2,5,7-trimethyl-1,5-dihydro-4H-pyrrolo[3,2-c]pyridin-4-one

To a mixture of N-allyl-N,5-dimethyl-1H-pyrrole-2-carboxamide (2 g), DMF (20 mL) and THF (40 mL) were added dichlorobis(acetonitrile)palladium(II) (295.7 mg) and 1,4-benzoquinone (1.22 g), and the mixture was stirred at 100° C. for 2 hr, and then overnight at 80° C. The insoluble substance was filtered through Celite, and washed with ethyl acetate. The filtrate was concentrated under reduced pressure, and the residue was purified by silica gel column chromatography (hexane/ethyl acetate/methanol) to give the title compound (678 mg).
MS: [M+H]$^+$ 177.2.

C) 1,2,5,7-tetramethyl-1,5-dihydro-4H-pyrrolo[3,2-c]pyridin-4-one

To a solution of 2,5,7-trimethyl-1,5-dihydro-4H-pyrrolo[3,2-c]pyridin-4-one (676.7 mg) in DMF (12 mL) was added sodium hydride (60% in oil, 211.2 mg), and the mixture was stirred at room temperature for 30 min. Iodomethane (0.36 mL) was added dropwise thereto at 0° C., and the mixture was stirred overnight at room temperature. To the reaction mixture were added aqueous sodium hydrogencarbonate solution and sodium chloride, and the mixture was extracted with a mixed solvent of ethyl acetate/THF=1/1. The organic layer was separated, dried over anhydrous sodium sulfate, and concentrated under reduced pressure. The residue was purified by silica gel column chromatography (NH, hexane/ethyl acetate/methanol) to give the title compound (574 mg).
MS: [M+H]$^+$ 191.2.

D) 1,2,5,7-tetramethyl-4-oxo-4,5-dihydro-1H-pyrrolo[3,2-c]pyridine-3-carbaldehyde To DMF (3 mL) was added oxalyl chloride (0.4 mL) at 0° C., and the mixture was stirred at room temperature for 1 hr. A suspension of 1,2,5,7-tetramethyl-1,5-dihydro-4H-pyrrolo[3,2-c]pyridin-4-one (573 mg) in DMF (8 mL) was added dropwise thereto at 0° C., and the mixture was stirred at room temperature for 2 hr, and then at 80° C. for 30 min. To the reaction mixture were added aqueous sodium hydrogencarbonate solution and sodium chloride, and the mixture was extracted with a mixed solvent of ethyl acetate/THF=1/1. The organic layer was separated, dried over anhydrous sodium sulfate, and concentrated under reduced pressure. The residue was purified by silica gel column chromatography (hexane/ethyl acetate/methanol) to give the title compound (605 mg).
MS: [M+H]$^+$ 219.2.

E) 1,2,5,7-tetramethyl-4-oxo-4,5-dihydro-1H-pyrrolo[3,2-c]pyridine-3-carboxylic Acid To a solution of 1,2,5,7-tetramethyl-4-oxo-4,5-dihydro-1H-pyrrolo[3,2-c]pyridine-3-carbaldehyde (606.3 mg) in DMSO (10 mL) were added an aqueous solution (1.5 mL) of sodium dihydrogenphosphate (671.7 mg), and an aqueous solution (1.5 mL) of sodium chlorite (639.3 mg) at 10° C., and the mixture was stirred at room temperature for 2 hr. An aqueous solution (1 mL) of sodium dihydrogenphosphate (338.2 mg), and an aqueous solution (1 mL) of sodium chlorite (328.1 mg) were added thereto, and the mixture was stirred overnight at room temperature. The reaction mixture was adjusted to pH=2-3 with 2M hydrochloric acid, and diluted with water. The precipitate was collected by filtration, and washed with water to give the title compound (497 mg).
MS: [M+H]$^+$ 235.0.

F) N-(trans-4-butoxycyclohexyl)-1,2,5,7-tetramethyl-4-oxo-4,5-dihydro-1H-pyrrolo[3,2-c]pyridine-3-carboxamide To a mixture of 1,2,5,7-tetramethyl-4-oxo-4,5-dihydro-1H-pyrrolo[3,2-c]pyridine-3-carboxylic acid (102.4 mg), THF (2 mL) and DMF (0.01 mL) was added dropwise oxalyl chloride (0.095 mL), and the mixture was stirred at room temperature for 1 hr. The reaction mixture was concentrated under reduced pressure, and the residue was suspended in THF (2 mL). TEA (0.24 mL) and trans-4-butoxycyclohexanamine hydrochloride (113.1 mg) were added thereto at 0° C., and the mixture was stirred at room temperature for 1 hr. To the reaction mixture were added aqueous sodium hydrogencarbonate solution and sodium chloride, and the mixture was extracted with a mixed solvent of ethyl acetate/THF=1/1, dried over anhydrous sodium sulfate, and concentrated under reduced pressure. The residue was purified by silica gel column chromatography (NH, hexane/ethyl acetate) to give the title compound (57.4 mg).
$^1$H NMR (300 MHz, DMSO-d$_6$) δ 0.81-0.94 (3H, m), 1.20-1.53 (8H, m), 1.81-2.05 (4H, m), 2.44 (3H, s), 2.73 (3H, s), 3.24-3.28 (1H, m), 3.39 (2H, t, J=6.4 Hz), 3.46 (3H, s), 3.70 (1H, brs), 3.82 (3H, s), 7.22 (1H, d, J=0.9 Hz), 11.69 (1H, d, J=7.0 Hz).

Example 93

N-(trans-4-butoxycyclohexyl)-1,5-dimethyl-4-oxo-4,5-dihydro-1H-pyrrolo[3,2-c]pyridine-3-carboxamide

A) Methyl 4-chloro-1-methyl-1H-pyrrolo[3,2-c]pyridine-3-carboxylate

To a mixture of 4-chloro-1-methyl-1H-pyrrolo[3,2-c]pyridine-3-carboxylic acid (6.2 g), which was synthesized according to the method described in US 2013/0197046, cesium carbonate (14.47 g) and DMF (80 mL) was added iodomethane (2.2 mL) at room temperature, and the mixture was stirred at room temperature for 2 hr. To the reaction mixture was added water, and the mixture was extracted with ethyl acetate. To the aqueous layer was added sodium chloride, and the mixture was extracted with a mixed solvent of ethyl acetate/THF=1/1. The organic layer was separated, washed with saturated brine, dried over anhydrous magnesium sulfate, and concentrated under reduced pressure. The precipitate was collected by filtration to give the title compound (6.00 g).
MS: [M+H]$^+$ 224.9.

B) Methyl 1-methyl-4-oxo-4,5-dihydro-1H-pyrrolo[3,2-c]pyridine-3-carboxylate To a solution of methyl 4-chloro-1-methyl-1H-pyrrolo[3,2-c]pyridine-3-carboxylate (5.95 g) in acetic acid (50 mL) was added sodium acetate (6.53 g) at room temperature, and the mixture was stirred at 130° C. for 6 hr, and then overnight at 100° C. The reaction mixture was concentrated under reduced pressure, the residue was diluted with water, and the mixture was extracted with ethyl acetate. To the aqueous layer was added sodium chloride, and the mixture was extracted with THF. The organic layers were combined, washed with saturated brine, dried over anhydrous sodium sulfate, and concentrated under reduced pressure to give the title compound (2.09 g).

MS: [M+H]$^+$ 207.0.

C) Methyl 1,5-dimethyl-4-oxo-4,5-dihydro-1H-pyrrolo[3,2-c]pyridine-3-carboxylate To a mixture of methyl 1-methyl-4-oxo-4,5-dihydro-1H-pyrrolo[3,2-c]pyridine-3-carboxylate (24.08 g, a mixture with an inorganic salt (purity about 10%)), cesium carbonate (18.9 g) and DMF (100 mL) was added iodomethane (3 mL), and the mixture was stirred at 60° C. for 1 hr. Iodomethane (2 mL) was again added thereto, and the mixture was stirred at 60° C. for 2 hr. The insoluble substance was removed by filtration, and washed with acetone, and the filtrate was concentrated under reduced pressure. The precipitate was suspended in ethanol, and the suspension was concentrated under reduced pressure until the solvent volume reduced to half. The precipitate was collected by filtration, and washed with ethyl acetate to give the title compound (2.27 g).

MS: [M+H]$^+$ 221.0.

D) 1,5-dimethyl-4-oxo-4,5-dihydro-1H-pyrrolo[3,2-c]pyridine-3-carboxylic Acid To a mixture of methyl 1,5-dimethyl-4-oxo-4,5-dihydro-1H-pyrrolo[3,2-c]pyridine-3-carboxylate (580 mg), THF (2 mL) and MeOH (6 mL) was added 8M aqueous sodium hydroxide solution (1.4 mL), and the mixture was stirred at room temperature for 4 hr. The reaction mixture was acidified with 6M hydrochloric acid at 0° C., and diluted with water. The organic solvent was concentrated under reduced pressure, and the precipitate was collected by filtration to give the title compound (157 mg).

MS: [M+H]$^+$ 207.0.

E) N-(trans-4-butoxycyclohexyl)-1,5-dimethyl-4-oxo-4,5-dihydro-1H-pyrrolo[3,2-c]pyridine-3-carboxamide To a mixture of 1,5-dimethyl-4-oxo-4,5-dihydro-1H-pyrrolo[3,2-c]pyridine-3-carboxylic acid (50 mg), THF (1 mL) and DMF (0.01 mL) was added oxalyl chloride (0.032 mL), and the mixture was stirred at room temperature for 1.5 hr. The reaction mixture was concentrated under reduced pressure, and suspended in THF (1.5 mL). TEA (0.14 mL) and trans-4-butoxycyclohexanamine hydrochloride (59.4 mg) were added thereto at 0° C., and the mixture was stirred at room temperature for 4 hr. To the reaction mixture was added aqueous sodium hydrogencarbonate solution, and the mixture was extracted with ethyl acetate. The organic layer was separated, dried over anhydrous magnesium sulfate, and concentrated under reduced pressure. The residue was purified by silica gel column chromatography (NH, hexane/ethyl acetate/methanol) to give the title compound (51.2 mg).

$^1$H NMR (300 MHz, DMSO-d$_6$) δ 0.82-0.94 (3H, m), 1.21-1.40 (6H, m), 1.40-1.53 (2H, m), 1.83-2.03 (4H, m), 3.21-3.28 (1H, m), 3.40 (2H, t, J=6.5 Hz), 3.53 (3H, s), 3.74 (4H, s), 6.70 (1H, d, J=7.4 Hz), 7.53 (1H, d, J=7.2 Hz), 7.70 (1H, s), 11.00 (1H, d, J=7.4 Hz).

Example 98

N-(trans-4-butoxycyclohexyl)-7-chloro-1,5-dimethyl-4-oxo-4,5-dihydro-1H-pyrrolo[3,2-c]pyridine-3-carboxamide

A) methyl 7-chloro-1,5-dimethyl-4-oxo-4,5-dihydro-1H-pyrrolo[3,2-c]pyridine-3-carboxylate To a solution of methyl 1,5-dimethyl-4-oxo-4,5-dihydro-1H-pyrrolo[3,2-c]pyridine-3-carboxylate (239.6 mg) in DMF (5 mL) was added N-chlorosuccinimide (227.4 mg) at 0° C., and the mixture was stirred at 60° C. for 2 hr. To the reaction mixture was added saturated aqueous sodium hydrogencarbonate solution, and the mixture was extracted with ethyl acetate. The organic layer was separated, dried over anhydrous magnesium sulfate, and concentrated under reduced pressure. The residue was purified by silica gel column chromatography (NH, hexane/ethyl acetate/methanol) to give the title compound (90 mg).

MS: [M+H]$^+$ 255.0.

B) 7-chloro-1,5-dimethyl-4-oxo-4,5-dihydro-1H-pyrrolo[3,2-c]pyridine-3-carboxylic Acid To a mixture of methyl 7-chloro-1,5-dimethyl-4-oxo-4,5-dihydro-1H-pyrrolo[3,2-c]pyridine-3-carboxylate (105 mg), MeOH (1.5 mL) and THF (0.5 mL) was added 8M aqueous sodium hydroxide solution (0.21 mL), and the mixture was stirred at room temperature for 2 hr, and then at 60° C. for 2 hr. The reaction mixture was acidified with 2M hydrochloric acid, and diluted with water. The organic solvent was concentrated under reduced pressure, and the precipitate was collected by filtration to give the title compound (71.4 mg).

MS: [M+H]$^+$ 240.9.

C) N-(trans-4-butoxycyclohexyl)-7-chloro-1,5-dimethyl-4-oxo-4,5-dihydro-1H-pyrrolo[3,2-c]pyridine-3-carboxamide To a mixture of 7-chloro-1,5-dimethyl-4-oxo-4,5-dihydro-1H-pyrrolo[3,2-c]pyridine-3-carboxylic acid (68.8 mg), THF (2 mL) and DMF (0.01 mL) was added oxalyl chloride (0.038 mL), and the mixture was stirred at room temperature for 2 hr. Oxalyl chloride (0.019 mL) was added thereto, and the mixture was stirred at room temperature for 1 hr. The reaction mixture was concentrated under reduced pressure, THF (2 mL), trans-4-butoxycyclohexanamine hydrochloride (71.1 mg) and TEA (0.159 mL) were added thereto at 0° C., and the mixture was stirred at room temperature for 2 hr. To the reaction mixture was added aqueous sodium hydrogencarbonate solution, and the mixture was extracted with ethyl acetate. The organic layer was separated, dried over anhydrous magnesium sulfate, and concentrated under reduced pressure. The residue was purified by silica gel column chromatography (hexane/ethyl acetate/methanol) to give the title compound (12.3 mg).

$^1$H NMR (300 MHz, DMSO-d$_6$) δ 0.82-0.94 (3H, m), 1.22-1.39 (6H, m), 1.40-1.54 (2H, m), 1.85-2.03 (4H, m), 3.20-3.26 (1H, m), 3.39 (2H, t, J=6.4 Hz), 3.51 (3H, s), 3.71 (1H, brs), 4.03 (3H, s), 7.79 (2H, d, J=1.9 Hz), 10.99 (1H, d, J=7.4 Hz).

Example 101

1,7-dimethyl-4-oxo-N,5-diphenyl-4,5-dihydro-1H-pyrrolo[3,2-c]pyridine-3-carboxamide

A) N-allyl-1-methyl-N-phenyl-1H-pyrrole-2-carboxamide

To a solution of 1-methyl-1H-pyrrole-2-carboxylic acid (2.07 g) in toluene (20 mL) was added thionyl chloride (5.5 mL), and the mixture was stirred at 100° C. for 3 hr. The reaction mixture was concentrated under reduced pressure, to a solution of the residue in dichloromethane (20 mL) were added N-allylaniline (2 mL) and TEA (4.2 mL), and the mixture was stirred at 25° C. for 9 hr. The reaction mixture was concentrated under reduced pressure, and the residue was purified by silica gel column chromatography (petroleum ether/ethyl acetate) to give the title compound (3.2 g).

MS: [M+H]$^+$ 241.3.

B) 1,7-dimethyl-5-phenyl-1,5-dihydro-4H-pyrrolo[3,2-c]pyridin-4-one

To a mixture of N-allyl-1-methyl-N-phenyl-1H-pyrrole-2-carboxamide (2 g), THF (20 mL) and DMF (10 mL) were added dichloro(bisacetonitrile)palladium(II) (324 mg) and 1,4-benzoquinone (899.7 mg), and the mixture was stirred under nitrogen atmosphere at 100° C. for 16 hr. To the reaction mixture was added saturated brine, and the mixture was extracted with ethyl acetate. The organic layers were combined, dried over anhydrous sodium sulfate, and concentrated under reduced pressure. The residue was purified by silica gel column chromatography (petroleum ether/ethyl acetate) to give the title compound (700 mg).

MS: [M+H]$^+$ 239.2.

C) 1,7-dimethyl-4-oxo-5-phenyl-4,5-dihydro-1H-pyrrolo[3,2-c]pyridine-3-carbaldehyde To a mixture of DMF (0.19 mL) and dichloromethane (8 mL) was added oxalyl chloride (0.18 mL) at 0° C., and the mixture was stirred at 0° C. for 1 hr. The reaction mixture was added to a solution of 1,7-dimethyl-5-phenyl-1,5-dihydro-4H-pyrrolo[3,2-c]pyridin-4-one (500 mg) in dichloromethane (8 mL), and the mixture was stirred at 50° C. for 11 hr. The reaction mixture was poured into cold water, saturated aqueous sodium hydrogencarbonate solution was added thereto, and the mixture was extracted with dichloromethane. The organic layers were combined, dried over anhydrous sodium sulfate, and concentrated under reduced pressure. The residue was purified by silica gel column chromatography (petroleum ether/ethyl acetate) to give the title compound (450 mg).

MS: [M+H]$^+$ 267.1.

D) 1,7-dimethyl-4-oxo-5-phenyl-4,5-dihydro-1H-pyrrolo[3,2-c]pyridine-3-carboxylic Acid To a mixture of 1,7-dimethyl-4-oxo-5-phenyl-4,5-dihydro-1H-pyrrolo[3,2-c]pyridine-3-carbaldehyde (480 mg), water (3 mL), THF (3 mL) and tert-butanol (3 mL) was added sulfamic acid (350 mg). Potassium dihydrogenphosphate (736 mg) and an aqueous solution (3 mL) of sodium chlorite (245 mg) were added thereto, and the mixture was stirred at 25° C. for 1 hr. The reaction mixture was diluted with water, and extracted with ethyl acetate. The organic layer was washed with saturated brine, dried over anhydrous sodium sulfate, and concentrated under reduced pressure to give the title compound (500 mg).

MS: [M+H]$^+$ 283.1.

E) 1,7-dimethyl-4-oxo-N,5-diphenyl-4,5-dihydro-1H-pyrrolo[3,2-c]pyridine-3-carboxamide To a solution of 1,7-dimethyl-4-oxo-5-phenyl-4,5-dihydro-1H-pyrrolo[3,2-c]pyridine-3-carboxylic acid (100 mg) in DMF (5 mL) were added HATU (202 mg), aniline (0.065 mL) and DIPEA (0.154 mL), and the mixture was stirred at 25° C. for 12 hr. The reaction mixture was diluted with water, and extracted with ethyl acetate. The organic layers were combined, washed with saturated brine, dried over anhydrous sodium sulfate, and concentrated under reduced pressure. The residue was purified by preparative high-performance liquid chromatography (Phenomenex Gemini 150*25 mm*10 um, acetonitrile/0.05% aqueous ammonia) to give the title compound (13.44 mg).

$^1$H NMR (400 MHz, CDCl$_3$) δ 2.48 (3H, s), 4.05 (3H, s), 6.92 (1H, s), 7.00-7.05 (1H, m), 7.27-7.31 (2H, m), 7.42-7.50 (3H, m), 7.51-7.57 (2H, m), 7.75-7.82 (3H, m), 13.21 (1H, s).

Example 103

7-bromo-N-(trans-4-butoxycyclohexyl)-1,5-dimethyl-4-oxo-4,5-dihydro-1H-pyrrolo[3,2-c]pyridine-3-carboxamide

A) Methyl 7-bromo-1,5-dimethyl-4-oxo-4,5-dihydro-1H-pyrrolo[3,2-c]pyridine-3-carboxylate To a solution of methyl 1,5-dimethyl-4-oxo-4,5-dihydro-1H-pyrrolo[3,2-c]pyridine-3-carboxylate (825.2 mg) in DMF (10 mL) was added N-bromosuccinimide (792.3 mg) at 0° C., and the mixture was stirred at 0° C. for 40 min, and then overnight at room temperature. The reaction mixture was diluted with diisopropyl ether, and stirred at 0° C. for 30 min. The precipitate was collected by filtration, and washed with ethyl acetate to give the title compound (655 mg).

$^1$H NMR (300 MHz, DMSO-d$_6$) δ 3.42 (3H, s), 3.72 (3H, s), 4.02 (3H, s), 7.77 (1H, s), 7.78 (1H, s).

B) 7-bromo-1,5-dimethyl-4-oxo-4,5-dihydro-1H-pyrrolo[3,2-c]pyridine-3-carboxylic Acid To a mixture of methyl 7-bromo-1,5-dimethyl-4-oxo-4,5-dihydro-1H-pyrrolo[3,2-c]pyridine-3-carboxylate (89.7 mg), MeOH (1.5 mL) and THF (0.5 mL) was added 8M aqueous sodium hydroxide solution (0.075 mL), and the mixture was stirred at room temperature for 2 hr, and then at 60° C. for 1 hr. The reaction mixture was acidified with 2M hydrochloric acid, and diluted with water. The precipitate was collected by filtration, and washed with water to give the title compound (56.8 mg).

$^1$H NMR (300 MHz, DMSO-d$_6$) δ 3.61 (3H, s), 4.09 (3H, s), 8.01 (1H, s), 8.03 (1H, s), 15.67 (1H, s).

C) 7-bromo-N-(trans-4-butoxycyclohexyl)-1,5-dimethyl-4-oxo-4,5-dihydro-1H-pyrrolo[3,2-c]pyridine-3-carboxamide To a mixture of 7-bromo-1,5-dimethyl-4-oxo-4,5-dihydro-1H-pyrrolo[3,2-c]pyridine-3-carboxylic acid (56 mg), THF (2 mL) and DMF (0.01 mL) was added oxalyl chloride (0.034 mL), and the mixture was stirred at room temperature for 2 hr. The reaction mixture was concentrated under reduced pressure, to the residue were added THF (2 mL), trans-4-butoxycyclohexanamine hydrochloride (52.0 mg) and TEA (0.137 mL) at 0° C., and the mixture was stirred at room temperature for 2 hr. To the reaction mixture was added aqueous sodium hydrogencarbonate solution, and the mixture was extracted with ethyl acetate. The organic layer was separated, dried over anhydrous magnesium sulfate, and concentrated under reduced pressure. The residue was purified by silica gel column chromatography (hexane/ethyl acetate/methanol) to give the title compound (69 mg).

$^1$H NMR (300 MHz, DMSO-$d_6$) δ 0.83-0.92 (3H, m), 1.22-1.39 (6H, m), 1.40-1.53 (2H, m), 1.83-2.05 (4H, m), 3.20-3.28 (1H, m), 3.35-3.44 (2H, m), 3.51 (3H, s), 3.61-3.79 (1H, m), 4.05 (3H, s), 7.79 (1H, s), 7.86 (1H, s), 11.02 (1H, d, J=7.2 Hz).

Example 107

N-cyclohexyl-5-(2-methoxyphenyl)-1,7-dimethyl-4-oxo-4,5-dihydro-1H-pyrrolo[3,2-c]pyridine-3-carboxamide A) N-allyl-2-methoxyaniline To a solution of 2-methoxyaniline in DMF (20 mL) were added 3-bromoprop-1-ene (2.16 g) and potassium carbonate (5.61 g), and the mixture was stirred at 90° C. for 3 hr. The insoluble substance was removed by filtration, to the filtrate was added water, and the mixture was extracted with ethyl acetate. The organic layers were combined, washed with saturated brine, dried over anhydrous sodium sulfate, and concentrated under reduced pressure. The residue was purified by silica gel column chromatography (petroleum ether/ethyl acetate) to give the title compound (1.9 g).

$^1$H NMR (400 MHz, CDCl$_3$) δ 3.81 (1H, d, J=5.2 Hz), 3.80-3.83 (1H, m), 3.87 (3H, s), 4.38 (1H, s), 5.16-5.20 (1H, m), 5.30 (1H, dq, J=17.2, 1.6 Hz), 5.95-6.04 (1H, m), 6.63 (1H, dd, J=8.0, 1.6 Hz), 6.66-6.72 (1H, m), 6.79 (1H, dd, J=8.0, 1.2 Hz), 6.85-6.89 (1H, m).

B) N-allyl-N-(2-methoxyphenyl)-1-methyl-1H-pyrrole-2-carboxamide

To a solution of 1-methyl-1H-pyrrole-2-carboxylic acid (2.07 g) in toluene (20 mL) was added thionyl chloride (5.45 mL), and the mixture was stirred at 100° C. for 3 hr. The reaction mixture was concentrated under reduced pressure. To a solution of the residue in dichloromethane (20 mL) were added N-allyl-2-methoxyaniline (2.04 mL) and TEA (4.18 mL) at 0° C., and the mixture was stirred at 25° C. 9 hr. The reaction mixture was purified by silica gel column chromatography (petroleum ether/ethyl acetate) to give the title compound (3.6 g).

MS: [M+H]$^+$ 271.1.

C) 5-(2-methoxyphenyl)-1,7-dimethyl-1,5-dihydro-4H-pyrrolo[3,2-c]pyridin-4-one

To a mixture of N-allyl-N-(2-methoxyphenyl)-1-methyl-1H-pyrrole-2-carboxamide (2 g), THF (20 mL) and DMF (10 mL) were added dichloro(bisacetonitrile)palladium(II) (288 mg) and 1,4-benzoquinone (800 mg), and the mixture was stirred under nitrogen atmosphere at 100° C. for 16 hr. To the reaction mixture was added saturated brine, and the mixture was extracted with ethyl acetate. The organic layers were combined, dried over anhydrous sodium sulfate, and concentrated under reduced pressure. The residue was purified by silica gel column chromatography (petroleum ether/ethyl acetate) to give the title compound (600 mg).

MS: [M+H]$^+$ 269.2.

D) 5-(2-methoxyphenyl)-1,7-dimethyl-4-oxo-4,5-dihydro-1H-pyrrolo[3,2-c]pyridine-3-carbaldehyde To a solution of DMF (0.138 mL) in dichloromethane (8 mL) was added oxalyl chloride (0.131 mL) at 0° C., and the mixture was stirred for 1 hr. The reaction mixture was added to a solution of 5-(2-methoxyphenyl)-1,7-dimethyl-1,5-dihydro-4H-pyrrolo[3,2-c]pyridin-4-one (400 mg) in dichloromethane (8 mL), and the mixture was stirred at 50° C. for 11 hr. The reaction mixture was poured into cold water, saturated aqueous sodium hydrogencarbonate solution was added thereto, and the mixture was extracted with dichloromethane. The organic layers were combined, dried over anhydrous sodium sulfate, and concentrated under reduced pressure. The residue was purified by silica gel column chromatography (petroleum ether/ethyl acetate) to give the title compound (400 mg).

MS: [M+H]$^+$ 297.1.

E) 5-(2-methoxyphenyl)-1,7-dimethyl-4-oxo-4,5-dihydro-1H-pyrrolo[3,2-c]pyridine-3-carboxylic Acid To a mixture of 5-(2-methoxyphenyl)-1,7-dimethyl-4-oxo-4,5-dihydro-1H-pyrrolo[3,2-c]pyridine-3-carbaldehyde (450 mg), water (2 mL), THF (2 mL) and tert-butanol (2 mL) was added sulfamic acid (295 mg). Sodium dihydrogenphosphate (620 mg) and an aqueous solution (2 mL) of sodium chlorite (206 mg) were added thereto, and the mixture was stirred at 25° C. for 1 hr. The reaction mixture was diluted with water, and extracted with ethyl acetate. The organic layers were combined, washed with saturated brine, dried over anhydrous sodium sulfate, and concentrated under reduced pressure to give the title compound (460 mg).

MS: [M+H]$^+$ 313.1.

F) N-cyclohexyl-5-(2-methoxyphenyl)-1,7-dimethyl-4-oxo-4,5-dihydro-1H-pyrrolo[3,2-c]pyridine-3-carboxamide To a solution of 5-(2-methoxyphenyl)-1,7-dimethyl-4-oxo-4,5-dihydro-1H-pyrrolo[3,2-c]pyridine-3-carboxylic acid (100 mg) in DMF (5 mL) were added HATU (183 mg), cyclohexanamine (0.073 mL) and DIPEA (0.139 mL), and the mixture was stirred at 25° C. for 12 hr. To the reaction mixture was added water, and the mixture was extracted with ethyl acetate. The organic layers were combined, washed with saturated brine, dried over anhydrous sodium sulfate, and concentrated under reduced pressure. The residue was purified by preparative high-performance liquid chromatography (Phenomenex Gemini 150*25 mm*10 um, acetonitrile/0.05% aqueous ammonia) to give the title compound (34.76 mg).

$^1$H NMR (400 MHz, CDCl$_3$) δ 1.14 (1H, d, J=12.0 Hz), 1.30-1.41 (4H, m), 1.56 (1H, s), 1.71 (2H, s), 1.96 (2H, s), 2.44 (3H, d, J=0.8 Hz), 3.82 (3H, s), 3.86-3.95 (1H, m), 3.99 (3H, s), 6.72 (1H, d, J=0.8 Hz), 7.04-7.10 (2H, m), 7.30 (1H, dd, J=8.0, 1.6 Hz), 7.39-7.45 (1H, m), 7.64 (1H, s), 10.88 (1H, d, J=7.6 Hz).

Example 117

N-(trans-4-butoxycyclohexyl)-7-cyclopropyl-1,5-dimethyl-4-oxo-4,5-dihydro-1H-pyrrolo[3,2-c]pyridine-3-carboxamide

A) 7-cyclopropyl-1,5-dimethyl-4-oxo-4,5-dihydro-1H-pyrrolo[3,2-c]pyridine-3-carboxylic Acid To a mixture of methyl 7-bromo-1,5-dimethyl-4-oxo-4,5-dihydro-1H-pyrrolo[3,2-c]pyridine-3-carboxylate (174 mg), cyclopropylboronic acid (74.8 mg), 2M aqueous sodium carbonate solution (0.9 mL) and dimethoxyethane (3 mL) was added dichloro[1,1'-bis(diphenylphosphino)ferrocene]palladium(II) dichloromethane complex (23.6 mg), and the mixture was stirred overnight at 70° C., and then under irradiation with microwave at 110° C. for 1 hr. Cyclopropylboronic acid (75 mg), dichloro[1,1'-bis(diphenylphosphino)ferrocene]palladium(II) dichloromethane complex (23 mg) and 2M aqueous sodium carbonate solution (1 mL) were added thereto, and the mixture was stirred under irradiation with microwave at 120° C. for 1 hr. The reaction mixture was concentrated under reduced pressure to give methyl 7-cyclopropyl-1,5-dimethyl-4-oxo-4,5-dihydro-1H-pyrrolo[3,2-c]pyridine-3-carboxylate as a crude product. To a mixture of the obtained crude product, THF (1 mL) and MeCOH (3 mL) was added 8M aqueous sodium hydroxide solution (0.75 mL), and the mixture was stirred at room temperature for 2 hr. To the reaction mixture were added 6M hydrochloric acid and sodium chloride, and the mixture was extracted with a mixed solvent of ethyl acetate/THF=1/2. The organic layers were combined, dried over anhydrous magnesium sulfate, and concentrated under reduced pressure. The residue was purified by silica gel column chromatography (hexane/ethyl acetate/methanol) to give the title compound (18 mg).
MS: [M+H]$^+$ 247.0.

B) N-(trans-4-butoxycyclohexyl)-7-cyclopropyl-1,5-dimethyl-4-oxo-4,5-dihydro-1H-pyrrolo[3,2-c]pyridine-3-carboxamide To a mixture of 7-cyclopropyl-1,5-dimethyl-4-oxo-4,5-dihydro-1H-pyrrolo[3,2-c]pyridine-3-carboxylic acid (18 mg) and THF (1.5 mL) were added oxalyl chloride (0.0106 mL) and DMF (0.01 mL) at 0° C., and the mixture was stirred at 0° C. for 2 hr. Oxalyl chloride (0.0106 mL) was added thereto, and the mixture was stirred at 0° C. for 1 hr. The reaction mixture was concentrated under reduced pressure, and the residue was suspended in THF (1.5 mL). trans-4-Butoxycyclohexanamine hydrochloride (21.7 mg) and TEA (0.0408 mL) at 0° C. were added thereto, and the mixture was stirred at room temperature for 2 hr. To the reaction mixture was added aqueous sodium hydrogencarbonate solution, and the mixture was extracted with ethyl acetate. The organic layer was separated, dried over anhydrous magnesium sulfate, and concentrated under reduced pressure. The residue was purified by silica gel column chromatography (ethyl acetate/methanol) to give the title compound (12.9 mg).
$^1$H NMR (300 MHz, DMSO-d$_6$) δ 0.72 (2H, q, J=5.1 Hz), 0.82-0.94 (5H, m), 1.18-1.39 (6H, m), 1.40-1.53 (2H, m), 1.82-2.03 (4H, m), 2.07-2.22 (1H, m), 3.19-3.26 (1H, m), 3.36-3.43 (2H, m), 3.47 (3H, s), 3.62-3.77 (1H, m), 4.12 (3H, s), 7.21 (1H, s), 7.69 (1H, s), 11.21 (1H, d, J=7.2 Hz).

Example 208

N-(trans-4-butoxycyclohexyl)-7-ethyl-1,5-dimethyl-4-oxo-4,5-dihydro-1H-pyrrolo[3,2-c]pyridine-3-carboxamide

A) Methyl 1,5-dimethyl-4-oxo-7-vinyl-4,5-dihydro-1H-pyrrolo[3,2-c]pyridine-3-carboxylate A mixture of methyl 7-bromo-1,5-dimethyl-4-oxo-4,5-dihydro-1H-pyrrolo[3,2-c]pyridine-3-carboxylate (198.2 mg), tributyl(vinyl)tin (315 mg), Pd(PPh$_3$)$_4$ (39.5 mg) and DMF (3 mL) was stirred at 100° C. for 1.5 hr. The reaction mixture was concentrated under reduced pressure, and the residue was purified by silica gel column chromatography (hexane/ethyl acetate/methanol) to give the title compound (99 mg).
MS: [M+H]$^+$ 247.0.

B) Methyl 7-ethyl-1,5-dimethyl-4-oxo-4,5-dihydro-1H-pyrrolo[3,2-c]pyridine-3-carboxylate A mixture of methyl 1,5-dimethyl-4-oxo-7-vinyl-4,5-dihydro-1H-pyrrolo[3,2-c]pyridine-3-carboxylate (98.7 mg), 10% palladium-carbon (24.8 mg) and MeOH (3 mL) was stirred under normal pressure of hydrogen atmosphere at room temperature for 3 hr. The catalyst was removed by filtration, and the filtrate was concentrated under reduced pressure to give the title compound (97.4 mg)
MS: [M+H]$^+$ 249.0.

C) 7-ethyl-1,5-dimethyl-4-oxo-4,5-dihydro-1H-pyrrolo[3,2-c]pyridine-3-carboxylic Acid To a mixture of methyl 7-ethyl-1,5-dimethyl-4-oxo-4,5-dihydro-1H-pyrrolo[3,2-c]pyridine-3-carboxylate (97 mg), THF (0.5 mL) and MeOH (2 mL) was added 8M aqueous sodium hydroxide solution (0.147 mL), and the mixture was stirred at room temperature for 2 hr. 8M Aqueous sodium hydroxide solution (0.147 mL) was added thereto, and the mixture was stirred at 60° C. for 1 hr. The reaction mixture was acidified with 6M hydrochloric acid, and diluted with water. The precipitate was collected by filtration, and washed with water to give the title compound (56 mg).
MS: [M+H]$^+$ 235.0.

D) N-(trans-4-butoxycyclohexyl)-7-ethyl-1,5-dimethyl-4-oxo-4,5-dihydro-1H-pyrrolo[3,2-c]pyridine-3-carboxamide To a mixture of 7-ethyl-1,5-dimethyl-4-oxo-4,5-dihydro-1H-pyrrolo[3,2-c]pyridine-3-carboxylic acid (55.8 mg), THF (2 mL) and DMF (0.01 mL) was added oxalyl chloride (0.031 mL), and the mixture was stirred at room temperature for 30 min. The reaction mixture was concentrated under reduced pressure, and the residue was suspended in THF (2 mL). trans-4-Butoxycyclohexanamine hydrochloride (58.2 mg) and TEA (0.133 mL) were added thereto at 0° C., and the mixture was stirred at room temperature for 3 hr. To the reaction mixture was added aqueous sodium hydrogencarbonate solution, and the mixture was extracted with ethyl acetate. The organic layer was separated, dried over anhydrous magnesium sulfate, and concentrated under reduced pressure. The residue was purified by silica gel column chromatography (hexane/ethyl acetate/methanol) to give the title compound (60.7 mg).

¹H NMR (300 MHz, DMSO-d₆) δ 0.82-0.94 (3H, m), 1.20 (3H, t, J=7.3 Hz), 1.24-1.39 (6H, m), 1.40-1.54 (2H, m), 1.83-2.05 (4H, m), 2.83 (2H, q, J=7.7 Hz), 3.19-3.28 (1H, m), 3.39 (2H, t, J=6.4 Hz), 3.50 (3H, s), 3.63-3.79 (1H, m), 3.96 (3H, s), 7.20 (1H, s), 7.68 (1H, s), 11.29 (1H, d, J=7.2 Hz).

Example 271

N-(trans-4-butoxycyclohexyl)-1,5-dimethyl-4-oxo-7-phenyl-4,5-dihydro-1H-pyrrolo[3,2-c]pyridine-3-carboxamide A) Methyl 1,5-dimethyl-4-oxo-7-phenyl-4,5-dihydro-1H-pyrrolo[3,2-c]pyridine-3-carboxylate A mixture of methyl 7-bromo-1,5-dimethyl-4-oxo-4,5-dihydro-1H-pyrrolo[3,2-c]pyridine-3-carboxylate (139.7 mg), phenylboronic acid (74.9 mg), dichloro[1,1'-bis(diphenylphosphino)ferrocene]palladium(II) dichloromethane complex (25.2 mg), 2M aqueous sodium carbonate solution (0.75 mL) and dimethoxyethane (3 mL) was stirred under irradiation with microwave at 120° C. for 1 hr. To the reaction mixture was added water, and the mixture was extracted with ethyl acetate. The organic layers were combined, dried over anhydrous magnesium sulfate, and concentrated under reduced pressure. The residue was purified by silica gel column chromatography (ethyl acetate/methanol) to give the title compound (57.4 mg).
MS: [M+H]⁺ 297.0.

B) 1,5-dimethyl-4-oxo-7-phenyl-4,5-dihydro-1H-pyrrolo[3,2-c]pyridine-3-carboxylic Acid To a mixture of methyl 1,5-dimethyl-4-oxo-7-phenyl-4,5-dihydro-1H-pyrrolo[3,2-c]pyridine-3-carboxylate (56.5 mg), MeCOH (1.5 mL) and TH (0.5 mL) was added 8M aqueous sodium hydroxide solution (0.071 mL), and the mixture was stirred at room temperature for 30 min, and then at 60° C. for 2 hr. The mixture was adjusted to pH=2-3 with 2M hydrochloric acid, diluted with water, and stirred at room temperature for 30 min. The precipitate was collected by filtration, and washed with water to give the title compound (49.2 mg).
MS: [M+H]⁺ 283.0.

C) N-(trans-4-butoxycyclohexyl)-1,5-dimethyl-4-oxo-7-phenyl-4,5-dihydro-1H-pyrrolo[3,2-c]pyridine-3-carboxamide To a mixture of 1,5-dimethyl-4-oxo-7-phenyl-4,5-dihydro-1H-pyrrolo[3,2-c]pyridine-3-carboxylic acid (45.6 mg), oxalyl chloride (0.021 mL) and THE (1.5 mL) was added DMF (0.01 mL) at 0° C., and the mixture was stirred at 0° C. for 30 min. Oxalyl chloride (0.017 mL) was added thereto, and the mixture was stirred at 0° C. for 1 hr. The reaction mixture was concentrated under reduced pressure, and the residue was suspended in TH (1.5 mL). trans-4-Butoxycyclohexanamine hydrochloride (41.4 mg) and TEA (0.09 mL) were added thereto at 0° C., and the mixture was stirred overnight at room temperature. To the reaction mixture was added saturated aqueous sodium hydrogencarbonate solution, and the mixture was extracted with ethyl acetate. The organic layer was separated, dried over anhydrous magnesium sulfate, and concentrated under reduced pressure. The residue was purified by silica gel column chromatography (hexane/ethyl acetate/methanol) to give the title compound (26.7 mg).
¹H NMR (300 MHz, DMSO-d₆) δ 0.82-0.95 (3H, m), 1.24-1.39 (6H, m), 1.40-1.53 (2H, m), 1.86-2.04 (4H, m), 3.22 (3H, s), 3.26-3.29 (1H, m), 3.40 (2H, t, J=6.4 Hz), 3.56 (3H, s), 3.64-3.83 (1H, m), 7.39 (1H, s), 7.41-7.52 (5H, m), 7.68 (1H, s), 11.20 (1H, d, J=7.4 Hz).

Example 272

N-benzyl-5,7-dimethyl-4-oxo-4,5-dihydrothieno[3,2-c]pyridine-3-carboxamide

A) Ethyl (2Z)-3-(4-bromo-2-thienyl)but-2-enoate

To a mixture of sodium hydride (60% in oil, 4.68 g) in THE (200 mL) was added ethyl diethylphosphonoacetate (26.2 g) at 0° C., and the mixture was stirred at 0° C. for 30 min. A solution of 1-(4-bromo-2-thienyl)ethanone (23.22 mL) in THE (20 mL) was added dropwise thereto at 0° C., and the mixture was stirred at room temperature for 1 hr, and then at 70° C. for 3 hr. The reaction mixture was concentrated under reduced pressure, to the residue was added aqueous sodium hydrogencarbonate solution, and the mixture was extracted with ethyl acetate. The organic layer was separated, washed with saturated brine, dried over anhydrous magnesium sulfate, and concentrated under reduced pressure. The residue was purified by silica gel column chromatography (hexane/ethyl acetate) to give the title compound (23.6 g).
¹H NMR (300 MHz, DMSO-d₆) δ 1.07-1.32 (3H, m), 2.24 (1H, d, J=1.4 Hz), 2.51 (2H, d, J=1.1 Hz), 4.01-4.22 (2H, m), 5.93-6.30 (1H, m), 7.42-7.88 (2H, m).

B) (2Z)-3-(4-bromo-2-thienyl)but-2-enoic Acid

To a mixture of ethyl (2Z)-3-(4-bromo-2-thienyl)but-2-enoate (23.6 g), THE (50 mL) and MeOH (150 mL) was added 8M aqueous sodium hydroxide solution (42.9 mL), and the mixture was stirred overnight at room temperature. The organic solvent was concentrated under reduced pressure, and the residue was diluted with water, and washed with ethyl acetate. The aqueous layer was acidified with 6M hydrochloric acid, and the precipitate was collected by filtration to give the title compound (13.6 g).
¹H NMR (300 MHz, DMSO-d₆) δ 2.48 (3H, d, J=1.2 Hz), 6.18 (1H, d, J=1.3 Hz), 7.54 (1H, d, J=1.4 Hz), 7.77 (1H, d, J=1.4 Hz), 12.37 (1H, brs).

C) 3-bromo-7-methylthieno[3,2-c]pyridin-4(5H)-one

To a mixture of (2Z)-3-(4-bromo-2-thienyl)but-2-enoic acid (201.4 mg), TEA (0.148 mL) and DMF (4 mL) was added DPPA (0.193 mL) at 0° C., and the mixture was stirred at room temperature for 2.5 hr. To the reaction mixture was added water, and the mixture was extracted with ethyl acetate. The organic layers were combined, dried over anhydrous magnesium sulfate, and concentrated under reduced pressure. The residue was purified by silica gel column chromatography (hexane/ethyl acetate) to give (2Z)-3-(4-bromo-2-thienyl)buta-2-enoyl azide. A solution of the obtained azide (168.7 mg) in o-dichlorobenzene (2 mL) was stirred at 110° C. for 20 min until the generation of nitrogen gas stopped. Catalytic amount of iodine was added thereto, and the mixture was stirred at 180° C. for 2 hr, and then overnight at 165° C. The mixture was cooled to room temperature, a mixed solvent of hexane/diisopropyl ether=1/1 was added thereto, and the precipitate was collected by filtration to give the title compound (101 mg).

$^1$H NMR (300 MHz, DMSO-$d_6$) δ 2.15 (3H, d, J=1.1 Hz), 7.13 (1H, d, J=4.5 Hz), 7.72 (1H, s), 11.37 (1H, brs).

D) 3-bromo-5,7-dimethylthieno[3,2-c]pyridin-4(5H)-one

To a solution of 3-bromo-7-methylthieno[3,2-c]pyridin-4(5H)-one (98.5 mg) in DMF (2 mL) was added sodium hydride (60% in oil, 21.4 mg) at 0° C., and the mixture was stirred at room temperature for 30 min. Iodomethane (0.038 mL) was added dropwise thereto, and the mixture was stirred at room temperature for 1 hr. To the reaction mixture was added aqueous sodium hydrogencarbonate solution, and the mixture was extracted with ethyl acetate. The organic layer was separated, dried over anhydrous magnesium sulfate, and concentrated under reduced pressure. The residue was purified by silica gel column chromatography (hexane/ethyl acetate) to give the title compound (77 mg).

$^1$H NMR (300 MHz, DMSO-$d_6$) δ 2.16 (3H, d, J=1.1 Hz), 3.45 (3H, s), 7.50 (1H, s), 7.74 (1H, s).

E) 5,7-dimethyl-4-oxo-4,5-dihydrothieno[3,2-c]pyridine-3-carbonitrile

A mixture of 3-bromo-5,7-dimethylthieno[3,2-c]pyridin-4(5H)-one (74.9 mg), copper(I) cyanide (77.9 mg) and DMA (1.5 mL) was stirred under irradiation with microwave at 150° C. for 1 hr. To the reaction mixture was added 10% aqueous ammonia, and the mixture was extracted with a mixed solvent of ethyl acetate/THF=1/1. The organic layer was separated, dried over anhydrous magnesium sulfate, and concentrated under reduced pressure. The residue was purified by silica gel column chromatography (hexane/ethyl acetate) to give the title compound (35.2 mg).

MS: [M+H]$^+$ 205.0.

F) 5,7-dimethyl-4-oxo-4,5-dihydrothieno[3,2-c]pyridine-3-carboxylic Acid

To a mixture of 5,7-dimethyl-4-oxo-4,5-dihydrothieno[3,2-c]pyridine-3-carbonitrile (241 mg) and MeCOH (6 mL) was added sulfuric acid (2 mL), and the mixture was stirred at 100° C. for 8 hr, and then overnight at 60° C. To the reaction mixture were added 8M aqueous sodium hydroxide solution and THF (2 mL) at 0° C., and the mixture was stirred at room temperature for 1 hr. The reaction mixture was acidified with 6M hydrochloric acid, and diluted with water. The precipitate was collected by filtration to give the title compound (261 mg).

MS: [M+H]$^+$ 224.0.

G) N-benzyl-5,7-dimethyl-4-oxo-4,5-dihydrothieno[3,2-c]pyridine-3-carboxamide To a mixture of 5,7-dimethyl-4-oxo-4,5-dihydrothieno[3,2-c]pyridine-3-carboxylic acid (50.0 mg), THF (1.5 mL) and DMF (0.01 mL) was added oxalyl chloride (0.0294 mL), and the mixture was stirred at room temperature for 1 hr. The reaction mixture was concentrated under reduced pressure, and the residue was dissolved in DMA (1.5 mL). Benzylamine (0.0294 mL) was added thereto at 0° C., and the mixture was stirred at room temperature for 72 hr. To the reaction mixture was added aqueous sodium hydrogencarbonate solution, and the mixture was extracted with ethyl acetate. The organic layer was separated, dried over anhydrous magnesium sulfate, and concentrated under reduced pressure. The residue was purified by silica gel column chromatography (NH, hexane/ethyl acetate) to give the title compound (38.3 mg).

$^1$H NMR (300 MHz, DMSO-$d_6$) δ 2.25 (3H, d, J=1.1 Hz), 3.55 (3H, s), 4.55 (2H, d, J=5.7 Hz), 7.19-7.41 (5H, m), 7.64 (1H, s), 8.48 (1H, s), 12.24 (1H, t, J=5.3 Hz).

Example 277

N-(trans-4-butoxycyclohexyl)-1,5,7-trimethyl-4-oxo-4,5-dihydro-1H-pyrazolo[4,3-c]pyridine-3-carboxamide

A) 2,4-dichloro-5-methylnicotinaldehyde

To a solution of 2,4-dichloro-5-methylpyridine (7.6 g) in THF (100 mL) was added dropwise 2M THF solution (24 mL) of lithium diisopropylamide at −78° C., and the mixture was stirred at −78° C. for 1 hr. DMF (4.11 g) was added dropwise thereto at −78° C., and the mixture was stirred at −78° C. for 2 hr. To the reaction mixture was added water, and the mixture was extracted with ethyl acetate. The organic layers were combined, washed with saturated brine, dried over anhydrous sodium sulfate, and concentrated under reduced pressure. The residue was purified by silica gel column chromatography (petroleum ether/ethyl acetate) to give the title compound (5.3 g).

$^1$H NMR (400 MHz, DMSO-$d_6$) δ 2.35 (3H, d, J=0.4 Hz), 8.56 (1H, d, J=0.4 Hz), 10.32 (1H, s).

B) 4-chloro-7-methyl-1H-pyrazolo[4,3-c]pyridine

A mixture of 2,4-dichloro-5-methylnicotinaldehyde (5.4 g), hydrazine hydrate (6.69 g) and 1,2-dimethoxyethane (60 mL) was stirred at 80° C. for 16 hr. The reaction mixture was diluted with ethyl acetate (100 mL), washed with water and saturated brine, dried over anhydrous sodium sulfate, and concentrated under reduced pressure. The residue was washed with a mixed solvent of petroleum ether/ethyl acetate=1/1 to give the title compound (3.07 g).

$^1$H NMR (400 MHz, DMSO-$d_6$) δ 2.47 (3H, d, J=0.8 Hz), 7.93 (1H, d, J=0.8 Hz), 8.28 (1H, s).

C) 4-chloro-3-iodo-7-methyl-1H-pyrazolo[4,3-c]pyridine

A mixture of 4-chloro-7-methyl-1H-pyrazolo[4,3-c]pyridine (1.5 g), potassium hydroxide (2.51 g), iodine (9.09 g) and DMF (30 mL) was stirred at 80° C. for 16 hr. To the reaction mixture was added water, and the mixture was extracted with ethyl acetate. The organic layers were combined, washed with saturated aqueous sodium sulfite solution and saturated brine, dried over anhydrous sodium sulfate, and concentrated under reduced pressure. The residue was washed with a mixed solvent of petroleum ether/ethyl acetate=5/1 to give the title compound (2.00 g).

$^1$H NMR (400 MHz, DMSO-$d_6$) δ 2.43 (3H, s), 7.53 (1H, s), 14.35 (1H, brs).

D) 3-iodo-7-methyl-1,5-dihydro-4H-pyrazolo[4,3-c]pyridin-4-one

A mixture of 4-chloro-3-iodo-7-methyl-1H-pyrazolo[4,3-c]pyridine (2.00 g), acetic acid (50 mL) and water (1 mL) was stirred at 100° C. for 16 hr. The reaction mixture was cooled, and concentrated under reduced pressure. The residue was washed with ethyl acetate to give the title compound (1.80 g).

$^1$H NMR (400 MHz, DMSO-$d_6$) δ 2.11 (3H, d, J=0.8 Hz), 6.91 (1H, d, J=5.2 Hz), 10.79 (1H, brs), 13.73 (1H, brs).

E) 3-iodo-1,5,7-trimethyl-1,5-dihydro-4H-pyrazolo[4,3-c]pyridin-4-one

To a mixture of 3-iodo-7-methyl-1,5-dihydro-4H-pyrazolo[4,3-c]pyridin-4-one (2.12 g), potassium carbonate (4.26 g) and DMF (20 mL) was added iodomethane (2.74 g), and the mixture was stirred at 25° C. for 16 hr. Potassium carbonate (2.00 g) and iodomethane (2.00 g) were added thereto, and the mixture was stirred at 25° C. for 16 hr. The insoluble substance was removed by filtration, and washed with ethyl acetate. The filtrate was concentrated under reduced pressure to give the title compound (3.20 g) as a mixture with 3-iodo-2,5,7-trimethyl-2,5-dihydro-4H-pyrazolo[4,3-c]pyridin-4-one.

MS: [M+H]$^+$ 303.8.

F) Methyl 1,5,7-trimethyl-4-oxo-4,5-dihydro-1H-pyrazolo[4,3-c]pyridine-3-carboxylate A mixture of a mixture (3.20 g) of 3-iodo-1,5,7-trimethyl-1,5-dihydro-4H-pyrazolo[4,3-c]pyridin-4-one and 3-iodo-2,5,7-trimethyl-2,5-dihydro-4H-pyrazolo[4,3-c]pyridin-4-one, TEA (2.50 g), dichloro(diphenylphosphinoferrocene)palladium(II) dichloromethane complex (340 mg), DMSO (15 mL) and MeOH (45 mL) was stirred under carbon monoxide atmosphere of 50 psi, at 80° C. for 16 hr. The insoluble substance was removed by filtration, and the filtrate was concentrated under reduced pressure. The residue was purified by preparative liquid chromatography (acetonitrile containing 0.05% aqueous ammonia/0.1% aqueous ammonia) to give the title compound (220 mg) and methyl 2,5,7-trimethyl-4-oxo-4,5-dihydro-2H-pyrazolo[4,3-c]pyridine-3-carboxylate (500 mg), respectively.

MS: [M+H]$^+$ 235.9.

G) 1,5,7-trimethyl-4-oxo-4,5-dihydro-1H-pyrazolo[4,3-c]pyridine-3-carboxylic Acid Hydrochloride To a mixture of methyl 1,5,7-trimethyl-4-oxo-4,5-dihydro-1H-pyrazolo[4,3-c]pyridine-3-carboxylate (60 mg), THF (2 mL), MeOH (2 mL) and water (0.3 mL) was added lithium hydroxide monohydrate (16 mg), and the mixture was stirred at 25° C. for 16 hr. The reaction mixture was adjusted to pH=3 with 1M hydrochloric acid, and concentrated under reduced pressure to give the title compound (100 mg).

MS: [M+H]$^+$ 221.8.

H) N-(trans-4-butoxycyclohexyl)-1,5,7-trimethyl-4-oxo-4,5-dihydro-1H-pyrazolo[4,3-c]pyridine-3-carboxamide A mixture of 1,5,7-trimethyl-4-oxo-4,5-dihydro-1H-pyrazolo[4,3-c]pyridine-3-carboxylic acid hydrochloride (40 mg), trans-4-butoxycyclohexanamine trifluoroacetate (46 mg), DIPEA (93 mg), HATU (103 mg) and DMF (5 mL) was stirred at 25° C. for 16 hr. The reaction mixture was diluted with ethyl acetate, washed with water and saturated brine, dried over anhydrous sodium sulfate, and concentrated under reduced pressure. The residue was purified by preparative liquid chromatography (acetonitrile containing 0.225% formic acid/water containing 0.225% formic acid) to give the title compound (21 mg).

$^1$H NMR (400 MHz, DMSO-$d_6$) δ 0.88 (3H, t, J=7.2 Hz), 1.25-1.38 (6H, m), 1.41-1.50 (2H, m), 1.91-2.02 (4H, m), 2.41 (3H, s), 3.22-3.33 (1H, m), 3.39 (2H, t, J=6.4 Hz), 3.48 (3H, s), 3.72-3.81 (1H, m), 4.19 (3H, s), 7.41 (1H, s), 11.23 (1H, d, J=6.8 Hz).

Example 281

N-(trans-4-butoxycyclohexyl)-2,5,7-trimethyl-4-oxo-4,5-dihydro-2H-pyrazolo[4,3-c]pyridine-3-carboxamide

A) 2,5,7-trimethyl-4-oxo-4,5-dihydro-2H-pyrazolo[4,3-c]pyridine-3-carboxylic Acid To a mixture of methyl 2,5,7-trimethyl-4-oxo-4,5-dihydro-2H-pyrazolo[4,3-c]pyridine-3-carboxylate (500 mg) obtained in Step F of Example 277, THF (6 mL), MeOH (6 mL) and water (1.5 mL) was added lithium hydroxide monohydrate (134 mg), and the mixture was stirred at 25° C. for 16 hr. The reaction mixture was diluted with water, and adjusted to pH=3 with 1M hydrochloric acid. The precipitate was collected by filtration to give the title compound (250 mg).

MS: [M+H]$^+$ 221.9.

B) N-(trans-4-butoxycyclohexyl)-2,5,7-trimethyl-4-oxo-4,5-dihydro-2H-pyrazolo[4,3-c]pyridine-3-carboxamide A mixture of 2,5,7-trimethyl-4-oxo-4,5-dihydro-2H-pyrazolo[4,3-c]pyridine-3-carboxylic acid (50 mg), trans-4-butoxycyclohexanamine trifluoroacetate (46 mg), DIPEA (88 mg), HATU (129 mg) and DMF (3 mL) was stirred at 25° C. for 16 hr. HATU (65 mg) was added thereto, and the mixture was stirred at 50° C. for 16 hr. The reaction mixture was diluted with ethyl acetate, washed with water and saturated brine, dried over anhydrous sodium sulfate, and concentrated under reduced pressure. The residue was purified by preparative high-performance liquid chromatography (acetonitrile containing 0.05% aqueous ammonia/0.05% aqueous ammonia) to give the title compound (34 mg).

$^1$H NMR (400 MHz, DMSO-$d_6$) δ 0.90 (3H, t, J=7.2 Hz), 1.27-1.39 (6H, m), 1.41-1.51 (2H, m), 1.93-2.02 (4H, m), 2.17 (3H, d, J=1.2 Hz), 3.24-3.33 (1H, m, overlap with water signal), 3.40 (2H, t, J=6.4 Hz), 3.46 (3H, s), 3.72-3.81 (1H, m), 4.36 (3H, s), 7.27 (1H, d, J=1.2 Hz), 11.57 (1H, d, J=6.8 Hz).

Example 283

N-(trans-4-butoxycyclohexyl)-5,7-dimethyl-4-oxo-4,5-dihydropyrazolo[1,5-a]pyrazine-3-carboxamide

A) N-methyl-N-(prop-2-yn-1-yl)-1H-pyrazole-5-carboxamide

To a solution of N-methylprop-2-yn-1-amine (3.76 mL) in DMF (20 mL) were added 1H-pyrazole-3-carboxylic acid (5.00 g), HATU (20.35 g) and DIPEA (9.35 mL) at 0° C., and the mixture was stirred at 70° C. for 5 hr. The mixture was purified by silica gel column chromatography (SI and NH, hexane/ethyl acetate) to give the title compound (3.50 g).

MS: [M+H]$^+$ 164.0.

B) 5,7-dimethylpyrazolo[1,5-a]pyrazin-4(5H)-one

A mixture of N-methyl-N-(prop-2-yn-1-yl)-1H-pyrazole-5-carboxamide (3.50 g), DBU (0.97 mL) and DMF (7 mL) was stirred at 120° C. for 1.5 hr. The mixture was purified by silica gel column chromatography (hexane/ethyl acetate) to give the title compound (3.09 g).

MS: [M+H]$^+$ 164.0.

C) 3-iodo-5,7-dimethylpyrazolo[1,5-a]pyrazin-4(5H)-one

A mixture of 5,7-dimethylpyrazolo[1,5-a]pyrazin-4(5H)-one (1.50 g), 1-iodopyrrolidine-2,5-dione (2.172 g) and acetonitrile (15 mL) was stirred at 80° C. for 7 hr. The mixture was concentrated under reduced pressure, and the residue was washed with a mixed solvent of diisopropyl ether/acetonitrile=4/1 to give the title compound (2.02 g).

MS: [M+H]$^+$ 289.8.

D) Ethyl 5,7-dimethyl-4-oxo-4,5-dihydropyrazolo[1,5-a]pyrazine-3-carboxylate At 90° C.

Under carbon monoxide (5 atm) atmosphere, a mixture of 3-iodo-5,7-dimethylpyrazolo[1,5-a]pyrazin-4(5H)-one (2.02 g), dichloro[1,1'-bis(diphenylphosphino)ferrocene]palladium(II) (0.511 g), TEA (1.948 mL), DMF (20 mL) and EtOH (20 mL) was stirred at 90° C. for 7 hr. To the mixture was added saturated brine, and the mixture was extracted with ethyl acetate. The organic layer was separated, dried over anhydrous magnesium sulfate, and concentrated under reduced pressure. The residue was purified by silica gel column chromatography (hexane/ethyl acetate) to give the title compound (1.77 g).

MS: [M+H]$^+$ 236.0.

E) 5,7-dimethyl-4-oxo-4,5-dihydropyrazolo[1,5-a]pyrazine-3-carboxylic Acid

A mixture of ethyl 5,7-dimethyl-4-oxo-4,5-dihydropyrazolo[1,5-a]pyrazine-3-carboxylate (1.77 g), EtOH (10 mL), THF (10 mL) and 2M aqueous sodium hydroxide solution (10 mL) was stirred at 70° C. for 1 hr. The mixture was concentrated under reduced pressure until reduced to half volume, and the residue was cooled to 0° C., and neutralized with 2M hydrochloric acid. The solid was collected by filtration, and washed with water and diethyl ether to give the title compound (700 mg).

MS: [M+H]$^+$ 208.0.

F) N-(trans-4-butoxycyclohexyl)-5,7-dimethyl-4-oxo-4,5-dihydropyrazolo[1,5-a]pyrazine-3-carboxamide To a mixture of 5,7-dimethyl-4-oxo-4,5-dihydropyrazolo[1,5-a]pyrazine-3-carboxylic acid (51.8 mg) and THF (1 mL) was added DMF (one drop) at room temperature, and the mixture was stirred at room temperature for 30 min. trans-4-Butoxycyclohexanamine hydrochloride (62.3 mg) was added thereto, and then TEA (0.139 mL) was added dropwise thereto at room temperature, and the mixture was stirred at room temperature for 1 hr. To the mixture was added water, and the mixture was extracted with ethyl acetate. The organic layer was separated, washed with saturated brine, dried over anhydrous magnesium sulfate, and concentrated under reduced pressure. The residue was crystallized from hexane/ethyl acetate to give the title compound (19.7 mg).

$^1$H NMR (300 MHz, DMSO-d$_6$) δ 0.88 (3H, t, J=7.2 Hz), 1.23-1.55 (8H, m), 1.95 (4H, d, J=6.0 Hz), 2.40 (3H, s), 3.22-3.34 (1H, m), 3.40 (2H, t, J=6.4 Hz), 3.49 (3H, s), 3.75 (1H, brs), 7.24 (1H, s), 8.32 (1H, s), 10.39 (1H, d, J=7.4 Hz).

Example 284

N-(trans-4-butoxycyclohexyl)-2,5,7-trimethyl-4-oxo-4,5-dihydropyrazolo[1,5-a]pyrazine-3-carboxamide

A) N,3-dimethyl-N-(prop-2-yn-1-yl)-1H-pyrazole-5-carboxamide

To a solution of N-methylprop-2-yn-1-amine (3.21 mL) in DMF (10 mL) were added 5-methyl-1H-pyrazole-3-carboxylic acid (4.80 g) and HATU (17.36 g), and then DIPEA (7.98 mL) was added dropwise thereto at 0° C., and the mixture was stirred at 70° C. for 5 hr. The reaction mixture was purified by silica gel column chromatography (NH, hexane/ethyl acetate) to give the title compound (4.82 g).

MS: [M+H]$^+$ 178.0.

B) 2,5,7-trimethylpyrazolo[1,5-a]pyrazin-4(5H)-one

A mixture of N,3-dimethyl-N-(prop-2-yn-1-yl)-1H-pyrazole-5-carboxamide (4.82 g), DBU (1.230 mL) and DMF (7 mL) was stirred at 120° C. for 1.5 hr. The reaction mixture was cooled to 0° C., and diisopropyl ether was added thereto. The precipitate was collected by filtration to give the title compound (3.70 g).

MS: [M+H]$^+$ 178.0.

C) 3-iodo-2,5,7-trimethylpyrazolo[1,5-a]pyrazin-4(5H)-one

A mixture of 2,5,7-trimethylpyrazolo[1,5-a]pyrazin-4(5H)-one (1.50 g), N-succinimide (2.00 g) and acetonitrile (15 mL) was stirred at 80° C. for 4 hr. The reaction mixture was cooled to 0° C., and the resulting solid was collected by filtration, and washed with diisopropyl ether to give the title compound (1.42 g)

MS: 303.9.

D) 2,5,7-trimethyl-4-oxo-4,5-dihydropyrazolo[1,5-a]pyrazine-3-carboxylic Acid A mixture of 3-iodo-2,5,7-trimethylpyrazolo[1,5-a]pyrazin-4(5H)-one (1.42 g), dichloro[1,1'-bis(diphenylphosphino)ferrocene]palladium(II) (0.343 g), TEA (0.784 mL), DMF (15 mL) and EtOH (15 mL) was stirred under carbon monoxide (5 atm) atmosphere at 90° C. for 7 hr. The insoluble substance was removed by filtration, and the filtrate was concentrated under reduced pressure. The residue was washed with diisopropyl ether to give ethyl 2,5,7-trimethyl-4-oxo-4,5-dihydropyrazolo[1,5-a]pyrazine-3-carboxylate (2.12 g) as a crude product. To a mixture of the obtained crude product (2.12 g), EtOH (10 mL) and THF (10 mL) was added 2M aqueous sodium hydroxide solution (10 mL), and the mixture was stirred at 70° C. for 1 hr. The reaction mixture was concentrated until the solvent volume reduced to half, cooled to 0° C., and neutralized with 2M hydrochloric acid. The resulting solid was collected by filtration, and washed with diethyl ether and ethyl acetate to give the title compound (715 mg).
MS: [M+H]$^+$ 222.0.

E) N-(trans-4-butoxycyclohexyl)-2,5,7-trimethyl-4-oxo-4,5-dihydropyrazolo[1,5-a]pyrazine-3-carboxamide To a mixture of 2,5,7-trimethyl-4-oxo-4,5-dihydropyrazolo[1,5-a]pyrazine-3-carboxylic acid (55.3 mg), oxalyl chloride (0.033 mL) and THF (1 mL) was added DMF (one drop), and the mixture was stirred at room temperature for 30 min. trans-4-Butoxycyclohexanamine hydrochloride (62.3 mg) and TEA (0.139 mL) were added thereto, and the mixture was stirred at room temperature for 1 hr. To the reaction mixture was added water, and the mixture was extracted with ethyl acetate. The organic layer was separated, washed with saturated brine, dried over anhydrous magnesium sulfate, and concentrated under reduced pressure. The residue was crystallized from ethyl acetate to give the title compound (47.5 mg).
$^1$H NMR (300 MHz, DMSO-d$_6$) δ 0.83-0.97 (3H, m), 1.21-1.53 (8H, m), 1.82-2.04 (4H, m), 2.37 (3H, d, J=1.1 Hz), 2.59 (3H, s), 3.21-3.34 (1H, m), 3.40 (2H, t, J=6.4 Hz), 3.47 (3H, s), 3.73 (1H, brs), 7.18 (1H, d, J=1.3 Hz), 10.54 (1H, d, J=7.2 Hz).

Example 287

N-(trans-4-butoxycyclohexyl)-5,7-dimethyl-4-oxo-4,5-dihydrofuro[3,2-c]pyridine-3-carboxamide A) Ethyl (2E)-3-(4-bromo-2-furyl)but-2-enoate To a solution of ethyl diethylphosphonoacetate (6.3 mL) in TH (100 mL) was added 1M THF solution (34.9 mL) of NaHMDS at 0° C., and the mixture was stirred at 0° C. for 30 min. The reaction mixture was cooled to −20° C., a solution of 1-(4-bromo-2-furyl)ethanone (6.00 g) in THF (50 mL) was added thereto, and the mixture was stirred under nitrogen atmosphere at 0° C. for 1 hr. To the reaction mixture were added saturated aqueous ammonium chloride solution and water, and the mixture was extracted with ethyl acetate. The organic layer was dried over anhydrous sodium sulfate, and concentrated under reduced pressure. The residue was purified by silica gel column chromatography (petroleum ether/ethyl acetate) to give the title compound (4.5 g).
MS: [M+H]$^+$ 259.

B) (2E)-3-(4-bromo-2-furyl)but-2-enoic Acid

To a solution of ethyl (2E)-3-(4-bromo-2-furyl)but-2-enoate (4.5 g) in MeOH (45 mL) was added 8M aqueous sodium hydroxide solution (4.34 mL), and the mixture was stirred at 25° C. for 16 hr. The reaction mixture was concentrated under reduced pressure, the residue was diluted with water, and the mixture was adjusted to pH=4 with 3M hydrochloric acid. The precipitate was collected by filtration, and washed with water to give the title compound (3.6 g).
$^1$H NMR (400 MHz, CDCl$_3$) δ 2.43-2.45 (3H, m), 5.74-5.88 (1H, m), 6.39 (1H, s), 6.73 (1H, s)

C) (2E)-3-(4-bromo-2-furyl)buta-2-enoyl Azide

To a solution of (2E)-3-(4-bromo-2-furyl)but-2-enoic acid (2.6 g) in THF (50 mL) were added DPPA (3.41 g) and TEA (2.28 g) at 25° C., and the mixture was stirred at 25° C. for 1 hr. The reaction mixture was concentrated under reduced pressure, and the residue was purified by silica gel column chromatography (petroleum ether/ethyl acetate) to give the title compound (1.60 g).
$^1$H NMR (400 MHz, CDCl$_3$) δ 2.47 (3H, d, J=1.0 Hz) 6.28 (1H, d, J=1.0 Hz), 6.77 (1H, s), 7.48 (1H, s).

D) 3-bromo-7-methylfuro[3,2-c]pyridin-4(5H)-one

Diphenyl ether (8 mL) was heated to 230° C., a solution of (2E)-3-(4-bromo-2-furyl)buta-2-enoyl azide (700 mg) in chloroform (4 mL) was added dropwise thereto, and the mixture was stirred at 230° C. for 1 hr. The reaction mixture was diluted with petroleum ether, and the precipitate was washed with petroleum ether to give the title compound (600 mg).
$^1$H NMR (400 MHz, CD$_3$OD) δ 2.26 (3H, s), 7.16 (1H, s), 7.86 (1H, s).

E) 3-bromo-5,7-dimethylfuro[3,2-c]pyridin-4(5H)-one

To a solution of 3-bromo-7-methylfuro[3,2-c]pyridin-4(5H)-one (700 mg) in DMF (20 mL) was added sodium hydride (60% in oil, 147 mg) at 0° C., and the mixture was stirred at 0° C. for 30 min. Iodomethane (523 mg) was added thereto at 0° C., and the reaction mixture was stirred at 25° C. for 1.5 hr. The reaction mixture was poured into cold water, and extracted with ethyl acetate. The organic layers were combined, dried over anhydrous sodium sulfate, and concentrated under reduced pressure. The residue was purified by silica gel column chromatography (petroleum ether/ethyl acetate) to give the title compound (600 mg).
$^1$H NMR (400 MHz, CDCl$_3$) δ 2.21 (3H, s), 3.57 (3H, s), 6.96 (1H, s), 7.53 (1H, s).

F) 5,7-dimethyl-4-oxo-4,5-dihydrofuro[3,2-c]pyridine-3-carbonitrile

A mixture of 3-bromo-5,7-dimethylfuro[3,2-c]pyridin-4(5H)-one (326.1 mg), copper(I) cyanide (241.5 mg) and DMA (3 so mL) was stirred under irradiation with microwave at 150° C. for 1 hr, and then at 170° C. for 2 hr. To the reaction mixture was added saturated aqueous sodium hydrogencarbonate solution, and the mixture was extracted with ethyl acetate. The organic layer was separated, dried over anhydrous magnesium sulfate, and concentrated under reduced pressure. The residue was purified by silica gel column chromatography (NH, hexane/ethyl acetate) to give the title compound (117 mg).
MS: [M+H]$^+$ 188.9.

G) 5,7-dimethyl-4-oxo-4,5-dihydrofuro[3,2-c]pyridine-3-carboxylic Acid

To a mixture of 5,7-dimethyl-4-oxo-4,5-dihydrofuro[3,2-c]pyridine-3-carbonitrile (116 mg) and MeOH (3 mL) was added sulfuric acid (1 mL) at room temperature, and the mixture was stirred at 100° C. for 4 hr. The reaction mixture was cooled to 0° C., 8M aqueous sodium hydroxide solution (3 mL) was added thereto, and the mixture was stirred overnight at room temperature. The mixture was adjusted to pH=2-3 with 2M hydrochloric acid, and diluted with water. The precipitate was collected by filtration, and washed with water to give the title compound (119 mg).
MS: [M+H]$^+$ 208.0.

H) N-(trans-4-butoxycyclohexyl)-5,7-dimethyl-4-oxo-4,5-dihydrofuro[3,2-c]pyridine-3-carboxamide To a mixture of 5,7-dimethyl-4-oxo-4,5-dihydrofuro[3,2-c]pyridine-3-carboxylic acid (29.8 mg), oxalyl chloride (0.019 mL) and THF (1.5 mL) was added DMF (0.01 mL) at 0° C., and the mixture was stirred at 0° C. for 1 hr. The reaction mixture was concentrated under reduced pressure, and the residue was suspended in THF (1.5 mL). trans-4-Butoxycyclohexanamine hydrochloride (40.9 mg) and TEA (0.08 mL) were added thereto at 0° C., and the mixture was stirred at room temperature for 3 hr. To the reaction mixture was added saturated aqueous sodium hydrogencarbonate solution, and the mixture was extracted with ethyl acetate. The organic layer was separated, dried over anhydrous magnesium sulfate, and concentrated under reduced pressure. The residue was purified by silica gel column chromatography (hexane/ethyl acetate/methanol) to give the title compound (18.3 mg).

$^1$H NMR (300 MHz, DMSO-d$_6$) δ 0.84-0.93 (3H, m), 1.20-1.40 (6H, m), 1.40-1.55 (2H, m), 1.95 (4H, d, J=9.8 Hz), 2.21 (3H, d, J=0.8 Hz), 3.24-3.28 (1H, m), 3.40 (2H, t, J=6.4 Hz), 3.55 (3H, s), 3.66-3.83 (1H, m), 7.67 (1H, d, J=0.8 Hz), 8.41 (1H, s), 10.79 (1H, d, J=7.4 Hz).

Example 291

N-(2-(4-chlorophenyl)propan-2-yl)-5-(2-methoxyphenyl)-1-methyl-4-oxo-4,5-dihydro-1H-pyrrolo[3,2-c]pyridine-3-carboxamide

A) Methyl 5-(2-methoxyphenyl)-1-methyl-4-oxo-4,5-dihydro-1H-pyrrolo[3,2-c]pyridine-3-carboxylate To a mixture of methyl 1-methyl-4-oxo-4,5-dihydro-1H-pyrrolo[3,2-c]pyridine-3-carboxylate (103.5 mg), (2-methoxyphenyl)boronic acid (222 mg), acetonitrile (6.5 mL) and DMF (0.5 mL) were added copper(II) acetate (182 mg), pyridine (0.081 mL), TEA (0.14 mL) and molecular sieve 3A (200 mg), and the mixture was stirred overnight at room temperature, and then at 60° C. for 3.5 hr. The reaction mixture was filtered through Celite, and the filtrate was concentrated under reduced pressure. The residue was purified by silica gel column chromatography (ethyl acetate/methanol) to give the title compound (41.3 mg).

MS: [M+H]$^+$ 313.0.

B) 5-(2-methoxyphenyl)-1-methyl-4-oxo-4,5-dihydro-1H-pyrrolo[3,2-c]pyridine-3-carboxylic Acid To a mixture of methyl 5-(2-methoxyphenyl)-1-methyl-4-oxo-4,5-dihydro-1H-pyrrolo[3,2-c]pyridine-3-carboxylate (72.2 mg), THF (0.3 mL) and MeOH (0.9 mL) was added 8M aqueous sodium hydroxide solution (0.087 mL) at room temperature, and the mixture was stirred at 50° C. for 2 hr, and cooled over 1 hr to room temperature. The reaction mixture was adjusted to pH=2-3 with 2M hydrochloric acid, and diluted with water. The precipitate was collected by filtration, and washed with water to give the title compound (56.2 mg).

MS: [M+H]$^+$ 299.0.

C) N-(2-(4-chlorophenyl)propan-2-yl)-5-(2-methoxyphenyl)-1-methyl-4-oxo-4,5-dihydro-1H-pyrrolo[3,2-c]pyridine-3-carboxamide To a mixture of 5-(2-methoxyphenyl)-1-methyl-4-oxo-4,5-dihydro-1H-pyrrolo[3,2-c]pyridine-3-carboxylic acid (55.0 mg), THF (1.5 mL) and DMF (0.01 mL) was added oxalyl chloride (0.02421 mL), and the mixture was stirred at room temperature for 1 hr. The reaction mixture was concentrated under reduced pressure, to the residue was added THF (1.5 mL), and the mixture was cooled to 0° C. TEA (0.09 mL) and 2-(4-chlorophenyl)propan-2-amine hydrochloride (42.0 mg) were added thereto, and the mixture was stirred at room temperature for 2 hr. To the reaction mixture was added saturated aqueous sodium hydrogencarbonate solution, and the mixture was extracted with ethyl acetate. The organic layer was separated, washed successively with saturated aqueous sodium hydrogencarbonate solution, 1M hydrochloric acid and saturated brine, dried over anhydrous magnesium sulfate, and concentrated under reduced pressure. The residue was purified by silica gel column chromatography (ethyl acetate/methanol) to give the title compound (74.4 mg).

$^1$H NMR (300 MHz, DMSO-d$_6$) δ 1.58 (6H, d, J=4.9 Hz), 3.78 (3H, s), 3.79 (3H, s), 6.79 (1H, d, J=7.5 Hz), 7.10 (1H, td, J=7.6, 0.9 Hz), 7.22-7.41 (7H, m), 7.44-7.52 (1H, m), 7.64 (1H, s), 11.21 (1H, s).

Example 292

5-(cyanomethyl)-1-methyl-N-(4-(morpholin-4-yl)phenyl)-4-oxo-4,5-dihydro-1H-pyrrolo[3,2-c]pyridine-3-carboxamide

A) 1-methyl-N-(4-(morpholin-4-yl)phenyl)-4-oxo-4,5-dihydro-1H-pyrrolo[3,2-c]pyridine-3-carboxamide To a solution of 1-methyl-4-oxo-4,5-dihydro-1H-pyrrolo[3,2-c]pyridine-3-carboxylic acid (202.8 mg) in DMF (3.5 mL) was added CDI (240 mg) at room temperature, and the mixture was stirred under nitrogen atmosphere at 110° C. for 2.5 hr. 4-(Morpholin-4-yl)aniline (226 mg) was added thereto, and the mixture was stirred at 80° C. for 3 hr. To the reaction mixture was added water, and the mixture was stirred at room temperature for 10 min. The precipitate was collected by filtration, and washed successively with water, ethyl acetate, methanol and THF to give the title compound (222 mg).

MS: [M+H]$^+$ 392.1.

B) 5-(cyanomethyl)-1-methyl-N-(4-(morpholin-4-yl)phenyl)-4-oxo-4,5-dihydro-1H-pyrrolo[3,2-c]pyridine-3-carboxamide To a mixture of 1-methyl-N-(4-(morpholin-4-yl)phenyl)-4-oxo-4,5-dihydro-1H-pyrrolo[3,2-c]pyridine-3-carboxamide (59.0 mg), potassium carbonate (46.3 mg) and DMF (0.85 mL) was added 2-bromoacetonitrile (0.015 mL) at room temperature, and the mixture was stirred overnight at room temperature. 2-Bromoacetonitrile (0.008 mL), potassium carbonate (12.5 mg) and DMF (0.35 mL) were added thereto, and the mixture was stirred at room temperature for additional 5 hr. To the reaction mixture was added water (5 mL), and the precipitate was collected by filtration, and washed with water. The filtered precipitate was suspended in a mixed solvent of ethyl acetate/methanol, and filtered again, and washed with ethyl acetate to give the title compound (40.3 mg).

$^1$H NMR (300 MHz, DMSO-d$_6$) δ 3.03-3.10 (4H, m), 3.71-3.77 (4H, m), 3.82 (3H, s), 5.22 (2H, s), 6.92-7.00 (3H, m), 7.61 (2H, d, J=9.0 Hz), 7.69 (1H, d, J=7.5 Hz), 7.94 (1H, s), 12.74 (1H, s).

Example 293

5-(2-methoxyphenyl)-1-methyl-N-(4-(morpholin-4-yl)phenyl)-4-oxo-4,5-dihydro-1H-pyrrolo[3,2-c]pyridine-3-carboxamide To a mixture of 1-methyl-N-(4-(morpholin-4-yl)phenyl)-4-oxo-4,5-dihydro-1H-pyrrolo[3,2-c]pyridine-3-carboxamide (105.9 mg), (2-methoxyphenyl)boronic acid (21.0 mg), molecular sieve 3A (200 mg), acetonitrile (3 mL) and DMF (1 mL) were added copper(II) acetate (11 mg), pyridine (0.018 mL) and TEA (0.098 mL), and the mixture was stirred at room temperature for 45 min. (2-Methoxyphenyl)boronic acid (21.0 mg), copper(II) acetate (11 mg) and pyridine (0.018 mL) were added thereto three times every 45 min, and the mixture was stirred at room temperature for 1.5 hr. The mixture was filtered through Celite, and the filtrate was purified by silica gel column chromatography (hexane/ethyl acetate/methanol) to give the title compound (20.2 mg).

$^1$H NMR (300 MHz, CDCl$_3$) δ 3.06-3.11 (4H, m), 3.80 (3H, s), 3.82 (3H, s), 3.83-3.86 (4H, m), 6.49 (1H, d, J=7.2 Hz), 6.81-6.88 (2H, m), 7.06-7.15 (3H, m), 7.34 (1H, dd, J=8.1, 1.7 Hz), 7.46 (1H, td, J=7.9, 1.5 Hz), 7.66-7.74 (2H, m), 7.78 (1H, s), 12.79 (1H, s).

Example 294

1-methyl-N-(4-(morpholin-4-yl)phenyl)-4-oxo-5-(2-(2,2,2-trifluoroethoxy)phenyl)-4,5-dihydro-1H-pyrrolo[3,2-c]pyridine-3-carboxamide A mixture of 1-methyl-N-(4-(morpholin-4-yl)phenyl)-4-oxo-4,5-dihydro-1H-pyrrolo[3,2-c]pyridine-3-carboxamide (60.3 mg), (2-(2,2,2-trifluoroethoxy)phenyl)boronic acid (45.1 mg), molecular sieve 3A (103.0 mg), copper(II) acetate (24.6 mg), TEA (0.056 mL), pyridine (0.0324 mL), acetonitrile (1 mL) and DMF (0.5 mL) was stirred at 50° C. for 2 hr. (2-(2,2,2-Trifluoroethoxy)phenyl)boronic acid (30.5 mg) was added thereto, and the mixture was stirred at 50° C. for 3 hr. The reaction mixture was purified by silica gel column chromatography (hexane/ethyl acetate/methanol) to give the title compound (8 mg).

$^1$H NMR (300 MHz, DMSO-d$_6$) δ 2.96-3.07 (4H, m), 3.65-3.78 (4H, m), 3.85 (3H, s), 4.72-4.92 (2H, m), 6.88 (3H, d, J=7.9 Hz), 7.16-7.32 (1H, m), 7.35-7.62 (6H, m), 7.92 (1H, s), 12.91 (1H, s).

Example 298

1-methyl-N-(4-(morpholin-4-yl)phenyl)-4-oxo-5-(2,2,2-trifluoroethyl)-4,5-dihydro-1H-pyrrolo[3,2-c]pyridine-3-carboxamide To a solution of 1-methyl-N-(4-(morpholin-4-yl)phenyl)-4-oxo-4,5-dihydro-1H-pyrrolo[3,2-c]pyridine-3-carboxamide (48.5 mg) in DMF (1 mL) was added sodium hydride (60% in oil, 7 mg) at 0° C., and the mixture was stirred at room temperature for 15 min. 2,2,2-Trifluoroethyl trifluoromethanesulfonate (0.03 mL) was added thereto, and the mixture was stirred at room temperature for 1 hr. To the reaction mixture was added water, and the mixture was stirred at room temperature for 10 min, and the precipitate was collected by filtration, and washed with water. The obtained precipitate was purified by silica gel column chromatography (hexane/ethyl acetate/methanol) to give the title compound (41.1 mg).

$^1$H NMR (300 MHz, DMSO-d$_6$) δ 3.06 (4H, brs), 3.74 (4H, brs), 3.82 (3H, s), 5.06 (2H, q, J=9.0 Hz), 6.82-7.07 (3H, m), 7.47-7.71 (3H, m), 7.93 (1H, s), 12.81 (1H, s).

Example 311

5-(2-methoxyphenyl)-7-methyl-N-(4-(morpholin-4-yl)phenyl)-4-oxo-4,5-dihydropyrazolo[1,5-a]pyrazine-3-carboxamide

A) 2-methoxy-N-(prop-2-yn-1-yl)aniline

To a solution of 2-methoxyaniline (11.4 mL) in acetonitrile (30 mL) were added potassium carbonate (6.97 g) and 3-bromoprop-1-yne (1.911 mL) at 0° C. The mixture was stirred overnight at room temperature. The precipitate was removed by filtration, and the filtrate was concentrated under reduced pressure. The residue was purified by silica gel column chromatography (hexane/ethyl acetate) to give the title compound (4.06 g).

MS: [M+H]$^+$ 162.0.

B) 4-bromo-N-(2-methoxyphenyl)-N-(prop-2-yn-1-yl)-1H-pyrazole-5-carboxamide

To a mixture of 4-bromo-1H-pyrazole-3-carboxylic acid (2.370 g), 2-methoxy-N-(prop-2-yn-1-yl)aniline (2.00 g) and DMF (5 mL) were added HATU (5.66 g) and DIPEA (2.60 mL) at 0° C. The mixture was stirred overnight at 70° C. The mixture was purified by silica gel column chromatography (Si and NH, hexane/ethyl acetate) to give the title compound (2.58 g).

$^1$H NMR (300 MHz, CDCl$_3$) δ 2.19 (1H, t, J=2.5 Hz), 3.78 (3H, s), 4.27 (1H, d, J=17.2 Hz), 4.98 (1H, d, J=16.8 Hz), 6.80-6.97 (2H, m), 7.20-7.30 (2H, m), 7.37 (1H, s), 10.34 (1H, brs).

C) 3-bromo-5-(2-methoxyphenyl)-7-methylpyrazolo[1,5-a]pyrazin-4(5H)-one

A mixture of 4-bromo-N-(2-methoxyphenyl)-N-(prop-2-yn-1-yl)-1H-pyrazole-5-carboxamide (2.58 g), DBU (0.349 mL) and DMF (3 mL) was stirred at 120° C. for 3 hr. The mixture was cooled to room temperature, and the precipitate was washed with ethyl acetate to give the title compound (920 mg).

$^1$H NMR (300 MHz, DMSO-d$_6$) δ 2.36 (3H, d, J=1.1 Hz), 3.78 (3H, s), 6.96 (1H, d, J=1.1 Hz), 7.09 (1H, td, J=7.6, 1.2 Hz), 7.24 (1H, dd, J=8.5, 1.1 Hz), 7.38 (1H, dd, J=7.7, 1.5 Hz), 7.44-7.55 (1H, m), 8.14 (1H, s).

D) Ethyl 5-(2-methoxyphenyl)-7-methyl-4-oxo-4,5-dihydropyrazolo[1,5-a]pyrazine-3-carboxylate A mixture of 3-bromo-5-(2-methoxyphenyl)-7-methylpyrazolo[1,5-a]pyrazin-4(5H)-one (1.33 g), dichloro[1,1'-bis(diphenylphosphino)ferrocene]palladium(II) (471.2 mg), TEA (2 mL), DMF (10 mL) and EtOH (10 mL) was stirred under carbon monoxide (5 atm) atmosphere, at 100° C. for 7 hr. The reaction mixture was filtered through Celite, and washed with ethyl acetate. The filtrate was concentrated under reduced pressure, and the residue was purified by silica gel column chromatography (NH, hexane/ethyl acetate) to give the title compound (1.13 g).

MS: [M+H]$^+$ 328.0.

E) 5-(2-methoxyphenyl)-7-methyl-4-oxo-4,5-dihydropyrazolo[1,5-a]pyrazine-3-carboxylic Acid A mixture of ethyl 5-(2-methoxyphenyl)-7-methyl-4-oxo-4,5-dihydropyrazolo[1,5-a]pyrazine-3-carboxylate (189 mg), EtOH (2 mL), THF (2 mL) and 2M aqueous sodium hydroxide solution (2 mL) was stirred at room temperature for 2 hr. The mixture was concentrated under reduced pressure until reduced to half volume, the residue was cooled to 0° C., and neutralized with 2M hydrochloric acid. The solid was collected by filtration, and washed with water to give the title compound (153 mg).
MS: [M+H]$^+$ 300.0.

F) 5-(2-methoxyphenyl)-7-methyl-N-(4-(morpholin-4-yl)phenyl)-4-oxo-4,5-dihydropyrazolo[1,5-a]pyrazine-3-carboxamide To a mixture of 5-(2-methoxyphenyl)-7-methyl-4-oxo-4,5-dihydropyrazolo[1,5-a]pyrazine-3-carboxylic acid (30.0 mg), oxalyl chloride (0.013 mL) and THF (1 mL) was added DMF (one drop) at room temperature, and the mixture was stirred at room temperature for 30 min. The mixture was cooled to 0° C., 4-(morpholin-4-yl)aniline (19.65 mg) and TEA (50.7 mg) were added thereto, and the mixture was stirred at room temperature for 1 hr. To the mixture was added water, and the mixture was extracted with ethyl acetate. The organic layer was separated, washed with saturated brine, dried over anhydrous magnesium sulfate, and concentrated under reduced pressure. The residue was washed with diisopropyl ether to give the title compound (36.0 mg).
$^1$H NMR (300 MHz, DMSO-d$_6$) δ 2.47 (3H, d, J=0.8 Hz), 3.00-3.11 (4H, m), 3.66-3.76 (4H, m), 3.81 (3H, s), 6.91 (2H, d, J=9.1 Hz), 7.09-7.19 (1H, m), 7.24 (1H, d, J=1.1 Hz), 7.30 (1H, d, J=7.6 Hz), 7.44-7.61 (4H, m), 8.53 (1H, s), 12.24 (1H, s).

Example 314

N-[(1S,3R)-3-butoxycyclopentyl]-1,5,7-trimethyl-4-oxo-4,5-dihydro-1H-pyrrolo[3,2-c]pyridine-3-carboxamide A) Tert-butyl {(1S,3R)-3-[(but-2-en-1-yl)oxy]cyclopentyl}carbamate To a solution of tert-butyl [(1S,3R)-3-hydroxycyclopentyl]carbamate (1 g) in DMF (15 mL) was added sodium hydride (60% in oil, 261.2 mg) at 0° C., and the mixture was stirred at room temperature for 30 min. Crotyl bromide (0.918 g) was added thereto, and the mixture was stirred at 60° C. for 3 hr. To the reaction mixture was added aqueous ammonium chloride solution, and the mixture was extracted with ethyl acetate. The organic layer was separated, washed with water and saturated brine, dried over anhydrous magnesium sulfate, and concentrated under reduced pressure. The residue was purified by silica gel column chromatography (hexane/ethyl acetate) to give the title compound (977 mg).
$^1$H NMR (300 MHz, DMSO-d$_6$) δ 1.27-1.53 (11H, m), 1.53-1.82 (6H, m), 2.01-2.18 (1H, m), 3.57-3.73 (1H, m), 3.74-3.87 (2.6H, m), 3.92 (0.4H, d, J=6.2 Hz), 5.40-5.72 (2H, m), 6.73 (1H, d, J=7.4 Hz).

B) Tert-butyl [(1S,3R)-3-butoxycyclopentyl]carbamate

A mixture of tert-butyl {(1S,3R)-3-[(but-2-en-1-yl)oxy]cyclopentyl}carbamate (976 mg), 10% palladium-carbon (120 mg) and MeOH (12 mL) was stirred under normal pressure of hydrogen atmosphere, at room temperature for 2 hr. The catalyst was removed by filtration, and the filtrate was concentrated under reduced pressure to give the title compound (882 mg).
$^1$H NMR (300 MHz, DMSO-d$_6$) δ 0.79-0.93 (3H, m), 1.21-1.53 (15H, m), 1.53-1.80 (3H, m), 2.08 (1H, dt, J=12.9, 6.8 Hz), 3.24-3.31 (2H, m), 3.57-3.84 (2H, m), 6.69 (1H, d, J=7.6 Hz).

C) (1S,3R)-3-butoxycyclopentan-1-amine Hydrochloride

To a solution of tert-butyl [(1S,3R)-3-butoxycyclopentyl]carbamate (881 mg) in ethyl acetate (10 mL) was added 4M hydrogen chloride-ethyl acetate solution (4 mL), and the mixture was stirred at 60° C. for 2 hr. The reaction mixture was concentrated under reduced pressure, and the precipitate was collected by filtration, and washed with diisopropyl ether and ethyl acetate to give the title compound (590 mg).
$^1$H NMR (300 MHz, DMSO-d$_6$) δ 0.81-0.93 (3H, m), 1.23-1.39 (2H, m), 1.39-1.80 (6H, m), 1.83-1.97 (1H, m), 2.12-2.26 (1H, m), 3.25-3.49 (3H, m), 3.77-3.94 (1H, m), 7.80 (3H, brs).

D) N-[(1S,3R)-3-butoxycyclopentyl]-1,5,7-trimethyl-4-oxo-4,5-dihydro-1H-pyrrolo[3,2-c]pyridine-3-carboxamide To a solution of 1,5,7-trimethyl-4-oxo-4,5-dihydro-1H-pyrrolo[3,2-c]pyridine-3-carboxylic acid (50.4 mg) in THF (1.5 mL) were added oxalyl chloride (0.030 mL) and DMF (0.01 mL), and the mixture was stirred at room temperature for 1 hr. Oxalyl chloride (0.015 mL) was added thereto, and the mixture was stirred at room temperature for 3 hr. The reaction mixture was concentrated under reduced pressure. To a suspension of the residue in THF (1.5 mL) were added (1S,3R)-3-butoxycyclopentan-1-amine hydrochloride (52.7 mg) and TEA (0.1 mL) at 0° C., and the mixture was stirred at room temperature for 72 hr. To the reaction mixture was added aqueous sodium hydrogencarbonate solution, and the mixture was extracted with ethyl acetate. The organic layer was separated, dried over anhydrous magnesium sulfate, and concentrated under reduced pressure. The residue was purified by silica gel column chromatography (ethyl acetate/methanol) to give the title compound (27.0 mg).
$^1$H NMR (300 MHz, DMSO-d$_6$) δ 0.79-0.89 (3H, m), 1.22-1.63 (6H, m), 1.65-1.78 (2H, m), 1.83-1.98 (1H, m), 2.21-2.35 (1H, m), 2.40 (3H, d, J=0.8 Hz), 3.29-3.35 (2H, m), 3.48 (3H, s), 3.77-3.90 (1H, m), 3.98 (3H, s), 4.05-4.20 (1H, m), 7.22 (1H, d, J=0.9 Hz), 7.66 (1H, s), 11.36 (1H, d, J=6.8 Hz).

Example 315

N-(cis-3-butoxycyclobutyl)-1,5,7-trimethyl-4-oxo-4,5-dihydro-1H-pyrrolo[3,2-c]pyridine-3-carboxamide A) Tert-butyl {cis-3-[(but-2-en-1-yl)oxy]cyclobutyl}carbamate To a solution of tert-butyl (cis-3-hydroxycyclobutyl)carbamate (1 g) in DMF (15 mL) was added sodium hydride (60% in oil, 282.5 mg) at 0° C., and the mixture was stirred at room temperature for 30 min. Crotyl bromide (0.75 mL) was added thereto, and the mixture was stirred at 60° C. for 3 hr. To the reaction mixture was added aqueous ammonium chloride solution, and the mixture was extracted with ethyl acetate. The organic layer was separated, dried over anhydrous magnesium sulfate, and concentrated under reduced pressure. The residue was purified by silica gel column chromatography (hexane/ethyl acetate) to give the title compound (959 mg).

$^1$H NMR (300 MHz, DMSO-$d_6$) δ 1.36 (9H, s), 1.54-1.82 (5H, m), 2.35-2.47 (2H, m), 3.40-3.65 (2H, m), 3.73 (1.6H, dt, J=6.0, 1.2 Hz), 3.86 (0.4H, d, J=6.4 Hz), 5.38-5.73 (2H, m), 7.07 (1H, d, J=8.3 Hz).

B) Tert-butyl (cis-3-butoxycyclobutyl)carbamate

A mixture of tert-butyl {cis-3-[(but-2-en-1-yl)oxy]cyclobutyl}carbamate (958 mg), 10% palladium-carbon (200.7 mg) and MeOH (15 mL) was stirred under normal pressure of hydrogen atmosphere, at room temperature for 2.5 hr. The catalyst was removed by filtration, and the filtrate was concentrated under reduced pressure to give the title compound (972 mg).

$^1$H NMR (300 MHz, DMSO-$d_6$) δ 0.80-0.91 (3H, m), 1.20-1.49 (13H, m), 1.63-1.80 (2H, m), 2.36-2.47 (2H, m), 3.23 (2H, t, J=6.4 Hz), 3.43-3.62 (2H, m), 7.06 (1H, d, J=7.9 Hz).

C) cis-3-butoxycyclobutan-1-amine Hydrochloride

To a solution of tert-butyl (cis-3-butoxycyclobutyl)carbamate (971 mg) in ethyl acetate (10 mL) was added 4M hydrogen chloride-ethyl acetate solution (5 mL), and the mixture was stirred at 60° C. for 2 hr. The reaction mixture was concentrated under reduced pressure, and the precipitate was washed with hexane and diisopropyl ether to give the title compound (680 mg).

$^1$H NMR (300 MHz, DMSO-$d_6$) δ 0.81-0.93 (3H, m), 1.22-1.38 (2H, m), 1.39-1.52 (2H, m), 1.85-2.03 (2H, m), 2.52-2.60 (2H, m), 3.18-3.30 (3H, m), 3.59-3.79 (1H, m), 7.96 (3H, brs).

D) N-(cis-3-butoxycyclobutyl)-1,5,7-trimethyl-4-oxo-4,5-dihydro-1H-pyrrolo[3,2-c]pyridine-3-carboxamide To a solution of 1,5,7-trimethyl-4-oxo-4,5-dihydro-1H-pyrrolo[3,2-c]pyridine-3-carboxylic acid (49 mg) in THF (1.5 mL) were added oxalyl chloride (0.029 mL) and DMF (0.01 mL) at 0° C., and the mixture was stirred at room temperature for 1 hr. Oxalyl chloride (0.01 mL) was added thereto, and the mixture was stirred at room temperature for 3 hr. The reaction mixture was concentrated under reduced pressure. To a suspension of the residue in TH (1.5 mL) were added cis-3-butoxycyclobutan-1-amine hydrochloride (50.3 mg) and TEA (0.1 mL) at 0° C., and the mixture was stirred at room temperature for 72 hr. To the reaction mixture was added aqueous sodium hydrogencarbonate solution, and the mixture was extracted with ethyl acetate. The organic layer was separated, dried over anhydrous magnesium sulfate, and concentrated under reduced pressure. The residue was purified by silica gel column chromatography (ethyl acetate/methanol) to give the title compound (22.3 mg).

$^1$H NMR (300 MHz, DMSO-$d_6$) δ 0.84-0.94 (3H, m), 1.24-1.39 (2H, m), 1.40-1.53 (2H, m), 1.65-1.82 (2H, m), 2.41 (3H, d, J=0.8 Hz), 2.57-2.70 (2H, m), 3.25-3.30 (2H, m), 3.50 (3H, s), 3.62-3.76 (1H, m), 3.91-4.04 (4H, m), 7.24 (1H, d, J=0.9 Hz), 7.67 (1H, s), 11.55 (1H, d, J=7.4 Hz).

Example 316

N-[rac-(1R,3S)-3-butoxycyclopentyl]-1,5,7-trimethyl-4-oxo-4,5-dihydro-1H-pyrrolo[3,2-c]pyridine-3-carboxamide A) Tert-butyl {rac-(1R,3S)-3-[(but-2-en-1-yl)oxy]cyclopentyl}carbamate To a solution of tert-butyl [rac-(1R,3S)-3-hydroxycyclopentyl]carbamate (1 g) in DMF (15 mL) was added sodium hydride (60% in oil, 258 mg) at 0° C., and the mixture was stirred at room temperature for 30 min. Crotyl bromide (0.678 mL) was added thereto, and the mixture was stirred at 60° C. for 3 hr. To the reaction mixture was added water, and the mixture was extracted with ethyl acetate. The organic layer was separated, washed with saturated brine, dried over anhydrous magnesium sulfate, and concentrated under reduced pressure. The residue was purified by silica gel column chromatography (hexane/ethyl acetate) to give the title compound (584 mg).

$^1$H NMR (300 MHz, DMSO-$d_6$) δ 1.26-1.84 (17H, m), 2.09 (1H, dt, J=13.2, 6.8 Hz), 3.56-3.95 (4H, m), 5.41-5.72 (2H, m), 6.72 (1H, d, J=7.4 Hz).

B) rac-(1R,3S)-3-butoxycyclopentan-1-amine Hydrochloride

A mixture of tert-butyl {rac-(1R,3S)-3-[(but-2-en-1-yl)oxy]cyclopentyl}carbamate (584 mg), 10% palladium-carbon (117 mg) and MecOH (6 mL) was stirred under normal pressure of hydrogen atmosphere, at room temperature for 3 hr. The catalyst was removed by filtration, and the filtrate was concentrated under reduced pressure. To the residue was added 4M hydrogen chloride-ethyl acetate solution (6 mL), and the mixture was stirred overnight at room temperature. The reaction mixture was concentrated under reduced pressure, and the precipitate was washed with diisopropyl ether to give the title compound (387 mg).

$^1$H NMR (300 MHz, DMSO-$d_6$) δ 0.84-0.95 (3H, m), 1.24-1.38 (2H, m), 1.40-1.77 (6H, m), 1.82-1.96 (1H, m), 2.11-2.29 (1H, m), 3.25-3.48 (3H, m), 3.76-3.93 (1H, m), 7.99 (3H, brs).

C) N-[rac-(1R,3S)-3-butoxycyclopentyl]-1,5,7-trimethyl-4-oxo-4,5-dihydro-1H-pyrrolo[3,2-c]pyridine-3-carboxamide To a solution of 1,5,7-trimethyl-4-oxo-4,5-dihydro-1H-pyrrolo[3,2-c]pyridine-3-carboxylic acid (50.7 mg) in THF (1.5 mL) were added oxalyl chloride (0.035 mL) and DMF (0.01 mL), and the mixture was stirred at room temperature for 1 hr. The reaction mixture was concentrated under reduced pressure. To a suspension of the residue in THF (1.5 mL) were added rac-(1R,3S)-3-butoxycyclopentan-1-amine hydrochloride (51.3 mg) and TEA (0.1 mL) at 0° C., and the mixture was stirred at room temperature for 48 hr. To the reaction mixture was added aqueous sodium hydrogencarbonate solution, and the mixture was extracted with ethyl acetate. The organic layer was separated, dried over anhydrous magnesium sulfate, and concentrated under reduced pressure. The residue was purified by silica gel column chromatography (ethyl acetate/methanol) to give the title compound (32 mg).

$^1$H NMR (300 MHz, DMSO-$d_6$) δ 0.79-0.89 (3H, m), 1.22-1.62 (6H, m), 1.65-1.78 (2H, m), 1.83-1.98 (1H, m), 2.28 (1H, dt, J=13.8, 6.8 Hz), 2.40 (3H, d, J=0.8 Hz), 3.26-3.37 (2H, m), 3.48 (3H, s), 3.79-3.90 (1H, m), 3.98 (3H, s), 4.06-4.17 (1H, m), 7.22 (1H, d, J=0.9 Hz), 7.66 (1H, s), 11.36 (1H, d, J=6.8 Hz).

Example 317

N-(trans-3-butoxycyclobutyl)-1,5,7-trimethyl-4-oxo-4,5-dihydro-1H-pyrrolo[3,2-c]pyridine-3-carboxamide A) Tert-butyl {trans-3-[(but-2-en-1-yl)oxy]cyclobutyl}carbamate To a solution of tert-butyl (trans-3-hydroxycyclobutyl)carbamate (1 g) in DMF (15 mL) was added sodium hydride (60% in oil, 278 mg) at 0° C., and the mixture was stirred at room temperature for 30 min. Crotyl bromide (0.728 mL) was added thereto, and the mixture was stirred at 60° C. for 3 hr. To the reaction mixture was added water, and the mixture was extracted with ethyl acetate. The organic layer was separated, dried over anhydrous magnesium sulfate, and concentrated under reduced pressure. The residue was purified by silica gel column chromatography (hexane/ethyl acetate) to give the title compound (350 mg).

$^1$H NMR (300 MHz, DMSO-$d_6$) δ 1.30-1.74 (12H, m), 2.00-2.19 (4H, m), 3.68-4.06 (4H, m), 5.35-5.77 (2H, m), 7.16 (1H, d, J=6.2 Hz).

B) trans-3-butoxycyclobutan-1-amine

A mixture of tert-butyl {trans-3-[(but-2-en-1-yl)oxy]cyclobutyl}carbamate (350 mg), 10% palladium-carbon (70 mg) and MeOH (4 mL) was stirred under normal pressure of hydrogen atmosphere, at room temperature for 3 hr. The catalyst was removed by filtration, and concentrated under reduced pressure. To the residue was added 4M hydrogen chloride-ethyl acetate solution (4 mL), and the mixture was stirred overnight at room temperature. The reaction mixture was concentrated under reduced pressure, saturated aqueous sodium hydrogencarbonate solution was added thereto, and the mixture was extracted with ethyl acetate. The organic layer was separated, dried over anhydrous magnesium sulfate, and concentrated under reduced pressure to give the title compound (6.0 mg).

$^1$H NMR (300 MHz, CDCl$_3$) δ 0.87-0.96 (3H, m), 1.30-1.44 (2H, m), 1.47-1.62 (2H, m), 1.94-2.11 (2H, m), 2.22-2.40 (2H, m), 3.31 (2H, t, J=6.7 Hz), 3.62-3.76 (1H, m), 4.07-4.22 (1H, m).

C) N-(trans-3-butoxycyclobutyl)-1,5,7-trimethyl-4-oxo-4,5-dihydro-1H-pyrrolo[3,2-c]pyridine-3-carboxamide To a solution of 1,5,7-trimethyl-4-oxo-4,5-dihydro-1H-pyrrolo[3,2-c]pyridine-3-carboxylic acid (50.0 mg) in THF (1.5 mL) were added oxalyl chloride (0.034 mL) and DMF (0.01 mL) at 0° C., and the mixture was stirred at room temperature for 1 hr. The reaction mixture was concentrated under reduced pressure. To a suspension of the residue in THF (1.5 mL) were added trans-3-butoxycyclobutan-1-amine (6.0 mg) and TEA (0.1 mL) at 0° C., and the mixture was stirred at room temperature for 2 hr. To the reaction mixture was added water, and the mixture was extracted with ethyl acetate. The organic layer was separated, dried over anhydrous magnesium sulfate, and concentrated under reduced pressure. The residue was purified by preparative high-performance liquid chromatography (acetonitrile containing 0.1% TFA/water containing 0.1% TFA) to give the title compound (2.7 mg).

MS: [M+H]$^+$ 346.2.

Example 318

3-[1-(5-chloropyridin-2-yl)-3-azabicyclo[3.1.0]hexane-3-carbonyl]-1,5,7-trimethyl-1,5-dihydro-4H-pyrrolo[3,2-c]pyridin-4-one A) Tert-butyl (5-chloropyridin-2-yl)(cyano)acetate To a suspension of sodium hydride (60% in oil, 3.38 g) in DMSO (75 mL) was added dropwise tert-butyl cyanoacetate (11.9 g) at 0° C., and the mixture was stirred at room temperature for 1 hr. A solution of 2,5-dichloropyridine (5.00 g) in DMSO (5 mL) was added dropwise thereto, and the mixture was stirred at 120° C. for 16 hr. To the reaction mixture was added saturated aqueous ammonium chloride solution, and the precipitate was collected by filtration, and washed successively with water and petroleum ether to give the title compound (4.48 g).

MS: [M+H]$^+$-(tBu) 196.7.

B) (5-chloropyridin-2-yl)acetonitrile

A mixture of tert-butyl (5-chloropyridin-2-yl)(cyano)acetate (4.48 g), 4-methylbenzenesulfonid acid (3.05 g) and acetonitrile (60 mL) was stirred at 81° C. for 16 hr. The mixture was concentrated under reduced pressure, ethyl acetate was added thereto, and the mixture was washed with aqueous sodium hydrogencarbonate solution and saturated brine, dried over anhydrous sodium sulfate, and concentrated under reduced pressure. The residue was purified by silica gel column chromatography (petroleum ether/ethyl acetate) to give the title compound (2.41 g).

MS: [M+H]$^+$ 152.8.

C) 1-(5-chloropyridin-2-yl)-2-(hydroxymethyl)cyclopropane-1-carbonitrile

To a solution of sodium amide (537 mg) in THF (30 mL) was added dropwise a solution of (5-chloropyridin-2-yl)acetonitrile (1.91 g) in THF (5 mL) under nitrogen atmosphere at −25° C., and the mixture was stirred at room temperature for 2 hr. The mixture was cooled to −25° C., 2-(chloromethyl)oxirane (1.39 g) and sodium amide (537 mg) were added successively thereto, and the mixture was stirred at room temperature for 5 hr. To the reaction mixture was added saturated aqueous ammonium chloride solution, and the mixture was extracted with ethyl acetate. The organic layers were combined, washed with saturated brine, dried over anhydrous sodium sulfate, and concentrated under reduced pressure. The residue was purified by silica gel column chromatography (petroleum ether/ethyl acetate) to give the title compound (1.10 g).

MS: [M+H]$^+$ 208.7.

D) [2-(aminomethyl)-2-(5-chloropyridin-2-yl)cyclopropyl]methanol

To a suspension of lithium aluminium hydride (500 mg) in THF (35 mL) was added dropwise a solution of 1-(5-chloropyridin-2-yl)-2-(hydroxymethyl)cyclopropane-1-carbonitrile (1.10 g) in THF (5 mL) at 0° C., and the mixture was stirred at 0° C. for 30 min. The reaction mixture was diluted with THF, and water and 15% aqueous sodium hydroxide solution were added thereto. The insoluble substance was removed by filtration, and the filtrate was concentrated under reduced pressure to give the title compound (1.00 g).

MS: [M+H]$^+$ 212.7.

E) 1-(5-chloropyridin-2-yl)-3-azabicyclo[3.1.0]hexane

To a solution of [2-(aminomethyl)-2-(5-chloropyridin-2-yl)cyclopropyl]methanol (1.00 g) in ethyl acetate (30 mL) was added thionyl chloride (2.80 g) at 0° C., and the mixture was stirred at 20° C. for 6 hr. The mixture was cooled to 0° C., 28% aqueous ammonia (11.8 g) was added dropwise thereto, and the mixture was stirred at 0° C. for 2 hr. The reaction mixture was diluted with water, and extracted with ethyl acetate. The organic layers were combined, washed with saturated brine, dried over anhydrous sodium sulfate, and concentrated under reduced pressure to give the title compound (560 mg).

MS: [M+H]$^+$ 194.7.

F) 3-[1-(5-chloropyridin-2-yl)-3-azabicyclo[3.1.0]hexane-3-carbonyl]-1,5,7-trimethyl-1,5-dihydro-4H-pyrrolo[3,2-c]pyridin-4-one A mixture of 1,5,7-trimethyl-4-oxo-4,5-dihydro-1H-pyrrolo[3,2-c]pyridine-3-carboxylic acid (300 mg) and thionyl chloride (5 mL) was stirred at 76° C. for 15 hr. The reaction mixture was concentrated under reduced pressure to give the corresponding acid chloride (400 mg). To a mixture of 1-(5-chloropyridin-2-yl)-3-azabicyclo[3.1.0]hexane (100 mg) and dichloromethane (10 mL) were added DIPEA (199 mg) and the above acid chloride (125 mg), and the mixture was stirred at 20° C. for 30 min. The reaction mixture was diluted with dichloromethane, washed with water and saturated brine, dried over anhydrous sodium sulfate, and concentrated under reduced pressure. The residue was purified by preparative high-performance liquid chromatography (acetonitrile containing 0.05% aqueous ammonia/0.1% aqueous ammonia) to give the title compound (29 mg).

$^1$H NMR (400 MHz, CDCl$_3$) δ 1.17-1.48 (2H, m), 2.07-2.12 (1H, m), 2.39 (3H, d, J=0.4 Hz), 3.47-3.54 (3.5H, m), 3.66-3.72 (0.5H, m), 3.77-3.85 (1H, m), 3.90-3.92 (3H, m), 3.98-4.08 (1H, m), 4.23-4.28 (0.5H, m), 4.47-4.53 (0.5H, m), 6.72 (1H, s), 6.83-6.88 (0.5H, m), 6.90 (1H, d, J=7.2 Hz), 7.13-7.17 (0.5H, m), 7.46-7.60 (1H, m), 8.33-8.41 (1H, m).

Example 319

N-[rac-(1R,3R)-3-butoxycyclohexyl]-1,5,7-trimethyl-4-oxo-4,5-dihydro-1H-pyrrolo[3,2-c]pyridine-3-carboxamide

A) rac-(1R,3R)-3-azidocyclohexan-1-ol

To a solution of rac-(1R,3S)-cyclohexane-1,3-diol (504.8 mg) in pyridine (12 mL) was added thionyl chloride (1.4 mL) at 0° C., and the mixture was stirred at 0° C. for 45 min. To the reaction mixture was added water, and the mixture was extracted with ethyl acetate. The organic layers were combined, washed successively with 1M hydrochloric acid and saturated aqueous sodium hydrogencarbonate, dried over anhydrous magnesium sulfate, and concentrated under reduced pressure. To a solution of the residue in DMF (10 mL) was added sodium azide (706 mg), and the mixture was stirred overnight at 100° C. To the reaction mixture was added water, and the mixture was extracted with ethyl acetate. The organic layer was separated, washed with water and saturated brine, dried over anhydrous magnesium sulfate, and concentrated under reduced pressure. The residue was purified by silica gel column chromatography (hexane/ethyl acetate) to give the title compound (215 mg).

$^1$H NMR (300 MHz, CDCl$_3$) δ 1.32 (1H, d, J=3.4 Hz), 1.47-1.81 (8H, m), 3.77-3.93 (1H, m), 4.01-4.17 (1H, m).

B) rac-(1R,3R)-1-azido-3-[(but-2-en-1-yl)oxy]cyclohexane

To a mixture of rac-(1R,3R)-3-azidocyclohexan-1-ol (212.8 mg), THF (3 mL) and DMF (1 mL) was added sodium hydride (60% in oil, 78 mg) at 0° C., and the mixture was stirred at 0° C. for 30 min. Crotyl bromide (0.257 mL) was added thereto, and the mixture was stirred at room temperature for 3 hr. To the reaction mixture was added saturated aqueous ammonium chloride solution, and the mixture was extracted with ethyl acetate. The organic layer was separated, washed with water and saturated brine, dried over anhydrous magnesium sulfate, and concentrated under reduced pressure. The residue was purified by silica gel column chromatography (hexane/ethyl acetate) to give the title compound (228 mg).

$^1$H NMR (300 MHz, CDCl$_3$) δ 1.40-1.74 (9H, m), 1.79 (1H, dd, J=12.4, 3.8 Hz), 1.85-1.97 (1H, m), 3.62-3.72 (1H, m), 3.73-3.84 (1H, m), 3.84-4.07 (2H, m), 5.50-5.78 (2H, m).

C) rac-(1R,3R)-3-butoxycyclohexan-1-amine

A mixture of rac-(1R,3R)-1-azido-3-[(but-2-en-1-yl)oxy]cyclohexane (225 mg), 10% palladium-carbon (30 mg) and MeOH (4 mL) was stirred under normal pressure of hydrogen atmosphere overnight at room temperature. The catalyst was removed by filtration, and the filtrate was concentrated under reduced pressure to give the title compound (177 mg).

$^1$H NMR (300 MHz, CDCl$_3$) δ 0.88-0.95 (3H, m), 1.03-1.83 (13H, m), 1.86-2.00 (1H, m), 2.99-3.11 (1H, m), 3.35-3.42 (2H, m), 3.58-3.66 (1H, m).

D) N-[rac-(1R,3R)-3-butoxycyclohexyl]-1,5,7-trimethyl-4-oxo-4,5-dihydro-1H-pyrrolo[3,2-c]pyridine-3-carboxamide To a solution of 1,5,7-trimethyl-4-oxo-4,5-dihydro-1H-pyrrolo[3,2-c]pyridine-3-carboxylic acid (53.4 mg) in DMF (0.75 mL) was added CDI (62.9 mg), and the mixture was stirred under nitrogen atmosphere at 110° C. for 1.5 hr. The reaction mixture was cooled to 60° C., rac-(1R,3R)-3-butoxycyclohexan-1-amine (64.6 mg) was added thereto, and the mixture was stirred at 60° C. for 1.5 hr. To the reaction mixture was added saturated aqueous sodium hydrogencarbonate solution, and the mixture was extracted with ethyl acetate. The organic layer was separated, washed with 1M hydrochloric acid and saturated brine, dried over anhydrous magnesium sulfate, and concentrated under reduced pressure. The residue was purified by silica gel column chromatography (NH, ethyl acetate/methanol) to give the title compound (70.5 mg).

$^1$H NMR (300 MHz, DMSO-d$_6$) δ0.89 (3H, t, J=7.3 Hz), 1.27-1.42 (3H, m), 1.42-1.64 (7H, m), 1.66-1.86 (2H, m), 2.40 (3H, s), 3.37 (2H, t, J=6.4 Hz), 3.47 (3H, s), 3.63 (1H, brs), 3.98 (3H, s), 4.02-4.15 (1H, m), 7.22 (1H, s), 7.66 (1H, s), 11.25 (1H, d, J=7.5 Hz).

Example 320

1,5,7-trimethyl-3-{1-[1-(2,2,2-trifluoroethyl)-1H-pyrazol-4-yl]-3-azabicyclo[3.1.0]hexane-3-carbonyl}-1,5-dihydro-4H-pyrrolo[3,2-c]pyridin-4-one A) Tert-butyl 1-(4,4,5,5-tetramethyl-1,3,2-dioxaborolan-2-yl)-3-azabicyclo[3.1.0]hexane-3-carboxylate To a solution of 1M toluene solution (40.7 mL) of diethylzinc in dichloromethane (45 mL) was added dropwise a solution of diiodomethane (21.8 g) in dichloromethane (15 mL) at −40° C., and the mixture was stirred under nitrogen atmosphere at −40° C. for 1 hr. A solution of trifluoroacetic acid (4.64 g) in dichloromethane (15 mL) was added dropwise thereto at −40° C., and the mixture was stirred at −15° C. for 1 hr. A solution of tert-butyl 3-(4,4,5,5-tetramethyl-1,3,2-dioxaborolan-2-yl)-2,5-dihydro-1H-pyrrole-1-carboxylate (1.50 g) in dichloromethane (15 mL) was added dropwise thereto, and the mixture was stirred at room temperature for 16 hr. THF (30 mL), ditert-butyl dicarbonate (5.55 g), TEA (5.14 g) and DMAP (155 mg) were added thereto, and the mixture was stirred at room temperature for 2 hr. The reaction mixture was diluted with ethyl acetate, saturated aqueous sodium hydrogencarbonate solution was added thereto, and the insoluble substance was removed by filtration. The filtrate was washed with saturated brine, dried over anhydrous sodium sulfate, and concentrated under reduced pressure. The residue was purified by silica gel column chromatography (petroleum ether/ethyl acetate) to give the title compound (800 mg).
$^1$H NMR (400 MHz, CDCl$_3$) δ 0.38-0.44 (1H, m), 0.91-0.98 (1H, m), 1.22 (12H, s), 1.41 (9H, s), 1.58-1.65 (1H, m), 3.28-3.66 (4H, m).

B) [3-(tert-butoxycarbonyl)-3-azabicyclo[3.1.0]hexan-1-yl](trifluoride)borate

To a solution of tert-butyl 1-(4,4,5,5-tetramethyl-1,3,2-dioxaborolan-2-yl)-3-azabicyclo[3.1.0]hexane-3-carboxylate (800 mg) in MeOH (20 mL) was added potassium hydrogen fluoride (1.41 g), and the mixture was stirred at 65° C. for 4 hr. The mixture was concentrated under reduced pressure, and the precipitate was washed with petroleum ether, hot acetonitrile was added thereto, and the insoluble substance was removed by filtration. The filtrate was concentrated under reduced pressure to give the title compound (650 mg).
$^1$H NMR (400 MHz, DMSO-d$_6$) δ −0.43-−0.39 (1H, m), 0.31-0.37 (1H, m), 0.90-0.96 (1H, m), 1.35 (9H, s), 3.05-3.14 (3H, m), 3.29-3.33 (1H, m).

C) 4-bromo-1-(2,2,2-trifluoroethyl)-1H-pyrazole

A mixture of 4-bromo-1H-pyrazole (2.00 g), 2,2,2-trifluoroethyl trifluoromethanesulfonate (3.47 g), potassium carbonate (2.82 g) and DMF (30 mL) was stirred at room temperature for 16 hr. To the reaction mixture was added water, and the mixture was extracted with ethyl acetate. The organic layers were combined, washed with saturated brine, dried over anhydrous sodium sulfate, and concentrated under reduced pressure. The residue was purified by silica gel column chromatography (petroleum ether/ethyl acetate) to give the title compound (1.80 g).
$^1$H NMR (400 MHz, DMSO-d$_6$) δ 5.14 (2H, q, J=9.2 Hz), 7.71 (1H, d, J=0.4 Hz), 8.11 (1H, s).

D) Tert-butyl 1-[1-(2,2,2-trifluoroethyl)-1H-pyrazol-4-yl]-3-azabicyclo[3.1.0]hexane-3-carboxylate A mixture of [3-(tert-butoxycarbonyl)-3-azabicyclo [3.1.0]hexan-1-yl](trifluoride)borate (300 mg), 4-bromo-1-(2,2,2-trifluoroethyl)-1H-pyrazole (475 mg), cesium carbonate (1.01 g), dichloro[1,1'-bis(diphenylphosphino)ferrocene] palladium(II) (76 mg), toluene (20 mL) and water (2 mL) was stirred under nitrogen atmosphere at 90° C. for 16 hr. The reaction mixture was diluted with ethyl acetate, washed with water and saturated brine, dried over anhydrous sodium sulfate, and concentrated under reduced pressure. The residue was purified by silica gel column chromatography (petroleum ether/ethyl acetate) to give the title compound (160 mg).
MS: [M+H]$^+$ 331.9.

E) 1-[1-(2,2,2-trifluoroethyl)-1H-pyrazol-4-yl]-3-azabicyclo[3.1.0]hexane Hydrochloride A mixture of tert-butyl 1-[1-(2,2,2-trifluoroethyl)-1H-pyrazol-4-yl]-3-azabicyclo[3.1.0]hexane-3-carboxylate (160 mg) and 4M hydrochloric acid-dioxane solution (5 mL) was stirred at room temperature for 1 hr. The reaction mixture was concentrated under reduced pressure to give the title compound (140 mg).
MS: [M+H]$^+$ 231.8.

F) 1,5,7-trimethyl-3-{1-[1-(2,2,2-trifluoroethyl)-1H-pyrazol-4-yl]-3-azabicyclo[3.1.0]hexane-3-carbonyl}-1,5-dihydro-4H-pyrrolo[3,2-c]pyridin-4-one A mixture of 1,5,7-trimethyl-4-oxo-4,5-dihydro-1H-pyrrolo[3,2-c]pyridine-3-carboxylic acid (200 mg) and thionyl chloride (5 mL) was stirred at 76° C. for 1 hr. The mixture was concentrated under reduced pressure to give the corresponding acid chloride (220 mg). To a mixture of 1-[1-(2,2,2-trifluoroethyl)-1H-pyrazol-4-yl]-3-azabicyclo[3.1.0] hexane hydrochloride (140 mg) and dichloromethane (10 mL) were added DIPEA (270 mg) and the acid chloride (220 mg) obtained above, and the mixture was stirred at 20° C. for 30 min. The reaction mixture was diluted with dichloromethane, washed with water and saturated brine, dried over anhydrous sodium sulfate, and concentrated under reduced pressure. The residue was purified by preparative high-performance liquid chromatography (acetonitrile containing 0.05% aqueous ammonia/0.1% aqueous ammonia) to give the title compound (85 mg).
$^1$H NMR (400 MHz, DMSO-d$_6$) δ 0.91-1.02 (2H, m), 1.56-1.75 (1H, m), 2.37 (3H, s), 3.25-3.30 (0.5H, m), 3.37-3.40 (3H, m), 3.42-3.54 (2.5H, m), 3.87-3.93 (3.5H, m), 4.08-4.13 (0.5H, m), 4.92-5.09 (2H, m), 7.07 (1H, s), 7.13 (1H, d, J=2.0 Hz), 7.39-7.78 (2H, m).

Example 321

1,5,7-trimethyl-3-{1-[1-(2,2,2-trifluoroethyl)-1H-pyrazol-3-yl]-3-azabicyclo[3.1.0]hexane-3-carbonyl}-1,5-dihydro-4H-pyrrolo[3,2-c]pyridin-4-one A) 3-bromo-1-(2,2,2-trifluoroethyl)-1H-pyrazole A mixture of 5-bromo-1H-pyrazole (1.00 g), 2,2,2-trifluoroethyl trifluoromethanesulfonate (1.90 g), potassium carbonate (1.41 g) and DMF (20 mL) was stirred at room temperature for 16 hr. To the reaction mixture was added water, and the mixture was extracted with ethyl acetate. The organic layers were combined, washed with saturated brine, dried over anhydrous sodium sulfate, and concentrated under reduced pressure. The residue was purified by silica gel column chromatography (petroleum ether/ethyl acetate) to give the title compound (1.20 g).

MS: [M+H]$^+$ 228.7.

B) Tert-butyl 1-[1-(2,2,2-trifluoroethyl)-1H-pyrazol-3-yl]-3-azabicyclo[3.1.0]hexane-3-carboxylate A mixture of 3-bromo-1-(2,2,2-trifluoroethyl)-1H-pyrazole (508 mg), [3-(tert-butoxycarbonyl)-3-azabicyclo[3.1.0]hexan-1-yl](trifluoride)borate (320 mg), cesium carbonate (1.08 g), dichloro[1,1'-bis(diphenylphosphino)ferrocene]palladium(II) (81 mg), toluene (30 mL) and water (3 mL) was stirred at 90° C. for 16 hr. The reaction mixture was diluted with ethyl acetate, washed with water and saturated brine, dried over anhydrous sodium sulfate, and concentrated under reduced pressure. The residue was purified by silica gel column chromatography (petroleum ether/ethyl acetate) to give the title compound (280 mg).

MS: [M+H]$^+$ 332.1.

C) 1-[1-(2,2,2-trifluoroethyl)-1H-pyrazol-3-yl]-3-azabicyclo[3.1.0]hexane Hydrochloride A mixture of tert-butyl 1-[1-(2,2,2-trifluoroethyl)-1H-pyrazol-3-yl]-3-azabicyclo[3.1.0]hexane-3-carboxylate (280 mg) and 4M hydrochloric acid-dioxane solution (5 mL) was stirred at room temperature for 1 hr. The reaction mixture was concentrated under reduced pressure to give the title compound (240 mg).

MS: [M+H]$^+$ 231.9.

D) 1,5,7-trimethyl-3-{1-[1-(2,2,2-trifluoroethyl)-1H-pyrazol-3-yl]-3-azabicyclo[3.1.0]hexane-3-carbonyl}-1,5-dihydro-4H-pyrrolo[3,2-c]pyridin-4-one A mixture of 1,5,7-trimethyl-4-oxo-4,5-dihydro-1H-pyrrolo[3,2-c]pyridine-3-carboxylic acid (200 mg) and thionyl chloride (5 mL) was stirred at 76° C. for 1 hr. The mixture was concentrated under reduced pressure to give the corresponding acid chloride (220 mg). To a mixture of 1-[1-(2,2,2-trifluoroethyl)-1H-pyrazol-3-yl]-3-azabicyclo[3.1.0]hexane hydrochloride (140 mg) and dichloromethane (10 mL) were added DIPEA (270 mg) and the above acid chloride (220 mg), and the mixture was stirred at room temperature for 30 min. The reaction mixture was diluted with dichloromethane, washed with water and saturated brine, dried over anhydrous sodium sulfate, and concentrated under reduced pressure. The residue was purified by preparative high-performance liquid chromatography so (acetonitrile containing 0.05% aqueous ammonia/0.1% aqueous ammonia) to give the title compound (22 mg).

$^1$H NMR (400 MHz, CDCl$_3$) δ 1.07-1.33 (2H, m), 1.76-1.84 (1H, m), 2.39 (3H, s), 3.45-3.52 (3H, m), 3.67-3.84 (2H, m), 3.85-4.01 (4H, m), 4.18-4.45 (1H, m), 4.52-4.66 (2H, m), 5.98-6.22 (1H, m), 6.68-6.74 (1H, m), 6.85-6.93 (1H, m), 7.33-7.42 (1H, m).

Example 322

3-[1-(5-chloropyrimidin-2-yl)-3-azabicyclo[3.1.0]hexane-3-carbonyl]-1,5,7-trimethyl-1,5-dihydro-4H-pyrrolo[3,2-c]pyridin-4-one A) Tert-butyl 1-(5-chloropyrimidin-2-yl)-3-azabicyclo[3.1.0]hexane-3-carboxylate A mixture of [3-(tert-butoxycarbonyl)-3-azabicyclo[3.1.0]hexan-1-yl](trifluoride)borate (300 mg), 2-bromo-5-chloropyrimidine (401 mg), cesium carbonate (1.01 g), dichloro[1,1'-bis(diphenylphosphino)ferrocene]palladium(II) (76 mg), toluene (30 mL) and water (3 mL) was stirred at 90° C. for 16 hr. The reaction mixture was diluted with ethyl acetate, washed with water and saturated brine, dried over anhydrous sodium sulfate, and concentrated under reduced pressure. The residue was purified by silica gel column chromatography (petroleum ether/ethyl acetate) to give the title compound (150 mg).

MS: [M+H]$^+$-(tBu) 239.8.

B) 1-(5-chloropyrimidin-2-yl)-3-azabicyclo[3.1.0]hexane Hydrochloride

A mixture of tert-butyl 1-(5-chloropyrimidin-2-yl)-3-azabicyclo[3.1.0]hexane-3-carboxylate (150 mg) and 4M hydrochloric acid-dioxane solution (5 mL) was stirred at room temperature for 1 hr. The reaction mixture was concentrated under reduced pressure to give the title compound (130 mg).

MS: [M+H]$^+$ 195.8.

C) 3-[1-(5-chloropyrimidin-2-yl)-3-azabicyclo[3.1.0]hexane-3-carbonyl]-1,5,7-trimethyl-1,5-dihydro-4H-pyrrolo[3,2-c]pyridin-4-one A mixture of 1,5,7-trimethyl-4-oxo-4,5-dihydro-1H-pyrrolo[3,2-c]pyridine-3-carboxylic acid (200 mg) and thionyl chloride (5 mL) was stirred at 76° C. for 1 hr. The mixture was concentrated under reduced pressure to give the corresponding acid chloride (220 mg). To a mixture of 1-(5-chloropyrimidin-2-yl)-3-azabicyclo[3.1.0]hexane hydrochloride (130 mg) and dichloromethane (10 mL) were DIPEA (290 mg) and the above acid chloride (220 mg), and the mixture was stirred at room temperature for 30 min. The reaction mixture was diluted with dichloromethane, washed with water and saturated brine, dried over anhydrous sodium sulfate, and concentrated under reduced pressure. The residue was purified by preparative high-performance liquid chromatography (acetonitrile containing 0.05% aqueous ammonia/0.1% aqueous ammonia) to give the title compound (42 mg).

$^1$H NMR (400 MHz, CDCl$_3$) b 1.24-1.53 (2H, m), 2.05-2.29 (1H, m), 2.40 (3H, s), 3.47-3.73 (4H, m), 3.79-3.86 (1H, m), 3.91 (3H, s), 4.15-4.50 (2H, m), 6.72 (1H, s), 6.88-6.93 (1H, m), 8.45-8.54 (2H, m).

Example 323

5-(2-methoxyphenyl)-1-methyl-4-oxo-N-[6-(2,2,2-trifluoroethoxy)pyridin-3-yl]-4,5-dihydro-1H-pyrrolo[3,2-c]pyridine-3-carboxamide A) 1-methyl-4-oxo-N-[6-(2,2,2-trifluoroethoxy)pyridin-3-yl]-4,5-dihydro-1H-pyrrolo[3,2-c]pyridine-3-carboxamide To a suspension of 1-methyl-4-oxo-4,5-dihydro-1H-pyrrolo[3,2-c]pyridine-3-carboxylic acid (77.8 mg) in DMF (1.5 mL) was added CDI (92.1 mg), and the mixture was stirred at 100° C. for 4 hr. 6-(2,2,2-Trifluoroethoxy)pyridin-3-amine (85.8 mg) was added thereto, and the mixture was stirred at 80° C. for 2 hr. 6-(2,2,2-Trifluoroethoxy)pyridin-3-amine (40 mg) was added thereto, and the mixture was stirred overnight at 80° C. To the reaction mixture was added water, and the mixture was stirred at room temperature for 30 min. The precipitate was collected by filtration to give the title compound (97 mg).

MS: [M+H]$^+$ 367.0.

B) 5-(2-methoxyphenyl)-1-methyl-4-oxo-N-[6-(2,2,2-trifluoroethoxy)pyridin-3-yl]-4,5-dihydro-1H-pyrrolo[3,2-c]pyridine-3-carboxamide To a mixture of 1-methyl-4-oxo-N-[6-(2,2,2-trifluoroethoxy)pyridin-3-yl]-4,5-dihydro-1H-pyrrolo[3,2-c]pyridine-3-carboxamide (97.6 mg), (2-methoxyphenyl)boronic acid (46 mg), pyridine (0.065 mL), TEA (0.105 mL), molecular sieve 3A (148.9 mg), acetonitrile (1 mL) and DMF (0.5 mL) was added copper(II) acetate (58.3 mg), and the mixture was stirred at 50° C. for 40 min. (2-Methoxyphenyl)boronic acid (42.3 mg) was added thereto, and the mixture was stirred at 50° C. for 3.5 hr. (2-Methoxyphenyl)boronic acid (40.3 mg) was added thereto, and the mixture was stirred at 50° C. for 3 hr. (2-Methoxyphenyl)boronic acid (42.9 mg) was added thereto, and the mixture was stirred overnight at 50° C. The reaction mixture was purified by silica gel column chromatography (NH, hexane/ethyl acetate) to give the title compound (5.7 mg).

$^1$H NMR (300 MHz, DMSO-d$_6$) δ 3.76 (3H, s), 3.86 (3H, s), 4.93 (2H, q, J=9.1 Hz), 6.89 (1H, d, J=7.4 Hz), 6.95 (1H, d, J=9.3 Hz), 7.11 (1H, td, J=7.6, 1.2 Hz), 7.26 (1H, dd, J=8.5, 1.1 Hz), 7.39 (1H, dd, J=7.8, 1.7 Hz), 7.42 (1H, d, J=7.4 Hz), 7.50 (1H, ddd, J=8.3, 7.5, 1.7 Hz), 7.91 (1H, dd, J=8.9, 2.7 Hz), 8.00 (1H, s), 8.52 (1H, d, J=2.1 Hz), 13.26 (1H, s).

Example 324

5-[(4-methoxyphenyl)methyl]-7-methyl-N-[4-(morpholin-4-yl)phenyl]-4-oxo-4,5-dihydropyrazolo[1,5-a]pyrazine-3-carboxamide A) N-[(4-methoxyphenyl)methyl]prop-2-yn-1-amine To a solution of 4-methoxybenzaldehyde (4 mL) in MeOH (16 mL) was added prop-2-yn-1-amine (2.55 mL), and the mixture was stirred at room temperature for 1.5 hr. The mixture was cooled to 0° C., sodium borohydride (2.20 g) was added thereto, and the mixture was stirred overnight at room temperature. To the reaction mixture was added 1M aqueous sodium hydroxide solution, and the mixture was extracted with a mixed solvent of hexane/ethyl acetate=1/3. The organic layers were combined, washed with saturated aqueous sodium hydrogencarbonate solution and saturated brine, dried over anhydrous magnesium sulfate, and concentrated under reduced pressure. The residue was purified by silica gel column chromatography (hexane/ethyl acetate) to give the title compound (2.94 g).

$^1$H NMR (300 MHz, CDCl$_3$) δ 1.26 (1H, s), 2.25 (1H, t, J=2.4 Hz), 3.41 (2H, d, J=2.3 Hz), 3.80 (3H, s), 3.82 (2H, s), 6.84-6.90 (2H, m), 7.24-7.30 (2H, m).

B) 4-bromo-N-[(4-methoxyphenyl)methyl]-N-(prop-2-yn-1-yl)-1H-pyrazole-3-carboxamide To a mixture of 4-bromo-1H-pyrazole-3-carboxylic acid (225.2 mg), DMAP (14.3 mg), THF (2 mL) and DMF (0.60 mL) was added N,N'-dicyclohexylcarbodiimide (263.8 mg) at 0° C., and the mixture was stirred at 0° C. for 20 min. A solution of N-[(4-methoxyphenyl)methyl]prop-2-yn-1-amine (220.1 mg) in THF (1 mL) was added thereto, and the mixture was stirred overnight at room temperature. The reaction mixture was diluted with a mixed solvent of hexane/ethyl acetate=1/1, and the insoluble substance was removed by filtration. The filtrate was concentrated under reduced pressure, and the residue was purified by silica gel column chromatography (hexane/ethyl acetate) to give the title compound (308.3 mg).

MS: [M+H]$^+$ 347.9.

C) 3-bromo-5-[(4-methoxyphenyl)methyl]-7-methylpyrazolo[1,5-a]pyrazin-4(5H)-one

A mixture of 4-bromo-N-[(4-methoxyphenyl)methyl]-N-(prop-2-yn-1-yl)-1H-pyrazole-3-carboxamide (307 mg), DBU (38.3 mg) and DMF (1.0 mL) was stirred under nitrogen atmosphere at 120° C. for 1.5 hr. The mixture was concentrated under reduced pressure, and the residue was purified by silica gel column chromatography (hexane/ethyl acetate) to give the title compound (218 mg).

MS: [M+H]$^+$ 347.9.

D) 5-[(4-methoxyphenyl)methyl]-7-methyl-4-oxo-4,5-dihydropyrazolo[1,5-a]pyrazine-3-carboxylic Acid To a solution of 3-bromo-5-[(4-methoxyphenyl)methyl]-7-methylpyrazolo[1,5-a]pyrazin-4(5H)-one (359.2 mg) in THF (4 mL) was added 1M THF solution (2 mL) of isopropylmagnesium chloride-lithium chloride complex at −78° C., and the mixture was stirred at 0° C. for 1 hr. The mixture was cooled to −78° C., dry ice (1.5 g) was added thereto, and the mixture was stirred at room temperature for 2 hr. The reaction mixture was adjusted to pH=2 with 1M hydrochloric acid, and diluted with water. The precipitate was collected by filtration, and washed with a mixed solvent of water and hexane/ethyl acetate=1/1 to give the title compound (281 mg).

MS: [M+H]$^+$ 314.0.

E) 5-[(4-methoxyphenyl)methyl]-7-methyl-N-[4-(morpholin-4-yl)phenyl]-4-oxo-4,5-dihydropyrazolo[1,5-a]pyrazine-3-carboxamide To a mixture of 5-[(4-methoxyphenyl)methyl]-7-methyl-4-oxo-4,5-dihydropyrazolo[1,5-a]pyrazine-3-carboxylic acid (205.9 mg), THF (2 mL) and DMF (0.02 mL) was added oxalyl chloride (0.086 mL), and the mixture was stirred at room temperature for 1 hr. The reaction mixture was concentrated under reduced pressure. To a solution of the residue in THF (2 mL) were added TEA (0.275 mL) and 4-(morpholin-4-yl)aniline (129 mg), and the mixture was stirred at room temperature for 1 hr. To the reaction mixture was added saturated aqueous sodium hydrogencarbonate solution, and the precipitate was collected by filtration, and washed with a mixed solvent of water and hexane/ethyl acetate=1/1 to give the title compound (291 mg).

$^1$H NMR (300 MHz, DMSO-d$_6$) δ 2.43 (3H, s), 3.03-3.11 (4H, m), 3.71-3.77 (7H, m), 5.15 (2H, s), 6.95 (4H, dd, J=11.9, 8.9 Hz), 7.34-7.45 (3H, m), 7.58 (2H, d, J=9.0 Hz), 8.46 (1H, s), 12.47 (1H, s).

Example 325

3-[4-(4-chlorophenoxy)piperidine-1-carbonyl]-5-[(4-methoxyphenyl)methyl]-7-methylpyrazolo[1,5-a]pyrazin-4(5H)-one To a mixture of 5-[(4-methoxyphenyl)methyl]-7-methyl-4-oxo-4,5-dihydropyrazolo[1,5-a]pyrazine-3-carboxylic acid (279.5 mg), THF (3.0 mL) and DMF (0.02 mL) was added oxalyl chloride (0.117 mL), and the mixture was stirred at room temperature for 1 hr. The reaction mixture was concentrated under reduced pressure. To a solution of the residue in THF (3 mL) were added TEA (0.497 mL) and 4-(4-chlorophenoxy)piperidine hydrochloride (244 mg), and the mixture was stirred at room temperature for 1 hr. To the reaction mixture was added saturated aqueous sodium hydrogencarbonate solution, and the mixture was extracted with ethyl acetate. The organic layers were combined, washed with saturated brine, dried over anhydrous magnesium sulfate, and concentrated under reduced pressure. The residue was purified by silica gel column chromatography (ethyl acetate/methanol) to give the title compound (396 mg).

$^1$H NMR (300 MHz, DMSO-d$_6$) δ 1.49-1.73 (2H, m), 1.82 (1H, brs), 1.98 (1H, brs), 2.37 (3H, s), 3.18-3.29 (1H, m), 3.37-3.51 (2H, m), 3.68-3.73 (3H, m), 3.98-4.07 (1H, m), 4.58-4.71 (1H, m), 4.93-5.07 (2H, m), 6.84-6.92 (2H, m), 6.97-7.06 (2H, m), 7.15 (1H, d, J=1.1 Hz), 7.27-7.36 (4H, m), 8.02 (1H, s).

Example 326

5-[(4-methoxyphenyl)methyl]-7-methyl-3-(4-phenoxypiperidine-1-carbonyl)pyrazolo[1,5-a]pyrazin-4(5H)-one A mixture of 3-[4-(4-chlorophenoxy)piperidine-1-carbonyl]-5-[(4-methoxyphenyl)methyl]-7-methylpyrazolo[1,5-a]pyrazin-4(5H)-one (88.0 mg), 10% palladium-carbon (15 mg), methanol (2 mL), THF (1 mL) and ethyl acetate (1 mL) was stirred under normal pressure of hydrogen atmosphere at room temperature for 48 hr. The catalyst was removed by filtration, and the filtrate was concentrated under reduced pressure. The residue was purified by silica gel column chromatography (ethyl acetate/methanol) to give the title compound (5.1 mg).

$^1$H NMR (300 MHz, CDCl$_3$) δ 1.73-1.86 (1H, m), 1.89-2.16 (3H, m), 2.41 (3H, d, J=1.1 Hz), 3.32-3.45 (1H, m), 3.60-3.73 (1H, m), 3.79 (3H, s), 3.97 (2H, t, J=5.7 Hz), 4.60 (1H, tt, J=6.3, 3.3 Hz), 4.94-5.10 (2H, m), 6.39 (1H, d, J=1.1 Hz), 6.83-7.00 (5H, m), 7.22-7.34 (4H, m), 7.91 (1H, s).

Example 327

7-methyl-N-[4-(morpholin-4-yl)phenyl]-4-oxo-5-(2,2,2-trifluoroethyl)-4,5-dihydropyrazolo[1,5-a]pyrazine-3-carboxamide A) 7-methyl-N-[4-(morpholin-4-yl)phenyl]-4-oxo-4,5-dihydropyrazolo[1,5-a]pyrazine-3-carboxamide To a solution of 5-[(4-methoxyphenyl)methyl]-7-methyl-N-[4-(morpholin-4-yl)phenyl]-4-oxo-4,5-dihydropyrazolo[1,5-a]pyrazine-3-carboxamide (300.7 mg) in trifluoroacetic acid (3.5 mL) were added anisole (1.2 mL) and trifluoromethanesulfonic acid (0.674 mL) at 0° C., and the mixture was stirred overnight at 40° C. The mixture was concentrated under reduced pressure, and to the residue was added saturated aqueous sodium hydrogencarbonate solution at 0° C. The precipitate was collected by filtration, and washed successively with water and a mixed solvent of hexane/ethyl acetate=1/1. The obtained solid was suspended in a mixed solvent of ethyl acetate/methanol, and the precipitate was collected by filtration, and washed with hexane to give the title compound (171 mg).

MS: [M+H]$^+$ 354.1.

B) 7-methyl-N-[4-(morpholin-4-yl)phenyl]-4-oxo-5-(2,2,2-trifluoroethyl)-4,5-dihydropyrazolo[1,5-a]pyrazine-3-carboxamide To a solution of 7-methyl-N-[4-(morpholin-4-yl)phenyl]-4-oxo-4,5-dihydropyrazolo[1,5-a]pyrazine-3-carboxamide (24.2 mg) in DMF (0.7 mL) was added sodium hydride (60% in oil, 4.0 mg) at 0° C., and the mixture was stirred at 0° C. for 15 min. 2,2,2-Trifluoroethyl trifluoromethanesulfonate (0.015 mL) was added thereto, and the mixture was stirred at room temperature for 2.5 hr. To the reaction mixture was added MeOH, and the mixture was concentrated under reduced pressure. The residue was purified by silica gel column chromatography (hexane/ethyl acetate/methanol) to give the title compound (1.9 mg).

$^1$H NMR (300 MHz, DMSO-d$_6$) δ 2.46 (3H, d, J=0.8 Hz), 3.02-3.12 (4H, m), 3.68-3.81 (4H, m), 4.99 (2H, q, J=9.0 Hz), 6.98 (2H, d, J=9.0 Hz), 7.31 (1H, s), 7.57 (2H, d, J=9.0 Hz), 8.51 (1H, s), 12.09 (1H, s).

Example 337

7-methyl-4-oxo-5-[2-(2,2,2-trifluoroethoxy)phenyl]-N-[6-(2,2,2-trifluoroethoxy)pyridin-3-yl]-4,5-dihydropyrazolo[1,5-a]pyrazine-3-carboxamide A) N-(prop-2-yn-1-yl)-2-(2,2,2-trifluoroethoxy)aniline To a mixture of 3-bromoprop-1-yne (1 g), 2-(2,2,2-trifluoroethoxy)aniline (6.38 g) and acetonitrile (10 mL) was added potassium carbonate (2.26 g), and the mixture was stirred overnight at room temperature. The insoluble substance was removed by filtration, and the filtrate was concentrated under reduced pressure. The residue was purified by silica gel column chromatography (hexane/ethyl acetate) to give the title compound (1.31 g).

MS: [M+H]$^+$ 229.9.

B) 4-bromo-N-(prop-2-yn-1-yl)-N-[2-(2,2,2-trifluoroethoxy)phenyl]-1H-pyrazole-5-carboxamide To a suspension of 4-bromo-1H-pyrazole-3-carboxylic acid (558 mg) in THF (5 mL) were added oxalyl chloride (0.332 mL) and DMF (0.1 mL) at 0° C., and the mixture was stirred at 0° C. for 1 hr. Oxalyl chloride (0.415 mL) was added thereto, and the mixture was stirred at room temperature for 3 hr. The reaction mixture was concentrated under reduced pressure. To a suspension of the residue in THF (3 mL) was added a solution of TEA (1.6 mL) and N-(prop-2-yn-1-yl)-2-(2,2,2-trifluoroethoxy)aniline (760 mg) in THF (5 mL) at 0° C., and the mixture was stirred at room temperature for 3 hr. To the reaction mixture was added aqueous sodium hydrogencarbonate solution, and the mixture was extracted with ethyl acetate. The organic layer was separated, dried over anhydrous magnesium sulfate, and concentrated under reduced pressure. The residue was purified by silica gel column chromatography (hexane/ethyl acetate) to give the title compound (584 mg).

$^1$H NMR (300 MHz, DMSO-d$_6$) δ 3.14 (1H, t, J=2.5 Hz), 4.11 (1H, d, J=18.7 Hz), 4.63-4.84 (2H, m), 4.92 (1H, d, J=16.4 Hz), 6.86-7.33 (4H, m), 7.78 (1H, brs), 13.26 (1H, brs).

C) 3-bromo-7-methyl-5-[2-(2,2,2-trifluoroethoxy)phenyl]pyrazolo[1,5-a]pyrazin-4(5H)-one A mixture of 4-bromo-N-(prop-2-yn-1-yl)-N-[2-(2,2,2-trifluoroethoxy)phenyl]-1H-pyrazole-5-carboxamide (820 mg), DBU (0.1 mL) and DMF (3 mL) was stirred at 110° C. for 1.5 hr. The reaction mixture was concentrated under reduced pressure, and the residue was purified by silica gel column chromatography (hexane/ethyl acetate) to give the title compound (578 mg).

$^1$H NMR (300 MHz, DMSO-d$_6$) δ 2.36 (3H, d, J=0.8 Hz), 4.81 (2H, d, J=9.0 Hz), 6.98 (1H, s), 7.17-7.26 (1H, m), 7.34-7.42 (1H, m), 7.43-7.57 (2H, m), 8.15 (1H, s).

D) Ethyl 7-methyl-4-oxo-5-[2-(2,2,2-trifluoroethoxy)phenyl]-4,5-dihydropyrazolo[1,5-a]pyrazine-3-carboxylate A mixture of 3-bromo-7-methyl-5-[2-(2,2,2-trifluoroethoxy)phenyl]pyrazolo[1,5-a]pyrazin-4(5H)-one (520 mg), dichloro[1,1'-bis(diphenylphosphino)ferrocene]palladium (II) dichloromethane complex (106.6 mg), DMF (6 mL) and EtOH (6 mL) was stirred under carbon monoxide atmosphere of 0.5 MPa, at 100° C. for 5 hr. The catalyst was removed by filtration, and the filtrate was concentrated under reduced pressure. The residue was purified by silica gel column chromatography (hexane/ethyl acetate) to give the title compound (257 mg).

MS: [M+H]$^+$ 396.0.

E) 7-methyl-4-oxo-5-[2-(2,2,2-trifluoroethoxy)phenyl]-4,5-dihydropyrazolo[1,5-a]pyrazine-3-carboxylic Acid To a mixture of ethyl 7-methyl-4-oxo-5-[2-(2,2,2-trifluoroethoxy)phenyl]-4,5-dihydropyrazolo[1,5-a]pyrazine-3-carboxylate (257.2 mg), THF (1 mL) and MeOH (2 mL) was added 8M aqueous sodium hydroxide solution (0.244 mL), and the mixture was stirred at 60° C. for 1 hr. To the reaction mixture were added 6M hydrochloric acid and water, and the mixture was stirred at 0° C. for 10 min. The precipitate was collected by filtration, and washed with water to give the title compound (233 mg).

MS: [M+H]$^+$ 368.0.

F) 7-methyl-4-oxo-5-[2-(2,2,2-trifluoroethoxy)phenyl]-N-[6-(2,2,2-trifluoroethoxy)pyridin-3-yl]-4,5-dihydropyrazolo[1,5-a]pyrazine-3-carboxamide To a mixture of 7-methyl-4-oxo-5-[2-(2,2,2-trifluoroethoxy)phenyl]-4,5-dihydropyrazolo[1,5-a]pyrazine-3-carboxylic acid (30.0 mg), oxalyl chloride (0.011 mL) and THF (1 mL) was added DMF (one drop), and the mixture was stirred at room temperature for 2 hr. Oxalyl chloride (0.011 mL) and DMF (one drop) were added thereto, and the mixture was stirred at room temperature for 30 min. The mixture was cooled to 0° C., 6-(2,2,2-trifluoroethoxy)pyridin-3-amine (18.83 mg) and TEA (0.057 mL) were added thereto, and the mixture was stirred at room temperature for 1 hr. To the reaction mixture was added water, and the precipitate was collected by filtration, and washed with water and diisopropyl ether. The solid was suspended in DMSO (2 mL), and washed with ethyl acetate to give the title compound (18.3 mg).

$^1$H NMR (300 MHz, DMSO-d$_6$) δ 2.47-2.49 (3H, m), 4.81-5.02 (4H, m), 6.99 (1H, d, J=8.9 Hz), 7.28 (1H, td, J=7.6, 1.1 Hz), 7.33 (1H, d, J=1.3 Hz), 7.41-7.50 (1H, m), 7.54-7.63 (2H, m), 7.97 (1H, dd, J=9.0, 2.7 Hz), 8.50 (1H, d, J=2.3 Hz), 8.59 (1H, s), 12.45 (1H, s).

Example 340

N-[4-(2-hydroxypropan-2-yl)phenyl]-7-methyl-4-oxo-5-[2-(2,2,2-trifluoroethoxy)phenyl]-4,5-dihydropyrazolo[1,5-a]pyrazine-3-carboxamide To a mixture of 7-methyl-4-oxo-5-[2-(2,2,2-trifluoroethoxy)phenyl]-4,5-dihydropyrazolo[1,5-a]pyrazine-3-carboxylic acid (32.0 mg), THF (1 mL) and DMF (0.01 mL) was added oxalyl chloride (0.011 mL), and the mixture was stirred at room temperature for 1 hr. The reaction mixture was concentrated under reduced pressure. To a solution of the residue in THF (0.5 mL) were added TEA (0.03 mL) and 2-(4-aminophenyl)propan-2-ol (15.81 mg) at 0° C., and the mixture was stirred at room temperature for 1 hr. To the reaction mixture was added saturated aqueous sodium hydrogencarbonate solution, and the precipitate was collected by filtration, and washed with water and hexane/ethyl acetate to give the title compound (23.1 mg).

$^1$H NMR (300 MHz, DMSO-d$_6$) δ 1.39 (6H, s), 2.48 (3H, brs), 4.88 (2H, q, J=8.8 Hz), 4.95 (1H, s), 7.24-7.34 (2H, m), 7.37-7.50 (3H, m), 7.51-7.63 (4H, m), 8.57 (1H, s), 12.35 (1H, s).

Example 344

N-[2-(benzyloxy)phenyl]-6,8-dimethyl-5-oxo-5,6-dihydroimidazo[1,2-c]pyrimidine-3-carboxamide

A) 8-methylimidazo[1,2-c]pyrimidin-5(6H)-one

To a mixture of 4-amino-5-methylpyrimidin-2(1H)-one (10 g), sodium acetate (16.4 g) and water (100 mL) was added 40% chloroacetaldehyde aqueous solution (31.4 g), and the mixture was stirred at 80° C. for 16 hr. The reaction mixture was extracted with ethyl acetate. The organic layers were combined, dried over anhydrous sodium sulfate, and concentrated under reduced pressure to give the title compound (10.5 g).

MS: [M+H]$^+$ 149.8.

B) 3-iodo-8-methylimidazo[1,2-c]pyrimidin-5(6H)-one

To a solution of 8-methylimidazo[1,2-c]pyrimidin-5(6H)-one (3.00 g) in DMF (40 mL) was added N-iodosuccinimide (4.53 g) at 0° C. over 30 min or longer, and the mixture was stirred at room temperature for 15.5 hr. The mixture was concentrated under reduced pressure, 0.1M aqueous sodium thiosulfate solution was added thereto, and the mixture was extracted with ethyl acetate. The organic layers were combined, dried over anhydrous sodium sulfate, and concentrated under reduced pressure. The residue was purified by silica gel column chromatography (petroleum ether/ethyl acetate) to give the title compound (2.10 g).

MS: [M+H]$^+$ 275.7.

C) 3-iodo-6,8-dimethylimidazo[1,2-c]pyrimidin-5(6H)-one

To a solution of 3-iodo-8-methylimidazo[1,2-c]pyrimidin-5(6H)-one (2.70 g) in DMF (30 mL) were added potassium carbonate (1.76 g) and iodomethane (1.67 g), and the mixture was stirred at room temperature for 2 hr. To the reaction mixture was added water, and the precipitate was collected by filtration, and washed with water. The obtained solid was suspended in toluene, and the suspension was concentrated under reduced pressure to give the title compound (1.90 g).

MS: [M+H]$^+$ 289.6.

D) Methyl 6,8-dimethyl-5-oxo-5,6-dihydroimidazo[1,2-c]pyrimidine-3-carboxylate A mixture of 3-iodo-6,8-dimethylimidazo[1,2-c]pyrimidin-5(6H)-one (1.90 g), TEA (1.33 g), dichloro[1,1'-bis(diphenylphosphino)ferrocene]palladium(II) (481 mg), MeOH (100 mL) and DMSO (20 mL) was stirred under carbon monoxide atmosphere of 50 psi, at 30° C. for 16 hr. The MeOH was evaporated under reduced pressure, and water was added thereto, and the mixture was extracted with dichloromethane. The organic layers were combined, and concentrated under reduced pressure. The residue was purified by silica gel column chromatography (petroleum ether/ethyl acetate) to give the title compound (1.25 g).

MS: [M+H]$^+$ 221.8.

E) N-[2-(benzyloxy)phenyl]-6,8-dimethyl-5-oxo-5,6-dihydroimidazo[1,2-c]pyrimidine-3-carboxamide A mixture of methyl 6,8-dimethyl-5-oxo-5,6-dihydroimidazo[1,2-c]pyrimidine-3-carboxylate (150 mg), 2-(benzyloxy)aniline (135 mg), 2M toluene solution (0.34 mL) of trimethylaluminium and toluene (5 mL) was stirred at 15° C. for 16 hr. The reaction mixture was diluted with ethyl acetate, washed successively with water and saturated brine, dried over so anhydrous sodium sulfate, and concentrated under reduced pressure. The residue was purified by preparative high-performance liquid chromatography (acetonitrile containing 0.225% formic acid/water containing 0.225% formic acid) to give the title compound (112 mg).

$^1$H NMR (400 MHz, CDCl$_3$) δ 2.30 (3H, s), 3.32 (3H, s), 5.15 (2H, s), 6.82 (1H, d, J=0.8 Hz), 6.96-7.07 (3H, m), 7.27-7.39 (3H, m), 7.53 (2H, d, J=6.8 Hz), 8.35 (1H, s), 8.56 (1H, d, J=8.0 Hz), 12.04 (1H, brs).

Example 346

N-(trans-4-butoxycyclohexyl)-6,8-dimethyl-5-oxo-5,6-dihydroimidazo[1,2-c]pyrimidine-3-carboxamide

A) 6,8-dimethyl-5-oxo-5,6-dihydroimidazo[1,2-c]pyrimidine-3-carboxylic Acid

A mixture of methyl 6,8-dimethyl-5-oxo-5,6-dihydroimidazo[1,2-c]pyrimidine-3-carboxylate (300 mg), lithium iodide (908 mg) and pyridine (8 mL) was stirred under nitrogen atmosphere at 100° C. for 16 hr. The reaction mixture was concentrated under reduced pressure, and water and ethyl acetate were added thereto. The aqueous layer was separated, adjusted to pH=4 with 1M hydrochloric acid, and extracted with dichloromethane. The organic layers were combined, and concentrated under reduced pressure to give the title compound (200 mg).

MS: [M+H]$^+$ 207.8.

B) N-(trans-4-butoxycyclohexyl)-6,8-dimethyl-5-oxo-5,6-dihydroimidazo[1,2-c]pyrimidine-3-carboxamide A mixture of 6,8-dimethyl-5-oxo-5,6-dihydroimidazo[1,2-c]pyrimidine-3-carboxylic acid (70 mg), trans-4-butoxycyclohexan-1-amine (65 mg), DIPEA (87 mg), HATU (193 mg) and DMF (3 mL) was stirred at 15° C. for 16 hr. The reaction mixture was diluted with ethyl acetate, washed successively with water and saturated brine, dried over anhydrous sodium sulfate, and concentrated under reduced pressure. The residue was purified by preparative high-performance liquid chromatography (acetonitrile containing 0.05% aqueous ammonia/0.1% aqueous ammonia) to give the title compound (40 mg).

$^1$H NMR (400 MHz, CDCl$_3$) δ 0.91 (3H, t, J=7.2 Hz), 1.31-1.58 (8H, m), 2.01-2.13 (4H, m), 2.30 (3H, d, J=0.8 Hz), 3.21-3.30 (1H, m), 3.44 (2H, t, J=6.8 Hz), 3.58 (3H, s), 3.90-3.96 (1H, m), 6.86 (1H, d, J=1.2 Hz), 8.24 (1H, s), 9.95 (1H, d, J=7.2 Hz).

Example 349

N-[2-(benzyloxy)phenyl]-6-(2-methoxyphenyl)-8-methyl-5-oxo-5,6-dihydroimidazo[1,2-c]pyrimidine-3-carboxamide

A) 6-(2-methoxyphenyl)-8-methylimidazo[1,2-c]pyrimidin-5(6H)-one

A mixture of 8-methylimidazo[1,2-c]pyrimidin-5(6H)-one (2.00 g), (2-methoxyphenyl)boronic acid (4.08 g), copper(II) acetate (4.87 g), molecular sieve 4A (8.00 g), pyridine (2.12 g), TEA (2.71 g) and dichloromethane (60 mL) was stirred at 15° C. for 16 hr. To the reaction mixture were added dichloromethane and water, and the insoluble substance was filtered off. The organic layer of the filtrate was separated, washed with saturated brine, dried over anhydrous sodium sulfate, and concentrated under reduced pressure. The residue was purified by silica gel column chromatography (petroleum ether/ethyl acetate) to give the title compound (800 mg).

MS: [M+H]$^+$ 255.9.

B) 3-iodo-6-(2-methoxyphenyl)-8-methylimidazo[1,2-c]pyrimidin-5(6H)-one

To a solution of 6-(2-methoxyphenyl)-8-methylimidazo[1,2-c]pyrimidin-5(6H)-one (800 mg) in DMF (15 mL) was added N-iodosuccinimide (846 mg), and the mixture was stirred at 15° C. for 15 hr. To the reaction mixture was added 0.1M aqueous sodium thiosulfate solution, and the precipitate was collected by filtration, and washed with a mixed solvent of water and petroleum ether/ethyl acetate=5/1 to give the title compound (1.07 g).

MS: [M+H]$^+$ 382.

C) Methyl 6-(2-methoxyphenyl)-8-methyl-5-oxo-5,6-dihydroimidazo[1,2-c]pyrimidine-3-carboxylate A mixture of 3-iodo-6-(2-methoxyphenyl)-8-methylimidazo[1,2-c]pyrimidin-5(6H)-one (1.07 g), TEA (568 mg), dichloro[1,1'-bis(diphenylphosphino)ferrocene]palladium (II) (205 mg), DMSO (10 mL) and MeCOH (50 mL) was stirred under carbon monoxide atmosphere of 50 psi, at 30° C. for 16 hr. The 1a MeOH was evaporated under reduced pressure, water was added thereto, and the mixture was extracted with ethyl acetate. The organic layers were combined, and concentrated under reduced pressure. The residue was purified by silica gel column chromatography (petroleum ether/ethyl acetate) to give the title compound (750 mg).

MS: [M+H]$^+$ 313.8.

D) N-[2-(benzyloxy)phenyl]-6-(2-methoxyphenyl)-8-methyl-5-oxo-5,6-dihydroimidazo[1,2-c]pyrimidine-3-carboxamide A mixture of methyl 6-(2-methoxyphenyl)-8-methyl-5-oxo-5,6-dihydroimidazo[1,2-c]pyrimidine-3-carboxylate (70 mg), 2-(benzyloxy)aniline (50 mg), 2M toluene solution (0.13 mL) of trimethylaluminium and toluene (3 mL) was stirred under nitrogen atmosphere at 15° C. for 16 hr. To the reaction mixture was added ethyl acetate, and the mixture was washed with water and saturated brine, dried over anhydrous sodium sulfate, and concentrated under reduced pressure. The residue was purified by preparative high-performance liquid chromatography (acetonitrile containing 0.05% aqueous ammonia/0.1% aqueous ammonia) to give the title compound (48 mg).

$^1$H NMR (400 MHz, CDCl$_3$) δ 2.36 (3H, d, J=0.8 Hz), 3.79 (3H, s), 5.04 (2H, s), 6.87-6.92 (2H, m), 6.95-7.02 (2H, m), 7.07 (2H, t, J=8.0 Hz), 7.13-7.24 (3H, m), 7.25-7.33 (3H, m), 7.47 (1H, td, J=8.0, 1.2 Hz), 8.35-8.41 (2H, m), 11.75 (1H, brs).

Example 351

N-(trans-4-butoxycyclohexyl)-6-(2-methoxyphenyl)-8-methyl-5-oxo-5,6-dihydroimidazo[1,2-c]pyrimidine-3-carboxamide

A) 6-(2-methoxyphenyl)-8-methyl-5-oxo-5,6-dihydroimidazo[1,2-c]pyrimidine-3-carboxylic Acid A mixture of methyl 6-(2-methoxyphenyl)-8-methyl-5-oxo-5,6-dihydroimidazo[1,2-c]pyrimidine-3-carboxylate (200 mg), lithium iodide (427 mg) and pyridine (5 mL) was stirred under nitrogen atmosphere at 100° C. for 16 hr. The reaction mixture was concentrated under reduced pressure, water and ethyl acetate were added thereto, and the aqueous layer was separated. The aqueous layer was adjusted to pH=4 with 1M hydrochloric acid, and extracted with dichloromethane. The organic layers were combined, washed with saturated brine, dried over anhydrous sodium sulfate, and concentrated under reduced pressure to give the title compound (160 mg).

MS: [M+H]$^+$299.8.

B) N-(trans-4-butoxycyclohexyl)-6-(2-methoxyphenyl)-8-methyl-5-oxo-5,6-dihydroimidazo[1,2-c]pyrimidine-3-carboxamide A mixture of 6-(2-methoxyphenyl)-8-methyl-5-oxo-5,6-dihydroimidazo[1,2-c]pyrimidine-3-carboxylic acid (80 mg), trans-4-butoxycyclohexan-1-amine (50 mg), DIPEA (70 mg), HATU (150 mg) and DMF (3 mL) was stirred at 15° C. for 16 hr. The reaction mixture was diluted with ethyl acetate, washed with water and saturated brine, dried over anhydrous sodium sulfate, and concentrated under reduced pressure. The residue was purified by preparative high-performance liquid chromatography (acetonitrile containing 0.05% aqueous ammonia/0.1% aqueous ammonia) to give the title compound (61 mg).

$^1$H NMR (400 MHz, CDCl$_3$) δ 0.89 (3H, t, J=7.2 Hz), 1.24-1.41 (6H, m), 1.45-1.55 (2H, m), 1.96-2.36 (4H, m), 2.33 (3H, d, J=1.2 Hz), 3.13-3.20 (1H, m), 3.40 (2H, t, J=6.8 Hz), 3.83-3.94 (4H, m), 6.84 (1H, d, J=1.2 Hz), 7.07-7.14 (2H, m), 7.32 (1H, dd, J=7.6, 1.2 Hz), 7.49 (1H, td, J=8.0, 1.6 Hz), 8.30 (1H, s), 9.77 (1H, d, J=7.2 Hz).

The compounds of Examples are shown in the following Table 1-1 to Table 1-45. MS in the tables means actual measured value. The compounds of Examples 6 to 92, 94 to 97, 99, 100, 102, 104 to 106, 108 to 116, 118 to 207, 209 to 270, 273 to 276, 278 to 280, 282, 285, 286, 288 to 290, 295 to 297, 299 to 310, 312, 313, 328 to 336, 338, 339, 341 to 343, 345, 347, 348, 350, 352 and 353 in the following tables were produced according to the methods described in the above-mentioned Examples, or methods analogous thereto.

TABLE 1-1

| Ex. No. | IUPAC Name | Structure | Additive | MS |
| --- | --- | --- | --- | --- |
| 1 | N-benzyl-1,5,7-trimethyl-4-oxo-4,5-dihydro-1H-pyrrolo[3,2-c]pyridine-3-carboxamide | 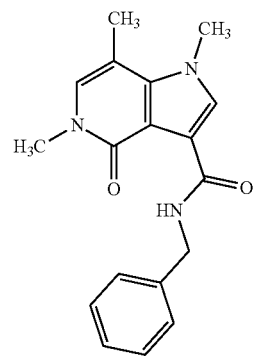 [SMILES: Cc1cn(C)c(=O)c2c(C(=O)NCc3ccccc3)cn(C)c12] | | 310.2 |

TABLE 1-1-continued

| Ex. No. | IUPAC Name | Structure | Additive | MS |
|---|---|---|---|---|
| 2 | N-(trans-4-butoxycyclohexyl)-1,5,7-trimethyl-4-oxo-4,5-dihydro-1H-pyrrolo[3,2-c]pyridine-3-carboxamide | 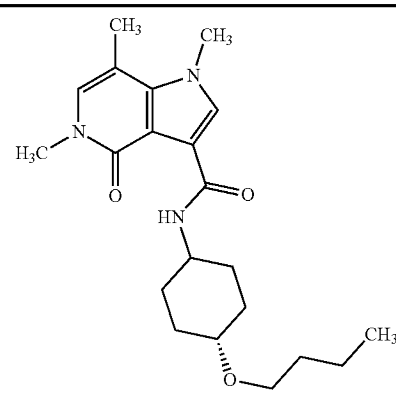 | | 374.14 |
| 3 | N-(trans-4-butoxycyclohexyl)-1-ethyl-5,7-dimethyl-4-oxo-4,5-dihydro-1H-pyrrolo[3,2-c]pyridine-3-carboxamide | 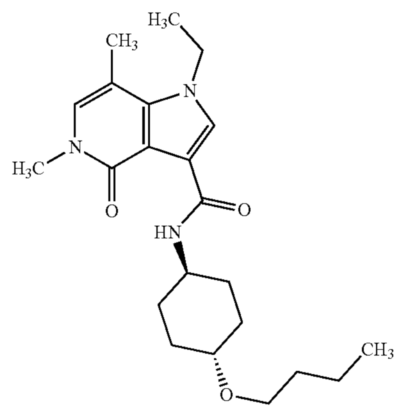 [SMILES: CCCCO[C@H]1CC[C@H](NC(=O)c2cn(CC)c3c(C)cn(C)c(=O)c23)CC1] | | 388.13 |
| 4 | 1-benzyl-N-(trans-4-butoxycyclohexyl)-5,7-dimethyl-4-oxo-4,5-dihydro-1H-pyrrolo[3,2-c]pyridine-3-carboxamide | 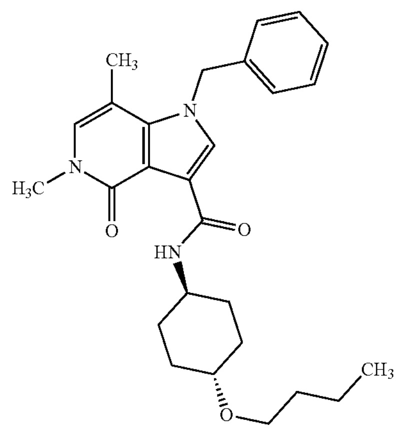 [SMILES: CCCCO[C@H]1CC[C@H](NC(=O)c2cn(Cc3ccccc3)c3c(C)cn(C)c(=O)c23)CC1] | | 450.12 |
| 5 | N-(trans-4-butoxycyclohexyl)-1,2,5,7-tetramethyl-4-oxo-4,5-dihydro-1H-pyrrolo[3,2-c]pyridine-3-carboxamide | 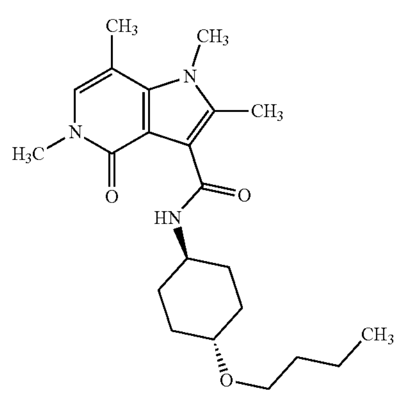 [SMILES: CCCCO[C@H]1CC[C@H](NC(=O)c2c(C)n(C)c3c(C)cn(C)c(=O)c23)CC1] | | 388.31 |

TABLE 1-1-continued

| Ex. No. | IUPAC Name | Structure | Additive | MS |
|---|---|---|---|---|
| 6 | N-((6-methoxypyridin-2-yl)methyl)-1,5,7-trimethyl-4-oxo-4,5-dihydro-1H-pyrrolo[3,2-c]pyridine-3-carboxamide | 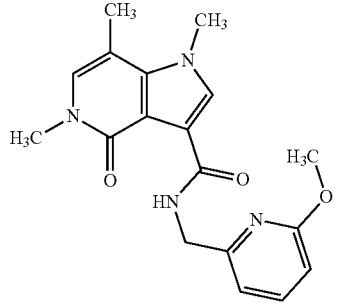 [SMILES: COc1cccc(CNC(=O)c2cn(C)c3c(C)cn(C)c(=O)c23)n1] | | 340.91 |
| 7 | 1,5,7-trimethyl-4-oxo-N-(1-(2,2,2-trifluoroethyl)-1H-pyrazol-5-yl)-4,5-dihydro-1H-pyrrolo[3,2-c]pyridine-3-carboxamide | 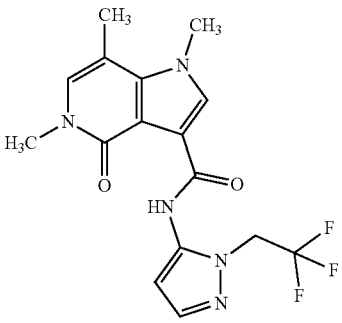 [SMILES: Cc1cn(C)c(=O)c2c(C(=O)Nc3ccnn3CC(F)(F)F)cn(C)c12] | | 367.94 |
| 8 | N-(2-(benzyloxy)phenyl)-1,5,7-trimethyl-4-oxo-4,5-dihydro-1H-pyrrolo[3,2-c]pyridine-3-carboxamide | 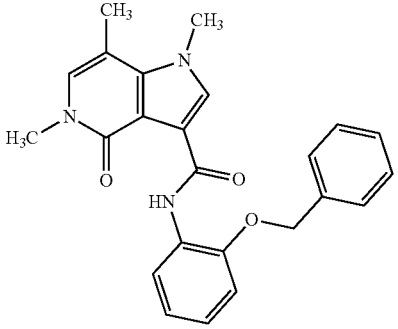 [SMILES: Cc1cn(C)c(=O)c2c(C(=O)Nc3ccccc3OCc3ccccc3)cn(C)c12] | | 402.02 |

TABLE 1-2

| Ex. No. | IUPAC Name | Structure | Additive | MS |
|---|---|---|---|---|
| 9 | tert-butyl ((1R,2R)-2-(((1,5,7-trimethyl-4-oxo-4,5-dihydro-1H-pyrrolo[3,2-c]pyridin-3-yl)carbonyl)amino)cyclohexyl)carbamate | 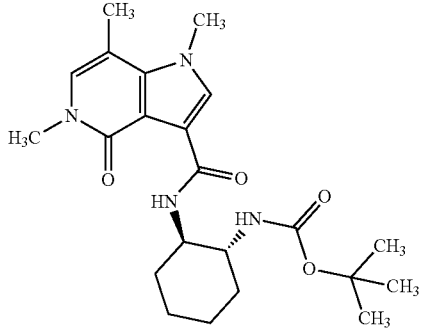 [SMILES: Cc1cn(C)c(=O)c2c(C(=O)N[C@@H]3CCCC[C@H]3NC(=O)OC(C)(C)C)cn(C)c12] | | 417.09 |

TABLE 1-2-continued

| Ex. No. | IUPAC Name | Structure | Additive | MS |
|---|---|---|---|---|
| 10 | tert-butyl (rac-(1S,2S)-2-(((1,5,7-trimethyl-4-oxo-4,5-dihydro-1H-pyrrolo[3,2-c]pyridin-3-yl)carbonyl)amino)cyclohexyl)carbamate | 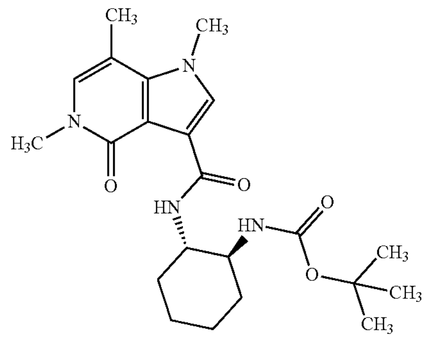 [SMILES: Cc1cn(C)c(=O)c2c(C(=O)N[C@H]3CCCC[C@@H]3NC(=O)OC(C)(C)C)cn(C)c12] | | 417.13 |
| 11 | tert-butyl ((1R,2S)-2-(((1,5,7-trimethyl-4-oxo-4,5-dihydro-1H-pyrrolo[3,2-c]pyridin-3-yl)carbonyl)amino)cyclohexyl)carbamate | 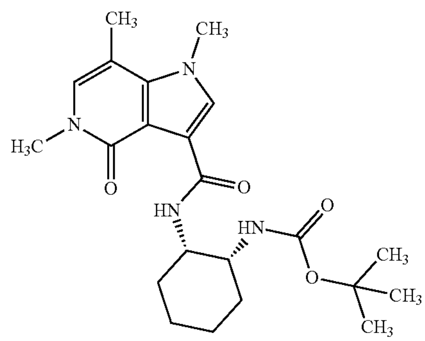 [SMILES: Cc1cn(C)c(=O)c2c(C(=O)N[C@H]3CCCC[C@H]3NC(=O)OC(C)(C)C)cn(C)c12] | | 417.09 |
| 12 | tert-butyl ((1S,2R)-2-(((1,5,7-trimethyl-4-oxo-4,5-dihydro-1H-pyrrolo[3,2-c]pyridin-3-yl)carbonyl)amino)cyclohexyl)carbamate | 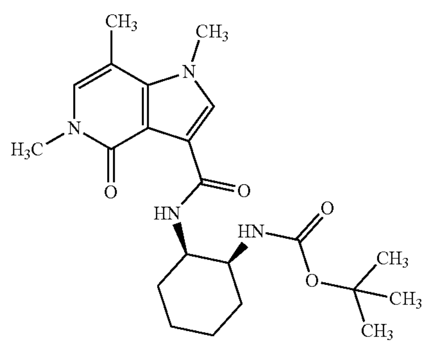 [SMILES: Cc1cn(C)c(=O)c2c(C(=O)N[C@@H]3CCCC[C@@H]3NC(=O)OC(C)(C)C)cn(C)c12] | | 417.06 |
| 13 | 1,5,7-trimethyl-3-((2-phenylpyrrolidin-1-yl)carbonyl)-1,5-dihydro-4H-pyrrolo[3,2-c]pyridin-4-one | 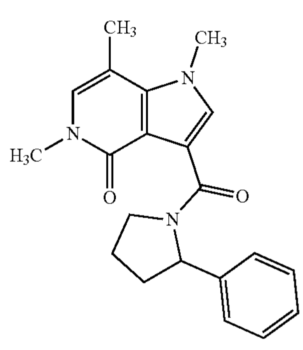 [SMILES: Cc1cn(C)c(=O)c2c(C(=O)N3CCCC3c3ccccc3)cn(C)c12] | | 349.95 |

TABLE 1-2-continued

| Ex. No. | IUPAC Name | Structure | Additive | MS |
|---|---|---|---|---|
| 14 | 1,5,7-trimethyl-3-((3-phenylpyrrolidin-1-yl)carbonyl)-1,5-dihydro-4H-pyrrolo[3,2-c]pyridin-4-one | 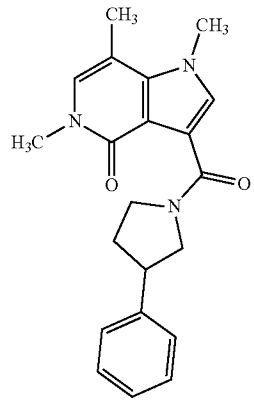 [SMILES: Cc1cn(C)c(=O)c2c(C(=O)N3CCC(c4ccccc4)C3)cn(C)c12] | | 350.02 |
| 15 | 3-(2,3-dihydro-1H-indol-1-ylcarbonyl)-1,5,7-trimethyl-1,5-dihydro-4H-pyrrolo[3,2-c]pyridin-4-one | 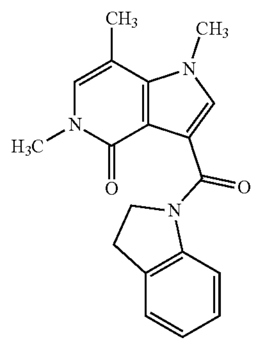 [SMILES: Cc1cn(C)c(=O)c2c(C(=O)N3CCc4ccccc43)cn(C)c12] | | 321.94 |
| 16 | 3-(1,3-dihydro-2H-isoindol-2-ylcarbonyl)-1,5,7-trimethyl-1,5-dihydro-4H-pyrrolo[3,2-c]pyridin-4-one | 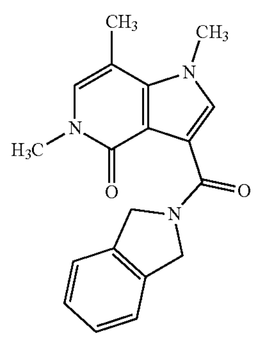 [SMILES: Cc1cn(C)c(=O)c2c(C(=O)N3Cc4ccccc4C3)cn(C)c12] | | 321.97 |

TABLE 1-3

| Ex. No. | IUPAC Name | Structure | Additive | MS |
|---|---|---|---|---|
| 17 | 1,5,7-trimethyl-N-(4-methyl-3,4-dihydro-2H-chromen-4-yl)-4-oxo-4,5-dihydro-1H-pyrrolo[3,2-c]pyridine-3-carboxamide | 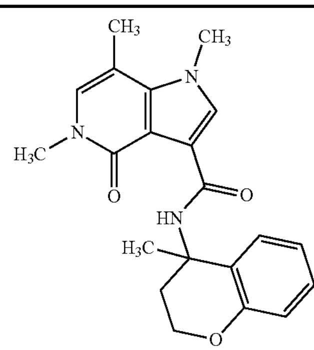 | | 366.01 |

TABLE 1-3-continued

| Ex. No. | IUPAC Name | Structure | Additive | MS |
|---|---|---|---|---|
| 18 | N-(cyclopropylmethyl)-1,5,7-trimethyl-4-oxo-4,5-dihydro-1H-pyrrolo[3,2-c]pyridine-3-carboxamide | 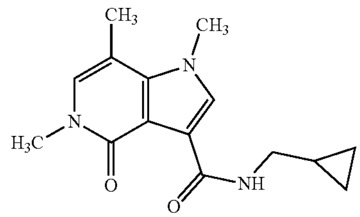 [SMILES: Cc1cn(C)c(=O)c2c(C(=O)NCC3CC3)cn(C)c12] | | 273.98 |
| 19 | 1,5,7-trimethyl-4-oxo-N-(3-(trifluoromethyl)bicyclo[1.1.1]pent-1-yl)-4,5-dihydro-1H-pyrrolo[3,2-c]pyridine-3-carboxamide | 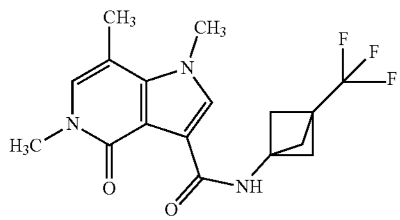 | | 353.92 |
| 20 | N-cyclohexyl-1,5,7-trimethyl-4-oxo-4,5-dihydro-1H-pyrrolo[3,2-c]pyridine-3-carboxamide | 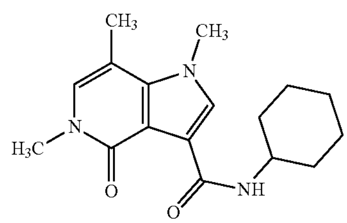 [SMILES: Cc1cn(C)c(=O)c2c(C(=O)NC3CCCCC3)cn(C)c12] | | 301.95 |
| 21 | 1,5,7-trimethyl-4-oxo-N-(4-phenylcyclohexyl)-4,5-dihydro-1H-pyrrolo[3,2-c]pyridine-3-carboxamide | 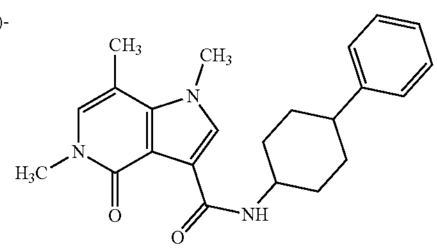 | | 378.06 |
| 22 | N-(2-methoxycyclohexyl)-1,5,7-trimethyl-4-oxo-4,5-dihydro-1H-pyrrolo[3,2-c]pyridine-3-carboxamide | 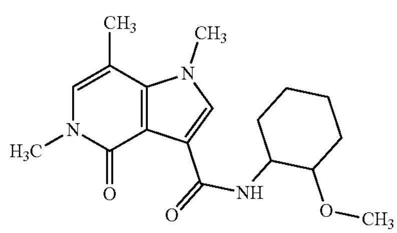 | | 331.98 |
| 23 | N-(3-methoxycyclohexyl)-1,5,7-trimethyl-4-oxo-4,5-dihydro-1H-pyrrolo[3,2-c]pyridine-3-carboxamide | 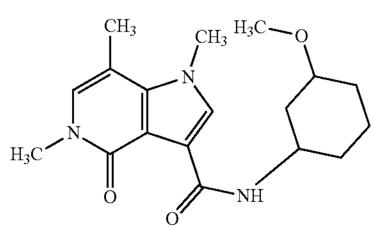 [SMILES: COC1CCCC(NC(=O)c2cn(C)c3c(C)cn(C)c(=O)c23)C1] | | 331.98 |

TABLE 1-3-continued

| Ex. No. | IUPAC Name | Structure | Additive | MS |
|---|---|---|---|---|
| 24 | N-(4-methoxycyclohexyl)-1,5,7-trimethyl-4-oxo-4,5-dihydro-1H-pyrrolo[3,2-c]pyridine-3-carboxamide | 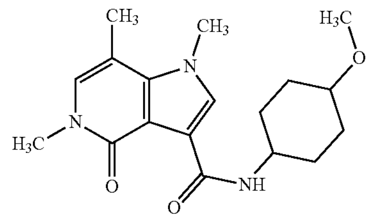 [SMILES: COC1CCC(NC(=O)c2cn(C)c3c(C)cn(C)c(=O)c23)CC1] | | 331.98 |

TABLE 1-4

| Ex. No. | IUPAC Name | Structure | Additive | MS |
|---|---|---|---|---|
| 25 | N-(cyclohexylmethyl)-1,5,7-trimethyl-4-oxo-4,5-dihydro-1H-pyrrolo[3,2-c]pyridine-3-carboxamide | 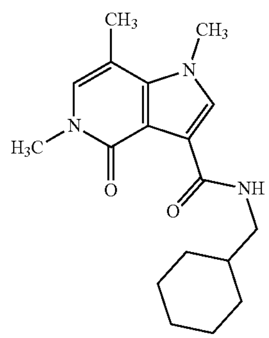 [SMILES: Cc1cn(C)c(=O)c2c(C(=O)NCC3CCCCC3)cn(C)c12] | | 316.01 |
| 26 | 1,5,7-trimethyl-4-oxo-N-(1-phenylpiperidin-4-yl)-4,5-dihydro-1H-pyrrolo[3,2-c]pyridine-3-carboxamide | 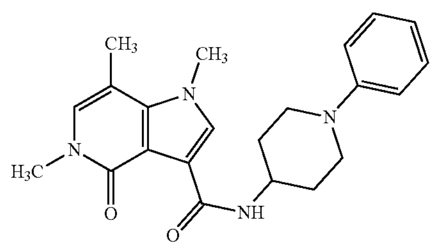 [SMILES: Cc1cn(C)c(=O)c2c(C(=O)NC3CCN(c4ccccc4)CC3)cn(C)c12] | | 379.04 |
| 27 | N-(1-benzylpiperidin-4-yl)-1,5,7-trimethyl-4-oxo-4,5-dihydro-1H-pyrrolo[3,2-c]pyridine-3-carboxamide | 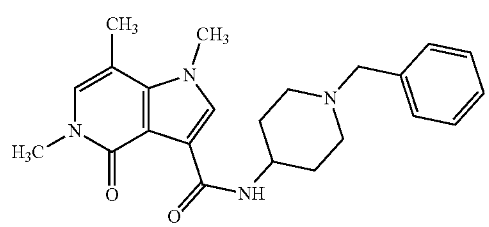 [SMILES: Cc1cn(C)c(=O)c2c(C(=O)NC3CCN(Cc4ccccc4)CC3)cn(C)c12] | | 393.09 |
| 28 | N-(1-(cyclopropylmethyl)piperidin-4-yl)-1,5,7-trimethyl-4-oxo-4,5-dihydro-1H-pyrrolo[3,2-c]pyridine-3-carboxamide | 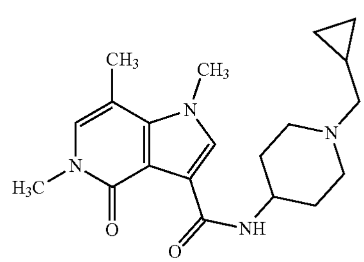 [SMILES: Cc1cn(C)c(=O)c2c(C(=O)NC3CCN(CC4CC4)CC3)cn(C)c12] | | 357.06 |

TABLE 1-4-continued

| Ex. No. | IUPAC Name | Structure | Additive | MS |
|---|---|---|---|---|
| 29 | 1,5,7-trimethyl-4-oxo-N-phenyl-4,5-dihydro-1H-pyrrolo[3,2-c]pyridine-3-carboxamide | 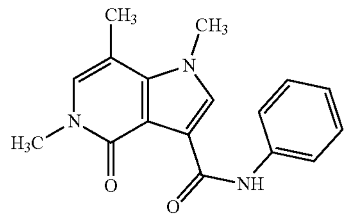 [SMILES: Cc1cn(C)c(=O)c2c(C(=O)Nc3ccccc3)cn(C)c12] | | 295.95 |
| 30 | 1,5,7-trimethyl-N-(4-(morpholin-4-yl)phenyl)-4-oxo-4,5-dihydro-1H-pyrrolo[3,2-c]pyridine-3-carboxamide | 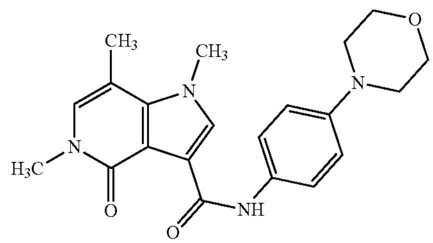 [SMILES: Cc1cn(C)c(=O)c2c(C(=O)Nc3ccc(N4CCOCC4)cc3)cn(C)c12] | | 381.02 |
| 31 | 1,5,7-trimethyl-4-oxo-N-(4-phenoxyphenyl)-4,5-dihydro-1H-pyrrolo[3,2-c]pyridine-3-carboxamide | 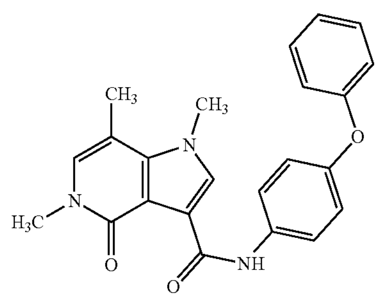 [SMILES: Cc1cn(C)c(=O)c2c(C(=O)Nc3ccc(Oc4ccccc4)cc3)cn(C)c12] | | 388.04 |
| 32 | 1,5,7-trimethyl-4-oxo-N-(5-phenoxypyridin-2-yl)-4,5-dihydro-1H-pyrrolo[3,2-c]pyridine-3-carboxamide | 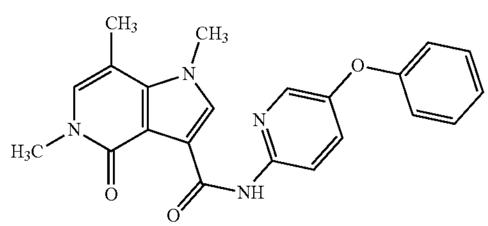 [SMILES: Cc1cn(C)c(=O)c2c(C(=O)Nc3ccc(Oc4ccccc4)cn3)cn(C)c12] | | 389.01 |

TABLE 1-5

| Ex. No. | IUPAC Name | Structure | Additive | MS |
|---|---|---|---|---|
| 33 | N-((5-(4-chlorophenyl)-1,2,4-oxadiazol-3-yl)methyl)-1,5,7-trimethyl-4-oxo-4,5-dihydro-1H-pyrrolo[3,2-c]pyridine-3-carboxamide | 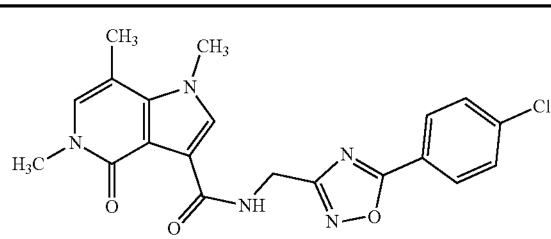 | | 411.96 |

TABLE 1-5-continued

| Ex. No. | IUPAC Name | Structure | Additive | MS |
|---|---|---|---|---|
| 34 | N-(1-(4-fluorobenzyl)-3,5-dimethyl-1H-pyrazol-4-yl)-1,5,7-trimethyl-4-oxo-4,5-dihydro-1H-pyrrolo[3,2-c]pyridine-3-carboxamide | 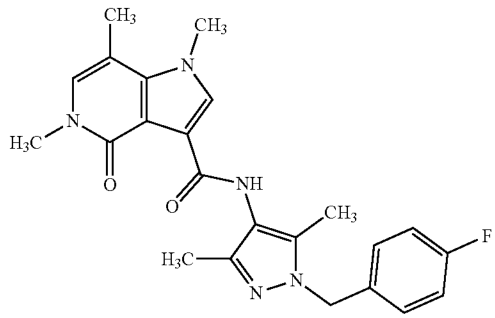 [SMILES: Cc1nn(Cc2ccc(F)cc2)c(C)c1NC(=O)c1cn(C)c2c(C)cn(C)c(=O)c12] | | 422.04 |
| 35 | N-(3-methoxypyridin-2-yl)-1,5,7-trimethyl-4-oxo-4,5-dihydro-1H-pyrrolo[3,2-c]pyridine-3-carboxamide | 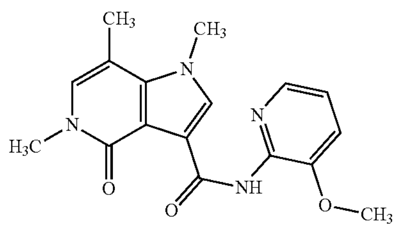 | | 326.93 |
| 36 | N-(2-methoxypyridin-4-yl)-1,5,7-trimethyl-4-oxo-4,5-dihydro-1H-pyrrolo[3,2-c]pyridine-3-carboxamide | 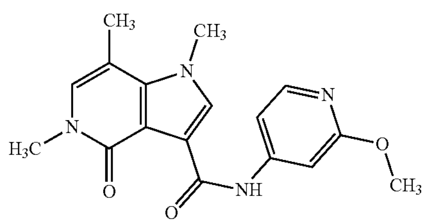 | | 326.96 |
| 37 | N-(4-methoxypyridin-2-yl)-1,5,7-trimethyl-4-oxo-4,5-dihydro-1H-pyrrolo[3,2-c]pyridine-3-carboxamide | 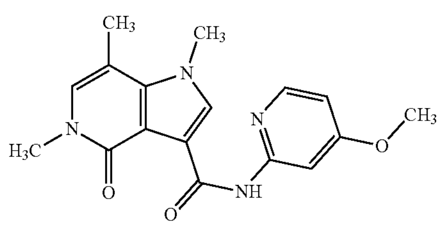 | | 326.96 |
| 38 | N-(5-methoxypyridin-2-yl)-1,5,7-trimethyl-4-oxo-4,5-dihydro-1H-pyrrolo[3,2-c]pyridine-3-carboxamide | 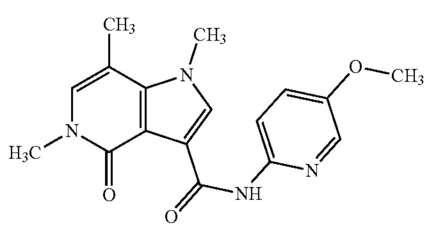 | | 326.93 |
| 39 | N-(6-methoxypyridin-2-yl)-1,5,7-trimethyl-4-oxo-4,5-dihydro-1H-pyrrolo[3,2-c]pyridine-3-carboxamide | 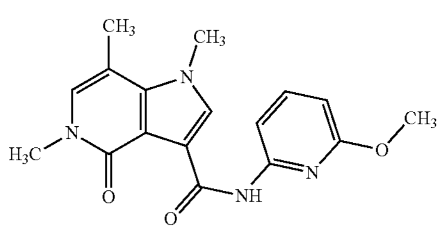 | | 326.93 |

TABLE 1-5-continued

| Ex. No. | IUPAC Name | Structure | Additive | MS |
|---|---|---|---|---|
| 40 | N-(5-cyanopyridin-2-yl)-1,5,7-trimethyl-4-oxo-4,5-dihydro-1H-pyrrolo[3,2-c]pyridine-3-carboxamide | 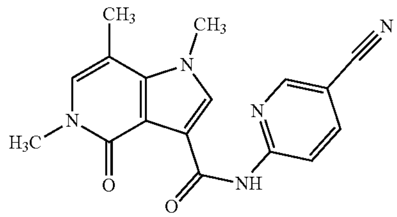 [SMILES: Cc1cn(C)c(=O)c2c(C(=O)Nc3ccc(C#N)cn3)cn(C)c12] | | 321.96 |

TABLE 1-6

| Ex. No. | IUPAC Name | Structure | Additive | MS |
|---|---|---|---|---|
| 41 | 1,5,7-trimethyl-4-oxo-N-(5-(trifluoromethyl)pyridin-2-yl)-4,5-dihydro-1H-pyrrolo[3,2-c]pyridine-3-carboxamide | 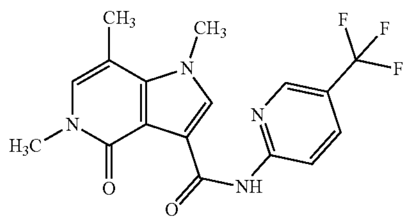 [SMILES: Cc1cn(C)c(=O)c2c(C(=O)Nc3ccc(C(F)(F)F)cn3)cn(C)c12] | | 364.94 |
| 42 | 1,5,7-trimethyl-4-oxo-N-(1-phenyl-1H-imidazol-4-yl)-4,5-dihydro-1H-pyrrolo[3,2-c]pyridine-3-carboxamide | 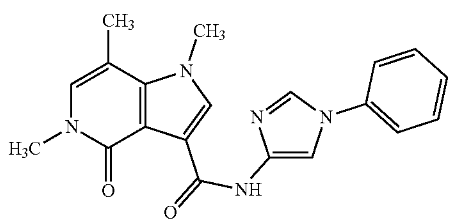 [SMILES: Cc1cn(C)c(=O)c2c(C(=O)Nc3cn(-c4ccccc4)cn3)cn(C)c12] | | 362.01 |
| 43 | N-(2-ethoxyphenyl)-1,5,7-trimethyl-4-oxo-4,5-dihydro-1H-pyrrolo[3,2-c]pyridine-3-carboxamide | 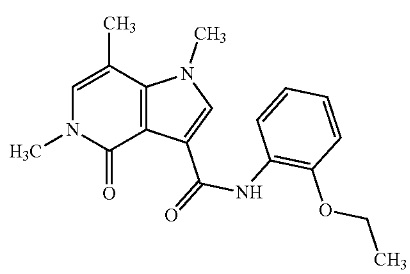 [SMILES: CCOc1ccccc1NC(=O)c1cn(C)c2c(C)cn(C)c(=O)c12] | | 339.94 |
| 44 | N-(2-ethylphenyl)-1,5,7-trimethyl-4-oxo-4,5-dihydro-1H-pyrrolo[3,2-c]pyridine-3-carboxamide | 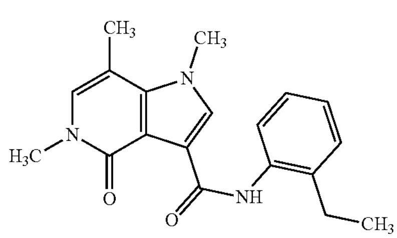 | | 324 |

TABLE 1-6-continued

| Ex. No. | IUPAC Name | Structure | Additive | MS |
|---|---|---|---|---|
| 45 | 1,5,7-trimethyl-4-oxo-N-((1-phenyl-1H-pyrazol-4-yl)methyl)-4,5-dihydro-1H-pyrrolo[3,2-c]pyridine-3-carboxamide | 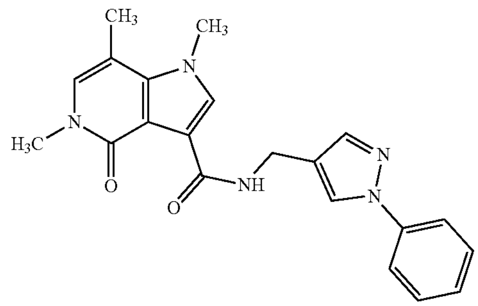 [SMILES: Cc1cn(C)c(=O)c2c(C(=O)NCc3cnn(-c4ccccc4)c3)cn(C)c12] | | 376.07 |
| 46 | N-(1-benzylpyrrolidin-3-yl)-1,5,7-trimethyl-4-oxo-4,5-dihydro-1H-pyrrolo[3,2-c]pyridine-3-carboxamide | 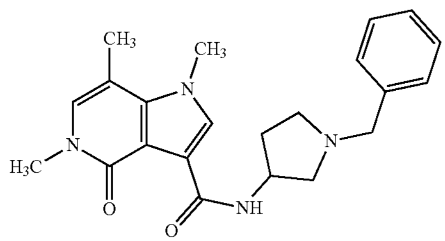 [SMILES: Cc1cn(C)c(=O)c2c(C(=O)NC3CCN(Cc4ccccc4)C3)cn(C)c12] | | 379.07 |
| 47 | 1,5,7-trimethyl-N-(1-methyl-3-(trifluoromethyl)-1H-pyrazol-5-yl)-4-oxo-4,5-dihydro-1H-pyrrolo[3,2-c]pyridine-3-carboxamide | 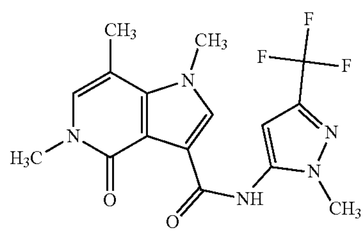 [SMILES: Cc1cn(C)c(=O)c2c(C(=O)Nc3cc(C(F)(F)F)nn3C)cn(C)c12] | | 367.98 |
| 48 | N-(2-methoxyphenyl)-1,5,7-trimethyl-4-oxo-4,5-dihydro-1H-pyrrolo[3,2-c]pyridine-3-carboxamide | 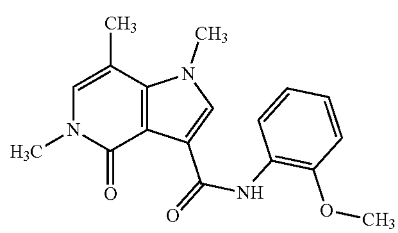 | | 325.95 |

TABLE 1-7

| Ex. No. | IUPAC Name | Structure | Additive | MS |
|---|---|---|---|---|
| 49 | N-(3-methoxyphenyl)-1,5,7-trimethyl-4-oxo-4,5-dihydro-1H-pyrrolo[3,2-c]pyridine-3-carboxamide | 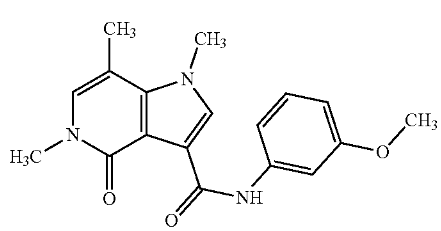 | | 325.95 |

TABLE 1-7-continued

| Ex. No. | IUPAC Name | Structure | Additive | MS |
|---|---|---|---|---|
| 50 | 1,5,7-trimethyl-4-oxo-N-(trans-4-phenoxycyclohexyl)-4,5-dihydro-1H-pyrrolo[3,2-c]pyridine-3-carboxamide | 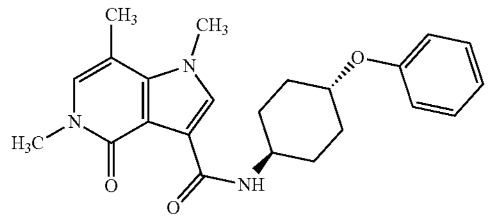 [SMILES: Cc1cn(C)c(=O)c2c(C(=O)N[C@H]3CC[C@H](Oc4ccccc4)CC3)cn(C)c12] | | 394.07 |
| 51 | N-((1S,3S)-3-butoxycyclopentyl)-1,5,7-trimethyl-4-oxo-4,5-dihydro-1H-pyrrolo[3,2-c]pyridine-3-carboxamide | 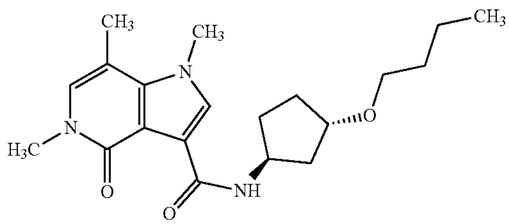 [SMILES: CCCCO[C@H]1CC[C@H](NC(=O)c2cn(C)c3c(C)cn(C)c(=O)c23)C1] | | 360.1 |
| 52 | N-(trans-4-(benzyloxy)cyclohexyl)-1,5,7-trimethyl-4-oxo-4,5-dihydro-1H-pyrrolo[3,2-c]pyridine-3-carboxamide | 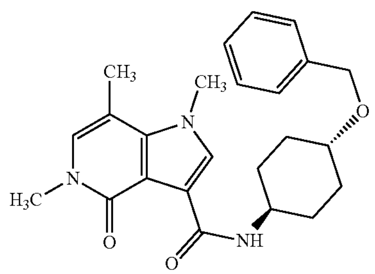 [SMILES: Cc1cn(C)c(=O)c2c(C(=O)N[C@H]3CC[C@H](OCc4ccccc4)CC3)cn(C)c12] | | 408.09 |
| 53 | 1,5,7-trimethyl-4-oxo-N-(3-phenoxycyclohexyl)-4,5-dihydro-1H-pyrrolo[3,2-c]pyridine-3-carboxamide | 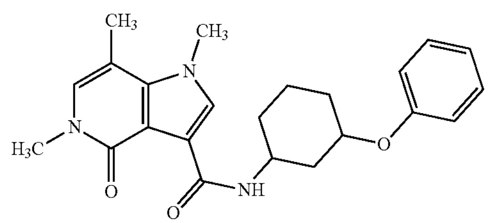 [SMILES: Cc1cn(C)c(=O)c2c(C(=O)NC3CCCC(Oc4ccccc4)C3)cn(C)c12] | | 394.1 |
| 54 | N-(3-(benzyloxy)cyclohexyl)-1,5,7-trimethyl-4-oxo-4,5-dihydro-1H-pyrrolo[3,2-c]pyridine-3-carboxamide | 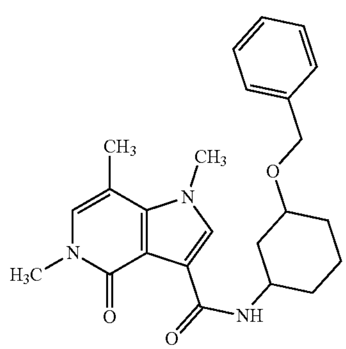 [SMILES: Cc1cn(C)c(=O)c2c(C(=O)NC3CCCC(OCc4ccccc4)C3)cn(C)c12] | | 408.09 |
| 55 | N-((1S,3R)-3-butoxycyclohexyl)-1,5,7-trimethyl-4-oxo-4,5-dihydro-1H-pyrrolo[3,2-c]pyridine-3-carboxamide | 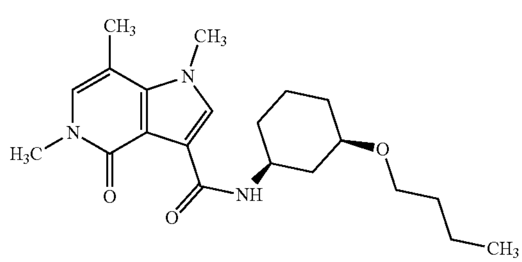 [SMILES: CCCCO[C@@H]1CCC[C@H](NC(=O)c2cn(C)c3c(C)cn(C)c(=O)c23)C1] | | 374.12 |

TABLE 1-7-continued

| Ex. No. | IUPAC Name | Structure | Additive | MS |
|---|---|---|---|---|
| 56 | N-((1S,2R)-2-butoxy-cyclohexyl)-1,5,7-trimethyl-4-oxo-4,5-dihydro-1H-pyrrolo[3,2-c]pyridine-3-carboxamide | 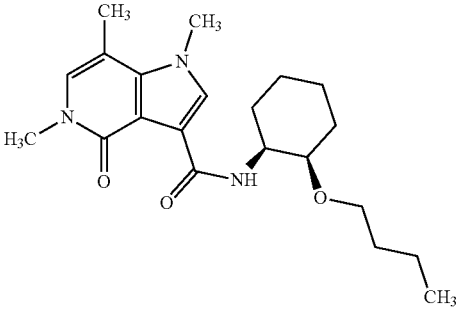 [SMILES: CCCCO[C@@H]1CCCC[C@@H]1NC(=O)c1cn(C)c2c(C)cn(C)c(=O)c12] | | 374.12 |

TABLE 1-8

| Ex. No. | IUPAC Name | Structure | Additive | MS |
|---|---|---|---|---|
| 57 | N-(3-butoxycyclohexyl)-1,5,7-trimethyl-4-oxo-4,5-dihydro-1H-pyrrolo[3,2-c]pyridine-3-carboxamide | 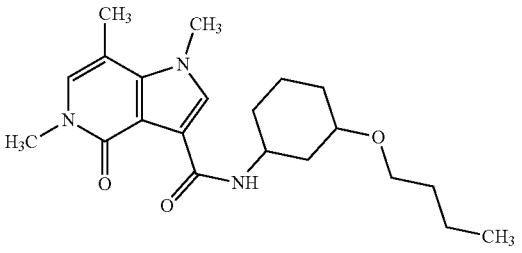 [SMILES: CCCCOC1CCCC(NC(=O)c2cn(C)c3c(C)cn(C)c(=O)c23)C1] | | 374.08 |
| 58 | N-((1S,2S)-2-butoxycyclohexyl)-1,5,7-trimethyl-4-oxo-4,5-dihydro-1H-pyrrolo[3,2-c]pyridine-3-carboxamide | 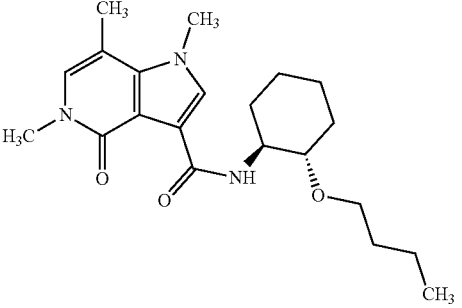 [SMILES: CCCCO[C@H]1CCCC[C@@H]1NC(=O)c1cn(C)c2c(C)cn(C)c(=O)c12] | | 374.15 |
| 59 | 1,5,7-trimethyl-4-oxo-N-(1-(pyridin-2-yl)cyclopropyl)-4,5-dihydro-1H-pyrrolo[3,2-c]pyridie-3-carboxamide | 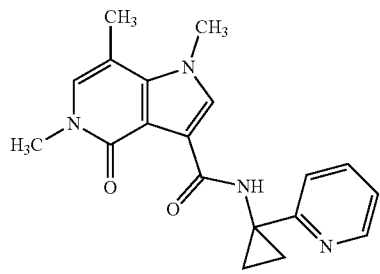 [SMILES: Cc1cn(C)c(=O)c2c(C(=O)NC3(c4ccccn4)CC3)cn(C)c12] | | 337.01 |
| 60 | 1,5,7-trimethyl-4-oxo-N-(1-(pyridin-2-yl)cyclobutyl)-4,5-dihydro-1H-pyrrolo[3,2-c]pyridine-3-carboxamide | 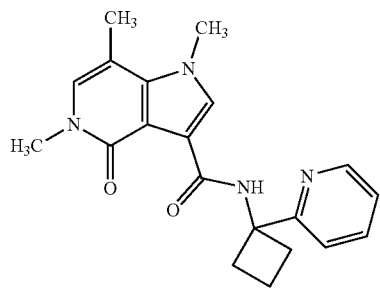 [SMILES: Cc1cn(C)c(=O)c2c(C(=O)NC3(c4ccccn4)CCC3)cn(C)c12] | | 350.99 |

TABLE 1-8-continued

| Ex. No. | IUPAC Name | Structure | Additive | MS |
|---|---|---|---|---|
| 61 | 1,5,7-trimethyl-4-oxo-N-(1-phenylcyclopropyl)-4,5-dihydro-1H-pyrrolo[3,2-c]pyridine-3-carboxamide | 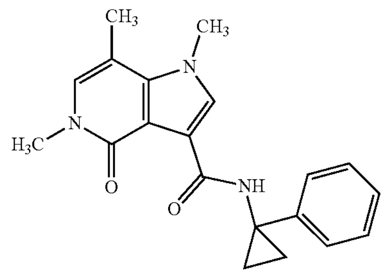 [SMILES: Cc1cn(C)c(=O)c2c(C(=O)NC3(c4ccccc4)CC3)cn(C)c12] | | 335.99 |
| 62 | 1,5,7-trimethyl-4-oxo-N-(1-phenylcyclobutyl)-4,5-dihydro-1H-pyrrolo[3,2-c]pyridine-3-carboxamide | 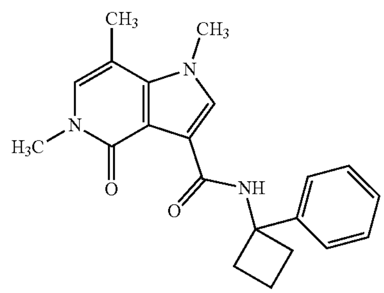 [SMILES: Cc1cn(C)c(=O)c2c(C(=O)NC3(c4ccccc4)CCC3)cn(C)c12] | | 350.02 |
| 63 | 3-((2-(2-methoxyphenyl)pyrrolidin-1-yl)carbonyl)-1,5,7-trimethyl-1,5-dihydro-4H-pyrrolo[3,2-c]pyridin-4-one | 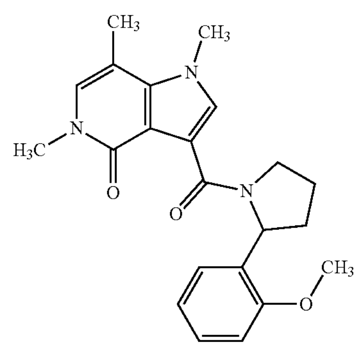 | | 380.05 |
| 64 | 3-((2-(3-methoxyphenyl)pyrrolidin-1-yl)carbonyl)-1,5,7-trimethyl-1,5-dihydro-4H-pyrrolo[3,2-c]pyridin-4-one | 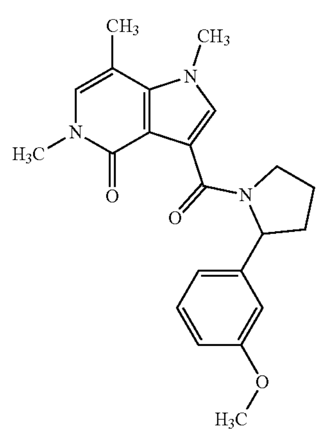 [SMILES: COc1cccc(C2CCCN2C(=O)c2cn(C)c3c(C)cn(C)c(=O)c23)c1] | | 380.05 |

TABLE 1-9

| Ex. No. | IUPAC Name | Structure | Additive | MS |
|---|---|---|---|---|
| 65 | 3-((2-(4-methoxyphenyl)pyrrolidin-1-yl)carbonyl)-1,5,7-trimethyl-1,5-dihydro-4H-pyrrolo[3,2-c]pyridin-4-one | 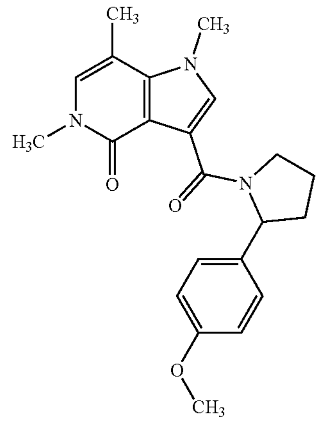 [SMILES: COc1ccc(C2CCCN2C(=O)c2cn(C)c3c(C)cn(C)c(=O)c23)cc1] | | 380.05 |
| 66 | 1,5,7-trimethyl-3-((2-(2-(trifluoromethyl)phenyl)pyrrolidin-1-yl)carbonyl)-1,5-dihydro-4H-pyrrolo[3,2-c]pyridin-4-one | 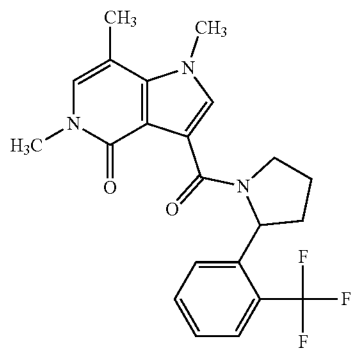 [SMILES: Cc1cn(C)c(=O)c2c(C(=O)N3CCCC3c3ccccc3C(F)(F)F)cn(C)c12] | | 418 |
| 67 | 1,5,7-trimethyl-3-((2-(3-(trifluoromethyl)phenyl)pyrrolidin-1-yl)carbonyl)-1,5-dihydro-4H-pyrrolo[3,2-c]pyridin-4-one | 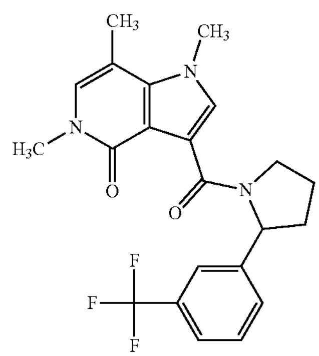 [SMILES: Cc1cn(C)c(=O)c2c(C(=O)N3CCCC3c3cccc(C(F)(F)F)c3)cn(C)c12] | | 418.03 |
| 68 | 1,5,7-trimethyl-3-((2-(4-(trifluoromethyl)phenyl)pyrrolidin-1-yl)carbonyl)-1,5-dihydro-4H-pyrrolo[3,2-c]pyridin-4-one | 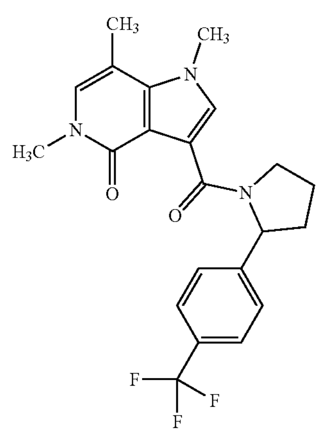 [SMILES: Cc1cn(C)c(=O)c2c(C(=O)N3CCCC3c3ccc(C(F)(F)F)cc3)cn(C)c12] | | 418.07 |

TABLE 1-9-continued

| Ex. No. | IUPAC Name | Structure | Additive | MS |
|---|---|---|---|---|
| 69 | 3-((2-benzylpyrrolidin-1-yl)carbonyl)-1,5,7-trimethyl-1,5-dihydro-4H-pyrrolo[3,2-c]pyridin-4-one | 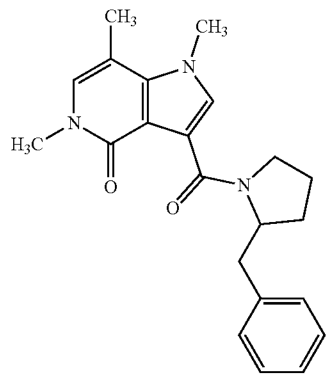 [SMILES: Cc1cn(C)c(=O)c2c(C(=O)N3CCCC3Cc3ccccc3)cn(C)c12] | | 360.04 |
| 70 | 3-((3-benzylpyrrolidin-1-yl)carbonyl)-1,5,7-trimethyl-1,5-dihydro-4H-pyrrolo[3,2-c]pyridin-4-one | 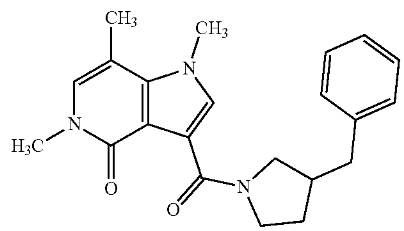 [SMILES: Cc1cn(C)c(=O)c2c(C(=O)N3CCC(Cc4ccccc4)C3)cn(C)c12] | | 364.04 |
| 71 | 3-((3-(4-chlorophenyl)pyrrolidin-1-yl)carbonyl)-1,5,7-trimethyl-1,5-dihydro-4H-pyrrolo[3,2-c]pyridin-4-one | 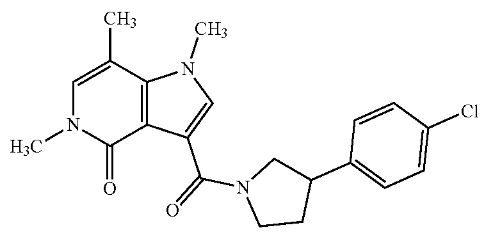 [SMILES: Cc1cn(C)c(=O)c2c(C(=O)N3CCC(c4ccc(Cl)cc4)C3)cn(C)c12] | | 384.06 |
| 72 | 3-((1-(4-chlorophenyl)-3-azabicyclo[3.1.0]hex-3-yl)carbonyl)-1,5,7-trimethyl-1,5-dihydro-4H-pyrrolo[3,2-c]pyridin-4-one | 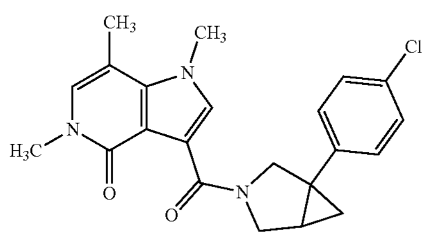 [SMILES: Cc1cn(C)c(=O)c2c(C(=O)N3CC4CC4(c4ccc(Cl)cc4)C3)cn(C)c12] | | 396.02 |

TABLE 1-10

| Ex. No. | IUPAC Name | Structure | Additive | MS |
|---|---|---|---|---|
| 73 | 3-((6,6-difluoro-1-phenyl-3-azabicyclo[3.1.0]hex-3-yl)carbonyl)-1,5,7-trimethyl-1,5-dihydro-4H-pyrrolo[3,2-c]pyridin-4-one | 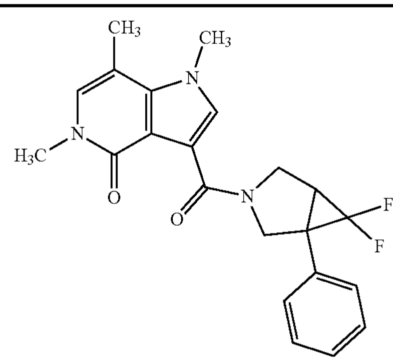 | | 398.05 |

TABLE 1-10-continued

| Ex. No. | IUPAC Name | Structure | Additive | MS |
|---|---|---|---|---|
| 74 | 1,5,7-trimethyl-3-((2-phenylpiperidin-1-yl)carbonyl)-1,5-dihydro-4H-pyrrolo[3,2-c]pyridin-4-one | 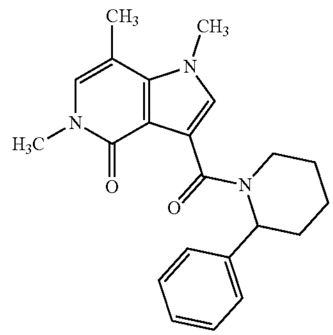 [SMILES: Cc1cn(C)c(=O)c2c(C(=O)N3CCCCC3c3ccccc3)cn(C)c12] | | 364.04 |
| 75 | 3-((2-(2-methoxyphenyl)piperidin-1-yl)carbonyl)-1,5,7-trimethyl-1,5-dihydro-4H-pyrrolo[3,2-c]pyridin-4-one | 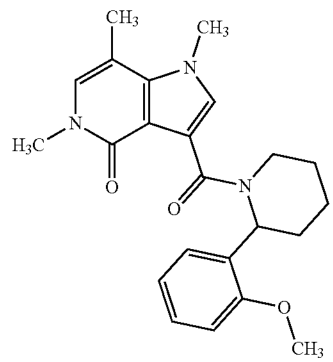 [SMILES: COc1ccccc1C1CCCCN1C(=O)c1cn(C)c2c(C)cn(C)c(=O)c12] | | 394.07 |
| 76 | 3-((2-(3-methoxyphenyl)piperidin-1-yl)carbonyl)-1,5,7-trimethyl-1,5-dihydro-4H-pyrrolo[3,2-c]pyridin-4-one | 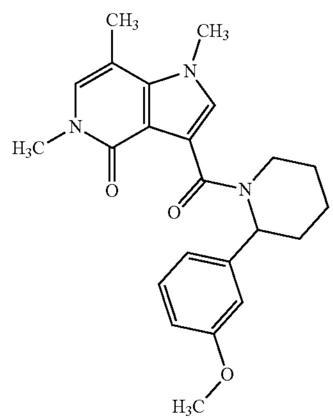 [SMILES: COc1cccc(C2CCCCN2C(=O)c2cn(C)c3c(C)cn(C)c(=O)c23)c1] | | 394.07 |
| 77 | 3-((2-(4-methoxyphenyl)piperidin-1-yl)carbonyl)-1,5,7-trimethyl-1,5-dihydro-4H-pyrrolo[3,2-c]pyridin-4-one | 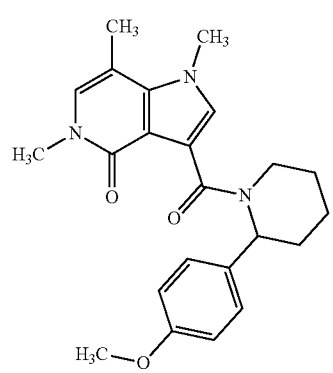 [SMILES: COc1ccc(C2CCCCN2C(=O)c2cn(C)c3c(C)cn(C)c(=O)c23)cc1] | | 394.07 |

TABLE 1-10-continued

| Ex. No. | IUPAC Name | Structure | Additive | MS |
|---|---|---|---|---|
| 78 | 1,5,7-trimethyl-3-((3-phenylpiperidin-1-yl)carbonyl)-1,5-dihydro-4H-pyrrolo[3,2-c]pyridin-4-one | 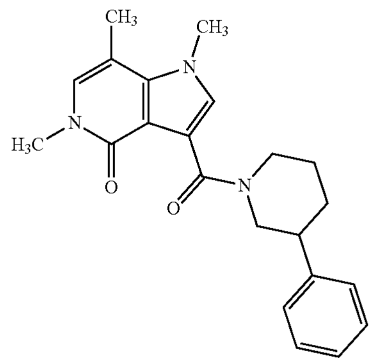 [SMILES: Cc1cn(C)c(=O)c2c(C(=O)N3CCCC(c4ccccc4)C3)cn(C)c12] | | 364.04 |
| 79 | 1,5,7-trimethyl-3-((4-phenylpiperidin-1-yl)carbonyl)-1,5-dihydro-4H-pyrrolo[3,2-c]pyridin-4-one | 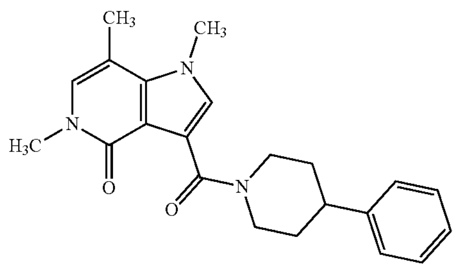 [SMILES: Cc1cn(C)c(=O)c2c(C(=O)N3CCC(c4ccccc4)CC3)cn(C)c12] | | 364.04 |
| 80 | 3-((2-benzylpiperidin-1-yl)carbonyl)-1,5,7-trimethyl-1,5-dihydro-4H-pyrrolo[3,2-c]pyridin-4-one | 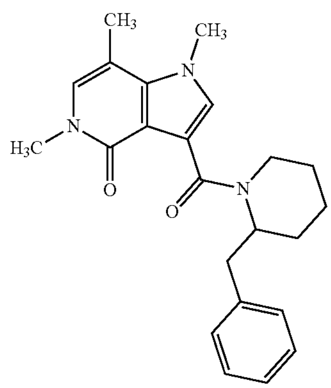 [SMILES: Cc1cn(C)c(=O)c2c(C(=O)N3CCCCC3Cc3ccccc3)cn(C)c12] | | 378.06 |

TABLE 1-11

| Ex. No. | IUPAC Name | Structure | Additive | MS |
|---|---|---|---|---|
| 81 | 3-((3-benzylpiperidin-1-yl)carbonyl)-1,5,7-trimethyl-1,5-dihydro-4H-pyrrolo[3,2-c]pyridin-4-one | 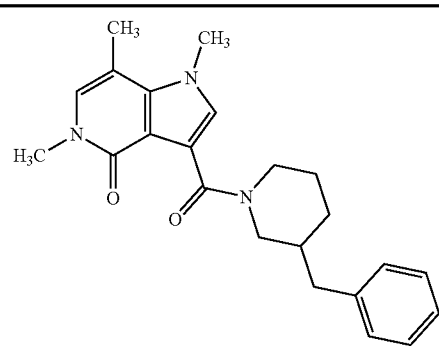 | | 378.06 |

TABLE 1-11-continued

| Ex. No. | IUPAC Name | Structure | Additive | MS |
|---|---|---|---|---|
| 82 | 3-((8-methoxy-3,4-dihydroquinolin-1(2H)-yl)carbonyl)-1,5,7-trimethyl-1,5-dihydro-4H-pyrrolo[3,2-c]pyridin-4-one | 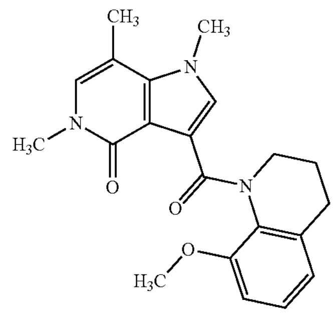 [SMILES: COc1cccc2c1N(C(=O)c1cn(C)c3c(C)cn(C)c(=O)c13)CCC2] | | 365.99 |
| 83 | 1,5,7-trimethyl-3-((2-phenylazetidin-1-yl)carbonyl)-1,5-dihydro-4H-pyrrolo[3,2-c]pyridin-4-one | 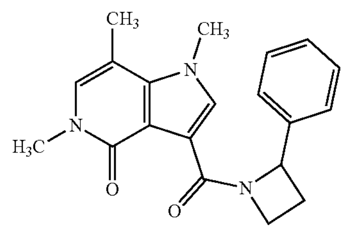 [SMILES: Cc1cn(C)c(=O)c2c(C(=O)N3CCC3c3ccccc3)cn(C)c12] | | 335.96 |
| 84 | 1,5,7-trimethyl-3-((3-phenylazetidin-1-yl)carbonyl)-1,5-dihydro-4H-pyrrolo[3,2-c]pyridin-4-one | 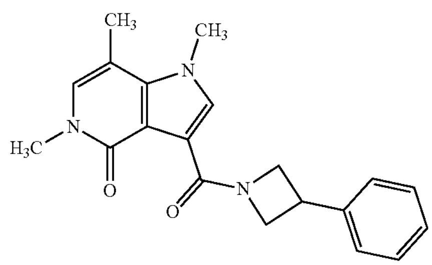 [SMILES: Cc1cn(C)c(=O)c2c(C(=O)N3CC(c4ccccc4)C3)cn(C)c12] | | 335.96 |
| 85 | 3-((3-benzylazetidin-1-yl)carbonyl)-1,5,7-trimethyl-1,5-dihydro-4H-pyrrolo[3,2-c]pyridin-4-one | 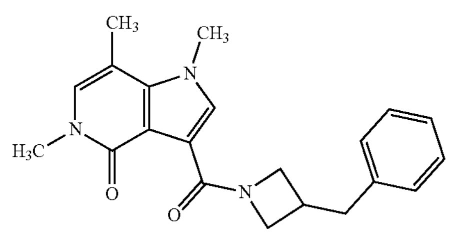 [SMILES: Cc1cn(C)c(=O)c2c(C(=O)N3CC(Cc4ccccc4)C3)cn(C)c12] | | 349.98 |
| 86 | 3-((4-methoxy-2,3-dihydro-1H-indol-1-yl)carbonyl)-1,5,7-trimethyl-1,5-dihydro-4H-pyrrolo[3,2-c]pyridin-4-one | 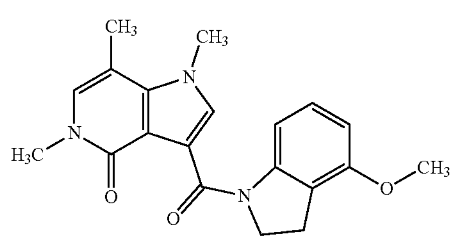 | | 351.97 |
| 87 | 3-((6-methoxy-2,3-dihydro-1H-indol-1-yl)carbonyl)-1,5,7-trimethyl-1,5-dihydro-4H-pyrrolo[3,2-c]pyridin-4-one | 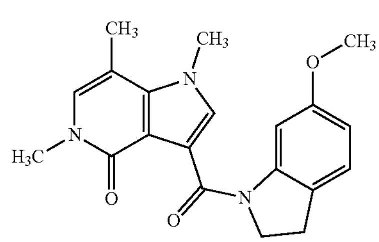 | | 351.93 |

TABLE 1-11-continued

| Ex. No. | IUPAC Name | Structure | Additive | MS |
|---|---|---|---|---|
| 88 | 3-((5-methoxy-2,3-dihydro-1H-indol-1-yl)carbonyl)-1,5,7-trimethyl-1,5-dihydro-4H-pyrrolo[3,2-c]pyridin-4-one | 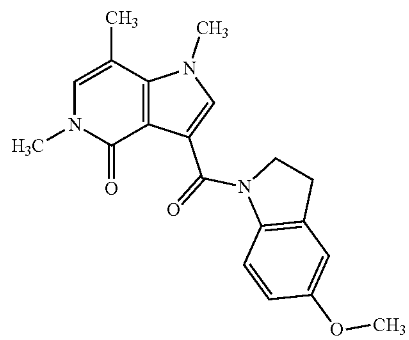 | | 351.93 |

TABLE 1-12

| Ex. No. | IUPAC Name | Structure | Additive | MS |
|---|---|---|---|---|
| 89 | 3-((7-methoxy-2,3-dihydro-1H-indol-1-yl)carbonyl)-1,5,7-trimethyl-1,5-dihydro-4H-pyrrolo[3,2-c]pyridin-4-one | 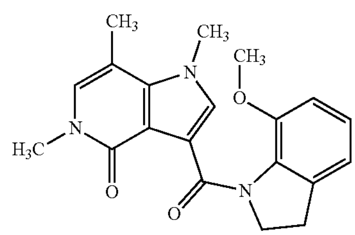 [SMILES: COc1cccc2c1N(C(=O)c1cn(C)c3c(C)cn(C)c(=O)c13)CC2] | | 352 |
| 90 | 3-((6-methoxy-3,4-dihydroquinolin-1(2H)-yl)carbonyl)-1,5,7-trimethyl-1,5-dihydro-4H-pyrrolo[3,2-c]pyridin-4-one | 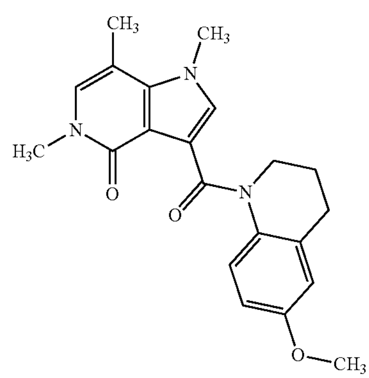 | | 366.03 |
| 91 | 3-((7-methoxy-3,4-dihydroisoquinolin-2(1H)-yl)carbonyl)-1,5,7-trimethyl-1,5-dihydro-4H-pyrrolo[3,2-c]pyridin-4-one | 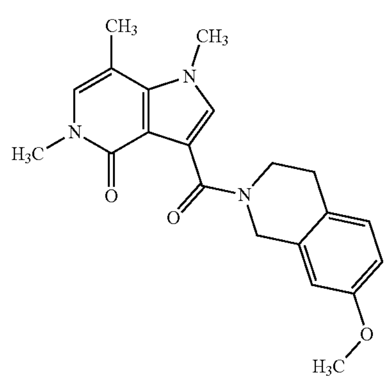 [SMILES: COc1ccc2c(c1)CN(C(=O)c1cn(C)c3c(C)cn(C)c(=O)c13)CC2] | | 366.06 |

TABLE 1-12-continued

| Ex. No. | IUPAC Name | Structure | Additive | MS |
|---|---|---|---|---|
| 92 | N-(cis-4-butoxycyclohexyl)-1,5,7-trimethyl-4-oxo-4,5-dihydro-1H-pyrrolo[3,2-c]pyridine-3-carboxamide | 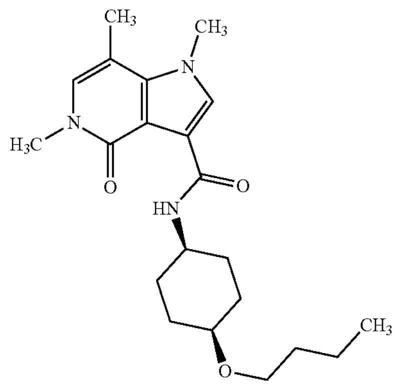 [SMILES: CCCCO[C@H]1CC[C@@H](NC(=O)c2cn(C)c3c(C)cn(C)c(=O)c23)CC1] | | 374.08 |
| 93 | N-(trans-4-butoxycyclohexyl)-1,5-dimethyl-4-oxo-4,5-dihydro-1H-pyrrolo[3,2-c]pyridine-3-carboxamide | 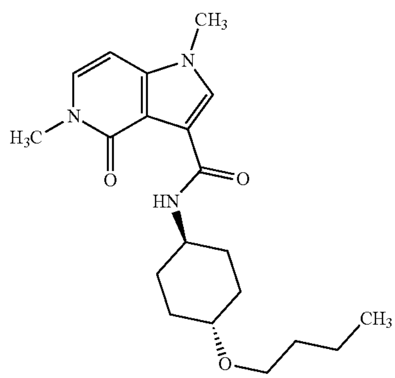 [SMILES: CCCCO[C@H]1CC[C@H](NC(=O)c2cn(C)c3ccn(C)c(=O)c23)CC1] | | 360.06 |
| 94 | 3-((8-methoxy-3,4-dihydroisoquinolin-2(1H)-yl)carbonyl)-1,5,7-trimethyl-1,5-dihydro-4H-pyrrolo[3,2-c]pyridin-4-one | 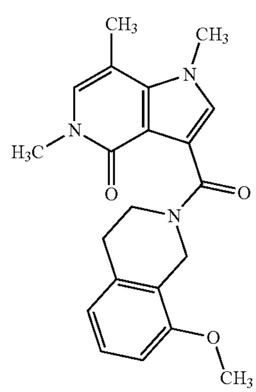 [SMILES: COc1cccc2c1CN(C(=O)c1cn(C)c3c(C)cn(C)c(=O)c13)CC2] | | 366.03 |
| 95 | 3-((6-methoxy-3,4-dihydroisoquinolin-2(1H)-yl)carbonyl)-1,5,7-trimethyl-1,5-dihydro-4H-pyrrolo[3,2-c]pyridin-4-one | 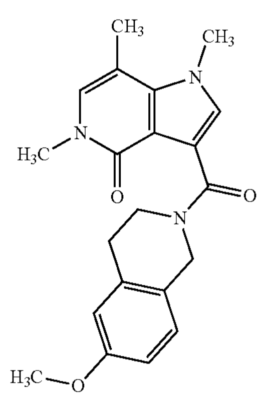 [SMILES: COc1ccc2c(c1)CCN(C(=O)c1cn(C)c3c(C)cn(C)c(=O)c13)C2] | | 365.99 |

TABLE 1-12-continued

| Ex. No. | IUPAC Name | Structure | Additive | MS |
|---|---|---|---|---|
| 96 | 3-((7-methoxy-3,4-dihydroquinolin-1(2H)-yl)carbonyl)-1,5,7-trimethyl-1,5-dihydro-4H-pyrrolo[3,2-c]pyridin-4-one | 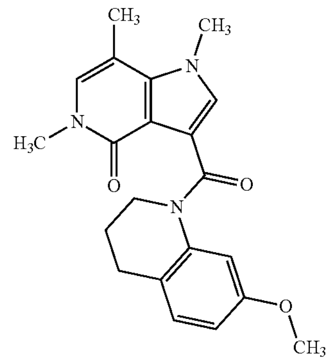 | | 366.03 |

TABLE 1-13

| Ex. No. | IUPAC Name | Structure | Additive | MS |
|---|---|---|---|---|
| 97 | 3-((4-benzylpiperidin-1-yl)carbonyl)-1,5,7-trimethyl-1,5-dihydro-4H-pyrrolo[3,2-c]pyridin-4-one | 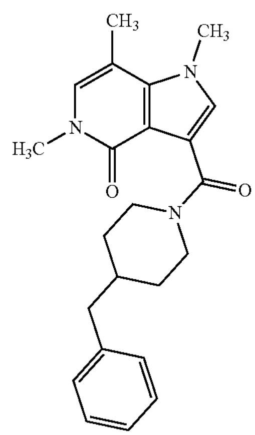 [SMILES: Cc1cn(C)c(=O)c2c(C(=O)N3CCC(Cc4ccccc4)CC3)cn(C)c12] | | 378.02 |
| 98 | N-(trans-4-butoxycyclohexyl)-7-chloro-1,5-dimethyl-4-oxo-4,5-dihydro-1H-pyrrolo[3,2-c]pyridine-3-carboxamide | 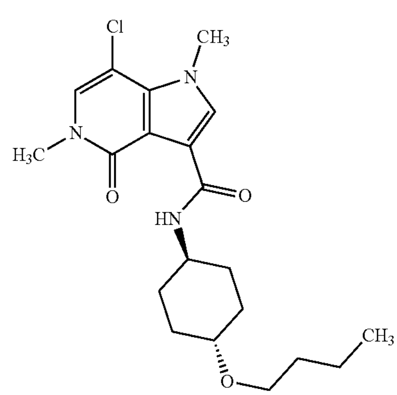 [SMILES: CCCCO[C@H]1CC[C@H](NC(=O)c2cn(C)c3c(Cl)cn(C)c(=O)c23)CC1] | | 394.27 |

TABLE 1-13-continued

| Ex. No. | IUPAC Name | Structure | Additive | MS |
|---|---|---|---|---|
| 99 | 3-((5-methoxy-3,4-dihydroisoquinolin-2(1H)-yl)carbonyl)-1,5,7-trimethyl-1,5-dihydro-4H-pyrrolo[3,2-c]pyridin-4-one | 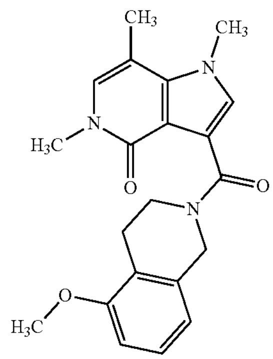 [SMILES: COc1cccc2c1CCN(C(=O)c1cn(C)c3c(C)cn(C)c(=O)c13)C2] | | 366.23 |
| 100 | 3-((5-methoxy-1,3-dihydro-2H-isoindol-2-yl)carbonyl)-1,5,7-trimethyl-1,5-dihydro-4H-pyrrolo[3,2-c]pyridin-4-one | 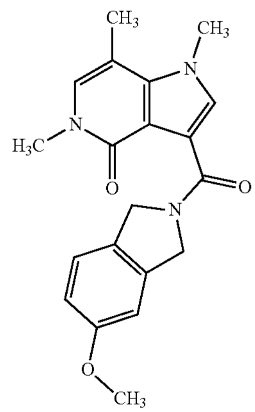 [SMILES: COc1ccc2c(c1)CN(C(=O)c1cn(C)c3c(C)cn(C)c(=O)c13)C2] | | 352.17 |
| 101 | 1,7-dimethyl-4-oxo-N,5-diphenyl-4,5-dihydro-1H-pyrrolo[3,2-c]pyridine-3-carboxamide | 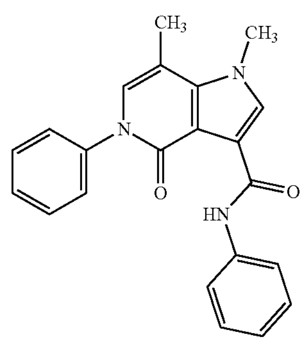 [SMILES: Cc1cn(-c2ccccc2)c(=O)c2c(C(=O)Nc3ccccc3)cn(C)c12] | | 358.13 |
| 102 | 3-((5-methoxy-3,4-dihydroquinolin-1(2H)-yl)carbonyl)-1,5,7-trimethyl-1,5-dihydro-4H-pyrrolo[3,2-c]pyridin-4-one | 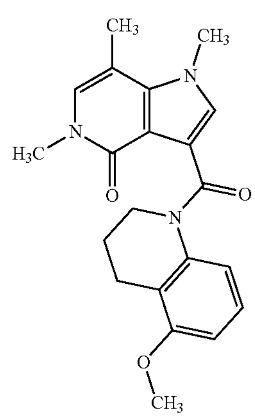 [SMILES: COc1cccc2c1CCCN2C(=O)c1cn(C)c2c(C)cn(C)c(=O)c12] | | 366.19 |

TABLE 1-13-continued

| Ex. No. | IUPAC Name | Structure | Additive | MS |
|---|---|---|---|---|
| 103 | 7-bromo-N-(trans-4-butoxycyclohexyl)-1,5-dimethyl-4-oxo-4,5-dihydro-1H-pyrrolo[3,2-c]pyridine-3-carboxamide | 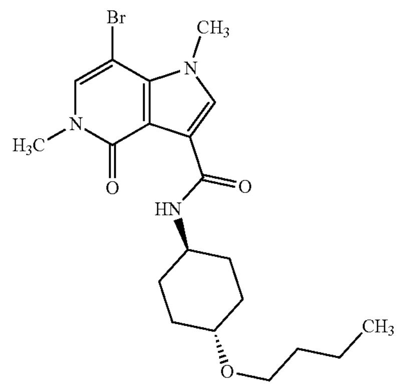 [SMILES: CCCCO[C@H]1CC[C@H](NC(=O)c2cn(C)c3c(Br)cn(C)c(=O)c23)CC1] | | 438.16 |
| 104 | 3-((2-(3-bromophenyl)azetidin-1-yl)carbonyl)-1,5,7-trimethyl-1,5-dihydro-4H-pyrrolo[3,2-c]pyridin-4-one | 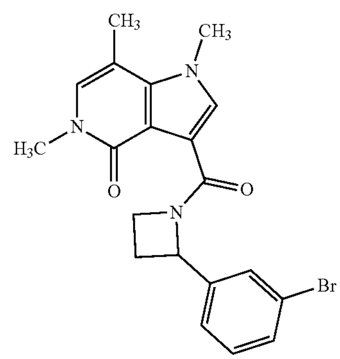 [SMILES: Cc1cn(C)c(=O)c2c(C(=O)N3CCC3c3cccc(Br)c3)cn(C)c12] | | 414.15 |

TABLE 1-14

| Ex. No. | IUPAC Name | Structure | Additive | MS |
|---|---|---|---|---|
| 105 | 3-((4-methoxy-1,3-dihydro-2H-isoindol-2-yl)carbonyl)-1,5,7-trimethyl-1,5-dihydro-4H-pyrrolo[3,2-c]pyridin-4-one | 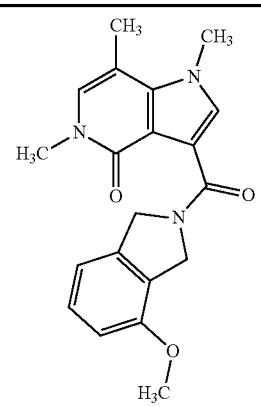 | | 352.2 |
| 106 | N-cyclohexyl-1,7-dimethyl-4-oxo-5-phenyl-4,5-dihydro-1H-pyrrolo[3,2-c]pyridine-3-carboxamide | 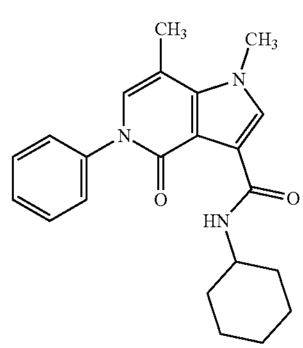 [SMILES: Cc1cn(-c2ccccc2)c(=O)c2c(C(=O)NC3CCCCC3)cn(C)c12] | | 364.27 |

TABLE 1-14-continued

| Ex. No. | IUPAC Name | Structure | Additive | MS |
|---|---|---|---|---|
| 107 | N-cyclohexyl-5-(2-methoxyphenyl)-1,7-dimethyl-4-oxo-4,5-dihydro-1H-pyrrolo[3,2-c]pyridine-3-carboxamide | 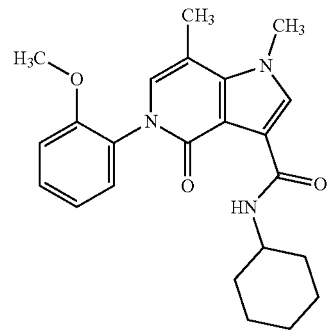 [SMILES: COc1ccccc1-n1cc(C)c2c(c(C(=O)NC3CCCCC3)cn2C)c1=O] | | 394.27 |
| 108 | 5-(2-methoxyphenyl)-1,7-dimethyl-4-oxo-N-phenyl-4,5-dihydro-1H-pyrrolo[3,2-c]pyridine-3-carboxamide | 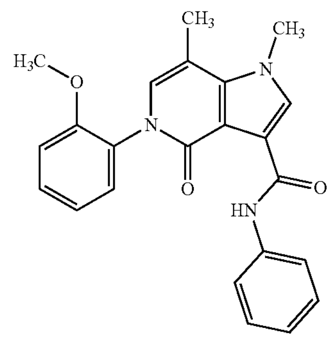 [SMILES: COc1ccccc1-n1cc(C)c2c(c(C(=O)Nc3ccccc3)cn2C)c1=O] | | 388.2 |
| 109 | 1,5,7-trimethyl-4-oxo-N-(2-phenyltetrahydrofuran-3-yl)-4,5-dihydro-1H-pyrrolo[3,2-c]pyridine-3-carboxamide | 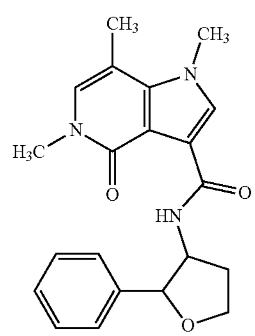 [SMILES: Cc1cn(C)c(=O)c2c(C(=O)NC3CCOC3c3ccccc3)cn(C)c12] | | 366.19 |
| 110 | 1,5,7-trimethyl-4-oxo-N-[rac-(1S,2R)-2-phenylcyclopentyl]-4,5-dihydro-1H-pyrrolo[3,2-c]pyridine-3-carboxamide | 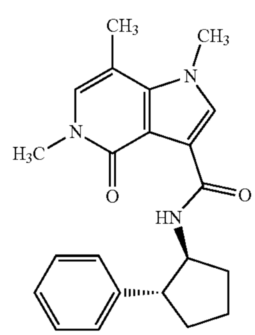 [SMILES: Cc1cn(C)c(=O)c2c(C(=O)N[C@H]3CCC[C@@H]3c3ccccc3)cn(C)c12] | | 364.24 |

TABLE 1-14-continued

| Ex. No. | IUPAC Name | Structure | Additive | MS |
|---|---|---|---|---|
| 111 | 1,5,7-trimethyl-4-oxo-N-[rac-(1S,2S)-2-phenylcyclopentyl]-4,5-dihydro-1H-pyrrolo[3,2-c]pyridine-3-carboxamide | 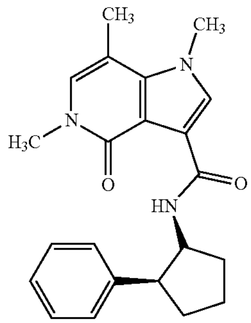 | | 364.24 |
| 112 | 1,5,7-trimethyl-4-oxo-N-[rac-(1S,2R)-2-phenylcyclohexyl]-4,5-dihydro-1H-pyrrolo[3,2-c]pyridine-3-carboxamide | 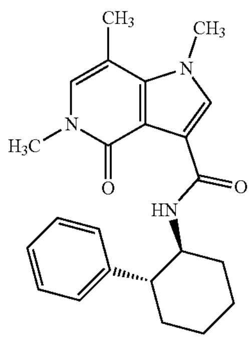 [SMILES: Cc1cn(C)c(=O)c2c(C(=O)N[C@H]3CCCC[C@@H]3c3ccccc3)cn(C)c12] | | 378.26 |

TABLE 1-15

| Ex. No. | IUPAC Name | Structure | Additive | MS |
|---|---|---|---|---|
| 113 | 1,5,7-trimethyl-4-oxo-N-[rac-(1S,2S)-2-phenylcyclohexyl]-4,5-dihydro-1H-pyrrolo[3,2-c]pyridine-3-carboxamide | 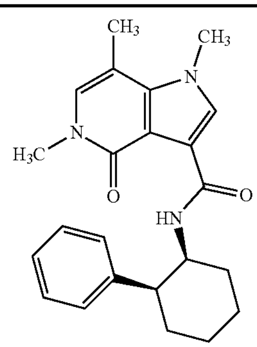 | | 378.29 |
| 114 | 1,5,7-trimethyl-4-oxo-N-[rac-(1S,3S)-3-phenylcyclohexyl]-4,5-dihydro-1H-pyrrolo[3,2-c]pyridine-3-carboxamide | 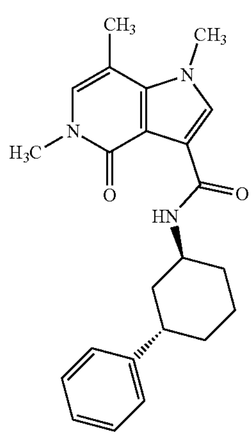 [SMILES: Cc1cn(C)c(=O)c2c(C(=O)N[C@H]3CCC[C@H](c4ccccc4)C3)cn(C)c12] | | 378.26 |

TABLE 1-15-continued

| Ex. No. | IUPAC Name | Structure | Additive | MS |
|---|---|---|---|---|
| 115 | 1,5,7-trimethyl-4-oxo-N-[rac-(1S,3R)-3-phenylcyclohexyl]-4,5-dihydro-1H-pyrrolo[3,2-c]pyridine-3-carboxamide | 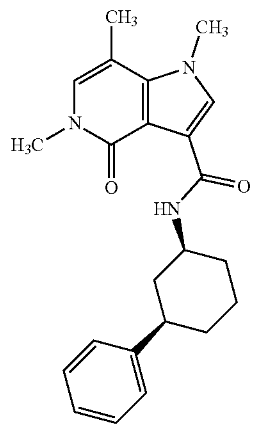 [SMILES: Cc1cn(C)c(=O)c2c(C(=O)N[C@H]3CCC[C@@H](c4ccccc4)C3)cn(C)c12] | | 378.29 |
| 116 | 1,5,7-trimethyl-4-oxo-N-[rac-(3R,4S)-4-phenyltetrahydrofuran-3-yl]-4,5-dihydro-1H-pyrrolo[3,2-c]pyridine-3-carboxamide | 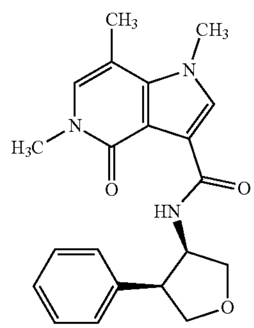 [SMILES: Cc1cn(C)c(=O)c2c(C(=O)N[C@H]3COC[C@H]3c3ccccc3)cn(C)c12] | | 366.23 |
| 117 | N-(trans-4-butoxycyclohexyl)-7-cyclopropyl-1,5-dimethyl-4-oxo-4,5-dihydro-1H-pyrrolo[3,2-c]pyridine-3-carboxamide | 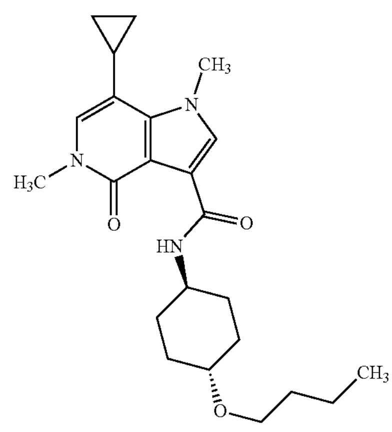 [SMILES: CCCCO[C@H]1CC[C@H](NC(=O)c2cn(C)c3c(C4CC4)cn(C)c(=O)c23)CC1] | | 400.34 |
| 118 | 3-((1-(3-chlorophenyl)-3-azabicyclo[3.1.0]hex-3-yl)carbonyl)-1,5,7-trimethyl-1,5-dihydro-4H-pyrrolo[3,2-c]pyridin-4-one | 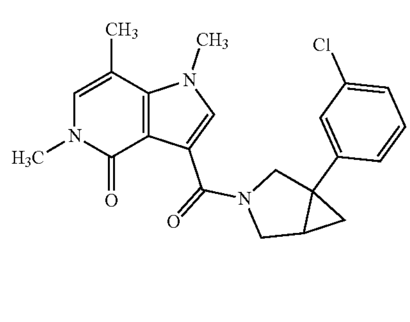 [SMILES: Cc1cn(C)c(=O)c2c(C(=O)N3CC4CC4(c4cccc(Cl)c4)C3)cn(C)c12] | | 395.95 |

TABLE 1-15-continued

| Ex. No. | IUPAC Name | Structure | Additive | MS |
|---|---|---|---|---|
| 119 | 3-((1-(2-chlorophenyl)-3-azabicyclo[3.1.0]hex-3-yl)carbonyl)-1,5,7-trimethyl-1,5-dihydro-4H-pyrrolo[3,2-c]pyridin-4-one | 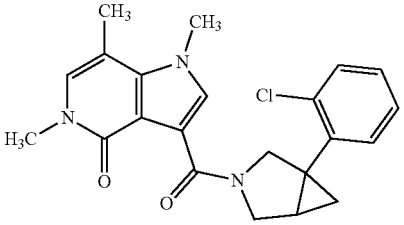 [SMILES: Cc1cn(C)c(=O)c2c(C(=O)N3CC4CC4(c4ccccc4Cl)C3)cn(C)c12] | | 395.95 |
| 120 | 3-((1-(3,4-dichlorophenyl)-3-azabicyclo[3.1.0]hex-3-yl)carbonyl)-1,5,7-trimethyl-1,5-dihydro-4H-pyrrolo[3,2-c]pyridin-4-one | 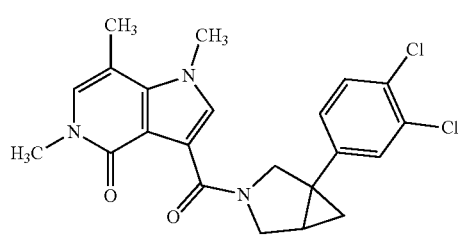 [SMILES: Cc1cn(C)c(=O)c2c(C(=O)N3CC4CC4(c4ccc(Cl)c(Cl)c4)C3)cn(C)c12] | | 429.96 |

TABLE 1-16

| Ex. No. | IUPAC Name | Structure | Additive | MS |
|---|---|---|---|---|
| 121 | 3-((1-(2,3-dichlorophenyl)-3-azabicyclo[3.1.0]hex-3-yl)carbonyl)-1,5,7-trimethyl-1,5-dihydro-4H-pyrrolo[3,2-c]pyridin-4-one | 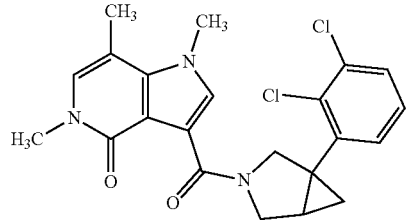 [SMILES: Cc1cn(C)c(=O)c2c(C(=O)N3CC4CC4(c4cccc(Cl)c4Cl)C3)cn(C)c12] | | 429.96 |
| 122 | 3-((1-(3,5-dichlorophenyl)-3-azabicyclo[3.1.0]hex-3-yl)carbonyl)-1,5,7-trimethyl-1,5-dihydro-4H-pyrrolo[3,2-c]pyridin-4-one | 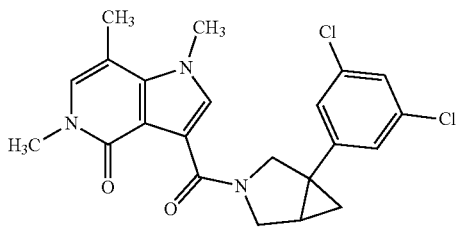 [SMILES: Cc1cn(C)c(=O)c2c(C(=O)N3CC4CC4(c4cc(Cl)cc(Cl)c4)C3)cn(C)c12] | | 430 |
| 123 | 3-((1-(2,5-dichlorophenyl)-3-azabicyclo[3.1.0]hex-3-yl)carbonyl)-1,5,7-trimethyl-1,5-dihydro-4H-pyrrolo[3,2-c]pyridin-4-one | 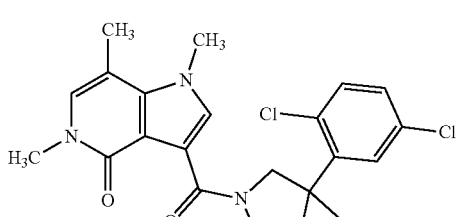 | | 429.96 |
| 124 | 3-((1-(4-fluorophenyl)-3-azabicyclo[3.1.0]hex-3-yl)carbonyl)-1,5,7-trimethyl-1,5-dihydro-4H-pyrrolo[3,2-c]pyridin-4-one | 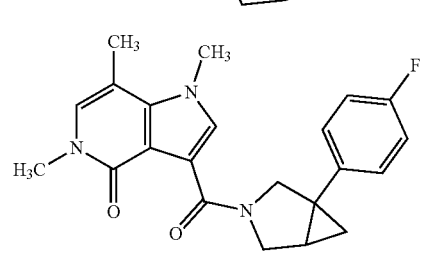 | | 380.25 |

TABLE 1-16-continued

| Ex. No. | IUPAC Name | Structure | Additive | MS |
|---|---|---|---|---|
| 125 | 3-((1-(3-fluorophenyl)-3-azabicyclo[3.1.0]hex-3-yl)carbonyl)-1,5,7-trimethyl-1,5-dihydro-4H-pyrrolo[3,2-c]pyridin-4-one | 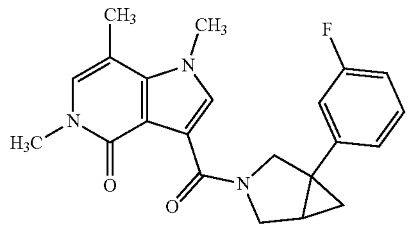 [SMILES: Cc1cn(C)c(=O)c2c(C(=O)N3CC4CC4(c4cccc(F)c4)C3)cn(C)c12] | | 380.21 |
| 126 | 3-((1-(2-fluorophenyl)-3-azabicyclo[3.1.0]hex-3-yl)carbonyl)-1,5,7-trimethyl-1,5-dihydro-4H-pyrrolo[3,2-c]pyridin-4-one | 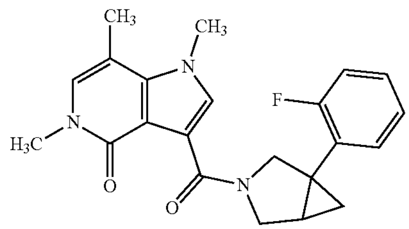 [SMILES: Cc1cn(C)c(=O)c2c(C(=O)N3CC4CC4(c4ccccc4F)C3)cn(C)c12] | | 380.21 |
| 127 | 3-((1-(4-methoxyphenyl)-3-azabicyclo[3.1.0]hex-3-yl)carbonyl)-1,5,7-trimethyl-1,5-dihydro-4H-pyrrolo[3,2-c]pyridin-4-one | 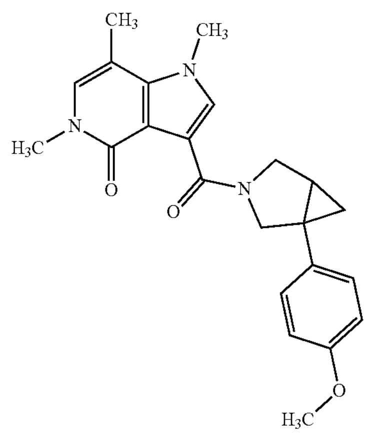 [SMILES: COc1ccc(C23CC2CN(C(=O)c2cn(C)c4c(C)cn(C)c(=O)c24)C3)cc1] | | 392.05 |
| 128 | 3-((1-(3-methoxyphenyl)-3-azabicyclo[3.1.0]hex-3-yl)carbonyl)-1,5,7-trimethyl-1,5-dihydro-4H-pyrrolo[3,2-c]pyridin-4-one | 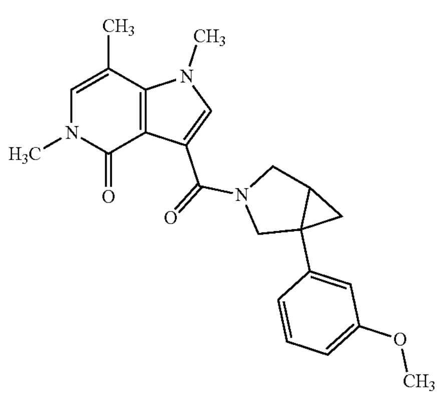 | | 392.01 |

TABLE 1-17

| Ex. No. | IUPAC Name | Structure | Additive | MS |
|---|---|---|---|---|
| 129 | 3-((1-(2-methoxyphenyl)-3-azabicyclo[3.1.0]hex-3-yl)carbonyl)-1,5,7-trimethyl-1,5-dihydro-4H-pyrrolo[3,2-c]pyridin-4-one | 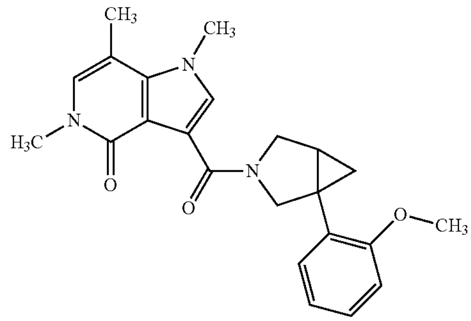 | | 392.08 |
| 130 | 1,5,7-trimethyl-3-((1-(4-(trifluoromethoxy)phenyl)-3-azabicyclo[3.1.0]hex-3-yl)carbonyl)-1,5-dihydro-4H-pyrrolo[3,2-c]pyridin-4-one | 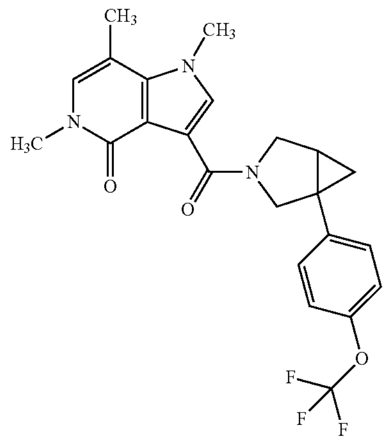 [SMILES: Cc1cn(C)c(=O)c2c(C(=O)N3CC4CC4(c4ccc(OC(F)(F)F)cc4)C3)cn(C)c12] | | 446.01 |
| 131 | 1,5,7-trimethyl-3-((1-(3-(trifluoromethoxy)phenyl)-3-azabicyclo[3.1.0]hex-3-yl)carbonyl)-1,5-dihydro-4H-pyrrolo[3,2-c]pyridin-4-one | 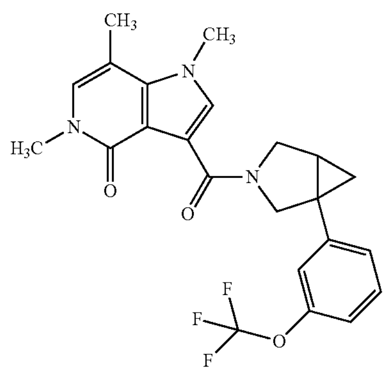 [SMILES: Cc1cn(C)c(=O)c2c(C(=O)N3CC4CC4(c4cccc(OC(F)(F)F)c4)C3)cn(C)c12] | | 446.01 |
| 132 | 1,5,7-trimethyl-3-((1-(4-methylphenyl)-3-azabicyclo[3.1.0]hex-3-yl)carbonyl)-1,5-dihydro-4H-pyrrolo[3,2-c]pyridin-4-one | 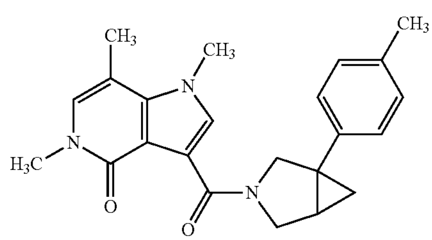 | | 376.04 |
| 133 | 1,5,7-trimethyl-3-((1-(3-methylphenyl)-3-azabicyclo[3.1.0]hex-3-yl)carbonyl)-1,5-dihydro-4H-pyrrolo[3,2-c]pyridin-4-one | 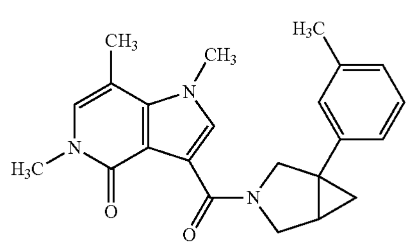 [SMILES: Cc1cccc(C23CC2CN(C(=O)c2cn(C)c4c(C)cn(C)c(=O)c24)C3)c1] | | 376.04 |

TABLE 1-17-continued

| Ex. No. | IUPAC Name | Structure | Additive | MS |
|---|---|---|---|---|
| 134 | 1,5,7-trimethyl-3-((1-(2-methylphenyl)-3-azabicyclo[3.1.0]hex-3-yl)carbonyl)-1,5-dihydro-4H-pyrrolo[3,2-c]pyridin-4-one | 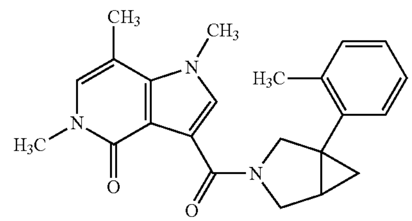 [SMILES: Cc1ccccc1C12CC1CN(C(=O)c1cn(C)c3c(C)cn(C)c(=O)c13)C2] | | 376.07 |
| 135 | 1,5,7-trimethyl-3-((1-(4-(trifluoromethyl)phenyl)-3-azabicyclo[3.1.0]hex-3-yl)carbonyl)-1,5-dihydro-4H-pyrrolo[3,2-c]pyridin-4-one | 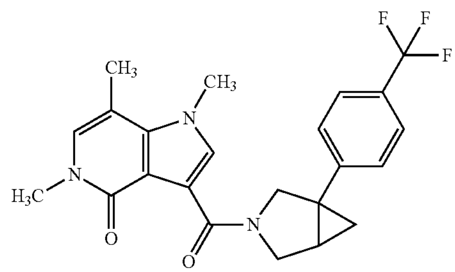 [SMILES: Cc1cn(C)c(=O)c2c(C(=O)N3CC4CC4(c4ccc(C(F)(F)F)cc4)C3)cn(C)c12] | | 430.03 |
| 136 | 1,5,7-trimethyl-3-((1-(3-(trifluoromethyl)phenyl)-3-azabicyclo[3.1.0]hex-3-yl)carbonyl)-1,5-dihydro-4H-pyrrolo[3,2-c]pyridin-4-one | 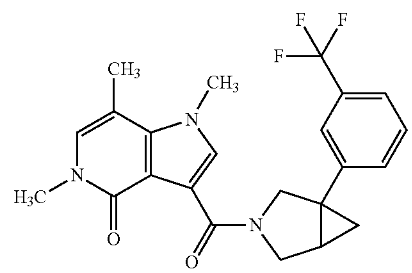 [SMILES: Cc1cn(C)c(=O)c2c(C(=O)N3CC4CC4(c4cccc(C(F)(F)F)c4)C3)cn(C)c12] | | 430 |

TABLE 1-18

| Ex. No. | IUPAC Name | Structure | Additive | MS |
|---|---|---|---|---|
| 137 | 1,5,7-trimethyl-3-((1-(2-(trifluoromethyl)phenyl)-3-azabicyclo[3.1.0]hex-3-yl)carbonyl)-1,5-dihydro-4H-pyrrolo[3,2-c]pyridin-4-one | 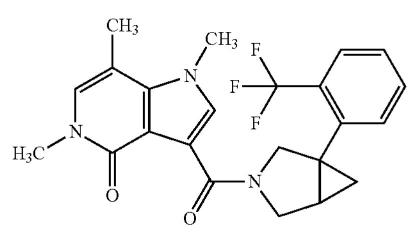 [SMILES: Cc1cn(C)c(=O)c2c(C(=O)N3CC4CC4(c4ccccc4C(F)(F)F)C3)cn(C)c12] | | 430.03 |
| 138 | 3-((1-(3-fluoro-4-(trifluoromethyl)phenyl)-3-azabicyclo[3.1.0]hex-3-yl)carbonyl)-1,5,7-trimethyl-1,5-dihydro-4H-pyrrolo[3,2-c]pyridin-4-one | 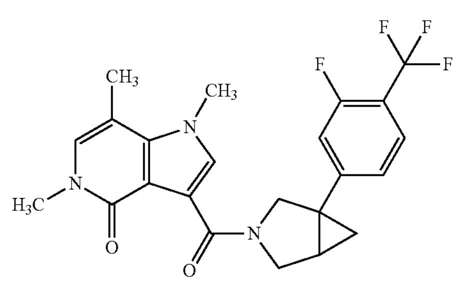 [SMILES: Cc1cn(C)c(=O)c2c(C(=O)N3CC4CC4(c4ccc(C(F)(F)F)c(F)c4)C3)cn(C)c12] | | 447.93 |

TABLE 1-18-continued

| Ex. No. | IUPAC Name | Structure | Additive | MS |
|---|---|---|---|---|
| 139 | 3-((1-(3-fluoro-4-(trifluoromethoxy)phenyl)-3-azabicyclo[3.1.0]hex-3-yl)carbonyl)-1,5,7-trimethyl-1,5-dihydro-4H-pyrrolo[3,2-c]pyridin-4-one | 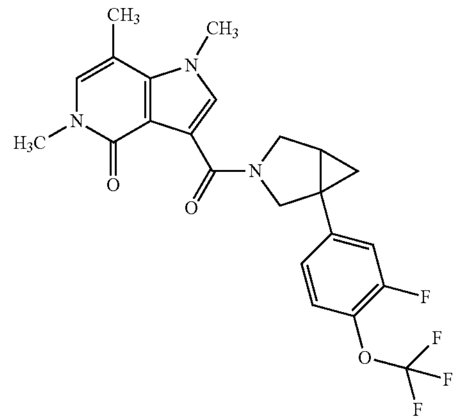 [SMILES: Cc1cn(C)c(=O)c2c(C(=O)N3CC4CC4(c4ccc(OC(F)(F)F)c(F)c4)C3)cn(C)c12] | | 463.96 |
| 140 | 3-((1-(3-chloro-5-(trifluoromethyl)phenyl)-3-azabicyclo[3.1.0]hex-3-yl)carbonyl)-1,5,7-trimethyl-1,5-dihydro-4H-pyrrolo[3,2-c]pyridin-4-one | 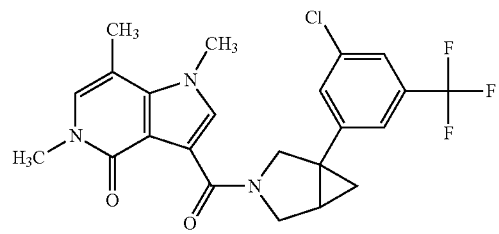 [SMILES: Cc1cn(C)c(=O)c2c(C(=O)N3CC4CC4(c4cc(Cl)cc(C(F)(F)F)c4)C3)cn(C)c12] | | 463.89 |
| 141 | 3-((1-(4-chloro-3-(trifluoromethyl)phenyl)-3-azabicyclo[3.1.0]hex-3-yl)carbonyl)-1,5,7-trimethyl-1,5-dihydro-4H-pyrrolo[3,2-c]pyridin-4-one | 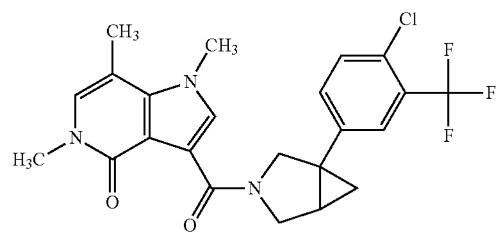 [SMILES: Cc1cn(C)c(=O)c2c(C(=O)N3CC4CC4(c4ccc(Cl)c(C(F)(F)F)c4)C3)cn(C)c12] | | 463.92 |
| 142 | 3-(((1R,5R)-1-(methoxymethyl)-3-azabicyclo[3.1.0]hex-3-yl)carbonyl)-1,5,7-trimethyl-1,5-dihydro-4H-pyrrolo[3,2-c]pyridin-4-one | 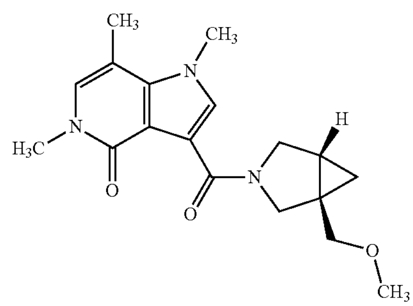 | | 329.96 |
| 143 | 3-(((1S,5R)-1-((dimethylamino)methyl)-3-azabicyclo[3.1.0]hex-3-yl)carbonyl)-1,5,7-trimethyl-1,5-dihydro-4H-pyrrolo[3,2-c]pyridin-4-one | 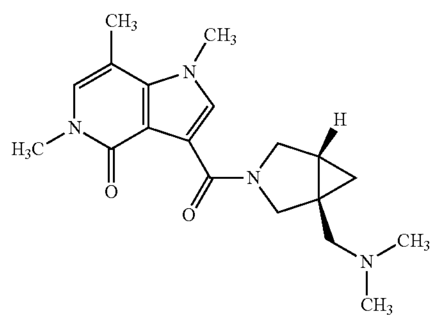 | | 343.04 |

TABLE 1-18-continued

| Ex. No. | IUPAC Name | Structure | Additive | MS |
| --- | --- | --- | --- | --- |
| 144 | 3-(((1R,5R)-1-(difluoromethyl)-3-azabicyclo[3.1.0]hex-3-yl)carbonyl)-1,5,7-trimethyl-1,5-dihydro-4H-pyrrolo[3,2-c]pyridin-4-one | 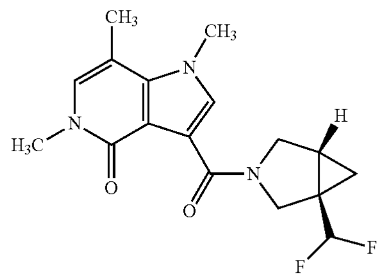 [SMILES: Cc1cn(C)c(=O)c2c(C(=O)N3C[C@@H]4C[C@]4(C(F)F)C3)cn(C)c12] | | 335.96 |

TABLE 1-19

| Ex. No. | IUPAC Name | Structure | Additive | MS |
| --- | --- | --- | --- | --- |
| 145 | ((1R,5R)-3-((1,5,7-trimethyl-4-oxo-4,5-dihydro-1H-pyrrolo[3,2-c]pyridin-3-yl)carbonyl)-3-azabicyclo[3.1.0]hex-1-yl)acetonitrile | 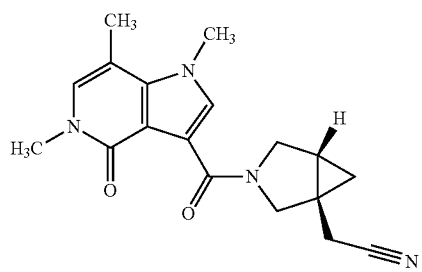 [SMILES: Cc1cn(C)c(=O)c2c(C(=O)N3C[C@@H]4C[C@]4(CC#N)C3)cn(C)c12] | | 324.94 |
| 146 | 3-((6,6-difluoro-1-(4-methylphenyl)-3-azabicyclo[3.1.0]hex-3-yl)carbonyl)-1,5,7-trimethyl-1,5-dihydro-4H-pyrrolo[3,2-c]pyridin-4-one | 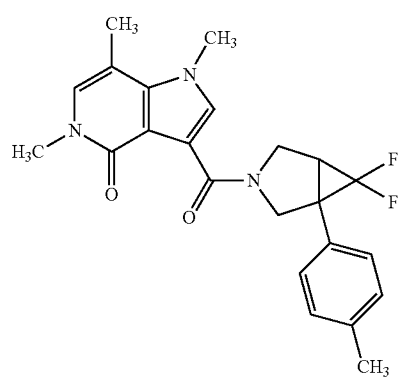 [SMILES: Cc1ccc(C23CN(C(=O)c4cn(C)c5c(C)cn(C)c(=O)c45)CC2C3(F)F)cc1] | | 412.03 |
| 147 | 3-((6,6-difluoro-1-(3-methylphenyl)-3-azabicyclo[3.1.0]hex-3-yl)carbonyl)-1,5,7-trimethyl-1,5-dihydro-4H-pyrrolo[3,2-c]pyridin-4-one | 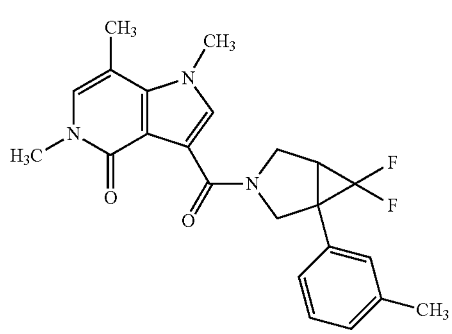 | | 412.03 |

TABLE 1-19-continued

| Ex. No. | IUPAC Name | Structure | Additive | MS |
|---|---|---|---|---|
| 148 | 3-((6,6-difluoro-1-(4-methoxyphenyl)-3-azabicyclo[3.1.0]hex-3-yl)carbonyl)-1,5,7-trimethyl-1,5-dihydro-4H-pyrrolo[3,2-c]pyridin-4-one | 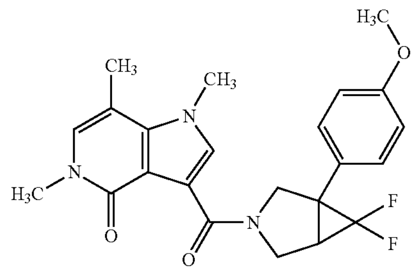 [SMILES: COc1ccc(C23CN(C(=O)c4cn(C)c5c(C)cn(C)c(=O)c45)CC2C3(F)F)cc1] | | 428.04 |
| 149 | 3-((6,6-difluoro-1-(3-methoxyphenyl)-3-azabicyclo[3.1.0]hex-3-yl)carbonyl)-1,5,7-trimethyl-1,5-dihydro-4H-pyrrolo[3,2-c]pyridin-4-one | 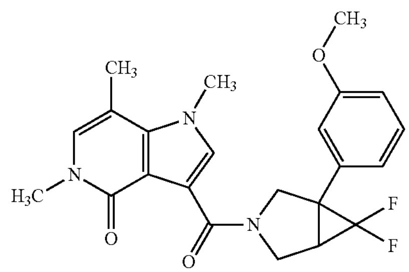 [SMILES: COc1cccc(C23CN(C(=O)c4cn(C)c5c(C)cn(C)c(=O)c45)CC2C3(F)F)c1] | | 428.01 |
| 150 | 3-((6,6-difluoro-1-(2-methoxyphenyl)-3-azabicyclo[3.1.0]hex-3-yl)carbonyl)-1,5,7-trimethyl-1,5-dihydro-4H-pyrrolo[3,2-c]pyridin-4-one | 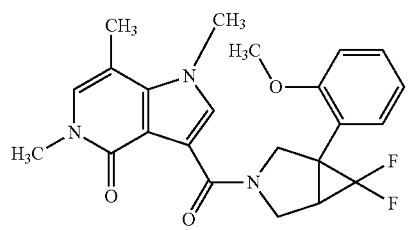 [SMILES: COc1ccccc1C12CN(C(=O)c3cn(C)c4c(C)cn(C)c(=O)c34)CC1C2(F)F] | | 428.04 |
| 151 | 1,5,7-trimethyl-3-((1-(2-(trifluoromethoxy)phenyl)-3-azabicyclo[3.1.0]hex-3-yl)carbonyl)-1,5-dihydro-4H-pyrrolo[3,2-c]pyridin-4-one | 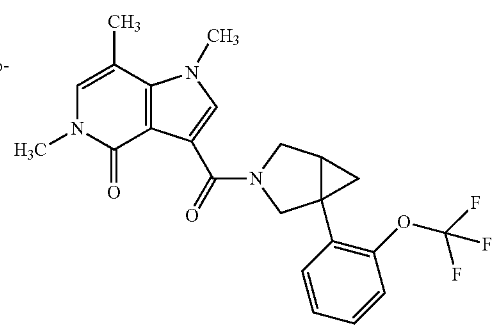 | | 445.97 |
| 152 | 3-((7,7-difluoro-6-phenyl-3-azabicyclo[4.1.0]hept-3-yl)carbonyl)-1,5,7-trimethyl-1,5-dihydro-4H-pyrrolo[3,2-c]pyridin-4-one | 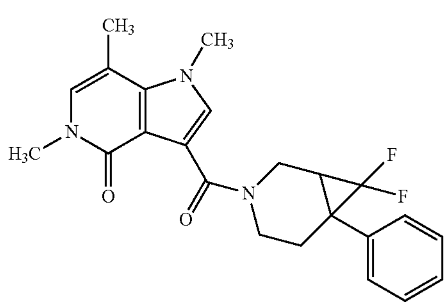 [SMILES: Cc1cn(C)c(=O)c2c(C(=O)N3CCC4(c5ccccc5)C(C3)C4(F)F)cn(C)c12] | | 412.03 |

TABLE 1-20

| Ex. No. | IUPAC Name | Structure | Additive | MS |
|---|---|---|---|---|
| 153 | 3-((6-(4-chlorophenyl)-7,7-difluoro-3-azabicyclo[4.1.0]hept-3-yl)carbonyl)-1,5,7-trimethyl-1,5-dihydro-4H-pyrrolo[3,2-c]pyridin-4-one | 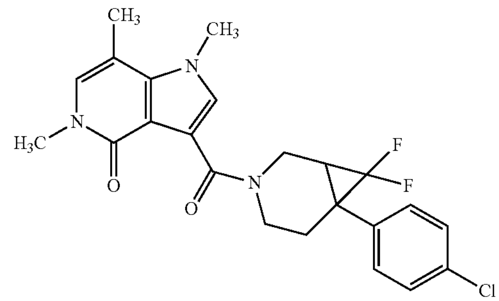 [SMILES: Cc1cn(C)c(=O)c2c(C(=O)N3CCC4(c5ccc(Cl)cc5)C(C3)C4(F)F)cn(C)c12] | | 445.94 |
| 154 | 3-((7,7-difluoro-6-(2-methoxyphenyl)-3-azabicyclo[4.1.0]hept-3-yl)carbonyl)-1,5,7-trimethyl-1,5-dihydro-4H-pyrrolo[3,2-c]pyridin-4-one | 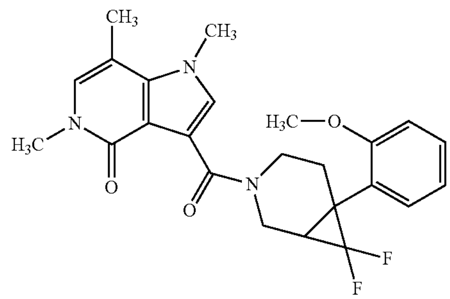 [SMILES: COc1ccccc1C12CCN(C(=O)c3cn(C)c4c(C)cn(C)c(=O)c34)CC1C2(F)F] | | 442 |
| 155 | 3-((6-(3-chlorophenyl)-7,7-difluoro-3-azabicyclo[4.1.0]hept-3-yl)carbonyl)-1,5,7-trimethyl-1,5-dihydro-4H-pyrrolo[3,2-c]pyridin-4-one | 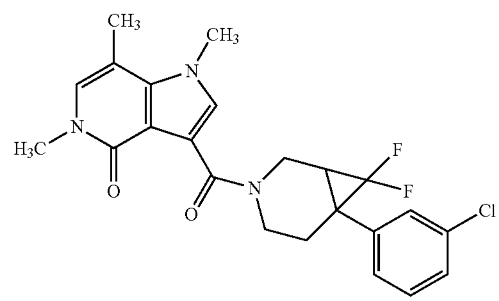 [SMILES: Cc1cn(C)c(=O)c2c(C(=O)N3CCC4(c5cccc(Cl)c5)C(C3)C4(F)F)cn(C)c12] | | 445.97 |
| 156 | 3-((7,7-difluoro-6-(3-methoxyphenyl)-3-azabicyclo[4.1.0]hept-3-yl)carbonyl)-1,5,7-trimethyl-1,5-dihydro-4H-pyrrolo[3,2-c]pyridin-4-one | 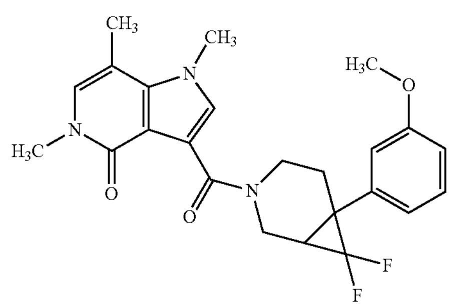 [SMILES: COc1cccc(C23CCN(C(=O)c4cn(C)c5c(C)cn(C)c(=O)c45)CC2C3(F)F)c1] | | 442.03 |
| 157 | 3-((7,7-difluoro-6-(4-methoxyphenyl)-3-azabicyclo[4.1.0]hept-3-yl)carbonyl)-1,5,7-trimethyl-1,5-dihydro-4H-pyrrolo[3,2-c]pyridin-4-one | 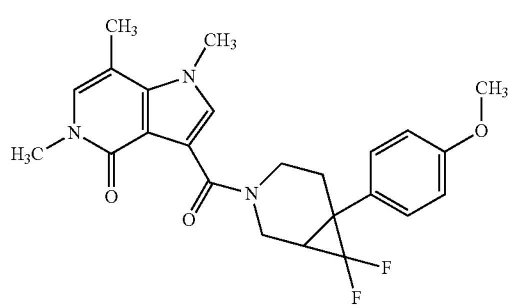 | | 442.03 |

TABLE 1-20-continued

| Ex. No. | IUPAC Name | Structure | Additive | MS |
|---|---|---|---|---|
| 158 | 3-((7,7-difluoro-6-(2-methylphenyl)-3-azabicyclo[4.1.0]hept-3-yl)carbonyl)-1,5,7-trimethyl-1,5-dihydro-4H-pyrrolo[3,2-c]pyridin-4-one | 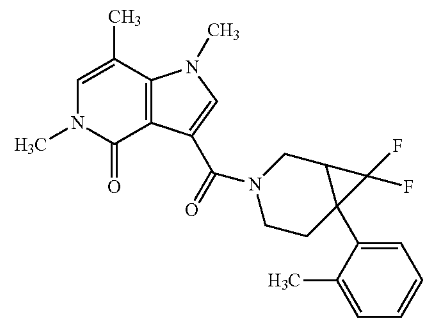 [SMILES: Cc1ccccc1C12CCN(C(=O)c3cn(C)c4c(C)cn(C)c(=O)c34)CC1C2(F)F] | | 426.06 |
| 159 | 3-((7,7-difluoro-6-(3-methylphenyl)-3-azabicyclo[4.1.0]hept-3-yl)carbonyl)-1,5,7-trimethyl-1,5-dihydro-4H-pyrrolo[3,2-c]pyridin-4-one | 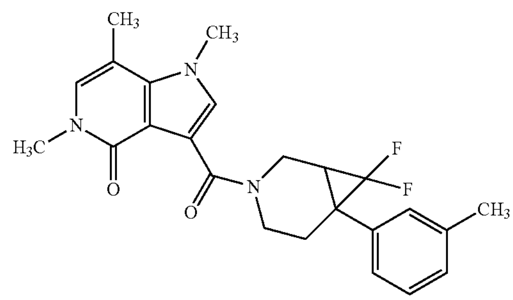 | | 426.06 |
| 160 | 3-((7,7-difluoro-6-(4-methylphenyl)-3-azabicyclo[4.1.0]hept-3-yl)carbonyl)-1,5,7-trimethyl-1,5-dihydro-4H-pyrrolo[3,2-c]pyridin-4-one | 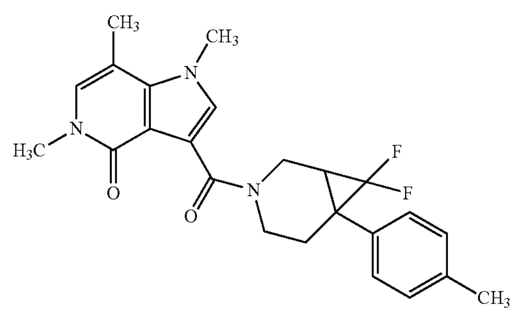 | | 426.06 |

TABLE 1-21

| Ex. No. | IUPAC Name | Structure | Additive | MS |
|---|---|---|---|---|
| 161 | 3-((6-(2-chlorophenyl)-7,7-difluoro-3-azabicyclo[4.1.0]hept-3-yl)carbonyl)-1,5,7-trimethyl-1,5-dihydro-4H-pyrrolo[3,2-c]pyridin-4-one | 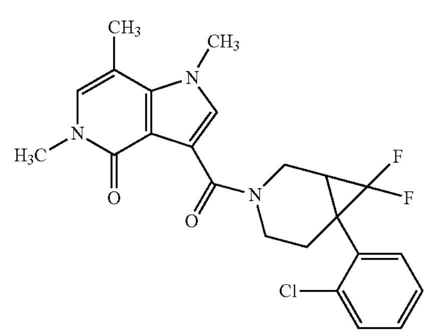 [SMILES: Cc1cn(C)c(=O)c2c(C(=O)N3CCC4(c5ccccc5Cl)C(C3)C4(F)F)cn(C)c12] | | 445.97 |

TABLE 1-21-continued

| Ex. No. | IUPAC Name | Structure | Additive | MS |
|---|---|---|---|---|
| 162 | 1,5,7-trimethyl-3-((6-phenyl-3-azabicyclo[4.1.0]hept-3-yl)carbonyl)-1,5-dihydro-4H-pyrrolo[3,2-c]pyridin-4-one | 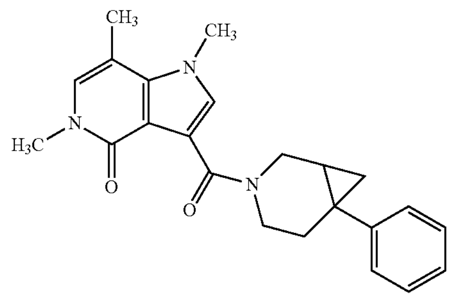 [SMILES: Cc1cn(C)c(=O)c2c(C(=O)N3CCC4(c5ccccc5)CC4C3)cn(C)c12] | | 376.04 |
| 163 | 3-((6-(3-chlorophenyl)-3-azabicyclo[4.1.0]hept-3-yl)carbonyl)-1,5,7-trimethyl-1,5-dihydro-4H-pyrrolo[3,2-c]pyridin-4-one | 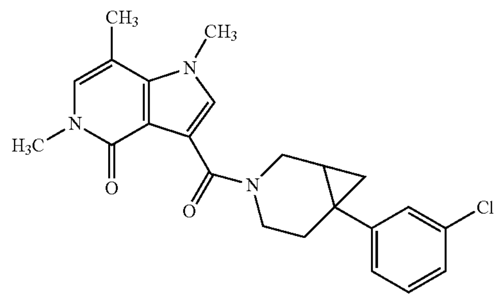 [SMILES: Cc1cn(C)c(=O)c2c(C(=O)N3CCC4(c5cccc(Cl)c5)CC4C3)cn(C)c12] | | 410.01 |
| 164 | 3-((6-(3-methoxyphenyl)-3-azabicyclo[4.1.0]hept-3-yl)carbonyl)-1,5,7-trimethyl-1,5-dihydro-4H-pyrrolo[3,2-c]pyridin-4-one | 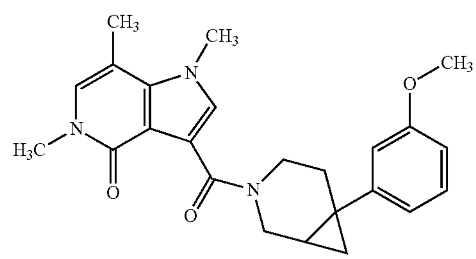 | | 406.07 |
| 165 | 1,5,7-trimethyl-3-((6-(2-methylphenyl)-3-azabicyclo[4.1.0]hept-3-yl)carbonyl)-1,5-dihydro-4H-pyrrolo[3,2-c]pyridin-4-one | 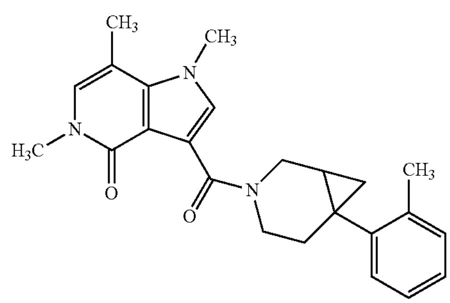 [SMILES: Cc1ccccc1C12CCN(C(=O)c3cn(C)c4c(C)cn(C)c(=O)c34)CC1C2] | | 390.06 |
| 166 | 1,5,7-trimethyl-3-((6-(3-methylphenyl)-3-azabicyclo[4.1.0]hept-3-yl)carbonyl)-1,5-dihydro-4H-pyrrolo[3,2-c]pyridin-4-one | 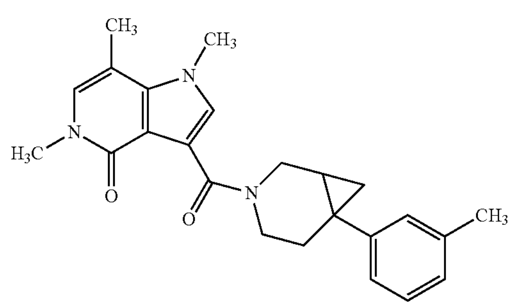 | | 390.02 |

TABLE 1-21-continued

| Ex. No. | IUPAC Name | Structure | Additive | MS |
|---|---|---|---|---|
| 167 | 3-((6-(2-methoxyphenyl)-3-azabicyclo[4.1.0]hept-3-yl)carbonyl)-1,5,7-trimethyl-1,5-dihydro-4H-pyrrolo[3,2-c]pyridin-4-one | 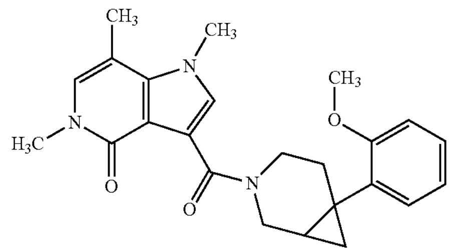 [SMILES: COc1ccccc1C12CCN(C(=O)c3cn(C)c4c(C)cn(C)c(=O)c34)CC1C2] | | 406.03 |
| 168 | 3-((3-(4-chlorophenyl)-3-fluoropyrrolidin-1-yl)carbonyl)-1,5,7-trimethyl-1,5-dihydro-4H-pyrrolo[3,2-c]pyridin-4-one | 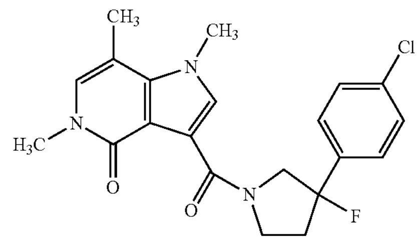 [SMILES: Cc1cn(C)c(=O)c2c(C(=O)N3CCC(F)(c4ccc(Cl)cc4)C3)cn(C)c12] | | 402.02 |

TABLE 1-22

| Ex. No. | IUPAC Name | Structure | Additive | MS |
|---|---|---|---|---|
| 169 | 1,5,7-trimethyl-3-((3-(trifluoromethoxy)pyrrolidin-1-yl)carbonyl)-1,5-dihydro-4H-pyrrolo[3,2-c]pyridin-4-one | 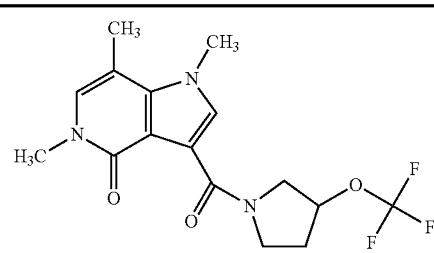 | | 357.97 |
| 170 | 3-((3-methoxypyrrolidin-1-yl)carbonyl)-1,5,7-trimethyl-1,5-dihydro-4H-pyrrolot[3,2-c]pyridin-4-one | 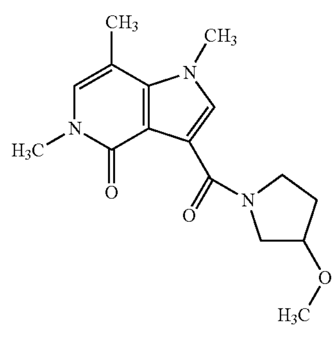 [SMILES: COC1CCN(C(=O)c2cn(C)c3c(C)cn(C)c(=O)c23)C1] | | 303.98 |
| 171 | 3-((4-(cyclopropylmethoxy)piperidin-1-yl)carbonyl)-1,5,7-trimethyl-1,5-dihydro-4H-pyrrolo[3,2-c]pyridin-4-one | 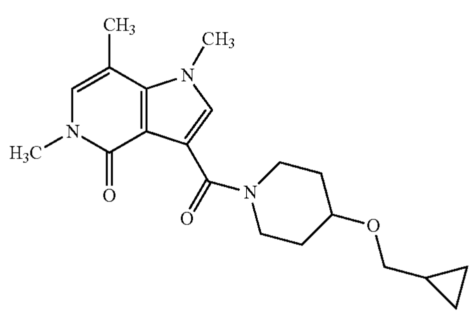 [SMILES: Cc1cn(C)c(=O)c2c(C(=O)N3CCC(OCC4CC4)CC3)cn(C)c12] | | 358.04 |

TABLE 1-22-continued

| Ex. No. | IUPAC Name | Structure | Additive | MS |
|---|---|---|---|---|
| 172 | 3-((4-methoxypiperidin-1-yl)carbonyl)-1,5,7-trimethyl-1,5-dihydro-4H-pyrrolo[3,2-c]pyridin-4-one | 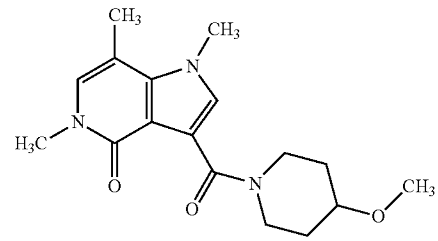 | | 318 |
| 173 | 3-((4-(2-chlorophenoxy)piperidin-1-yl)carbonyl)-1,5,7-trimethyl-1,5-dihydro-4H-pyrrolo[3,2-c]pyridin-4-one | 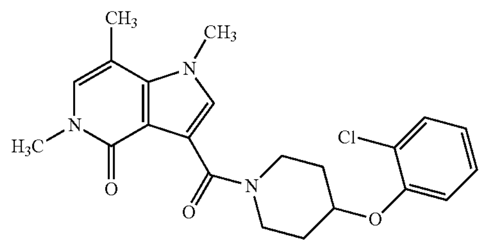 [SMILES: Cc1cn(C)c(=O)c2c(C(=O)N3CCC(Oc4ccccc4Cl)CC3)cn(C)c12] | | 414.02 |
| 174 | 1,5,7-trimethyl-3-((4-(2-methylphenoxy)piperidin-1-yl)carbonyl)-1,5-dihydro-4H-pyrrolo[3,2-c]pyridin-4-one | 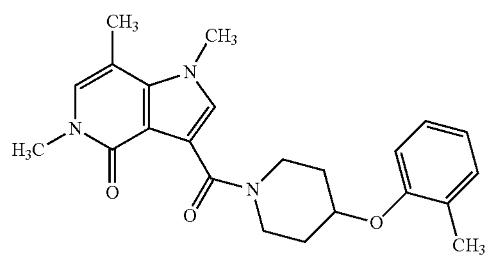 [SMILES: Cc1ccccc1OC1CCN(C(=O)c2cn(C)c3c(C)cn(C)c(=O)c23)CC1] | | 394.04 |
| 175 | 1,5,7-trimethyl-3-((4-phenoxypiperidin-1-yl)carbonyl)-1,5-dihydro-4H-pyrrolo[3,2-c]pyridin-4-one | 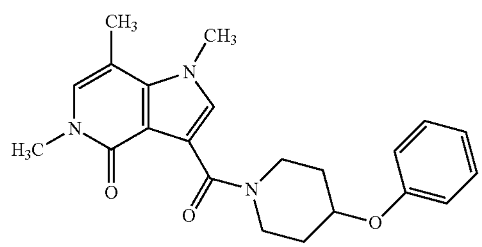 [SMILES: Cc1cn(C)c(=O)c2c(C(=O)N3CCC(Oc4ccccc4)CC3)cn(C)c12] | | 380.05 |
| 176 | 1,5,7-trimethyl-3-((4-(3-(trifluoromethyl)phenoxy)piperidin-1-yl)carbonyl)-1,5-dihydro-4H-pyrrolo[3,2-c]pyridin-4-one | 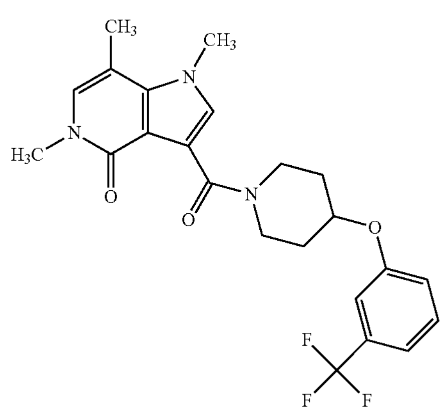 [SMILES: Cc1cn(C)c(=O)c2c(C(=O)N3CCC(Oc4cccc(C(F)(F)F)c4)CC3)cn(C)c12] | | 447.96 |

TABLE 1-23

| Ex. No. | IUPAC Name | Structure | Additive | MS |
|---|---|---|---|---|
| 177 | 3-((4-(difluoromethoxy)piperidin-1-yl)carbonyl)-1,5,7-trimethyl-1,5-dihydro-4H-pyrrolo[3,2-c]pyridin-4-one | 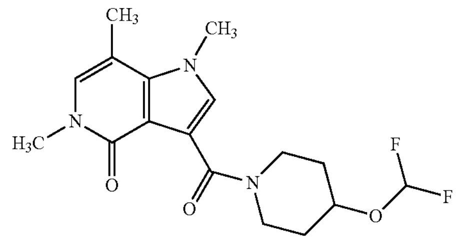 [SMILES: Cc1cn(C)c(=O)c2c(C(=O)N3CCC(OC(F)F)CC3)cn(C)c12] | | 353.99 |
| 178 | 3-((4-(3,4-dichlorophenoxy)piperidin-1-yl)carbonyl)-1,5,7-trimethyl-1,5-dihydro-4H-pyrrolo[3,2-c]pyridin-4-one | 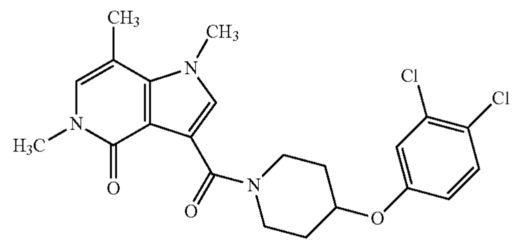 [SMILES: Cc1cn(C)c(=O)c2c(C(=O)N3CCC(Oc4ccc(Cl)c(Cl)c4)CC3)cn(C)c12] | | 447.93 |
| 179 | 1,5,7-trimethyl-3-((4-(4-methylphenoxy)piperidin-1-yl)carbonyl)-1,5-dihydro-4H-pyrrolo[3,2-c]pyridin-4-one | 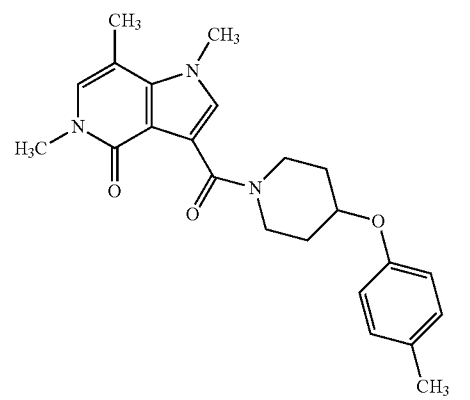 [SMILES: Cc1ccc(OC2CCN(C(=O)c3cn(C)c4c(C)cn(C)c(=O)c34)CC2)cc1] | | 394.07 |
| 180 | 3-((4-(benzyloxy)piperidin-1-yl)carbonyl)-1,5,7-trimethyl-1,5-dihydro-4H-pyrrolo[3,2-c]pyridin-4-one | 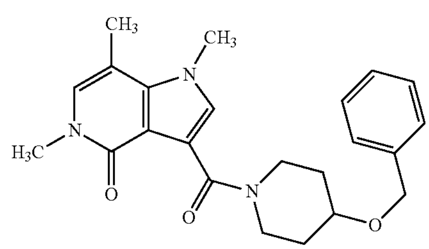 [SMILES: Cc1cn(C)c(=O)c2c(C(=O)N3CCC(OCc4ccccc4)CC3)cn(C)c12] | | 394.07 |
| 181 | 3-((4-(4-fluorophenoxy)piperidin-1-yl)carbonyl)-1,5,7-trimethyl-1,5-dihydro-4H-pyrrolo[3,2-c]pyridin-4-one | 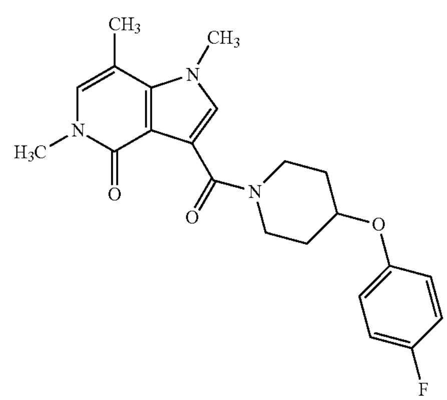 [SMILES: Cc1cn(C)c(=O)c2c(C(=O)N3CCC(Oc4ccc(F)cc4)CC3)cn(C)c12] | | 398.05 |

TABLE 1-23-continued

| Ex. No. | IUPAC Name | Structure | Additive | MS |
|---|---|---|---|---|
| 182 | 1,5,7-trimethyl-3-((4-(trifluoromethoxy)piperidin-1-yl)carbonyl)-1,5-dihydro-4H-pyrrolo[3,2-c]pyridin-4-one | 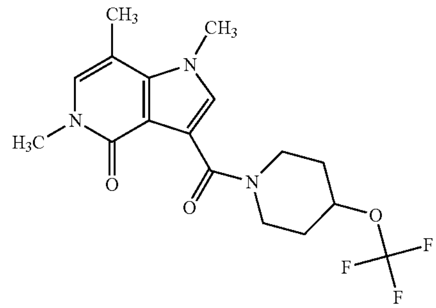 [SMILES: Cc1cn(C)c(=O)c2c(C(=O)N3CCC(OC(F)(F)F)CC3)cn(C)c12] | | 371.99 |
| 183 | 1,5,7-trimethyl-3-((4-(2-(trifluoromethyl)phenoxy)piperidin-1-yl)carbonyl)-1,5-dihydro-4H-pyrrolo[3,2-c]pyridin-4-one | 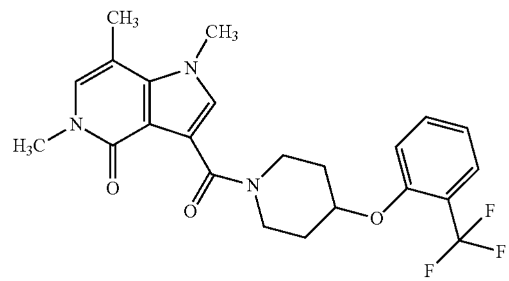 [SMILES: Cc1cn(C)c(=O)c2c(C(=O)N3CCC(Oc4ccccc4C(F)(F)F)CC3)cn(C)c12] | | 447.96 |
| 184 | 2-((1-((1,5,7-trimethyl-4-oxo-4,5-dihydro-1H-pyrrolo[3,2-c]pyridin-3-yl)carbonyl)piperidin-4-yl)oxy)benzonitrile | 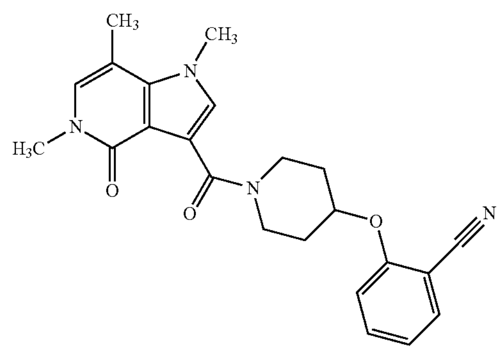 [SMILES: Cc1cn(C)c(=O)c2c(C(=O)N3CCC(Oc4ccccc4C#N)CC3)cn(C)c12] | | 404.99 |

TABLE 1-24

| Ex. No. | IUPAC Name | Structure | Additive | MS |
|---|---|---|---|---|
| 185 | 3-((4-(4-methoxyphenoxy)piperidin-1-yl)carbonyl)-1,5,7-trimethyl-1,5-dihydro-4H-pyrrolo[3,2-c]pyridin-4-one | 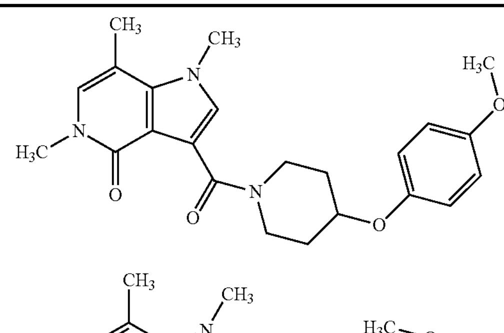 | | 410.05 |
| 186 | 3-((4-(3-methoxyphenoxy)piperidin-1-yl)carbonyl)-1,5,7-trimethyl-1,5-dihydro-4H-pyrrolo[3,2-c]pyridin-4-one | 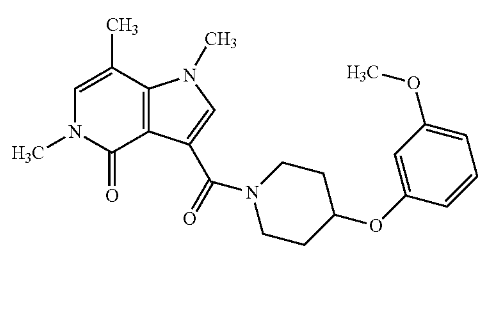 [SMILES: COc1cccc(OC2CCN(C(=O)c3cn(C)c4c(C)cn(C)c(=O)c34)CC2)c1] | | 410.05 |

TABLE 1-24-continued

| Ex. No. | IUPAC Name | Structure | Additive | MS |
|---|---|---|---|---|
| 187 | 3-((4-(2-methoxyphenoxy)piperidin-1-yl)carbonyl)-1,5,7-trimethyl-1,5-dihydro-4H-pyrrolo[3,2-c]pyridin-4-one | 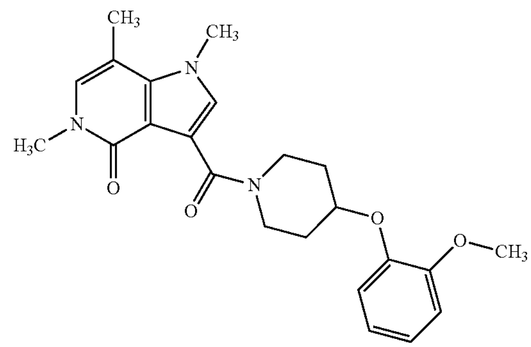 | | 410.05 |
| 188 | 3-((4-(3-chlorophenoxy)piperidin-1-yl)carbonyl)-1,5,7-trimethyl-1,5-dihydro-4H-pyrrolo[3,2-c]pyridin-4-one | 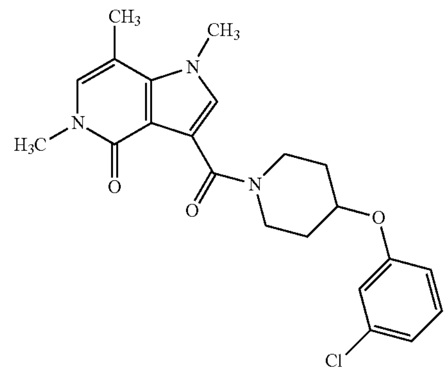 [SMILES: Cc1cn(C)c(=O)c2c(C(=O)N3CCC(Oc4cccc(Cl)c4)CC3)cn(C)c12] | | 414.02 |
| 189 | 3-((4-(4-chlorophenoxy)piperidin-1-yl)carbonyl)-1,5,7-trimethyl-1,5-dihydro-4H-pyrrolo[3,2-c]pyridin-4-one | 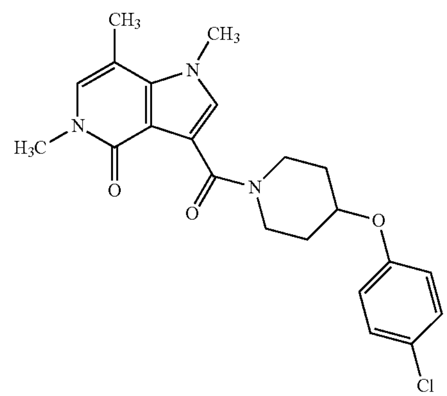 [SMILES: Cc1cn(C)c(=O)c2c(C(=O)N3CCC(Oc4ccc(Cl)cc4)CC3)cn(C)c12] | | 413.99 |
| 190 | 1,5,7-trimethyl-3-((4-(4-(trifluoromethyl)phenoxy)piperidin-1-yl)carbonyl)-1,5-dihydro-4H-pyrrolo[3,2-c]pyridin-4-one | 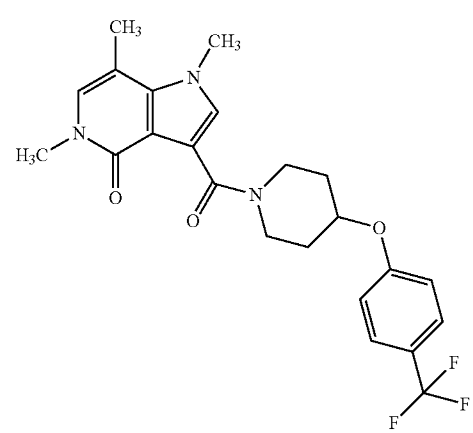 [SMILES: Cc1cn(C)c(=O)c2c(C(=O)N3CCC(Oc4ccc(C(F)(F)F)cc4)CC3)cn(C)c12] | | 448 |

TABLE 1-24-continued

| Ex. No. | IUPAC Name | Structure | Additive | MS |
|---|---|---|---|---|
| 191 | 1,5,7-trimethyl-3-((3-phenoxyazetidin-1-yl)carbonyl)-1,5-dihydro-4H-pyrrolo[3,2-c]pyridin-4-one | 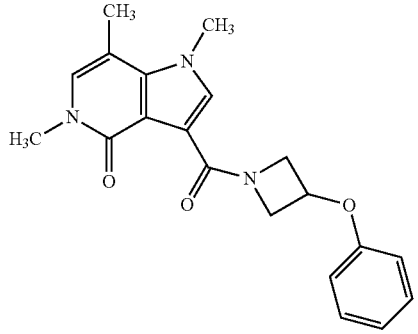 [SMILES: Cc1cn(C)c(=O)c2c(C(=O)N3CC(Oc4ccccc4)C3)cn(C)c12] | | 351.97 |
| 192 | 3-((3-methoxyazetidin-1-yl)carbonyl)-1,5,7-trimethyl-1,5-dihydro-4H-pyrrolo[3,2-c]pyridin-4-one | 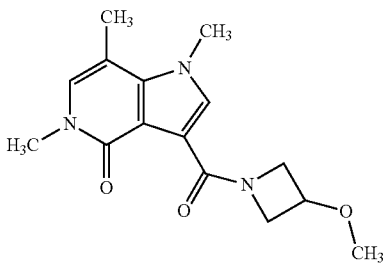 | | 289.99 |

TABLE 1-25

| Ex. No. | IUPAC Name | Structure | Additive | MS |
|---|---|---|---|---|
| 193 | 3-((3-(difluoromethoxy)azetidin-1-yl)carbonyl)-1,5,7-trimethyl-1,5-dihydro-4H-pyrrolo[3,2-c]pyridin-4-one | 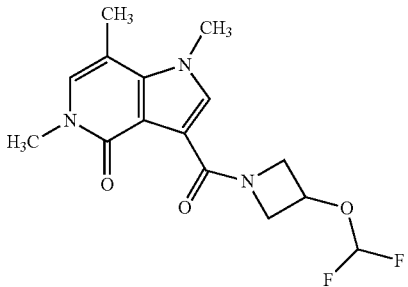 [SMILES: Cc1cn(C)c(=O)c2c(C(=O)N3CC(OC(F)F)C3)cn(C)c12] | | 325.91 |
| 194 | 3-((3-(benzyloxy)azetidin-1-yl)carbonyl)-1,5,7-trimethyl-1,5-dihydro-4H-pyrrolo[3,2-c]pyridin-4-one | 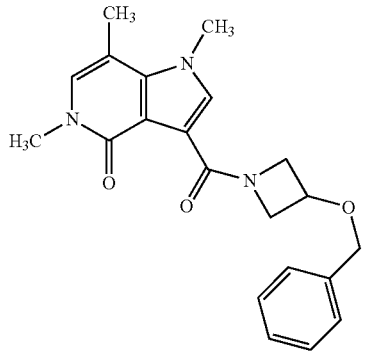 [SMILES: Cc1cn(C)c(=O)c2c(C(=O)N3CC(OCc4ccccc4)C3)cn(C)c12] | | 366.03 |

TABLE 1-25-continued

| Ex. No. | IUPAC Name | Structure | Additive | MS |
|---|---|---|---|---|
| 195 | 3-((2-isopropylazetidin-1-yl)carbonyl)-1,5,7-trimethyl-1,5-dihydro-4H-pyrrolo[3,2-c]pyridin-4-one | 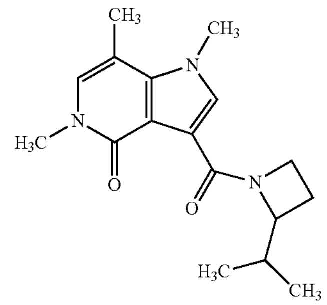 [SMILES: Cc1cn(C)c(=O)c2c(C(=O)N3CCC3C(C)C)cn(C)c12] | | 301.99 |
| 196 | 3-((2-cyclopropylazetidin-1-yl)carbonyl)-1,5,7-trimethyl-1,5-dihydro-4H-pyrrolo[3,2-c]pyridin-4-one | 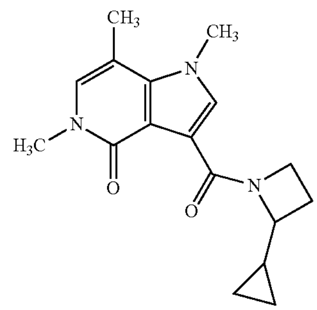 [SMILES: Cc1cn(C)c(=O)c2c(C(=O)N3CCC3C3CC3)cn(C)c12] | | 300 |
| 197 | 3-(1-azaspiro[3.3]hept-1-ylcarbonyl)-1,5,7-trimethyl-1,5-dihydro-4H-pyrrolo[3,2-c]pyridin-4-one | 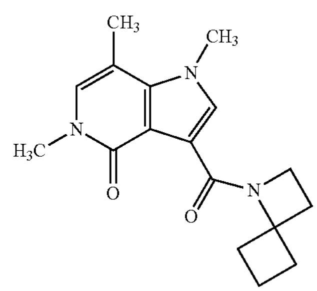 [SMILES: Cc1cn(C)c(=O)c2c(C(=O)N3CCC34CCC4)cn(C)c12] | | 300 |
| 198 | 3-(((2R)-2-(methoxymethyl)azetidin-1-yl)carbonyl)-1,5,7-trimethyl-1,5-dihydro-4H-pyrrolo[3,2-c]pyridin-4-one | 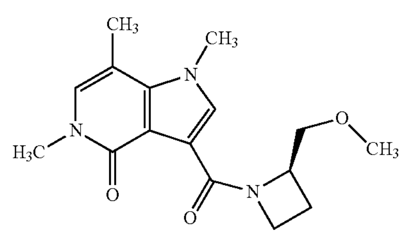 | | 303.94 |
| 199 | 1,5,7-trimethyl-3-(6-oxa-1-azaspiro[3.5]non-1-ylcarbonyl)-1,5-dihydro-4H-pyrrolo[3,2-c]pyridin-4-one | 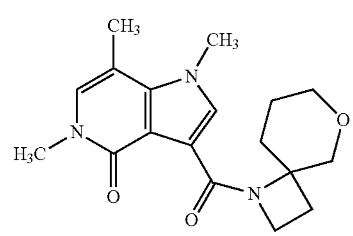 [SMILES: Cc1cn(C)c(=O)c2c(C(=O)N3CCC34CCCOC4)cn(C)c12] | | 329.96 |

TABLE 1-25-continued

| Ex. No. | IUPAC Name | Structure | Additive | MS |
|---|---|---|---|---|
| 200 | 1,5,7-trimethyl-3-(6-oxa-1-azaspiro[3.3]hept-1-ylcarbonyl)-1,5-dihydro-4H-pyrrolo[3,2-c]pyridin-4-one | 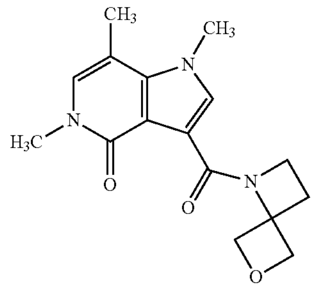 [SMILES: Cc1cn(C)c(=O)c2c(C(=O)N3CCC34COC4)cn(C)c12] | | 301.95 |

TABLE 1-26

| Ex. No. | IUPAC Name | Structure | Additive | MS |
|---|---|---|---|---|
| 201 | 3-(azetidin-1-ylcarbonyl)-1,5,7-trimethyl-1,5-dihydro-4H-pyrrolo[3,2-c]pyridin-4-one | 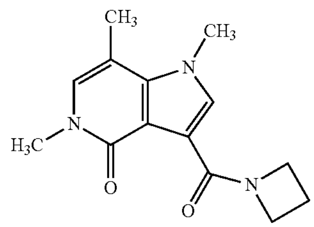 [SMILES: Cc1cn(C)c(=O)c2c(C(=O)N3CCC3)cn(C)c12] | | 259.99 |
| 202 | 1,5,7-trimethyl-3-((2-methylazetidin-1-yl)carbonyl)-1,5-dihydro-4H-pyrrolo[3,2-c]pyridin-4-one | 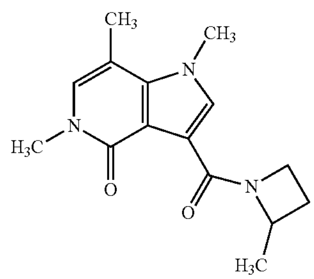 [SMILES: Cc1cn(C)c(=O)c2c(C(=O)N3CCC3C)cn(C)c12] | | 274.01 |
| 203 | 3-((2,2-dimethylazetidin-1-yl)carbonyl)-1,5,7-trimethyl-1,5-dihydro-4H-pyrrolo[3,2-c]pyridin-4-one | 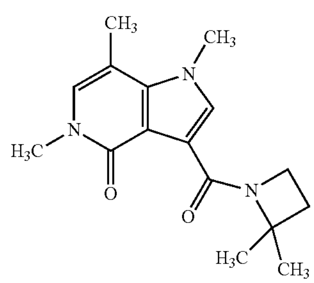 [SMILES: Cc1cn(C)c(=O)c2c(C(=O)N3CCC3(C)C)cn(C)c12] | | 287.97 |
| 204 | 1,5,7-trimethyl-3-(6-oxa-1-azaspiro[3.4]oct-1-ylcarbonyl)-1,5-dihydro-4H-pyrrolo[3,2-c]pyridin-4-one | 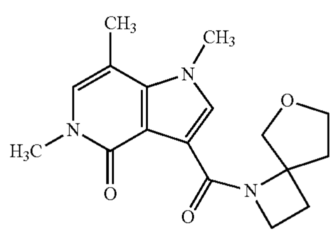 [SMILES: Cc1cn(C)c(=O)c2c(C(=O)N3CCC34CCOC4)cn(C)c12] | | 315.97 |

TABLE 1-26-continued

| Ex. No. | IUPAC Name | Additive | MS |
|---|---|---|---|
| 205 | 3-(((1R,5S)-1-(3,4-dichlorophenyl)-3-azabicyclo[3.1.0]hex-3-yl)carbonyl)-1,5,7-trimethyl-1,5-dihydro-4H-pyrrolo[3,2-c]pyridin-4-one | | 430 |
| 206 | 3-(((1S,5R)-1-(3,4-dichlorophenyl)-3-azabicyclo[3.1.0]hex-3-yl)carbonyl)-1,5,7-trimethyl-1,5-dihydro-4H-pyrrolo[3,2-c]pyridin-4-one | | 429.96 |
| 207 | 3-((2-(4-chlorophenyl)azetidin-1-yl)carbonyl)-1,5,7-trimethyl-1,5-dihydro-4H-pyrrolo[3,2-c]pyridin-4-one | | 370.19 |
| 208 | N-(trans-4-butoxycyclohexyl)-7-ethyl-1,5-dimethyl-4-oxo-4,5-dihydro-1H-pyrrolo[3,2-c]pyridine-3-carboxamide | | 388.14 |

TABLE 1-27

| Ex. No. | IUPAC Name | Structure | Additive | MS |
|---|---|---|---|---|
| 209 | 3-((2-(4-fluorophenyl)azetidin-1-yl)carbonyl)-1,5,7-trimethyl-1,5-dihydro-4H-pyrrolo[3,2-c]pyridin-4-one | 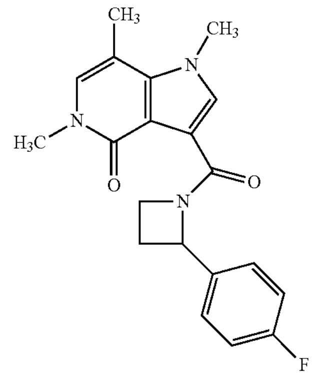 [SMILES: Cc1cn(C)c(=O)c2c(C(=O)N3CCC3c3ccc(F)cc3)cn(C)c12] | | 353.99 |
| 210 | 3-((2-(4-chlorophenyl)azetidin-1-yl)carbonyl)-1,5,7-trimethyl-1,5-dihydro-4H-pyrrolo[3,2-c]pyridin-4-one | 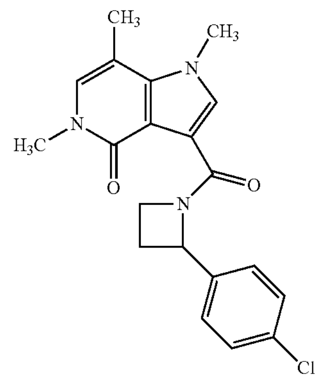 [SMILES: Cc1cn(C)c(=O)c2c(C(=O)N3CCC3c3ccc(Cl)cc3)cn(C)c12] | | 370 |
| 211 | 3-((2-(4-chlorophenyl)azetidin-1-yl)carbonyl)-1,5,7-trimethyl-1,5-dihydro-4H-pyrrolo[3,2-c]pyridin-4-one | 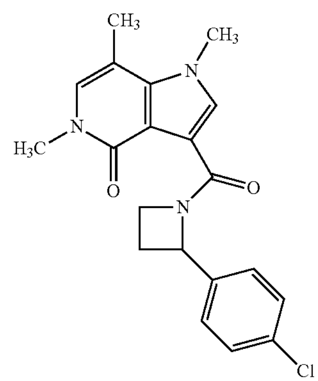 [SMILES: Cc1cn(C)c(=O)c2c(C(=O)N3CCC3c3ccc(Cl)cc3)cn(C)c12] | | 369.97 |
| 212 | 1,5,7-trimethyl-N-((3-methyl-1-phenyl-1H-pyrazol-4-yl)methyl)-4-oxo-4,5-dihydro-1H-pyrrolo[3,2-c]pyridine-3-carboxamide | 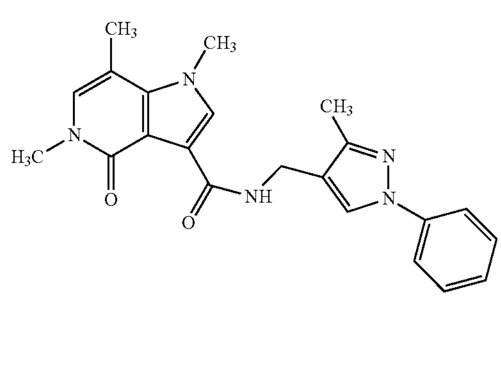 [SMILES: Cc1nn(-c2ccccc2)cc1CNC(=O)c1cn(C)c2c(C)cn(C)c(=O)c12] | | 390.19 |

TABLE 1-27-continued

| Ex. No. | IUPAC Name | Structure | Additive | MS |
|---|---|---|---|---|
| 213 | 1,5,7-trimethyl-N-((5-methyl-2-phenyl-2H-1,2,3-triazol-4-yl)methyl)-4-oxo-4,5-dihydro-1H-pyrrolo[3,2-c]pyridine-3-carboxamide | 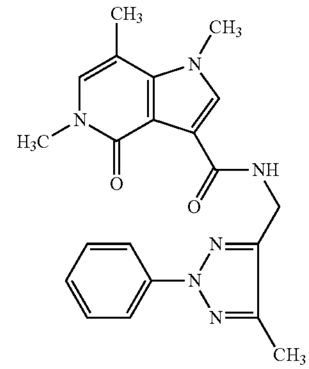 | | 391.24 |
| 214 | 1,5,7-trimethyl-N-((4-methyl-2-phenyl-1,3-thiazol-5-yl)methyl)-4-oxo-4,5-dihydro-1H-pyrrolo[3,2-c]pyridine-3-carboxamide | 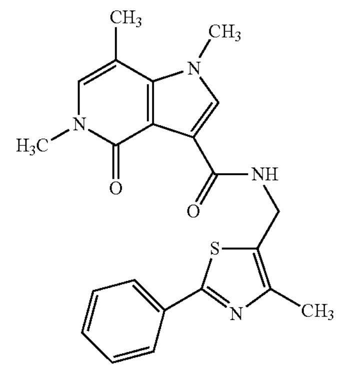 | | 407.18 |
| 215 | N-((3,5-dimethyl-1-(2-methylphenyl)-1H-pyrazol-4-yl)methyl)-1,5,7-trimethyl-4-oxo-4,5-dihydro-1H-pyrrolo[3,2-c]pyridine-3-carboxamide | 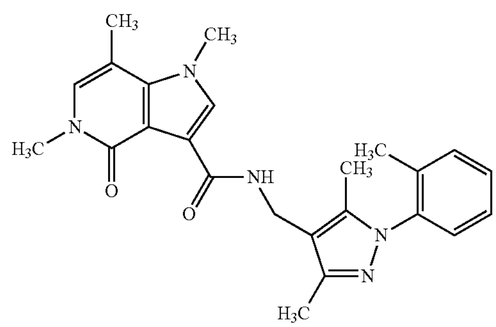 [SMILES: Cc1ccccc1-n1nc(C)c(CNC(=O)c2cn(C)c3c(C)cn(C)c(=O)c23)c1C] | | 418.27 |
| 216 | N-((3,5-dimethyl-1-(3-methylphenyl)-1H-pyrazol-4-yl)methyl)-1,5,7-trimethyl-4-oxo-4,5-dihydro-1H-pyrrolo[3,2-c]pyridine-3-carboxamide | 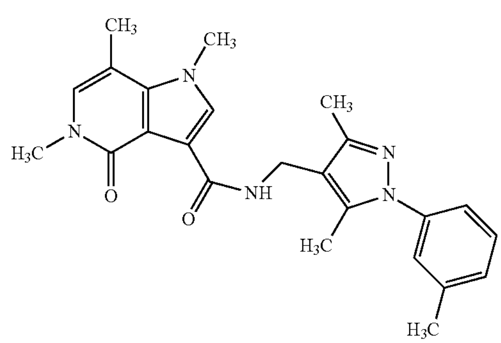 [SMILES: Cc1cccc(-n2nc(C)c(CNC(=O)c3cn(C)c4c(C)cn(C)c(=O)c34)c2C)c1] | | 418.3 |

TABLE 1-28

| Ex. No. | IUPAC Name | Structure | Additive | MS |
|---|---|---|---|---|
| 217 | N-((5-(4-chlorophenyl)-2-thienyl)methyl)-1,5,7-trimethyl-4-oxo-4,5-dihydro-1H-pyrrolo[3,2-c]pyridine-3-carboxamide | 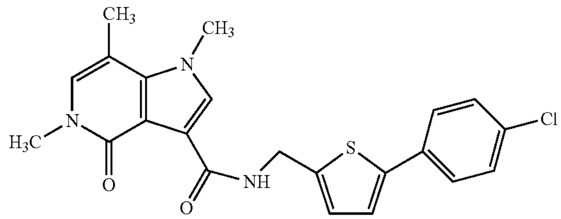 [SMILES: Cc1cn(C)c(=O)c2c(C(=O)NCc3ccc(-c4ccc(Cl)cc4)s3)cn(C)c12] | | 426.15 |
| 218 | N-tert-butyl-1,5,7-trimethyl-4-oxo-4,5-dihydro-1H-pyrrolo[3,2-c]pyridine-3-carboxamide | 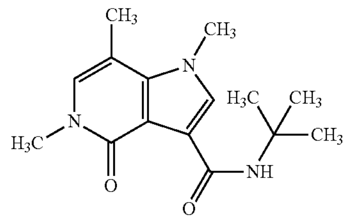 [SMILES: Cc1cn(C)c(=O)c2c(C(=O)NC(C)(C)C)cn(C)c12] | | 276.14 |
| 219 | 1,5,7-trimethyl-4-oxo-N-(2-phenylpropan-2-yl)-4,5-dihydro-1H-pyrrolo[3,2-c]pyridine-3-carboxamide | 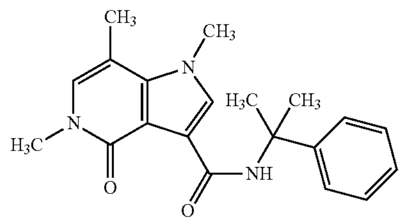 [SMILES: Cc1cn(C)c(=O)c2c(C(=O)NC(C)(C)c3ccccc3)cn(C)c12] | | 338.18 |
| 220 | N-(2-cyanopropan-2-yl)-1,5,7-trimethyl-4-oxo-4,5-dihydro-1H-pyrrolo[3,2-c]pyridine-3-carboxamide | 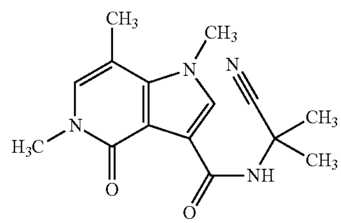 [SMILES: Cc1cn(C)c(=O)c2c(C(=O)NC(C)(C)C#N)cn(C)c12] | | 287.13 |
| 221 | N-(2-(4-chlorophenyl)propan-2-yl)-1,5,7-trimethyl-4-oxo-4,5-dihydro-1H-pyrrolo[3,2-c]pyridine-3-carboxamide | 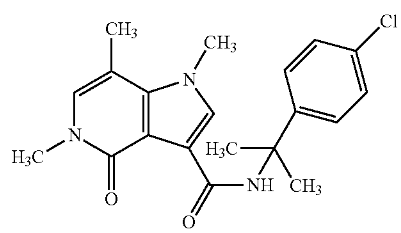 [SMILES: Cc1cn(C)c(=O)c2c(C(=O)NC(C)(C)c3ccc(Cl)cc3)cn(C)c12] | | 372.18 |
| 222 | 1,5,7-trimethyl-4-oxo-N-(2-(pyridin-2-yl)propan-2-yl)-4,5-dihydro-1H-pyrrolo[3,2-c]pyridine-3-carboxamide | 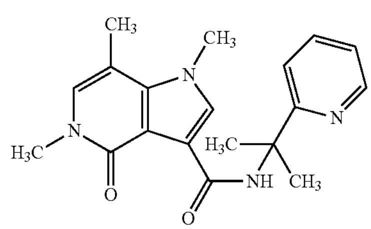 [SMILES: Cc1cn(C)c(=O)c2c(C(=O)NC(C)(C)c3ccccn3)cn(C)c12] | | 339.16 |
| 223 | N-(4,4-difluorocyclohexyl)-1,5,7-trimethyl-4-oxo-4,5-dihydro-1H-pyrrolo[3,2-c]pyridine-3-carboxamide | 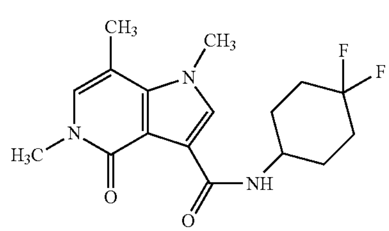 [SMILES: Cc1cn(C)c(=O)c2c(C(=O)NC3CCC(F)(F)CC3)cn(C)c12] | | 338.15 |

TABLE 1-28-continued

| Ex. No. | IUPAC Name | Structure | Additive | MS |
|---|---|---|---|---|
| 224 | 1,5,7-trimethyl-4-oxo-N-(4-(trifluoromethyl)cyclohexyl)-4,5-dihydro-1H-pyrrolo[3,2-c]pyridine-3-carboxamide | 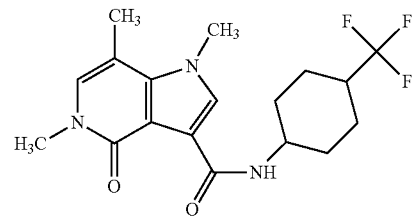 [SMILES: Cc1cn(C)c(=O)c2c(C(=O)NC3CCC(C(F)(F)F)CC3)cn(C)c12] | | 370.2 |

TABLE 1-29

| Ex. No. | IUPAC Name | Structure | Additive | MS |
|---|---|---|---|---|
| 225 | N-(trans-4-cyanocyclohexyl)-1,5,7-trimethyl-4-oxo-4,5-dihydro-1H-pyrrolo[3,2-c]pyridine-3-carboxamide | 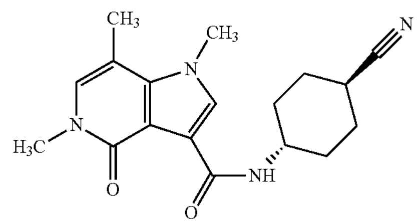 [SMILES: Cc1cn(C)c(=O)c2c(C(=O)N[C@H]3CC[C@H](C#N)CC3)cn(C)c12] | | 327.16 |
| 226 | N-(1-(2-chlorophenyl)cyclobutyl)-1,5,7-trimethyl-4-oxo-4,5-dihydro-1H-pyrrolo[3,2-c]pyridine-3-carboxamide | 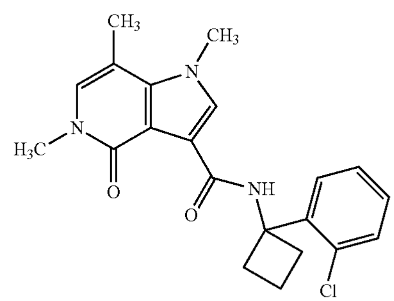 [SMILES: Cc1cn(C)c(=O)c2c(C(=O)NC3(c4ccccc4Cl)CCC3)cn(C)c12] | | 384.15 |
| 227 | N-(1-(3-chlorophenyl)cyclobutyl)-1,5,7-trimethyl-4-oxo-4,5-dihydro-1H-pyrrolo[3,2-c]pyridine-3-carboxamide | 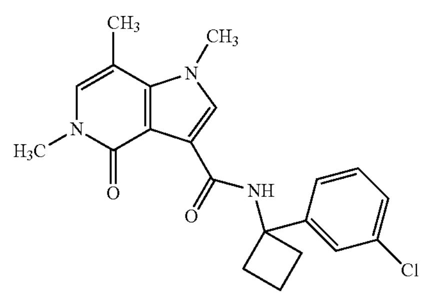 [SMILES: Cc1cn(C)c(=O)c2c(C(=O)NC3(c4cccc(Cl)c4)CCC3)cn(C)c12] | | 384.15 |
| 228 | N-(1-(4-chlorophenyl)cyclobutyl)-1,5,7-trimethyl-4-oxo-4,5-dihydro-1H-pyrrolo[3,2-c]pyridine-3-carboxamide | 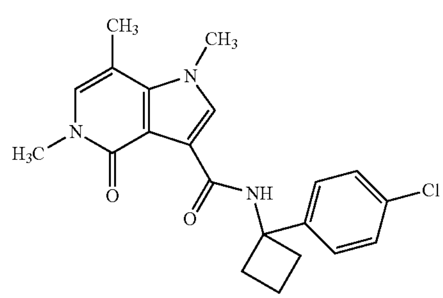 [SMILES: Cc1cn(C)c(=O)c2c(C(=O)NC3(c4ccc(Cl)cc4)CCC3)cn(C)c12] | | 384.19 |

TABLE 1-29-continued

| Ex. No. | IUPAC Name | Structure | Additive | MS |
|---|---|---|---|---|
| 229 | 1,5,7-trimethyl-4-oxo-N-(3-phenylcyclobutyl)-4,5-dihydro-1H-pyrrolo[3,2-c]pyridine-3-carboxamide | 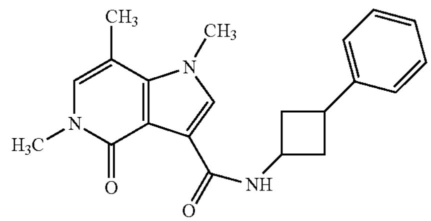 [SMILES: Cc1cn(C)c(=O)c2c(C(=O)NC3CC(c4ccccc4)C3)cn(C)c12] | | 350.18 |
| 230 | 1,5,7-trimethyl-4-oxo-N-(3-phenylbicyclo[1.1.1]pent-1-yl)-4,5-dihydro-1H-pyrrolo[3,2-c]pyridine-3-carboxamide | 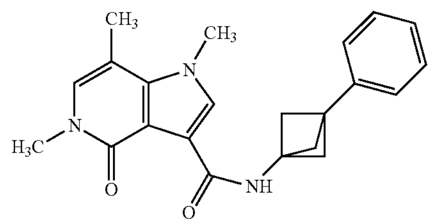 [SMILES: Cc1cn(C)c(=O)c2c(C(=O)NC34CC(c5ccccc5)(C3)C4)cn(C)c12] | | 362.21 |
| 231 | N-(3-(benzyloxy)phenyl)-1,5,7-trimethyl-4-oxo-4,5-dihydro-1H-pyrrolo[3,2-c]pyridine-3-carboxamide | 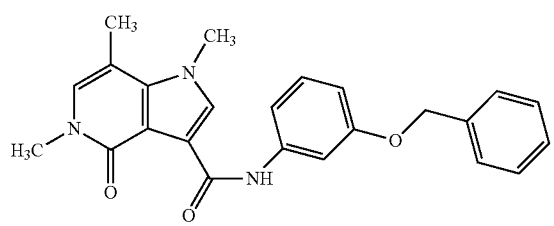 [SMILES: Cc1cn(C)c(=O)c2c(C(=O)Nc3cccc(OCc4ccccc4)c3)cn(C)c12] | | 402.22 |
| 232 | N-(4-(benzyloxy)phenyl)-1,5,7-trimethyl-4-oxo-4,5-dihydro-1H-pyrrolo[3,2-c]pyridine-3-carboxamide | 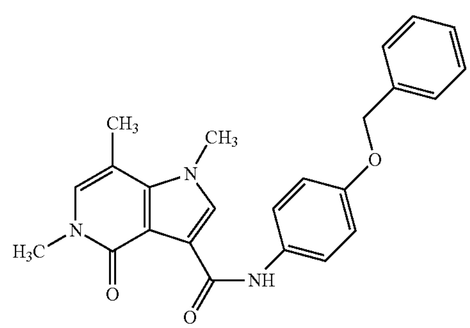 [SMILES: Cc1cn(C)c(=O)c2c(C(=O)Nc3ccc(OCc4ccccc4)cc3)cn(C)c12] | | 402.22 |

TABLE 1-30

| Ex. No. | IUPAC Name | Structure | Additive | MS |
|---|---|---|---|---|
| 233 | N-((1-(4-chlorophenyl)-1H-pyrazol-4-yl)methyl)-1,5,7-trimethyl-4-oxo-4,5-dihydro-1H-pyrrolo[3,2-c]pyridine-3-carboxamide | 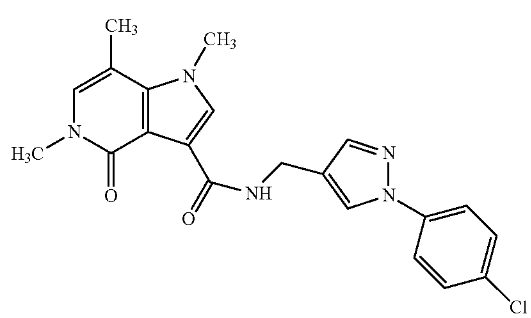 [SMILES: Cc1cn(C)c(=O)c2c(C(=O)NCc3cnn(-c4ccc(Cl)cc4)c3)cn(C)c12] | | 410.14 |

TABLE 1-30-continued

| Ex. No. | IUPAC Name | Structure | Additive | MS |
|---|---|---|---|---|
| 234 | 1,5,7-trimethyl-4-oxo-N-(1,2,3,4-tetrahydronaphthalen-2-yl)-4,5-dihydro-1H-pyrrolo[3,2-c]pyridine-3-carboxamide | 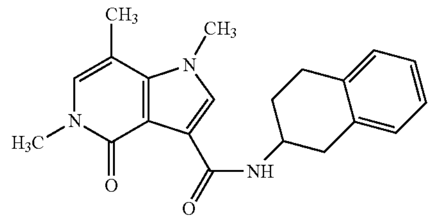 [SMILES: Cc1cn(C)c(=O)c2c(C(=O)NC3CCc4ccccc4C3)cn(C)c12] | | 350.18 |
| 235 | N-(2,3-dihydro-1H-inden-1-yl)-1,5,7-trimethyl-4-oxo-4,5-dihydro-1H-pyrrolo[3,2-c]pyridine-3-carboxamide | 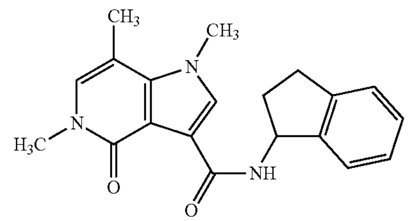 [SMILES: Cc1cn(C)c(=O)c2c(C(=O)NC3CCc4ccccc43)cn(C)c12] | | 336.16 |
| 236 | N-(5-chloro-2,3-dihydro-1H-inden-1-yl)-1,5,7-trimethyl-4-oxo-4,5-dihydro-1H-pyrrolo[3,2-c]pyridine-3-carboxamide | 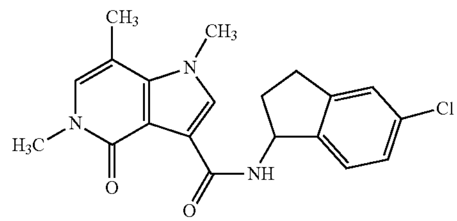 [SMILES: Cc1cn(C)c(=O)c2c(C(=O)NC3CCc4cc(Cl)ccc43)cn(C)c12] | | 370.13 |
| 237 | N-(bicyclo[4.2.0]octa-1,3,5-trien-7-yl)-1,5,7-trimethyl-4-oxo-4,5-dihydro-1H-pyrrolo[3,2-c]pyridine-3-carboxamide | 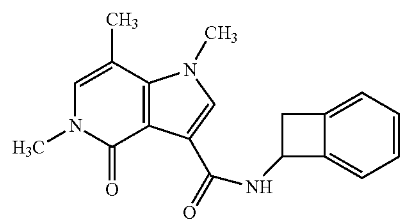 [SMILES: Cc1cn(C)c(=O)c2c(C(=O)NC3Cc4ccccc43)cn(C)c12] | | 322.11 |
| 238 | 3-((3-(benzyloxy)pyrrolidin-1-yl)carbonyl)-1,5,7-trimethyl-1,5-dihydro-4H-pyrrolo[3,2-c]pyridin-4-one | 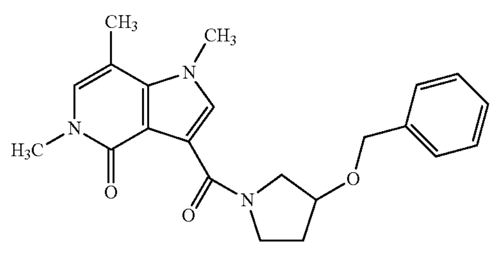 [SMILES: Cc1cn(C)c(=O)c2c(C(=O)N3CCC(OCc4ccccc4)C3)cn(C)c12] | | 380.25 |
| 239 | 1,5,7-trimethyl-3-((4-(pyridin-2-yloxy)piperidin-1-yl)carbonyl)-1,5-dihydro-4H-pyrrolo[3,2-c]pyridin-4-one | 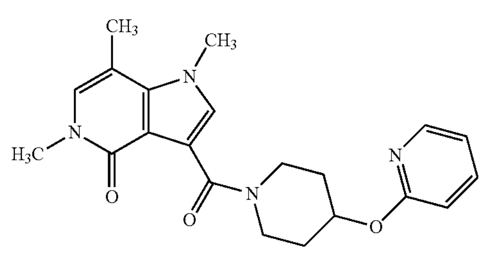 [SMILES: Cc1cn(C)c(=O)c2c(C(=O)N3CCC(Oc4ccccn4)CC3)cn(C)c12] | | 381.19 |

TABLE 1-30-continued

| Ex. No. | IUPAC Name | Structure | Additive | MS |
| --- | --- | --- | --- | --- |
| 240 | 1,5,7-trimethyl-3-((4-(1,3-thiazol-2-yloxy)piperidin-1-yl)carbonyl)-1,5-dihydro-4H-pyrrolo[3,2-c]pyridin-4-one | 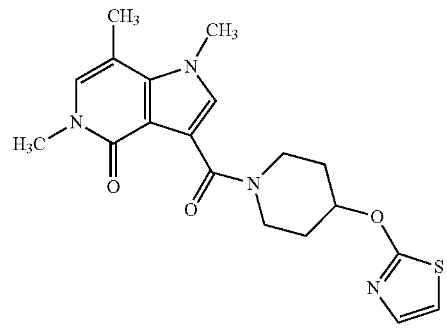 [SMILES: Cc1cn(C)c(=O)c2c(C(=O)N3CCC(Oc4nccs4)CC3)cn(C)c12] | | 387.15 |

TABLE 1-31

| Ex. No. | IUPAC Name | Structure | Additive | MS |
| --- | --- | --- | --- | --- |
| 241 | 1,5,7-trimethyl-3-((4-(pyridin-4-yloxy)piperidin-1-yl)carbonyl)-1,5-dihydro-4H-pyrrolo[3,2-c]pyridin-4-one | 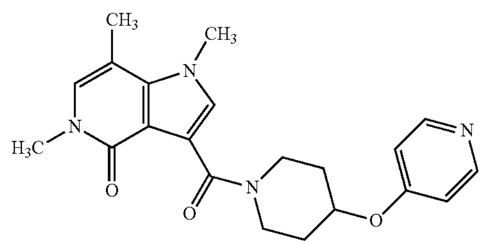 [SMILES: Cc1cn(C)c(=O)c2c(C(=O)N3CCC(Oc4ccncc4)CC3)cn(C)c12] | | 381.19 |
| 242 | tert-butyl 4-((1-((1,5,7-trimethyl-4-oxo-4,5-dihydro-1H-pyrrolo[3,2-c]pyridin-3-yl)carbonyl)piperidin-4-yl)oxy)piperidine-1-carboxylate | 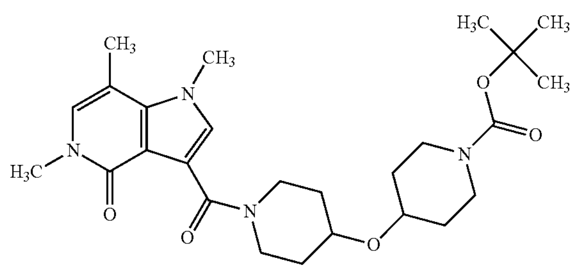 [SMILES: Cc1cn(C)c(=O)c2c(C(=O)N3CCC(OC4CCN(C(=O)OC(C)(C)C)CC4)CC3)cn(C)c12] | | 487.26 |
| 243 | 1,5,7-trimethyl-3-((4-(pyrazin-2-yloxy)piperidin-1-yl)carbonyl)-1,5-dihydro-4H-pyrrolo[3,2-c]pyridin-4-one | 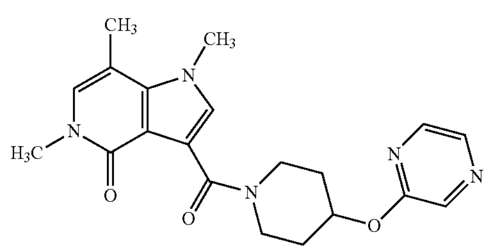 [SMILES: Cc1cn(C)c(=O)c2c(C(=O)N3CCC(Oc4cnccn4)CC3)cn(C)c12] | | 382.17 |
| 244 | 1,5,7-trimethyl-3-((4-(pyrimidin-2-yloxy)piperidin-1-yl)carbonyl)-1,5-dihydro-4H-pyrrolo[3,2-c]pyridin-4-one | 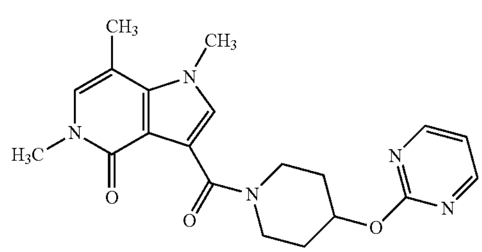 [SMILES: Cc1cn(C)c(=O)c2c(C(=O)N3CCC(Oc4ncccn4)CC3)cn(C)c12] | | 382.2 |

TABLE 1-31-continued

| Ex. No. | IUPAC Name | Structure | Additive | MS |
|---|---|---|---|---|
| 245 | 3-((3-(difluoromethoxy)piperidin-1-yl)carbonyl)-1,5,7-trimethyl-1,5-dihydro-4H-pyrrolo[3,2-c]pyridin-4-one | 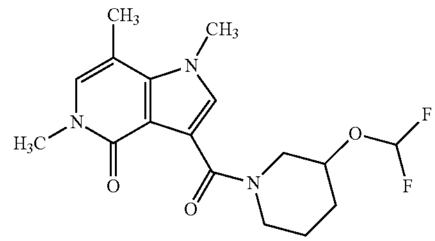 [SMILES: Cc1cn(C)c(=O)c2c(C(=O)N3CCCC(OC(F)F)C3)cn(C)c12] | | 354.19 |
| 246 | 3-((3-ethoxypiperidin-1-yl)carbonyl)-1,5,7-trimethyl-1,5-dihydro-4H-pyrrolo[3,2-c]pyridin-4-one | 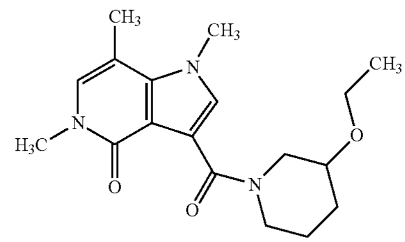 [SMILES: CCOC1CCCN(C(=O)c2cn(C)c3c(C)cn(C)c(=O)c23)C1] | | 332.15 |
| 247 | 3-((3-methoxypiperidin-1-yl)carbonyl)-1,5,7-trimethyl-1,5-dihydro-4H-pyrrolo[3,2-c]pyridin-4-one | 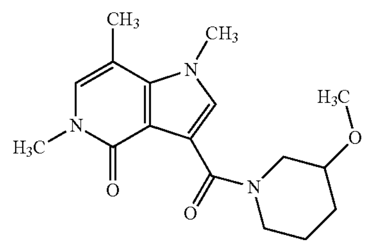 [SMILES: COC1CCCN(C(=O)c2cn(C)c3c(C)cn(C)c(=O)c23)C1] | | 318.13 |
| 248 | 1,5,7-trimethyl-3-((3-(trifluoromethoxy)piperidin-1-yl)carbonyl)-1,5-dihydro-4H-pyrrolo[3,2-c]pyridin-4-one | 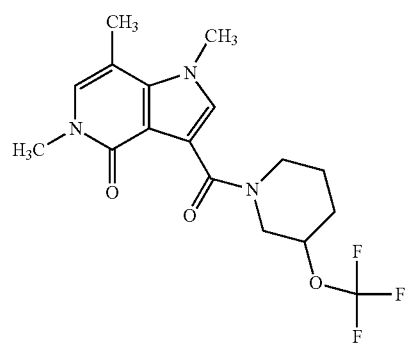 [SMILES: Cc1cn(C)c(=O)c2c(C(=O)N3CCCC(OC(F)(F)F)C3)cn(C)c12] | | 372.19 |

TABLE 1-32

| Ex. No. | IUPAC Name | Structure | Additive | MS |
|---|---|---|---|---|
| 249 | 3-((6-chloro-3,4-dihydroisoquinolin-2(1H)-yl)carbonyl)-1,5,7-trimethyl-1,5-dihydro-4H-pyrrolo[3,2-c]pyridin-4-one | 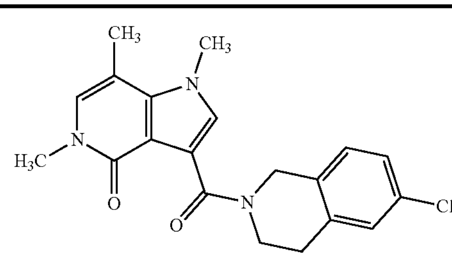 | | 370.17 |

TABLE 1-32-continued

| Ex. No. | IUPAC Name | Structure | Additive | MS |
|---|---|---|---|---|
| 250 | 1,5,7-trimethyl-3-((7-methyl-3,4-dihydroisoquinolin-2(1H)-yl)carbonyl)-1,5-dihydro-4H-pyrrolo[3,2-c]pyridin-4-one | 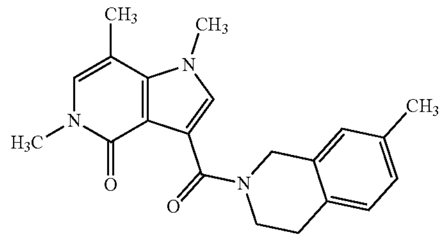 | | 350.18 |
| 251 | 1,5,7-trimethyl-3-((6-methyl-3,4-dihydroisoquinolin-2(1H)-yl)carbonyl)-1,5-dihydro-4H-pyrrolo[3,2-c]pyridin-4-one | 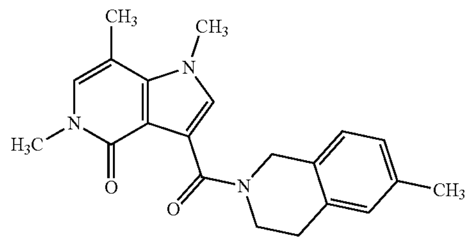 | | 350.18 |
| 252 | 3-((7-chloro-3,4-dihydroisoquinolin-2(1H)-yl)carbonyl)-1,5,7-trimethyl-1,5-dihydro-4H-pyrrolo[3,2-c]pyridin-4-one | 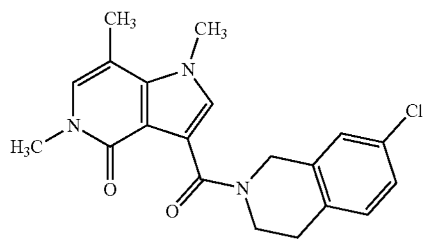 [SMILES: Cc1cn(C)c(=O)c2c(C(=O)N3CCc4ccc(Cl)cc4C3)cn(C)c12] | | 370.13 |
| 253 | 3-(3,4-dihydroisoquinolin-2(1H)-ylcarbonyl)-1,5,7-trimethyl-1,5-dihydro-4H-pyrrolo[3,2-c]pyridin-4-one | 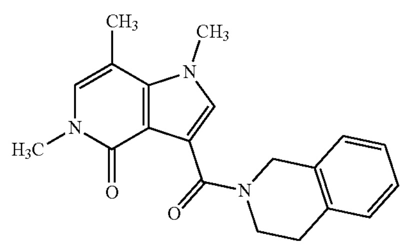 [SMILES: Cc1cn(C)c(=O)c2c(C(=O)N3CCc4ccccc4C3)cn(C)c12] | | 336.16 |
| 254 | 3-((6-bromo-3,4-dihydroisoquinolin-2(1H)-yl)carbonyl)-1,5,7-trimethyl-1,5-dihydro-4H-pyrrolo[3,2-c]pyridin-4-one | 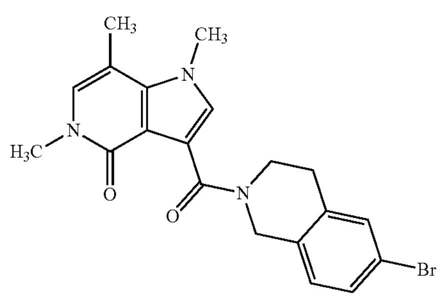 [SMILES: Cc1cn(C)c(=O)c2c(C(=O)N3CCc4cc(Br)ccc4C3)cn(C)c12] | | 414.12 |
| 255 | 3-((7-bromo-3,4-dihydroisoquinolin-2(1H)-yl)carbonyl)-1,5,7-trimethyl-1,5-dihydro-4H-pyrrolo[3,2-c]pyridin-4-one | 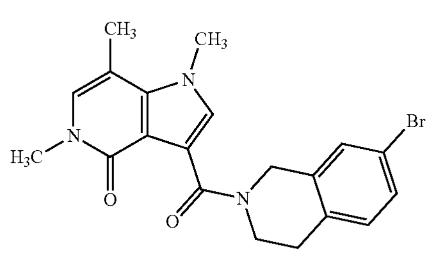 [SMILES: Cc1cn(C)c(=O)c2c(C(=O)N3CCc4ccc(Br)cc4C3)cn(C)c12] | | 414.12 |

TABLE 1-32-continued

| Ex. No. | IUPAC Name | Structure | Additive | MS |
|---|---|---|---|---|
| 256 | 3-((6,7-dimethoxy-3,4-dihydroisoquinolin-2(1H)-yl)carbonyl)-1,5,7-trimethyl-1,5-dihydro-4H-pyrrolo[3,2-c]pyridin-4-one | 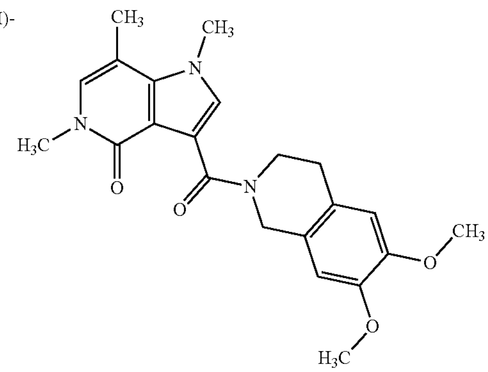 | | 396.22 |

TABLE 1-33

| Ex. No. | IUPAC Name | Structure | Additive | MS |
|---|---|---|---|---|
| 257 | 3-((4-(2-chlorophenyl)piperidin-1-yl)carbonyl)-1,5,7-trimethyl-1,5-dihydro-4H-pyrrolo[3,2-c]pyridin-4-one | 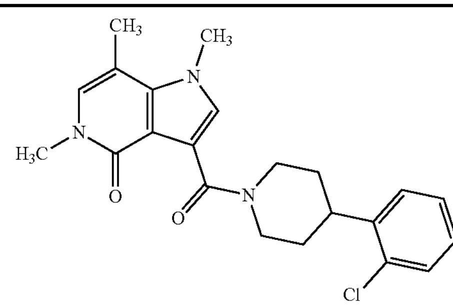 | | 398.21 |
| 258 | 3-((4-(4-chlorophenyl)piperidin-1-yl)carbonyl)-1,5,7-trimethyl-1,5-dihydro-4H-pyrrolo[3,2-c]pyridin-4-one | 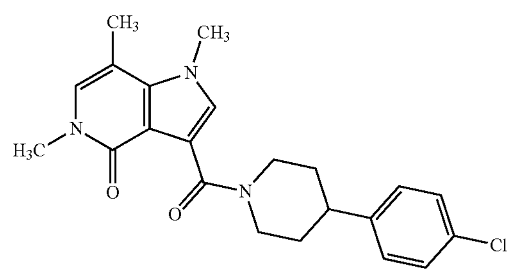 [SMILES: Cc1cn(C)c(=O)c2c(C(=O)N3CCC(c4ccc(Cl)cc4)CC3)cn(C)c12] | | 398.21 |
| 259 | 1,5,7-trimethyl-3-((1-(3-thienyl)-3-azabicyclo[3.1.0]hex-3-yl)carbonyl)-1,5-dihydro-4H-pyrrolo[3,2-c]pyridin-4-one | 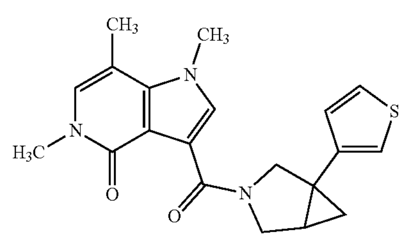 [SMILES: Cc1cn(C)c(=O)c2c(C(=O)N3CC4CC4(c4ccsc4)C3)cn(C)c12] | | 368.18 |
| 260 | 1,5,7-trimethyl-3-((1-(2-thienyl)-3-azabicyclo[3.1.0]hex-3-yl)carbonyl)-1,5-dihydro-4H-pyrrolo[3,2-c]pyridin-4-one | 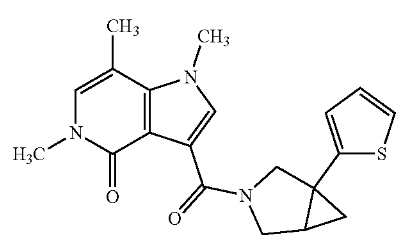 [SMILES: Cc1cn(C)c(=O)c2c(C(=O)N3CC4CC4(c4cccs4)C3)cn(C)c12] | | 368.14 |

TABLE 1-33-continued

| Ex. No. | IUPAC Name | Structure | Additive | MS |
|---|---|---|---|---|
| 261 | 1,5,7-trimethyl-3-((1-(2-naphthyl)-3-azabicyclo[3.1.0]hex-3-yl)carbonyl)-1,5-dihydro-4H-pyrrolo[3,2-c]pyridin-4-one | 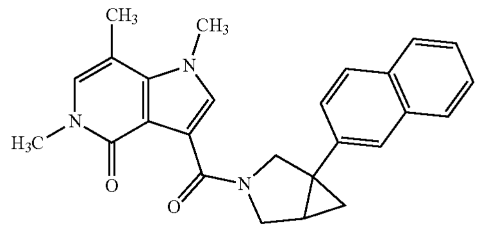 [SMILES: Cc1cn(C)c(=O)c2c(C(=O)N3CC4CC4(c4ccc5ccccc5c4)C3)cn(C)c12] | | 412.23 |
| 262 | 1,5,7-trimethyl-3-((1-(1-naphthyl)-3-azabicyclo[3.1.0]hex-3-yl)carbonyl)-1,5-dihydro-4H-pyrrolo[3,2-c]pyridin-4-one | 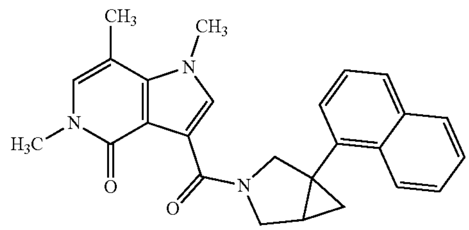 [SMILES: Cc1cn(C)c(=O)c2c(C(=O)N3CC4CC4(c4cccc5ccccc45)C3)cn(C)c12] | | 412.23 |
| 263 | 3-((2-(4-bromophenyl)azetidin-1-yl)carbonyl)-1,5,7-trimethyl-1,5-dihydro-4H-pyrrolo[3,2-c]pyridin-4-one | 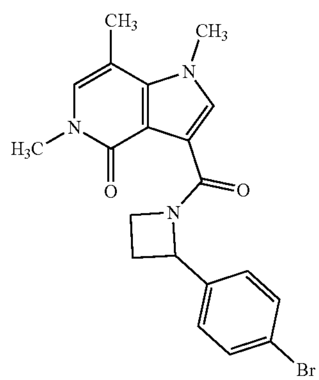 [SMILES: Cc1cn(C)c(=O)c2c(C(=O)N3CCC3c3ccc(Br)cc3)cn(C)c12] | | 413.95 |
| 264 | 3-((1-(4-chlorophenyl)-3-azabicyclo[3.1.0]hex-3-yl)carbonyl)-1,5,7-trimethyl-1,5-dihydro-4H-pyrrolo[3,2-c]pyridin-4-one | 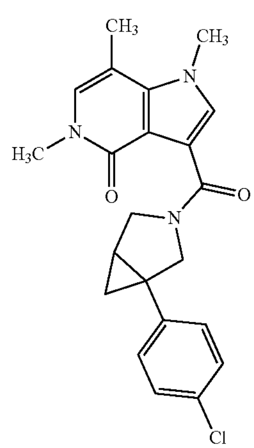 [SMILES: Cc1cn(C)c(=O)c2c(C(=O)N3CC4CC4(c4ccc(Cl)cc4)C3)cn(C)c12] | | 396.19 |

TABLE 1-34

| Ex. No. | IUPAC Name | Structure | Additive | MS |
|---|---|---|---|---|
| 265 | 3-((1-(4-chlorophenyl)-3-azabicyclo[3.1.0]hex-3-yl)carbonyl)-1,5,7-trimethyl-1,5-dihydro-4H-pyrrolo[3,2-c]pyridin-4-one | 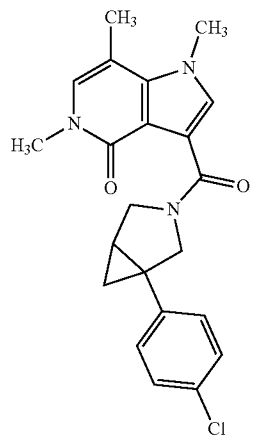 [SMILES: Cc1cn(C)c(=O)c2c(C(=O)N3CC4CC4(c4ccc(Cl)cc4)C3)cn(C)c12] | | 396.15 |
| 266 | 3-((2-(4-fluorophenyl)azetidin-1-yl)carbonyl)-1,5,7-trimethyl-1,5-dihydro-4H-pyrrolo[3,2-c]pyridin-4-one | 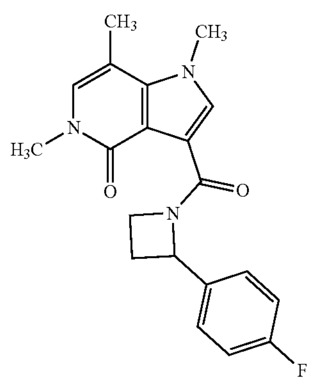 [SMILES: Cc1cn(C)c(=O)c2c(C(=O)N3CCC3c3ccc(F)cc3)cn(C)c12] | | 354.25 |
| 267 | 3-((2-(4-fluorophenyl)azetidin-1-yl)carbonyl)-1,5,7-trimethyl-1,5-dihydro-4H-pyrrolo[3,2-c]pyridin-4-one | 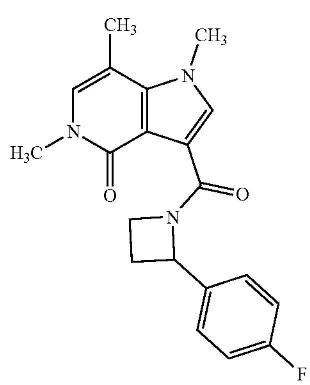 [SMILES: Cc1cn(C)c(=O)c2c(C(=O)N3CCC3c3ccc(F)cc3)cn(C)c12] | | 354.22 |
| 268 | 1,5,7-trimethyl-3-((2-phenylazetidin-1-yl)carbonyl)-1,5-dihydro-4H-pyrrolo[3,2-c]pyridin-4-one | 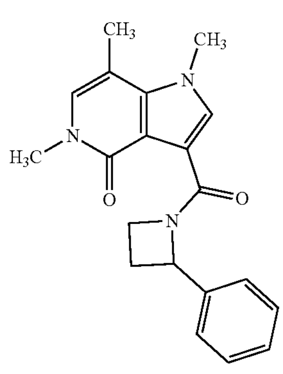 [SMILES: Cc1cn(C)c(=O)c2c(C(=O)N3CCC3c3ccccc3)cn(C)c12] | | 336.25 |

TABLE 1-34-continued

| Ex. No. | IUPAC Name | Structure | Additive | MS |
|---|---|---|---|---|
| 269 | 1,5,7-trimethyl-3-((2-phenylazetidin-1-yl)carbonyl)-1,5-dihydro-4H-pyrrolo[3,2-c]pyridin-4-one | 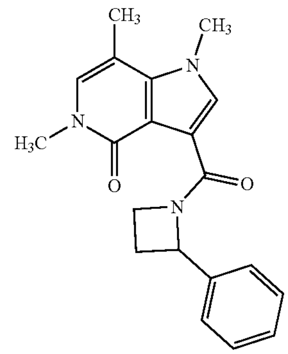 [SMILES: Cc1cn(C)c(=O)c2c(C(=O)N3CCC3c3ccccc3)cn(C)c12] | | 336.22 |
| 270 | 5-(2-methoxyphenyl)-1,7-dimethyl-4-oxo-N-(1,1,1-trifluoropropan-2-yl)-4,5-dihydro-1H-pyrrolo[3,2-c]pyridine-3-carboxamide | 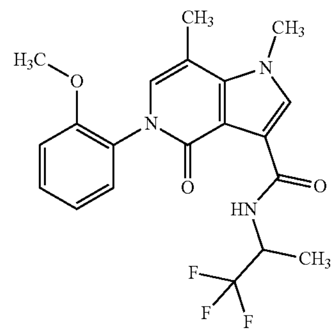 [SMILES: COc1ccccc1-n1cc(C)c2c(c(C(=O)NC(C)C(F)(F)F)cn2C)c1=O] | | 408.26 |
| 271 | N-(trans-4-butoxycyclohexyl)-1,5-dimethyl-4-oxo-7-phenyl-4,5-dihydro-1H-pyrrolo[3,2-c]pyridine-3-carboxamide | 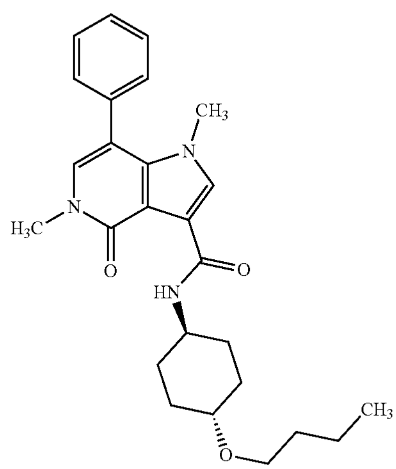 [SMILES: CCCCO[C@H]1CC[C@H](NC(=O)c2cn(C)c3c(-c4ccccc4)cn(C)c(=O)c23)CC1] | | 436.42 |
| 272 | N-benzyl-5,7-dimethyl-4-oxo-4,5-dihydrothieno[3,2-c]pyridine-3-carboxamide | 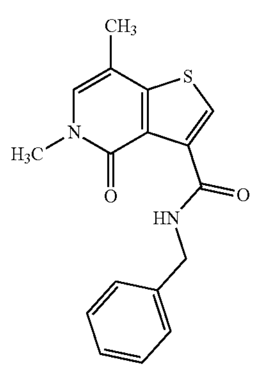 [SMILES: Cc1cn(C)c(=O)c2c(C(=O)NCc3ccccc3)csc12] | | 313.2 |

TABLE 1-35

| Ex. No. | IUPAC Name | Structure | Additive | MS |
|---|---|---|---|---|
| 273 | N-(trans-4-butoxycyclohexyl)-5,7-dimethyl-4-oxo-4,5-dihydrothieno[3,2-c]pyridine-3-carboxamide | 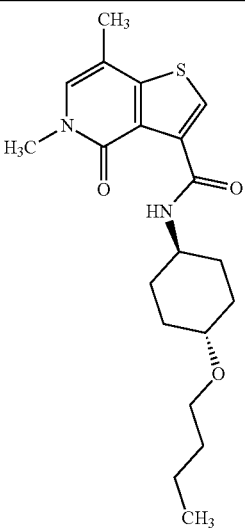 | | 377.2 |
| 274 | 5,7-dimethyl-4-oxo-N-(1-(2,2,2-trifluoroethyl)-1H-pyrazol-5-yl)-4,5-dihydrothieno[3,2-c]pyridine-3-carboxamide | 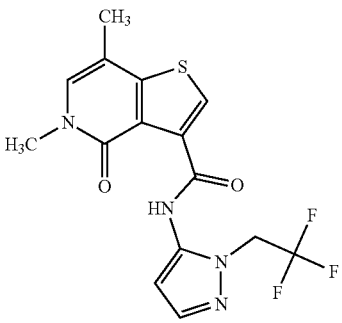 [SMILES: Cc1cn(C)c(=O)c2c(C(=O)Nc3ccnn3CC(F)(F)F)csc12] | | 371.14 |
| 275 | N-((6-methoxypyridin-2-yl)methyl)-5,7-dimethyl-4-oxo-4,5-dihydrothieno[3,2-c]pyridine-3-carboxamide | 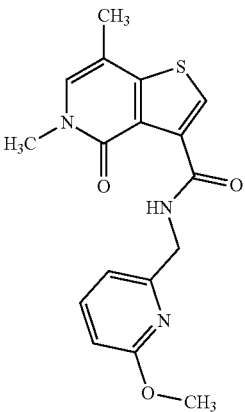 [SMILES: COc1cccc(CNC(=O)c2csc3c(C)cn(C)c(=O)c23)n1] | | 343.97 |
| 276 | N-(cyclopropylmethyl)-5,7-dimethyl-4-oxo-4,5-dihydrothieno[3,2-c]pyridine-3-carboxamide | 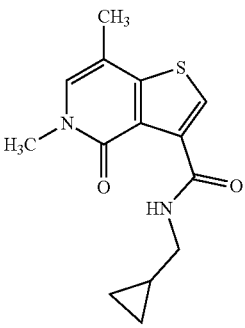 [SMILES: Cc1cn(C)c(=O)c2c(C(=O)NCC3CC3)csc12] | | 277.1 |

TABLE 1-35-continued

| Ex. No. | IUPAC Name | Structure | Additive | MS |
|---|---|---|---|---|
| 277 | N-(trans-4-butoxycyclohexyl)-1,5,7-trimethyl-4-oxo-4,5-dihydro-1H-pyrazolo[4,3-c]pyridine-3-carboxamide | 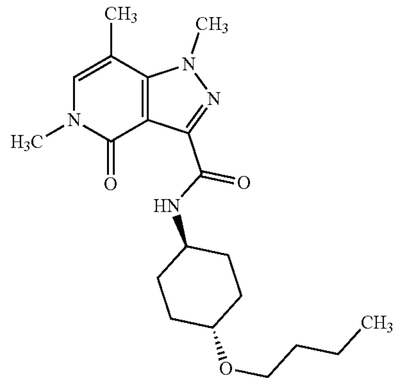 [SMILES: CCCCO[C@H]1CC[C@H](NC(=O)c2nn(C)c3c(C)cn(C)c(=O)c23)CC1] | | 375.29 |
| 278 | N-(2-(benzyloxy)phenyl)-1,5,7-trimethyl-4-oxo-4,5-dihydro-1H-pyrazolo[4,3-c]pyridine-3-carboxamide | 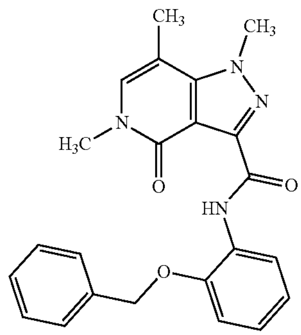 [SMILES: Cc1cn(C)c(=O)c2c(C(=O)Nc3ccccc3OCc3ccccc3)nn(C)c12] | | 403.2 |
| 279 | N-cyclohexyl-1,5,7-trimethyl-4-oxo-4,5-dihydro-1H-pyrazolo[4,3-c]pyridine-3-carboxamide | 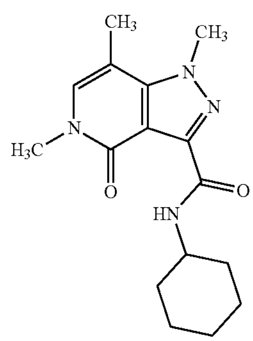 [SMILES: Cc1cn(C)c(=O)c2c(C(=O)NC3CCCCC3)nn(C)c12] | | 303.13 |
| 280 | 1,5,7-trimethyl-4-oxo-N-(1-(2,2,2-trifluoroethyl)-1H-pyrazol-5-yl)-4,5-dihydro-1H-pyrazolo[4,3-c]pyridine-3-carboxamide | 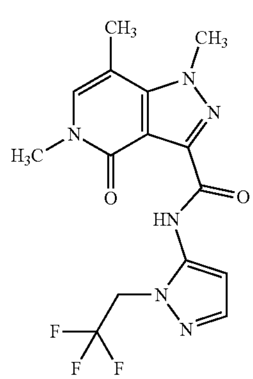 [SMILES: Cc1cn(C)c(=O)c2c(C(=O)Nc3ccnn3CC(F)(F)F)nn(C)c12] | | 369.19 |

TABLE 1-36

| Ex. No. | IUPAC Name | Structure | Additive | MS |
|---|---|---|---|---|
| 281 | N-(trans-4-butoxycyclohexyl)-2,5,7-trimethyl-4-oxo-4,5-dihydro-2H-pyrazolo[4,3-c]pyridine-3-carboxamide | 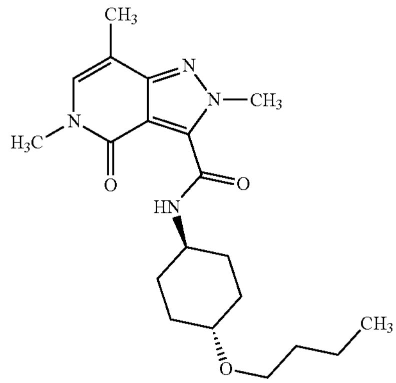 [SMILES: CCCCO[C@H]1CC[C@H](NC(=O)c2c3c(=O)n(C)cc(C)c3nn2C)CC1] | | 375.26 |
| 282 | N-(2-(benzyloxy)phenyl)-2,5,7-trimethyl-4-oxo-4,5-dihydro-2H-pyrazolo[4,3-c]pyridine-3-carboxamide | 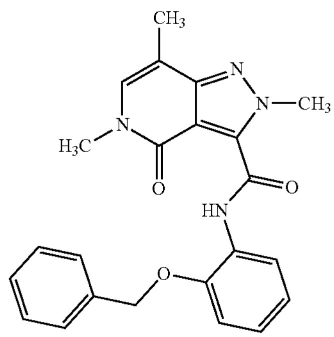 [SMILES: Cc1cn(C)c(=O)c2c(C(=O)Nc3ccccc3OCc3ccccc3)n(C)nc12] | | 403.23 |
| 283 | N-(trans-4-butoxycyclohexyl)-5,7-dimethyl-4-oxo-4,5-dihydropyrazolo[1,5-a]pyrazine-3-carboxamide | 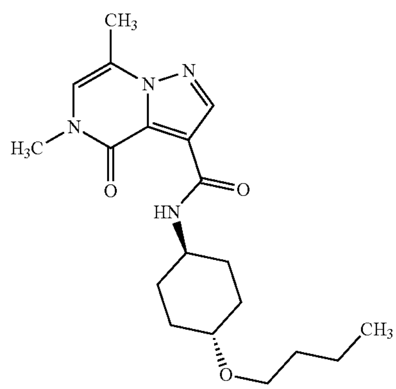 [SMILES: CCCCO[C@H]1CC[C@H](NC(=O)c2cnn3c(C)cn(C)c(=O)c23)CC1] | | 361.24 |
| 284 | N-(trans-4-butoxycyclohexyl)-2,5,7-trimethyl-4-oxo-4,5-dihydropyrazolo[1,5-a]pyrazine-3-carboxamide | 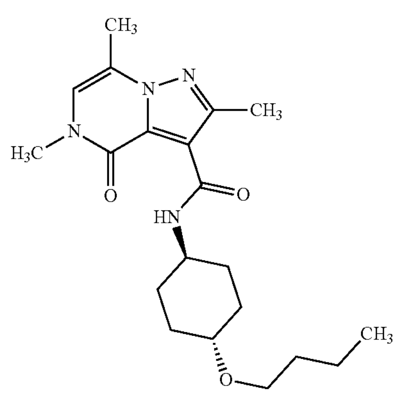 [SMILES: CCCCO[C@H]1CC[C@H](NC(=O)c2c(C)nn3c(C)cn(C)c(=O)c23)CC1] | | 375.26 |

TABLE 1-36-continued

| Ex. No. | IUPAC Name | Structure | Additive | MS |
|---|---|---|---|---|
| 285 | 5,7-dimethyl-N-(4-(morpholin-4-yl)phenyl)-4-oxo-4,5-dihydropyrazolo[1,5-a]pyrazine-3-carboxamide | 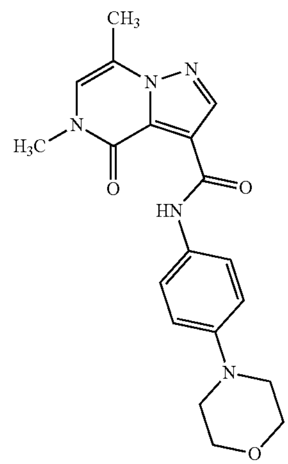 [SMILES: Cc1cn(C)c(=O)c2c(C(=O)Nc3ccc(N4CCOCC4)cc3)cnn12] | | 368.21 |
| 286 | N-((5-(4-chlorophenyl)-1,2,4-oxadiazol-3-yl)methyl)-5,7-dimethyl-4-oxo-4,5-dihydropyrazolo[1,5-a]pyrazine-3-carboxamide | 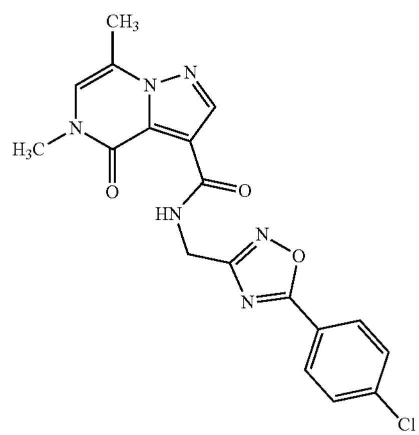 [SMILES: Cc1cn(C)c(=O)c2c(C(=O)NCc3noc(-c4ccc(Cl)cc4)n3)cnn12] | | 399.19 |
| 287 | N-(trans-4-butoxycyclohexyl)-5,7-dimethyl-4-oxo-4,5-dihydrofuro[3,2-c]pyridine-3-carboxamide | 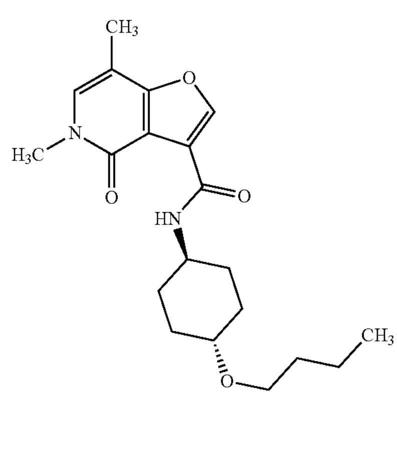 [SMILES: CCCCO[C@H]1CC[C@H](NC(=O)c2coc3c(C)cn(C)c(=O)c23)CC1] | | 361.3 |

TABLE 1-36-continued

| Ex. No. | IUPAC Name | Structure | Additive | MS |
|---|---|---|---|---|
| 288 | 1,5,7-trimethyl-3-((4-(4-(trifluoromethoxy)phenoxy)piperidin-1-yl)carbonyl)-1,5-dihydro-4H-pyrrolo[3,2-c]pyridin-4-one | 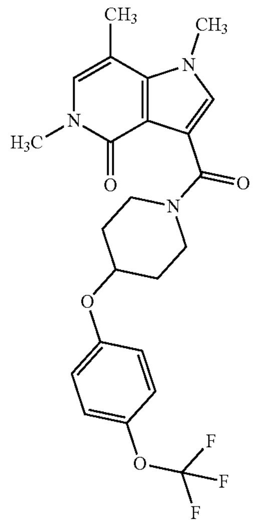 [SMILES: Cc1cn(C)c(=O)c2c(C(=O)N3CCC(Oc4ccc(OC(F)(F)F)cc4)CC3)cn(C)c12] | | 464.16 |

TABLE 1-37

| Ex. No. | IUPAC Name | Structure | Additive | MS |
|---|---|---|---|---|
| 289 | tert-butyl (3S,4S)-3-(4-chloro-3-fluorophenyl)-4-(((1,5,7-trimethyl-4-oxo-4,5-dihydro-1H-pyrrolo[3,2-c]pyridin-3-yl)carbonyl)amino)piperidine-1-carboxylate | 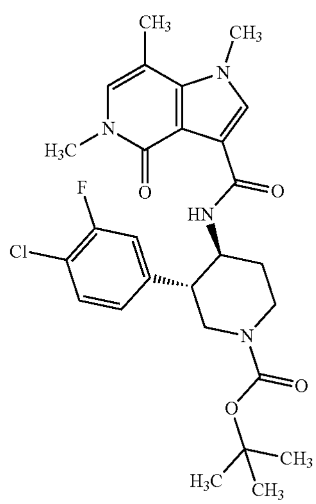 [SMILES: Cc1cn(C)c(=O)c2c(C(=O)N[C@H]3CCN(C(=O)OC(C)(C)C)C[C@@H]3c3ccc(Cl)c(F)c3)cn(C)c12] | | 531.18 |
| 290 | 1,5,7-trimethyl-4-oxo-N-[rac-(1R,3R)-3-propoxycyclohexyl]-4,5-dihydro-1H-pyrrolo[3,2-c]pyridine-3-carboxamide | 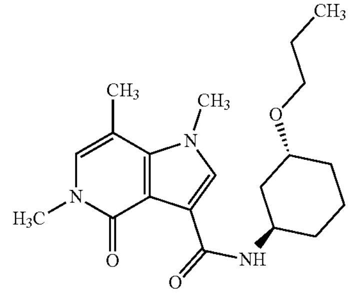 [SMILES: CCCO[C@@H]1CCC[C@@H](NC(=O)c2cn(C)c3c(C)cn(C)c(=O)c23)C1] | | 360.23 |

TABLE 1-37-continued

| Ex. No. | IUPAC Name | Structure | Additive | MS |
|---|---|---|---|---|
| 291 | N-(2-(4-chlorophenyl)propan-2-yl)-5-(2-methoxyphenyl)-1-methyl-4-oxo-4,5-dihydro-1H-pyrrolo[3,2-c]pyridine-3-carboxamide | 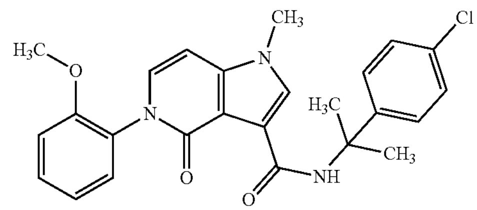 [SMILES: COc1ccccc1-n1ccc2c(c(C(=O)NC(C)(C)c3ccc(Cl)cc3)cn2C)c1=O] | | 450.27 |
| 292 | 5-(cyanomethyl)-1-methyl-N-(4-(morpholin-4-yl)phenyl)-4-oxo-4,5-dihydro-1H-pyrrolo[3,2-c]pyridine-3-carboxamide | 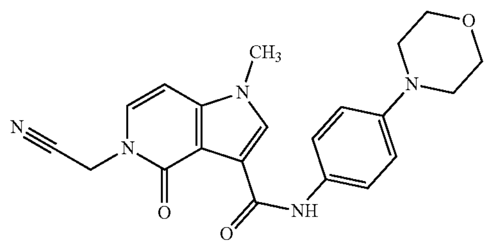 [SMILES: Cn1cc(C(=O)Nc2ccc(N3CCOCC3)cc2)c2c(=O)n(CC#N)ccc21] | | 392.28 |
| 293 | 5-(2-methoxyphenyl)-1-methyl-N-(4-(morpholin-4-yl)phenyl)-4-oxo-4,5-dihydro-1H-pyrrolo[3,2-c]pyridine-3-carboxamide | 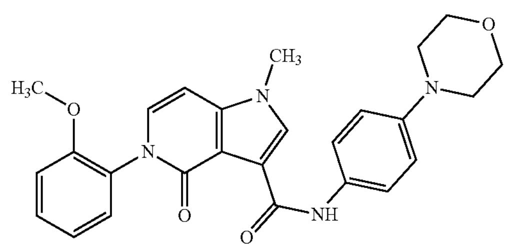 [SMILES: COc1ccccc1-n1ccc2c(c(C(=O)Nc3ccc(N4CCOCC4)cc3)cn2C)c1=O] | | 459.23 |
| 294 | 1-methyl-N-(4-(morpholin-4-yl)phenyl)-4-oxo-5-(2-(2,2,2-trifluoroethoxy)phenyl)-4,5-dihydro-1H-pyrrolo[3,2-c]pyridine-3-carboxamide | 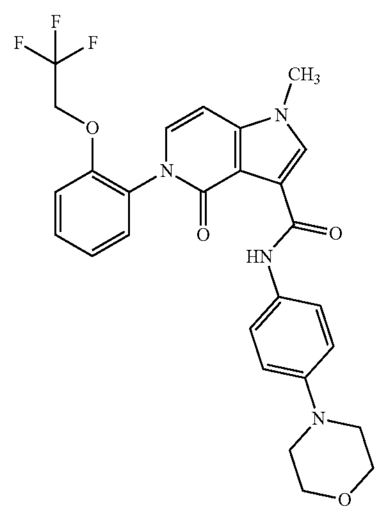 [SMILES: Cn1cc(C(=O)Nc2ccc(N3CCOCC3)cc2)c2c(=O)n(-c3ccccc3OCC(F)(F)F)ccc21] | | 527.23 |
| 295 | 5-(4-fluoro-2-methoxyphenyl)-1-methyl-N-(4-(morpholin-4-yl)phenyl)-4-oxo-4,5-dihydro-1H-pyrrolo[3,2-c]pyridine-3-carboxamide | 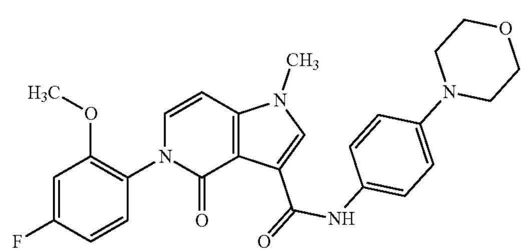 [SMILES: COc1cc(F)ccc1-n1ccc2c(c(C(=O)Nc3ccc(N4CCOCC4)cc3)cn2C)c1=O] | | 477.3 |

TABLE 1-37-continued

| Ex. No. | IUPAC Name | Structure | Additive | MS |
|---|---|---|---|---|
| 296 | N-(2-(4-chlorophenyl)propan-2-yl)-5-(cyanomethyl)-1-methyl-4-oxo-4,5-dihydro-1H-pyrrolo[3,2-c]pyridine-3-carboxamide | 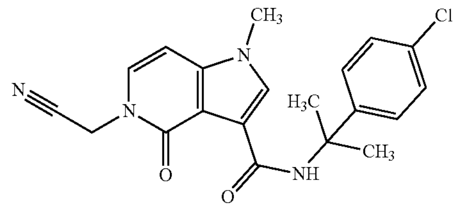 [SMILES: Cn1cc(C(=O)NC(C)(C)c2ccc(Cl)cc2)c2c(=O)n(CC#N)ccc21] | | 381.03 |

TABLE 1-38

| Ex. No. | IUPAC Name | Structure | Additive | MS |
|---|---|---|---|---|
| 297 | N-(2-(4-chlorophenyl)propan-2-yl)-1-methyl-4-oxo-5-(2,2,2-trifluoroethyl)-4,5-dihydro-1H-pyrrolo[3,2-c]pyridine-3-carboxamide | 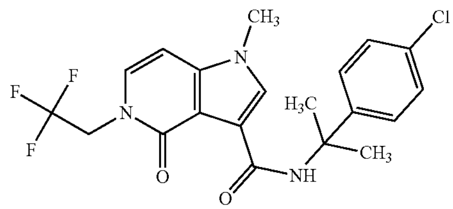 [SMILES: Cn1cc(C(=O)NC(C)(C)c2ccc(Cl)cc2)c2c(=O)n(CC(F)(F)F)ccc21] | | 426.2 |
| 298 | 1-methyl-N-(4-(morpholin-4-yl)phenyl)-4-oxo-5-(2,2,2-trifluoroethyl)-4,5-dihydro-1H-pyrrolo[3,2-c]pyridine-3-carboxamide | 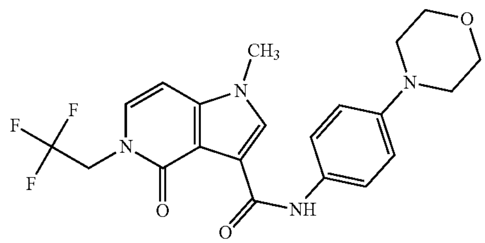 [SMILES: Cn1cc(C(=O)Nc2ccc(N3CCOCC3)cc2)c2c(=O)n(CC(F)(F)F)ccc21] | | 435.22 |
| 299 | 1,5,7-trimethyl-N-(4-(morpholin-4-yl)phenyl)-4-oxo-4,5-dihydro-1H-pyrazolo[4,3-c]pyridine-3-carboxamide | 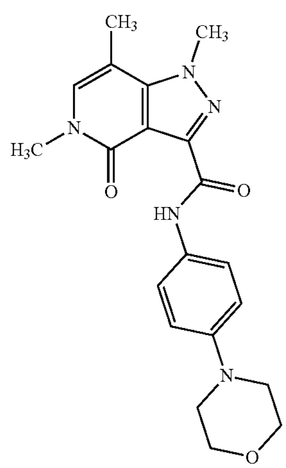 [SMILES: Cc1cn(C)c(=O)c2c(C(=O)Nc3ccc(N4CCOCC4)cc3)nn(C)c12] | | 382.27 |
| 300 | N-((5-(4-chlorophenyl)-1,2,4-oxadiazol-3-yl)methyl)-1,5,7-trimethyl-4-oxo-4,5-dihydro-1H-pyrazolo[4,3-c]pyridine-3-carboxamide | 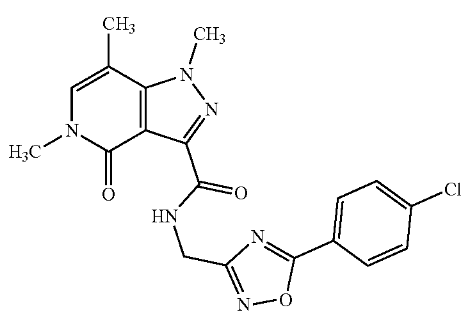 [SMILES: Cc1cn(C)c(=O)c2c(C(=O)NCc3noc(-c4ccc(Cl)cc4)n3)nn(C)c12] | | 413.21 |

TABLE 1-38-continued

| Ex. No. | IUPAC Name | Structure | Additive | MS |
|---|---|---|---|---|
| 301 | 1,5,7-trimethyl-4-oxo-N-(cis-4-phenylcyclohexyl)-4,5-dihydro-1H-pyrazolo[4,3-c]pyridine-3-carboxamide | 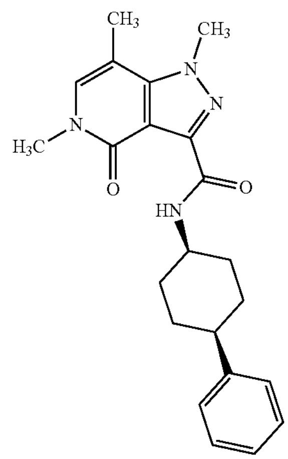 [SMILES: Cc1cn(C)c(=O)c2c(C(=O)N[C@H]3CC[C@@H](c4ccccc4)CC3)nn(C)c12] | | 379.27 |
| 302 | 1,5,7-trimethyl-4-oxo-N-(trans-4-phenylcyclohexyl)-4,5-dihydro-1H-pyrazolo[4,3-c]pyridine-3-carboxamide | 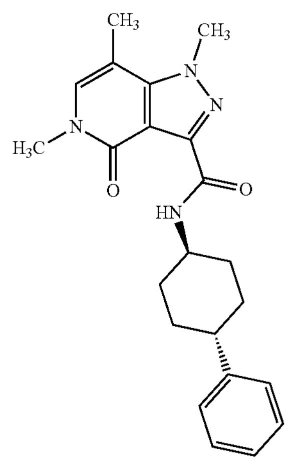 [SMILES: Cc1cn(C)c(=O)c2c(C(=O)N[C@H]3CC[C@H](c4ccccc4)CC3)nn(C)c12] | | 379.31 |
| 303 | 5,7-dimethyl-3-((4-(4-(trifluoromethoxy)phenoxy)piperidin-1-yl)carbonyl)pyrazolo[1,5-a]pyrazin-4(5H)-one | 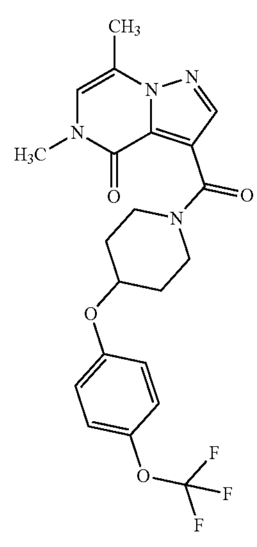 [SMILES: Cc1cn(C)c(=O)c2c(C(=O)N3CCC(Oc4ccc(OC(F)(F)F)cc4)CC3)cnn12] | | 451.15 |

TABLE 1-38-continued

| Ex. No. | IUPAC Name | Structure | Additive | MS |
|---|---|---|---|---|
| 304 | 3-((1-(4-chlorophenyl)-3-azabicyclo[3.1.0]hex-3-yl)carbonyl)-5,7-dimethylpyrazolo[1,5-a]pyrazin-4(5H)-one | 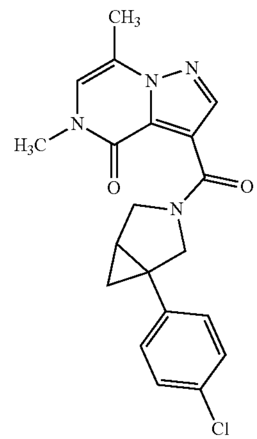 [SMILES: Cc1cn(C)c(=O)c2c(C(=O)N3CC4CC4(c4ccc(Cl)cc4)C3)cnn12] | | 383.14 |

TABLE 1-39

| Ex. No. | IUPAC Name | Structure | Additive | MS |
|---|---|---|---|---|
| 305 | 5,7-dimethyl-3-((1-(4-(trifluoromethoxy)phenyl)-3-azabicyclo[3.1.0]hex-3-yl)carbonyl)pyrazolo[1,5-a]pyrazin-4(5H)-one | 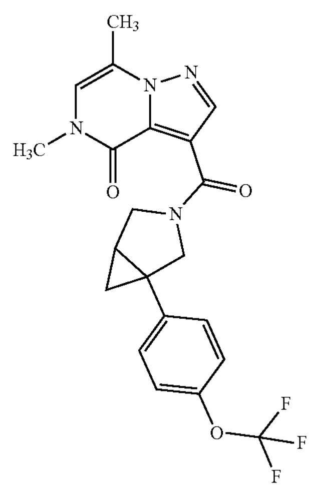 [SMILES: Cc1cn(C)c(=O)c2c(C(=O)N3CC4CC4(c4ccc(OC(F)(F)F)cc4)C3)cnn12] | | 433.13 |
| 306 | N-(2-(4-chlorophenyl)propan-2-yl)-5,7-dimethyl-4-oxo-4,5-dihydropyrazolo[1,5-a]pyrazine-3-carboxamide | 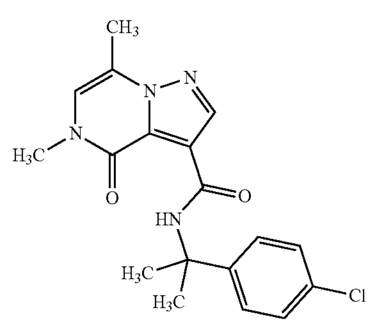 [SMILES: Cc1cn(C)c(=O)c2c(C(=O)NC(C)(C)c3ccc(Cl)cc3)cnn12] | | 359.11 |

TABLE 1-39-continued

| Ex. No. | IUPAC Name | Structure | Additive | MS |
|---|---|---|---|---|
| 307 | 3-((1-(4-chlorophenyl)-3-azabicyclo[3.1.0]hex-3-yl)carbonyl)-5,7-dimethylpyrazolo[1,5-a]pyrazin-4(5H)-one | 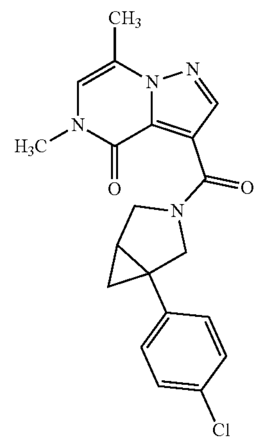 [SMILES: Cc1cn(C)c(=O)c2c(C(=O)N3CC4CC4(c4ccc(Cl)cc4)C3)cnn12] | | 383.25 |
| 308 | 3-((1-(4-chlorophenyl)-3-azabicyclo[3.1.0]hex-3-yl)carbonyl)-5,7-dimethylpyrazolo[1,5-a]pyrazin-4(5H)-one | 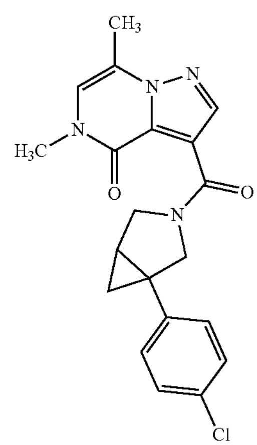 [SMILES: Cc1cn(C)c(=O)c2c(C(=O)N3CC4CC4(c4ccc(Cl)cc4)C3)cnn12] | | 383.25 |
| 309 | 5,7-dimethyl-3-((1-(4-(trifluoromethoxy)phenyl)-3-azabicyclo[3.1.0]hex-3-yl)carbonyl)pyrazolo[1,5-a]pyrazin-4(5H)-one | 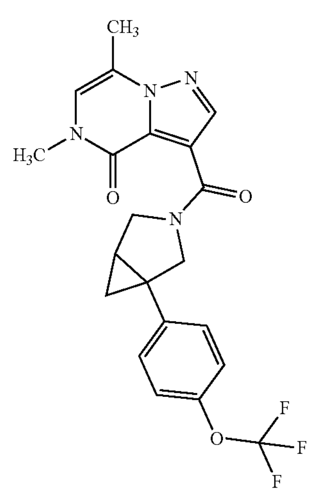 [SMILES: Cc1cn(C)c(=O)c2c(C(=O)N3CC4CC4(c4ccc(OC(F)(F)F)cc4)C3)cnn12] | | 433.24 |

TABLE 1-39-continued

| Ex. No. | IUPAC Name | Structure | Additive | MS |
|---|---|---|---|---|
| 310 | 5,7-dimethyl-3-((1-(4-(trifluoromethoxy)phenyl)-3-azabicyclo[3.1.0]hex-3-yl)carbonyl)pyrazolo[1,5-a]pyrazin-4(5H)-one | 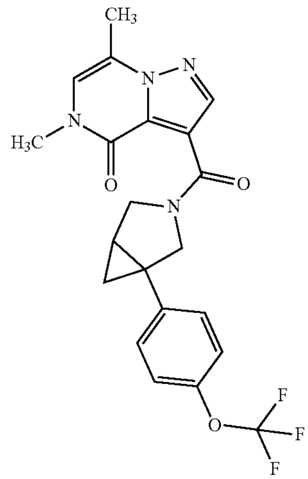 [SMILES: Cc1cn(C)c(=O)c2c(C(=O)N3CC4CC4(c4ccc(OC(F)(F)F)cc4)C3)cnn12] | | 433.21 |
| 311 | 5-(2-methoxyphenyl)-7-methyl-N-(4-(morpholin-4-yl)phenyl)-4-oxo-4,5-dihydropyrazolo[1,5-a]pyrazine-3-carboxamide | 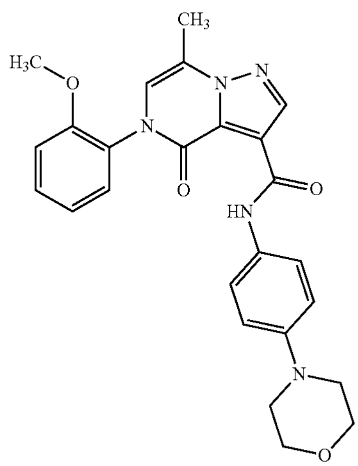 [SMILES: COc1ccccc1-n1cc(C)n2ncc(C(=O)Nc3ccc(N4CCOCC4)cc3)c2c1=O] | | 460.31 |
| 312 | N-(2-(4-chlorophenyl)propan-2-yl)-5-(2-methoxyphenyl)-7-methyl-4-oxo-4,5-dihydropyrazolo[1,5-a]pyrazine-3-carboxamide | 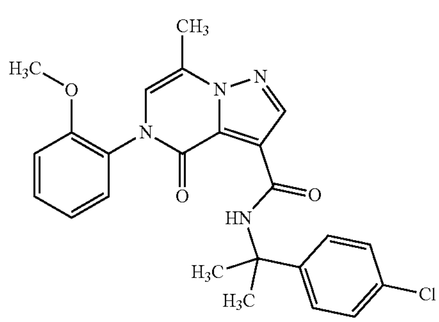 [SMILES: COc1ccccc1-n1cc(C)n2ncc(C(=O)NC(C)(C)c3ccc(Cl)cc3)c2c1=O] | | 451.27 |

TABLE 1-40

| Ex. No. | IUPAC Name | Structure | Additive | MS |
|---|---|---|---|---|
| 313 | 5,7-dimethyl-3-((4-(4-(trifluoromethyl)phenoxy)piperidin-1-yl)carbonyl)pyrazolo[1,5-a]pyrazin-4(5H)-one | 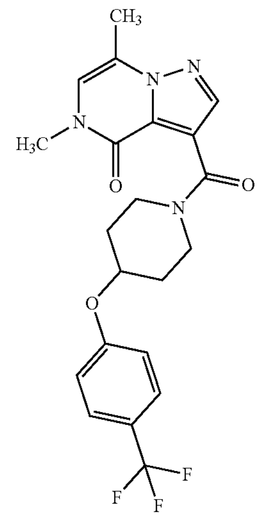 [SMILES: Cc1cn(C)c(=O)c2c(C(=O)N3CCC(Oc4ccc(C(F)(F)F)cc4)CC3)cnn12] | | 435.27 |
| 314 | N-[(1S,3R)-3-butoxycyclopentyl]-1,5,7-trimethyl-4-oxo-4,5-dihydro-1H-pyrrolo[3,2-c]pyridine-3-carboxamide | 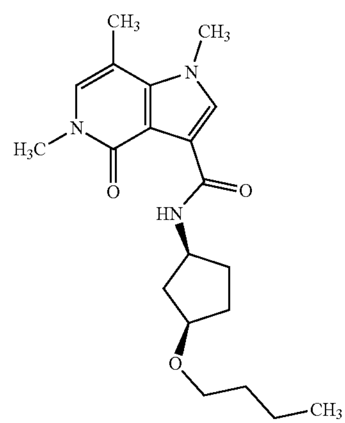 [SMILES: CCCCO[C@@H]1CC[C@H](NC(=O)c2cn(C)c3c(C)cn(C)c(=O)c23)C1] | | 360.2 |
| 315 | N-[cis-3-butoxycyclobutyl]-1,5,7-trimethyl-4-oxo-4,5-dihydro-1H-pyrrolo[3,2-c]pyridine-3-carboxamide | 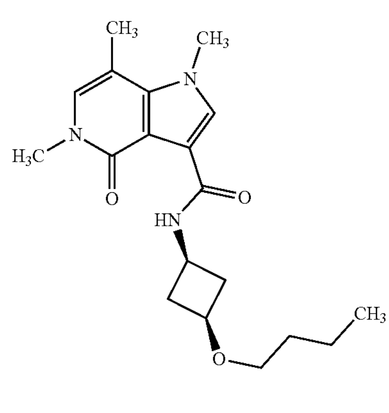 [SMILES: CCCCO[C@H]1C[C@@H](NC(=O)c2cn(C)c3c(C)cn(C)c(=O)c23)C1] | | 346.2 |

TABLE 1-40-continued

| Ex. No. | IUPAC Name | Structure | Additive | MS |
|---|---|---|---|---|
| 316 | N-[rac-(1R,3S)-3-butoxycyclopentyl]-1,5,7-trimethyl-4-oxo-4,5-dihydro-1H-pyrrolo[3,2-c]pyridine-3-carboxamide | 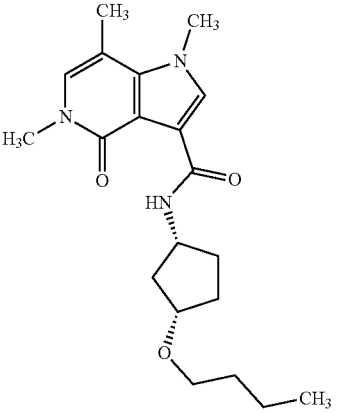 [SMILES: CCCCO[C@H]1CC[C@@H](NC(=O)c2cn(C)c3c(C)cn(C)c(=O)c23)C1] | | 360.2 |
| 317 | N-[trans-3-butoxycyclobutyl]-1,5,7-trimethyl-4-oxo-4,5-dihydro-1H-pyrrolo[3,2-c]pyridine-3-carboxamide | 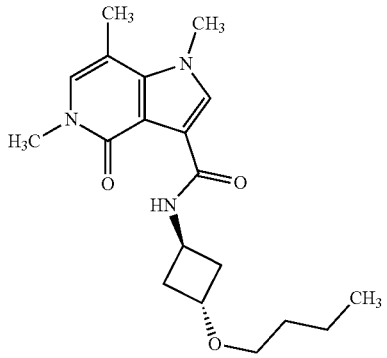 [SMILES: CCCCO[C@H]1C[C@H](NC(=O)c2cn(C)c3c(C)cn(C)c(=O)c23)C1] | | 346.2 |
| 318 | 3-[1-(5-chloropyridin-2-yl)-3-azabicyclo[3.1.0]hexane-3-carbonyl]-1,5,7-trimethyl-1,5-dihydro-4H-pyrrolo[3,2-c]pyridin-4-one | 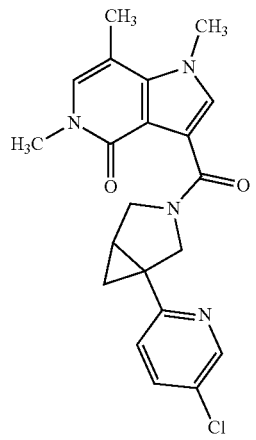 | | 397.2 |
| 319 | N-[rac-(1R,3R)-3-butoxycyclohexyl]-1,5,7-trimethyl-4-oxo-4,5-dihydro-1H-pyrrolo[3,2-c]pyridine-3-carboxamide | 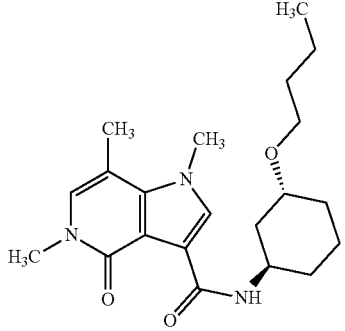 [SMILES: CCCCO[C@@H]1CCC[C@@H](NC(=O)c2cn(C)c3c(C)cn(C)c(=O)c23)C1] | | 374.3 |

TABLE 1-40-continued

| Ex. No. | IUPAC Name | Structure | Additive | MS |
|---|---|---|---|---|
| 320 | 1,5,7-trimethyl-3-{1-[1-(2,2,2-trifluoroethyl)-1H-pyrazol-4-yl]-3-azabicyclo[3.1.0]hexane-3-carbonyl}-1,5-dihydro-4H-pyrrolo[3,2-c]pyridin-4-one | 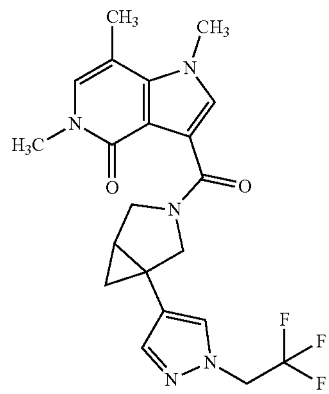 [SMILES: Cc1cn(C)c(=O)c2c(C(=O)N3CC4CC4(c4cnn(CC(F)(F)F)c4)C3)cn(C)c12] |  | 434.0 |

TABLE 1-41

| Ex. No. | IUPAC Name | Structure | Additive | MS |
|---|---|---|---|---|
| 321 | 1,5,7-trimethyl-3-{1-[1-(2,2,2-trifluoroethyl)-1H-pyrazol-3-yl]-3-azabicyclo[3.1.0]hexane-3-carbonyl}-1,5-dihydro-4H-pyrrolo[3,2-c]pyridin-4-one | 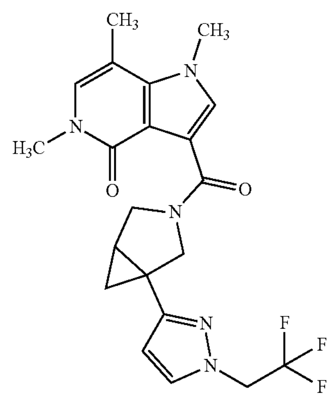 [SMILES: Cc1cn(C)c(=O)c2c(C(=O)N3CC4CC4(c4ccn(CC(F)(F)F)n4)C3)cn(C)c12] |  | 434.1 |
| 322 | 3-[1-(5-chloropyrimidin-2-yl)-3-azabicyclo[3.1.0]hexane-3-carbonyl]-1,5,7-trimethyl-1,5-dihydro-4H-pyrrolo[3,2-c]pyridin-4-one | 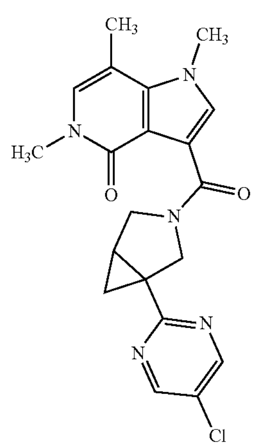 [SMILES: Cc1cn(C)c(=O)c2c(C(=O)N3CC4CC4(c4ncc(Cl)cn4)C3)cn(C)c12] |  | 398.1 |

TABLE 1-41-continued

| Ex. No. | IUPAC Name | Structure | Additive | MS |
|---|---|---|---|---|
| 323 | 5-(2-methoxyphenyl)-1-methyl-4-oxo-N-[6-(2,2,2-trifluoroethoxy)pyridin-3-yl]-4,5-dihydro-1H-pyrrolo[3,2-c]pyridine-3-carboxamide | 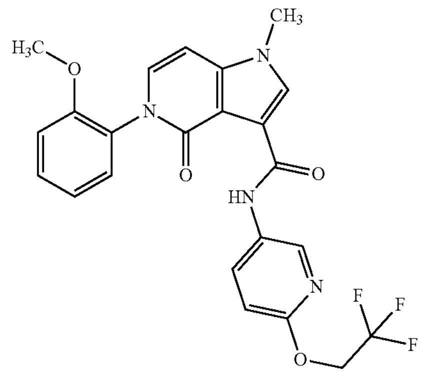 [SMILES: COc1ccccc1-n1ccc2c(c(C(=O)Nc3ccc(OCC(F)(F)F)nc3)cn2C)c1=O] | | 471.3 |
| 324 | 5-[(4-methoxyphenyl)methyl]-7-methyl-N-[4-(morpholin-4-yl)phenyl]-4-oxo-4,5-dihydropyrazolo[1,5-a]pyrazine-3-carboxamide | 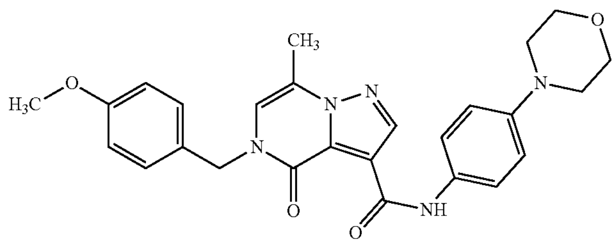 [SMILES: COc1ccc(Cn2cc(C)n3ncc(C(=O)Nc4ccc(N5CCOCC5)cc4)c3c2=O)cc1] | | 474.2 |
| 325 | 3-[4-(4-chlorophenoxy)piperidine-1-carbonyl]-5-[(4-methoxyphenyl)methyl]-7-methylpyrazolo[1,5-a]pyrazin-4(5H)-one | 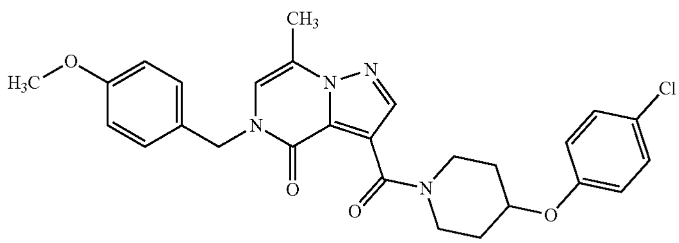 [SMILES: COc1ccc(Cn2cc(C)n3ncc(C(=O)N4CCC(Oc5ccc(Cl)cc5)CC4)c3c2=O)cc1] | | 507.2 |
| 326 | 5-[(4-methoxyphenyl)methyl]-7-methyl-3-(4-phenoxypiperidine-1-carbonyl)pyrazolo[1,5-a]pyrazin-4(5H)-one | 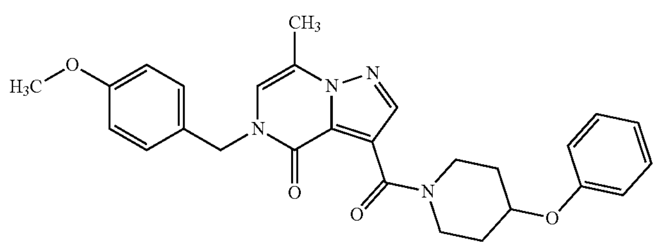 [SMILES: COc1ccc(Cn2cc(C)n3ncc(C(=O)N4CCC(Oc5ccccc5)CC4)c3c2=O)cc1] | | 473.2 |
| 327 | 7-methyl-N-[4-(morpholin-4-yl)phenyl]-4-oxo-5-(2,2,2-trifluoroethyl)-4,5-dihydropyrazolo[1,5-a]pyrazine-3-carboxamide | 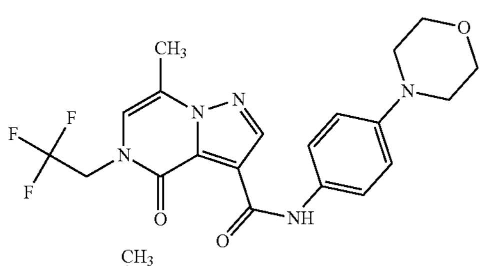 | | 436.2 |
| 328 | 3-[4-(4-chlorophenoxy)piperidine-1-carbonyl]-7-methyl-5-(2,2,2-trifluoroethyl)pyrazolo[1,5-a]pyrazin-4(5H)-one | 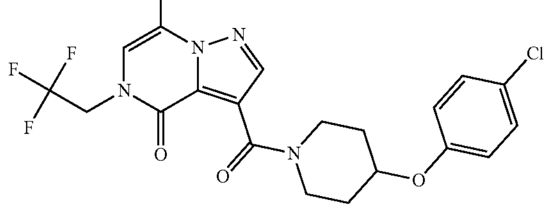 | | 469.4 |

TABLE 1-42

| Ex. No. | IUPAC Name | Structure | Additive | MS |
|---|---|---|---|---|
| 329 | 5-(cyanomethyl)-7-methyl-N-[4-(morpholin-4-yl)phenyl]-4-oxo-4,5-dihydropyrazolo[1,5-a]pyrazine-3-carboxamide | 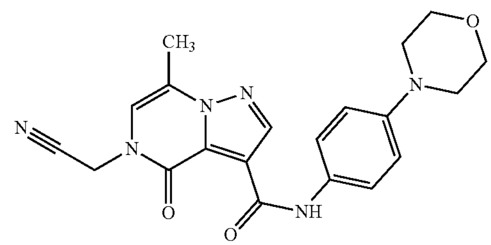 [SMILES: Cc1cn(CC#N)c(=O)c2c(C(=O)Nc3ccc(N4CCOCC4)cc3)cnn12] | | 393.4 |
| 330 | {3-[4-(4-chlorophenoxy)piperidine-1-carbonyl]-7-methyl-4-oxopyrazolo[1,5-a]pyrazin-5(4H)-yl}acetonitrile | 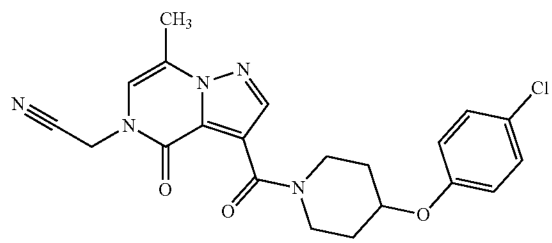 [SMILES: Cc1cn(CC#N)c(=O)c2c(C(=O)N3CCC(Oc4ccc(Cl)cc4)CC3)cnn12] | | 426.3 |
| 331 | 3-[4-(4-chlorophenoxy)piperidine-1-carbonyl]-5-(2-methoxyphenyl)-7-methylpyrazolo[1,5-a]pyrazin-4(5H)-one | 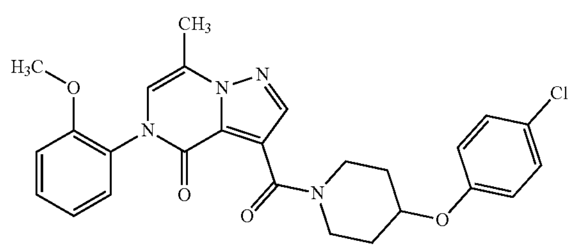 [SMILES: COc1ccccc1-n1cc(C)n2ncc(C(=O)N3CCC(Oc4ccc(Cl)cc4)CC3)c2c1=O] | | 493.3 |
| 332 | 3-[4-(4-chlorophenoxy)piperidine-1-carbonyl]-5-(4-fluoro-2-methoxyphenyl)-7-methylpyrazolo[1,5-a]pyrazin-4(5H)-one | 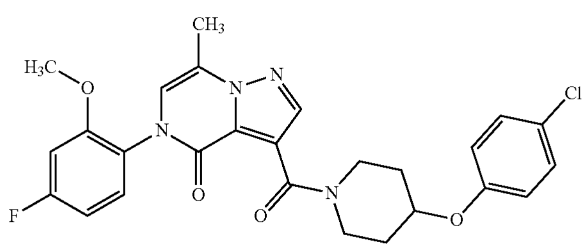 [SMILES: COc1cc(F)ccc1-n1cc(C)n2ncc(C(=O)N3CCC(Oc4ccc(Cl)cc4)CC3)c2c1=O] | | 511.1 |
| 333 | 5-(4-fluoro-2-methoxyphenyl)-7-methyl-N-[4-(morpholin-4-yl)phenyl]-4-oxo-4,5-dihydropyrazolo[1,5-a]pyrazine-3-carboxamide | 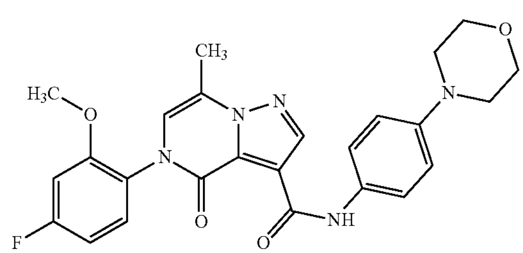 [SMILES: COc1cc(F)ccc1-n1cc(C)n2ncc(C(=O)Nc3ccc(N4CCOCC4)cc3)c2c1=O] | | 478.2 |
| 334 | 7-methyl-N-[4-(morpholin-4-yl)phenyl]-4-oxo-5-[2-(2,2,2-trifluoroethoxy)phenyl]-4,5-dihydropyrazolo[1,5-a]pyrazine-3-carboxamide | 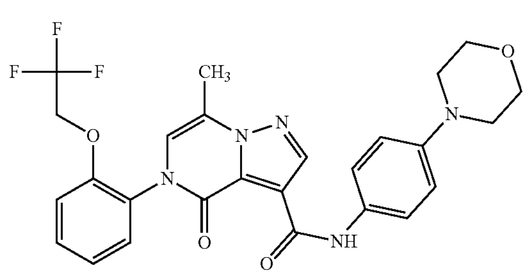 [SMILES: Cc1cn(-c2ccccc2OCC(F)(F)F)c(=O)c2c(C(=O)Nc3ccc(N4CCOCC4)cc3)cnn12] | | 528.1 |

TABLE 1-42-continued

| Ex. No. | IUPAC Name | Additive | MS |
|---|---|---|---|
| 335 | 3-[4-(4-chlorophenoxy)piperidine-1-carbonyl]-7-methyl-5-[2-(2,2,2-trifluoroethoxy)phenyl]pyrazolo[1,5-a]pyrazin-4(5H)-one | | 561.3 |
| 336 | 5-[4-fluoro-2-(2,2,2-trifluoroethoxy)phenyl]-7-methyl-N-[4-(morpholin-4-yl)phenyl]-4-oxo-4,5-dihydropyrazolo[1,5-a]pyrazine-3-carboxamide | | 546.1 |

TABLE 1-43

| Ex. No. | IUPAC Name | Additive | MS |
|---|---|---|---|
| 337 | 7-methyl-4-oxo-5-[2-(2,2,2-trifluoroethoxy)phenyl]-N-[6-(2,2,2-trifluoroethoxy)pyridin-3-yl]-4,5-dihydropyrazolo[1,5-a]pyrazine-3-carboxamide | | 541.8 |
| 338 | N-[6-(difluoromethoxy)pyridin-3-yl]-7-methyl-4-oxo-5-[2-(2,2,2-trifluoroethoxy)phenyl]-4,5-dihydropyrazolo[1,5-a]pyrazine-3-carboxamide | | 509.8 |

TABLE 1-43-continued

| Ex. No. | IUPAC Name | Structure | Additive | MS |
|---|---|---|---|---|
| 339 | N-[trans-4-butoxycyclohexyl]-7-methyl-4-oxo-5-[2-(2,2,2-trifluoroethoxy)phenyl]-4,5-dihydropyrazolo[1,5-a]pyrazine-3-carboxamide | 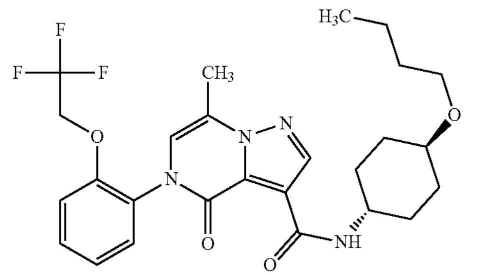 [SMILES: CCCCO[C@H]1CC[C@H](NC(=O)c2cnn3c(C)cn(-c4ccccc4OCC(F)(F)F)c(=O)c23)CC1] | | 521.0 |
| 340 | N-[4-(2-hydroxypropan-2-yl)phenyl]-7-methyl-4-oxo-5-[2-(2,2,2-trifluoroethoxy)phenyl]-4,5-dihydropyrazolo[1,5-a]pyrazine-3-carboxamide | 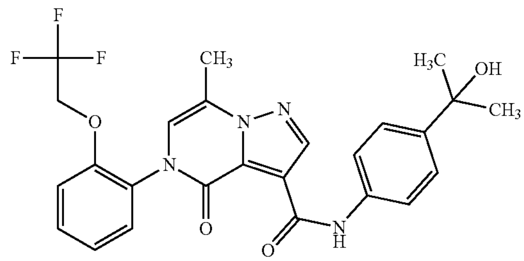 [SMILES: Cc1cn(-c2ccccc2OCC(F)(F)F)c(=O)c2c(C(=O)Nc3ccc(C(C)(C)O)cc3)cnn12] | | 500.9 |
| 341 | N-(6-cyclopropylpyridin-3-yl)-7-methyl-4-oxo-5-[2-(2,2,2-trifluoroethoxy)phenyl]-4,5-dihydropyrazolo[1,5-a]pyrazine-3-carboxamide | 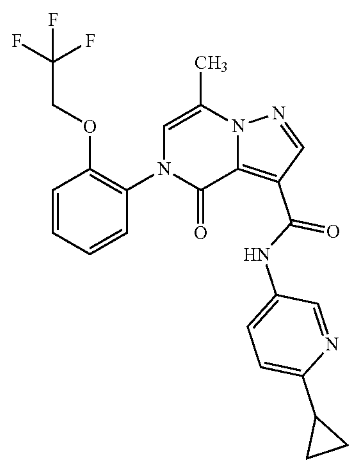 [SMILES: Cc1cn(-c2ccccc2OCC(F)(F)F)c(=O)c2c(C(=O)Nc3ccc(C4CC4)nc3)cnn12] | | 483.9 |
| 342 | N-(6-cyanopyridin-3-yl)-7-methyl-4-oxo-5-[2-(2,2,2-trifluoroethoxy)phenyl]-4,5-dihydropyrazolo[1,5-a]pyrazine-3-carboxamide | 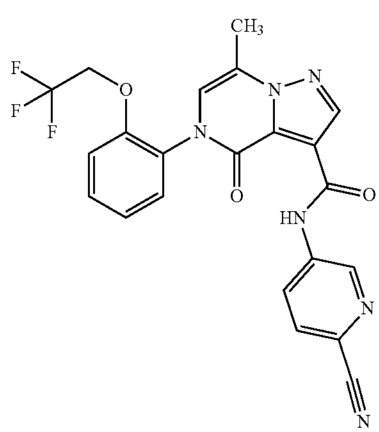 [SMILES: Cc1cn(-c2ccccc2OCC(F)(F)F)c(=O)c2c(C(=O)Nc3ccc(C#N)nc3)cnn12] | | 468.9 |

TABLE 1-43-continued

| Ex. No. | IUPAC Name | Structure | Additive | MS |
|---|---|---|---|---|
| 343 | N-(5-cyanopyridin-2-yl)-7-methyl-4-oxo-5-[2-(2,2,2-trifluoroethoxy)phenyl]-4,5-dihydropyrazolo[1,5-a]pyrazine-3-carboxamide | 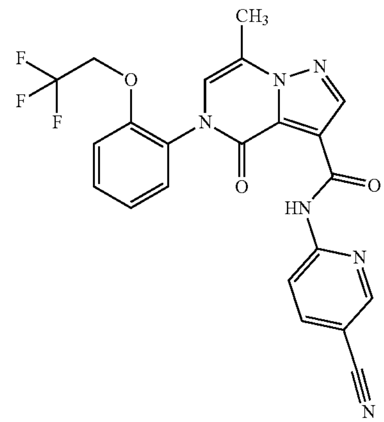 [SMILES: Cc1cn(-c2ccccc2OCC(F)(F)F)c(=O)c2c(C(=O)Nc3ccc(C#N)cn3)cnn12] | | 468.9 |
| 344 | N-[2-(benzyloxy)phenyl]-6,8-dimethyl-5-oxo-5,6-dihydroimidazo[1,2-c]pyrimidine-3-carboxamide | 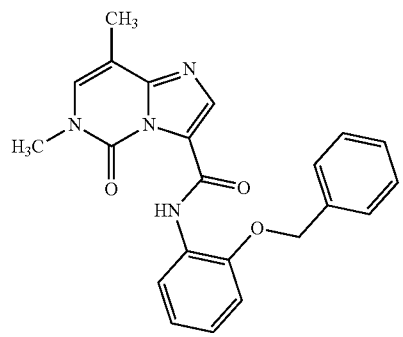 [SMILES: Cc1cn(C)c(=O)n2c(C(=O)Nc3ccccc3OCc3ccccc3)cnc12] | | 389.2 |

TABLE 1-44

| Ex. No. | IUPAC Name | Structure | Additive | MS |
|---|---|---|---|---|
| 345 | 6,8-dimethyl-N-[4-(morpholin-4-yl)phenyl]-5-oxo-5,6-dihydroimidazo[1,2-c]pyrimidine-3-carboxamide | 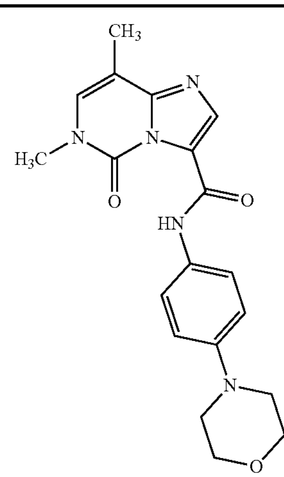 | | 368.2 |

TABLE 1-44-continued

| Ex. No. | IUPAC Name | Structure | Additive | MS |
|---|---|---|---|---|
| 346 | N-[trans-4-butoxycyclohexyl]-6,8-dimethyl-5-oxo-5,6-dihydroimidazo[1,2-c]pyrimidine-3-carboxamide | 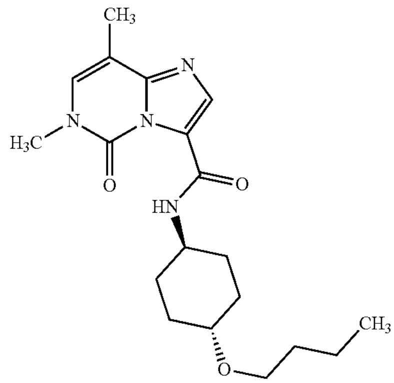 [SMILES: CCCCO[C@H]1CC[C@H](NC(=O)c2cnc3c(C)cn(C)c(=O)n23)CC1] | | 361.2 |
| 347 | N-[2-(4-chlorophenyl)propan-2-yl]-6,8-dimethyl-5-oxo-5,6-dihydroimidazo[1,2-c]pyrimidine-3-carboxamide | 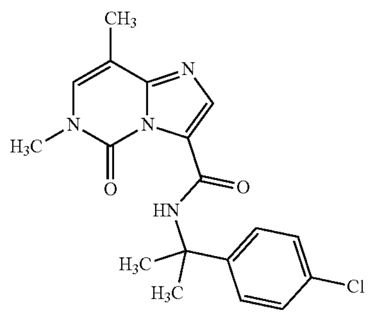 [SMILES: Cc1cn(C)c(=O)n2c(C(=O)NC(C)(C)c3ccc(Cl)cc3)cnc12] | | 359.1 |
| 348 | 3-[4-(4-chlorophenoxy)piperidine-1-carbonyl]-6,8-dimethylimidazo[1,2-c]pyrimidin-5(6H)-one | 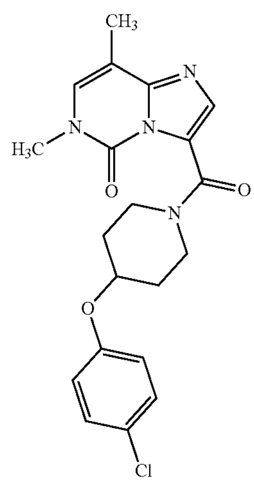 [SMILES: Cc1cn(C)c(=O)n2c(C(=O)N3CCC(Oc4ccc(Cl)cc4)CC3)cnc12] | | 401.1 |
| 349 | N-[2-(benzyloxy)phenyl]-6-(2-methoxyphenyl)-8-methyl-5-oxo-5,6-dihydroimidazo[1,2-c]pyrimidine-3-carboxamide | 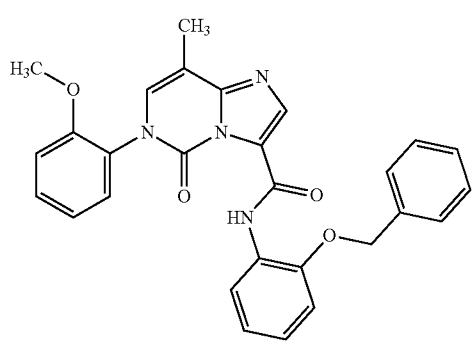 [SMILES: COc1ccccc1-n1cc(C)c2ncc(C(=O)Nc3ccccc3OCc3ccccc3)n2c1=O] | | 481.2 |

TABLE 1-44-continued
| Ex. No. | IUPAC Name | Structure | Additive | MS |
|---|---|---|---|---|
| 350 | 6-(2-methoxyphenyl)-8-methyl-N-[4-(morpholin-4-yl)phenyl]-5-oxo-5,6-dihydroimidazo[1,2-c]pyrimidine-3-carboxamide | 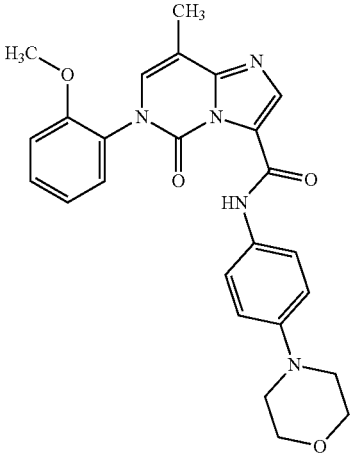 [SMILES: COc1ccccc1-n1cc(C)c2ncc(C(=O)Nc3ccc(N4CCOCC4)cc3)n2c1=O] | | 460.2 |
| 351 | N-[trans-4-butoxycyclohexyl]-6-(2-methoxyphenyl)-8-methyl-5-oxo-5,6-dihydroimidazo[1,2-c]pyrimidine-3-carboxamide | 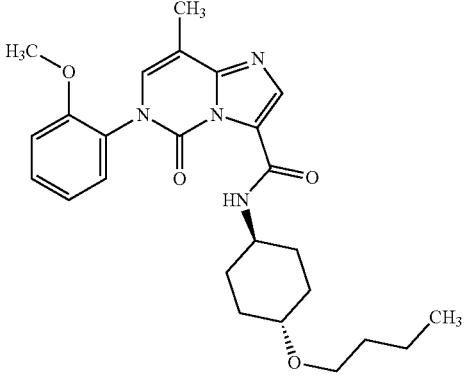 [SMILES: CCCCO[C@H]1CC[C@H](NC(=O)c2cnc3c(C)cn(-c4ccccc4OC)c(=O)n23)CC1] | | 453.3 |
| 352 | N-[2-(4-chlorophenyl)propan-2-yl]-6-(2-methoxyphenyl)-8-methyl-5-oxo-5,6-dihydroimidazo[1,2-c]pyrimidine-3-carboxamide | 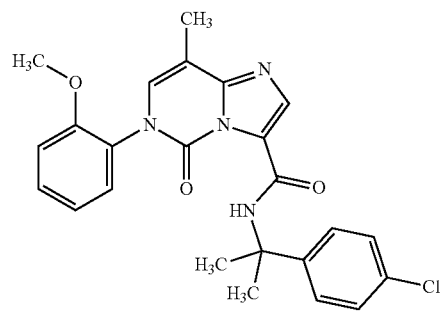 [SMILES: COc1ccccc1-n1cc(C)c2ncc(C(=O)NC(C)(C)c3ccc(Cl)cc3)n2c1=O] | | 451.1 |

TABLE 1-45

| Ex. No. | IUPAC Name | Structure | Additive | MS |
|---|---|---|---|---|
| 353 | 3-[4-(4-chlorophenoxy)piperidine-1-carbonyl]-6-(2-methoxyphenyl)-8-methylimidazo[1,2-c]pyrimidin-5(6H)-one | 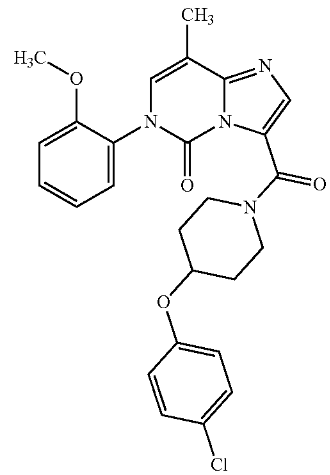 [SMILES: COc1ccccc1-n1cc(C)c2ncc(C(=O)N3CCC(Oc4ccc(Cl)cc4)CC3)n2c1=O] | | 493.2 |

Experimental Example

Glucosylceramide Lowering Assay

Using GBA mutant human fibroblasts containing mutated glucosylceramidase, the effect of test compounds on glucosylceramide reduction was evaluated.

GBA mutant human fibroblasts GM008760 (Coriel Institute) were seeded in a 96-well multiwell plate at a density of 5,000 cells/100 μL culture solution/well. GlutaMAX (Thermo Fishcer Scientific), penicillin-streptomycin, and Minimum Essential Media (Thermo Fishcer Scientific) supplemented with 15% fetal bovine serum were used as a culture solution. After culturing for 2 days, a 10 mM DMSO solution of the test compound diluted with the culture solution was added to a 96-well plate by 100 μL to adjust a final test compound concentration to 10 μM. After culturing the cells for 4 days in the presence of the test compound, the culture solution was removed, and the cells adhered to the 96-well plate were washed with a phosphate buffer (ThermoFisher Scientific, product number 14190-144). A solvent composed of 50% ethanol and 50% isopropanol was added to the 96-well plate by 100 μL, and the intracellular lipids were dissolved by pipetting. A solution prepared by dissolving N-Octadecanoyl-D35-psychosine (50 ng/mL, Matreya LLC Inc.) as an internal standard in 50% ethanol and 50% isopropanol was added to the sample in an equal volume, and 2.5 μL of the centrifuged supernatant was used as the test compound group.

In the same manner as above, a control group was prepared by using DMSO instead of the 10 mM DMSO solution of the test compound.

For the test compound group and the control group, molar concentrations of glucosylceramide [GlcCer (C16:0)] and ceramide [Cer (C16:0)] were quantified using Rapidfire-MS/MS (API-5000, Turbo-ESI, SRM), and the glucosylceramide lowering effect of the test compound group relative to the control group was evaluated by the following formula.

(GlcCer/Cer of test compound group)/(GlcCer/Cer of control group)×100 wherein GlcCer/Cer is the ratio of the molar concentration of glucosylceramide to that of ceramide.

In this test, when the numerical value obtained by the above calculation formula is small, glucosylceramide is metabolized to ceramide by the test compound, or the synthesis of glucosylceramide from ceramide is inhibited by the test compound, that is, it can be said that the test compound has a glucosylceramide lowering effect.

The results are shown in the following Table 2-1 and Table 2-2.

TABLE 2-1

| Example | 10 μM GlcCer/Cer (% of control) |
|---|---|
| 2 | 87 |
| 21 | 67 |
| 36 | 65 |
| 37 | 68 |
| 40 | 62 |
| 57 | 65 |
| 71 | 68 |
| 72 | 38 |
| 83 | 49 |
| 107 | 50 |
| 108 | 67 |
| 110 | 58 |
| 111 | 61 |
| 112 | 61 |
| 113 | 41 |
| 114 | 58 |
| 118 | 59 |
| 120 | 50 |
| 121 | 68 |
| 122 | 54 |
| 123 | 47 |
| 124 | 56 |
| 126 | 61 |
| 127 | 65 |
| 130 | 21 |
| 131 | 63 |
| 137 | 64 |
| 138 | 39 |
| 139 | 37 |
| 140 | 49 |
| 141 | 47 |
| 146 | 65 |
| 151 | 46 |
| 153 | 60 |
| 155 | 53 |
| 168 | 40 |
| 176 | 56 |
| 178 | 42 |
| 188 | 65 |

TABLE 2-1-continued

| Example | 10 µM GlcCer/Cer (% of control) |
|---|---|
| 189 | 36 |
| 190 | 29 |
| 205 | 62 |
| 206 | 49 |
| 217 | 64 |
| 219 | 63 |
| 221 | 44 |
| 227 | 59 |
| 228 | 43 |
| 231 | 59 |
| 258 | 64 |
| 261 | 65 |
| 262 | 51 |
| 265 | 34 |
| 277 | 77 |
| 282 | 66 |
| 283 | 75 |
| 286 | 67 |
| 288 | 27 |
| 292 | 89 |
| 293 | 52 |
| 294 | 36 |
| 295 | 66 |
| 296 | 52 |
| 303 | 60 |
| 304 | 64 |
| 305 | 47 |
| 306 | 51 |
| 307 | 65 |
| 309 | 44 |
| 310 | 68 |
| 311 | 54 |
| 313 | 52 |

TABLE 2-2

| Example | 10 µM GlcCer/Cer (% of control) |
|---|---|
| 330 | 68 |
| 334 | 27 |
| 335 | 68 |
| 336 | 42 |
| 337 | 37 |
| 338 | 40 |
| 339 | 30 |
| 340 | 33 |
| 341 | 32 |
| 342 | 28 |
| 343 | 23 |
| 347 | 44 |
| 350 | 54 |

As is clear from Table 2-1 and Table 2-2, since GlcCer/Cer was lower in the test compound group than in the control group, it was confirmed that the compound of the present invention had a glucosylceramide lowering effect.

Formulation Examples

Medicaments containing the compound of the present invention as an active ingredient can be produced, for example, by the following formulations.

1. Capsule

| (1) compound obtained in Example 1 | 10 mg |
|---|---|
| (2) lactose | 90 mg |
| (3) microcrystalline cellulose | 70 mg |
| (4) magnesium stearate | 10 mg |
| 1 capsule | 180 mg |

The total amount of the above-mentioned (1), (2) and (3) and 5 mg of (4) are blended and granulated, and 5 mg of the remaining (4) is added. The whole mixture is sealed in a gelatin capsule.

2. Tablet

| (1) compound obtained in Example 1 | 10 mg |
|---|---|
| (2) lactose | 35 mg |
| (3) cornstarch | 150 mg |
| (4) microcrystalline cellulose | 30 mg |
| (5) magnesium stearate | 5 mg |
| 1 tablet | 230 mg |

The total amount of the above-mentioned (1), (2) and (3), 20 mg of (4) and 2.5 mg of (5) are blended and granulated, and 10 mg of the remaining (4) and 2.5 mg of the remaining (5) are added and the mixture is compression formed to give a tablet.

INDUSTRIAL APPLICABILITY

According to the present invention, a compound having an excellent glucosylceramide lowering action (e.g., promoting glucosylceramide metabolism, inhibition of glucosylceramide synthesis, promoting glucosylceramide catabolism, etc.), which is expected to be useful as an agent for the prophylaxis or treatment of lysosome diseases (e.g., Gaucher's disease), neurodegenerative diseases (e.g., Parkinson's disease, Lewy body dementia, multiple-system atrophy) and the like, can be provided.

This application is based on patent application No. 2018-015264 filed on Jan. 31, 2018 in Japan, the contents of which are encompassed in full herein.

The invention claimed is:

1. A compound represented by the formula (I):

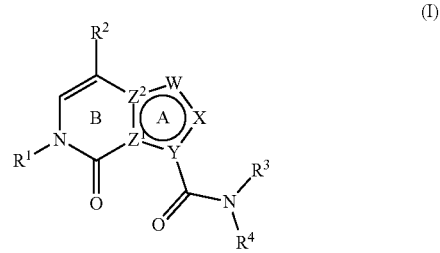

wherein
Ring A is a 5-membered aromatic heterocycle,
Ring B is an optionally further substituted 6-membered nitrogen-containing non-aromatic heterocycle,
W is $CR^5$, $NR^6$, N, O or S,
X is $CR^7$, $NR^8$ or N,
Y is C or N, $Z^1$ and $Z^2$ are each independently C or N,
$R^1$ is a substituent,
as to $R^2$
(1) when W is $CR^5$, $NR^6$ or N, then $R^2$ is a hydrogen atom or a substituent,
(2) when W is O or S, then $R^2$ is a substituent,
$R^3$ and $R^4$ are each independently
(1) a hydrogen atom,
(2) a $C_{1-6}$ alkyl group optionally substituted by 1 to 3 substituents selected from
  (a) a halogen atom,
  (b) a cyano group,
  (c) a $C_{3-10}$ cycloalkyl group,
  (d) a $C_{6-14}$ aryl group optionally substituted by 1 to 3 halogen atoms, and
  (e) a 5- to 14-membered aromatic heterocyclic group optionally substituted by 1 to 3 substituents selected from
    (i) a $C_{1-6}$ alkyl group,
    (ii) a $C_{1-6}$ alkoxy group, and
    (iii) a $C_{6-14}$ aryl group optionally substituted by 1 to 3 substituents selected from a halogen atom and a $C_{1-6}$ alkyl group,
(3) a $C_{3-10}$ cycloalkyl group optionally fused with a benzene ring (the $C_{3-10}$ cycloalkyl may be a bridged ring group), which is optionally substituted by 1 to 3 substituents selected from
  (a) a halogen atom,
  (b) a cyano group,
  (c) an optionally halogenated $C_{1-6}$ alkyl group,
  (d) a $C_{1-6}$ alkoxy group,
  (e) a $C_{1-6}$ alkoxy-carbonylamino group,
  (f) a $C_{6-14}$ aryl group optionally substituted by 1 to 3 halogen atoms,
  (g) a $C_{6-14}$ aryloxy group,
  (h) a $C_{7-16}$ aralkyloxy group, and
  (i) a 5- to 14-membered aromatic heterocyclic group,
(4) a $C_{6-14}$ aryl group optionally substituted by 1 to 3 substituents selected from
  (a) a $C_{1-6}$ alkyl group optionally substituted by 1 to 3 hydroxy groups,
  (b) a $C_{1-6}$ alkoxy group,
  (c) a $C_{6-14}$ aryloxy group,
  (d) a $C_{7-16}$ aralkyloxy group, and
  (e) a 3- to 14-membered non-aromatic heterocyclic group,
(5) a 5- to 14-membered aromatic heterocyclic group optionally substituted by 1 to 3 substituents selected from
  (a) a cyano group,
  (b) an optionally halogenated $C_{1-6}$ alkyl group,
  (c) an optionally halogenated $C_{1-6}$ alkoxy group,
  (d) a $C_{6-14}$ aryl group,
  (e) a $C_{6-14}$ aryloxy group,
  (f) a $C_{7-16}$ aralkyl group optionally substituted by 1 to 3 halogen atoms, and
  (g) a $C_{3-10}$ cycloalkyl group, or
(6) a 3- to 14-membered non-aromatic heterocyclic group optionally substituted by 1 to 3 substituents selected from
  (a) a $C_{1-6}$ alkyl group optionally substituted by 1 to 3 $C_{3-10}$ cycloalkyl groups,
  (b) a $C_{1-6}$ alkoxy-carbonyl group,
  (c) a $C_{6-14}$ aryl group optionally substituted by 1 to 3 halogen atoms, and
  (d) a $C_{7-16}$ aralkyl group, or $R^3$ and $R^4$ are bonded to each other to form, together with the adjacent nitrogen atom, a 3- to 14-membered non-aromatic nitrogen-containing heterocycle optionally further substituted by 1 to 3 substituents selected from
  (a) a halogen atom,
  (b) a $C_{1-6}$ alkyl group optionally substituted by 1 to 3 substituents selected from
    (i) a halogen atom,
    (ii) a cyano group,
    (iii) a $C_{1-6}$ alkoxy group, and
    (iv) a mono- or di-$C_{1-6}$ alkylamino group,
  (c) a $C_{1-6}$ alkoxy group optionally substituted by 1 to 3 substituents selected from
    (i) a halogen atom, and
    (ii) a $C_{3-10}$ cycloalkyl group,
  (d) a $C_{3-10}$ cycloalkyl group,
  (e) a $C_{6-14}$ aryl group optionally substituted by 1 to 3 substituents selected from
    (i) a halogen atom,
    (ii) an optionally halogenated $C_{1-6}$ alkyl group, and
    (iii) an optionally halogenated $C_{1-6}$ alkoxy group,
  (f) a $C_{6-14}$ aryloxy group optionally substituted by 1 to 3 substituents selected from
    (i) a halogen atom,
    (ii) a cyano group,
    (iii) an optionally halogenated $C_{1-6}$ alkyl group, and
    (iv) an optionally halogenated $C_{1-6}$ alkoxy group,
  (g) a $C_{7-16}$ aralkyl group,
  (h) a $C_{7-16}$ aralkyloxy group,
  (i) a 5- to 14-membered aromatic heterocyclic group optionally substituted by 1 to 3 substituents selected from
    (i) a halogen atom, and
    (ii) an optionally halogenated $C_{1-6}$ alkyl group,
  (j) a 5- to 14-membered aromatic heterocyclyloxy group, and
  (k) a 3- to 14-membered non-aromatic heterocyclyloxy group optionally substituted by 1 to 3 $C_{1-6}$ alkoxy-carbonyl groups,
$R^5$ and $R^7$ are each independently a hydrogen atom or a substituent, and
$R^6$ and $R^8$ are each independently a substituent,
or a salt thereof.

2. The compound or salt according to claim 1, wherein
Ring A is pyrrole, pyrazole, thiophene, furan or imidazole;
Ring B is dihydropyridine, tetrahydropyridine, tetrahydropyrazine or tetrahydropyrimidine;
W is $NR^6$ wherein $R^6$ is a $C_{1-6}$ alkyl group or a benzyl group, N, O or S;
X is $CR^7$ wherein $R^7$ is a hydrogen atom or a $C_{1-6}$ alkyl group, $NR^8$ wherein $R^8$ is a $C_{1-6}$ alkyl group, or N;
Y is C;
$Z^1$—$Z^2$ is C=C, C—C, C—N or N—C;
$R^1$ is
(1) a $C_{1-6}$ alkyl group optionally substituted by 1 to 3 substituents selected from
  (a) a halogen atom, and
  (b) a cyano group,
(2) a phenyl group optionally substituted by 1 to 3 substituents selected from
  (a) an optionally halogenated $C_{1-6}$ alkoxy group, and
  (b) a halogen atom, or (3) a benzyl group optionally substituted by 1 to 3 $C_{1-6}$ alkoxy groups;

as to $R^2$ (1) when W is $NR^6$ or N, then $R^2$ is a hydrogen atom, a halogen atom, a $C_{1-6}$ alkyl group, a $C_{3-6}$ cycloalkyl group or a phenyl group, (2) when W is O or S, then $R^2$ is a $C_{1-6}$ alkyl group; and $R^3$ and $R^4$ are each independently (1) a hydrogen atom, (2) a $C_{1-6}$ alkyl group optionally substituted by 1 to 3 substituents selected from
   (a) a halogen atom,
   (b) a cyano group,
   (c) a $C_{3-6}$ cycloalkyl group,
   (d) a phenyl group optionally substituted by 1 to 3 halogen atoms,
   (e) a pyridyl group optionally substituted by 1 to 3 $C_{1-6}$ alkoxy groups,
   (f) a pyrazolyl group optionally substituted by 1 to 3 substituents selected from
      (i) a $C_{1-6}$ alkyl group, and
      (ii) a phenyl group optionally substituted by 1 to 3 substituents selected from a halogen atom and a $C_{1-6}$ alkyl group,
   (g) a triazolyl group optionally substituted by 1 or 2 substituents selected from
      (i) a $C_{1-6}$ alkyl group, and
      (ii) a phenyl group,
   (h) an oxadiazolyl group optionally substituted by phenyl group(s) optionally substituted by 1 to 3 halogen atoms,
   (i) a thiazolyl group optionally substituted by 1 or 2 substituents selected from
      (i) a $C_{1-6}$ alkyl group, and
      (ii) a phenyl group, and
   (j) a thienyl group optionally substituted by 1 to 3 phenyl groups optionally substituted by 1 to 3 halogen atoms, (3) a $C_{3-6}$ cycloalkyl group optionally substituted by 1 to 3 substituents selected from
   (a) a halogen atom,
   (b) a cyano group,
   (c) an optionally halogenated $C_{1-6}$ alkyl group,
   (d) a $C_{1-6}$ alkoxy group,
   (e) a $C_{1-6}$ alkoxy-carbonylamino group,
   (f) a phenyl group optionally substituted by 1 to 3 halogen atoms,
   (g) a phenoxy group,
   (h) a benzyloxy group, and
   (i) a pyridyl group, (4) a bicyclo[1.1.1]pentyl group optionally substituted by 1 to 3 substituents selected from
   (a) an optionally halogenated $C_{1-6}$ alkyl group, and
   (b) a phenyl group, (5) an indanyl group optionally substituted by 1 to 3 halogen atoms, (6) a tetrahydronaphthyl group, (7) a dihydrobenzocyclobutenyl group, (8) a phenyl group optionally substituted by 1 to 3 substituents selected from
   (a) a $C_{1-6}$ alkyl group optionally substituted by 1 to 3 hydroxy groups,
   (b) a $C_{1-6}$ alkoxy group,
   (c) a phenoxy group,
   (d) a benzyloxy group, and
   (e) a morpholinyl group, (9) a pyrazolyl group optionally substituted by 1 to 3 substituents selected from
   (a) an optionally halogenated $C_{1-6}$ alkyl group, and
   (b) a benzyl group optionally substituted by 1 to 3 halogen atoms,

(10) an imidazolyl group optionally substituted by 1 to 3 phenyl groups,

(11) a pyridyl group optionally substituted by 1 to 3 substituents selected from
   (a) a cyano group,
   (b) an optionally halogenated $C_{1-6}$ alkyl group,
   (c) an optionally halogenated $C_{1-6}$ alkoxy group,
   (d) a phenoxy group, and
   (e) a $C_{3-10}$ cycloalkyl group,

(12) a pyrrolidinyl group optionally substituted by 1 to 3 benzyl groups,

(13) a piperidyl group optionally substituted by 1 to 3 substituents selected from
   (a) a $C_{1-6}$ alkyl group optionally substituted by 1 to 3 $C_{3-6}$ cycloalkyl groups,
   (b) a $C_{1-6}$ alkoxy-carbonyl group,
   (c) a phenyl group optionally substituted by 1 to 3 halogen atoms, and
   (d) a benzyl group,

(14) a tetrahydrofuryl group optionally substituted by 1 to 3 phenyl groups, or

(15) a dihydrochromenyl group optionally substituted by 1 to 3 $C_{1-6}$ alkyl groups, or $R^3$ and $R^4$ are bonded to each other to form, together with the adjacent nitrogen atom, (1) an azetidine ring optionally further substituted by 1 to 3 substituents selected from
   (a) a $C_{1-6}$ alkyl group optionally substituted by 1 to 3 $C_{1-6}$ alkoxy groups,
   (b) an optionally halogenated $C_{1-6}$ alkoxy group,
   (c) a $C_{3-6}$ cycloalkyl group,
   (d) a phenyl group optionally substituted by 1 to 3 halogen atoms,
   (e) a phenoxy group,
   (f) a benzyl group, and
   (g) a benzyloxy group, (2) a pyrrolidine ring optionally further substituted by 1 to 3 substituents selected from
   (a) a halogen atom,
   (b) an optionally halogenated $C_{1-6}$ alkoxy group,
   (c) a phenyl group optionally substituted by 1 to 3 substituents selected from
      (i) a halogen atom,
      (ii) an optionally halogenated $C_{1-6}$ alkyl group, and
      (iii) a $C_{1-6}$ alkoxy group,
   (d) a benzyl group, and
   (e) a benzyloxy group, (3) a piperidine ring optionally further substituted by 1 to 3 substituents selected from
   (a) a $C_{1-6}$ alkoxy group optionally substituted by 1 to 3 substituents selected from
      (i) a halogen atom, and
      (ii) a $C_{3-6}$ cycloalkyl group,
   (b) a phenyl group optionally substituted by 1 to 3 substituents selected from
      (i) a halogen atom, and
      (ii) a $C_{1-6}$ alkoxy group,
   (c) a phenoxy group optionally substituted by 1 to 3 substituents selected from
      (i) a halogen atom,
      (ii) a cyano group, (iii) an optionally halogenated $C_{1-6}$ alkyl group, and
(iv) an optionally halogenated $C_{1-6}$ alkoxy group,
(d) a benzyl group,
(e) a benzyloxy group,
(f) a pyridyloxy group,
(g) a pyrazinyloxy group,
(h) a pyrimidinyloxy group,
(i) a thiazolyloxy group, and
(j) a piperidyloxy group optionally substituted by 1 to 3 $C_{1-6}$ alkoxy-carbonyl groups,
(4) an indoline ring optionally further substituted by 1 to 3 $C_{1-6}$ alkoxy groups,
(5) an isoindoline ring optionally further substituted by 1 to 3 $C_{1-6}$ alkoxy groups,
(6) a tetrahydroquinoline ring optionally further substituted by 1 to 3 $C_{1-6}$ alkoxy groups,
(7) a tetrahydroisoquinoline ring optionally further substituted by 1 to 3 substituents selected from
(a) a halogen atom,
(b) a $C_{1-6}$ alkyl group, and
(c) a $C_{1-6}$ alkoxy group,
(8) a 3-azabicyclo[3.1.0]hexane ring optionally further substituted by 1 to 3 substituents selected from
(a) a halogen atom,
(b) a $C_{1-6}$ alkyl group optionally substituted by 1 to 3 substituents selected from
(i) a halogen atom,
(ii) a cyano group,
(iii) a $C_{1-6}$ alkoxy group, and
(iv) a mono- or di-$C_{1-6}$ alkylamino group,
(c) a phenyl group optionally substituted by 1 to 3 substituents selected from
(i) a halogen atom,
(ii) an optionally halogenated $C_{1-6}$ alkyl group, and
(iii) an optionally halogenated $C_{1-6}$ alkoxy group,
(d) a naphthyl group, and
(e) a thienyl group,
(f) a pyrazolyl group optionally substituted by 1 to 3 of optionally halogenated $C_{1-6}$ alkyl groups,
(g) a pyridyl group optionally substituted by 1 to 3 halogen atoms, and
(h) a pyrimidinyl group optionally substituted by 1 to 3 halogen atoms,
(9) a 3-azabicyclo[4.1.0]heptane ring optionally further substituted by 1 to 3 substituents selected from
(a) a halogen atom, and
(b) a phenyl group optionally substituted by 1 to 3 substituents selected from
(i) a halogen atom,
(ii) a $C_{1-6}$ alkyl group, and
(iii) a $C_{1-6}$ alkoxy group,
(10) a 1-azaspiro[3.3]heptane ring,
(11) a 6-oxa-1-azaspiro[3.5]nonane ring,
(12) a 6-oxa-1-azaspiro[3.3]heptane ring, or
(13) a 6-oxa-1-azaspiro[3.4]octane ring.

3. The compound or salt according to claim 2, wherein the partial structure represented by the following formula:

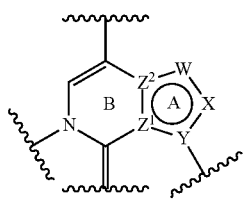

is a partial structure represented by the following formula:

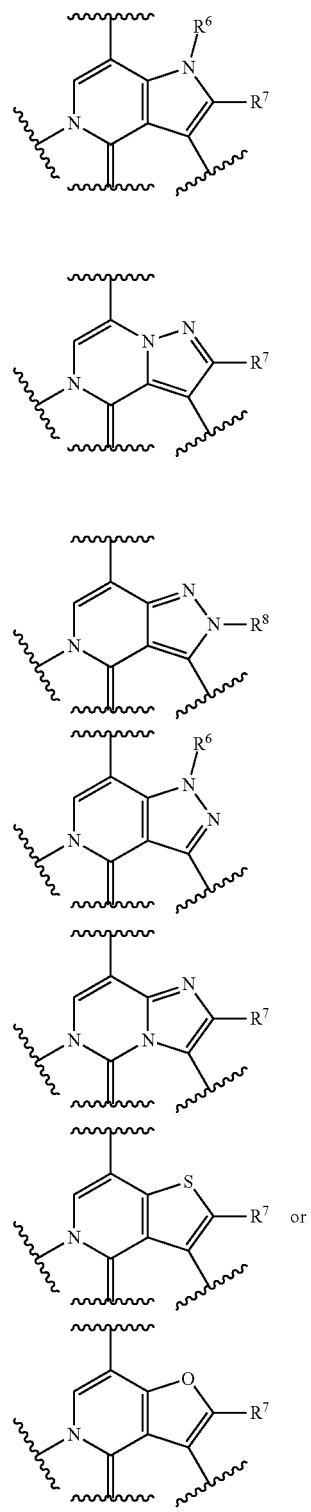

wherein $R^6$ is a $C_{1-6}$ alkyl group or a benzyl group, $R^7$ is a hydrogen atom or a $C_{1-6}$ alkyl group, and $R^8$ is a $C_{1-6}$ alkyl group.

4. The compound or salt according to claim 1, wherein the partial structure represented by the following formula:

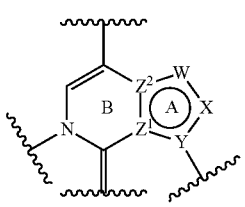

is a partial structure represented by the following formula:

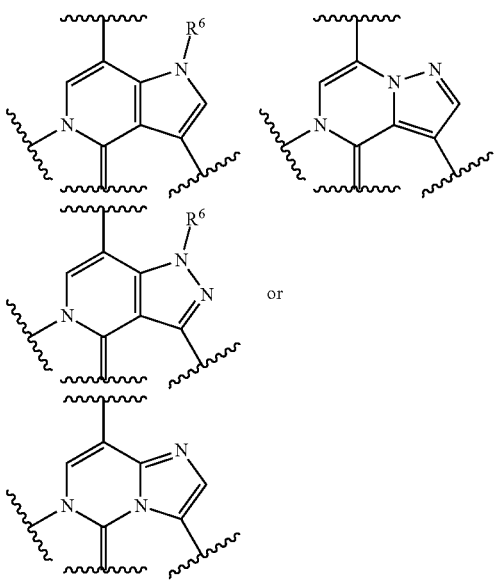

wherein $R^6$ is a $C_{1-6}$ alkyl group;

$R^1$ is (1) a $C_{1-6}$ alkyl group optionally substituted by 1 to 3 substituents selected from
  (a) a halogen atom, and
  (b) a cyano group, or
(2) a phenyl group optionally substituted by 1 to 3 substituents selected from
  (a) an optionally halogenated $C_{1-6}$ alkoxy group, and
  (b) a halogen atom;

$R^2$ is a hydrogen atom or a $C_{1-6}$ alkyl group;

$R^3$ is a hydrogen atom, and $R^4$ is (1) a $C_{1-6}$ alkyl group optionally substituted by 1 to 3 substituents selected from
  (a) a phenyl group optionally substituted by 1 to 3 halogen atoms,
  (b) an oxadiazolyl group optionally substituted by phenyl group(s) optionally substituted by 1 to 3 halogen atoms, and
  (c) a thienyl group optionally substituted by 1 to 3 phenyl groups optionally substituted by 1 to 3 halogen atoms,
(2) a $C_{3-6}$ cycloalkyl group optionally substituted by 1 to 3 substituents selected from
  (a) a $C_{1-6}$ alkoxy group, and
  (b) a phenyl group optionally substituted by 1 to 3 halogen atoms,
(3) a phenyl group optionally substituted by 1 to 3 substituents selected from
  (a) a benzyloxy group,
  (b) a morpholinyl group, and
  (c) a $C_{1-6}$ alkyl group optionally substituted by 1 to 3 hydroxy groups, or
(4) a pyridyl group optionally substituted by 1 to 3 substituents selected from
  (a) a cyano group,
  (b) an optionally halogenated $C_{1-6}$ alkoxy group, and
  (c) a $C_{3-10}$ cycloalkyl group, or $R^3$ and $R^4$ are bonded to each other to form, together with the adjacent nitrogen atom,
(1) an azetidine ring optionally further substituted by 1 to 3 phenyl groups,
(2) a pyrrolidine ring optionally further substituted by 1 to 3 substituents selected from
  (a) a halogen atom, and
  (b) a phenyl group optionally substituted by 1 to 3 halogen atoms,
(3) a piperidine ring optionally further substituted by 1 to 3 substituents selected from
  (a) a phenyl group optionally substituted by 1 to 3 halogen atoms, and
  (b) a phenoxy group optionally substituted by 1 to 3 substituents selected from
    (i) a halogen atom,
    (ii) an optionally halogenated $C_{1-6}$ alkyl group, and
    (iii) an optionally halogenated $C_{1-6}$ alkoxy group, or
(4) a 3-azabicyclo[3.1.0]hexane ring optionally further substituted by 1 to 3 substituents selected from
  (a) a halogen atom,
  (b) a phenyl group optionally substituted by 1 to 3 substituents selected from
    (i) a halogen atom,
    (ii) an optionally halogenated $C_{1-6}$ alkyl group, and
    (iii) an optionally halogenated $C_{1-6}$ alkoxy group, and
  (c) a naphthyl group.

5. N-(trans-4-Butoxycyclohexyl)-1,5,7-trimethyl-4-oxo-4,5-dihydro-1H-pyrrolo[3,2-c]pyridine-3-carboxamide or a salt thereof.

6. 1-Methyl-N-(4-(morpholin-4-yl)phenyl)-4-oxo-5-(2-(2,2,2-trifluoroethoxy)phenyl)-4,5-dihydro-1H-pyrrolo[3,2-c]pyridine-3-carboxamide or a salt thereof.

7. N-[4-(2-Hydroxypropan-2-yl)phenyl]-7-methyl-4-oxo-5-[2-(2,2,2-trifluoroethoxy)phenyl]-4,5-dihydropyrazolo[1,5-a]pyrazine-3-carboxamide or a salt thereof.

8. A pharmaceutical composition comprising the compound or salt according to claim 1, and a pharmaceutically acceptable carrier.

9. A method of lowering glucosylceramide in a mammal, which comprises administering an effective amount of the compound or salt according to claim 1 to the mammal.

10. A method for the treatment of Gaucher's disease, Parkinson's disease or Lewy body dementia in a mammal, which comprises administering an effective amount of the compound or salt according to claim 1 to the mammal.

* * * * *